US012780832B2

(12) United States Patent
Yoshinari et al.

(10) Patent No.: US 12,780,832 B2
(45) Date of Patent: Nov. 3, 2026

(54) HETEROCYCLIC COMPOUND ACTING ON G12D MUTANT KRAS PROTEIN

(71) Applicant: Astellas Pharma Inc., Tokyo (JP)

(72) Inventors: Tomohiro Yoshinari, Tokyo (JP); Hideyuki Watanabe, Tokyo (JP); Hiroki Ishioka, Tokyo (JP); Eiji Kawaminami, Tokyo (JP); Kenichi Kawaguchi, Tokyo (JP); Fumie Takahashi, Tokyo (JP); Takashi Kamikubo, Tokyo (JP); Tomoyoshi Imaizumi, Tokyo (JP); Takahiro Morikawa, Tokyo (JP); Hisao Hamaguchi, Tokyo (JP); Kazuyuki Kuramoto, Tokyo (JP); Hiroshi Inami, Tokyo (JP); Takeyuki Nagashima, Tokyo (JP); Kohei Inamura, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 18/684,845

(22) PCT Filed: Jul. 20, 2023

(86) PCT No.: PCT/JP2023/026522

§ 371 (c)(1),
(2) Date: Feb. 20, 2024

(87) PCT Pub. No.: WO2024/019103

PCT Pub. Date: Jan. 25, 2024

(65) Prior Publication Data

US 2025/0145631 A1 May 8, 2025

(30) Foreign Application Priority Data

Jul. 21, 2022 (JP) ................................. 2022-116367

(51) Int. Cl.

| | |
|---|---|
| ***C07D 487/08*** | (2006.01) |
| ***A61P 35/00*** | (2006.01) |
| ***C07D 401/14*** | (2006.01) |

(52) U.S. Cl.

CPC ......... *C07D 487/08* (2013.01); *C07D 401/14* (2013.01)

(58) Field of Classification Search

CPC .. C07D 487/08; C07D 401/14; C07D 405/14; C07D 417/14; C07D 519/00; A61K 31/4995; A61K 31/519; A61K 47/55; A61P 1/18; A61P 35/00

See application file for complete search history.

(56) References Cited

U.S. PATENT DOCUMENTS

2018/0015087 A1 1/2018 Liu et al.

FOREIGN PATENT DOCUMENTS

| | | | |
|---|---|---|---|
| CN | 115785199 A | 3/2023 | |
| CN | 116375742 A | 7/2023 | |
| WO | WO 2013/106643 A2 | 7/2013 | |
| WO | WO 2015/160845 A2 | 10/2015 | |
| WO | WO 2016/049565 A1 | 3/2016 | |
| WO | WO 2016/049568 A1 | 3/2016 | |
| WO | WO 2017/172979 A1 | 10/2017 | |
| WO | WO 2019/195609 A2 | 10/2019 | |
| WO | WO 2020/018788 A1 | 1/2020 | |
| WO | WO-2020132561 A1 * | 6/2020 | .......... C07D 401/14 |
| WO | WO 2021/041671 A1 | 3/2021 | |
| WO | WO 2021/051034 A1 | 3/2021 | |
| WO | WO 2021/106231 A1 | 6/2021 | |
| WO | WO 2021/107160 A1 | 6/2021 | |
| WO | WO 2021/188948 A1 | 9/2021 | |
| WO | WO 2021/207172 A1 | 10/2021 | |
| WO | WO 2022/002102 A1 | 1/2022 | |
| WO | WO 2022/015375 A1 | 1/2022 | |
| WO | WO 2022/031678 A1 | 2/2022 | |
| WO | WO 2022/098625 A1 | 5/2022 | |
| WO | WO 2022/105855 A1 | 5/2022 | |
| WO | WO 2022/148421 A1 | 7/2022 | |
| WO | WO 2022/148422 A1 | 7/2022 | |
| WO | WO 2022/173032 A1 | 8/2022 | |
| WO | WO 2022/173033 A1 | 8/2022 | |

(Continued)

OTHER PUBLICATIONS

M. Zeng et al., “Exploring Targeted Degradation Strategy for Oncogenic KRAS$^{G12C}$,” Cell Chem. Biol. 27, 19-31, Jan. 16, 2020, 20 pages.

M. J. Bond, et al., “Targeted Degradation of Oncogenic KRAS$^{G12C}$ by VHL-Recruiting PROTACs,” ACS Cent. Sci. 2020, 6, 1367-1375, 9 pages.

Wan Y et al. “Small-molecule PROTACs: novel agents for cancer therapy,” Future Med. Chem. (2020) 12(10), 915-938.

*Primary Examiner* — Renee Claytor

*Assistant Examiner* — Elena V Vishnyakova

(74) *Attorney, Agent, or Firm* — Finnegan, Henderson, Farabow, Garrett & Dunner, LLP

(57) ABSTRACT

[Problem] To provide a compound useful as an active ingredient of a pharmaceutical composition for treating pancreatic cancer.

[Means for resolution] The present inventors have studied about a compound that is useful as an active ingredient of a pharmaceutical composition for treating pancreatic cancer and have found that heterocyclic compounds represented by the formula (I) have an excellent degradation-inducing action on a G12D mutant KRAS protein and/or a G12D mutant KRAS inhibition activity and can be used as a therapeutic agent for pancreatic cancer, thus completing the present invention. The heterocyclic compound or a salt thereof of the present invention can be used as a therapeutic agent for pancreatic cancer.

10 Claims, No Drawings

(56) References Cited

FOREIGN PATENT DOCUMENTS

| | | | |
|---|---|---|---|
| WO | WO 2022/228576 | A1 | 11/2022 |
| WO | WO 2022/266206 | A1 | 12/2022 |
| WO | WO 2023/280026 | A1 | 1/2023 |
| WO | WO 2023/077441 | A1 | 5/2023 |
| WO | WO 2023/081476 | A1 | 5/2023 |
| WO | WO 2023/116934 | A1 | 6/2023 |
| WO | WO 2023/171781 | A1 | 9/2023 |

* cited by examiner

HETEROCYCLIC COMPOUND ACTING ON G12D MUTANT KRAS PROTEIN

RELATED APPLICATIONS

This application is a U.S. National Stage Application under 35 U.S.C. § 371 of International Application No. PCT/JP2023/026522 filed Jul. 20, 2023, which claims priority to Japanese Patent Application No. 2022-116367, filed on Jul. 21, 2022, all of which are incorporated herein by reference in their entirety.

TECHNICAL FIELD

The present invention relates to pharmaceutical compositions and, in particular, to a heterocyclic compound that is excellent in a degradation-inducing action on a G12D mutant KRAS protein and/or that is expected to be useful as a G12D mutant KRAS inhibitor and to be useful as an active ingredient of, for example, a pharmaceutical composition for treating pancreatic cancer.

BACKGROUND ART

Pancreatic cancer mainly including pancreatic ductal adenocarcinoma is a cancer with a very poor prognosis having a five-years survival rate of 10% or less (CA Cancer J. Clin., 2016, 66, p. 7-30), and about 460,000 new cases are reported per year in the world (CA Cancer J. Clin., 2018, 68, p. 394-424). The most effective therapy for treating pancreatic cancer is a surgery. However, the cancer has often metastasized since early detection is difficult, and the therapeutic effect of a surgery cannot be expected in many cases. When the cancer is not treated by operation, chemotherapy or radiotherapy is adopted, but the survival rate is not so good. Today, the FOLFRINOX therapy (multidrug treatment of three chemotherapy agents of 5-FU, irinotecan and oxaliplatin, plus levofolinate) is used as a standard therapy of pancreatic cancer. However, due to the strong toxicity, the subject patient has to be cautiously selected, for example, the therapy is to be applied only to patients of an ECOG performance status of 1 or less (J. Clin. Oncol., 2018, 36, p. 2545-2556). As a molecular target drug, an epidermal growth factor receptor (EGFR) inhibitor, Erlotinib, has been approved in a combination therapy with Gemcitabine. However, the extension of the overall survival is only about two weeks as compared with Gemcitabine alone, and no satisfying therapeutic effect has been achieved. A highly effective therapeutic agent remains needed (J. Clin. Oncol., 2007, 25, p. 1960-1966).

RAS proteins are low molecular weight guanosine triphosphate (GTP)-binding proteins of about 21 kDa constituted of 188-189 amino acids and include four main types of proteins (KRAS (KRAS 4A and KRAS 4B), NRAS and HRAS) produced by three genes of a KRAS gene, an NRAS gene and an HRAS gene. RAS proteins are divided into an active GTP-binding type and an inactive GDP-binding type. A RAS protein is activated by replacement of guanosine diphosphate (GDP) with GTP due to, for example, ligand stimulation to a membrane receptor, such as EGFR. The active RAS binds to effector proteins as much as twenty, such as RAF, PI3K and RALGDS, to activate the downstream signal cascade. On the other hand, the active RAS is converted to the inactive type by replacement of GTP with GDP due to the intrinsic GTP hydrolysis (GTPase) activity. The GTPase activity is enhanced by a GTPase-activating protein (GAP). As can be seen from the above statement, RAS bears an important function of "molecular switch" in an intracellular signal transduction pathway for EGFR or the like and plays a critical role in the processes of cell growth, proliferation, angiogenesis and the like (Nature Rev. Cancer, 2011, 11, p. 761-774, Nature Rev. Drug Discov., 2014, 13, p. 828-851, Nature Rev. Drug Discov., 2016, 15, p. 771-785).

Substitution of an amino acid by spontaneous mutation of the RAS gene results in a constant activated state due to hypofunction of RAS as GTPase or hyporeactivity to GAP, and then, signals are continuously sent downstream. The excessive signaling causes carcinogenesis or cancer growth acceleration. It is said that pancreatic ductal adenocarcinoma occurs through a weakly heteromorphic stage and a subsequent highly heteromorphic stage in the pancreatic intraepithelial neoplasia (PanIN), and mutation of the KRAS gene has already been recognized in an initial stage of PanIN. Subsequently, abnormality occurs in INK4A, p53 and SMAD4, which are tumor suppression genes, leading to malignancy (Nature Rev. Cancer, 2010, 10, p. 683-695). Furthermore, in 90% or more of the cases of pancreatic ductal adenocarcinoma, mutation is seen in the KRAS gene, and a majority of them are a spontaneous point mutation in the codon 12 located in the KRAS exon 2 (Cancer Cell 2017, 32, p. 185-203). As can be seen from the above statement, KRAS plays a critical role in the processes of carcinogenesis and development of pancreatic cancer.

As a mutation of a KRAS gene, KRAS G12C mutation, KRAS G12D mutation and the like are known. G12C mutant KRAS frequently occurs in non-small-cell lung cancer but occurs few percent in pancreatic cancer (Cancer Cell 2014, 25, p. 272-281), and a therapeutic agent against another KRAS mutation is desired. G12D mutant KRAS is seen in about 34% of the cases of pancreatic cancer, and this rate is reported to be the highest in KRAS mutations (Nat. Rev. Cancer, 2018, 18, p. 767-777).

Patent Documents 1, 2 and 3 disclose RAS inhibitors, and Patent Documents 2 and 3 disclose compounds represented by the following formula (A) and formula (B), respectively. Patent Documents 1, 2 and 3 state that the compounds are useful for a cancer with a mutation in the codon 12 of KRAS. The G12D mutation is one of such mutations, but any effect on the G12D mutant KRAS-positive cancer is not described.

[Chem.1]

(A)

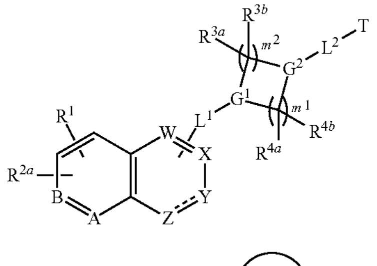

(B)

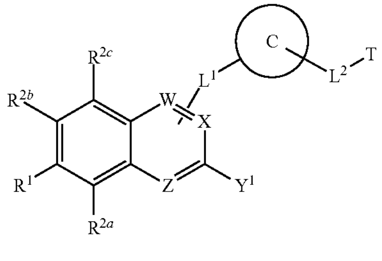

(The meanings of the symbols in the formulae can be found in the patent documents.)

Moreover, Patent Documents 9, 10, 11, 12, 13, 14, 15 and 16 disclose a KRAS G12D inhibitor.

In recent years, as a technique for inducing degradation of a target protein, bifunctional compounds collectively called as PROTAC (PROteolysis-TArgeting Chimera) or SNIPER (Specific and Nongenetic IAP-dependent Protein Eraser) are found and are expected as one novel technique of drug development modality (Drug. Discov. Today Technol., 2019, 31, p 15-27). Such a bifunctional compound promotes formation of a composite of the target protein and an E3 ligase in a cell, and degradation of the target protein is induced using the ubiquitin-proteasome system. The ubiquitin-proteasome system is one of intracellular protein degradation mechanisms. A protein called E3 ligase recognizes a protein to be degraded to convert the protein into ubiquitin, whereby degradation by proteasome is promoted.

600 or more E3 ligases are present in an organism and are roughly divided into four types of HECT-domain E3s, U-box E3s, monomeric RING E3s and multi-subunit E3s. E3 ligases used as a bifunctional degradation inducer which are called PROTAC, SNIPER or the like are currently limited, and typical examples thereof include Von Hippel-Lindau (VHL), celebron (CRBN), inhibitor of apoptosis protein (IAP) and mouse double minute 2 homolog (MDM2). In particular, VHL is reported in Patent Document 4, and CRBN is reported in Patent Document 5.

The bifunctional compounds are compounds in which a ligand of a target protein and a ligand of an E3 ligase are bound via a Linker, and some bifunctional compounds for degrading a KRAS protein have ever been reported (Non-patent Document 1, Non-patent Document 2, Patent Document 6, Patent Document 7, Patent Document 8, Patent Document 12 and Patent Document 17). Furthermore, bifunctional compounds for reducing G12D mutant KRAS protein levels have been reported in Patent Document 18 and Patent Document 19, and quinazoline compounds for inducing degradation of G12D mutant KRAS protein have been reported in Patent Document 20, Patent Document 21 and Patent Document 22. However, there is no report suggesting that a bifunctional compound degrades the G12D mutant KRAS protein other than Patent Documents 18 to 22 now.

CITATION LIST

Patent Document

[Patent Document 1] WO 2016/049565
[Patent Document 2] WO 2016/049568
[Patent Document 3] WO 2017/172979
[Patent Document 4] WO 2013/106643
[Patent Document 5] WO 2015/160845
[Patent Document 6] US Patent Application Publication No. 2018/0015087
[Patent Document 7] WO 2019/195609
[Patent Document 8] WO 2020/018788
[Patent Document 9] WO 2021/041671
[Patent Document 10] WO 2021/106231
[Patent Document 11] WO 2021/107160
[Patent Document 12] WO 2022/002102
[Patent Document 13] WO 2022/015375
[Patent Document 14] WO 2022/098625
[Patent Document 15] WO 2022/105855
[Patent Document 16] WO 2022/031678
[Patent Document 17] WO 2021/207172
[Patent Document 18] WO 2022/148421
[Patent Document 19] WO 2022/148422
[Patent Document 20] WO 2022/173032
[Patent Document 21] WO 2022/228576
[Patent Document 22] WO 2023/280026

Non-Patent Document

[Non-patent Document 1] Cell. Chem. Biol., 2020, 27, p. 19-31
[Non-patent Document 2] ACS Cent. Sci., 2020, 6, p. 1367-1375

SUMMARY OF INVENTION

Technical Problem

A pharmaceutical composition, for example, a heterocyclic compound that is excellent in a degradation-inducing action on a G12D mutant KRAS protein and/or that is expected to be useful as a G12D mutant KRAS inhibitor and to be useful as an active ingredient of a pharmaceutical composition for treating pancreatic cancer, in particular, G12D mutant KRAS-positive pancreatic cancer, is provided.

Solution to Problem

The present inventors have intensively and extensively studied about a compound that is useful as an active ingredient of a pharmaceutical composition for treating pancreatic cancer. As a result, the present inventors have found that a heterocyclic compound of a formula (I), for example, a bifunctional compound of the formula (I) characterized in that a substituent on the 8-position of a heterocyclic compound selected from the group consisting of quinazoline and quinoline is bound to a ligand of an E3 ligase via a linker, has an excellent degradation-inducing action on a G12D mutant KRAS protein and/or a G12D mutant KRAS inhibition activity, thus completing the present invention.

Specifically, the present invention relates to a compound of the formula (I) or a salt thereof and a pharmaceutical composition that contains a compound of the formula (I) or a salt thereof and one or more pharmaceutically acceptable excipients.

[Chem. 2]

(I)

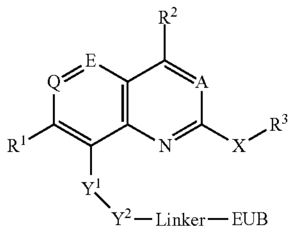

(In the formula,

A is $CR^A$ or N, $R^A$ is H, optionally substituted $C_{1-3}$ alkyl or cyano,

Q is $CR^Q$ or N, $R^Q$ is H, halogen, optionally substituted $C_{1-3}$ alkyl, $C_{3-6}$ cycloalkyl or vinyl, E is CH or N, $R^1$ is naphthyl optionally substituted with one or two groups selected from the group consisting of optionally substituted $C_{1-3}$ alkyl, cyano, OH and halogen, or $R^1$ is a group selected from the group consisting of the formula (II), the formula (III) and the formula (IV) below,

[Chem. 3]

(II)

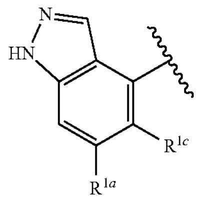

(III)

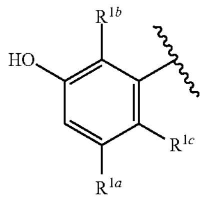

(IV)

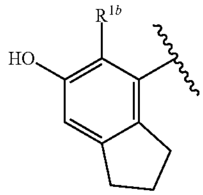

$R^{1a}$, $R^{1b}$ and $R^{1c}$, which are the same as or different from each other, are H, optionally substituted $C_{1-3}$ alkyl, vinyl or halogen, $R^2$ is —$V^1$—$V^2$ or W, $V^1$ is a bond, —$CH_2$—, —O—, —S— or —N($R^{V1}$)—, $R^{V1}$ is H or optionally substituted $C_{1-3}$ alkyl, $V^2$ is the formula (V) or the formula (VI) below,

[Chem. 4]

(V)

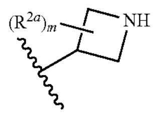

(VI)

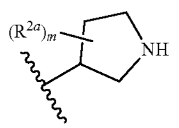

W is the formula (VII) or the formula (VII-2) below or 7-membered to 9-membered bridged heterocycloalkyl containing one to two nitrogen atoms,

[Chem. 5]

(VII)

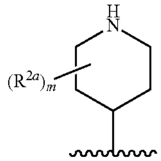

(VII-2)

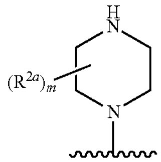

each $R^{2a}$, which is the same as or different from each other, are OH, $OCH_3$, F or optionally substituted $C_{1-3}$ alkyl, where $R^{2a}$ is attached only to a carbon atom that is an atom forming a ring selected from the group consisting of an azetidine ring represented by the formula (V), a pyrrolidine ring represented by the formula (VI), a piperidine ring represented by the formula (VII) and a piperazine ring represented by the formula (VII-2), m is an integer of 0 to 2, $R^3$ is optionally substituted $C_{1-6}$ alkyl, optionally substituted heterocycloalkyl or optionally substituted heteroaryl, X is a bond, —$CH_2$—, —O—, —S— or —$NR^{4X}$—, $R^{4X}$ is H or optionally substituted $C_{1-3}$ alkyl, $Y^1$ is —O-(optionally substituted $C_{1-3}$ alkylene)-$^{*Y2}$, —S-(optionally substituted $C_{1-3}$ alkylene)-$^{*Y2}$, —$SO_2$-(optionally substituted $C_{1-3}$ alkylene)-$^{*Y2}$, —$NR^Y$-(optionally substituted $C_{1-3}$ alkylene)-$^{*Y2}$, -(optionally substituted $C_{1-3}$ alkylene)-O-$^{*Y2}$, -(optionally substituted $C_{1-3}$ alkylene)-S-$^{*Y2}$, -(optionally substituted $C_{1-3}$ alkylene)-$SO_2$-$^{*Y2}$ or -(optionally substituted $C_{1-3}$ alkylene)-$NR^Y$-$^{*Y2}$ ($^{*Y2}$ represents a linking moiety to $Y^2$), $R^Y$ is H or optionally substituted $C_{1-3}$ alkyl, $Y^2$ is a bond, optionally substituted phenylene or optionally substituted heteroarylene, Linker is one group chemically linking $Y^2$ to EUB, and EUB is a group capable of binding to one E3 ubiquitin ligase selected from the group consisting of cereblon, IAP, MDM2, DCAF11, DCAF15, DCAF16, BIRC2, KEAP1, RNF4, RNF114, FEM1B and AhR.)

Furthermore, the compound that has a degradation-inducing action on a G12D mutant KRAS protein and/or a G12D mutant KRAS inhibition activity may be, for example, a bifunctional compound of the formula (XXI) characterized in that a substituent on the 2-position of a heterocyclic compound selected from the group consisting of quinazoline and quinoline is bound to a ligand of an E3 ligase via Linker.

Specifically, the present invention also relates to a compound of the formula (XXI) or a salt thereof and a pharmaceutical composition that contains a compound of the formula (XXI) or a salt thereof and one or more pharmaceutically acceptable excipients.

[Chem. 6]

(XXI)

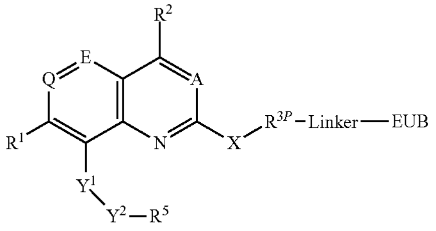

(In the formula,

A is $CR^A$ or N, $R^A$ is H, optionally substituted $C_{1-3}$ alkyl or cyano,

Q is $CR^Q$ or N, $R^Q$ is H, halogen, optionally substituted $C_{1-3}$ alkyl, $C_{3-6}$ cycloalkyl or vinyl, E is CH or N, $R^1$ is naphthyl optionally substituted with one or two groups selected from the group consisting of optionally substituted $C_{1-3}$ alkyl, cyano, OH and halogen, or $R^1$ is a group selected from the group consisting of the formula (II), the formula (III) and the formula (IV) below,

[Chem. 7]

(II)

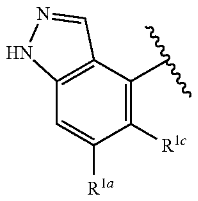

(III)

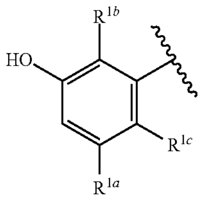

(IV)

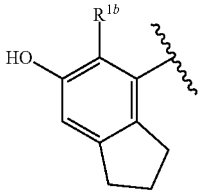

$R^{1a}$, $R^{1b}$ and $R^{1c}$, which are the same as or different from each other, are H, optionally substituted $C_{1-3}$ alkyl, vinyl or halogen, $R^2$ is —$V^1$—$V^2$ or W, $V^1$ is a bond, —$CH_2$—, —O—, —S— or —$N(R^{V1})$—, $R^{V1}$ is H or optionally substituted $C_{1-3}$ alkyl, $V^2$ is the formula (V) or the formula (VI) below,

[Chem. 8]

(V)

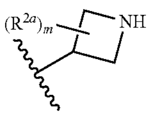

(VI)

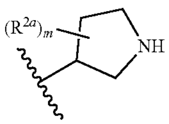

W is the formula (VII) or the formula (VII-2) below or 7-membered to 9-membered bridged heterocycloalkyl containing one to two nitrogen atoms,

[Chem. 9]

(VII)

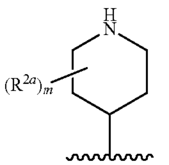

(VII-2)

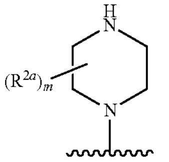

each $R^{2a}$, which is the same as or different from each other, are OH, $OCH_3$, F or optionally substituted $C_{1-3}$ alkyl, where $R^{2a}$ is attached only to a carbon atom that is an atom forming a ring selected from the group consisting of an azetidine ring represented by the formula (V), a pyrrolidine ring represented by the formula (VI), a piperidine ring represented by the formula (VII) and a piperazine ring represented by the formula (VII-2), m is an integer of 0 to 2, $R^{3P}$ is optionally substituted $C_{1-6}$ alkylene, optionally substituted heterocycloalkylene or optionally substituted heteroarylene, X is a bond, —$CH_2$—, —O—, —S— or —$NR^{4X}$—, $R^{4X}$ is H or optionally substituted $C_{1-3}$ alkyl, $Y^1$ is —O-(optionally substituted $C_{1-3}$ alkylene)-$^{*Y2}$, —S-(optionally substituted $C_{1-3}$ alkylene)-$^{*Y2}$, —$SO_2$-(optionally substituted $C_{1-3}$ alkylene)-$^{*Y2}$, —$NR^Y$-(optionally substituted $C_{1-3}$ alkylene)-$^{*Y2}$, -(optionally substituted $C_{1-3}$ alkylene)-O-$^{*Y2}$, -(optionally substituted $C_{1-3}$ alkylene)-S-$^{*Y2}$, -(optionally substituted $C_{1-3}$ alkylene)-$SO_2$-$^{*Y2}$ or -(optionally substituted $C_{1-3}$ alkylene)-$NR^Y$-$^{*Y2}$ ($^{*Y2}$ represents a linking moiety to $Y^2$), $R^Y$ is H or optionally substituted $C_{1-3}$ alkyl, $Y^2$ is a bond, optionally substituted phenylene or optionally substituted heteroarylene, $R^5$ is H, $CONR^6R^7$ or a group selected from the group consisting of the formulae (XXIV), (XXV), (XXVI), (XXVII), (XXVIII), (XXIX), (XXX), (XXXI), (XXXII), (XXXIII), (XXXIV) and (XXXV) below,

[Chem. 10]

(XXIV)

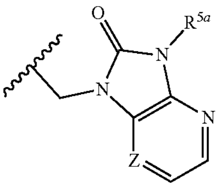

(XXV)

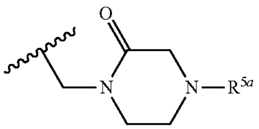

(XXVI)

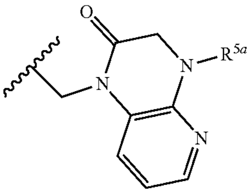

(XXVII)

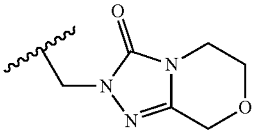

(XXVIII)

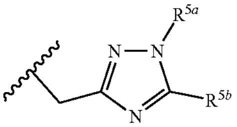

(XXIX)

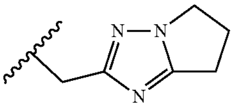

(XXX)

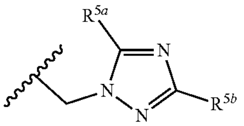

(XXXI)

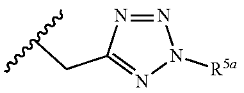

(XXXII)

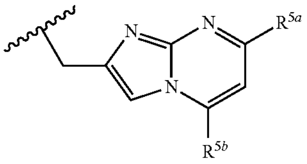

(XXXIII)

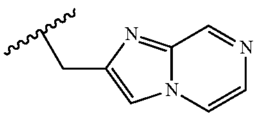

-continued (XXXIV)

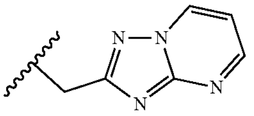

(XXXV)

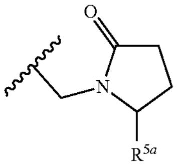

$R^{5a}$ and $R^{5b}$, which are the same as or different from each other, are H, optionally substituted $C_{1-3}$ alkyl, cyclopropyl, cyclopropylmethyl, oxetanyl, tetrahydropyranyl, optionally substituted oxazolyl, thiazolyl or pyrazinyl, $R^6$ and $R^7$, which are the same as or different from each other, are H or optionally substituted $C_{1-6}$ alkyl, or $R^6$ and $R^7$ form a 4-membered to 8-membered saturated heterocyclic ring when taken together with a nitrogen atom to which they are attached, wherein the 4-membered to 8-membered saturated heterocyclic ring is optionally substituted with optionally substituted $C_{1-6}$ alkyl, Linker is a group chemically linking $R^{3P}$ to EUB, and EUB is a group capable of binding to one E3 ubiquitin ligase selected from the group consisting of cereblon, IAP, MDM2, DCAF11, DCAF15, DCAF16, BIRC2, KEAP1, RNF4, RNF114, FEM1B and AhR).

Furthermore, the compound that has a degradation-inducing action on a G12D mutant KRAS protein and/or a G12D mutant KRAS inhibition activity may be, for example, a bifunctional compound of the formula (XXII) characterized in that a substituent on the 7-position of a heterocyclic compound selected from the group consisting of quinazoline and quinoline is bound to a ligand of an E3 ligase via Linker.

Specifically, the present invention also relates to a compound of the formula (XXII) or a salt thereof and a pharmaceutical composition that contains a compound of the formula (XXII) or a salt thereof and one or more pharmaceutically acceptable excipients.

[Chem. 11]

(XXII)

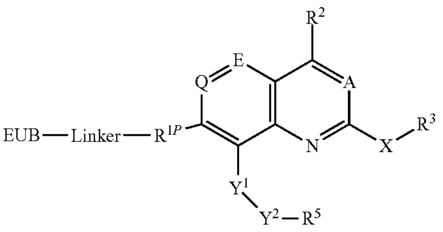

(In the formula,

A is $CR^A$ or N, $R^A$ is H, optionally substituted $C_{1-3}$ alkyl or cyano,

Q is $CR^Q$ or N, $R^Q$ is H, halogen, optionally substituted $C_{1-3}$ alkyl, $C_{3-6}$ cycloalkyl or vinyl, E is CH or N, $R^{1P}$ is naphthylene optionally substituted with one or two groups selected from the group consisting of optionally substituted $C_{1-3}$ alkyl, cyano, OH and halogen or one group selected from the group consisting of the formula (II-22A), the formula (II-22B), the formula (II-22C), the formula (III-22A), the formula (III-22B), the formula (III-22C) and the formula (III-22D) below,

[Chem. 12-1]

(II-22A)

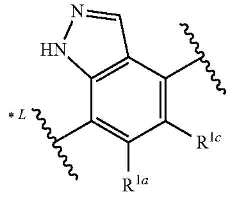

(II-22B)

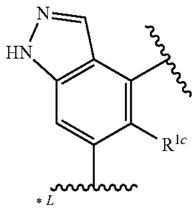

(II-22C)

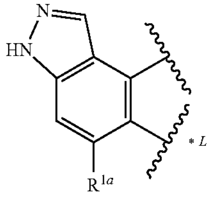

[Chem. 12-2]

(III-22A)

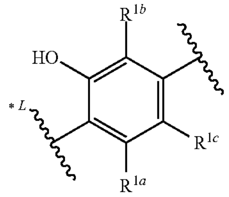

(III-22B)

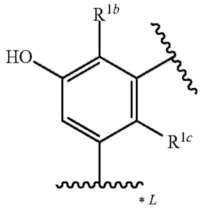

(III-22C)

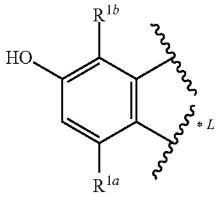

-continued (III-22D)

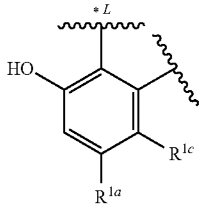

$R^{1a}$, $R^{1b}$ and $R^{1c}$, which are the same as or different from each other, are H, optionally substituted $C_{1-3}$ alkyl, vinyl or halogen, $R^2$ is $—V^1—V^2$ or W, $V^1$ is a bond, $—CH_2—$, —O—, —S— or $—N(R^{V1})—$, $R^{V1}$ is H or optionally substituted $C_{1-3}$ alkyl, $V^2$ is the formula (V) or the formula (VI) below,

[Chem. 13]

(V)

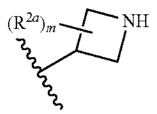

(VI)

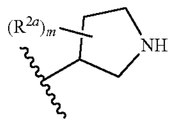

W is the formula (VII) or the formula (VII-2) below or 7-membered to 9-membered bridged heterocycloalkyl containing one to two nitrogen atoms,

[Chem. 14]

(VII)

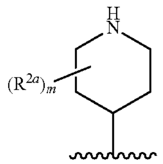

(VII-2)

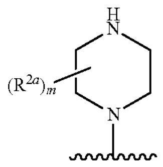

each $R^{2a}$, which is the same as or different from each other, are OH, $OCH_3$, F or optionally substituted $C_{1-3}$ alkyl, where $R^{2a}$ is attached only to a carbon atom that is an atom forming a ring selected from the group consisting of an azetidine ring represented by the formula (V), a pyrrolidine ring represented by the formula (VI), a piperidine ring represented by the formula (VII) and a piperazine ring represented by the formula (VII-2), m is an integer of 0 to 2, $R^3$ is optionally substituted $C_{1-6}$ alkyl, optionally substituted heterocycloalkyl or optionally substituted heteroaryl, X is a bond, —$CH_2$—, —O—, —S— or —$NR^{4X}$—, $R^{4X}$ is H or optionally substituted $C_{1-3}$ alkyl, $Y^1$ is —O-(optionally substituted $C_{1-3}$ alkylene)-$^{*Y2}$, —S-(optionally substituted $C_{1-3}$ alkylene)-$^{*Y2}$, —$SO_2$-(optionally substituted $C_{1-3}$ alkylene)-$^{*Y2}$, —$NR^Y$-(optionally substituted $C_{1-3}$ alkylene)-$^{*Y2}$, -(optionally substituted $C_{1-3}$ alkylene)-O-$^{*Y2}$, -(optionally substituted $C_{1-3}$ alkylene)-S-$^{*Y2}$, -(optionally substituted $C_{1-3}$ alkylene)-$SO_2$-$^{*Y2}$ or -(optionally substituted $C_{1-3}$ alkylene)-$NR^Y$-$^{*Y2}$ ($^{*Y2}$ represents a linking moiety to $Y^2$), $R^Y$ is H or optionally substituted $C_{1-3}$ alkyl, $Y^2$ is a bond, optionally substituted phenylene or optionally substituted heteroarylene, $R^5$ is H, $CONR^6R^7$ or a group selected from the group consisting of the formulae (XXIV), (XXV), (XXVI), (XXVII), (XXVIII), (XXIX), (XXX), (XXXI), (XXXII), (XXXIII), (XXXIV) and (XXXV) below,

[Chem. 10]

(XXIV)

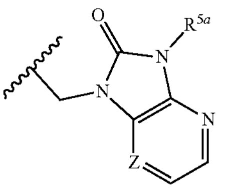

(XXV)

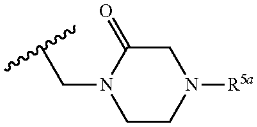

(XXVI)

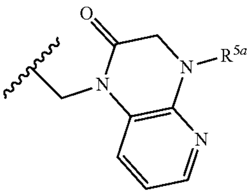

(XXVII)

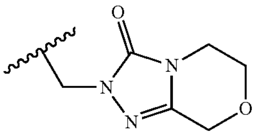

(XXVIII)

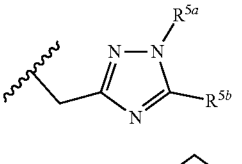

(XXIX)

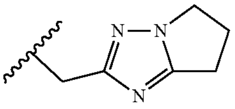

(XXX)

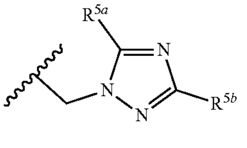

-continued (XXXI)

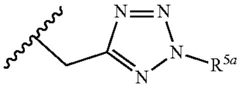

(XXXII)

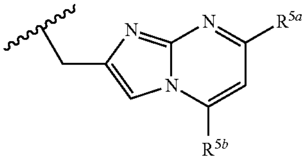

(XXXIII)

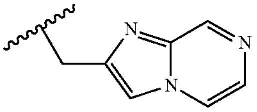

(XXXIV)

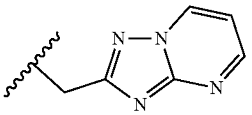

(XXXV)

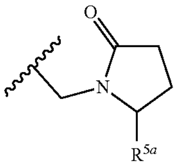

$R^{5a}$ and $R^{5b}$, which are the same as or different from each other, are H, optionally substituted $C_{1-3}$ alkyl, cyclopropyl, cyclopropylmethyl, oxetanyl, tetrahydropyranyl, optionally substituted oxazolyl, thiazolyl or pyrazinyl, $R^6$ and $R^7$, which are the same as or different from each other, are H or optionally substituted $C_{1-6}$ alkyl, or $R^6$ and $R^7$ form a 4-membered to 8-membered saturated heterocyclic ring together with a nitrogen atom to which they are attached, wherein the 4-membered to 8-membered saturated heterocyclic ring is optionally substituted with optionally substituted $C_{1-6}$ alkyl, Linker is a group chemically linking $R^{1P}$ to EUB, and EUB is a group capable of binding to one E3 ubiquitin ligase selected from the group consisting of cereblon, IAP, MDM2, DCAF11, DCAF15, DCAF16, BIRC2, KEAP1, RNF4, RNF114, FEM1B and AhR.)

Furthermore, the compound that has a degradation-inducing action on a G12D mutant KRAS protein and/or a G12D mutant KRAS inhibition activity may be, for example, a bifunctional compound of the formula (XXIII) characterized in GDB-Linker-EUB.

Specifically, the present invention also relates to a compound of the formula (XXIII) or a salt thereof and a pharmaceutical composition that contains a compound of the formula (XXIII) or a salt thereof and one or more pharmaceutically acceptable excipients.

[Chem. 16]

GDB-Linker-EUB (XXIII)

(In the formula,

GDB is a group capable of binding to a G12D mutant KRAS protein, and

-Linker-EUB is one group selected from the group consisting of the formula (LE-1) to the formula (LE-40).)

[Chem. 17-1]
(LE-1)
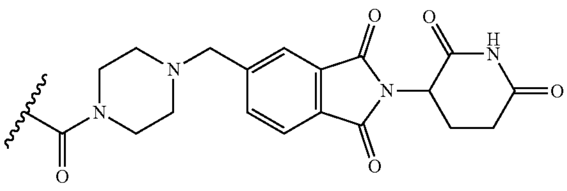
(LE-2)
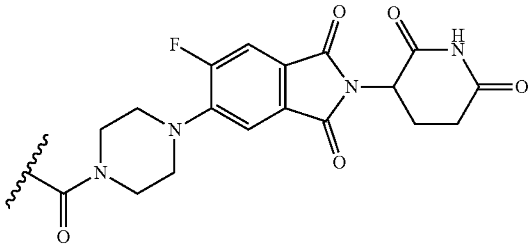
(LE-3)
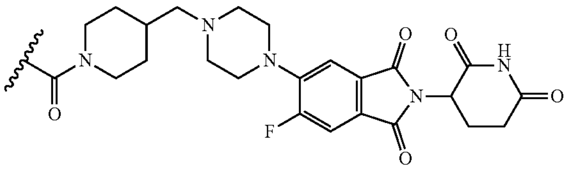
(LE-4)
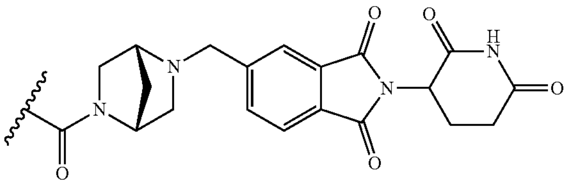
[Chem. 17-2]
(LE-5)
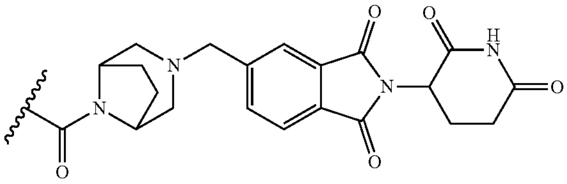
(LE-6)
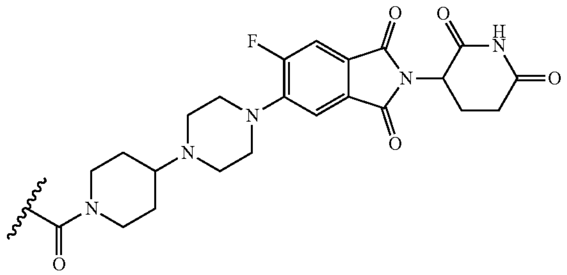
-continued
(LE-7)
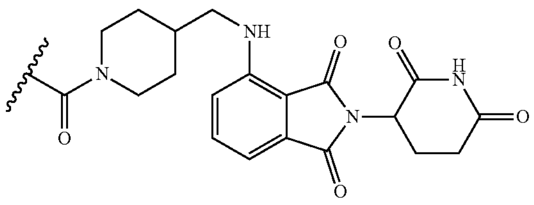
(LE-8)
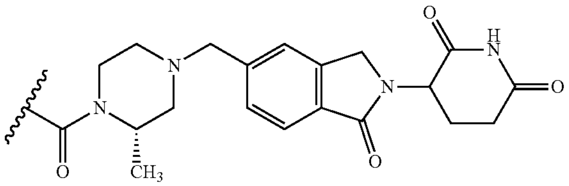
[Chem. 17-3]
(LE-9)
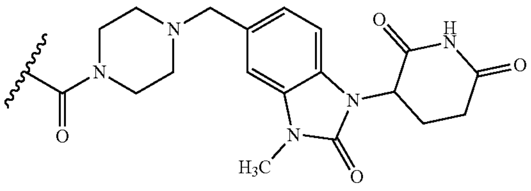
(LE-10)
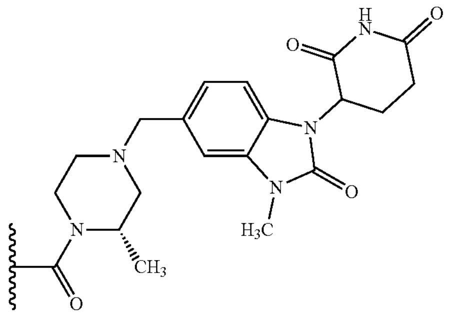
(LE-11)
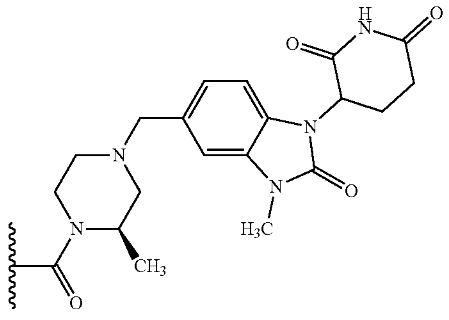

-continued
(LE-12)
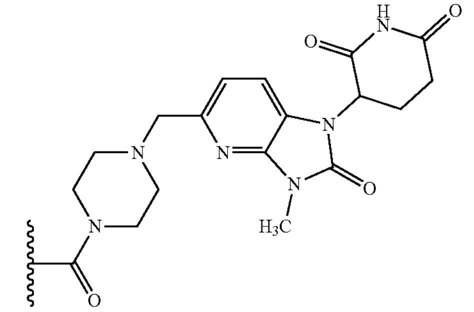
[Chem. 17-4]
(LE-13)
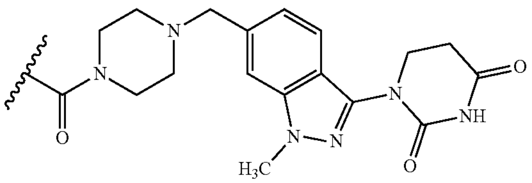
(LE-14)
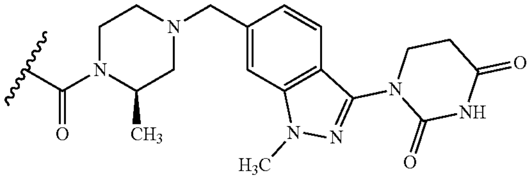
(LE-15)
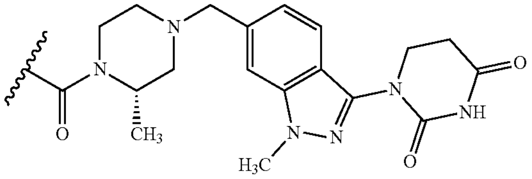
(LE-16)
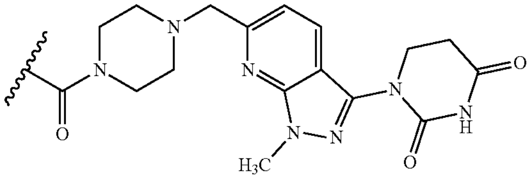
[Chem. 17-5]
(LE-17)
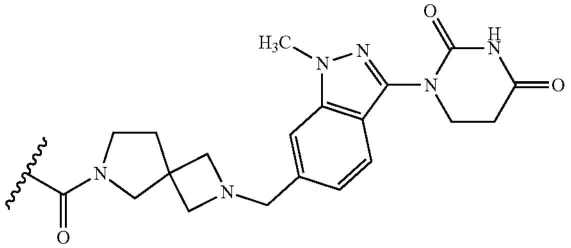
-continued
(LE-18)
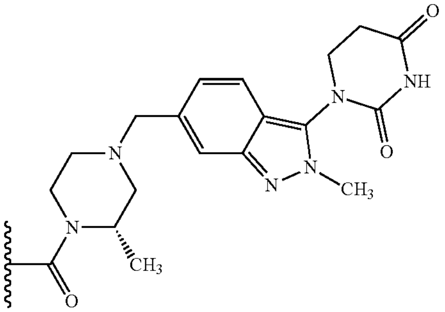
(LE-19)
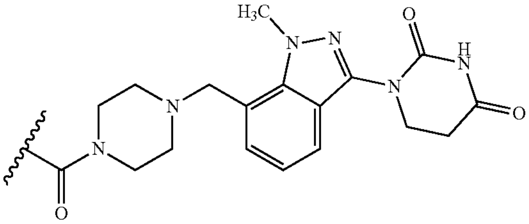
(LE-20)
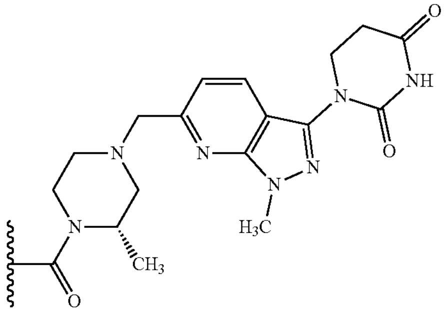
[Chem. 17-6]
(LE-21)
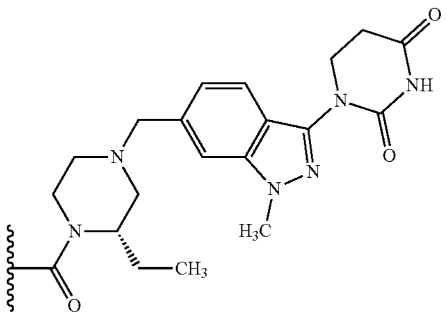

-continued
(LE-22)
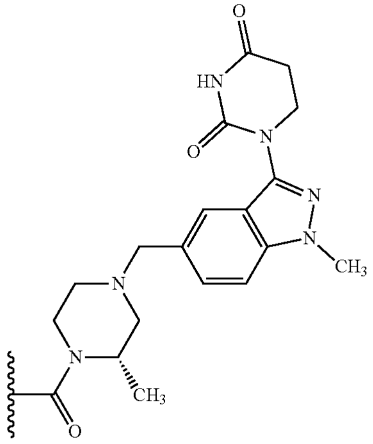
(LE-23)
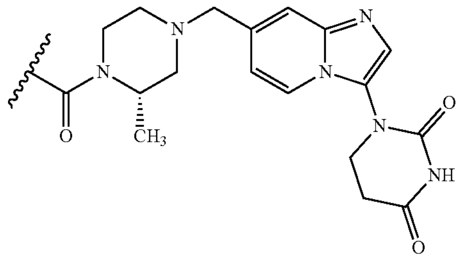
(LE-24)
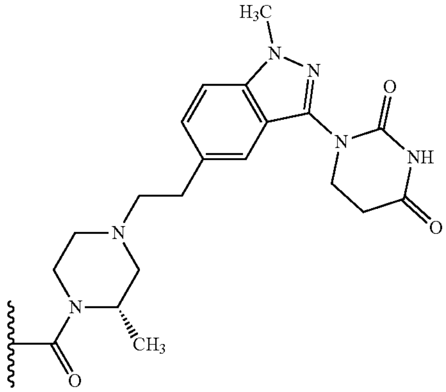
[Chem. 17-7]
(LE-25)
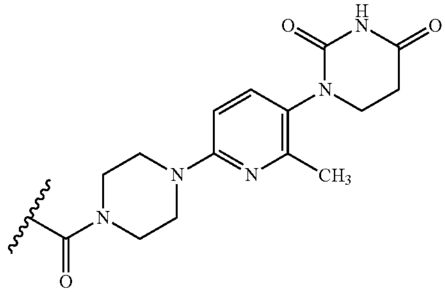
-continued
(LE-26)
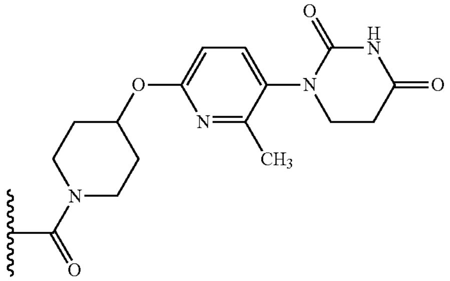
(LE-27)
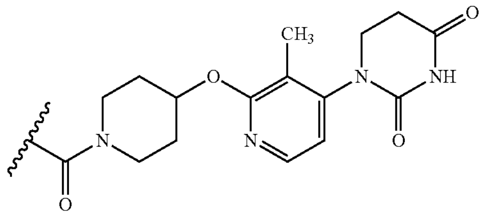
(LE-28)
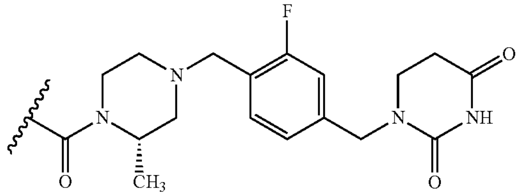
[Chem. 17-8]
(LE-29)
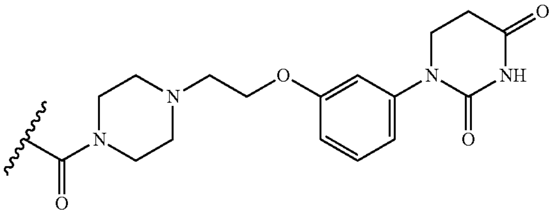
(LE-30)
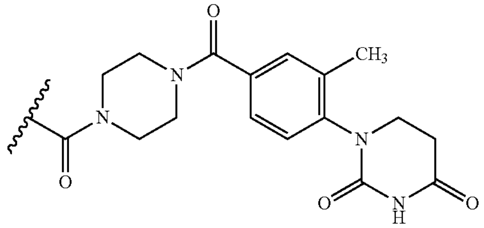
(LE-31)
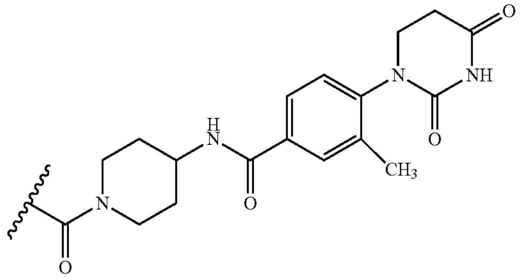

-continued (LE-32)

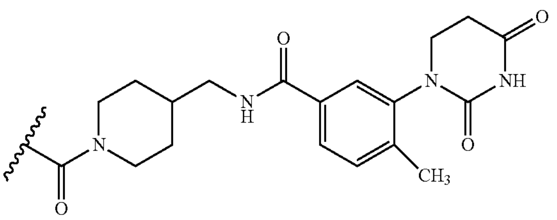

[Chem. 17-9]

(LE-33)

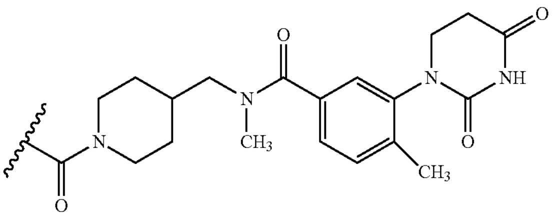

(LE-34)

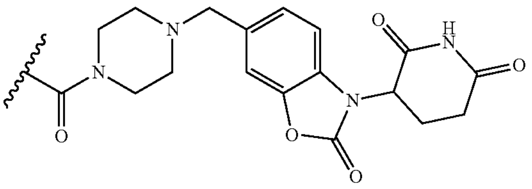

(LE-35)

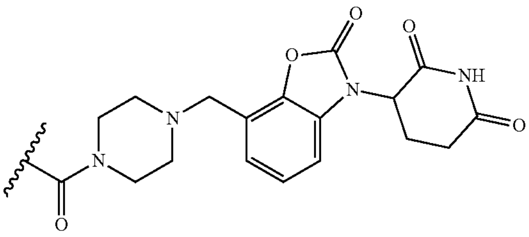

(LE-36)

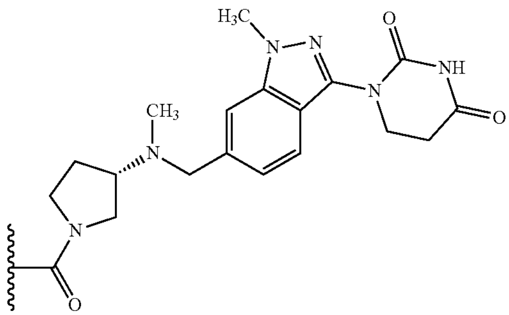

-continued

[Chem. 17-10]

(LE-37)

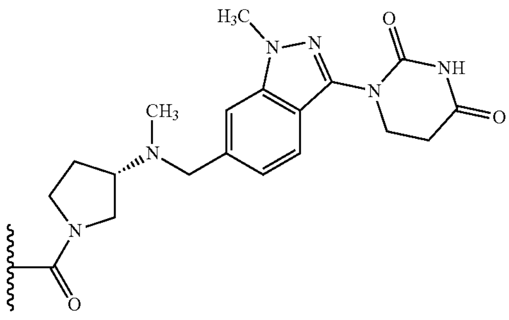

[Chem. 17-11]

(LE-38)

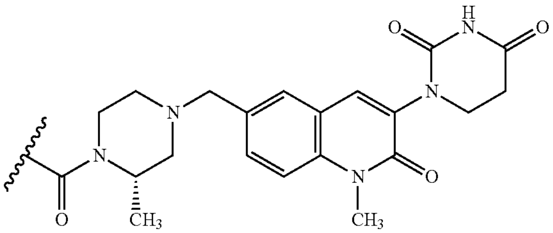

(LE-39)

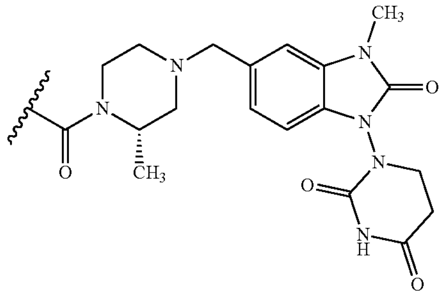

(LE-40)

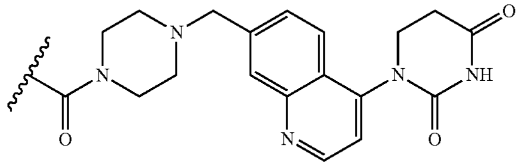

Note that, when a symbol in a chemical formula herein is used in another chemical formula, the same symbol represents the same meaning unless otherwise specified.

The present invention also relates to a pharmaceutical composition containing the compound of the formula (I) or a salt thereof and one or more pharmaceutically acceptable excipients, in one embodiment, a pharmaceutical composition for treating pancreatic cancer, in one embodiment, a pharmaceutical composition for treating G12D mutant KRAS-positive pancreatic cancer, in one embodiment, a pharmaceutical composition for treating metastatic pancreatic cancer, in one embodiment, a pharmaceutical composition for treating locally advanced pancreatic cancer, in one embodiment, a pharmaceutical composition for treating recurrent or refractory pancreatic cancer, in one embodiment, a pharmaceutical composition for treating pancreatic cancer of a patient who is untreated and/or has a treatment history, in one embodiment, a pharmaceutical composition for treating metastatic G12D mutant KRAS-positive pancreatic cancer, in one embodiment, a pharmaceutical composition for treating locally advanced G12D mutant KRAS-positive pancreatic cancer, in one embodiment, a pharmaceutical composition for treating recurrent or refractory G12D mutant KRAS-positive pancreatic cancer, in one embodiment, a pharmaceutical composition for treating G12D mutant KRAS-positive pancreatic cancer of a patient who is untreated and/or has a treatment history. Note that the pharmaceutical composition containing the compound of the formula (I) or a salt thereof and one or more pharmaceutically acceptable excipients includes a therapeutic agent containing the compound of the formula (I) or a salt thereof for pancreatic cancer, and in one embodiment, for G12D mutant KRAS-positive pancreatic cancer.

The present invention also relates to use of the compound of the formula (I) or a salt thereof for the manufacture of a pharmaceutical composition for treating pancreatic cancer, in one embodiment, G12D mutant KRAS-positive pancreatic cancer, in one embodiment, metastatic pancreatic cancer, in one embodiment, locally advanced pancreatic cancer, in one embodiment, recurrent or refractory pancreatic cancer, in one embodiment, pancreatic cancer of a patient who is untreated and/or has a treatment history, in one embodiment, metastatic G12D mutant KRAS-positive pancreatic cancer, in one embodiment, locally advanced G12D mutant KRAS-positive pancreatic cancer, in one embodiment, recurrent or refractory G12D mutant KRAS-positive pancreatic cancer, in one embodiment, G12D mutant KRAS-positive pancreatic cancer of a patient who is untreated and/or has a treatment history, to use of the compound of the formula (I) or a salt thereof for treating pancreatic cancer, in one embodiment, G12D mutant KRAS-positive pancreatic cancer, in one embodiment, metastatic pancreatic cancer, in one embodiment, locally advanced pancreatic cancer, in one embodiment, recurrent or refractory pancreatic cancer, in one embodiment, pancreatic cancer of a patient who is untreated and/or has a treatment history, in one embodiment, metastatic G12D mutant KRAS-positive pancreatic cancer, in one embodiment, locally advanced G12D mutant KRAS-positive pancreatic cancer, in one embodiment, recurrent or refractory G12D mutant KRAS-positive pancreatic cancer, in one embodiment, G12D mutant KRAS-positive pancreatic cancer of a patient who is untreated and/or has a treatment history, to the compound of the formula (I) or a salt thereof for use in treatment of pancreatic cancer, in one embodiment, G12D mutant KRAS-positive pancreatic cancer, in one embodiment, metastatic pancreatic cancer, in one embodiment, locally advanced pancreatic cancer, in one embodiment, recurrent or refractory pancreatic cancer, in one embodiment, pancreatic cancer of a patient who is untreated and/or has a treatment history, in one embodiment, metastatic G12D mutant KRAS-positive pancreatic cancer, in one embodiment, locally advanced G12D mutant KRAS-positive pancreatic cancer, in one embodiment, recurrent or refractory G12D mutant KRAS-positive pancreatic cancer, in one embodiment, G12D mutant KRAS-positive pancreatic cancer of a patient who is untreated and/or has a treatment history and to a method for treating pancreatic cancer, in one embodiment, G12D mutant KRAS-positive pancreatic cancer, in one embodiment, metastatic pancreatic cancer, in one embodiment, locally advanced pancreatic cancer, in one embodiment, recurrent or refractory pancreatic cancer, in one embodiment, pancreatic cancer of a patient who is untreated and/or has a treatment history, in one embodiment, metastatic G12D mutant KRAS-positive pancreatic cancer, in one embodiment, locally advanced G12D mutant KRAS-positive pancreatic cancer, in one embodiment, recurrent or refractory G12D mutant KRAS-positive pancreatic cancer, in one embodiment, G12D mutant KRAS-positive pancreatic cancer of a patient who is untreated and/or has a treatment history, the method comprising administering an effective amount of the compound of the formula (I) or a salt thereof to a subject.

The present invention also relates to the compound of the formula (I) or a salt thereof that is a G12D mutant KRAS protein degradation inducer and/or a G12D mutant KRAS inhibitor, to the compound of the formula (I) or a salt thereof for use as a G12D mutant KRAS protein degradation inducer and/or a G12D mutant KRAS inhibitor and to a G12D mutant KRAS protein degradation inducer and/or a G12D mutant KRAS inhibitor comprising the compound of the formula (I) or a salt thereof.

The present invention also relates to a pharmaceutical composition containing the compound of the formula (XXI), the formula (XXII) or the formula (XXIII) or a salt thereof and one or more pharmaceutically acceptable excipients, in one embodiment, a pharmaceutical composition for treating pancreatic cancer, in one embodiment, a pharmaceutical composition for treating G12D mutant KRAS-positive pancreatic cancer, in one embodiment, a pharmaceutical composition for treating metastatic pancreatic cancer, in one embodiment, a pharmaceutical composition for treating locally advanced pancreatic cancer, in one embodiment, a pharmaceutical composition for treating recurrent or refractory pancreatic cancer, in one embodiment, a pharmaceutical composition for treating pancreatic cancer of a patient who is untreated and/or has a treatment history, in one embodiment, a pharmaceutical composition for treating metastatic G12D mutant KRAS-positive pancreatic cancer, in one embodiment, a pharmaceutical composition for treating locally advanced G12D mutant KRAS-positive pancreatic cancer, in one embodiment, a pharmaceutical composition for treating recurrent or refractory G12D mutant KRAS-positive pancreatic cancer, in one embodiment, a pharmaceutical composition for treating G12D mutant KRAS-positive pancreatic cancer of a patient who is untreated and/or has a treatment history. Note that the pharmaceutical composition containing the compound of the formula (XXI), the formula (XXII) or the formula (XXIII) or a salt thereof and one or more pharmaceutically acceptable excipients includes a therapeutic agent for pancreatic cancer, the agent containing the compound of the formula (XXI), the formula (XXII) or the formula (XXIII) or a salt thereof, and G12D mutant KRAS-positive pancreatic cancer in one embodiment, the agent containing the compound of the formula (XXI), the formula (XXII) or the formula (XXIII) or a salt thereof.

The present invention also relates to the following:

use of the compound of the formula (XXI), the formula (XXII) or the formula (XXIII) or a salt thereof for the manufacture of a pharmaceutical composition for treating pancreatic cancer, in one embodiment, G12D mutant KRAS-positive pancreatic cancer, in one embodiment, metastatic pancreatic cancer, in one embodiment, locally advanced pancreatic cancer, in one embodiment, recurrent or refractory pancreatic cancer, in one embodiment, pancreatic cancer of a patient who is untreated and/or has a treatment history, in one embodiment, metastatic G12D mutant KRAS-positive pancreatic cancer, in one embodiment, locally advanced G12D mutant KRAS-positive pancreatic cancer, in one embodiment, recurrent or refractory G12D mutant KRAS-positive pancreatic cancer, in one embodiment, G12D mutant KRAS-positive pancreatic cancer of a patient who is untreated and/or has a treatment history;

use of the compound of the formula (XXI), the formula (XXII) or the formula (XXIII) or a salt thereof for treating pancreatic cancer, in one embodiment, G12D mutant KRAS-positive pancreatic cancer, in one embodiment, metastatic pancreatic cancer, in one embodiment, locally advanced pancreatic cancer, in one embodiment, recurrent or refractory pancreatic cancer, in one embodiment, pancreatic cancer of a patient who is untreated and/or has a treatment history, in one embodiment, metastatic G12D mutant KRAS-positive pancreatic cancer, in one embodiment, locally advanced G12D mutant KRAS-positive pancreatic cancer, in one embodiment, recurrent or refractory G12D mutant KRAS-positive pancreatic cancer, in one embodiment, G12D mutant KRAS-positive pancreatic cancer of a patient who is untreated and/or has a treatment history;

the compound of the formula (XXI), the formula (XXII) or the formula (XXIII) or a salt thereof for use in treatment of pancreatic cancer, in one embodiment, G12D mutant KRAS-positive pancreatic cancer, in one embodiment, metastatic pancreatic cancer, in one embodiment, locally advanced pancreatic cancer, in one embodiment, recurrent or refractory pancreatic cancer, in one embodiment, pancreatic cancer of a patient who is untreated and/or has a treatment history, in one embodiment, metastatic G12D mutant KRAS-positive pancreatic cancer, in one embodiment, locally advanced G12D mutant KRAS-positive pancreatic cancer, in one embodiment, recurrent or refractory G12D mutant KRAS-positive pancreatic cancer, in one embodiment, G12D mutant KRAS-positive pancreatic cancer of a patient who is untreated and/or has a treatment history;

a method for treating pancreatic cancer, comprising administering an effective amount of the compound of the formula the formula (XXI), the formula (XXII) or the formula (XXIII) or a salt thereof to a subject, in one embodiment, G12D mutant KRAS-positive pancreatic cancer, in one embodiment, metastatic pancreatic cancer, in one embodiment, locally advanced pancreatic cancer, in one embodiment, recurrent or refractory pancreatic cancer, in one embodiment, pancreatic cancer of a patient who is untreated and/or has a treatment history, in one embodiment, metastatic G12D mutant KRAS-positive pancreatic cancer, in one embodiment, locally advanced G12D mutant KRAS-positive pancreatic cancer, in one embodiment, recurrent or refractory G12D mutant KRAS-positive pancreatic cancer, in one embodiment, G12D mutant KRAS-positive pancreatic cancer of a patient who is untreated and/or has a treatment history;

the compound of the formula (XXI), the formula (XXII) or the formula (XXIII) or a salt thereof that is a G12D mutant KRAS protein degradation inducer and/or a G12D mutant KRAS inhibitor;

the compound of the formula (XXI), the formula (XXII) or the formula (XXIII) or a salt thereof for use as a G12D mutant KRAS protein degradation inducer and/or a G12D mutant KRAS inhibitor; and a G12D mutant KRAS protein degradation inducer and/or a G12D mutant KRAS inhibitor containing the compound of the formula (XXI), the formula (XXII) or the formula (XXIII) or a salt thereof.

Note that the "subject" is a human or another animal that needs the treatment, and in one embodiment, the "subject" is a human who needs the prevention or treatment.

Advantageous Effects of Invention

The compound of the formula (I), the formula (XXI), the formula (XXII) or the formula (XXIII) or a salt thereof has a degradation-inducing action on a G12D mutant KRAS protein and/or a G12D mutant KRAS inhibition activity and can be used as a therapeutic agent for pancreatic cancer, in particular, G12D mutant KRAS-positive pancreatic cancer.

DESCRIPTION OF EMBODIMENTS

The present invention will be described in detail below.

As used herein, "optionally substituted" means being unsubstituted or having one to five substituents. In one embodiment, the "optionally substituted" means being unsubstituted or having one to three substituents. Note that when there are multiple substituents, the substituents may be the same as or different from each other.

"$C_{1-12}$ Alkyl" is linear or branched alkyl having 1 to 12 carbon atoms, and examples thereof include methyl, ethyl, n-propyl, isopropyl, n-butyl, isobutyl, sec-butyl, tert-butyl, n-pentyl, n-hexyl, dodecyl and the like (the carbon atom numbers are described similarly hereinafter). The "$C_{1-12}$ alkyl" is ethyl or dodecyl in one embodiment.

Similarly, "$C_{1-6}$ alkyl" is linear or branched alkyl having 1 to 6 carbon atoms, and examples thereof include methyl, ethyl, n-propyl, isopropyl, n-butyl, isobutyl, sec-butyl, tert-butyl, n-pentyl and n-hexyl. The "$C_{1-6}$ alkyl" is methyl, ethyl, n-propyl, isopropyl or sec-butyl in one embodiment, methyl, ethyl, n-propyl, isopropyl or tert-butyl in one embodiment, methyl, ethyl, n-propyl, isopropyl or n-butyl in one embodiment, methyl, ethyl or n-propyl in one embodiment, methyl or n-propyl in one embodiment, methyl in one embodiment, ethyl in one embodiment or n-propyl in one embodiment.

Similarly, "$C_{1-3}$ alkyl" is linear or branched alkyl having 1 to 3 carbon atoms, and examples thereof include methyl, ethyl, n-propyl, isopropyl. The "$C_{1-3}$ alkyl" is methyl or ethyl in one embodiment, n-propyl or isopropyl in one embodiment, methyl or isopropyl in one embodiment, methyl or n-propyl in one embodiment ethyl or isopropyl in one embodiment, methyl in one embodiment, ethyl in one embodiment, isopropyl in one embodiment or n-propyl in one embodiment.

"$C_{3-6}$ Cycloalkyl" is cycloalkyl having 3 to 6 carbon atoms, and examples thereof include cyclopropyl, cyclobutyl, cyclopentyl and cyclohexyl. The "$C_{3-6}$ cycloalkyl" is cyclobutyl, cyclopentyl or cyclohexyl in one embodiment, cyclobutyl or cyclopentyl in one embodiment, cyclopentyl or cyclohexyl in one embodiment, cyclopropyl or cyclobutyl in one embodiment, cyclopropyl in one embodiment, cyclobutyl in one embodiment, cyclopentyl in one embodiment or cyclohexyl in one embodiment.

"$C_{1-3}$ Alkylene" is a divalent group in which the carbon atom of the "$C_{1-3}$ alkyl" has yet another bond. Examples thereof include methylene, ethylene, trimethylene, methylmethylene, 1,1-dimethylmethylene and the like. The "$C_{1-3}$ alkylene" is linear or branched $C_{1-3}$ alkylene in one embodiment, methylene, ethylene or trimethylene in one embodiment, methylene or ethylene in one embodiment, methylene in one embodiment or ethylene in one embodiment.

"Heterocycloalkyl" is a 4-membered to 7-membered saturated heterocyclic group containing one to four hetero atoms selected from the group consisting of oxygen, sulfur and nitrogen as ring-forming atoms and may partially contain an unsaturated bond. Further, the sulfur atom as a ring-forming atom of the saturated heterocyclic group is optionally oxidized. The “heterocycloalkyl” in one embodiment is a “4-membered to 6-membered heterocycloalkyl containing one or two hetero atoms selected from the group consisting of oxygen, sulfur and nitrogen as ring-forming atoms”, a “4-membered to 6-membered heterocycloalkyl containing one or two oxygen atoms as ring-forming atoms” in one embodiment, a “4-membered to 6-membered heterocycloalkyl containing one oxygen atom as a ring-forming atom” in one embodiment, a “4-membered to 6-membered heterocycloalkyl containing one or two nitrogen atoms as ring-forming atoms” in one embodiment, oxetanyl, tetrahydrofuranyl, tetrahydropyranyl, azetidinyl, pyrrolidinyl, piperidinyl, oxazolidinyl, imidazolidinyl, piperazinyl, morpholinyl, thiomorpholinyl, dioxothiomorpholinyl in one embodiment, oxetanyl, tetrahydropyranyl or tetrahydrofuranyl in one embodiment, tetrahydropyranyl or tetrahydrofuranyl in one embodiment, tetrahydropyranyl in one embodiment, tetrahydrofuranyl in one embodiment, azetidinyl, pyrrolidinyl, piperidinyl or piperazinyl in one embodiment, piperidinyl or piperazinyl in one embodiment, piperidinyl in one embodiment or piperazinyl in one embodiment.

“Heterocycloalkylene” is a divalent group of the “heterocycloalkyl” in which the nitrogen or carbon atom forming the ring has yet another bond. The “heterocycloalkylene” in one embodiment is a “4-membered to 6-membered heterocycloalkylene containing one or two hetero atoms selected from the group consisting of oxygen, sulfur and nitrogen as ring-forming atoms”, a “4-membered to 6-membered heterocycloalkylene containing one or two oxygen atoms as ring-forming atoms” in one embodiment, a “4-membered to 6-membered heterocycloalkylene containing one oxygen atom as a ring-forming atom” in one embodiment, a “4-membered to 6-membered heterocycloalkylene containing one or two nitrogen atoms as ring-forming atoms” in one embodiment, oxetandiyl, tetrahydrofurandiyl, tetrahydropyrandiyl, azetidinediyl, pyrrolidinediyl, piperidinediyl, oxazolidinediyl, imidazolidinediyl, piperazinediyl, morpholinediyl, thiomorpholinediyl, or dioxothiomorpholinediyl in one embodiment, oxetandiyl, tetrahydropyrandiyl or tetrahydrofurandiyl in one embodiment, tetrahydropyrandiyl or tetrahydrofurandiyl in one embodiment, tetrahydropyrandiyl in one embodiment, tetrahydrofurandiyl in one embodiment, azetidinediyl, pyrrolidinediyl, piperidinediyl or piperazinediyl in one embodiment, piperidinediyl or piperazinediyl in one embodiment, piperidinediyl in one embodiment or piperazinediyl in one embodiment.

“Bridged heterocycloalkyl” is a 7-membered to 9-membered bridged heterocyclic group containing one or two nitrogen atoms as ring-forming atoms. The “bridged heterocycloalkyl” is a saturated 7-membered to 9-membered bridged heterocyclic group containing one or two nitrogen atoms as ring-forming atoms in one embodiment, a saturated 7-membered to 9-membered bridged heterocycloalkyl containing two nitrogen atoms as ring-forming atoms in one embodiment or a saturated 7-membered to 9-membered bridged heterocycloalkyl containing two nitrogen atoms as ring-forming atoms in which one of the two nitrogen atoms bonds to one hydrogen atom in one embodiment. Examples thereof include diazabicyclo[2.2.2]octanyl, diazabicyclo[3.2.1]octanyl, diazabicyclo[3.1.1]heptanyl, diazabicyclo[2.2.1]heptanyl and diazabicyclo[3.3.1]nonanyl. The “bridged heterocycloalkyl” is diazabicyclo[2.2.2]octanyl, diazabicyclo[3.2.1]octanyl, diazabicyclo[3.2.1]oct-6-enyl, diazabicyclo[3.2.1]oct-2-enyl, diazabicyclo[3.1.1]heptanyl, diazabicyclo[2.2.1]heptanyl or diazabicyclo[2.2.1]hept-5-enyl in one embodiment, diazabicyclo[2.2.2]octanyl, diazabicyclo[3.2.1]octanyl, diazabicyclo[3.1.1]heptanyl or diazabicyclo[2.2.1]heptanyl in one embodiment, diazabicyclo[2.2.1]heptanyl or diazabicyclo[3.2.1]octanyl in one embodiment, diazabicyclo[2.2.1]heptanyl in one embodiment, diazabicyclo[3.2.1]octanyl in one embodiment, 2,5-diazabicyclo[2.2.1]heptanyl in one embodiment, 3,8-diazabicyclo[3.2.1]octanyl in one embodiment, 2,5-diazabicyclo[2.2.1]heptanyl in one embodiment or 3,8-diazabicyclo[3.2.1]octanyl in one embodiment.

“Bridged heterocycloalkylene” is a divalent group of the “bridged heterocycloalkyl” in which the nitrogen or carbon atom forming the ring has yet another bond. The “bridged heterocycloalkylene” is a saturated 7-membered or 9-membered bridged heterocycloalkylene containing two nitrogen atoms in one embodiment or a saturated 7-membered or 9-membered bridged heterocycloalkylene containing two nitrogen atoms in which one of the two nitrogen atoms bonds to one hydrogen atom in one embodiment. Examples thereof include diazabicyclo[2.2.2]octanediyl, diazabicyclo[3.2.1]octanediyl, diazabicyclo[3.1.1]heptanediyl, diazabicyclo[2.2.1]heptanediyl and diazabicyclo[3.3.1]nonanediyl. The “bridged heterocycloalkylene” is diazabicyclo[2.2.2]octanediyl, diazabicyclo[3.2.1]octanediyl, diazabicyclo[3.2.1]oct-6-enediyl, diazabicyclo[3.2.1]oct-2-enediyl, diazabicyclo[3.1.1]heptanediyl, diazabicyclo[2.2.1]heptanediyl or diazabicyclo[2.2.1]hept-5-enediyl in one embodiment, diazabicyclo[2.2.2]octanediyl, diazabicyclo[3.2.1]octanediyl, diazabicyclo[3.1.1]heptanediyl or diazabicyclo[2.2.1]heptanediyl in one embodiment, diazabicyclo[2.2.1]heptanediyl or diazabicyclo[3.2.1]octanediyl in one embodiment, diazabicyclo[2.2.1]heptanediyl in one embodiment, diazabicyclo[3.2.1]octanediyl in one embodiment, 2,5-diazabicyclo[2.2.1]heptanediyl or 3,8-diazabicyclo[3.2.1]ocnediyl in one embodiment, 2,5-diazabicyclo[2.2.1]heptanediyl in one embodiment or 3,8-diazabicyclo[3.2.1]octanediyl in one embodiment.

“Bridged piperazinyl” is piperazinyl having a bridging structure at a carbon atom on the ring, where the bridging structure is composed of carbon atoms. Examples thereof include diazabicyclo[2.2.1]heptanyl, diazabicyclo[3.2.1]octanyl and diazabicyclo[3.1.1]heptanyl. The “bridged piperazinyl” is diazabicyclo[2.2.1]heptanyl in one embodiment, diazabicyclo[3.2.1]octanyl in one embodiment, diazabicyclo[3.1.1]heptanyl in one embodiment, 2,5-diazabicyclo[2.2.1]heptanyl in one embodiment, 3,8-diazabicyclo[3.2.1]octanyl in one embodiment, 2,5-diazabicyclo[2.2.1]heptanyl in one embodiment or 3,8-diazabicyclo[3.2.1]octanyl in one embodiment.

“Bridged piperazinediyl” is a divalent group in which the nitrogen atom forming the ring of the “bridged piperazinyl” has yet another bond. Examples thereof include diazabicyclo[2.2.1]heptanediyl, diazabicyclo[3.2.1]octanediyl and diazabicyclo[3.1.1]heptanediyl. The “bridged piperazinediyl” is diazabicyclo[2.2.1]heptanediyl in one embodiment, diazabicyclo[3.2.1]octanediyl in one embodiment, diazabicyclo[3.1.1]heptanediyl in one embodiment, 2,5-diazabicyclo[2.2.1]heptanediyl in one embodiment, 3,8-diazabicyclo[3.2.1]octanediyl in one embodiment, 2,5-diazabicyclo[2.2.1]heptanediyl in one embodiment or 3,8-diazabicyclo[3.2.1]octanediyl in one embodiment.

“Spiroheterocycloalkyl” is a saturated 7-membered to 9-membered heterocyclo ring group containing one or two nitrogen atoms as ring-forming atoms and having a spiro atom. The “spiroheterocycloalkyl” is a saturated 7-membered to 9-membered heterocyclo ring group containing two nitrogen atoms as ring-forming atoms and having a spiro atom in one embodiment. Examples thereof include diazaspiro[3.3]heptanyl, diazaspiro[3.4]octanyl, diazaspiro[3.5]nonanyl and diazaspiro[4.4]nonanyl. The "spiroheterocycloalkyl" is 2,6-diazaspiro[3.4]octanyl in one embodiment or 2,6-diazaspiro[3.3]heptanyl in one embodiment.

"Spiroheterocycloalkylene" is a divalent group of the "spirocycloalkyl" having two nitrogen atoms as ring-forming atoms, in which the two nitrogen atoms each have a bond. Examples thereof include 2,6-diazaspiro[3.3]heptanediyl, 2,6-diazaspiro[3.4]octanediyl, 2,7-diazaspiro[3.5]nonanediyl and 2,7-diazaspiro[4.4]nonanediyl. The "spiroheterocycloalkylene" is 2,6-diazaspiro[3.4]octanediyl in one embodiment or 2,6-diazaspiro[3.3]heptanediyl in one embodiment. The "spiroheterocycloalkylene" may also be a divalent group of the "spiroheterocycloalkyl" in which the nitrogen or carbon atom forming the ring has yet another bond. Specifically, the "spiroheterocycloalkylene" is a saturated 7-membered to 9-membered spiroheterocycloalkylene containing one or two nitrogen atoms as ring-forming atoms in one embodiment, and examples thereof include 2,6-diazaspiro[3.3]heptanediyl, 2,6-diazaspiro[3.4]octanediyl, 2,7-diazaspiro[3.5]nonanediyl, 2,7-diazaspiro[4.4]nonanediyl, 2-azaspiro[3.3]heptanediyl, 2-azaspiro[3.4]octanediyl, 6-azaspiro[3.4]octanediyl, 2-azaspiro[3.5]nonanediyl, 7-azaspiro[3.5]nonanediyl, 2-azaspiro[4.4]nonanediyl and 7-azaspiro[4.4]nonanediyl. The "spiroheterocycloalkylene" is 2,6-diazaspiro[3.4]octanediyl in one embodiment or 2,6-diazaspiro[3.3]heptanediyl in one embodiment.

"Hetero ring" is an aromatic heterocyclic ring containing one to four hetero atoms selected from the group consisting of oxygen, sulfur and nitrogen as ring-forming atoms.

"5-Membered hetero ring" is a 5-membered hetero ring containing one to four hetero atoms selected from the group consisting of oxygen, sulfur and nitrogen as ring-forming atoms. The "5-membered hetero ring" in one embodiment is a pyrazole ring, an imidazole ring, a triazole ring, a tetrazole ring, an oxazole ring, an isoxazole ring, a thiazole ring, an isothiazole ring, an oxadiazole ring or a thiadiazole ring or a pyrazole ring, an imidazole ring, a triazole ring, an oxazole ring, an isoxazole ring, a thiazole ring, an isothiazole ring, an oxadiazole ring or a thiadiazole ring in one embodiment.

"6-Membered hetero ring" is a 6-membered hetero ring containing one to three nitrogen atoms as ring-forming atoms. The "6-membered hetero ring" in one embodiment is a 6-membered hetero ring containing one to three nitrogen atoms as ring-forming atoms or a pyridine ring, a pyrimidine ring, a pyrazine ring, a pyridazine ring or a triazine ring in one embodiment.

"5- or 6-Membered hetero ring" is a 5-membered hetero ring or a 6-membered hetero ring. The "5- or 6-membered hetero ring" in one embodiment is a 5-membered hetero ring or a 6-membered hetero ring in one embodiment.

"Heteroaryl" is a 5-membered or 6-membered aromatic heterocyclic group containing one to four hetero atoms selected from the group consisting of oxygen, sulfur and nitrogen as ring-forming atoms. The "heteroaryl" is 5-membered ring heteroaryl containing one to four hetero atoms selected from the group consisting of oxygen, sulfur and nitrogen as ring-forming atoms or 6-membered ring heteroaryl containing one to three nitrogen atoms as ring-forming atoms in one embodiment, 5-membered ring heteroaryl containing one to four hetero atoms selected from the group consisting of oxygen, sulfur and nitrogen as ring-forming atoms in one embodiment, 6-membered ring heteroaryl containing one to three nitrogen atoms as ring-forming atoms in one embodiment, pyrazolyl, imidazolyl, triazolyl, tetrazolyl, oxazolyl, isoxazolyl, thiazolyl, isothiazolyl, oxadiazolyl, thiadiazolyl, pyridyl, pyrimidinyl, pyrazinyl, pyridazinyl or triazinyl in one embodiment, pyrazolyl, imidazolyl, triazolyl, tetrazolyl, oxazolyl, isoxazolyl, thiazolyl, isothiazolyl, oxadiazolyl or thiadiazolyl in one embodiment or pyridyl, pyrimidinyl, pyrazinyl, pyridazinyl or triazinyl in one embodiment.

"Heteroarylene" is a divalent group of the "heteroaryl" in which two different carbon atoms and/or nitrogen atoms forming the ring have a bond. The "heteroarylene" in one embodiment is 5-membered ring heteroarylene containing one to four hetero atoms selected from the group consisting of oxygen, sulfur and nitrogen as ring-forming atoms or 6-membered ring heteroarylene containing one to three nitrogen atoms as ring-forming atoms in one embodiment, 5-membered ring heteroarylene containing one to four hetero atoms selected from the group consisting of oxygen, sulfur and nitrogen as ring-forming atoms in one embodiment, 6-membered ring heteroarylene containing one to three nitrogen atoms as ring-forming atoms in one embodiment, pyrazolediyl, imidazolediyl, triazolediyl, tetrazolediyl, oxazolediyl, isoxazolediyl, thiazolediyl, isothiazolediyl, oxadiazolediyl, thiadiazolediyl, pyridindiyl, pyrimidinediyl, pyrazinediyl, pyridazinediyl or triazinediyl in one embodiment, pyrazolediyl, imidazolediyl, triazolediyl, tetrazolediyl, oxazolediyl, isoxazolediyl, thiazolediyl, isothiazolediyl, oxadiazolediyl, thiadiazolediyl in one embodiment or pyridindiyl, pyrimidinediyl, pyrazinediyl, pyridazinediyl or triazinediyl in one embodiment.

"4-Membered to 8-membered saturated heterocyclic group" is a 4-membered to 8-membered saturated heterocyclic group containing one to two hetero atoms selected from the group consisting of oxygen, sulfur and nitrogen as ring-forming atoms, which may partially contain an unsaturated bond, have a bridge and form a spiro ring. Furthermore, the sulfur atom contained in the heterocyclic group is optionally oxidized. The "4-membered to 8-membered saturated heterocyclic group" is oxetane, tetrahydrofurane, tetrahydropyrane, azetidine, pyrrolidine, piperidine, azepane, oxazolidine, imidazolidine, piperazine, morpholine, thiomorpholine, dioxothiomorpholine, azabicyclo[2.2.1]heptane, diazabicyclo[2.2.1]heptane, azaspiro[3.3]heptane, azaspiro[3.4]octane, oxaazaspiro[3.3]heptane or diazaspiro[3.3]heptane in one embodiment, oxetane, tetrahydrofurane, tetrahydropyrane, azetidine, pyrrolidine, piperidine, piperazine, morpholine, thiomorpholine, dioxothiomorpholine, azaspiro[3.3]heptane or oxaazaspiro[3.3]heptane in one embodiment, azetidine, tetrahydropyrane, morpholine or oxaazaspiro[3.3]heptane in one embodiment, azetidine or tetrahydropyrane in one embodiment, morpholine or oxaazaspiro[3.3]heptane in one embodiment or tetrahydropyrane in one embodiment.

Substituents acceptable in "optionally substituted heterocycloalkyl", "optionally substituted heterocycloalkylene" and "optionally substituted $C_{1-6}$ alkylene" are $C_{1-3}$ alkyl, —O($C_{1-3}$ alkyl), C═O, halogen or OH in one embodiment, $C_{1-3}$ alkyl, —O($C_{1-3}$ alkyl) or halogen in one embodiment, —O($C_{1-3}$ alkyl) or halogen in one embodiment, $C_{1-3}$ alkyl in one embodiment, OH in one embodiment, F in one embodiment, methyl in one embodiment or ethyl in one embodiment.

Substituents acceptable in "optionally substituted $C_{1-6}$ alkyl", "optionally substituted $C_{1-3}$ alkyl" and "optionally substituted $C_{1-3}$ alkylene" are $C_{1-3}$ alkyl, —O($C_{1-3}$ alkyl), C═O, halogen or OH in one embodiment, $C_{1-3}$ alkyl, —O($C_{1-3}$ alkyl) or halogen in one embodiment, —O($C_{1-3}$ alkyl) or halogen in one embodiment, $C_{1-3}$ alkyl in one embodiment, OH in one embodiment, F in one embodiment, methyl in one embodiment or ethyl in one embodiment.

Substituents acceptable in "optionally substituted heteroarylene", "optionally substituted phenylene" and "optionally substituted heteroaryl" in one embodiment are $C_{1-3}$ alkyl, —O($C_{1-3}$ alkyl), halogen or OH, $C_{1-3}$ alkyl, —O($C_{1-3}$ alkyl) or halogen in one embodiment, $C_{1-3}$ alkyl in one embodiment, methyl in one embodiment, ethyl in one embodiment, halogen in one embodiment or F in one embodiment.

Substituents acceptable in "optionally substituted oxazolyl" are $C_{1-3}$ alkyl in one embodiment, methyl or isopropyl in one embodiment, methyl in one embodiment or isopropyl in one embodiment.

"Halogen" means F, Cl, Br and I. The "halogen" is F, Cl or Br in one embodiment, F or Cl in one embodiment, F or Br in one embodiment, F in one embodiment, Cl in one embodiment or Br in one embodiment.

"EUB" is a group capable of binding to a E3 ubiquitin ligase. "EUB" is a group capable of binding to one E3 ubiquitin ligase selected from the group consisting of cereblon, IAP, MDM2, DCAF11, DCAF15, DCAF16, BIRC2, KEAP1, RNF4, RNF114, FEMIB and AhR in one embodiment. The "EUB" is a group capable of binding to cereblon, IAP, and MDM2 in one embodiment or a group capable of binding to cereblon in one embodiment. It can be understood by those skilled in the art by reference to, but not limited to, the following references.

REFERENCE

Current Research in Chemical Biology., 2022, 2, 100020
Front. Chem., 2021, 9, 707317
J. Am. Chem. Soc., 2021, 143, 5141
Signal Transduct. Target. Ther., 2020, 5, 129
Nat. Chain. Biol., 2019, 15(7), 737
Communications Biology., 2020, 3, 140
Sci. Rep., 2020, 10(1), 15543
ACS Chain. Biol., 2019, 14, 2430
Cell Chem. Biol., 2021, 28(4), 559
J. Am. Chem. Soc., 2022, 144, 701
ACS Chain. Biol., 2019, 14, 2822

"GDB" is a group capable of binding to the G12D mutant KRAS protein and is limited to example compounds described in the following references.

REFERENCE

WO 2021/041671
WO 2021/106231
WO 2021/107160
WO 2022/002102
WO 2022/105855
WO 2022/161443
WO 2022/171013
WO 2022/171147
WO 2022/184178
WO 2022/187528
WO 2022/194066
WO 2022/199586
WO 2022/246092
WO 2022/266069

"G12D Mutation" represents a mutation in which the amino acid residue corresponding to the codon 12 in a wildtype protein is converted from glycine to aspartic acid.

"G12D Mutant KRAS" represents KRAS having the "G12D mutation".

"Pancreatic cancer" is a malignant tumor occurring in the pancreas. Examples thereof include pancreatic ductal carcinoma and pancreatic ductal adenocarcinoma, and the "pancreatic cancer" is pancreatic ductal carcinoma in one embodiment or pancreatic ductal adenocarcinoma in one embodiment. Moreover, the "pancreatic cancer" is metastatic pancreatic cancer in one embodiment, locally advanced pancreatic cancer in one embodiment, recurrent or refractory pancreatic cancer in one embodiment or pancreatic cancer of a patient who is untreated and/or has a treatment history in one embodiment.

"G12D Mutant KRAS-positive pancreatic cancer" is pancreatic cancer that is positive for G12D mutant KRAS. Examples thereof include a pancreatic cancer in which the KRAS G12D mutation occurs and a pancreatic cancer which has a high positive rate for G12D mutant KRAS. The "G12D mutant KRAS-positive pancreatic cancer" is G12D mutant KRAS-positive pancreatic ductal carcinoma in one embodiment or G12D mutant KRAS-positive pancreatic ductal adenocarcinoma in one embodiment.

"$Z^{N1}$" is the following one group selected from the group consisting of the formulae ($Z^{N1}$-1) to ($Z^{N1}$-15) ($^{*LGZ}$ represents a linking moiety to $LG^Z$ or Linker; each $R^{Z1'}$, which is the same as or different from each other, is optionally substituted $C_{1-6}$ alkyl, halogen, cyano, —OH, —O-(optionally substituted $C_{1-6}$ alkyl), —S-(optionally substituted $C_{1-6}$ alkyl), —NH-(optionally substituted $C_{1-6}$ alkyl) or —N-(optionally substituted $C_{1-6}$ alkyl)$_2$; n' is an integer of 0 to 2; $R^{Z2'}$, $R^{Z3'}$ and $R^{Z4'}$, which are the same as or different from each other, are H or optionally substituted $C_{1-6}$ alkyl; and ring B1' is a benzene ring or a 6-membered hetero ring, where $R^{Z1'}$ and -$^{*LGN}$ form a bond with a carbon atom forming the ring B1').

[Chem. 18-1]

($Z^{N1}$-1)

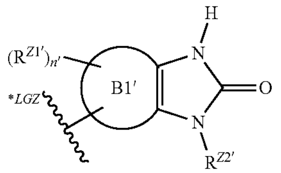

($Z^{N1}$-2)

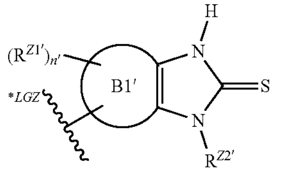

($Z^{N1}$-3)

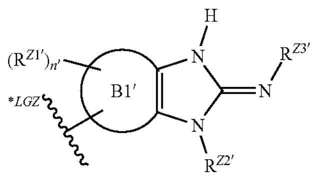

-continued ($Z^{N1}$-4)

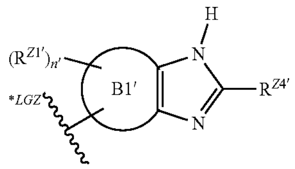

($Z^{N1}$-5)

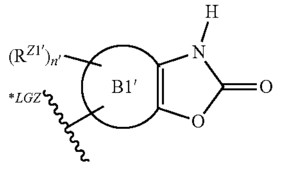

($Z^{N1}$-6

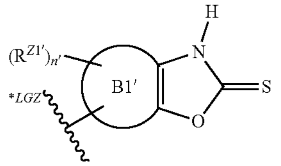

[Chem. 18-2]

($Z^{N1}$-7)

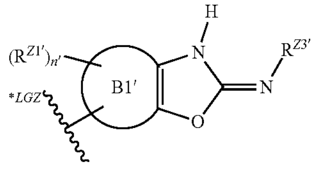

($Z^{N1}$-8)

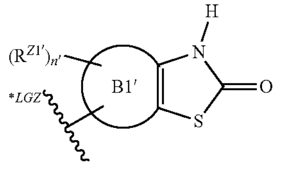

($Z^{N1}$-9)

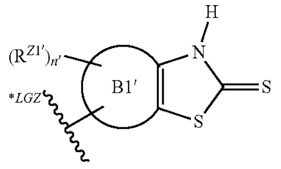

($Z^{N1}$-10)

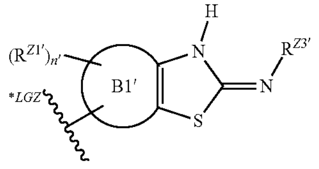

($Z^{N1}$-11)

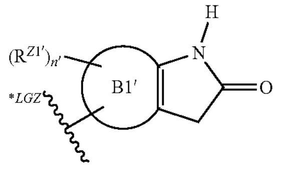

-continued ($Z^{N1}$-12)

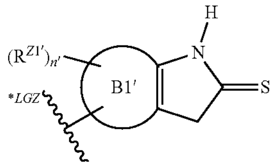

[Chem. 18-3]

($Z^{N1}$-13)

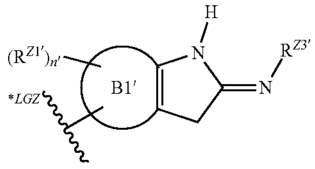

($Z^{N1}$-14)

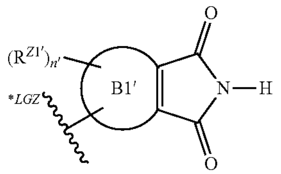

($Z^{N1}$-15)

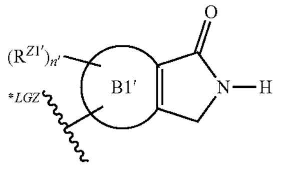

"$Z^{N2}$" is the following one group selected from the group consisting of the formulae ($Z^{N2}$-1) to ($Z^{N2}$-15) ($^{*LG}Z$ represents a linking moiety to $LG^Z$ or Linker; each $R^{Z1}$, which is the same as or different from each other, is optionally substituted $C_{1-6}$ alkyl, halogen, cyano, —OH, —O-(optionally substituted $C_{1-6}$ alkyl), —S-(optionally substituted $C_{1-6}$ alkyl), —NH-(optionally substituted $C_{1-6}$ alkyl) or —N-(optionally substituted $C_{1-6}$ alkyl)$_2$; n' is an integer of 0 to 2; $R^{Z2'}$ and $R^{Z3'}$, which are the same as or different from each other, are H or optionally substituted $C_{1-6}$ alkyl; and ring B1' is a benzene ring or a 6-membered hetero ring, where $R^{Z1'}$ and -$^{*LGN}$ form a bond with a carbon atom forming the ring B1').

[Chem. 19-1]

($Z^{N2}$-1)

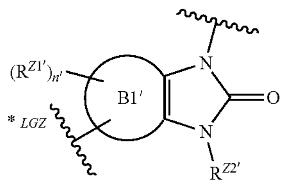

($Z^{N2}$-2)

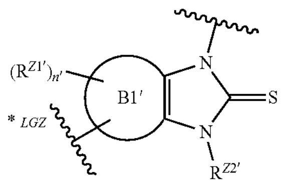

-continued ($Z^{N2}$-3)

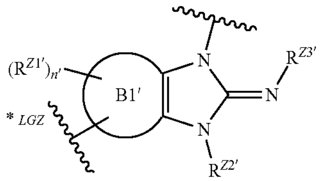

($Z^{N2}$-4)

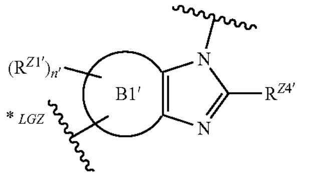

($Z^{N2}$-5)

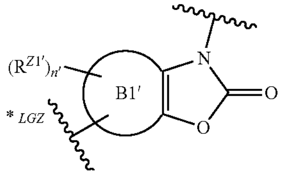

($Z^{N2}$-6)

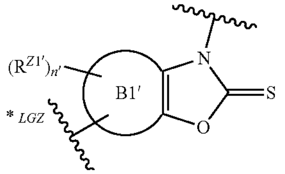

[Chem. 19-2]

($Z^{N2}$-7)

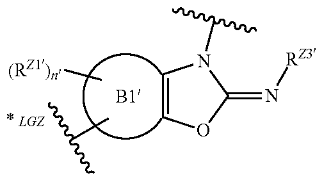

($Z^{N2}$-8)

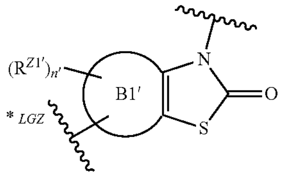

($Z^{N2}$-9)

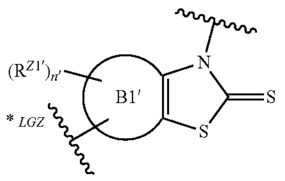

($Z^{N2}$-10)

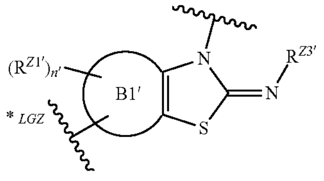

-continued ($Z^{N2}$-11)

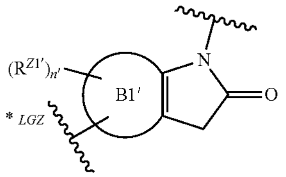

($Z^{N2}$-12)

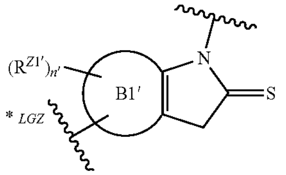

[Chem. 19-3]

($Z^{N2}$-13)

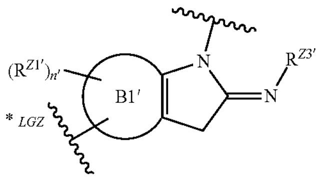

($Z^{N2}$-14)

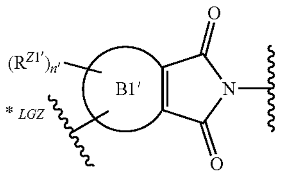

($Z^{N2}$-15)

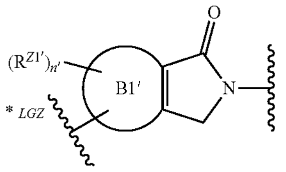

"$Z^C$" is the following one group selected from the group consisting of the formulae ($Z^c$-16) to ($Z^c$-27) ($^{*LGZ}$ represents a linking moiety to $LG^Z$ or Linker, each $R^{Z1}$, which is the same as or different from each other, optionally substituted $C_{1-6}$ alkyl, halogen, cyano, —OH, —O-(optionally substituted $C_{1-6}$ alkyl), —S-(optionally substituted $C_{1-6}$ alkyl), —NH-(optionally substituted $C_{1-6}$ alkyl) or —N-(optionally substituted $C_{1-6}$ alkyl)$_2$; n' is an integer of 0 to 2; $R^{Z2'}$, $R^{Z4'}$ and $R^{Z5'}$ which are the same as or different from each other, are H or optionally substituted $C_{1-6}$ alkyl; M' is a bond, —O—, —S—, —N($R^{M'}$)— or optionally substituted $C_{1-3}$ alkylene; $R^{M'}$ is H or optionally substituted $C_{1-3}$ alkyl; and ring B2' is a benzene ring or a 5- or 6-membered hetero ring, where $R^{z1'}$ and -$^{*LGC}$ form a bond with a carbon atom forming the ring B1', and M', $R^{z1'}$ and -$^{*LGC}$ form a bond with a carbon atom forming the ring B2').

[Chem. 20-1]

($Z^C$-16)

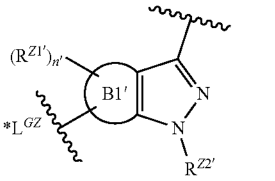

($Z^C$-17)

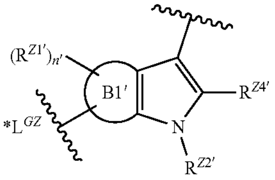

($Z^C$-18)

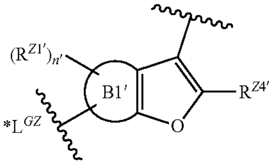

[Chem 20-2]

($Z^C$-19)

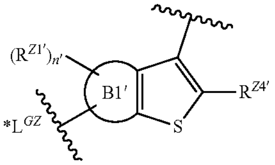

($Z^C$-20)

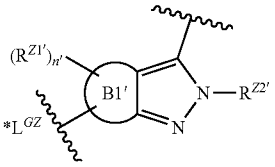

($Z^C$-21)

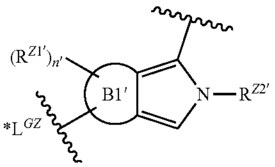

($Z^C$-22)

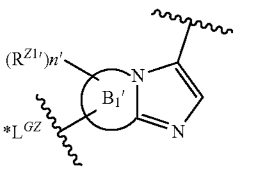

($Z^C$-23)

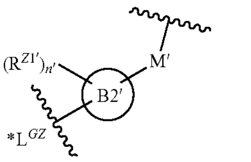

-continued

[Chem. 20-3]

($Z^C$-24)

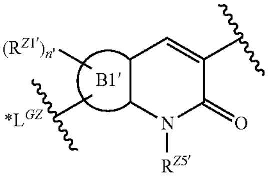

($Z^C$-25)

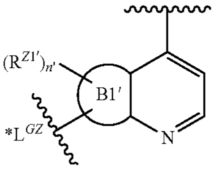

($Z^C$-26)

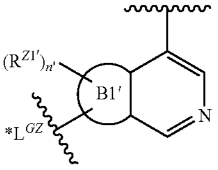

($Z^C$-27)

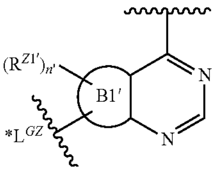

Embodiments of the compound of the formula (I) or a salt thereof of the present invention are shown below.

(1-1) The compound or a salt thereof in which A is $CR^A$ or N, and $R^A$ is H, optionally substituted $C_{1-3}$ alkyl or cyano.

(1-2) The compound or a salt thereof in which A is CH or N.

(1-3) The compound or a salt thereof in which A is CH.

(1-4) The compound or a salt thereof in which A is N.

(2-1) The compound or a salt thereof in which Q is $CR^Q$ or N, and $R^Q$ is H, halogen, optionally substituted $C_{1-3}$ alkyl, $C_{3-6}$ cycloalkyl or vinyl.

(2-2) The compound or a salt thereof in which Q is $CR^Q$, and $R^Q$ is $C_{3-6}$ cycloalkyl.

(2-3) The compound or a salt thereof in which Q is $CR^Q$, and $R^Q$ is cyclopropyl.

(3-1) The compound or a salt thereof in which E is CH or N.

(3-2) The compound or a salt thereof in which E is CH.

(4-1) The compound or a salt thereof in which $R^1$ is naphthyl optionally substituted with one or two groups selected from the group consisting of optionally substituted $C_{1-3}$ alkyl, cyano, OH and halogen, or $R^1$ is a group selected from the group consisting of the formula (II), the formula (III) and the formula (IV) below,

[Chem. 21]

(II)

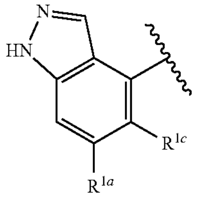

(III)

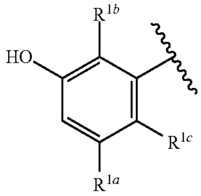

(IV)

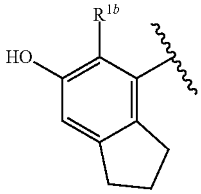

, and $R^{1a}$, $R^{1b}$ and $R^{1c}$, which are the same as or different from each other, are H, optionally substituted $C_{1-3}$ alkyl, vinyl or halogen.

(4-2) The compound or a salt thereof in which $R^1$ is the formula (II) below,

[Chem. 22]

(II)

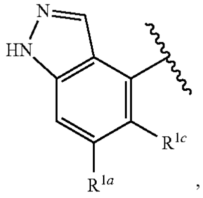

, and $R^{1a}$ and $R^{1c}$, which are the same as or different from each other, are $C_{1-3}$ alkyl or halogen.

(4-3) The compound or a salt thereof in which $R^1$ is the formula (II) below,

[Chem. 23]

(II)

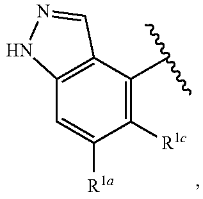

, and $R^{1a}$ is halogen, and $R^{1c}$ is $C_{1-3}$ alkyl.

(4-4) The compound or a salt thereof in which $R^1$ is the formula (II-2) below.

[Chem. 24]

(II-2)

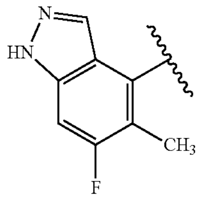

(5-1) The compound or a salt thereof in which $R^2$ is —$V^1$—$V^2$ or W, $V^1$ is a bond, —$CH_2$—, —O—, —S— or —N($R^{V1}$)—, $R^{V1}$ is H or optionally substituted $C_{1-3}$ alkyl, $V^2$ is the formula (V) or the formula (VI) below,

[Chem. 25]

(V)

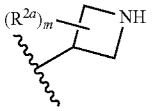

(VI)

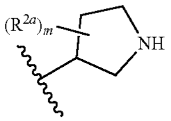

W is the formula (VII) or the formula (VII-2) below or 7-membered to 9-membered bridged heterocycloalkyl containing one to two nitrogen atoms,

[Chem. 26]

(VII)

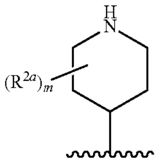

(VII-2)

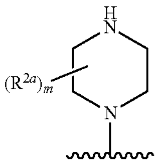

each $R^{2a}$, which is the same as or different from each other, are OH, $OCH_3$, F or optionally substituted $C_{1-3}$ alkyl, where $R^{2a}$ is attached only to a carbon atom that is an atom forming a ring selected from the group consisting of an azetidine ring represented by the formula (V), a pyrrolidine ring represented by the formula (VI), a piperidine ring represented by the formula (VII) and a piperazine ring represented by the formula (VII-2), and m is an integer of 0 to 2.

(5-2) The compound or a salt thereof in which $R^2$ is —$V^1$—$V^2$ or W, $V^1$ is a bond, —$CH_2$—, —O—, —S— or —N($R^{V1}$)—, $R^{V1}$ is $C_{1-3}$ alkyl optionally substituted with one group selected from the group consisting of $C_{3-6}$ cycloalkyl, halogen and —OH, $V^2$ is the formula (V-2) or (VI-2) below,

[Chem. 27]

(V-2)

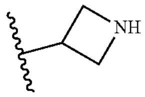

(VI-2)

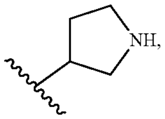

and

W is one group selected from the group consisting of the formulae (VII-3), (VII-4), (VIII), (IX), (X), (XI), (XII), (XIII) and (XIV) below.

[Chem. 28]

(VII-3)

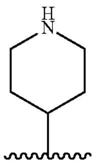

(VII-4)

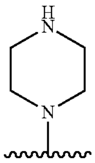

(VIII)

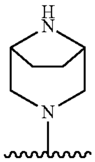

(IX)

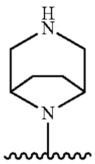

(X)

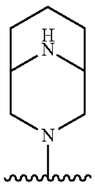

-continued (XI)

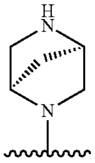

(XII)

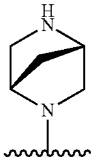

(XIII)

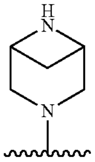

(XIV)

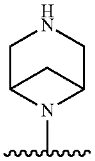

(5-3) The compound or a salt thereof in which $R^2$ is —$V^1$—$V^2$ or W, $V^1$ is a bond, —O— or —N($R^{V1}$)—, $R^{V1}$ is $C_{1-3}$ alkyl, $V^2$ is the formula (VI-2) below,

[Chem. 29]

(VI-2)

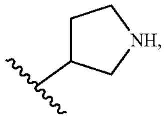

and

W is the formula (XII) below.

[Chem. 30]

(XII)

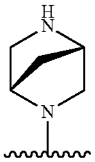

(5-4) The compound or a salt thereof in which $R^2$ is —$V^1$—$V^2$ or W, $V^1$ is —O— or —N($CH_3$)—, $V^2$ is the formula (VI-2) below,

[Chem. 31]

(VI-2)

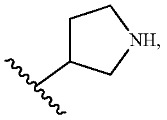

and

W is the formula (XII) below.

[Chem. 32]

(XII)

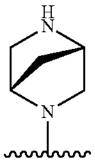

(5-5) The compound or a salt thereof in which $R^2$ is $—V^1—V^2$ or W, $V^1$ is —O—, $V^2$ is the formula (VI-2) below,

[Chem. 33]

(VI-2)

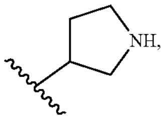

and

W is the formula (XII) below.

[Chem. 34]

(XII)

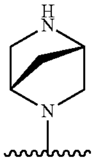

(5-6) The compound or a salt thereof in which $R^2$ is $—V^1—V^2$ or W, $V^1$ is a bond, $—CH_2—$, —O—, —S— or $—N(R^{V1})—$, $R^{V1}$ is $C_{1-3}$ alkyl optionally substituted with one group selected from the group consisting of $C_{3-6}$ cycloalkyl, halogen and —OH, $V^2$ is the formula (V-2) or (VI-2) below,

[Chem. 35]

(V-2)

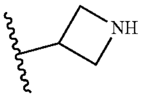

-continued (VI-2)

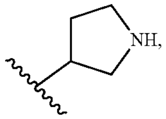

and

W is one group selected from the group consisting of the formulae (VII-4), (XI) and (XII).

[Chem. 36]

(VII-4)

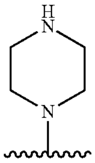

(XI)

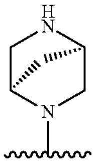

(XII)

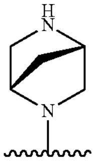

(5-6-2) The compound or a salt thereof in which $R^2$ is $—V^1—V^2$ or W, $V^1$ is —O— or $—N(R^{V1})—$, $R^{V1}$ is $C_{1-3}$ alkyl, $V^2$ is the formula (V-2) or (VI-2) below,

[Chem. 37]

(V-2)

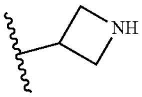

(VI-2)

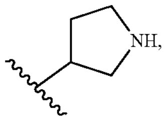

and

W is one group selected from the group consisting of the formulae (VII-4), (XI) and

[Chem. 38]

(VII-4)

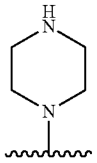

(XI)

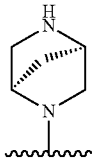

(XII)

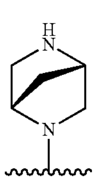

(5-7) The compound or a salt thereof in which $R^2$ is $-V^1-V^2$ or W, $V^1$ is —O— or $-N(CH_3)-$, $V^2$ is the formula (VI-2) below,

[Chem. 39]

(VI-2)

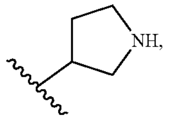

and

W is the formula (VII-4) or (XII) below.

[Chem. 40]

(VII-4)

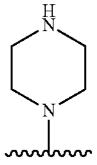

(XII)

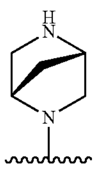

(6-1) The compound or a salt thereof in which $R^3$ is optionally substituted $C_{1-6}$ alkyl, optionally substituted heterocycloalkyl or optionally substituted heteroaryl.

(6-2) The compound or a salt thereof in which $R^3$ is $C_{1-6}$ alkyl optionally substituted with one group selected from the group consisting of —O—($C_{1-6}$ alkyl), —S—($C_{1-6}$ alkyl), —N—($C_{1-6}$ alkyl)$_2$ and heterocycloalkyl or optionally substituted heterocycloalkyl.

(6-3) The compound or a salt thereof in which $R^3$ is $C_{1-6}$ alkyl optionally substituted with one group selected from the group consisting of —O($C_{1-6}$ alkyl), oxetanyl, tetrahydrofuranyl and tetrahydropyranyl, oxetanyl, tetrahydrofuranyl or tetrahydropyranyl.

(6-4) The compound or a salt thereof in which $R^3$ is $C_{1-3}$ alkyl optionally substituted with $-OCH_3$ or tetrahydrofuranyl, tetrahydrofuranyl or tetrahydropyranyl.

(6-5) The compound or a salt thereof in which $R^3$ is n-propyl optionally substituted with $-OCH_3$ or tetrahydropyranyl.

(7-1) The compound or a salt thereof in which X is a bond, $-CH_2-$, —O—, —S— or $-NR^{4X}-$, and $R^{4X}$ is H or optionally substituted $C_{1-3}$ alkyl.

(7-2) The compound or a salt thereof in which X is —O— or $-NR^{4X}-$, $R^{4X}$ is $C_{1-3}$ alkyl.

(7-3) The compound or a salt thereof in which X is —O—.

(8-1) The compound or a salt thereof in which $Y^1$ is —O-(optionally substituted $C_{1-3}$ alkylene)-$^{*Y2}$, —S-(optionally substituted $C_{1-3}$ alkylene)-$^{*Y2}$, $-SO_2$-(Optionally substituted $C_{1-3}$ alkylene)-$^{*Y2}$, $-NR^Y$-(optionally substituted $C_{1-3}$ alkylene)-$^{*Y2}$, -(optionally substituted $C_{1-3}$ alkylene)-O-$^{*Y2}$, -(optionally substituted $C_{1-3}$ alkylene)-S-$^{*Y2}$, -(optionally substituted $C_{1-3}$ alkylene)-$SO_2$-$^{*Y2}$ or -(optionally substituted $C_{1-3}$ alkylene)-$NR^Y$-$^{*Y2}$ ($^{*Y2}$ represents a linking moiety to $Y^2$), and $R^Y$ is H or optionally substituted $C_{1-3}$ alkyl.

(8-2) The compound or a salt thereof in which $Y^1$ is —O—($C_{1-3}$ alkylene)-$^{*Y2}$ or ($C_{1-3}$ alkylene)-O-$^{*Y2}$ ($^{*Y2}$ represents a linking moiety to $Y^2$).

(8-3) The compound or a salt thereof in which $Y^1$ is —O—($C_{1-3}$ alkylene)-$^{*Y2}$ ($^{*Y2}$ represents a linking moiety to $Y^2$).

(8-4) The compound or a salt thereof in which $Y^1$ is —O-(methylene)-$^{*Y2}$ ($^{*Y2}$ represents a linking moiety to $Y^2$).

(9-1) The compound or a salt thereof in which $Y^2$ is a bond, optionally substituted phenylene or optionally substituted heteroarylene.

(9-2) The compound or a salt thereof in which $Y^2$ is phenylene or pyridinediyl.

(9-3) The compound or a salt thereof in which $Y^2$ is phenylene optionally substituted with fluorine.

(9-4) The compound or a salt thereof in which $Y^2$ is phenylene.

(9-5) The compound or a salt thereof in which $Y^2$ is optionally substituted phenylene or pyridinediyl.

(10-1) The compound or a salt thereof in which Linker is one group chemically linking $Y^2$ to EUB.

(10-2) The compound or a salt thereof in which Linker is -($L^1$-$L^2$-$L^3$-$L^4$)-, $L^1$, $L^2$, $L^3$ and $L^4$, which are the same as or different from each other, are one group selected from the group consisting of a bond, C═O, —O—, —S—, $-SO_2-$, $-NR^L-$, acetylene-1,2-diyl, optionally substituted heterocycloalkylene, optionally substituted heteroarylene, saturated 7-membered to 9-membered spiroheterocycloalkylene containing one or two nitrogen atoms, saturated 7-membered to 9-membered bridged heterocycloalkylene containing two nitrogen atoms and optionally substituted $C_{1-6}$ alkylene, and $R^L$ is H or $C_{1-6}$ alkyl.

(10-3) The compound or a salt thereof in which Linker is -($L^1$-$L^2$-$L^3$-$L^4$)-, $L^1$ is C═O, $L^2$ is piperidinediyl optionally substituted with $C_{1-3}$ alkyl, piperazinediyl optionally substituted with $C_{1-3}$ alkyl, pyrrolidinediyl optionally substituted with $C_{1-3}$ alkyl, bridged piperazinediyl or 2,6-diazaspiro[3.4]octanediyl, $L^3$ is a bond, —N($R^{L3}$)—, $C_{1-3}$ alkylene or piperazinediyl, $L^4$ is a bond, —N($R^{L4}$)—, —O— or $C_{1-3}$ alkylene, $R^{L3}$ is H or $C_{1-3}$ alkyl, and $R^{L4}$ is H or $C_{1-3}$ alkyl.

(10-3-2) The compound or a salt thereof in which Linker is -($L^1$-$L^2$-$L^3$-$L^4$)-, $L^1$ is C═O, $L^2$ is piperidinediyl optionally substituted with $C_{1-3}$ alkyl, piperazinediyl optionally substituted with $C_{1-3}$ alkyl, pyrrolidinediyl optionally substituted with $C_{1-3}$ alkyl, bridged piperazinediyl or 2,6-diazaspiro[3.4]octanediyl, $L^3$ is a bond, —N($R^{L3}$)—, $C_{1-3}$ alkylene or piperazinediyl, $L^4$ is a bond, —N($R^{L4}$)—, —O—, piperazinediyl or $C_{1-3}$ alkylene, $R^{L3}$ is H or $C_{1-3}$ alkyl, and $R^{L4}$ is H or $C_{1-3}$ alkyl.

(10-4) The compound or a salt thereof in which Linker is one group selected from the group consisting of the formulae (L-1), (L-2), (L-3), (L-4), (L-5), (L-6) and (L-7) below, wherein C═O in the formulae (L-1), (L-2), (L-3), (L-4), (L-5), (L-6) and (L-7) forms a bond with $Y^2$,

[Chem. 41]

(L-1)

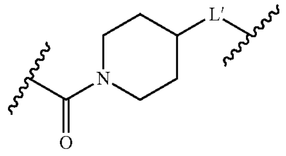

(L-2)

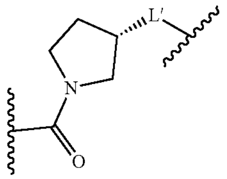

(L-3)

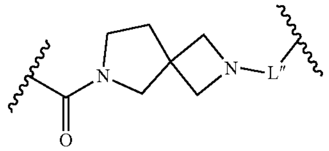

(L-4)

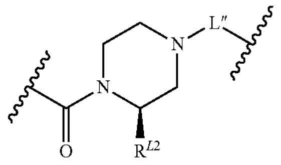

-continued (L-5)

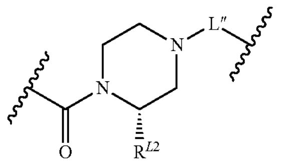

(L-6)

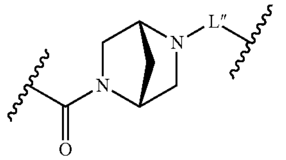

(L-7)

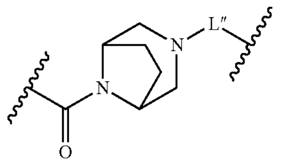

L' is —O—, —($C_{1-3}$ alkylene)-NH—, —N($CH_3$)($C_{1-3}$ alkylene)-, piperazinediyl or —($C_{1-3}$ alkylene)-piperazinediyl, L" is a bond, $C_{1-3}$ alkylene or —($C_{1-3}$ alkylene)-O—, and $R^{L2}$ is H or $C_{1-3}$ alkyl.

(10-5) The compound or a salt thereof in which Linker is -($L^1$-$L^2$-$L^3$-$L^4$)-, $L^1$ is C═O, $L^2$ is piperidinediyl optionally substituted with $C_{1-3}$ alkyl, piperazinediyl optionally substituted with $C_{1-3}$ alkyl, pyrrolidinediyl optionally substituted with $C_{1-3}$ alkyl, 3,8-diazabicyclo[3.2.1]octanediyl or 2,6-diazaspiro[3.4]octanediyl, $L^3$ is a bond, —N($R^{L3}$)—, $C_{1-3}$ alkylene or piperazinediyl, $L^4$ is a bond, —N($R^{L4}$)—, —O— or $C_{1-3}$ alkylene, $R^{L3}$ is H or $C_{1-3}$ alkyl, and $R^{L4}$ is H or $C_{1-3}$ alkyl.

(10-5-2) The compound or a salt thereof in which Linker is -($L^1$-$L^2$-$L^3$-$L^4$)-, $L^1$ is C═O, $L^2$ is piperidinediyl optionally substituted with $C_{1-3}$ alkyl, piperazinediyl optionally substituted with $C_{1-3}$ alkyl, pyrrolidinediyl optionally substituted with $C_{1-3}$ alkyl, 3,8-diazabicyclo[3.2.1]octanediyl or 2,6-diazaspiro[3.4]octanediyl, $L^3$ is a bond, —N($R^{L3}$)—, $C_{1-3}$ alkylene or piperazinediyl, $L^4$ is a bond, —N($R^{L4}$)—, —O—, piperazinediyl or $C_{1-3}$ alkylene, $R^{L3}$ is H or $C_{1-3}$ alkyl, and $R^{L4}$ is H or $C_{1-3}$ alkyl.

(10-6) The compound or a salt thereof in which Linker is one group selected from the group consisting of the formulae (L-1), (L-2), (L-3), (L-4), (L-5) and (L-7) below, wherein C═O in the formulae (L-1), (L-2), (L-3), (L-4), (L-5) and (L-7) forms a bond with $Y^2$,

[Chem. 42]

(L-1)

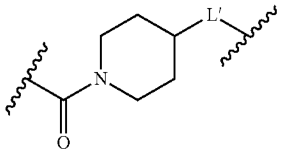

(L-2)

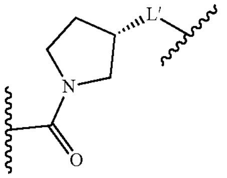

(L-3)

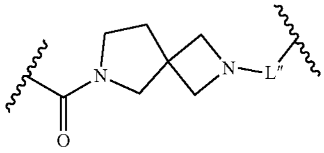

(L-4)

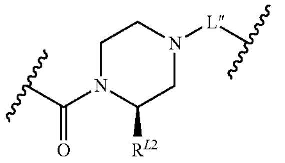

(L-5)

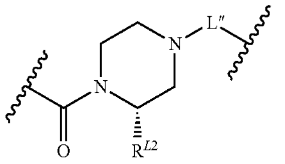

(L-7)

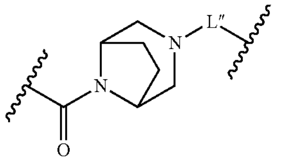

L' is —O—, —($C_{1-3}$ alkylene)-NH—, —N($CH_3$)($C_{1-3}$ alkylene)-, piperazinediyl or —($C_{1-3}$ alkylene)-piperazinediyl, L" is a bond, $C_{1-3}$ alkylene or —($C_{1-3}$ alkylene)-O—, and $R^{L2}$ is H or $C_{1-3}$ alkyl.

(10-7) The compound or a salt thereof in which Linker is the formula (L-5A) or (L-7A) below.

[Chem. 43]

(L-5A)

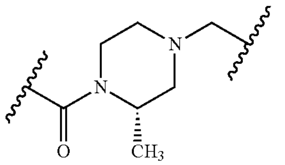

-continued (L-7A)

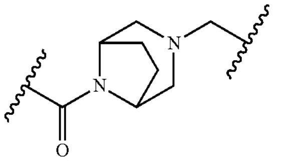

(11-1) The compound or a salt thereof in which EUB is a group capable of binding to one E3 ubiquitin ligase selected from the group consisting of cereblon, IAP, MDM2, DCAF11, DCAF15, DCAF16, BIRC2, KEAP1, RNF4, RNF114, FEM1B and AhR.

(11-2) The compound or a salt thereof in which EUB is a group capable of binding to cereblon.

(11-3) The compound or a salt thereof in which EUB is the formula (XV) below,

[Chem. 44]

(XV)

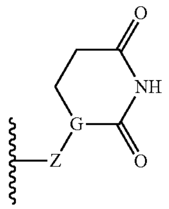

G is $CR^G$ or N, $R^G$ is H or $C_{1-6}$ alkyl,

Z is one group selected from the group consisting of the formulae (Z-1), (Z-2), (Z-3), (Z-4), (Z-5), (Z-6), (Z-7), (Z-8), (Z-9), (Z-10), (Z-11), (Z-12), (Z-13), (Z-14), (Z-15), (Z-16), (Z-17), (Z-18), (Z-19), (Z-20), (Z-21), (Z-22) and (Z-23) below, wherein ring B1 and ring B2 in the formulae (Z-1), (Z-2), (Z-3), (Z-4), (Z-5), (Z-6), (Z-7), (Z-8), (Z-9), (Z-10), (Z-11), (Z-12), (Z-13), (Z-14), (Z-15), (Z-16), (Z-17), (Z-18), (Z-19), (Z-20), (Z-21), (Z-22) and (Z-23) form a bond with Linker, provided that when G is N, Z is one group selected from the group consisting of the formulae (Z-16), (Z-17), (Z-18), (Z-19), (Z-20), (Z-21), (Z-22) and (Z-23),

[Chem. 45-1]

(Z-1)

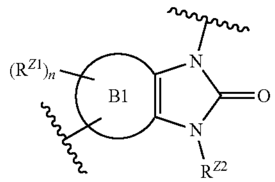

(Z-2)

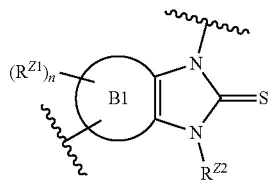

-continued
(Z-3)
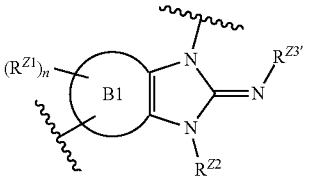
(Z-4)
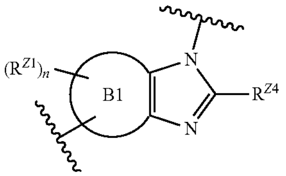
(Z-5)
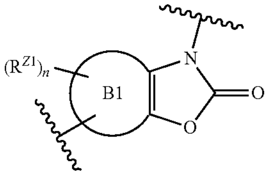
(Z-6)
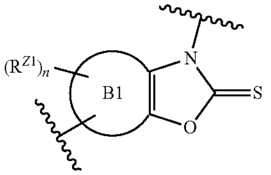
[Chem. 45-2]
(Z-7)
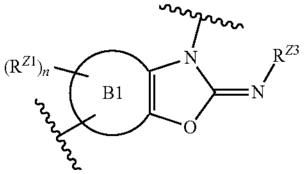
(Z-8)
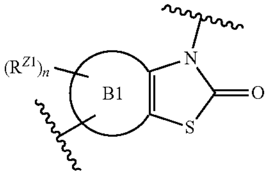
(Z-9)
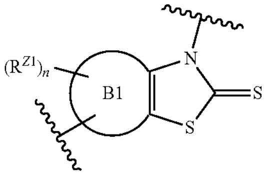
(Z-10)
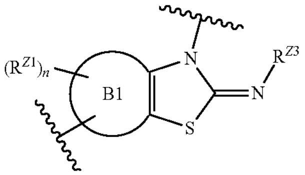
-continued
(Z-11)
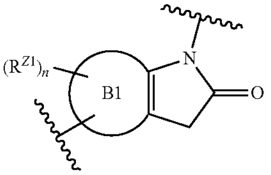
(Z-12)
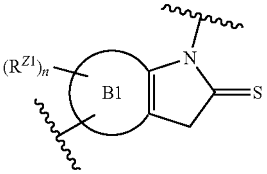
[Chem. 45-3]
(Z-13)
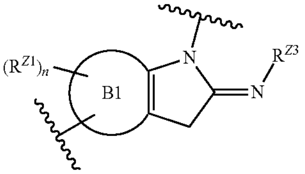
(Z-14)
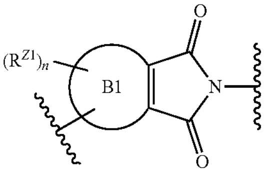
(Z-15)
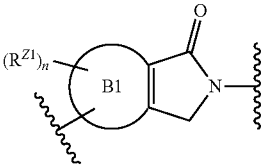
(Z-16)
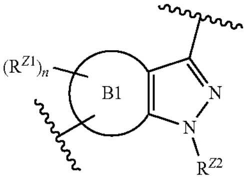
(Z-17)
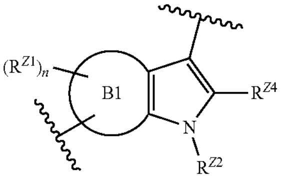
(Z-18)
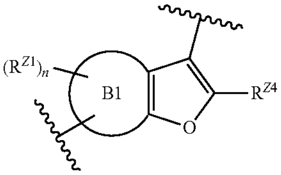

-continued

[Chem. 45-4]

(Z-19)

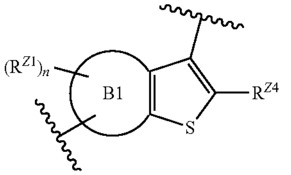

(Z-20)

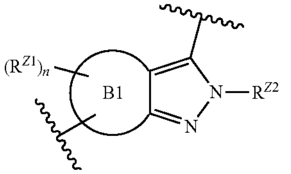

(Z-21)

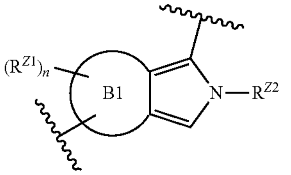

(Z-22)

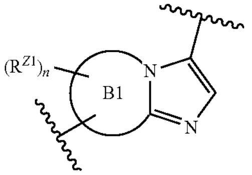

(Z-23)

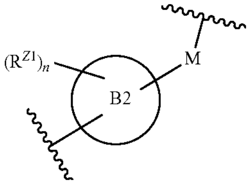

each $R^{Z1}$, which is the same as or different from each other, is optionally substituted $C_{1-6}$ alkyl, halogen, cyano, —OH, —O-(optionally substituted $C_{1-6}$ alkyl), —S-(optionally substituted $C_{1-6}$ alkyl), —NH-(optionally substituted $C_{1-6}$ alkyl) or —N-(optionally substituted $C_{1-6}$ alkyl)$_2$, n is an integer of 0 to 2, $R^{Z2}$, $R^{Z3}$ and $R^{Z4}$, which are the same as or different from each other, are H or optionally substituted $C_{1-6}$ alkyl, M is a bond, —O—, —S—, —N($R^M$)— or optionally substituted $C_{1-3}$ alkylene, $R^M$ is H or optionally substituted $C_{1-3}$ alkyl, ring B1 is a benzene ring or a 6-membered hetero ring, wherein $R^{Z1}$ and Linker form a bond with a carbon atom forming the ring B1, and ring B2 is a benzene ring or a 5- or 6-membered hetero ring, wherein M, $R^{Z1}$ and Linker form a bond with a carbon atom forming the ring B2.

(11-3-2) The compound or a salt thereof in which EUB is a group capable of binding to cereblon, where the group capable of binding to cereblon is the formula (XV) below,

[Chem. 46]

(XV)

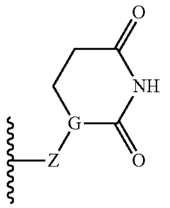

G is $CR^G$ or N, $R^G$ is H or $C_{1-6}$ alkyl,

Z is one group selected from the group consisting of the formulae (Z-1), (Z-2), (Z-3), (Z-4), (Z-5), (Z-6), (Z-7), (Z-8), (Z-9), (Z-10), (Z-11), (Z-12), (Z-13), (Z-14), (Z-15), (Z-16), (Z-17), (Z-18), (Z-19), (Z-20), (Z-21), (Z-22) and (Z-23) below, wherein ring B1 and ring B2 in the formulae (Z-1), (Z-2), (Z-3), (Z-4), (Z-5), (Z-6), (Z-7), (Z-8), (Z-9), (Z-10), (Z-11), (Z-12), (Z-13), (Z-14), (Z-15), (Z-16), (Z-17), (Z-18), (Z-19), (Z-20), (Z-21), (Z-22) and (Z-23) form a bond with Linker, provided that when G is N, Z is one group selected from the group consisting of the formulae (Z-16), (Z-17), (Z-18), (Z-19), (Z-20), (Z-21), (Z-22) and (Z-23),

[Chem. 47-1]

(Z-1)

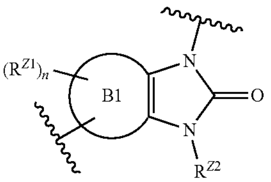

(Z-2)

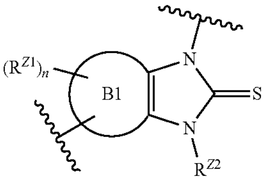

(Z-3)

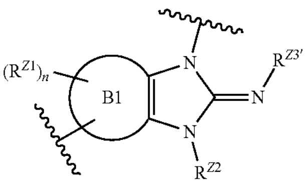

(Z-4)

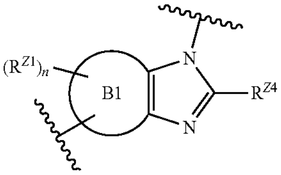

-continued
(Z-5)
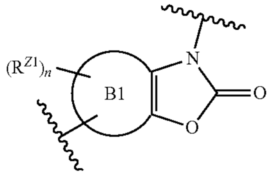
(Z-6)
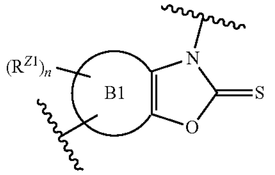
[Chem. 47-2]
(Z-7)
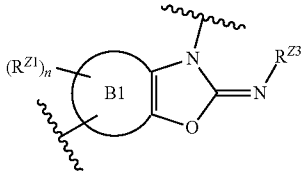
(Z-8)
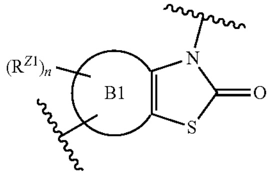
(Z-9)
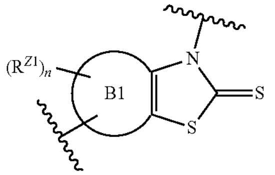
(Z-10)
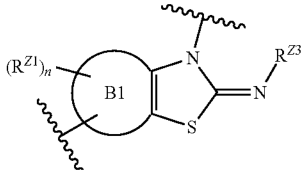
(Z-11)
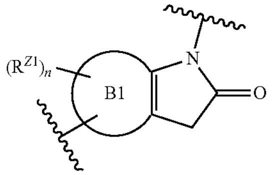
(Z-12)
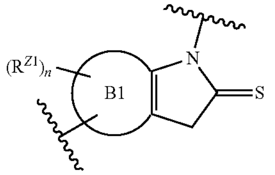
-continued
[Chem. 45-3]
(Z-13)
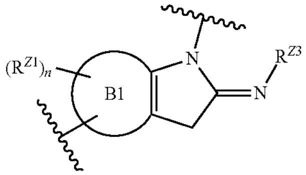
(Z-14)
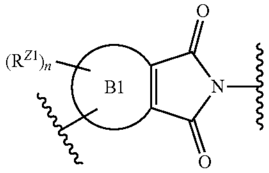
(Z-15)
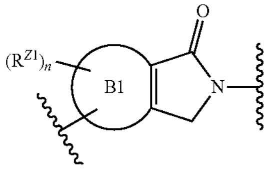
(Z-16)
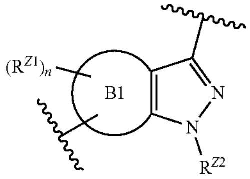
(Z-17)
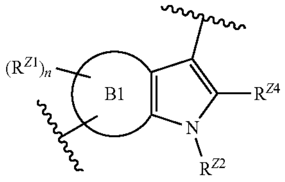
(Z-18)
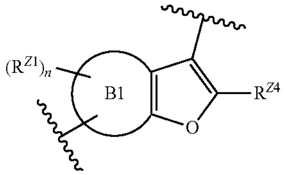
[Chem. 45-4]
(Z-19)
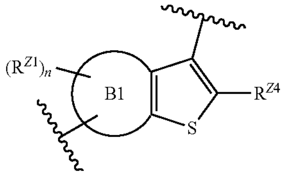
(Z-20)
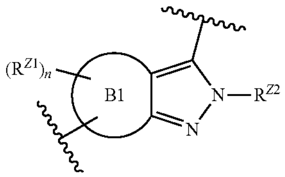

-continued (Z-21)

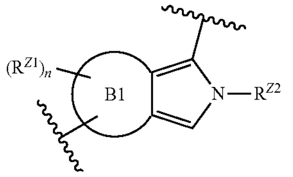

(Z-22)

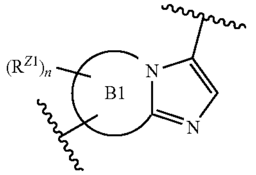

(Z-23)

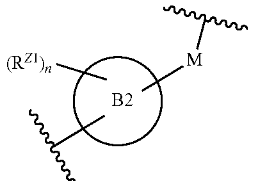

each $R^{Z1}$, which is the same as or different from each other, is optionally substituted $C_{1-6}$ alkyl, halogen, cyano, —OH, —O-(optionally substituted $C_{1-6}$ alkyl), —S-(optionally substituted $C_{1-6}$ alkyl), —NH-(optionally substituted $C_{1-6}$ alkyl) or —N-(optionally substituted $C_{1-6}$ alkyl)$_2$, n is an integer of 0 to 2, $R^{Z2}$, $R^{Z3}$ and $R^{Z4}$, which are the same as or different from each other, are H or optionally substituted $C_{1-6}$ alkyl, M is a bond, —O—, —S—, —N($R^M$)— or optionally substituted $C_{1-3}$ alkylene, $R^M$ is H or optionally substituted $C_{1-3}$ alkyl, ring B1 is a benzene ring or a 6-membered hetero ring, wherein $R^{Z1}$ and Linker form a bond with a carbon atom forming the ring B1, and ring B2 is a benzene ring or a 5- or 6-membered hetero ring, wherein M, $R^{Z1}$ and Linker form a bond with a carbon atom forming the ring B2.

(11-4) The compound or a salt thereof in which EUB is the formula (XV) below,

[Chem. 46]

(XV)

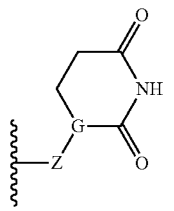

G is CH or N,

Z is one group selected from the group consisting of the formulae (Z-1), (Z-4), (Z-5), (Z-11), (Z-14), (Z-15), (Z-16), (Z-18), (Z-19), (Z-20), (Z-22) and (Z-23), wherein ring B1 and ring B2 in the formulae (Z-1), (Z-4), (Z-5), (Z-11), (Z-14), (Z-15), (Z-16), (Z-18), (Z-19), (Z-20), (Z-22) and (Z-23) form a bond with Linker, provided that when G is N, Z is one group selected from the group consisting of the formulae (Z-16), (Z-18), (Z-19), (Z-20), (Z-22) and (Z-23),

[Chem. 49-1]

(Z-1)

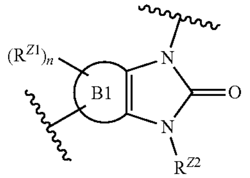

(Z-4)

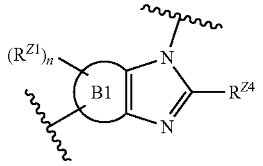

(Z-5)

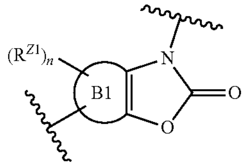

(Z-11)

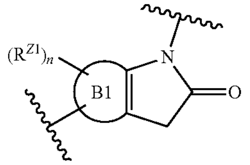

(Z-14)

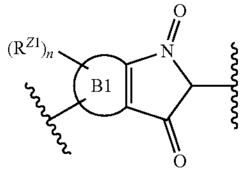

(Z-15)

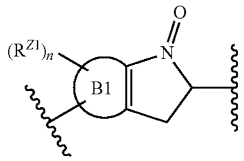

[Chem. 49-2]

(Z-16)

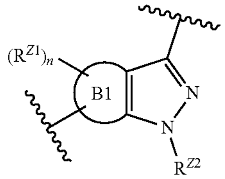

(Z-18)

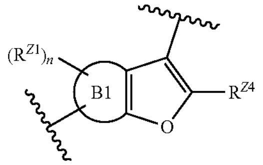

-continued (Z-19)

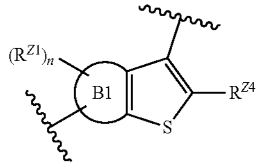

(Z-20)

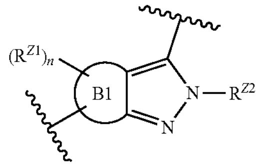

(Z-22)

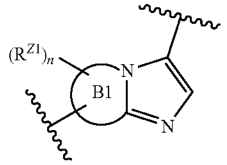

(Z-23)

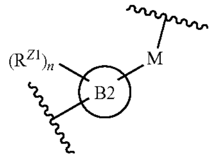

$R^{Z1}$ is $C_{1-6}$ alkyl or halogen, n is an integer of 0 or 1, $R^{Z2}$ and $R^{Z4}$, which are the same as or different from each other, are H or $C_{1-6}$ alkyl, M is a bond or $C_{1-3}$ alkylene, ring B1 is a benzene ring or a pyridine ring, wherein $R^{Z1}$ and Linker form a bond with a carbon atom forming the ring B1, and ring B2 is a benzene ring or a pyridine ring, wherein M, $R^{Z1}$ and Linker form a bond with a carbon atom forming the ring B2.

(11-5) The compound or a salt thereof in which EUB is the formula (XV) below,

[Chem. 50]

(XV)

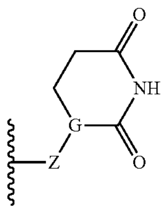

G is CH or N,

Z is one group selected from the group consisting of the formulae (Z-1), (Z-5), (Z-11), (Z-14), (Z-15), (Z-16), (Z-20), (Z-22) and (Z-23), wherein ring B1 and ring B2 in the formulae (Z-1), (Z-5), (Z-11), (Z-14), (Z-15), (Z-16), (Z-20), (Z-22) and (Z-23) form a bond with Linker, provided that when G is N, Z is one group selected from the group consisting of the formulae (Z-16), (Z-20), (Z-22) and (Z-23),

[Chem. 51-1]

(Z-1)

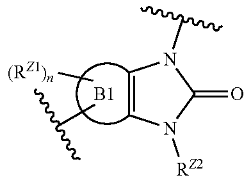

(Z-5)

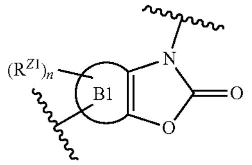

(Z-11)

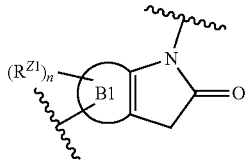

(Z-14)

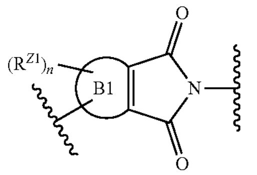

(Z-15)

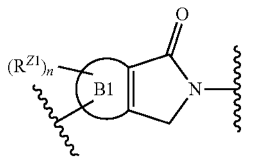

(Z-16)

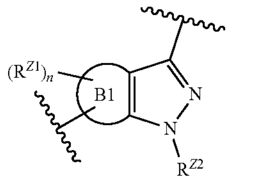

[Chem. 51-2]

(Z-20)

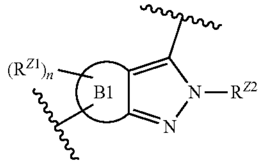

(Z-22)

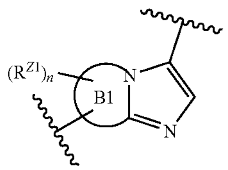

-continued (Z-23)

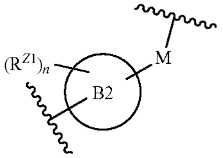

$R^{Z1}$ is $C_{1-3}$ alkyl or halogen, n is an integer of 0 or 1, $R^{Z2}$ is $C_{1-3}$ alkyl, M is a bond or $C_{1-3}$ alkylene, ring B1 is a benzene ring or a pyridine ring, wherein $R^{Z1}$ and Linker form a bond with a carbon atom forming the ring B1, and ring B2 is a benzene ring or a pyridine ring, wherein M, $R^{Z1}$ and Linker form a bond with a carbon atom forming the ring B2.

(11-6) The compound or a salt thereof in which EUB is the formula (XV) below,

[Chem. 52]

(XV)

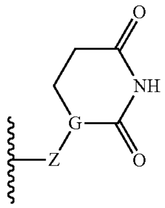

G is CH or N,

Z is one group selected from the group consisting of the formulae (Z-1A), (Z-1B), (Z-5A), (Z-5B), (Z-14A), (Z-14B), (Z-14C), (Z-15A), (Z-16A), (Z-16B), (Z-16C), (Z-16D), (Z-20A), (Z-22A), (Z-23A), (Z-23B), (Z-23C), (Z-23D), (Z-23E) and (Z-23F) below, and wherein a benzene ring or a 6-membered hetero ring in the formulae (Z-1A), (Z-1B), (Z-5A), (Z-5B), (Z-14A), (Z-14B), (Z-14C), (Z-15A), (Z-16A), (Z-16B), (Z-16C), (Z-16D), (Z-20A), (Z-22A), (Z-23A), (Z-23B), (Z-23C), (Z-23D), (Z-23E) and (Z-23F) form a bond with Linker, provided that when G is N, Z is one group selected from the group consisting of (Z-16A), (Z-16B), (Z-16C), (Z-16D), (Z-20A), (Z-22A), (Z-23A), (Z-23B), (Z-23C), (Z-23D), (Z-23E) and (Z-23F).

[Chem. 53-1]

(Z-1A)

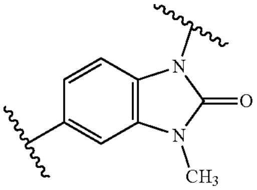

-continued (Z-1B)

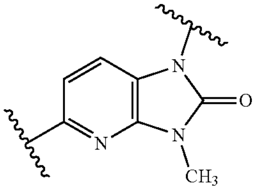

(Z-5A)

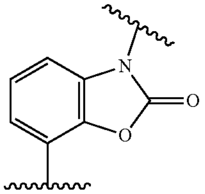

(Z-5B)

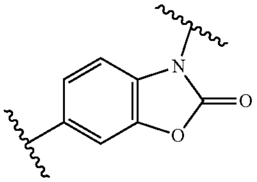

(Z-14A)

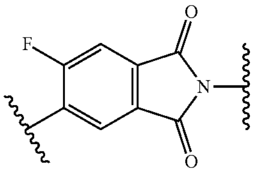

(Z-14B)

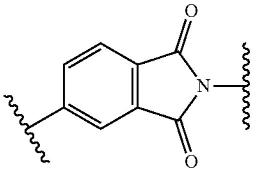

[Chem. 53-2]

(Z-14C)

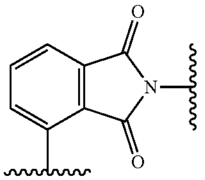

(Z-15A)

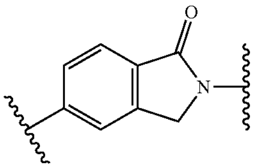

(Z-16A)

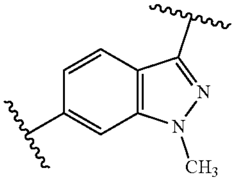

-continued
(Z-16B)
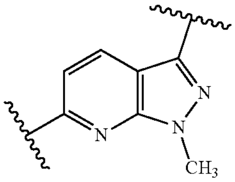
(Z-16C)
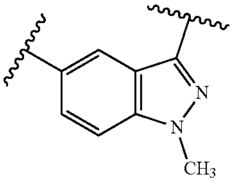
(Z-16D)
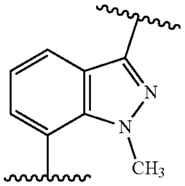
[Chem. 53-3]
(Z-20A)
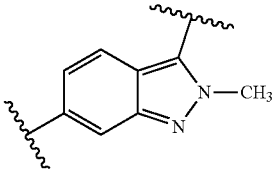
(Z-22A)
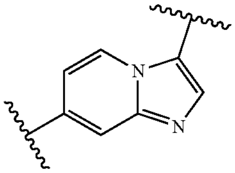
(Z-23A)
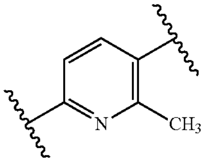
(Z-23B)
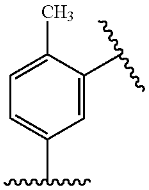
(Z-23C)
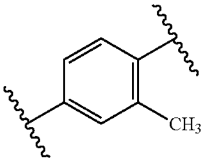
-continued
(Z-23D)
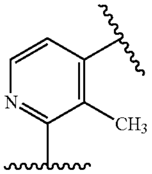
(Z-23E)
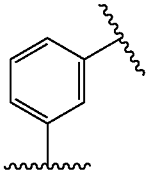
(Z-23F)
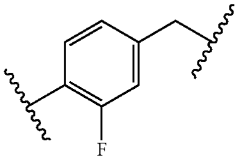
(11-7) The compound or a salt thereof in which EUB is the formula (XV) below,
[Chem. 54]
(XV)
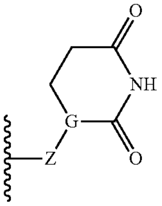
G is CH, and
Z is one group selected from the group consisting of the formulae (Z-1A), (Z-1B), (Z-5A), (Z-5B), (Z-14A), (Z-14B), (Z-14C) and (Z-15A),
wherein a benzene ring or a 6-membered hetero ring in the formulae (Z-1A), (Z-1B), (Z-5A), (Z-5B), (Z-14A), (Z-14B), (Z-14C) and (Z-15A) forms a bond with Linker.
[Chem. 55-1]
(Z-1A)
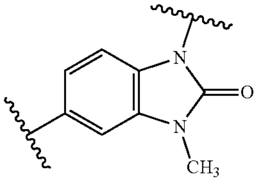
(Z-1B)
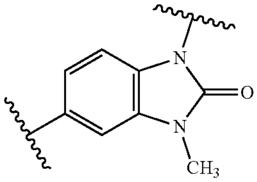

-continued (Z-5A)

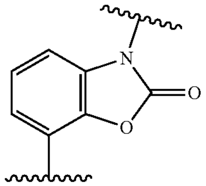

(Z-5B)

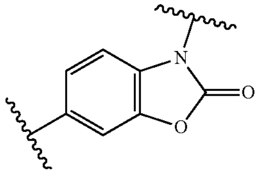

(Z-14A)

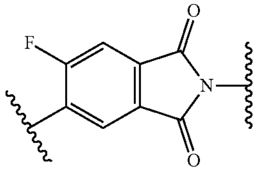

(Z-14B)

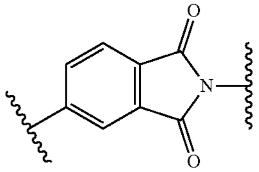

[Chem. 55-2]

(Z-14C)

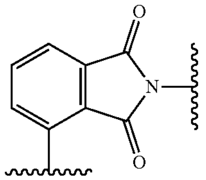

(Z-15A)

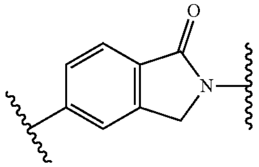

(11-8) The compound or a salt thereof in which EUB is the formula (XV) below,

[Chem. 56]

(XV)

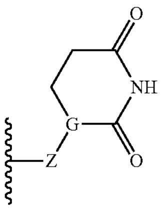

G is CH or N, and

Z is one group selected from the group consisting of the formulae (Z-1A), (Z-14B), (Z-15A), (Z-16A) and (Z-22A) below, wherein a benzene ring or a 6-membered hetero ring in the formulae (Z-1A), (Z-14B), (Z-15A), (Z-16A) and (Z-22A) forms a bond with Linker, provided that when G is N, Z is (Z-16A) or (Z-22A).

[Chem. 57]

(Z-1A)

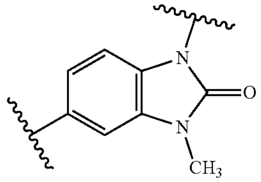

(Z-14B)

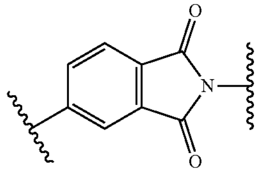

(Z-15A)

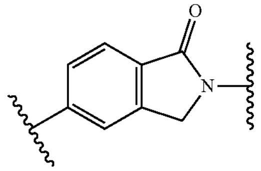

(Z-16A)

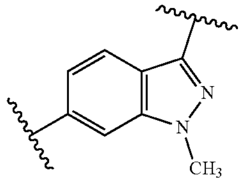

(Z-22A)

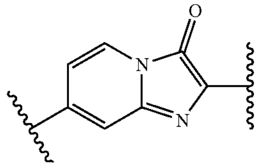

(11-9) The compound or a salt thereof in which EUB is the formula (XV) below,

[Chem. 58]

(XV)

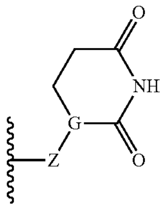

G is $CR^G$ or N, $R^G$ is H or $C_{1-6}$ alkyl,

Z is one group selected from the group consisting of the formulae (Z-1), (Z-2), (Z-3), (Z-4), (Z-5), (Z-6), (Z-7), (Z-8), (Z-9), (Z-10), (Z-11), (Z-12), (Z-13), (Z-14), (Z-15), (Z-16), (Z-17), (Z-18), (Z-19), (Z-20), (Z-21), (Z-22), (Z-23), (Z-24), (Z-25), (Z-26) and (Z-27) below,
wherein ring B1 and ring B2 in the formulae (Z-1), (Z-2), (Z-3), (Z-4), (Z-5), (Z-6), (Z-7), (Z-8), (Z-9), (Z-10), (Z-11), (Z-12), (Z-13), (Z-14), (Z-15), (Z-16), (Z-17), (Z-18), (Z-19), (Z-20), (Z-21), (Z-22), (Z-23), (Z-24), (Z-25), (Z-26) and (Z-27) form a bond with Linker,
provided that when G is N, Z is one group selected from the group consisting of the formulae (Z-1), (Z-16), (Z-17), (Z-18), (Z-19), (Z-20), (Z-21), (Z-22), (Z-23), (Z-24), (Z-25), (Z-26) and (Z-27),
[Chem. 59-1]
(Z-1)
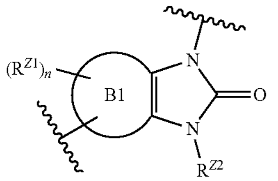
(Z-2)
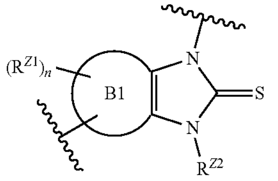
(Z-3)
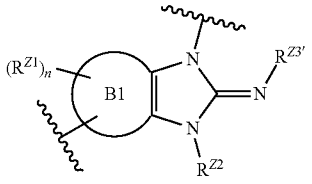
(Z-4)
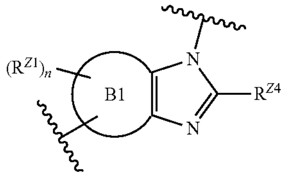
(Z-5)
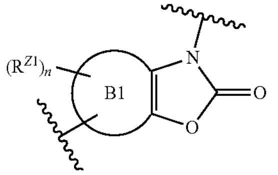
(Z-6)
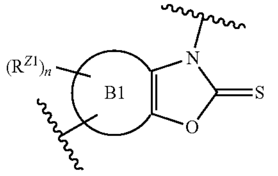
-continued
[Chem. 59-2]
(Z-7)
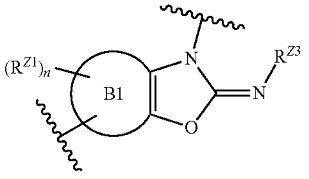
(Z-8)
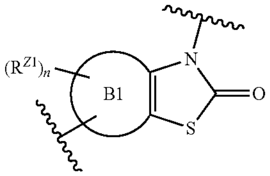
(Z-9)
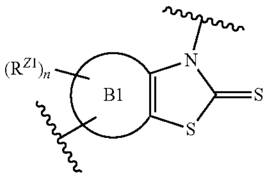
(Z-10)
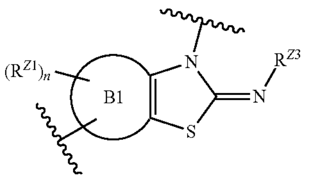
(Z-11)
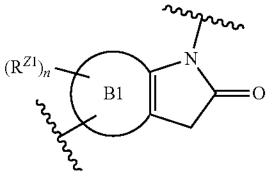
(Z-12)
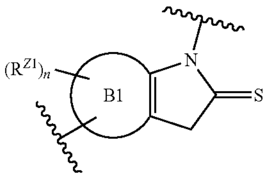
[Chem. 59-3]
(Z-13)
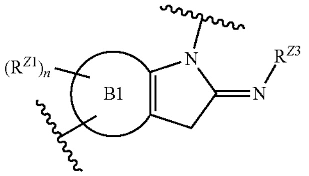
(Z-14)
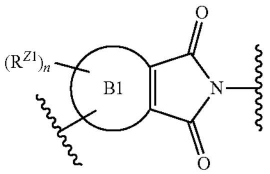

-continued (Z-15)

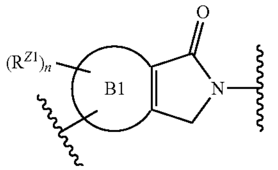

(Z-16)

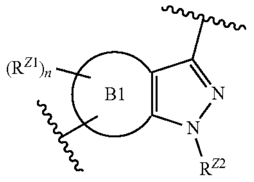

(Z-17)

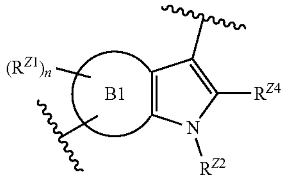

(Z-18)

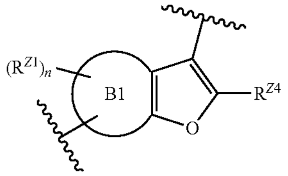

[Chem. 59-4]

(Z-19)

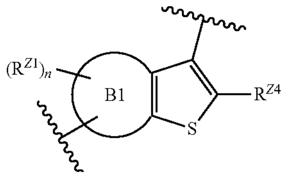

(Z-20)

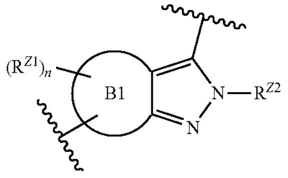

(Z-21)

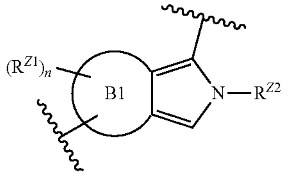

(Z-22)

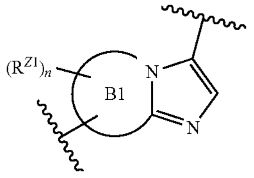

-continued (Z-23)

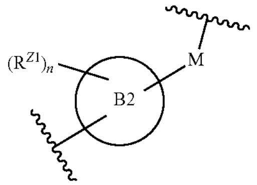

[Chem. 59-5]

(Z-24)

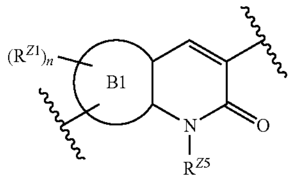

(Z-25)

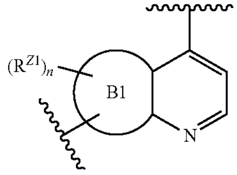

(Z-26)

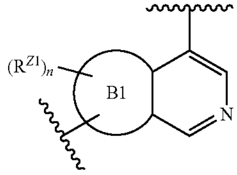

(Z-27)

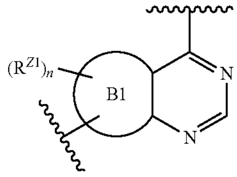

each $R^{Z1}$, which is the same as or different from each other, is optionally substituted $C_{1-6}$ alkyl, halogen, cyano, —OH, —O-(optionally substituted $C_{1-6}$ alkyl), —S-(optionally substituted $C_{1-6}$ alkyl), —NH-(optionally substituted $C_{1-6}$ alkyl) or —N-(optionally substituted $C_{1-6}$ alkyl)$_2$, n is an integer of 0 to 2, $R^{Z2}$, $R^{Z3}$, $R^{Z4}$ and $R^{Z5}$, which are the same as or different from each other, are H or optionally substituted $C_{1-6}$ alkyl, M is a bond, —O—, —S—, —N($R^M$)— or optionally substituted $C_{1-3}$ alkylene, $R^M$ is H or optionally substituted $C_{1-3}$ alkyl, ring B1 is a benzene ring or a 6-membered hetero ring, wherein $R^{Z1}$ and Linker form a bond with a carbon atom forming the ring B1, and ring B2 is a benzene ring or a 5- or 6-membered hetero ring, wherein M, $R^{Z1}$ and Linker form a bond with a carbon atom forming the ring B2.

(11-10) The compound or a salt thereof in which EUB is the formula (XV) below,
[Chem. 60]
(XV)
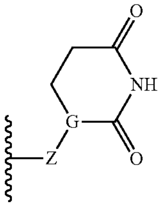
G is CH or N, and
Z is one group selected from the group consisting of the formulae (Z-1A), (Z-1B), (Z-5A), (Z-5B), (Z-14A), (Z-14B), (Z-14C), (Z-15A), (Z-16A), (Z-16B), (Z-16C), (Z-16D), (Z-20A), (Z-22A), (Z-23A), (Z-23B), (Z-23C), (Z-23D), (Z-23E), (Z-23F) and (Z-24A) below,
[Chem. 61-1]
(Z-1A)
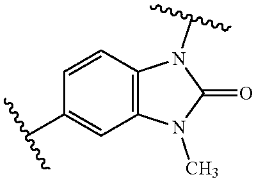
(Z-1B)
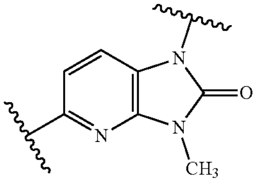
(Z-5A)
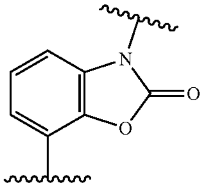
(Z-5B)
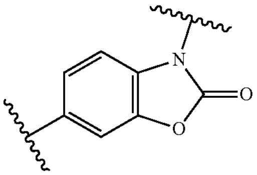
(Z-14A)
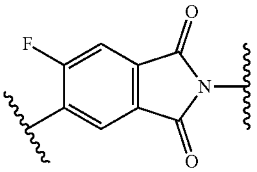
-continued
(Z-14B)
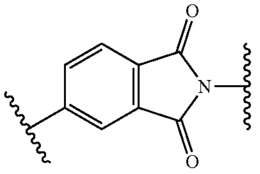
[Chem. 61-2]
(Z-14C)
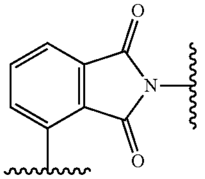
(Z-15A)
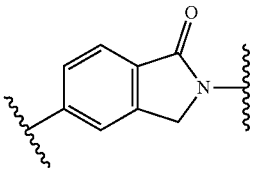
(Z-16A)
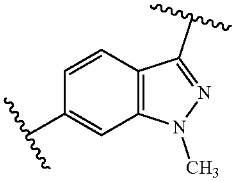
(Z-16B)
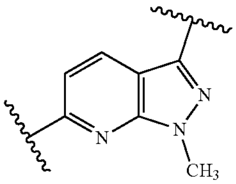
(Z-16C)
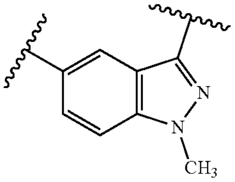
(Z-16D)
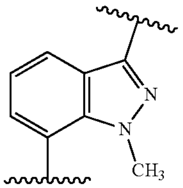
[Chem. 61-3]
(Z-20A)
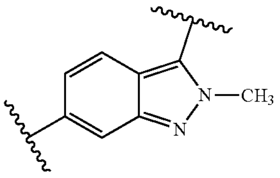

-continued (Z-22A)

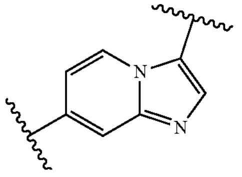

(Z-23A)

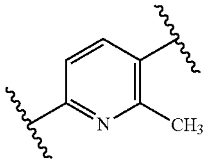

(Z-23B)

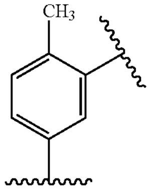

(Z-23C)

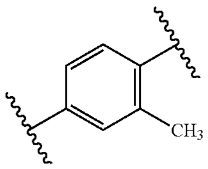

(Z-23D)

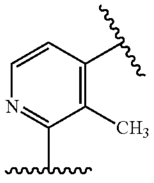

(Z-23E)

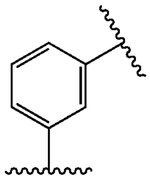

(Z-23F)

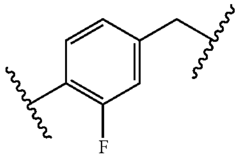

[Chem. 61-4]

(Z-24A)

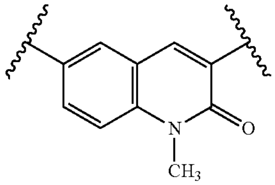

wherein a benzene ring or a 6-membered hetero ring in the formulae (Z-1A), (Z-1B), (Z-5A), (Z-5B), (Z-14A), (Z-14B), (Z-14C), (Z-15A), (Z-16A), (Z-16B), (Z-16C), (Z-16D), (Z-20A), (Z-22A), (Z-23A), (Z-23B), (Z-23C), (Z-23D), (Z-23E) and (Z-23F) form a bond with Linker, and a benzene ring in the formula (Z-24A) forms a bond with Linker, provided that when G is N, Z is one group selected from the group consisting of (Z-1A), (Z-16A), (Z-16B), (Z-16C), (Z-16D), (Z-20A), (Z-22A), (Z-23A), (Z-23B), (Z-23C), (Z-23D), (Z-23E), (Z-23F) and (Z-24A).

(12) The compound or a salt thereof which is a combination of two or more of the embodiments compatible with each other described in (1-1) to (11-10) above. Examples thereof include, but are not limited to, the following combinations.

(12-1) A compound of the formula (I) or a salt thereof,

[Chem. 62]

(I)

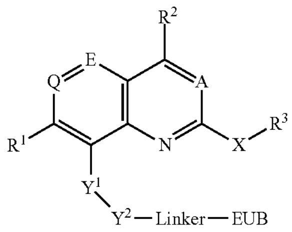

(wherein in the formula,

A is $CR^A$ or N, $R^A$ is H, optionally substituted $C_{1-3}$ alkyl or cyano,

Q is $CR^Q$ or N, $R^Q$ is H, halogen, optionally substituted $C_{1-3}$ alkyl, $C_{3-6}$ cycloalkyl or vinyl, E is CH or N, $R^1$ is naphthyl optionally substituted with one or two groups selected from the group consisting of optionally substituted $C_{1-3}$ alkyl, cyano, OH and halogen, or $R^1$ is a group selected from the group consisting of the formula (II), the formula (III) and the formula (IV) below,

[Chem. 63]

(II)

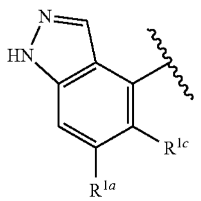

(III)

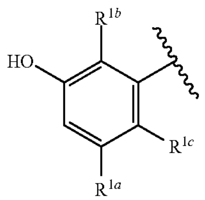

-continued (IV)

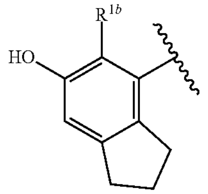

$R^{1a}$, $R^{1b}$ and $R^{1c}$, which are the same as or different from each other, are H, optionally substituted $C_{1-3}$ alkyl, vinyl or halogen, $R^2$ is —$V^1$—$V^2$ or W, $V^1$ is a bond, —$CH_2$—, —O—, —S— or —$N(R^{V1})$—, $R^{V1}$ is H or optionally substituted $C_{1-3}$ alkyl, $V^2$ is the formula (V) or the formula (VI) below,

[Chem. 64]

(V)

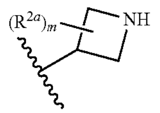

(VI)

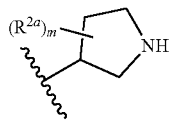

W is the formula (VII) or the formula (VII-2) below or 7-membered to 9-membered bridged heterocycloalkyl containing one to two nitrogen atoms,

[Chem. 65]

(VII)

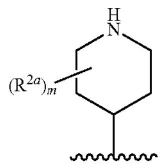

(VII-2)

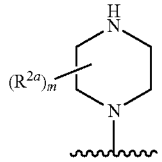

each $R^{2a}$, which is the same as or different from each other, are OH, $OCH_3$, F or optionally substituted $C_{1-3}$ alkyl, where $R^{2a}$ is attached only to a carbon atom that is an atom forming a ring selected from the group consisting of an azetidine ring represented by the formula (V), a pyrrolidine ring represented by the formula (VI), a piperidine ring represented by the formula (VII) and a piperazine ring represented by the formula (VII-2), m is an integer of 0 to 2, $R^3$ is optionally substituted $C_{1-6}$ alkyl, optionally substituted heterocycloalkyl or optionally substituted heteroaryl, X is a bond, —$CH_2$—, —O—, —S— or —$NR^{4X}$—, $R^{4X}$ is H or optionally substituted $C_{1-3}$ alkyl, $Y^1$ is —O-(optionally substituted $C_{1-3}$ alkylene)-$^{*Y2}$, —S-(optionally substituted $C_{1-3}$ alkylene)-$^{*Y2}$, —$SO_2$-(optionally substituted $C_{1-3}$ alkylene)-$^{*Y2}$, —$NR^Y$-(optionally substituted $C_{1-3}$ alkylene)-$^{*Y2}$, -(optionally substituted $C_{1-3}$ alkylene)-O-$^{*Y2}$, -(optionally substituted $C_{1-3}$ alkylene)-S-$^{*Y2}$, -(optionally substituted $C_{1-3}$ alkylene)-$SO_2$-$^{*Y2}$ or -(optionally substituted $C_{1-3}$ alkylene)-$NR^Y$-$^{*Y2}$ ($^{*Y2}$ represents a linking moiety to $Y^2$), $R^Y$ is H or optionally substituted $C_{1-3}$ alkyl, $Y^2$ is a bond, optionally substituted phenylene or optionally substituted heteroarylene, Linker is one group chemically linking $Y^2$ to EUB, and EUB is a group capable of binding to one E3 ubiquitin ligase selected from the group consisting of cereblon, IAP, MDM2, DCAF11, DCAF15, DCAF16, BIRC2, KEAP1, RNF4, RNF114, FEM1B and AhR).

(12-2) The compound or a salt thereof according to (12-1), wherein EUB is a group capable of binding to cereblon.

(12-3) The compound or a salt thereof according to (12-2), wherein EUB is the formula (XV) below,

[Chem. 66]

(XV)

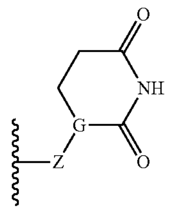

G is $CR^G$ or N, $R^G$ is H or $C_{1-6}$ alkyl,

Z is one group selected from the group consisting of the formulae (Z-1), (Z-2), (Z-3), (Z-4), (Z-5), (Z-6), (Z-7), (Z-8), (Z-9), (Z-10), (Z-11), (Z-12), (Z-13), (Z-14), (Z-15), (Z-16), (Z-17), (Z-18), (Z-19), (Z-20), (Z-21), (Z-22) and (Z-23) below, wherein ring B1 and ring B2 in the formulae (Z-1), (Z-2), (Z-3), (Z-4), (Z-5), (Z-6), (Z-7), (Z-8), (Z-9), (Z-10), (Z-11), (Z-12), (Z-13), (Z-14), (Z-15), (Z-16), (Z-17), (Z-18), (Z-19), (Z-20), (Z-21), (Z-22) and (Z-23) form a bond with Linker, provided that when G is N, Z is one group selected from the group consisting of the formulae (Z-16), (Z-17), (Z-18), (Z-19), (Z-20), (Z-21), (Z-22) and (Z-23),

[Chem. 67-1]

(Z-1)

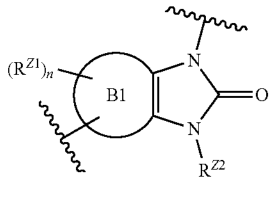

-continued
(Z-2)
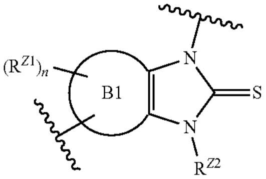
(Z-3)
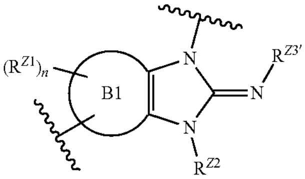
(Z-4)
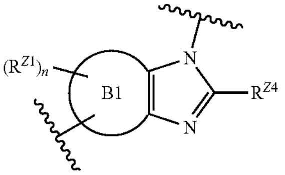
(Z-5)
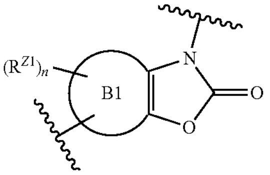
(Z-6)
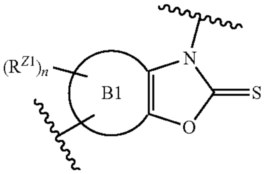
[Chem. 67-2]
(Z-7)
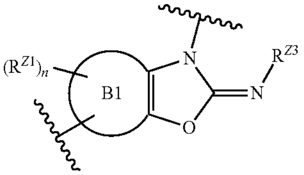
(Z-8)
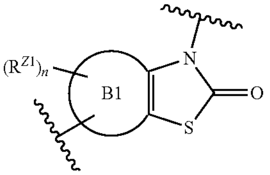
(Z-9)
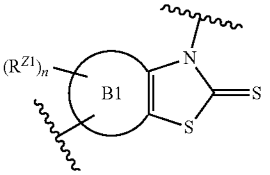
-continued
(Z-10)
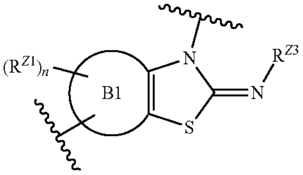
(Z-11)
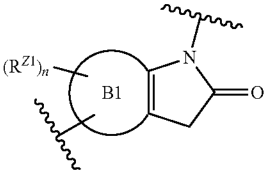
(Z-12)
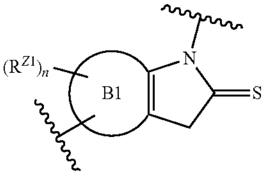
[Chem. 67-3]
(Z-13)
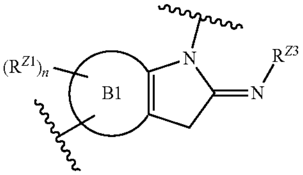
(Z-14)
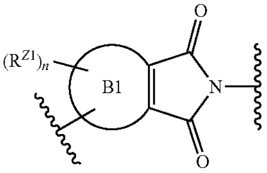
(Z-15)
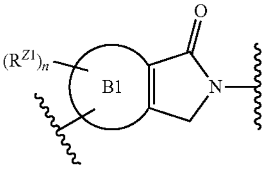
(Z-16)
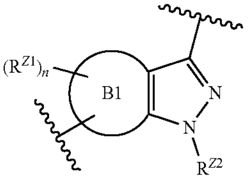
(Z-17)
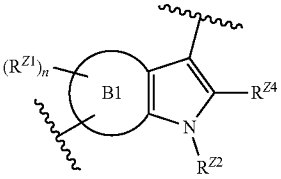

-continued (Z-18)

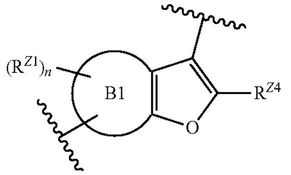

[Chem. 67-4]

(Z-19)

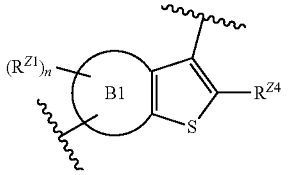

(Z-20)

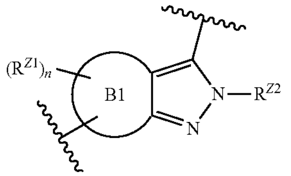

(Z-21)

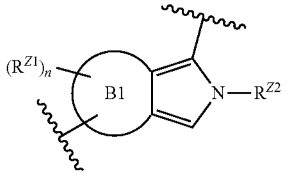

(Z-22)

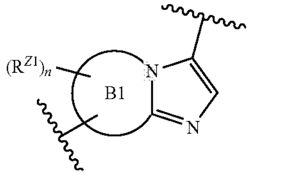

(Z-23)

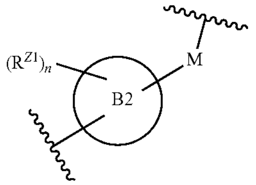

each $R^{Z1}$, which is the same as or different from each other, is optionally substituted $C_{1-6}$ alkyl, halogen, cyano, —OH, —O-(optionally substituted $C_{1-6}$ alkyl), —S-(optionally substituted $C_{1-6}$ alkyl), —NH-(optionally substituted $C_{1-6}$ alkyl) or —N-(optionally substituted $C_{1-6}$ alkyl)$_2$, n is an integer of 0 to 2, $R^{Z2}$, $R^{Z3}$ and $R^{Z4}$, which are the same as or different from each other, are H or optionally substituted $C_{1-6}$ alkyl, M is a bond, —O—, —S—, —N($R^M$)— or optionally substituted $C_{1-3}$ alkylene, $R^M$ is H or optionally substituted $C_{1-3}$ alkyl, ring B1 is a benzene ring or a 6-membered hetero ring, wherein $R^{Z1}$ and Linker form a bond with a carbon atom forming the ring B1, and ring B2 is a benzene ring or a 5- or 6-membered hetero ring, wherein M, $R^{Z1}$ and Linker form a bond with a carbon atom forming the ring B2.

(12-4) The compound or a salt thereof according to (12-3), wherein EUB is the formula (XV) below,

[Chem. 68]

(XV)

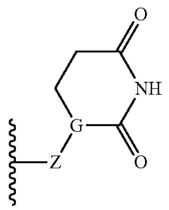

G is CH or N,

Z is one group selected from the group consisting of the formulae (Z-1), (Z-4), (Z-5), (Z-11), (Z-14), (Z-15), (Z-16), (Z-18), (Z-19), (Z-20), (Z-22) and (Z-23), wherein ring B1 and ring B2 in the formulae (Z-1), (Z-4), (Z-5), (Z-11), (Z-14), (Z-15), (Z-16), (Z-18), (Z-19), (Z-20), (Z-22) and (Z-23) form a bond with Linker, provided that when G is N, Z is one group selected from the group consisting of the formulae (Z-16), (Z-18), (Z-19), (Z-20), (Z-22) and (Z-23),

[Chem. 69-1]

(Z-1)

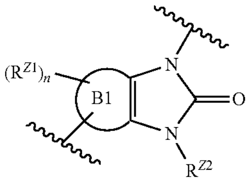

(Z-4)

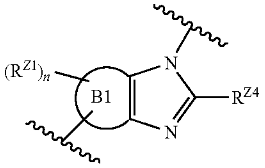

(Z-5)

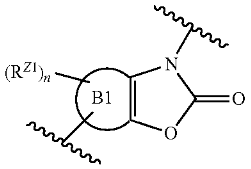

(Z-11)

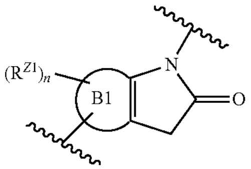

-continued (Z-14)

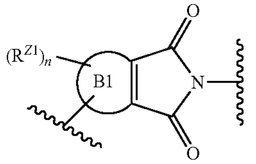

(Z-15)

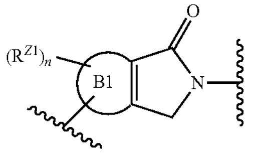

[Chem. 69-2]

(Z-16)

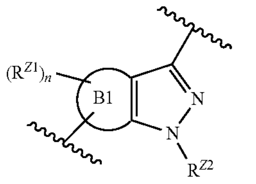

(Z-18)

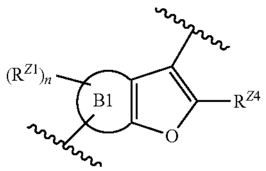

(Z-19)

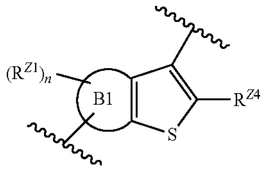

(Z-20)

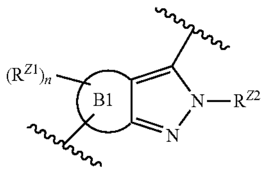

(Z-22)

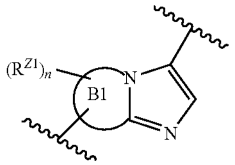

(Z-23)

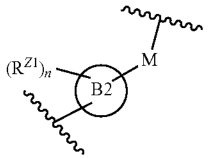

$R^{Z1}$ is $C_{1-6}$ alkyl or halogen, n is an integer of 0 or 1, $R^{Z2}$ and $R^{Z4}$, which are the same as or different from each other, are H or $C_{1-6}$ alkyl, M is a bond or $C_{1-3}$ alkylene, ring B1 is a benzene ring or a pyridine ring, wherein $R^{Z1}$ and Linker form a bond with a carbon atom forming the ring B1, and ring B2 is a benzene ring or a pyridine ring, wherein M, $R^{Z1}$ and Linker form a bond with a carbon atom forming the ring B2.

(12-5) The compound or a salt thereof according to (12-4), wherein A is CH or N, Q is $CR^Q$, $R^Q$ is $C_{3-6}$ cycloalkyl, E is CH, $R^1$ is the formula (II) below,

[Chem. 70]

(II)

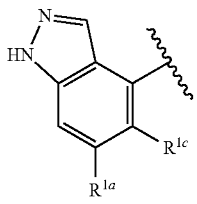

$R^{1a}$ and $R^{1c}$, which are the same as or different from each other, are $C_{1-3}$ alkyl or halogen, $R^2$ is —$V^1$—$V^2$ or W, $V^1$ is a bond, —$CH_2$—, —O—, —S— or —$N(R^{V1})$—, $R^{V1}$ is $C_{1-3}$ alkyl optionally substituted with one group selected from the group consisting of $C_{3-6}$ cycloalkyl, halogen and —OH, $V^2$ is the formula (V-2) or (VI-2) below,

[Chem. 71]

(V-2)

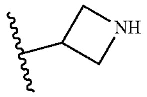

(VI-2)

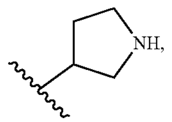

W is one group selected from the group consisting of the formulae (VII-3), (VII-4), (VIII), (IX), (X), (XI), (XII), (XIII) and (XIV) below,

[Chem. 72]

(VII-3)

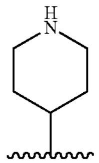

-continued (VII-4)

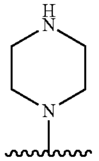

(VIII)

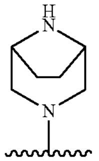

(IX)

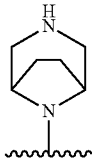

(X)

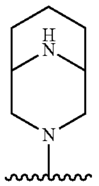

(XI)

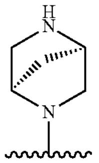

(XII)

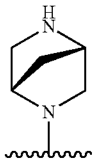

(XIII)

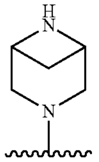

(XIV)

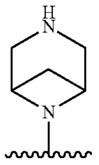

$R^3$ is $C_{1-6}$ alkyl optionally substituted with one group selected from the group consisting of —O—($C_{1-6}$ alkyl), —S—($C_{1-6}$ alkyl), —N—($C_{1-6}$ alkyl)$_2$ and heterocycloalkyl or optionally substituted heterocycloalkyl, X is —O— or —$NR^{4X}$—, $R^{4X}$ is $C_{1-3}$ alkyl, $Y^1$ is —O—($C_{1-3}$ alkylene)-$^{*Y2}$ or ($C_{1-3}$ alkylene)-O-$^{*Y2}$ ($^{*Y2}$ represents a linking moiety to $Y^2$), $Y^2$ is phenylene or pyridinediyl, Linker is -($L^1$-$L^2$-$L^3$-$L^4$)-, $L^1$, $L^2$, $L^3$ and $L^4$, which are the same as or different from each other, are one group selected from the group consisting of a bond, C═O, —O—, —S—, —$SO_2$—, —$NR^L$—, acetylene-1,2-diyl, optionally substituted heterocycloalkylene, optionally substituted heteroarylene, saturated 7-membered to 9-membered spiroheterocycloalkylene containing one or two nitrogen atoms, saturated 7-membered to 9-membered bridged heterocycloalkylene containing two nitrogen atoms and optionally substituted $C_{1-6}$ alkylene, and $R^L$ is H or $C_{1-6}$ alkyl.

(12-6) The compound or a salt thereof according to (12-5), wherein $R^1$ is the formula (II) below,

[Chem. 73]

(II)

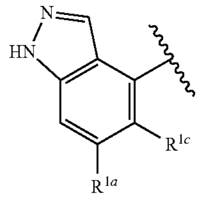

$R^{1a}$ is halogen, and $R^{1c}$ is $C_{1-3}$ alkyl, $R^2$ is —$V^1$—$V^2$ or W, $V^1$ is a bond, —O— or —N($R^{V1}$)—, $R^{V1}$ is $C_{1-3}$ alkyl, $V^2$ is the formula (VI-2) below,

[Chem. 74]

(VI-2)

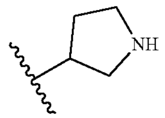

W is the formula (XII) below,

[Chem. 75]

(XII)

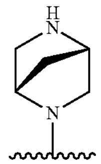

$R^3$ is $C_{1-6}$ alkyl optionally substituted with one group selected from the group consisting of —O($C_{1-6}$ alkyl), oxetanyl, tetrahydrofuranyl and tetrahydropyranyl, oxetanyl, tetrahydrofuranyl or tetrahydropyranyl, X is —O—, $Y^1$ is —O—($C_{1-3}$ alkylene)-$^{*Y2}$ ($^{*Y2}$ represents a linking moiety to $Y^2$), $Y^2$ is phenylene, Linker is -($L^1$-$L^2$-$L^3$-$L^4$)-, $L^1$ is C═O, $L^2$ is piperidinediyl optionally substituted with $C_{1-3}$ alkyl, piperazinediyl optionally substituted with $C_{1-3}$ alkyl, pyrrolidinediyl optionally substituted with $C_{1-3}$ alkyl, 3,8-diazabicyclo[3.2.1]octanediyl or 2,6-diazaspiro[3.4]octanediyl, $L^3$ is a bond, —N($R^{L3}$)—, $C_{1-3}$ alkylene or piperazinediyl, $L^4$ is a bond, —N($R^{L4}$)—, —O— or $C_{1-3}$ alkylene, $R^{L3}$ is H or $C_{1-3}$ alkyl, $R^{L4}$ is H or $C_{1-3}$ alkyl, EUB is the formula (XV) below,

[Chem. 76]

(XV)

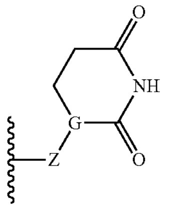

G is CH or N,

Z is one group selected from the group consisting of the formulae (Z-1), (Z-5), (Z-11), (Z-14), (Z-15), (Z-16), (Z-20), (Z-22) and (Z-23), wherein ring B1 and ring B2 in the formulae (Z-1), (Z-5), (Z-11), (Z-14), (Z-15), (Z-16), (Z-20), (Z-22) and (Z-23) form a bond with Linker, provided that when G is N, Z is one group selected from the group consisting of the formulae (Z-16), (Z-20), (Z-22) and (Z-23),

[Chem. 77-1]

(Z-1)

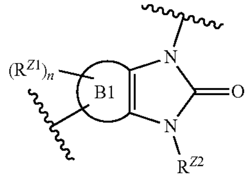

(Z-5)

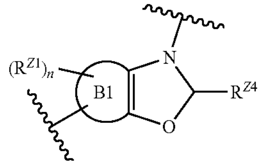

(Z-11)

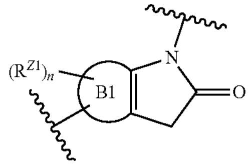

(Z-14)

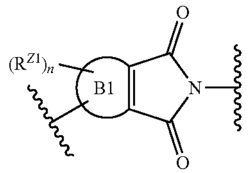

-continued (Z-15)

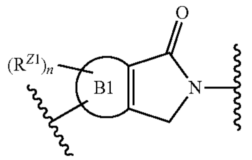

(Z-16)

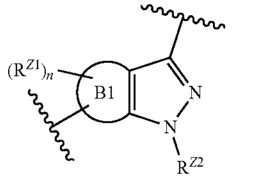

[Chem. 77-2]

(Z-20)

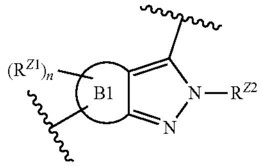

(Z-22)

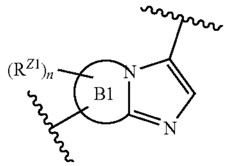

(Z-23)

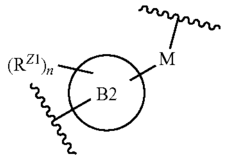

$R^{Z1}$ is $C_{1-3}$ alkyl or halogen, n is an integer of 0 or 1, $R^{Z2}$ is $C_{1-3}$ alkyl, M is a bond or $C_{1-3}$ alkylene, ring B1 is a benzene ring or a pyridine ring, wherein $R^{Z1}$ and Linker form a bond with a carbon atom forming the ring B1, and ring B2 is a benzene ring or a pyridine ring, wherein M, $R^{Z1}$ and Linker form a bond with a carbon atom forming the ring B2.

(12-6-2) The compound or a salt thereof according to (12-5), wherein $R^1$ is the formula (II) below,

[Chem. 78]

(II)

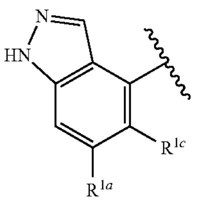

$R^{1a}$ is halogen, and $R^{1c}$ is $C_{1-3}$ alkyl, $R^2$ is —$V^1$—$V^2$ or W, $V^1$ is a bond, —O— or —N($R^{V1}$)—, $R^{V1}$ is $C_{1-3}$ alkyl, $V^2$ is the formula (VI-2) below,

[Chem. 79]

(VI-2)

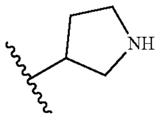

W is the formula (XII) below,

[Chem. 80]

(XII)

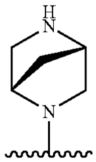

$R^3$ is $C_{1-6}$ alkyl optionally substituted with one group selected from the group consisting of —O($C_{1-6}$ alkyl), oxetanyl, tetrahydrofuranyl and tetrahydropyranyl, oxetanyl, tetrahydrofuranyl or tetrahydropyranyl, X is —O—, $Y^1$ is —O—($C_{1-3}$ alkylene)-$^{*Y2}$ ($^{*Y2}$ represents a linking moiety to $Y^2$), $Y^2$ is phenylene, Linker is -($L^1$-$L^2$-$L^3$-$L^4$)-, $L^1$ is C═O, $L^2$ is piperidinediyl optionally substituted with $C_{1-3}$ alkyl, piperazinediyl optionally substituted with $C_{1-3}$ alkyl, pyrrolidinediyl optionally substituted with $C_{1-3}$ alkyl, 3,8-diazabicyclo[3.2.1]octanediyl or 2,6-diazaspiro[3.4]octanediyl, $L^3$ is a bond, —N($R^{L3}$)—, $C_{1-3}$ alkylene or piperazinediyl, $L^4$ is a bond, —N($R^{L4}$)—, —O—, piperazinediyl or $C_{1-3}$ alkylene, $R^{L3}$ is H or $C_{1-3}$ alkyl, $R^{L4}$ is H or $C_{1-3}$ alkyl, EUB is the formula (XV) below,

[Chem. 81]

(XV)

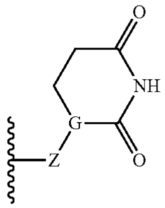

G is CH or N,

Z is one group selected from the group consisting of the formulae (Z-1), (Z-5), (Z-11), (Z-14), (Z-15), (Z-16), (Z-20), (Z-22) and (Z-23), wherein ring B1 and ring B2 in the formulae (Z-1), (Z-5), (Z-11), (Z-14), (Z-15), (Z-16), (Z-20), (Z-22) and (Z-23) form a bond with Linker, provided that when G is N, Z is one group selected from the group consisting of the formulae (Z-16), (Z-20), (Z-22) and (Z-23),

[Chem. 82-1]

(Z-1)

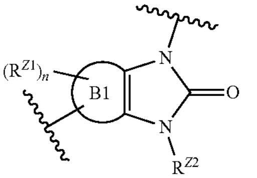

(Z-5)

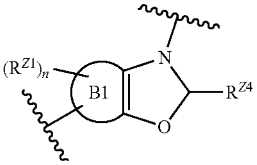

(Z-11)

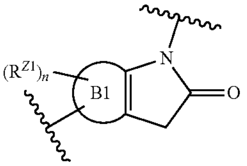

(Z-14)

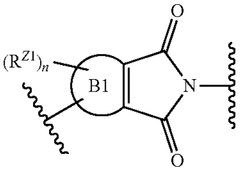

(Z-15)

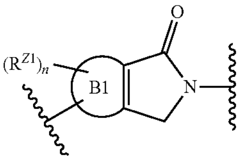

(Z-16)

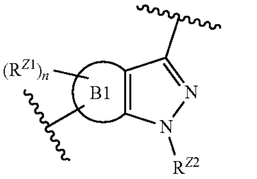

[Chem. 82-2]

(Z-20)

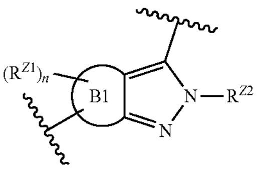

(Z-22)

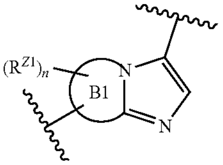

-continued (Z-23)

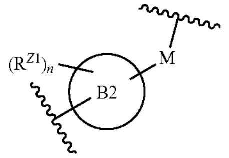

$R^{Z1}$ is $C_{1-3}$ alkyl or halogen, n is an integer of 0 or 1, $R^{Z2}$ is $C_{1-3}$ alkyl, M is a bond or $C_{1-3}$ alkylene, ring B1 is a benzene ring or a pyridine ring, wherein $R^{Z1}$ and Linker form a bond with a carbon atom forming the ring B1, and ring B2 is a benzene ring or a pyridine ring, wherein M, $R^{Z1}$ and Linker form a bond with a carbon atom forming the ring B2.

(12-7) The compound or a salt thereof according to (12-6), wherein Q is $CR^Q$, $R^Q$ is cyclopropyl, $R^1$ is the formula (II-2) below,

[Chem. 83]

(II-2)

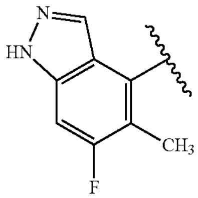

$R^2$ is —$V^1$—$V^2$ or W, $V^1$ is —O— or —$N(CH_3)$—, $V^2$ is the formula (VI-2) below,

[Chem. 84]

(VI-2)

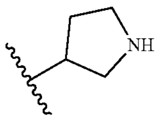

W is the formula (XII) below,

[Chem. 85]

(XII)

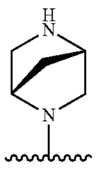

$R^3$ is $C_{1-3}$ alkyl optionally substituted with —$OCH_3$ or tetrahydrofuranyl, tetrahydrofuranyl or tetrahydropyranyl, $Y^1$ is —O-(methylene)-$^{*Y2}$ ($^{*Y2}$ represents a linking moiety to $Y^2$), Linker is one group selected from the group consisting of the formulae (L-1), (L-2), (L-3), (L-4), (L-5) and (L-7) below, wherein C═O in the formulae (L-1), (L-2), (L-3), (L-4), (L-5) and (L-7) forms a bond with $Y^2$,

[Chem. 86]

(L-1)

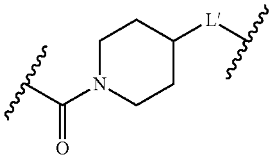

(L-2)

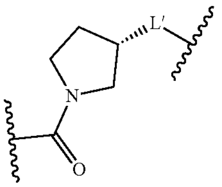

(L-3)

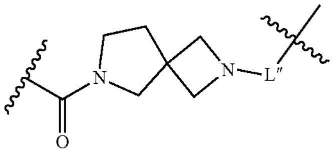

(L-4)

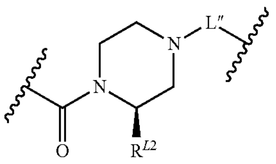

(L-5)

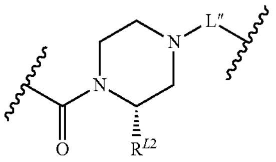

(L-6)

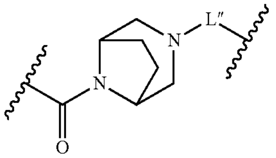

L' is —O—, —($C_{1-3}$ alkylene)-NH—, —$N(CH_3)$($C_{1-3}$ alkylene)-, piperazinediyl or —($C_{1-3}$ alkylene)-piperazinediyl, L" is a bond, $C_{1-3}$ alkylene or —($C_{1-3}$ alkylene)-O—, $R^{L2}$ is H or $C_{1-3}$ alkyl, EUB is the formula (XV) below,

[Chem. 87]

(XV)

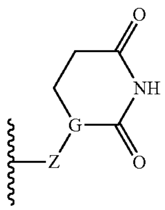

G is CH or N, and

Z is one group selected from the group consisting of the formulae (Z-1A), (Z-1B), (Z-5A), (Z-5B), (Z-14A), (Z-14B), (Z-14C), (Z-15A), (Z-16A), (Z-16B), (Z-16C), (Z-16D), (Z-20A), (Z-22A), (Z-23A), (Z-23B), (Z-23C), (Z-23D), (Z-23E) and (Z-23F) below, wherein a benzene ring or a 6-membered hetero ring in the formulae (Z-1A), (Z-1B), (Z-5A), (Z-5B), (Z-14A), (Z-14B), (Z-14C), (Z-15A), (Z-16A), (Z-16B), (Z-16C), (Z-16D), (Z-20A), (Z-22A), (Z-23A), (Z-23B), (Z-23C), (Z-23D), (Z-23E) and (Z-23F) form a bond with Linker, provided that when G is N, Z is one group selected from the group consisting of (Z-16A), (Z-16B), (Z-16C), (Z-16D), (Z-20A), (Z-22A), (Z-23A), (Z-23B), (Z-23C), (Z-23D), (Z-23E) and (Z-23F).

[Chem. 88-1]

(Z-1A)

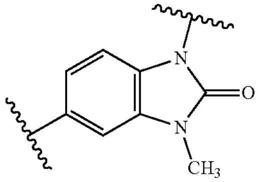

(Z-1B)

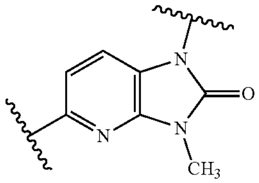

(Z-5A)

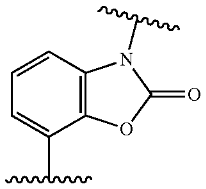

(Z-5B)

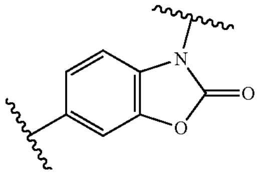

-continued (Z-14A)

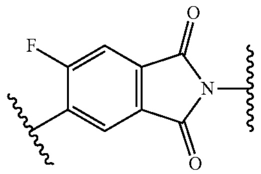

(Z-14B)

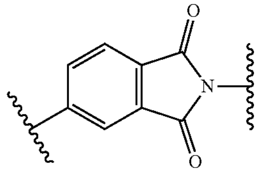

[Chem. 88-2]

(Z-14C)

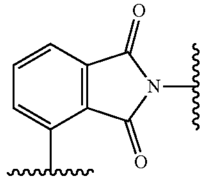

(Z-15A)

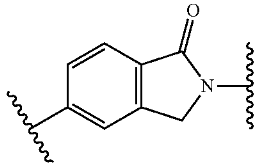

(Z-16A)

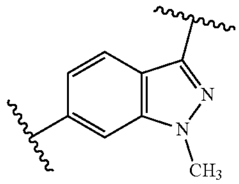

(Z-16B)

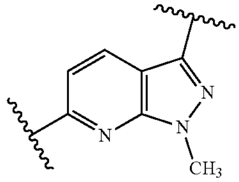

(Z-16C)

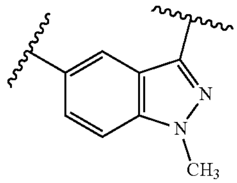

(Z-16D)

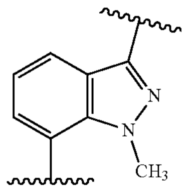

-continued

[Chem. 88-3]

(Z-20A)

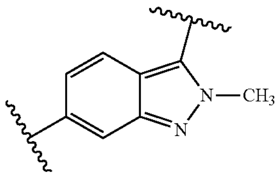

(Z-22A)

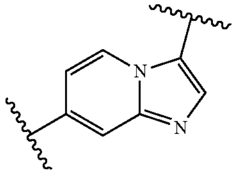

(Z-23A)

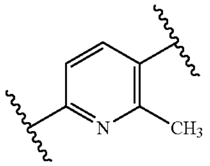

(Z-23B)

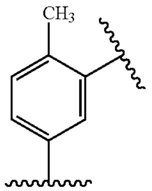

(Z-23C)

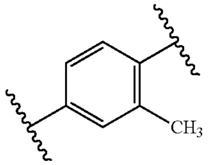

(Z-23D)

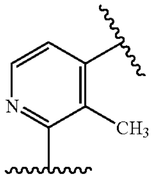

(Z-23E)

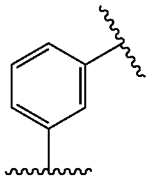

(Z-23F)

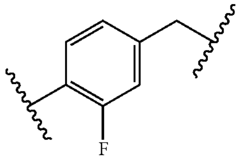

(12-8) The compound of the formula (I) or a salt thereof which is the combination of the embodiments of (1-2), (2-3), (3-2), (4-4), (5-5), (6-5), (7-3), (8-4), (9-4), (10-7) and (11-8) above.

(12-9) The compound of the formula (I) or a salt thereof which is the combination of the embodiments of (1-2), (2-2), (3-2), (4-3), (5-2), (6-3), (7-2), (8-2), (9-3), (10-5), (11-4) above.

(12-10) The compound of the formula (I) or a salt thereof which is the combination of the embodiments of (1-2), (2-2), (3-2), (4-2), (5-6), (6-2), (7-2), (8-2), (9-2), (10-2), (11-4) above.

(12-11) The compound of the formula (I) or a salt thereof which is the combination of the embodiments of (1-2), (2-2), (3-2), (4-1), (5-6), (6-2), (7-2), (8-2), (9-2), (10-2), (11-4) above.

(12-12) The compound of the formula (I) or a salt thereof which is the combination of the embodiments of (1-2), (2-2), (3-2), (4-1), (5-6), (6-2), (7-2), (8-2), (9-2), (10-2), (11-6) above.

(12-13) The compound of the formula (I) or a salt thereof which is the combination of the embodiments of (1-2), (2-2), (3-2), (4-3), (5-3), (6-3), (7-3), (8-4), (9-4), (10-5), (11-5) above.

(12-14) The compound of the formula (I) or a salt thereof which is the combination of the embodiments of (1-2), (2-2), (3-2), (4-3), (5-3), (6-3), (7-3), (8-3), (9-4), (10-5), (11-5) above.

(12-15) The compound of the formula (I) or a salt thereof which is the combination of the embodiments of (1-2), (2-3), (3-2), (4-4), (5-4), (6-4), (7-3), (8-4), (9-4), (10-6), (11-6) above.

(12-16) The compound of the formula (I) or a salt thereof which is the combination of the embodiments of (1-2), (2-2), (3-2), (4-3), (5-3), (6-3), (7-3), (8-3), (9-4), (10-3), (11-5) above.

(12-17) The compound of the formula (I) or a salt thereof which is the combination of the embodiments of (1-2), (2-3), (3-2), (4-4), (5-4), (6-4), (7-3), (8-4), (9-4), (10-4), (11-6) above.

(12-18) The compound of the formula (I) or a salt thereof which is the combination of the embodiments of (1-3), (2-2), (3-2), (4-3), (5-3), (6-3), (7-3), (8-3), (9-4), (10-5), (11-5) above.

(12-19) The compound of the formula (I) or a salt thereof which is the combination of the embodiments of (1-4), (2-2), (3-2), (4-3), (5-3), (6-3), (7-3), (8-3), (9-4), (10-5), (11-5) above.

(12-20) The compound of the formula (I) or a salt thereof which is the combination of the embodiments of (1-3), (2-3), (3-2), (4-4), (5-4), (6-4), (7-3), (8-4), (9-4), (10-6), (11-6) above.

(12-21) The compound of the formula (I) or a salt thereof which is the combination of the embodiments of (1-4), (2-3), (3-2), (4-4), (5-4), (6-4), (7-3), (8-4), (9-4), (10-6), (11-6) above.

(12-22) The compound or a salt thereof according to (12-7), wherein $R^2$ is $—V^1—V^2$ or W, $V^1$ is —O—, $V^2$ is the formula (VI-2) below,

[Chem. 89]

(VI-2)

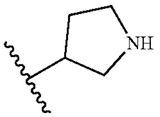

W is the formula (XII) below,

[Chem. 90]

(XII)

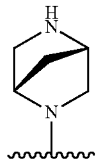

$R^3$ is n-propyl optionally substituted with —$OCH_3$ or tetrahydropyranyl,

Linker is the formula (L-5A) or (L-7A) below,

[Chem. 91]

(L-5A)

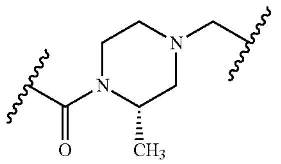

(L-7A)

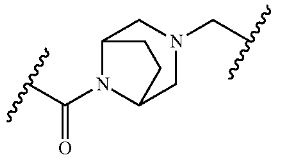

EUB is the formula (XV) below,

[Chem. 92]

(XV)

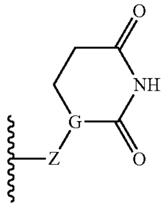

G is CH or N, and

Z is one group selected from the group consisting of the formulae (Z-1A), (Z-14B), (Z-15A), (Z-16A) and (Z-22A) below,

[Chem. 93]

(Z1-A)

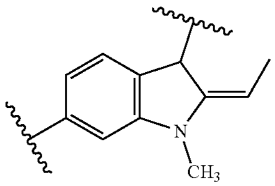

-continued (Z-14B)

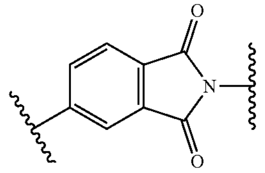

(Z-15B)

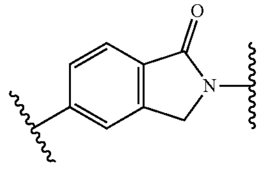

(Z-16A)

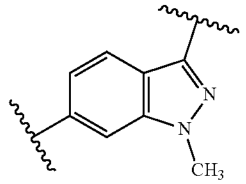

(Z-22A)

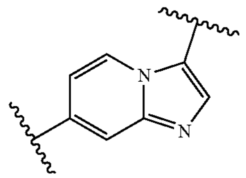

wherein a benzene ring or a 6-membered hetero ring in the formulae (Z-1A), (Z-14B), (Z-15A), (Z-16A) and (Z-22A) forms a bond with Linker, provided that when G is N, Z is (Z-16A) or (Z-22A).

(12-23) The compound or a salt thereof according to (12-2), wherein EUB is the formula (XV) below,

[Chem. 94]

(XV)

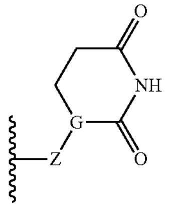

G is $CR^G$ or N, $R^G$ is H or $C_{1-6}$ alkyl,

Z is one group selected from the group consisting of the formulae (Z-1), (Z-2), (Z-3), (Z-4), (Z-5), (Z-6), (Z-7), (Z-8), (Z-9), (Z-10), (Z-11), (Z-12), (Z-13), (Z-14), (Z-15), (Z-16), (Z-17), (Z-18), (Z-19), (Z-20), (Z-21), (Z-22), (Z-23), (Z-24), (Z-25), (Z-26) and (Z-27) below, wherein ring B1 and ring B2 in the formulae (Z-1), (Z-2), (Z-3), (Z-4), (Z-5), (Z-6), (Z-7), (Z-8), (Z-9), (Z-10), (Z-11), (Z-12), (Z-13), (Z-14), (Z-15), (Z-16), (Z-17), (Z-18), (Z-19), (Z-20), (Z-21), (Z-22), (Z-23), (Z-24), (Z-25), (Z-26) and (Z-27) form a bond with Linker, provided that when G is N, Z is one group selected from the group consisting of the formulae (Z-1), (Z-16), (Z-17), (Z-18), (Z-19), (Z-20), (Z-21), (Z-22), (Z-23), (Z-24), (Z-25), (Z-26) and (Z-27),
[Chem. 95-1]
(Z-1)
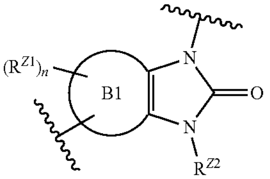
(Z-2)
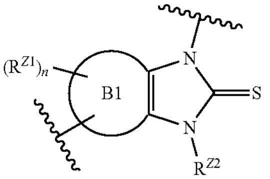
(Z-3)
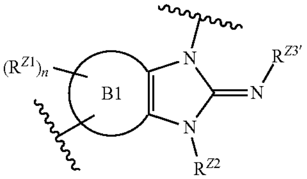
(Z-4)
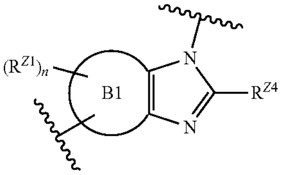
(Z-5)
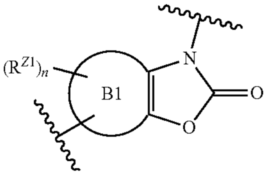
(Z-6)
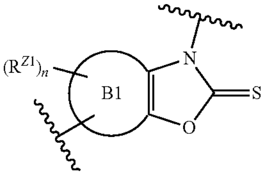
[Chem. 95-2]
(Z-7)
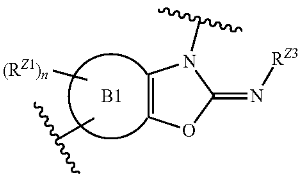
-continued
(Z-8)
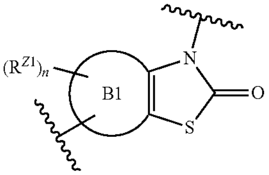
(Z-9)
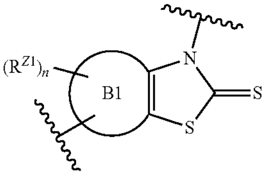
(Z-10)
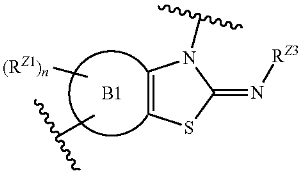
(Z-11)
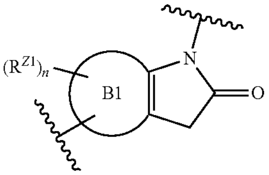
(Z-12)
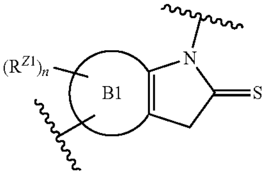
[Chem. 95-3]
(Z-13)
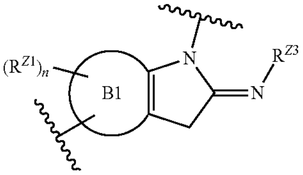
(Z-14)
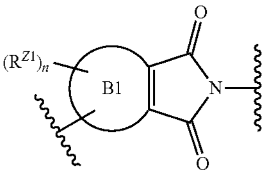
(Z-15)
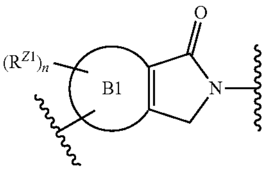

-continued (Z-16)

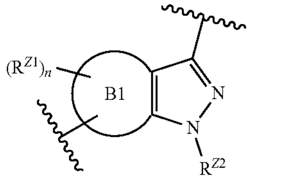

(Z-17)

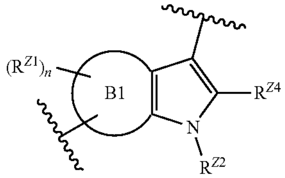

(Z-18)

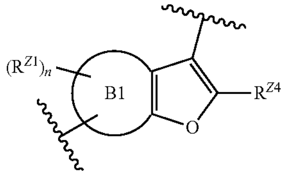

[Chem. 95-4]

(Z-19)

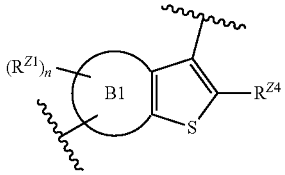

(Z-20)

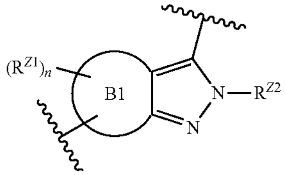

(Z-21)

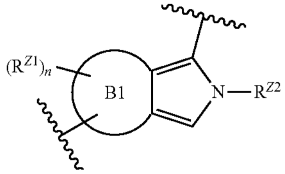

(Z-22)

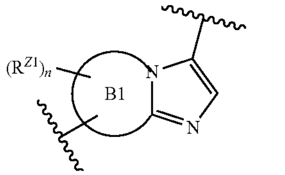

(Z-23)

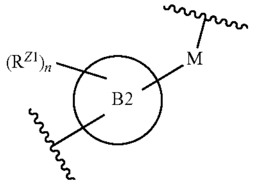

-continued

[Chem. 95-5]

(Z-24)

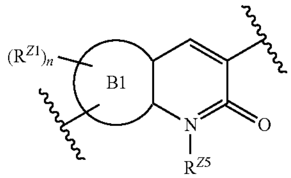

(Z-25)

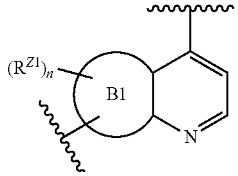

(Z-26)

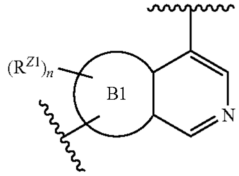

(Z-27)

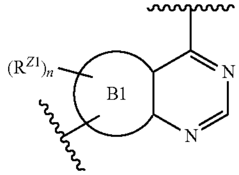

each $R^{Z1}$, which is the same as or different from each other, is optionally substituted $C_{1-6}$ alkyl, halogen, cyano, —OH, —O-(optionally substituted $C_{1-6}$ alkyl), —S-(optionally substituted $C_{1-6}$ alkyl), —NH-(optionally substituted $C_{1-6}$ alkyl) or —N-(optionally substituted $C_{1-6}$ alkyl)$_2$, n is an integer of 0 to 2, $R^{Z2}$, $R^{Z3}$, $R^{Z4}$ and $R^{Z5}$, which are the same as or different from each other, are H or optionally substituted $C_{1-6}$ alkyl, M is a bond, —O—, —S—, —N($R^M$)— or optionally substituted $C_{1-3}$ alkylene, $R^M$ is H or optionally substituted $C_{1-3}$ alkyl, ring B1 is a benzene ring or a 6-membered hetero ring, wherein $R^{Z1}$ and Linker form a bond with a carbon atom forming the ring B1, and ring B2 is a benzene ring or a 5- or 6-membered hetero ring, wherein M, $R^{Z1}$ and Linker form a bond with a carbon atom forming the ring B2.

(12-24) The compound or a salt thereof according to (12-23), wherein A is CH or N, Q is $CR^Q$, $R^Q$ is cyclopropyl, $R^1$ is the formula (II-2) below,

[Chem. 96]

(II-2)

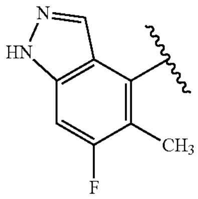

$R^2$ is —$V^1$—$V^2$ or W, $V^1$ is —O— or —$N(CH_3)$—, $V^2$ is the formula (VI-2) below,

[Chem. 97]

(VI-2)

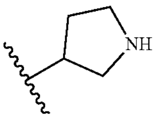

W is the formula (VII-4) or (XII) below,

[Chem. 98]

(VII-4)

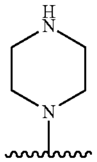

(XII)

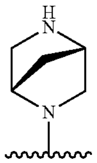

$R^3$ is $C_{1-3}$ alkyl optionally substituted with —$OCH_3$ or tetrahydrofuranyl, tetrahydrofuranyl or tetrahydropyranyl, X is —O—, $Y^1$ is —O-(methylene)-$^{*Y2}$ ($^{*Y2}$ represents a linking moiety to $Y^2$), $Y^2$ is phenylene, Linker is one group selected from the group consisting of the formulae (L-1), (L-2), (L-3), (L-4), (L-5) and (L-7) below, wherein C═O in the formulae (L-1), (L-2), (L-3), (L-4), (L-5) and (L-7) forms a bond with $Y^2$,

[Chem. 99]

(L-1)

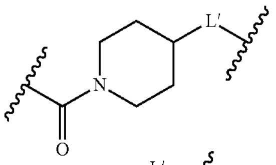

(L-2)

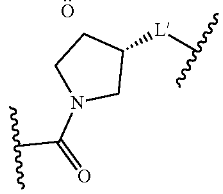

(L-3)

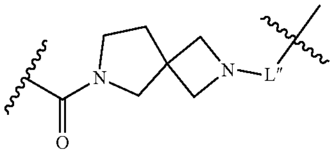

(L-4)

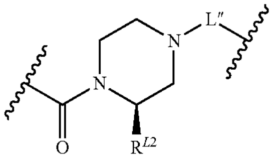

(L-5)

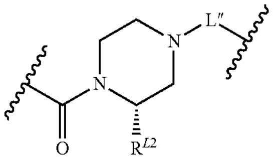

(L-6)

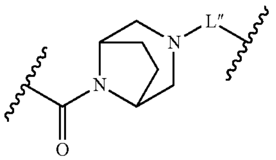

L' is —O—, —($C_{1-3}$ alkylene)-NH—, —$N(CH_3)$($C_{1-3}$ alkylene)-, piperazinediyl or —($C_{1-3}$ alkylene)-piperazinediyl, L" is a bond, $C_{1-3}$ alkylene or —($C_{1-3}$ alkylene)-O—, $R^{L2}$ is H or $C_{1-3}$ alkyl, EUB is the formula (XV) below,

[Chem. 100]

(XV)

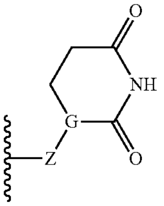

G is CH or N, and

Z is one group selected from the group consisting of the formulae (Z-1A), (Z-1B), (Z-5A), (Z-5B), (Z-14A), (Z-14B), (Z-14C), (Z-15A), (Z-16A), (Z-16B), (Z-16C), (Z-16D), (Z-20A), (Z-22A), (Z-23A), (Z-23B), (Z-23C), (Z-23D), (Z-23E), (Z-23F) and (Z-24A) below,
[Chem. 101-1]
(Z-1A)
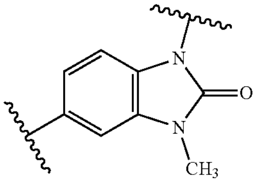
(Z-1B)
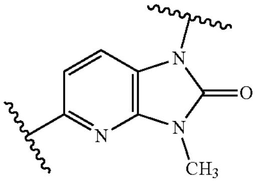
(Z-5A)
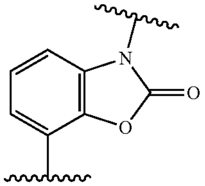
(Z-5B)
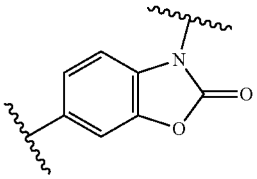
(Z-14A)
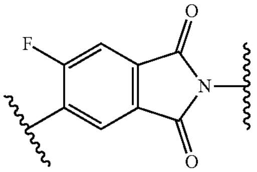
(Z-14B)
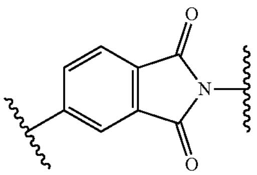
[Chem. 101-2]
(Z-14C)
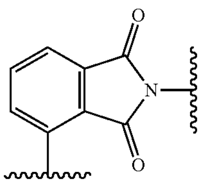
-continued
(Z-15A)
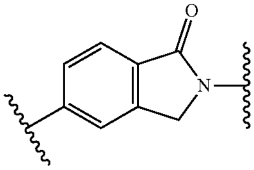
(Z-16A)
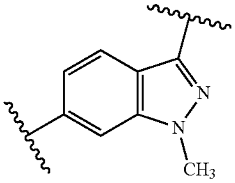
(Z-16B)
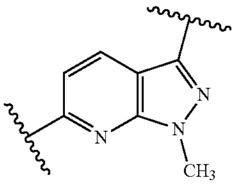
(Z-16C)
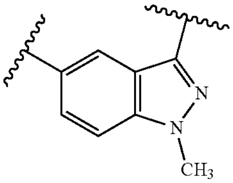
(Z-16D)
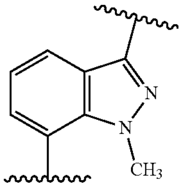
[Chem. 101-3]
(Z-20A)
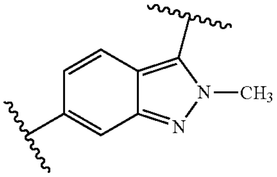
(Z-22A)
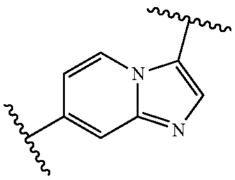
(Z-23A)
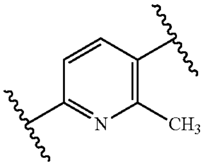

-continued (Z-23B)

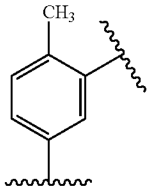

(Z-23C)

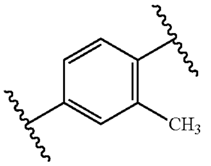

(Z-23D)

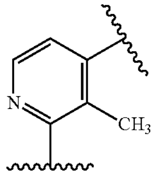

(Z-23E)

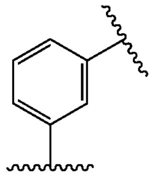

(Z-23F)

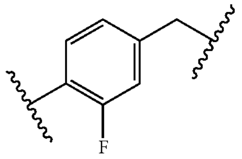

[Chem. 101-4]

(Z-24A)

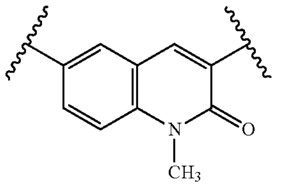

wherein a benzene ring or a 6-membered hetero ring in the formulae (Z-1A), (Z-1B), (Z-5A), (Z-5B), (Z-14A), (Z-14B), (Z-14C), (Z-15A), (Z-16A), (Z-16B), (Z-16C), (Z-16D), (Z-20A), (Z-22A), (Z-23A), (Z-23B), (Z-23C), (Z-23D), (Z-23E) and (Z-23F) form a bond with Linker, a benzene ring in the formula (Z-24A) forms a bond with Linker, provided that when G is N, Z is one group selected from the group consisting of (Z-1A), (Z-16A), (Z-16B), (Z-16C), (Z-16D), (Z-20A), (Z-22A), (Z-23A), (Z-23B), (Z-23C), (Z-23D), (Z-23E), (Z-23F) and (Z-24A).

Examples of specific compounds included in the present invention include the following compounds in one embodiment:

the compound or a salt thereof which is selected from the group consisting of

5-[(8-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3,8-diazabicyclo[3.2.1]octan-3-yl)methyl]-2-(2,6-dioxopiperidin-3-yl)-1H-isoindole-1,3(2H)-dione, 3-(5-{[(3S)-4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione, 3-(5-{[(3S)-4-{4-[({6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione, 3-[5-({(3S)-4-[4-({[6-cyclopropyl-7-(6-fluoro-5-methyl-1H-indazol-4-yl)-2-[(2S)-2-methoxypropoxy]-4-{[(3S)-pyrrolidin-3-yl]oxy}quinolin-8-yl]oxy}methyl)benzoyl]-3-methylpiperazin-1-yl}methyl)-3-methyl-2-oxo-2,3-dihydro-1H-benzimidazol-1-yl]piperidine-2,6-dione, 1-(6-{[(3S)-4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-1-methyl-1H-indazol-3-yl)-1,3-diazinane-2,4-dione, 3-(5-{[(3S)-4-{4-[({6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione, 3-(5-{[(3S)-4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-1-oxo-1,3-dihydro-2H-isoindol-2-yl)piperidine-2,6-dione and 1-(7-{[(3S)-4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}imidazo[1,2-a]pyridin-3-yl)-1,3-diazinane-2,4-dione.

Examples of specific compounds included in the present invention include the following compounds in one embodiment:

the compound or a salt thereof which is selected from the group consisting of

5-[(8-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3,8-diazabicyclo[3.2.1]octan-3-yl)methyl]-2-(2,6-dioxopiperidin-3-yl)-1H-isoindole-1,3(2H)-dione, 3-(5-{[(3S)-4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione, 3-(5-{[(3S)-4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione, 3-[5-({(3S)-4-[4-({[(7M)-6-cyclopropyl-7-(6-fluoro-5-methyl-1H-indazol-4-yl)-2-[(2S)-2-methoxypropoxy]-4-{[(3S)-pyrrolidin-3-yl]oxy}quinolin-8-yl]oxy}methyl)

benzoyl]-3-methylpiperazin-1-yl}methyl)-3-methyl-2-oxo-2,3-dihydro-1H-benzimidazol-1-yl]piperidine-2,6-dione, 1-(6-{[(3S)-4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-1-methyl-1H-indazol-3-yl)-1,3-diazinane-2,4-dione, 3-(5-{[(3S)-4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione, 3-(5-{[(3S)-4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-1-oxo-1,3-dihydro-2H-isoindol-2-yl)piperidine-2,6-dione and 1-(7-{[(3S)-4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}imidazo[1,2-a]pyridin-3-yl)-1,3-diazinane-2,4-dione.

Examples of specific compounds included in the present invention include the following compounds in one embodiment:

the compound or a salt thereof which is selected from the group consisting of

5-[(8-{4-[({(7P)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3,8-diazabicyclo[3.2.1]octan-3-yl)methyl]-2-(2,6-dioxopiperidin-3-yl)-1H-isoindole-1,3(2H)-dione, 3-(5-{[(3S)-4-{4-[({(7P)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione, 3-(5-{[(3S)-4-{4-[({(7P)-6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione, 3-[5-({(3S)-4-[4-({[(7P)-6-cyclopropyl-7-(6-fluoro-5-methyl-1H-indazol-4-yl)-2-[(2S)-2-methoxypropoxy]-4-{[(3S)-pyrrolidin-3-yl]oxy}quinolin-8-yl]oxy}methyl)benzoyl]-3-methylpiperazin-1-yl}methyl)-3-methyl-2-oxo-2,3-dihydro-1H-benzimidazol-1-yl]piperidine-2,6-dione, 1-(6-{[(3S)-4-{4-[({(7P)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-1-methyl-1H-indazol-3-yl)-1,3-diazinane-2,4-dione, 3-(5-{[(3S)-4-{4-[({(7P)-6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione, 3-(5-{[(3S)-4-{4-[({(7P)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-1-oxo-1,3-dihydro-2H-isoindol-2-yl)piperidine-2,6-dione and 1-(7-{[(3S)-4-{4-[({(7P)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}imidazo[1,2-a]pyridin-3-yl)-1,3-diazinane-2,4-dione.

Examples of specific compounds included in the present invention include the following compounds in one embodiment:

the compound or a salt thereof which is selected from the group consisting of 3-(5-{[(3S)-4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione n phosphate and 3-(5-{[(3S)-4-{4-[({6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione n phosphate.

Examples of specific compounds included in the present invention include the following compounds in one embodiment:

the compound or a salt thereof which is selected from the group consisting of 3-(5-{[(3S)-4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione n phosphate and 3-(5-{[(3S)-4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione n phosphate.

Examples of specific compounds included in the present invention include the following compounds in one embodiment:

the compound or a salt thereof which is selected from the group consisting of 3-(5-{[(3S)-4-{4-[({(7P)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione n phosphate and 3-(5-{[(3S)-4-{4-[({(7P)-6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione n phosphate.

Embodiments of the compound of the formula (XXI) or a salt thereof of the present invention are shown below.

(21-1) The compound of formula (XXI) or a salt thereof,

[Chem. 102]

(XXI)

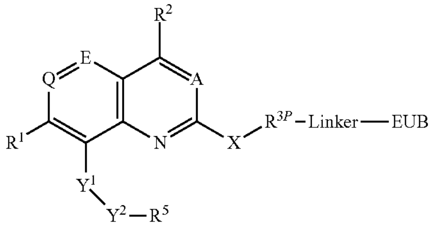

(In the formula,

A is $CR^A$ or N, $R^A$ is H, optionally substituted $C_{1-3}$ alkyl or cyano,

Q is $CR^Q$ or N, $R^Q$ is H, halogen, optionally substituted $C_{1-3}$ alkyl, $C_{3-6}$ cycloalkyl or vinyl, E is CH or N, $R^1$ is naphthyl optionally substituted with one or two groups selected from the group consisting of optionally substituted $C_{1-3}$ alkyl, cyano, OH and halogen, or $R^1$ is a group selected from the group consisting of the formula (II), the formula (III) and the formula (IV) below,

[Chem. 103]

(II)

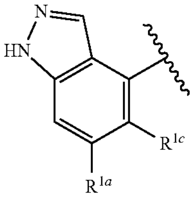

(III)

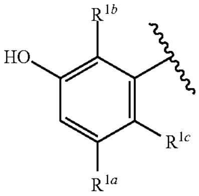

(IV)

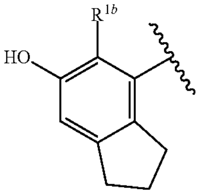

$R^{1a}$, $R^{1b}$ and $R^{1c}$, which are the same as or different from each other, are H, optionally substituted $C_{1-3}$ alkyl, vinyl or halogen, $R^2$ is —$V^1$—$V^2$ or W, $V^1$ is a bond, —$CH_2$—, —O—, —S— or —N($R^{V1}$)—, $R^{V1}$ is H or optionally substituted $C_{1-3}$ alkyl, $V^2$ is the formula (V) or the formula (VI) below,

[Chem. 104]

(V)

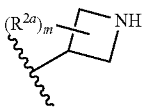

(VI)

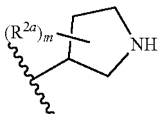

W is the formula (VII) or the formula (VII-2) below or 7-membered to 9-membered bridged heterocycloalkyl containing one to two nitrogen atoms,

[Chem. 105]

(VII)

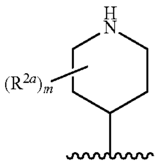

(VII-2)

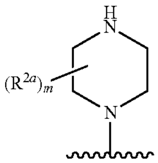

each $R^{2a}$, which is the same as or different from each other, are OH, $OCH_3$, F or optionally substituted $C_{1-3}$ alkyl, where $R^{2a}$ is attached only to a carbon atom that is an atom forming a ring selected from the group consisting of an azetidine ring represented by the formula (V), a pyrrolidine ring represented by the formula (VI), a piperidine ring represented by the formula (VII) and a piperazine ring represented by the formula (VII-2), m is an integer of 0 to 2, $R^{3P}$ is optionally substituted $C_{1-6}$ alkylene, optionally substituted heterocycloalkylene or optionally substituted heteroarylene, X is a bond, —$CH_2$—, —O—, —S— or —$NR^{4X}$—, $R^{4X}$ is H or optionally substituted $C_{1-3}$ alkyl, $Y^1$ is —O-(optionally substituted $C_{1-3}$ alkylene)-$^{*Y2}$, —S-(optionally substituted $C_{1-3}$ alkylene)-$^{*Y2}$, —$SO_2$-(optionally substituted $C_{1-3}$ alkylene)-$^{*Y2}$, —$NR^Y$-(optionally substituted $C_{1-3}$ alkylene)-$^{*Y2}$, -(optionally substituted $C_{1-3}$ alkylene)-O-$^{*Y2}$, -(optionally substituted $C_{1-3}$ alkylene)-S-$^{*Y2}$, -(optionally substituted $C_{1-3}$ alkylene)-$SO_2$-$^{*Y2}$ or -(optionally substituted $C_{1-3}$ alkylene)-$NR^Y$-$^{*Y2}$ ($^{*Y2}$ represents a linking moiety to $Y^2$), $R^Y$ is H or optionally substituted $C_{1-3}$ alkyl, $Y^2$ is a bond, optionally substituted phenylene or optionally substituted heteroarylene, $R^5$ is H, $CONR^6R^7$ or a group selected from the group consisting of the formulae (XXIV), (XXV), (XXVI), (XXVII), (XXVIII), (XXIX), (XXX), (XXXI), (XXXII), (XXXIII), (XXXIV) and (XXXV) below,

[Chem. 106]

(XXIV)

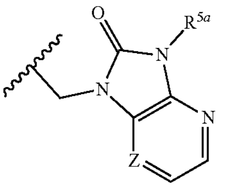

(XXV)

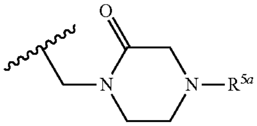

(XXVI)

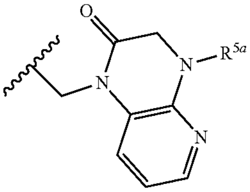

(XXVII)

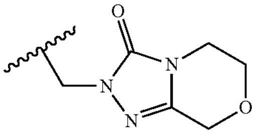

(XXVIII)

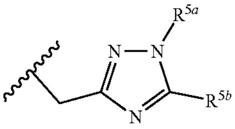

(XXIX)

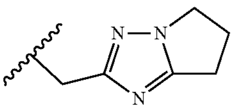

(XXX)

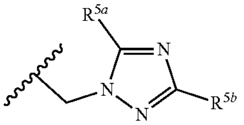

(XXXI)

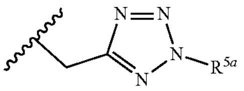

(XXXII)

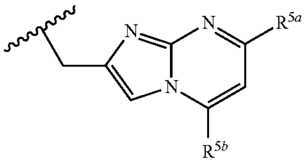

(XXXIII)

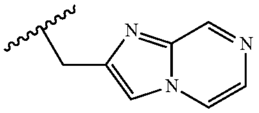

-continued (XXXIV)

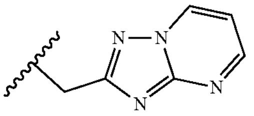

(XXXV)

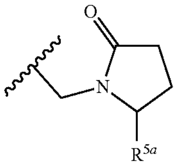

$R^{5a}$ and $R^{5b}$, which are the same as or different from each other, are H, optionally substituted $C_{1-3}$ alkyl, cyclopropyl, cyclopropylmethyl, oxetanyl, tetrahydropyranyl, optionally substituted oxazolyl, thiazolyl or pyrazinyl, $R^6$ and $R^7$, which are the same as or different from each other, are H or optionally substituted $C_{1-6}$ alkyl, or $R^6$ and $R^7$ form a 4-membered to 8-membered saturated heterocyclic ring together with a nitrogen atom to which they are attached, wherein the 4-membered to 8-membered saturated heterocyclic ring is optionally substituted with optionally substituted $C_{1-6}$ alkyl, Linker is a group chemically linking $R^{3P}$ to EUB, and EUB is a group capable of binding to one E3 ubiquitin ligase selected from the group consisting of cereblon, IAP, MDM2, DCAF11, DCAF15, DCAF16, BIRC2, KEAP1, RNF4, RNF114, FEM1B and AhR).

(21-2) The compound or a salt thereof according to (21-1), wherein A is CH or N, Q is $CR^Q$, $R^Q$ is $C_{3-6}$ cycloalkyl, E is CH, $R^1$ is the formula (II) below,

[Chem. 107]

(II)

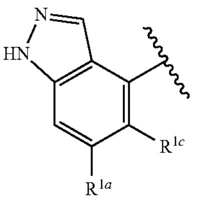

$R^{1a}$ is halogen, and $R^{1c}$ is $C_{1-3}$ alkyl, $R^2$ is —$V^1$—$V^2$ or W, $V^1$ is a bond, —O— or —N($R^{V1}$)—, $R^{V1}$ is $C_{1-3}$ alkyl, $V^2$ is the formula (VI-2) below,

[Chem. 108]

(VI-2)

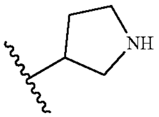

W is the formula (XII) below,

[Chem.109]

(XII)

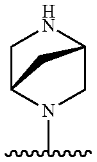

$R^{3P}$ is $C_{1-6}$ alkylene optionally substituted with one group selected from the group consisting of —O($C_{1-6}$ alkyl), oxetanyl, tetrahydrofuranyl and tetrahydropyranyl, oxetandiyl, tetrahydrofurandiyl or tetrahydropyrandiyl, $R^5$ is H or a group selected from the group consisting of the formulae (XXIV), (XXV), (XXVI), (XXVII), (XXVIII), (XXIX), (XXX), (XXXI), (XXXII), (XXXIII), (XXXIV) and (XXXV),

[Chem. 110]

(XXIV)

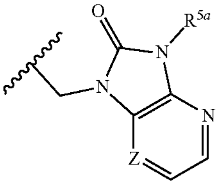

(XXV)

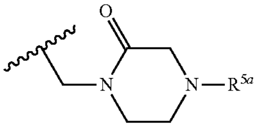

(XXVI)

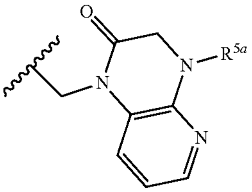

(XXVII)

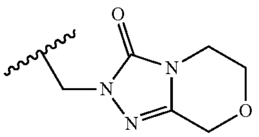

(XXVIII)

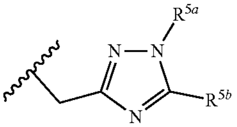

(XXIX)

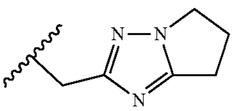

-continued (XXX)

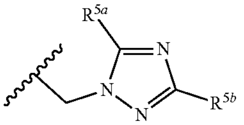

(XXXI)

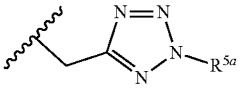

(XXXII)

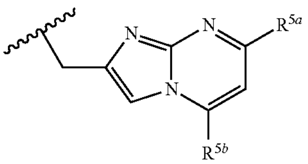

(XXXIII)

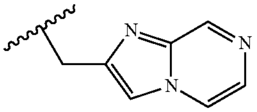

(XXXIV)

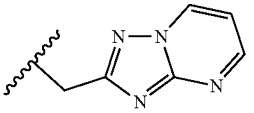

(XXXV)

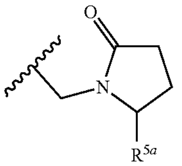

$R^{5a}$ and $R^{5b}$, which are the same as or different from each other, are H, optionally substituted $C_{1-3}$ alkyl, cyclopropyl, cyclopropylmethyl, oxetanyl, tetrahydropyranyl, thiazolyl or pyrazinyl, X is —O—, $Y^1$ is —O—($C_{1-3}$ alkylene)-$^{*Y2}$ ($^{*Y2}$ represents a linking moiety to $Y^2$), $Y^2$ is phenylene, Linker is -($L^1$-$L^2$-$L^3$-$L^4$)-, $L^1$ is C═O, $L^2$ is piperidinediyl optionally substituted with $C_{1-3}$ alkyl, piperazinediyl optionally substituted with $C_{1-3}$ alkyl, pyrrolidinediyl optionally substituted with $C_{1-3}$ alkyl, bridged piperazinediyl or 2,6-diazaspiro[3.4]octanediyl, $L^3$ is a bond, —N($R^{L3}$)—, $C_{1-3}$ alkylene or piperazinediyl, $L^4$ is a bond, —N($R^{L4}$)—, —O—, piperazinediyl or $C_{1-3}$ alkylene, $R^{L3}$ is H or $C_{1-3}$ alkyl, $R^{L4}$ is H or $C_{1-3}$ alkyl, EUB is a group capable of binding to cereblon, where the group capable of binding to cereblon is the formula (XV) below,

[Chem. 111]

(XV)

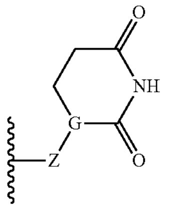

G is CH or N,

Z is one group selected from the group consisting of the formulae (Z-1), (Z-5), (Z-11), (Z-14), (Z-15), (Z-16), (Z-20), (Z-22) and (Z-23), wherein ring B1 and ring B2 in the formulae (Z-1), (Z-5), (Z-11), (Z-14), (Z-15), (Z-16), (Z-20), (Z-22) and (Z-23) form a bond with Linker, provided that when G is N, Z is one group selected from the group consisting of the formulae (Z-16), (Z-20), (Z-22) and (Z-23),

[Chem. 112-1]

(Z-1)

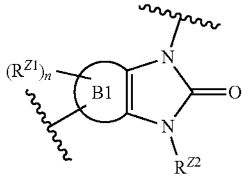

(Z-5)

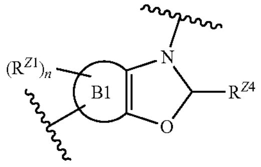

(Z-11)

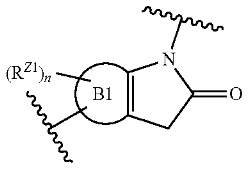

(Z-14)

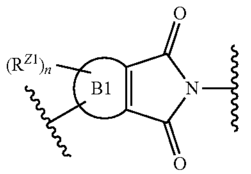

(Z-15)

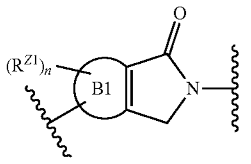

-continued (Z-16)

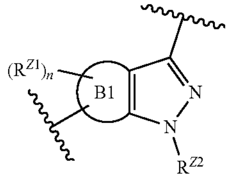

[Chem. 112-2]

(Z-20)

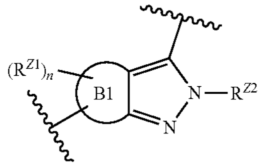

(Z-22)

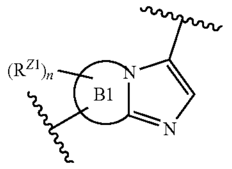

(Z-23)

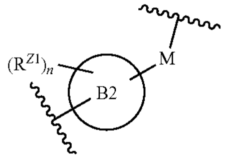

$R^{Z1}$ is $C_{1-3}$ alkyl or halogen, n is an integer of 0 or 1, $R^{Z2}$ is $C_{1-3}$ alkyl, M is a bond or $C_{1-3}$ alkylene, ring B1 is a benzene ring or a pyridine ring, wherein $R^{Z1}$ and Linker form a bond with a carbon atom forming the ring B1, and ring B2 is a benzene ring or a pyridine ring, wherein M, $R^{Z1}$ and Linker form a bond with a carbon atom forming the ring B2.

(21-3) The compound or a salt thereof according to (21-2), wherein A is CH or N, Q is $CR^{Q}$, $R^{Q}$ is cyclopropyl, E is CH, $R^1$ is the formula (II-2) below,

[Chem. 113]

(II-2)

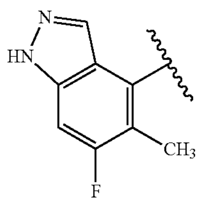

$R^2$ is —$V^1$—$V^2$ or W, $V^1$ is —O— or —$N(CH_3)$—, $V^2$ is the formula (VI-2) below,

[Chem. 114]

(VI-2)

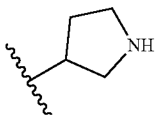

W is the formula (XII) below,

[Chem. 115]

(XII)

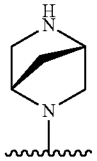

$R^{3P}$ is $C_{1-6}$ alkylene optionally substituted with —O($C_{1-3}$ alkyl), $R^5$ is H, X is —O—, $Y^1$ is —O-(methylene)-$^{*Y2}$ ($^{*Y2}$ represents a linking moiety to $Y^2$), $Y^2$ is phenylene, Linker is one group selected from the group consisting of the formulae (L-1), (L-2), (L-3), (L-4), (L-5), (L-6) and (L-7) below, wherein C═O in the formulae (L-1), (L-2), (L-3), (L-4), (L-5), (L-6) and (L-7) forms a bond with $Y^2$,

[Chem. 116]

(L-1)

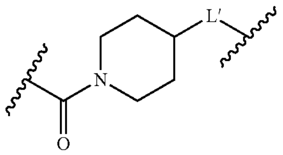

(L-2)

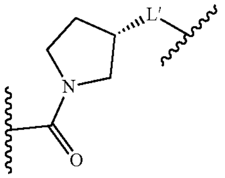

(L-3)

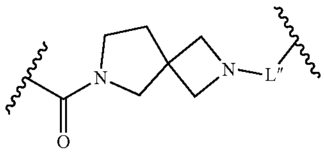

-continued (L-4)

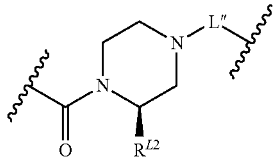

(L-5)

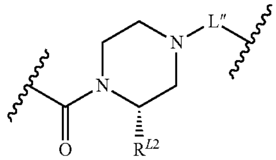

(L-6)

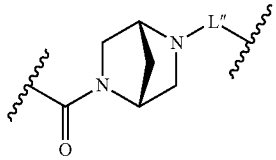

(L-7)

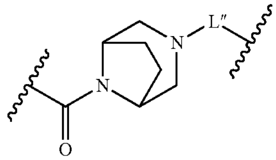

L' is —O—, —($C_{1-3}$ alkylene)-NH—, —$N(CH_3)$($C_{1-3}$ alkylene)-, piperazinediyl or —($C_{1-3}$ alkylene)-piperazinediyl, L" is a bond, $C_{1-3}$ alkylene or —($C_{1-3}$ alkylene)-O—, $R^{L2}$ is H or $C_{1-3}$ alkyl, EUB is a group capable of binding to cereblon, where the group capable of binding to cereblon is the formula (XV) below,

[Chem. 117]

(XV)

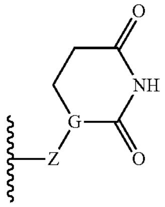

G is CH or N, and

Z is one group selected from the group consisting of the formulae (Z-1A), (Z-1B), (Z-5A), (Z-5B), (Z-14A), (Z-14B), (Z-14C), (Z-15A), (Z-16A), (Z-16B), (Z-16C), (Z-16D), (Z-20A), (Z-22A), (Z-23A), (Z-23B), (Z-23C), (Z-23D), (Z-23E) and (Z-23F) below, wherein a benzene ring or a 6-membered hetero ring in the formulae (Z-1A), (Z-1B), (Z-5A), (Z-5B), (Z-14A), (Z-14B), (Z-14C), (Z-15A), (Z-16A), (Z-16B), (Z-16C), (Z-16D), (Z-20A), (Z-22A), (Z-23A), (Z-23B), (Z-23C), (Z-23D), (Z-23E) and (Z-23F) form a bond with Linker, provided that when G is N, Z is one group selected from the group consisting of (Z-16A), (Z-16B), (Z-16C), (Z-16D), (Z-20A), (Z-22A), (Z-23A), (Z-23B), (Z-23C), (Z-23D), (Z-23E) and (Z-23F).

[Chem. 118-1]

(Z-1A)

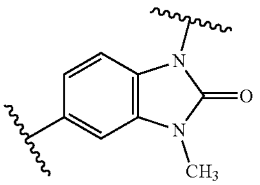

(Z-1B)

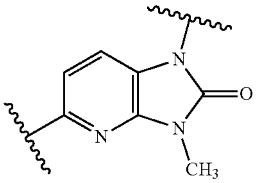

(Z-5A)

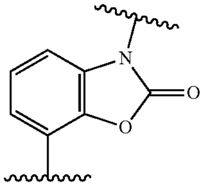

(Z-5B)

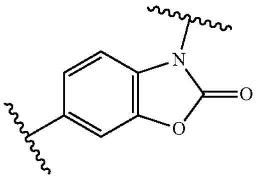

(Z-14A)

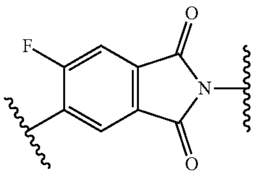

(Z-14B)

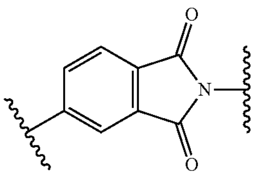

[Chem. 118-2]

(Z-14C)

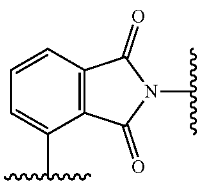

-continued (Z-15A)

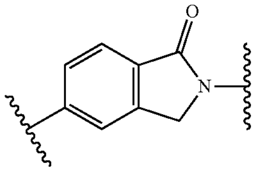

(Z-16A)

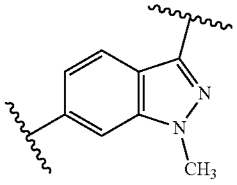

(Z-16B)

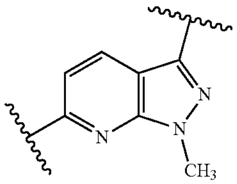

(Z-16C)

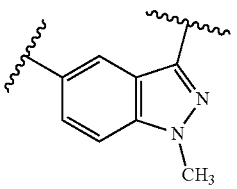

(Z-16D)

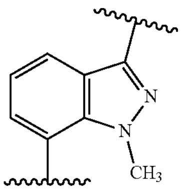

Embodiments of the compound of the formula (XXII) or a salt thereof of the present invention are shown below.

(22-1) The compound of formula (XXII) or a salt thereof,

[Chem. 119]

(XXII)

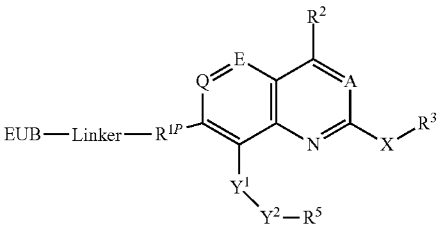

(In the formula, A is $CR^A$ or N, $R^A$ is H, optionally substituted $C_{1-3}$ alkyl or cyano, Q is $CR^Q$ or N, $R^Q$ is H, halogen, optionally substituted $C_{1-3}$ alkyl, $C_{3-6}$ cycloalkyl or vinyl, E is CH or N, $R^{1P}$ is naphthylene optionally substituted with one or two groups selected from the group consisting of optionally substituted $C_{1-3}$ alkyl, cyano, OH and halogen or one group selected from the group consisting of the formula (II-22A), the formula (II-22B), the formula (II-22C), the formula (III-22A), the formula (III-22B), the formula (III-22C) and the formula (III-22D) below,

[Chem. 120-1]

(II-22A)

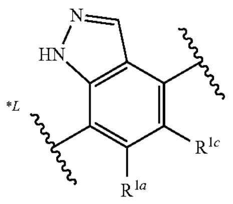

(II-22B)

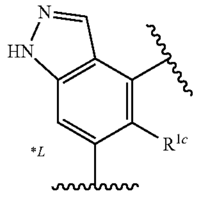

(II-22C)

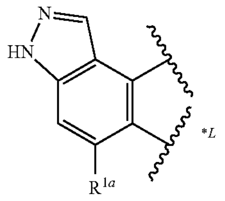

[Chem. 120-2]

(III22A0

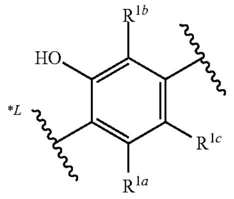

(III-22B)

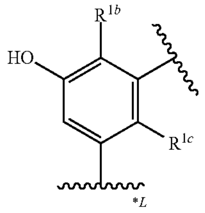

(III-22C)

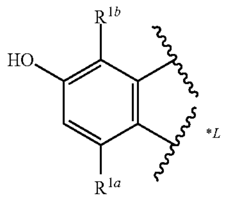

-continued (III=22D)

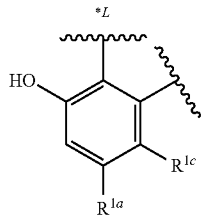

$R^{1a}$, $R^{1b}$ and $R^{1c}$, which are the same as or different from each other, are H, optionally substituted $C_{1-3}$ alkyl, vinyl or halogen, $R^2$ is —$V^1$—$V^2$ or W, $V^1$ is a bond, —$CH_2$—, —O—, —S— or —N($R^{V1}$)—, $R^{V1}$ is H or optionally substituted $C_{1-3}$ alkyl, $V^2$ is the formula (V) or the formula (VI) below,

[Chem. 121]

(V)

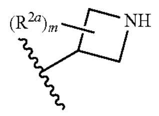

(VI)

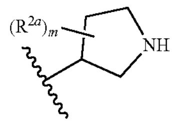

W is the formula (VII) or the formula (VII-2) below or 7-membered to 9-membered bridged heterocycloalkyl containing one to two nitrogen atoms,

[Chem. 122]

(VII)

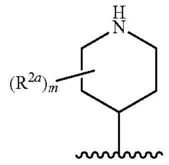

(VII-2)

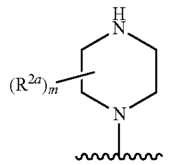

each $R^{2a}$, which is the same as or different from each other, are OH, $OCH_3$, F or optionally substituted $C_{1-3}$ alkyl, where $R^{2a}$ is attached only to a carbon atom that is an atom forming a ring selected from the group consisting of an azetidine ring represented by the formula (V), a pyrrolidine ring represented by the formula (VI), a piperidine ring represented by the formula (VII) and a piperazine ring represented by the formula (VII-2), m is an integer of 0 to 2, $R^3$ is optionally substituted $C_{1-6}$ alkyl, optionally substituted heterocycloalkyl or optionally substituted heteroaryl, X is a bond, —$CH_2$—, —O—, —S— or —$NR^{4X}$—, $R^{4X}$ is H or optionally substituted $C_{1-3}$ alkyl, $Y^1$ is —O-(optionally substituted $C_{1-3}$ alkylene)-$^{*Y2}$, —S-(optionally substituted $C_{1-3}$ alkylene)-$^{*Y2}$, —$SO_2$-(optionally substituted $C_{1-3}$ alkylene)-$^{*Y2}$, —$NR^Y$-(optionally substituted $C_{1-3}$ alkylene)-$^{*Y2}$, -(optionally substituted $C_{1-3}$ alkylene)-O-$^{*Y2}$, -(optionally substituted $C_{1-3}$ alkylene)-S-$^{*Y2}$, -(optionally substituted $C_{1-3}$ alkylene)-$SO_2$-$^{*Y2}$ or -(optionally substituted $C_{1-3}$ alkylene)-$NR^Y$-$^{*Y2}$ ($^{*Y2}$ represents a linking moiety to $Y^2$), $R^Y$ is H or optionally substituted $C_{1-3}$ alkyl, $Y^2$ is a bond, optionally substituted phenylene or optionally substituted heteroarylene, $R^5$ is H, $CONR^6R^7$ or a group selected from the group consisting of the formulae (XXIV), (XXV), (XXVI), (XXVII), (XXVIII), (XXIX), (XXX), (XXXI), (XXXII), (XXXIII), (XXXIV) and (XXXV) below,

[Chem. 123]

(XXIV)

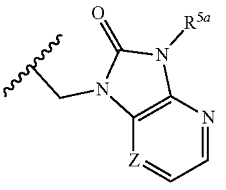

(XXV)

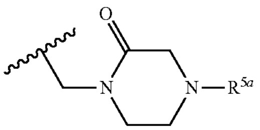

(XXVI)

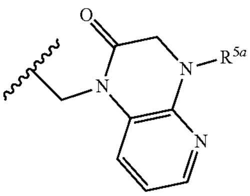

(XXVII)

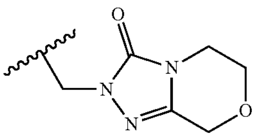

(XXVIII)

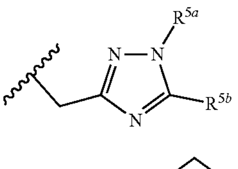

(XXIX)

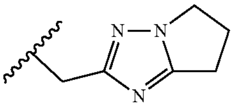

(XXX)

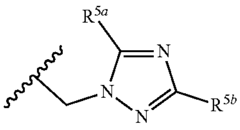

-continued (XXXI)

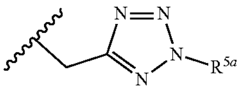

(XXXII)

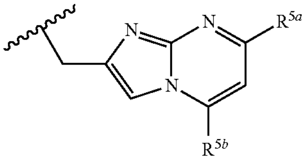

(XXXIII)

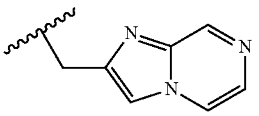

(XXXIV)

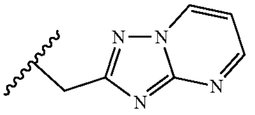

(XXXV)

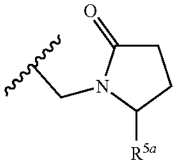

$R^{5a}$ and $R^{5b}$, which are the same as or different from each other, are H, optionally substituted $C_{1-3}$ alkyl, cyclopropyl, cyclopropylmethyl, oxetanyl, tetrahydropyranyl, optionally substituted oxazolyl, thiazolyl or pyrazinyl, $R^6$ and $R^7$, which are the same as or different from each other, are H or optionally substituted $C_{1-6}$ alkyl, or $R^6$ and $R^7$ form a 4-membered to 8-membered saturated heterocyclic ring together with a nitrogen atom to which they are attached, wherein the 4-membered to 8-membered saturated heterocyclic ring is optionally substituted with optionally substituted $C_{1-6}$ alkyl, Linker is a group chemically linking $R^{1P}$ to EUB, and EUB is a group capable of binding to one E3 ubiquitin ligase selected from the group consisting of cereblon, IAP, MDM2, DCAF11, DCAF15, DCAF16, BIRC2, KEAP1, RNF4, RNF114, FEM1B and AhR).

(22-2) The compound or a salt thereof according to (22-1), wherein A is CH or N, Q is $CR^Q$, $R^Q$ is $C_{3-6}$ cycloalkyl, E is CH, $R^{1P}$ is naphthylene optionally substituted with one or two groups selected from the group consisting of optionally substituted $C_{1-3}$ alkyl, cyano, OH and halogen or one group selected from the group consisting of the formula (II-22A), the formula (II-22B) and the formula (II-22C) below,

[Chem. 124]

(II-22A)

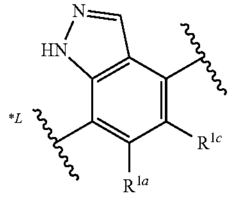

(II-22B)

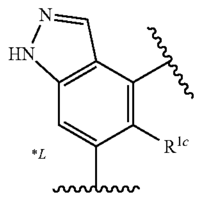

(II-22C)

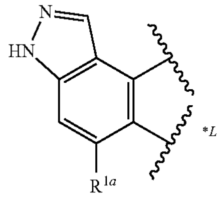

$R^{1a}$ is halogen, and R1c is $C_{1-3}$ alkyl, $R^2$ is —$V^1$—$V^2$ or W, $V^1$ is a bond, —O— or —N($R^{V1}$)—, $R^{V1}$ is $C_{1-3}$ alkyl, $V^2$ is the formula (VI-2) below,

[Chem. 125]

(VI-2)

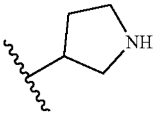

W is the formula (XII) below,

[Chem.126]

(XII)

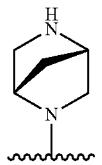

$R^3$ is optionally substituted $C_{1-6}$ alkyl, optionally substituted heterocycloalkyl or optionally substituted heteroaryl, $R^5$ is H or a group selected from the group consisting of the formulae (XXIV), (XXV), (XXVI), (XXVII), (XXVIII), (XXIX), (XXX), (XXXI), (XXXII), (XXXIII), (XXXIV) and (XXXV),

[Chem. 127]

(XXIV)

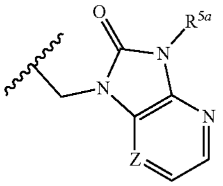

(XXV)

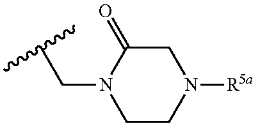

(XXVI)

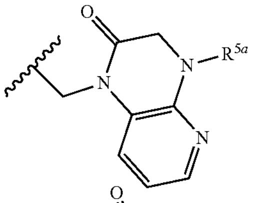

(XXVII)

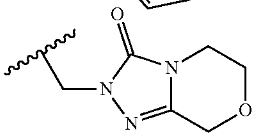

(XXVIII)

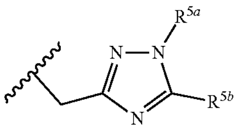

(XXIX)

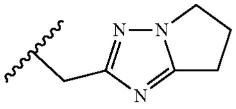

(XXX)

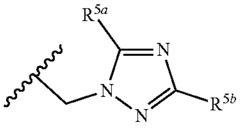

(XXXI)

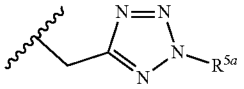

(XXXII)

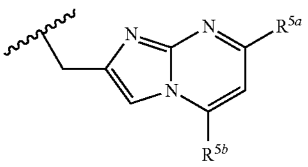

(XXXIII)

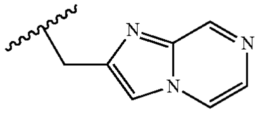

(XXXIV)

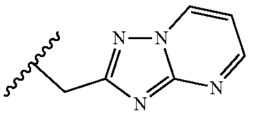

-continued (XXXV)

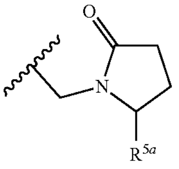

$R^{5a}$ and $R^{5b}$, which are the same as or different from each other, are H, optionally substituted $C_{1-3}$ alkyl, cyclopropyl, cyclopropylmethyl, oxetanyl, tetrahydropyranyl, thiazolyl or pyrazinyl, X is —O—, $Y^1$ is —O—($C_{1-3}$ alkylene)-$^{*Y2}$ ($^{*Y2}$ represents a linking moiety to $Y^2$), $Y^2$ is phenylene, Linker is -($L^1$-$L^2$-$L^3$-$L^4$)-, $L^1$ is C═O, $L^2$ is piperidinediyl optionally substituted with $C_{1-3}$ alkyl, piperazinediyl optionally substituted with $C_{1-3}$ alkyl, pyrrolidinediyl optionally substituted with $C_{1-3}$ alkyl, bridged piperazinediyl or 2,6-diazaspiro[3.4]octanediyl, $L^3$ is a bond, —N($R^{L3}$)—, $C_{1-3}$ alkylene or piperazinediyl, $L^4$ is a bond, —N($R^{L4}$)—, —O—, piperazinediyl or $C_{1-3}$ alkylene, $R^{L3}$ is H or $C_{1-3}$ alkyl, $R^{L4}$ is H or $C_{1-3}$ alkyl, EUB is a group capable of binding to cereblon, where the group capable of binding to cereblon is the formula (XV) below,

[Chem. 128]

(XV)

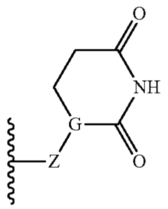

G is CH or N,

Z is one group selected from the group consisting of the formulae (Z-1), (Z-5), (Z-11), (Z-14), (Z-15), (Z-16), (Z-20), (Z-22) and (Z-23), wherein ring B1 and ring B2 in the formulae (Z-1), (Z-5), (Z-11), (Z-14), (Z-15), (Z-16), (Z-20), (Z-22) and (Z-23) form a bond with Linker, provided that when G is N, Z is one group selected from the group consisting of the formulae (Z-16), (Z-20), (Z-22) and (Z-23),

[Chem. 129-1]

(Z-1)

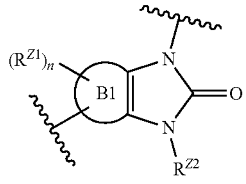

-continued (Z-5)

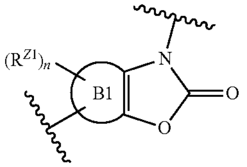

(Z-11)

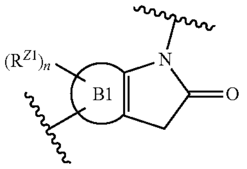

(Z-14)

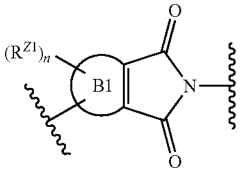

(Z-15)

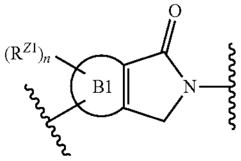

(Z-16)

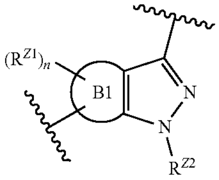

[Chem. 129-2]

(Z-20)

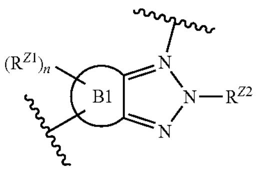

(Z-22)

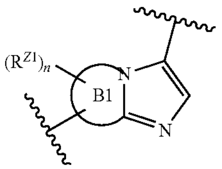

(Z-23)

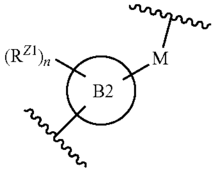

$R^{Z1}$ is $C_{1-3}$ alkyl or halogen, n is an integer of 0 or 1, $R^{Z2}$ is $C_{1-3}$ alkyl, M is a bond or $C_{1-3}$ alkylene, ring B1 is a benzene ring or a pyridine ring, wherein $R^{Z1}$ and Linker form a bond with a carbon atom forming the ring B1, and ring B2 is a benzene ring or a pyridine ring, wherein M, $R^{Z1}$ and Linker form a bond with a carbon atom forming the ring B2.

(22-3) The compound or a salt thereof according to (22-2), wherein A is CH or N, Q is $CR^{Q}$, $R^{Q}$ is cyclopropyl, E is CH, $R^{1P}$ is naphthylene optionally substituted with one or two groups selected from the group consisting of optionally substituted $C_{1-3}$ alkyl, cyano, OH and halogen or one group selected from the group consisting of the formula (II-22A), the formula (II-22B) and the formula (II-22C) below,

[Chem. 130]

(II-22A)

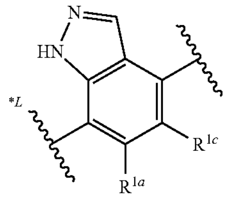

(II-22B)

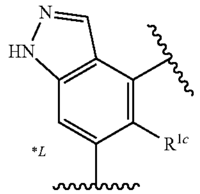

(II-22C)

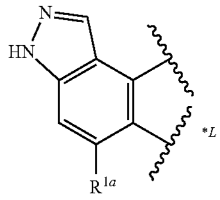

$R^{1a}$ is F, and $R^{1c}$ is methyl, $R^2$ is —$V^1$—$V^2$ or W, $V^1$ is —O— or —$N(CH_3)$—, $V^2$ is the formula (VI-2) below,

[Chem. 131]

(VI-2)

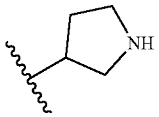

W is the formula (XII) below,

[Chem.132]

(XII)

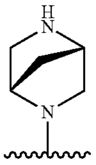

$R^3$ is $C_{1-3}$ alkyl optionally substituted with —$OCH_3$ or tetrahydrofuranyl, tetrahydrofuranyl or tetrahydropyranyl, $R^5$ is H, X is —O—, $Y^1$ is —O-(methylene)-$^{*Y2}$ ($^{*Y2}$ represents a linking moiety to $Y^2$), $Y^2$ is phenylene, Linker is one group selected from the group consisting of the formulae (L-1), (L-2), (L-3), (L-4), (L-5), (L-6) and (L-7) below, wherein C═O in the formulae (L-1), (L-2), (L-3), (L-4), (L-5), (L-6) and (L-7) forms a bond with $Y^2$,

[Chem. 133]

(L-1)

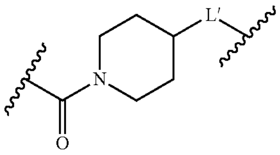

(L-2)

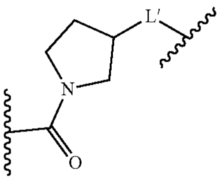

(L-3)

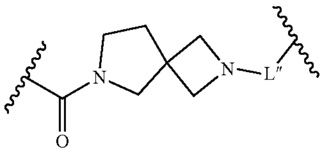

(L-4)

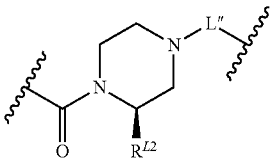

(L-5)

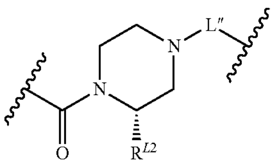

-continued (L-6)

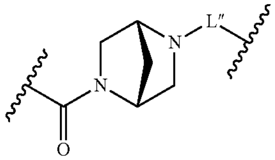

(L-7)

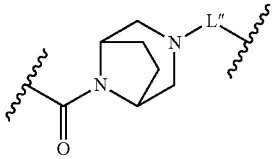

L' is —O—, —($C_{1-3}$ alkylene)-NH—, —N($CH_3$)($C_{1-3}$ alkylene)-, piperazinediyl or —($C_{1-3}$ alkylene)-piperazinediyl, L" is a bond, $C_{1-3}$ alkylene or —($C_{1-3}$ alkylene)-O—, $R^{L2}$ is H or $C_{1-3}$ alkyl, EUB is a group capable of binding to cereblon, where the group capable of binding to cereblon is the formula (XV) below,

[Chem. 134]

(XV)

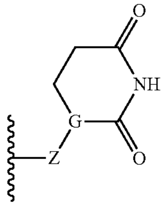

G is CH or N, and

Z is one group selected from the group consisting of the formulae (Z-1A), (Z-1B), (Z-5A), (Z-5B), (Z-14A), (Z-14B), (Z-14C), (Z-15A), (Z-16A), (Z-16B), (Z-16C), (Z-16D), (Z-20A), (Z-22A), (Z-23A), (Z-23B), (Z-23C), (Z-23D), (Z-23E) and (Z-23F) below, wherein a benzene ring or a 6-membered hetero ring in the formulae (Z-1A), (Z-1B), (Z-5A), (Z-5B), (Z-14A), (Z-14B), (Z-14C), (Z-15A), (Z-16A), (Z-16B), (Z-16C), (Z-16D), (Z-20A), (Z-22A), (Z-23A), (Z-23B), (Z-23C), (Z-23D), (Z-23E) and (Z-23F) form a bond with Linker, provided that when G is N, Z is one group selected from the group consisting of (Z-16A), (Z-16B), (Z-16C), (Z-16D), (Z-20A), (Z-22A), (Z-23A), (Z-23B), (Z-23C), (Z-23D), (Z-23E) and (Z-23F).

[Chem. 135-1]

(Z-1A)

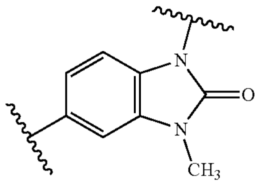

-continued (Z-1B)

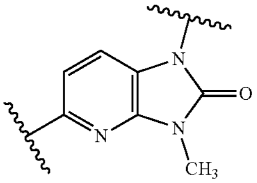

(Z-5A)

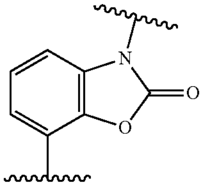

(Z-5B)

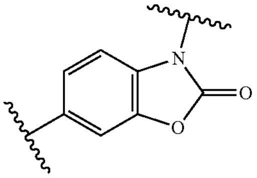

(Z-14A)

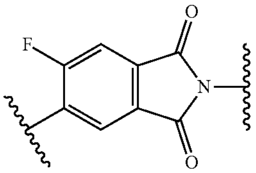

(Z-14B)

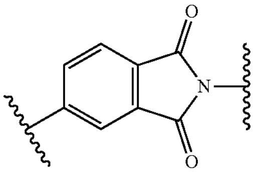

[Chem. 135-2]

(Z-14C)

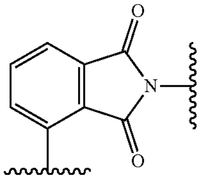

(Z-15A)

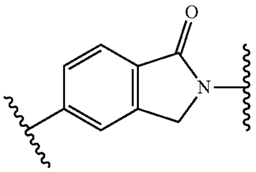

(Z-16A)

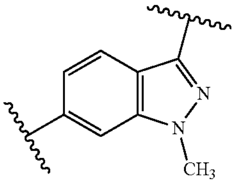

-continued (Z-16B)

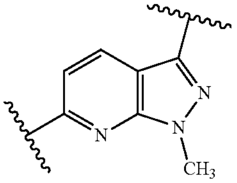

(Z-16C)

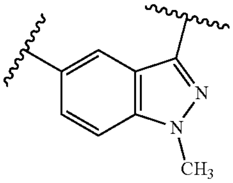

(Z-16D)

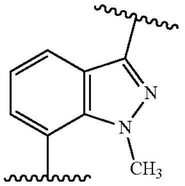

Embodiments of the compound of the formula (XXIII) or a salt thereof of the present invention are shown below.

(23-1) The compound of formula (XXIII) or a salt thereof,

[Chem. 136]

GDB-Linker-EUB (XXIII)

(In the formula,

GDB is a group capable of binding to a G12D mutant KRAS protein,

-Linker-EUB is one group selected from the group consisting of the formula (LE-1) to the formula (LE-37).)

[Chem. 137-1]

(LE-1)

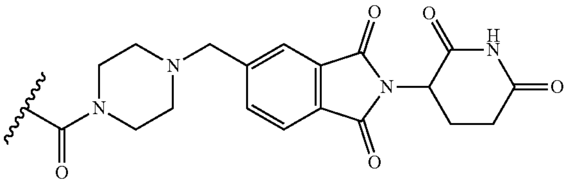

(LE-2)

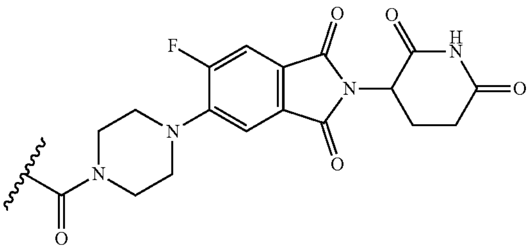

-continued (LE-3)

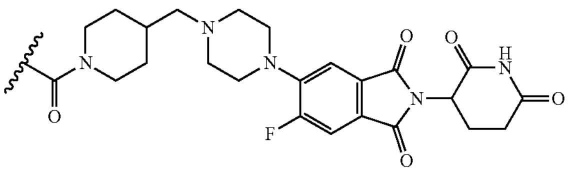

(LE-4)

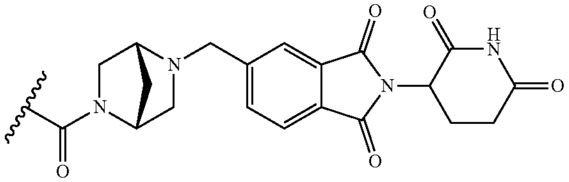

[Chem. 137-2]

(LE-5)

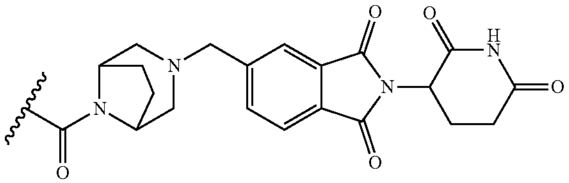

(LE-6)

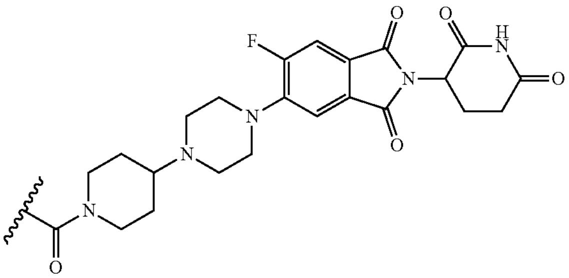

(LE-7)

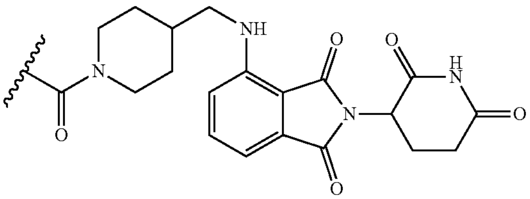

(LE-8)

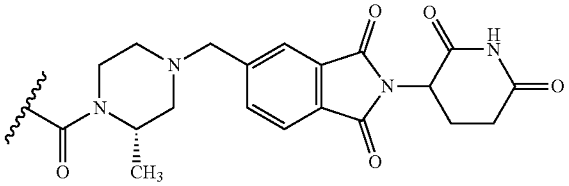

-continued
[Chem. 137-3]
(LE-9)
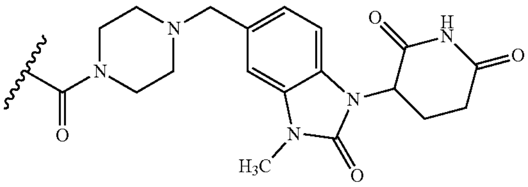
(LE-10)
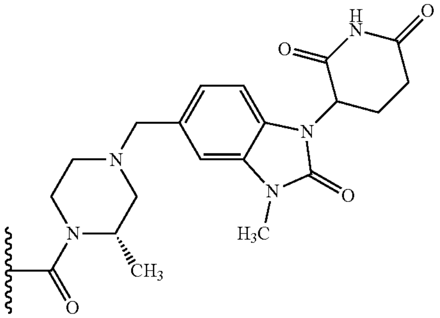
(LE-11)
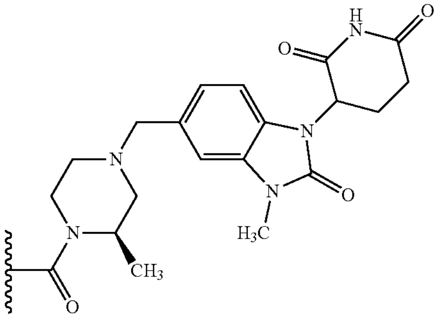
(LE-12)
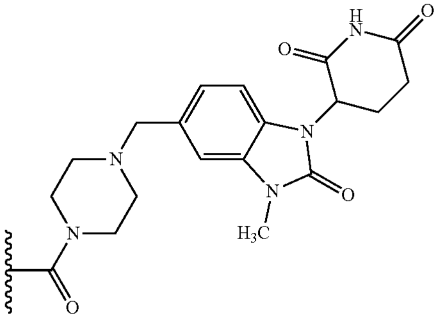
[Chem. 137-4]
(LE-13)
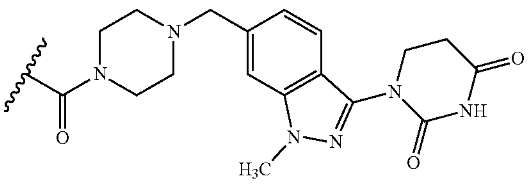
-continued
(LE-14)
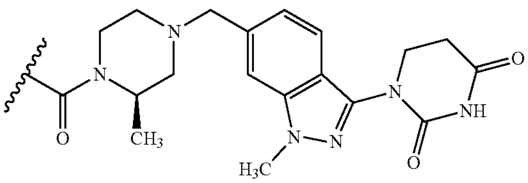
(LE-15)
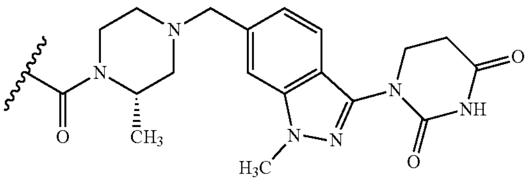
(LE-16)
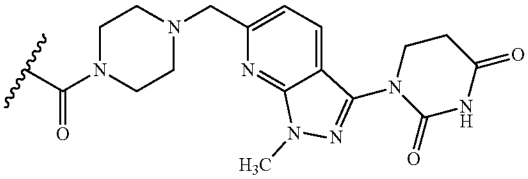
[Chem. 137-5]
(LE-17)
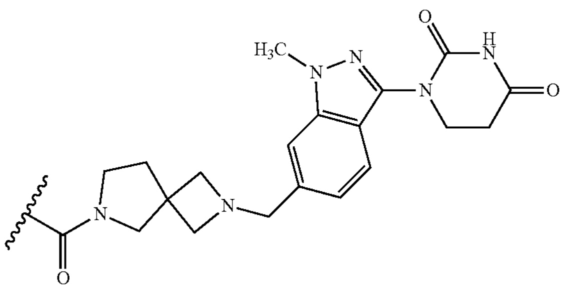
(LE-18)
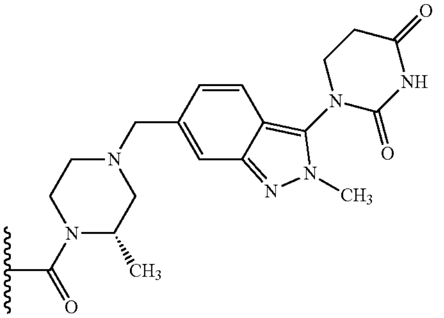
(LE-19)
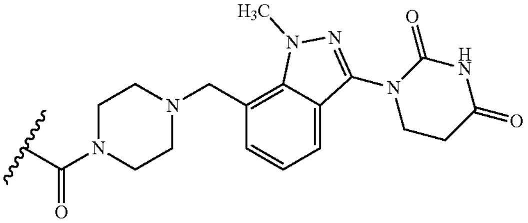

-continued
(LE-20)
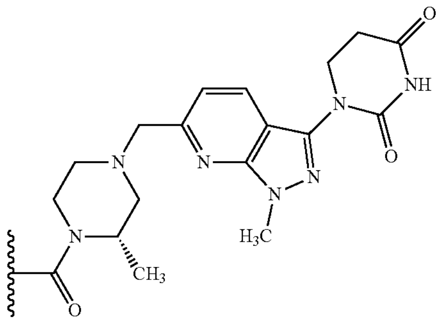
[Chem. 137-6]
(LE-21)
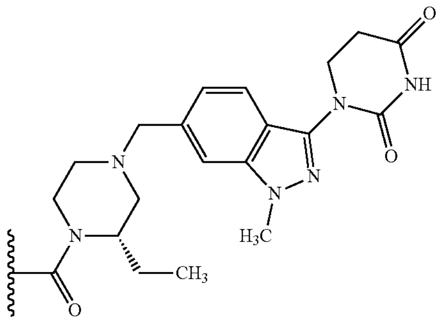
(LE-22)
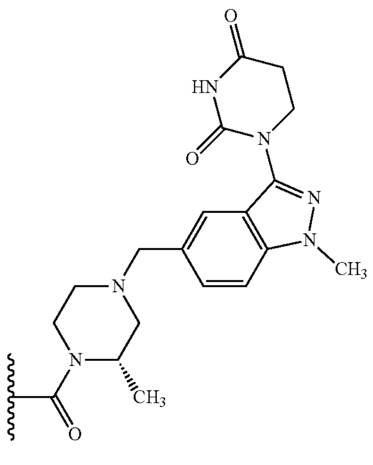
(LE-23)
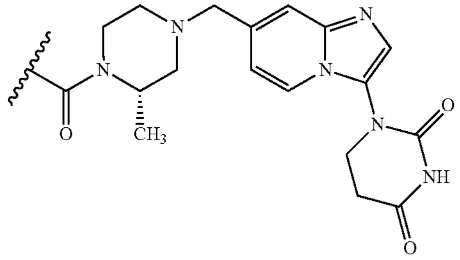
-continued
(LE-24)
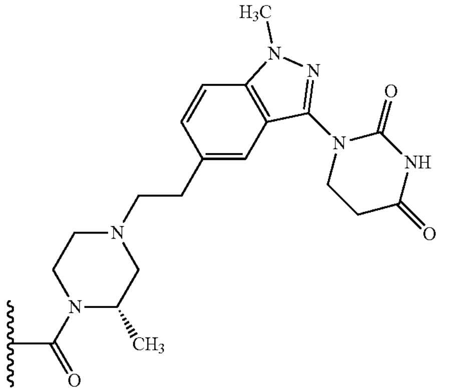
[Chem. 137-7]
(LE-25)
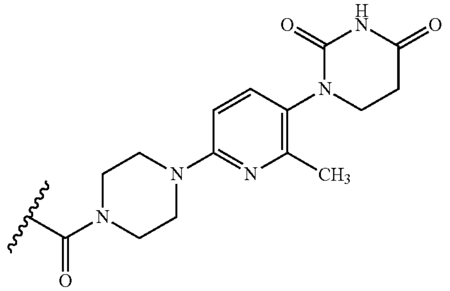
(LE-26)
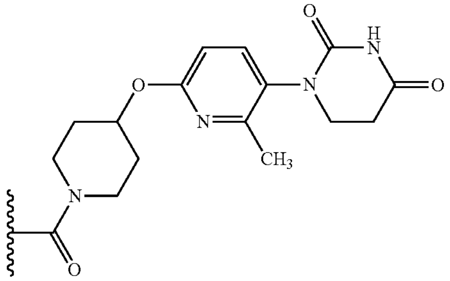
(LE-27)
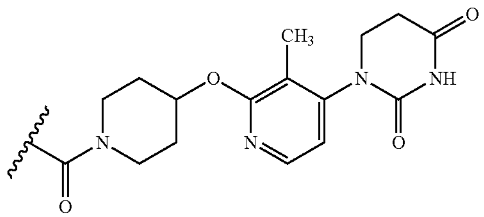
(LE-28)
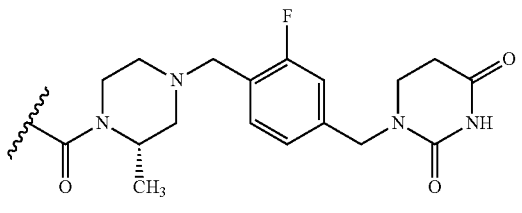

-continued
[Chem. 137-8]
(LE-29)
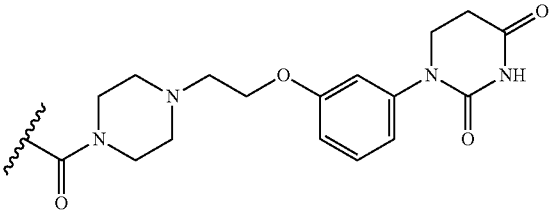
(LE-30)
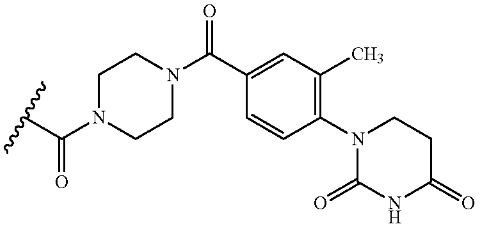
(LE-31)
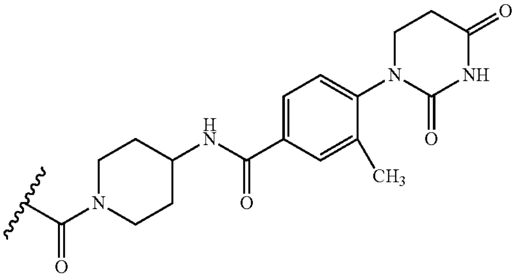
(LE-32)
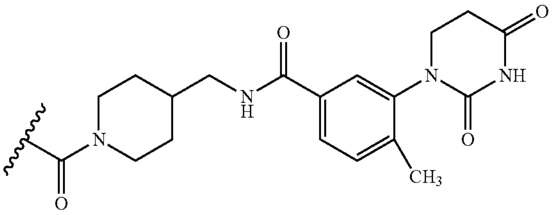
[Chem. 137-9]
(LE-33)
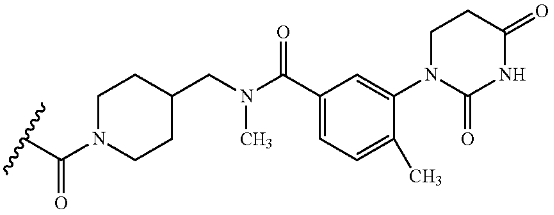
(LE-34)
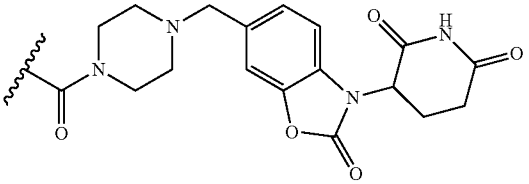
-continued
(LE-35)
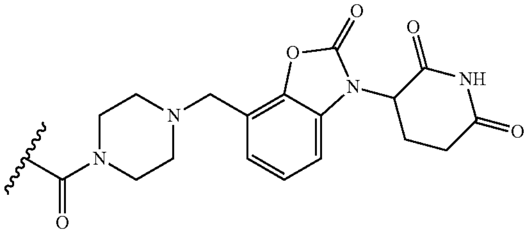
(LE-36)
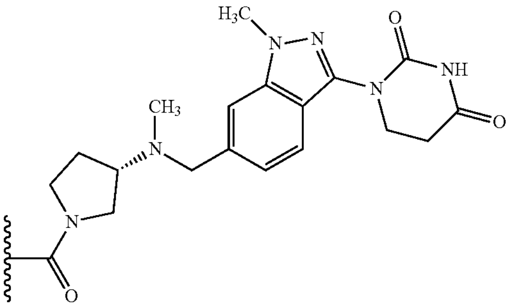
[Chem. 137-10]
(LE-37)
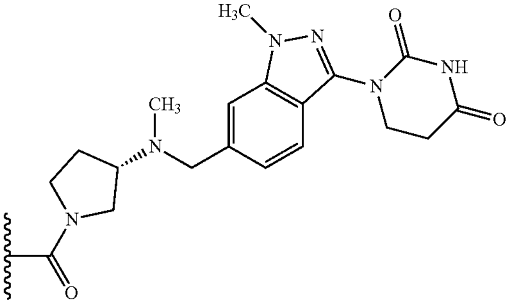
(23-2) The compound or a salt thereof described in (23-1) in which GDB is a group capable of binding to a G12D mutant KRAS protein, and
-Linker-EUB is one group selected from the group consisting of the formula (LE-5), the formula (LE-8), the formula (LE-10), the formula (LE-20) and (LE-23) below.
[Chem. 138]
(LE-5)
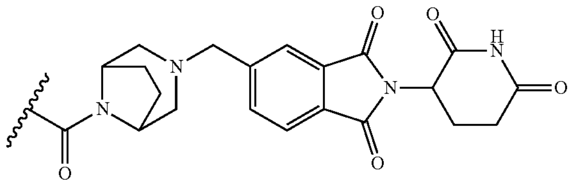

-continued (LE-8)

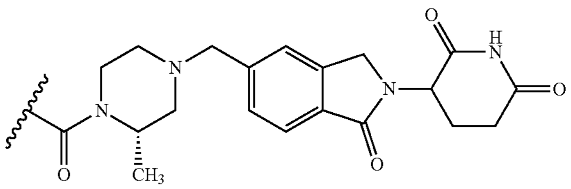

(LE-10)

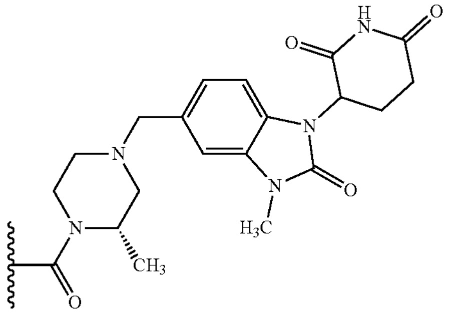

(LE-20)

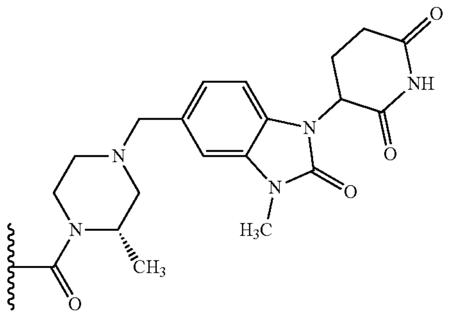

(LE-23)

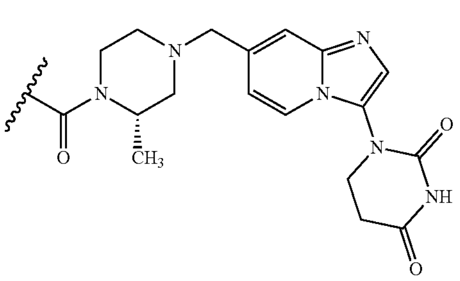

(23-3) The compound or a salt thereof described in (23-2) in which GDB is a group capable of binding to a G12D mutant KRAS protein, and -Linker-EUB is the formula (LE-10) below.

[Chem. 139]

(LE-10)

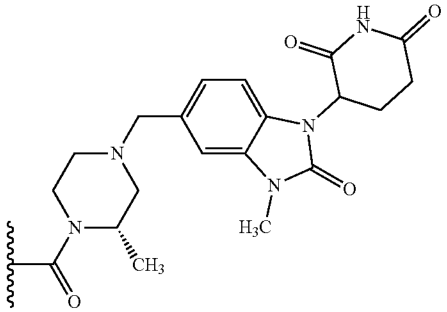

(23-4) The compound of formula (XXIII) or a salt thereof,

[Chem. 140]

GDB-Linker-EUB (XXIII)

(In the formula,

GDB is a group capable of binding to a G12D mutant KRAS protein, and

-Linker-EUB is one group selected from the group consisting of the formula (LE-1) to the formula (LE-40)).

[Chem. 141-1]

(LE-1)

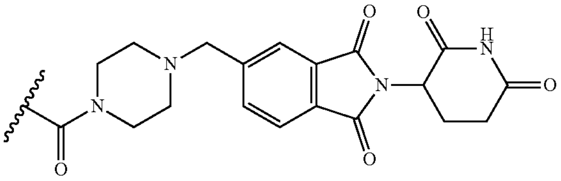

(LE-2)

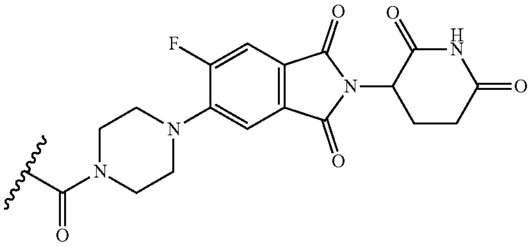

(LE-3)

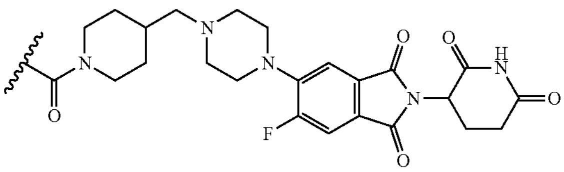

(LE-4)

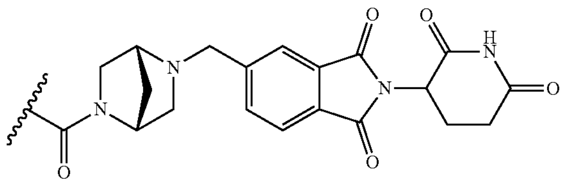

-continued
[Chem. 141-2]
(LE-5)
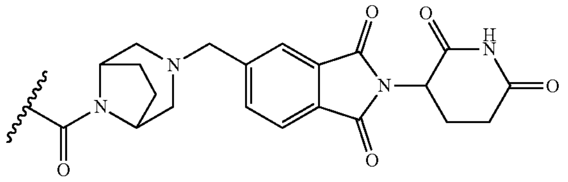
(LE-6)
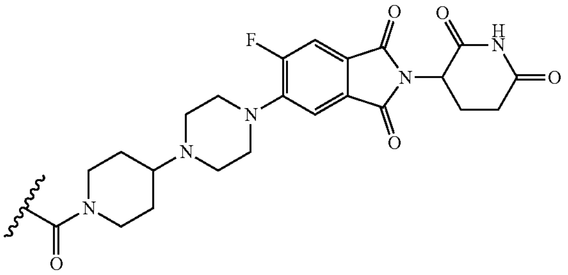
(LE-7)
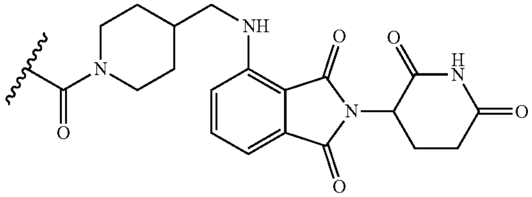
(LE-8)
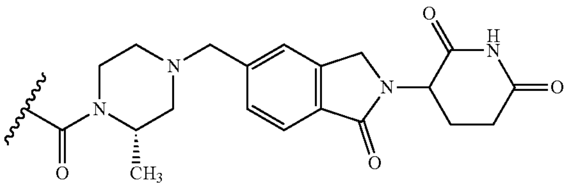
[Chem. 141-3]
(LE-9)
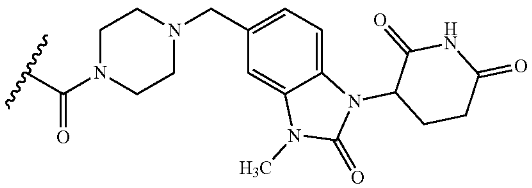
(LE-10)
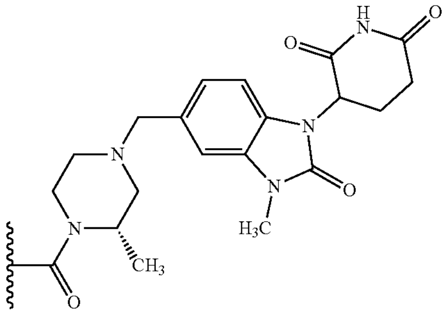
-continued
(LE-11)
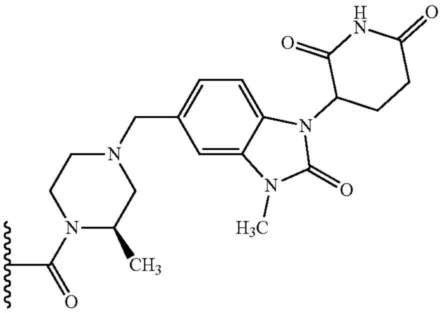
(LE-12)
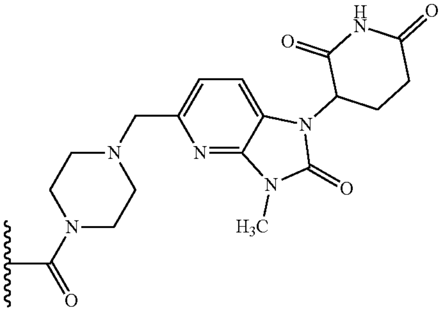
[Chem. 141-4]
(LE-13)
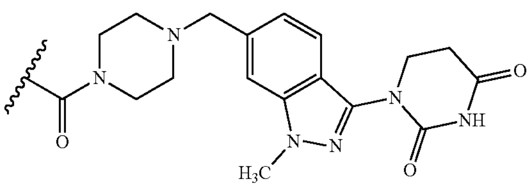
(LE-14)
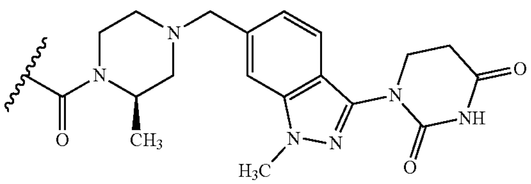
(LE-15)
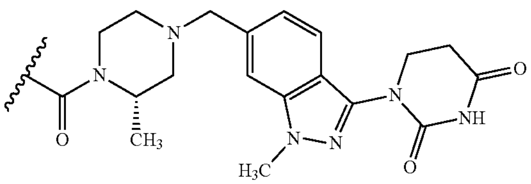
(LE-16)
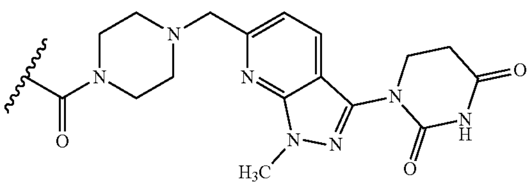

[Chem. 141-5]
(LE-17)
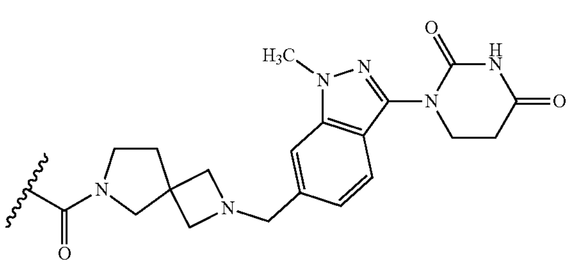
(LE-18)
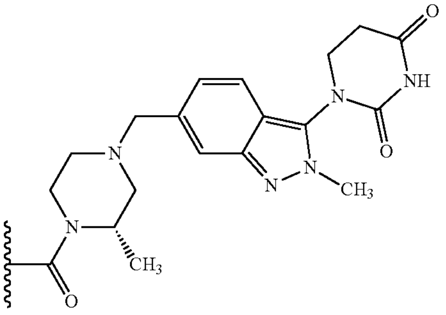
(LE-19)
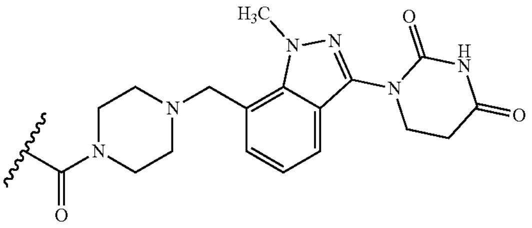
(LE-20)
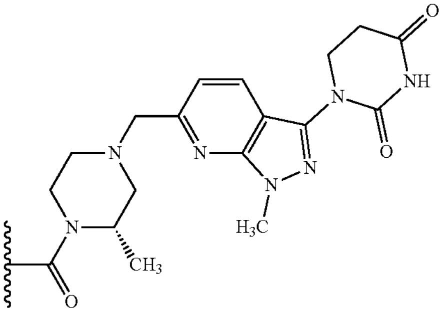
[Chem. 141-6]
(LE-21)
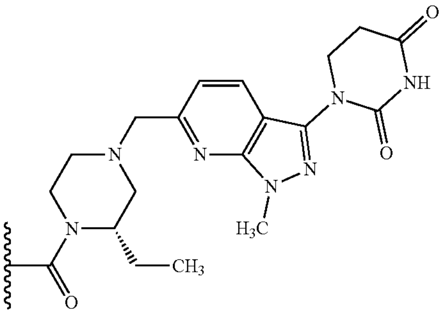
(LE-22)
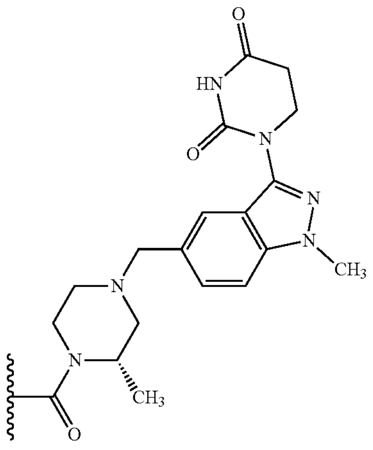
(LE-23)
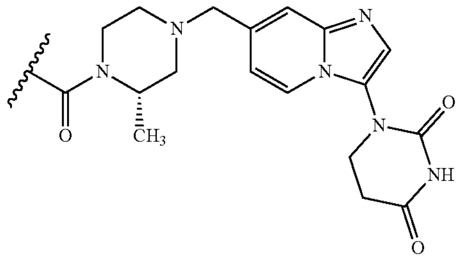
(LE-24)
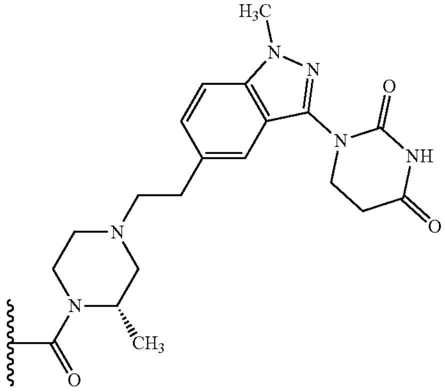
[Chem. 141-7]
(LE-25)
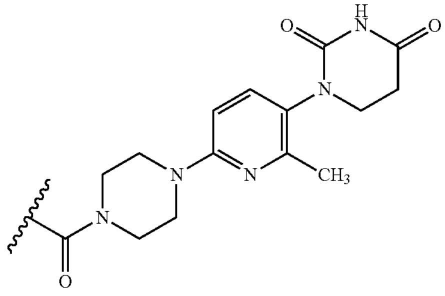

-continued
(LE-26)
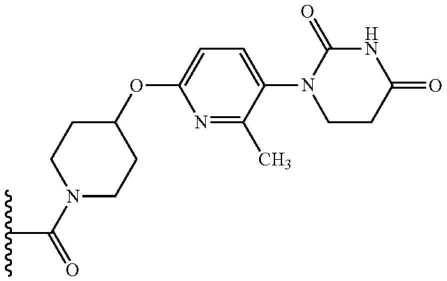
(LE-27)
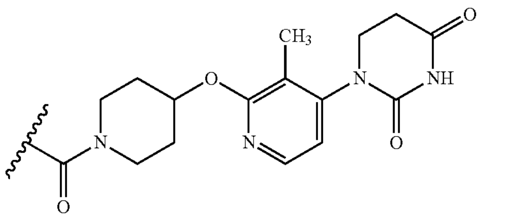
(LE-28)
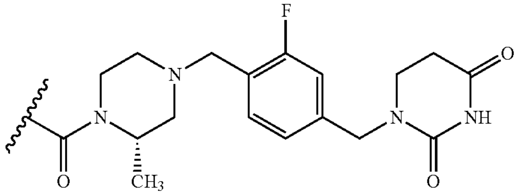
[Chem. 141-8]
(LE-29)
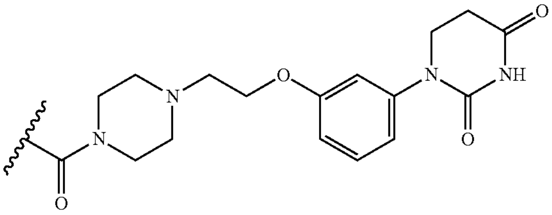
(LE-30)
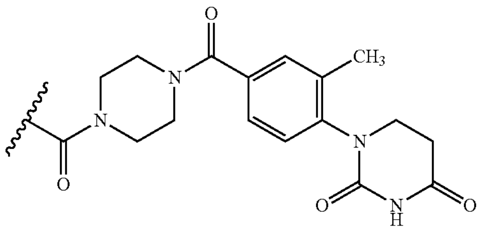
(LE-31)
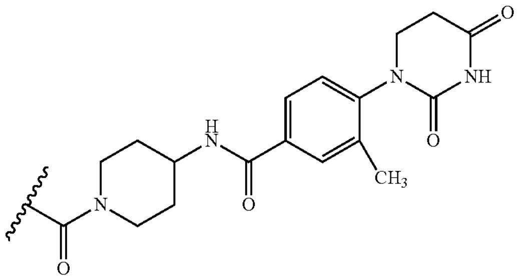
-continued
(LE-32)
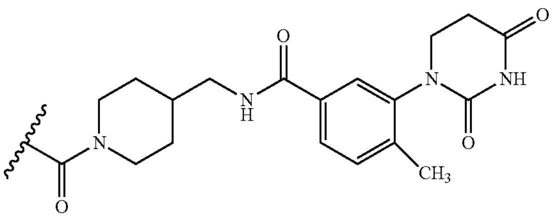
[Chem. 141-9]
(LE-33)
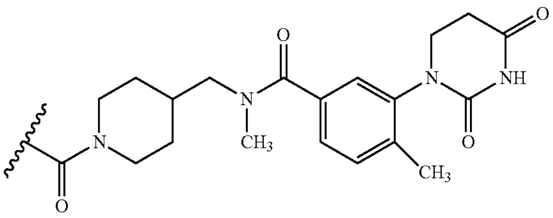
(LE-34)
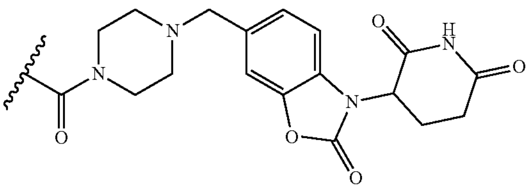
(LE-35)
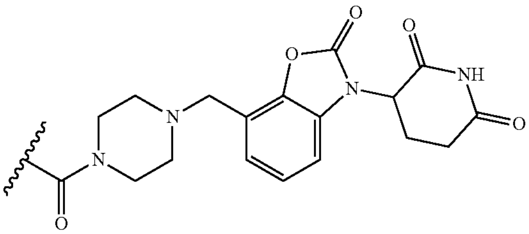
(LE-36)
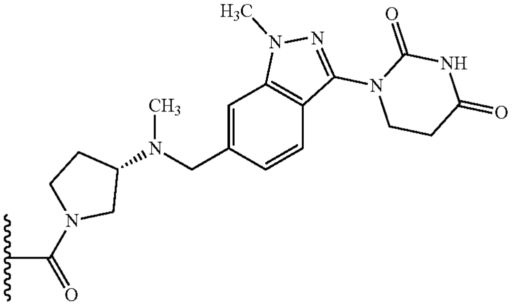

-continued

[Chem. 141-10]

(LE-37)

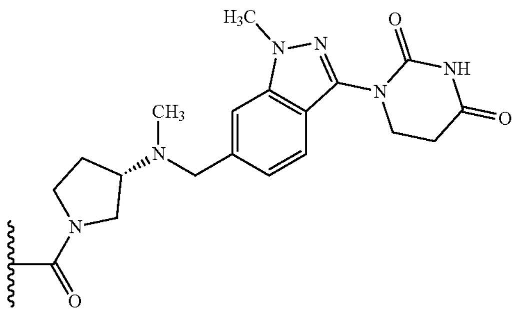

[Chem. 141-11]

(LE-38)

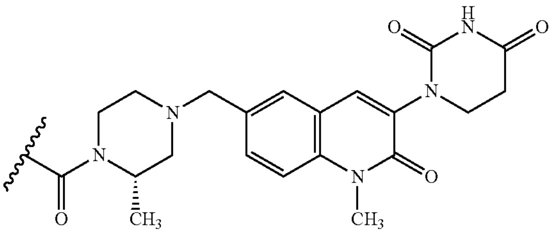

(LE-39)

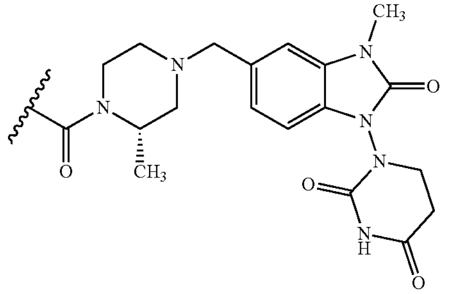

(LE-40)

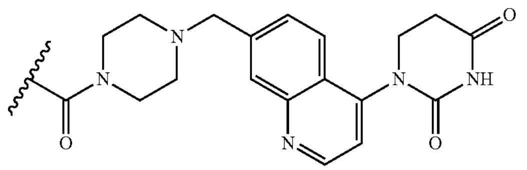

(23-5) The compound or a salt thereof described in (23-4) in which GDB is a group capable of binding to a G12D mutant KRAS protein, and -Linker-EUB is one group selected from the group consisting of the formula (LE-5), the formula (LE-8), the formula (LE-10), the formula (LE-15) and (LE-23) below.

[Chem. 142]

(LE-5)

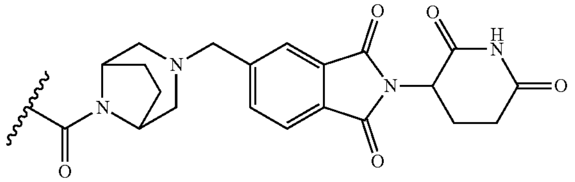

(LE-8)

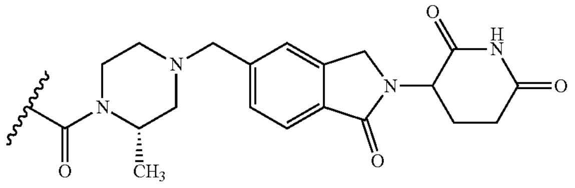

(LE-10)

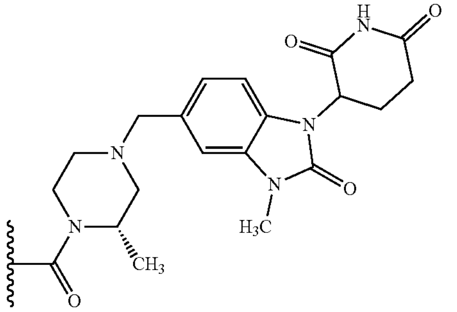

(LE-20)

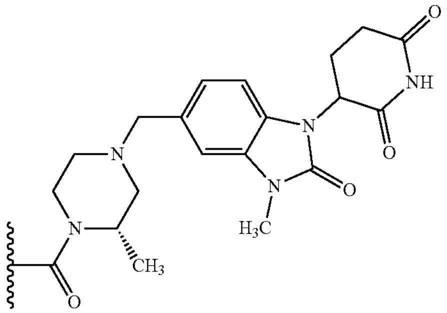

(LE-23)

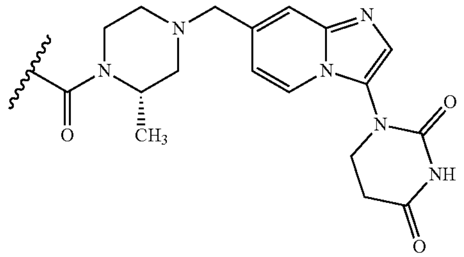

The compound of the formula (I), the formula (XXI), the formula (XXII) or the formula (XXIII) may have tautomers or geometrical isomers depending on the type of the substituent. In this specification, the compound of the formula (I), the formula (XXI), the formula (XXII) or the formula (XXIII) is sometimes described only as one of isomers, but the present invention includes isomers other than the above one and includes separated isomers or mixtures thereof.

In addition, the compound of the formula (I), the formula (XXI), the formula (XXII) or the formula (XXIII) may have an asymmetric carbon atom or an axial chirality and may have diastereomers based on them. The present invention includes separated diastereomers of the compound of the formula (I), the formula (XXI), the formula (XXII) or the formula (XXIII) or mixtures thereof.

Furthermore, the present invention also includes a pharmaceutically acceptable prodrug of the compound represented by the formula (I), the formula (XXI), the formula (XXII) or the formula (XXIII). The pharmaceutically acceptable prodrug is a compound having a group which can be converted to an amino group, a hydroxy group, a carboxyl group or the like by solvolysis or under physiological conditions. Examples of a prodrug-forming group include groups described in Prog. Med., 1985, 5, p. 2157-2161 and "Pharmaceutical Research and Development", Vol. 7, Molecular Design, Hirokawa Shoten, 1990, p. 163-198.

In addition, the salt of the compound of the formula (I), the formula (XXI), the formula (XXII) or the formula (XXIII) is a pharmaceutically acceptable salt of the compound of the formula (I) and may be an acid addition salt or a salt formed with a base depending on the type of the substituent. Examples thereof include salts shown in P. Heinrich Stahl, Handbook of Pharmaceutical Salts Properties, Selection, and Use, Wiley-VCH, 2008. Specific examples include an acid addition salt with an inorganic acid, such as hydrochloric acid, hydrobromic acid, hydroiodic acid, sulfuric acid, nitric acid or phosphoric acid, or with an organic acid, such as formic acid, acetic acid, propionic acid, oxalic acid, malonic acid, succinic acid, fumaric acid, maleic acid, lactic acid, malic acid, mandelic acid, tartaric acid, dibenzoiltartaric acid, ditoluoyltartaric acid, citric acid, methanesulfonic acid, ethanesulfonic acid, benzenesulfonic acid, p-toluenesulfonic acid, aspartic acid or glutamic acid, a salt with an inorganic metal, such as sodium, potassium, magnesium, calcium or aluminum, a salt with an organic base, such as methylamine, ethylamine or ethanolamine, a salt with various amino acids and amino acid derivatives, such as acetylleucine, lysine or ornithine, an ammonium salt and the like.

Furthermore, the present invention also includes various hydrates, solvates and crystal polymorphism substances of the compound of the formula (I), the formula (XXI), the formula (XXII) or the formula (XXIII) and a salt thereof.

The present invention also includes all the compounds of the formula (I), the formula (XXI), the formula (XXII) or the formula (XXIII) or salts thereof which are labeled with one or more pharmaceutically acceptable radioactive or non-radioactive isotopes. Examples of suitable isotopes used for isotopic labeling of the compound of the present invention include isotopes of hydrogen ($^{2}H$, $^{3}H$ and the like), carbon ($^{11}C$, $^{13}C$, $^{14}C$ and the like), nitrogen ($^{13}N$, $^{15}N$ and the like), oxygen ($^{15}O$, $^{17}O$, $^{18}O$ and the like), fluorine ($^{18}F$ and the like), chlorine ($^{36}Cl$ and the like), iodine ($^{123}I$, $^{125}I$ and the like) and sulfur ($^{35}S$ and the like).

The isotope-labeled compound of the invention of the present application can be used for research and the like such as research on tissue distribution of drugs and/or substrates. For example, radioactive isotopes such as tritium ($^{3}H$) and carbon 14 ($^{14}C$) can be used for this purpose due to the easiness of labeling and the convenience of detection.

Substitution by a heavier isotope, for example, substitution of hydrogen by deuterium (2H), is therapeutically advantageous through the improvement of metabolic stability in some cases (for example, increase in the in vivo half-life, decrease in the required dose or decrease in the interaction between drugs).

Substitution by a positron-emitting isotope ($^{11}C$, $^{18}F$, $^{15}O$, $^{13}N$ or the like) can be used in a positron emission tomography (PET) test for testing occupancy of a substrate receptor.

The isotope-labeled compound of the present invention can be generally produced by a conventional method known to a person skilled in the art or by the same production methods as in the Examples or the Production Examples and the like using suitable reagents which are labeled with an isotope in place of unlabeled reagents.

(Production Method)

The compound of the formula (I), the formula (XXI), the formula (XXII) or the formula (XXIII) and a salt thereof can be produced by applying various known synthetic methods using characteristics based on the basic structure or the type of substituent thereof. Here, depending on the type of functional group, it is sometimes effective as a production technique to substitute the functional group with an appropriate protective group (a group that can be easily converted to the functional group) in the process from a raw material to an intermediate. Examples of the protective group include protective groups described in P. G. M. Wuts and T. W. Greene, "Greene's Protective Groups in Organic Synthesis", 5th edition, John Wiley & Sons Inc., 2014 and the like, and a group appropriately selected from the protective groups is used depending on the reaction conditions. In such a method, a reaction is carried out with the protective group introduced, and then the protective group is removed, as required, whereby a desired compound can be obtained.

In addition, the prodrug of the compound of the formula (I), the formula (XXI), the formula (XXII) or the formula (XXIII) can be produced in the same manner as the above protecting group by introducing a specific group in the process from a raw material to an intermediate or by further performing a reaction using the resulting compound of formula (I), formula (XXI), formula (XXII) or formula (XXIII). The reaction can be performed by applying a method known to a person skilled in the art, such as common esterification, amidation and dehydration.

Typical methods for producing the compound of the formula (I), the formula (XXI), the formula (XXII) or the formula (XXIII) will be described below. The production methods can also be carried out with reference to a reference attached to the description. Note that the production method of the present invention is not limited to the examples described below.

In this specification, the following abbreviations are sometimes used.

DMF: N,N-dimethylformamide, DMAc: N,N-dimethylacetamide, THF: tetrahydrofuran, MeCN: acetonitrile, MeOH: methanol, EtOH: ethanol, iPrOH: isopropyl alcohol, tBuOH: tert-butyl alcohol, DOX: 1,4-dioxane, DMSO: dimethyl sulfoxide, TEA: triethylamine, DIPEA: N,N-diisopropylethylamine, tBuOK: potassium tert-butoxide, $PdCl_2(dppf)$-$CH_2Cl_2$: [1,1'-bis(diphenylphosphino)ferrocene] palladium(II) dichloride-dichloromethane adduct, Pd/C: palladium on carbon, PyBOP: (benzotriazol-1-yloxy)tripyrrolidinophosphonium hexafluorophosphate, $iPr_2O$: diisopropyl ether, HATU: 1-[bis(dimethylamino)methylene]-1H-1,2,3-triazolo[4,5-b]pyridinium 3-oxide hexafluorophosphate, DABCO: 1,4-diazabicyclo[2.2.2]octane, TfOH: trifluoromethanesulfonic acid, COMU: N-[({[(1Z)-1-cyano-2-ethoxy-2-oxoethylidene]amino}oxy)(morpholin-4-yl)methylene]-N-methylmethanaminium hexafluorophosphate, NMM: N-methylmorpholin, CDI: 1,1'carbodiimidazole, NMO: N-methylmorpholine N-oxide, LHMDS: lithium bis(trimethylsilyl)amide, NHMDS: (sodium bis(trimethylsilyl)

amide, DMEDA: N,N'-dimethylethylenediamine, Triton B: benzyltrimethylammonium hydroxide, Xantphos: 4,5-bis(diphenylphosphino)-9,9-dimethylxanthene, Ruphos: 2-dicyclohexylphosphino-2',6'-diisopropoxybiphenyl, Xphos: 2-dicyclohexylphosphino-2',4',6'-triisopropylbiphenyl, BINAP: 2,2'-bis(diphenylphosphino)-1,1'-binaphthyl.

(First Production Method)

This production method is a first method for producing a compound of the formula (I) or a salt thereof.

[Chem. 143]

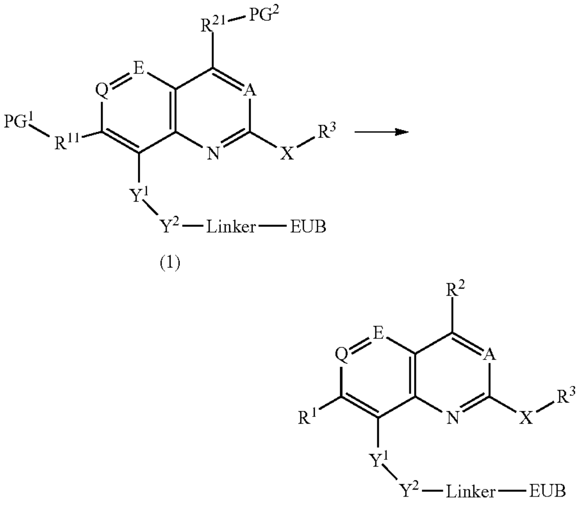

(1)

(I)

(In the formula, $PG^1$-$R^{11}$ is a group in which $PG^1$, which is a protective group, is bonded to NH or OH contained in $R^1$, and $PG^2$-$R^{21}$ is a group in which $PG^2$, which is a protecting group, is bonded to NH or OH contained in $R^2$. The same shall apply hereinafter.)

The compound of the formula (I) can be obtained by subjecting a compound (1) to deprotection reaction conditions under acidic conditions. Here, examples of the protective group which can be removed under acidic conditions include a tert-butoxycarbonyl group, a triphenylmethyl group, a tetrahydro-2H-pyran-2-yl group, a methoxymethyl group, a dimethylmethanediyl group, a tert-butylsulfinyl group and the like.

This reaction is performed by stirring the compound (1) using a deprotection reagent in an equivalent amount or an excess equivalent amount to the compound (1) in a solvent inactive for the reaction under cooling to under reflux with heat, generally for 0.1 hours to 5 days. Examples of the deprotection reagent used here include, but are not particularly limited to, acids such as hydrogen chloride (DOX solution), trifluoroacetic acid, methanesulfonic acid, phosphoric acid, p-toluenesulfonic acid and trifluoromethanesulfonic acid and a mixture thereof. Examples of the solvent used here include, but are not particularly limited to, an alcohol, such as MeOH or EtOH, a halogenated hydrocarbon, such as dichloromethane, 1,2-dichloromethane or chloroform, an ether, such as diethyl ether, THF, DOX or dimethoxyethane, DMF, DMSO, MeCN, TfOH or water and a mixture thereof.

By selecting a protective group, deprotection can also be performed by a catalytic hydrogenation reaction or under basic conditions. Examples of the protective group which can be removed by a catalytic hydrogenation reaction include a benzyl group, a p-methoxybenzyl group, a benzyloxycarbonyl group and the like. Moreover, deprotection can also be performed with a fluoride ion source such as tetra-n-butylammonium fluoride. Examples of the protective group include a tert-butyl(dimethyl)silyl group, a (trimethylsilyl)ethoxymethyl group and the like. Examples of the protective group which can be removed under basic conditions include an acetyl group, a trifluoroacetyl group, a benzoyl group and the like. Moreover, the deprotection can also be performed in stages by selecting protective groups which can be removed under different deprotection conditions as $PG^1$ and $PG^2$.

For example, the following can be referred as a reference about this reaction.

Wuts (P. G. M. Wuts) and Greene (T. W. Greene), "Greene's Protective Groups in Organic Synthesis, (5th edition, 2014)".

Note that, when the compound (1) as a raw material has an axial chirality, a stereoisomer which is obtained by once separating the compound (1) may be used for this reaction.

(Second Production Method)

This production method is a second method for producing a salt of the compound of the formula (I).

[Chem. 144]

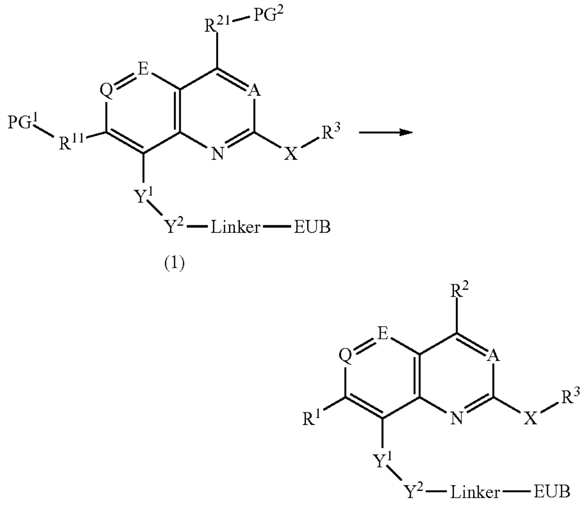

(1)

(I)

The compound of the formula (I) or a salt thereof can be obtained by subjecting the compound (1) to deprotection reaction conditions under acidic conditions, followed by isolation as a free form through treatment under basic conditions, then subjecting the compound to salt-forming reaction conditions. Here, examples of the protective group which can be removed under acidic conditions include a tert-butoxycarbonyl group, a triphenylmethyl group, a tetrahydro-2H-pyran-2-yl group, a methoxymethyl group, a dimethylmethanediyl group, a tert-butylsulfinyl group and the like.

In this reaction, the compound (1) and a deprotection reagent in an equivalent amount or an excess equivalent amount to the compound (1) are stirred in a solvent inactive for the reaction under cooling to under reflux with heat, generally for 0.1 hours to 5 days, treated with a basic aqueous solution, and then isolated as a free form. There-after, the reaction is performed by stirring the compound (1) using an acid reagent in an equivalent amount or an excess equivalent amount to the compound (1) in a solvent inactive for the reaction under cooling to under reflux with heat, generally for 0.1 hours to 5 days. Examples of the deprotection reagent used here include, but are not particularly limited to, acids such as hydrogen chloride (DOX solution), trifluoroacetic acid, methanesulfonic acid, phosphoric acid, p-toluenesulfonic acid and trifluoromethanesulfonic acid and a mixture thereof. Examples of the solvent used here include, but are not particularly limited to, an alcohol, such as MeOH or EtOH, a halogenated hydrocarbon, such as dichloromethane, 1,2-dichloromethane or chloroform, an ether, such as diethyl ether, THF, DOX or dimethoxyethane, DMF, DMSO, MeCN, TfOH or water and a mixture thereof. Examples of the acid reagent used here include acids such as hydrogen chloride (DOX solution), phosphoric acid and p-toluenesulfonic acid. Examples of the basic aqueous solution used here include, but are not particularly limited to, aqueous sodium hydrogen carbonate solution and the like.

By selecting a protective group, deprotection can also be performed by a catalytic hydrogenation reaction or under basic conditions. Examples of the protective group which can be removed by a catalytic hydrogenation reaction include a benzyl group, a p-methoxybenzyl group, a benzyloxycarbonyl group and the like. Moreover, deprotection can also be performed with a fluoride ion source such as tetra-n-butylammonium fluoride. Examples of the protective group include a tert-butyl(dimethyl)silyl group, a (trimethylsilyl)ethoxymethyl group and the like. Examples of the protective group which can be removed under basic conditions include an acetyl group, a trifluoroacetyl group, a benzoyl group and the like. Moreover, the deprotection can also be performed in stages by selecting protective groups which can be removed under different deprotection conditions as PG1 and PG2.

For example, the following can be referred as a reference about this reaction.

Wuts (P. G. M. Wuts) and Greene (T. W. Greene), "Greene's Protective Groups in Organic Synthesis, (5th edition, 2014)".

Note that, when the compound (1) as a raw material has an axial chirality, a stereoisomer which is obtained by once separating the compound (1) may be used for this reaction.

(Raw Material Production Method 1)

The production method is a method for producing a compound (1)-1 included in the compound (1), which is a raw material of the first production method and the second production method.

[Chem. 145]

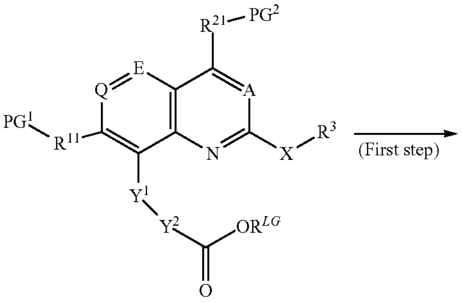

(2)

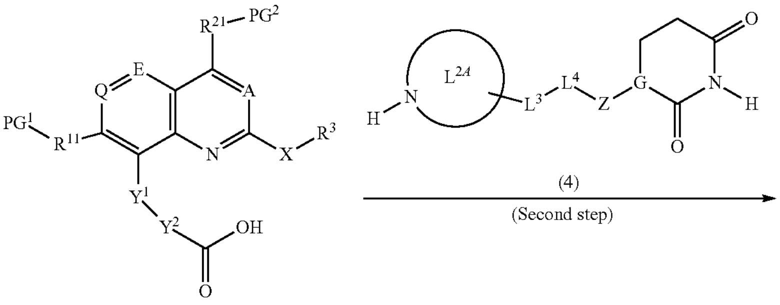

(3)

-continued

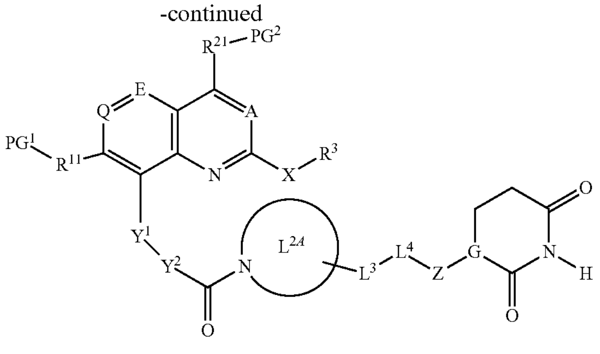

(1)-1

(In the formulae, $L^{2A}$ represents piperidinediyl optionally substituted with $C_{1-3}$ alkyl, piperazinediyl optionally substituted with $C_{1-3}$ alkyl, pyrrolidinediyl optionally substituted with $C_{1-3}$ alkyl, bridged piperazinediyl or 2,6-diazaspiro[3.4]octanediyl, and $R^{LG}$ represents a $C_{1-12}$ alkyl group. The same shall apply hereinafter.)

(First Step)

This step is a step of producing a compound (3) by subjecting the compound (2) to hydrolysis conditions.

This reaction is performed by stirring the compound (2) and a hydrolysis reagent in an equivalent amount or an excess equivalent amount to the compound (2) in a solvent inactive for the reaction under cooling to under reflux with heat, generally for 1 hours to 5 days. Examples of the hydrolysis reagent used here include, but are not particularly limited to, an aqueous sodium hydroxide solution, an aqueous potassium hydroxide solution, an aqueous lithium hydroxide solution, trimethyltin hydroxide and the like. Examples of the solvent include, but are not particularly limited to, an alcohol, such as methanol, ethanol or n-propanol, an ether-based solvent, such as tetrahydrofuran, diethyl ether or 1,4-dioxane, a halogenated hydrocarbon, such as dichloromethane, 1,2-dichloroethane or chloroform, acetonitrile, water and a mixture thereof.

(Second Step)

This step is a step of producing a compound (1)-1 by subjecting the compound (3) and the compound (4) to condensation reaction conditions.

This reaction is performed by adding a condensing agent and a base to a mixture of the compound (3) and the compound (4) in an equivalent amount or with one compound thereof in an excess equivalent amount and stirring the mixture in a solvent inactive for the reaction at room temperature, generally for 1 hour to 1 day. Examples of the condensing agent used here include, but are not particularly limited to, HATU, 1-(3-dimethylaminopropyl)-3-ethylcarbodiimide or the hydrochloride thereof, dicyclohexylcarbodiimide, 1,1'-carbonyldiimidazole, COMU, PyBOP and the like. Examples of the base include, but are not particularly limited to, an organic base, such as triethylamine, N,N-diisopropylethylamine or pyridine, and an inorganic base, such as potassium carbonate, sodium carbonate and cesium carbonate. Examples of the solvent include, but are not particularly limited to, a halogenated hydrocarbon, such as dichloromethane, 1,2-dichloroethane or chloroform, an ether-based solvent, such as tetrahydrofuran, diethyl ether or 1,4-dioxane, an alcohol, such as methanol, ethanol or n-propanol, N,N-dimethylformamide and a mixture thereof.

(Raw Material Production Method 2)

The production method is a method for producing a compound (2)-1 included in the compound (2), which is a raw material of Raw Material Production Method 1.

[Chem. 146-1]

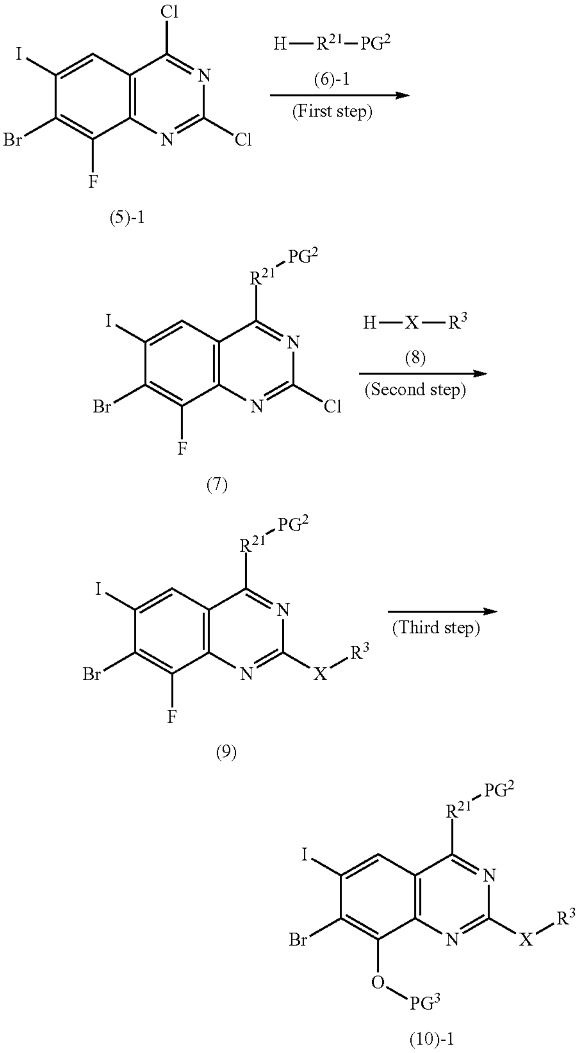

(5)-1

(7)

(9)

(10)-1

-continued

[Chem. 146-2]

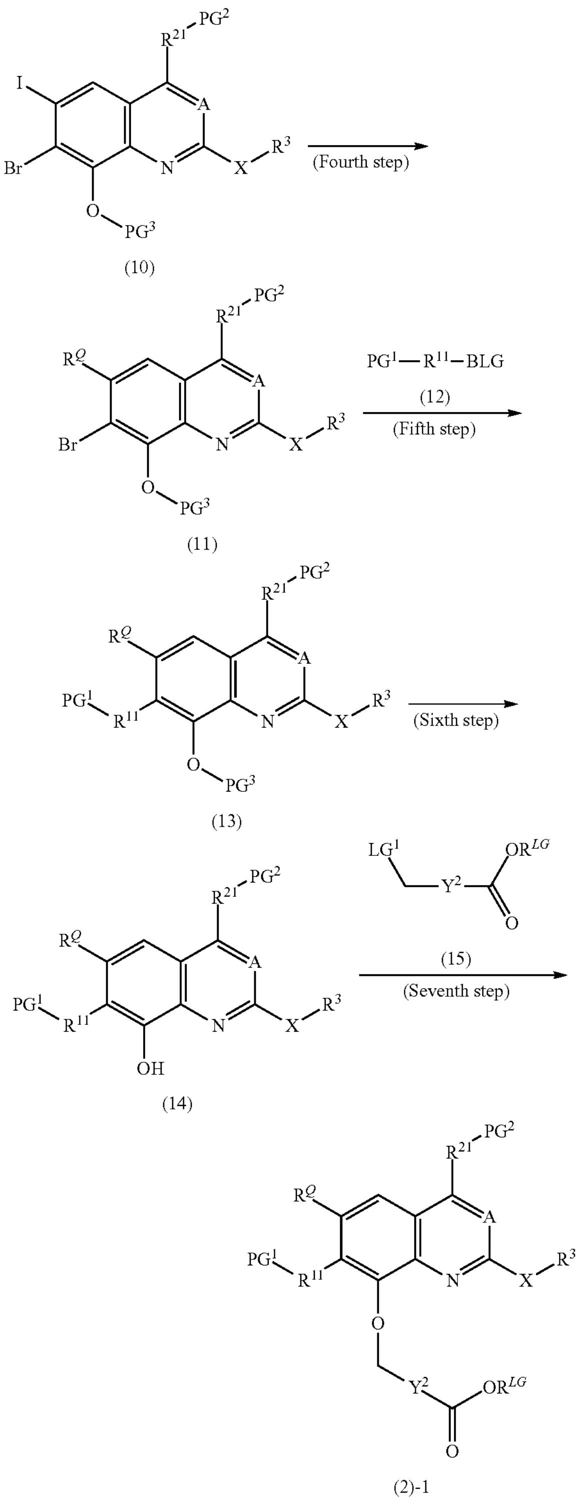

(In the formulae, $PG^3$ represents a protective group of OH, $LG^1$ represents a leaving group, and BLG represents a boronic acid group, a boronic acid group protected with a protective group of boronic acid such as a boronic acid pinacol ester group or a trifluoroboric acid salt group (hereinafter sometimes described as a boronic acid group or the like). Examples of the leaving group shown here include Cl, Br, a methanesulfonyloxy group, p-toluenesulfonyloxy group and the like. The same shall apply hereinafter.)

(First Step)

This step is a method for producing a compound (7) by an ipso substitution reaction of a compound (5)-1 and a compound (6)-1.

In this reaction, the compound (5)-1 and the compound (6)-1 are used in an equivalent amount or with one compound thereof in an excess equivalent amount, and the mixture of the compounds is stirred in a solvent inactive for the reaction or with no solvent, from under cooling to under reflux with heat, preferably at 0° C. to 120° C., generally for 0.1 hours to 5 days. Examples of the solvent used here include, but are not particularly limited to, a halogenated hydrocarbon, such as dichloromethane, 1,2-dichloroethane or chloroform, an aromatic hydrocarbon, such as benzene, toluene or xylene, an ether, such as diethyl ether, THF, dehydrated THF, DOX or 1,2-dimethoxyethane, DMF, DMAc, DMSO, ethyl acetate, MeCN, NMP and a mixture thereof. Performing the reaction in the presence of an organic base, such as TEA, DIPEA, NMM, DABCO or tBuOK, or an inorganic base, such as sodium hydride, potassium carbonate, sodium carbonate or cesium carbonate, is sometimes advantageous for smoothly promoting the reaction.

Moreover, the compound (7) can be produced by a catalytic hydrogenation reaction of the compound obtained by a Mizoroki-Heck reaction of the compound (5)-1 and the compound (6)-1.

REFERENCE

Chem. Rev., 2003, 103, p. 2945-2964

(Second Step)

This step is a method for producing a compound (9) by an ipso substitution reaction of the compound (7) and a compound (8).

The reaction conditions are the same as in the first step of the Raw Material Production Method 2.

Moreover, the compound (9) can be produced by the Negishi coupling of a compound in which a hydrogen atom of the compound (8) is converted to halogen and the compound (7).

REFERENCE

ACC. Chem. Res., 1982, 15, p. 340-348

(Third Step)

This step is a method for producing a compound (10)-1 by an ipso substitution reaction of the compound (9) and $PG^3$-OH.

Examples of the $PG^3$-OH used here include benzyl alcohol, p-methoxybenzyl alcohol and 1-phenylethanol.

The reaction conditions are the same as in the first step of the Raw Material Production Method 2.

(Fourth Step)

This step is a method for producing a compound (11) by a Suzuki-Miyaura coupling reaction of the compound (10) including both of the compound (10)-1 obtained in the third step of this synthesis method and the compound (10)-2 obtained in (Third Step of Raw Material Production Method 9) described below and a boronic acid derivative composed of a $R^Q$-boronic acid group or the like. Examples of the boronic acid group or the like used here include, but are not particularly limited to, a boronic acid group, a boronic acid ester group, a boronic acid pinacol ester group, a triol borate salt group and a trifluoroboric acid salt group.

In this reaction, the compound (10) and the boronic acid derivative composed of the $R^Q$-boronic acid group or the like are used in an equivalent amount or with one compound thereof in an excess equivalent amount, and the mixture of the compounds is stirred in a solvent inactive for the reaction, in the presence of a base and a palladium catalyst, from at room temperature to under reflux with heat, preferably at 20° C. to 140° C., generally for 0.1 hours to 5 days. Examples of the solvent used here include, but are not particularly limited to, a halogenated hydrocarbon, such as dichloromethane, 1,2-dichloroethane or chloroform, an aromatic hydrocarbon, such as benzene, toluene or xylene, an ether, such as diethyl ether, THF, DOX or 1,2-dimethoxyethane, an alcohol, such as MeOH, EtOH, isopropyl alcohol, butanol or amyl alcohol, DMF, DMSO, MeCN, 1,3-dimethylimidazolidin-2-one, water and a mixture thereof. Examples of the base include inorganic bases, such as tripotassium phosphate, sodium carbonate, potassium carbonate, sodium hydroxide, barium hydroxide and cesium carbonate. Examples of the palladium catalyst include tetrakis(triphenylphosphine)palladium, bis(triphenylphosphine)palladium(II) dichloride, [1,1'-bis(diphenylphosphino)ferrocene]palladium(II) dichloride-dichloromethane additive, (1E,4E)-1,5-diphenylpenta-1,4-dien-3-one/palladium (3:2), (2-dicyclohexylphosphino-2',6'-diisopropoxy-1,1'-biphenyl)[2-(2'-amino-1,1'-biphenyl)]palladium(II) methanesulfonate, palladium(II) acetate, mesyl[(tri-t-butylphosphine)-2-(2-aminobiphenyl)]palladium(II) and the like. Performing the reaction in the presence of a ligand, such as dicyclohexyl(2',6'-dimethoxybiphenyl-2-yl)phosphine, dicyclohexyl(2',6'-diisopropoxy-[1,1'-biphenyl]-2-yl) phosphine, 1,1'-bis(diphenylphosphino)ferrocene, butyldi-1-adamantylphosphine or di(adamantan-1-yl)(butyl) phosphine is sometimes advantageous for smoothly promoting the reaction. Alternatively, a pre-catalyst of (2-dicyclohexylphosphino-2',6'-diisopropoxy-1,1'-biphenyl)[2-(2'-amino-1,1'-biphenyl)]palladium(II) may be used as a palladium catalyst for this reaction. In addition, heating the mixture by microwave irradiation is sometimes advantageous for smoothly promoting the reaction.

REFERENCE

J. Am. Chem. Soc., 2005, 127, p. 4685-4696
Org. Lett. 2011, 13, p. 3948-3951
Org. Lett. 2012, 14, p. 1278-1281

The compound (11) (where $R^Q$ is hydrogen) can be produced by a deiodization reaction of the compound (10) with a Pd catalyst and a reducing agent.

REFERENCE

J. Org. Chem., 1977, 42, p. 3491-3494
Tetrahedron Letters 2013, 54, 5207-5210

(Fifth Step)

This step is a method for producing a compound (13) by a Suzuki-Miyaura coupling reaction of the compound (11) and a compound (12).

The reaction conditions are the same as in the fourth step of the Raw Material Production Method 2.

The compound (13) sometimes has an axial chirality and may be obtained as a mixture of stereoisomers, and each stereoisomer can be isolated by subjecting the compound (13) in which $PG^1$ is a protective group or a compound obtained by subjecting the compound (13) to a deprotection reaction (for example, compound (14)) to separation using a common separation operation, for example, ODS column chromatography or silica gel column chromatography.

(Sixth Step)

This step is a method for producing a compound (14) by deprotection by a catalytic hydrogenation reaction of the compound (13).

This reaction can be performed by stirring the compound (13) under hydrogen atmosphere, from under normal pressure to under increased pressure, in a solvent inactive for the reaction, such as MeOH, EtOH or ethyl acetate, in the presence of a metal catalyst, from under cooling to under heating, preferably at room temperature, for 1 hour to 5 days. As the metal catalyst, a palladium catalyst, such as Pd/C or palladium black, a platinum catalyst, such as a platinum plate or platinum oxide, a nickel catalyst, such as reduced nickel or Raney nickel, or the like is used. When a tetrahydro-2H-pyran-2-yl group or the like is used as a protective group of $PG^1$, a base may be used to suppress the deprotection thereof. Examples of the base used here include, but are not particularly limited to, sodium hydrogen carbonate, sodium carbonate, potassium carbonate, cesium carbonate and the like.

The compound (14) sometimes has an axial chirality and is obtained as a mixture of stereoisomers, and each stereoisomer can be isolated by subjecting the compound (14) in which $PG^1$ is a protective group or a compound obtained by subjecting the compound (14) to a deprotection reaction to separation using a common separation operation, for example, ODS column chromatography or silica gel column chromatography.

For example, the following can be referred as a reference about this reaction.

The Chemical Society of Japan, "Jikken Kagaku Koza (Courses in Experimental Chemistry)" (5th edition), Vol. 13, Maruzen, 2004

(Seventh Step)

This step is a method for producing the compound (2)-1 by a reaction of the compound (14) and a compound (15).

This reaction is performed by reacting a mixture of the compound (14) and the compound (15) in an equivalent amount or with one compound thereof in an excess equivalent amount in the presence of a base, in a solvent inactive for the reaction, from under cooling to under reflux with heat, preferably at 0° C. to 80° C., generally for 0.1 hours to 5 days. The solvent used here is not particularly limited, and examples thereof include an aromatic hydrocarbon, such as benzene, toluene or xylene, an alcohol, such as MeOH or EtOH, an ether, such as diethyl ether, THF, DOX or 1,2-dimethoxyethane, a halogenated hydrocarbon, such as dichloromethane, 1,2-dichloroethane or chloroform, DMF, DMSO, ethyl acetate, MeCN and a mixture thereof. Examples of the base include, but are not particularly limited to, an organic base, for example, such as TEA, DIPEA, 1,8-diazabicyclo[5.4.0]-7-undecene, n-butyllithium or tBuOK, and an inorganic base, such as sodium hydroxide, sodium carbonate, potassium carbonate, cesium carbonate or sodium hydride. Performing the reaction in the presence of a phase transfer catalyst, such as tetra-n-butylammonium chloride, is sometimes advantageous.

For example, the following can be referred as a reference about this reaction.

The Chemical Society of Japan, "Jikken Kagaku Koza (Courses in Experimental Chemistry)", 5th edition, Vol. 14, Maruzen, 2005

The compound (2)-1 sometimes has an axial chirality and is obtained as a mixture of stereoisomers, and each stereoisomer can be isolated by subjecting the compound (2)-1 in which $PG^1$ is a protective group or a compound obtained by subjecting the compound (2)-1 to a deprotection reaction to separation using a common separation operation, for example, ODS column chromatography or silica gel column chromatography.

The compound (15) in which $LG^1$ is a sulfonyloxy group can be produced by sulfonylation of a compound in which the moiety corresponding to $LG^1$ is a hydroxy group in the presence of a base. Examples of the sulfonylating reagent used here include, but are not particularly limited to, for example, methanesulfonylchloride, p-toluenesulfonylchloride, methanesulfonic anhydride and the like. Examples of the base include, but are not particularly limited to, for example, TEA, DIPEA, pyridine, tetramethylethylenediamine and the like.

For example, the following can be referred as a reference about this reaction.

Synthesis 1999, 9, p. 1633-1636

(Raw Material Production Method 3)

The Production Method is the Second Method for Producing a Compound (2)-1 included in the compound (2), which is a raw material of Raw Material Production Method 1.

[Chem. 147-1]

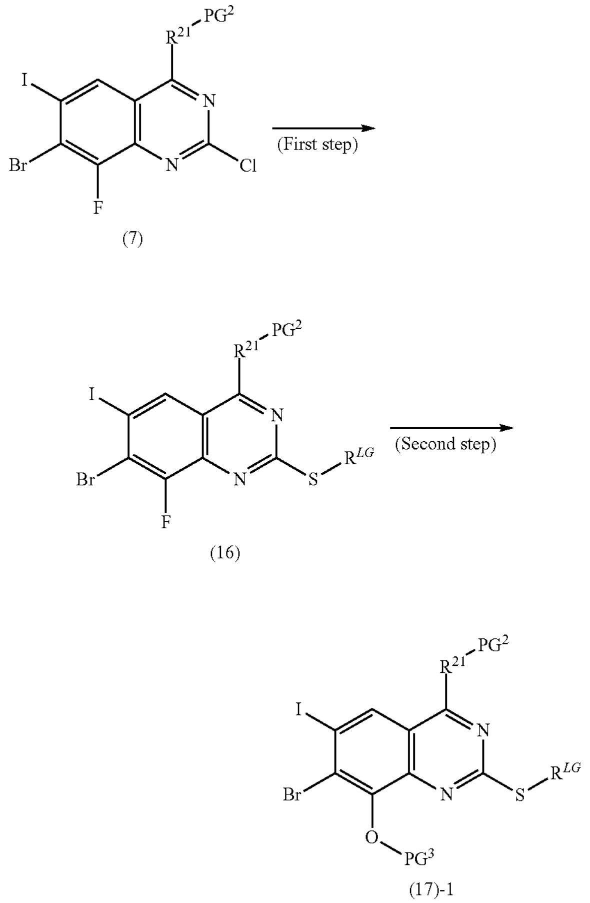

(7) (16) (17)-1

-continued

[Chem. 147-2]

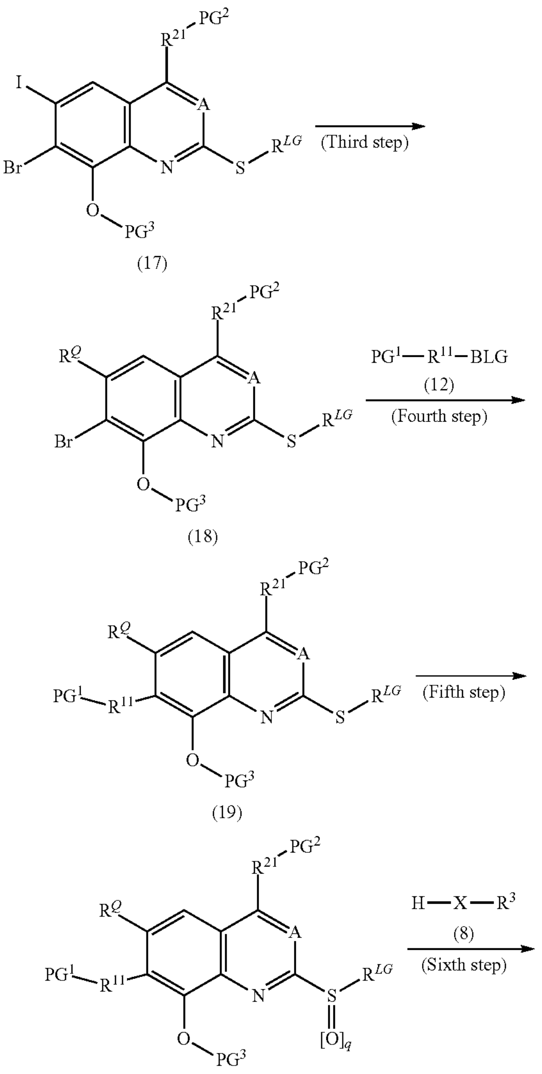

(17) (18) (19) (20)

[Chem. 147-3]

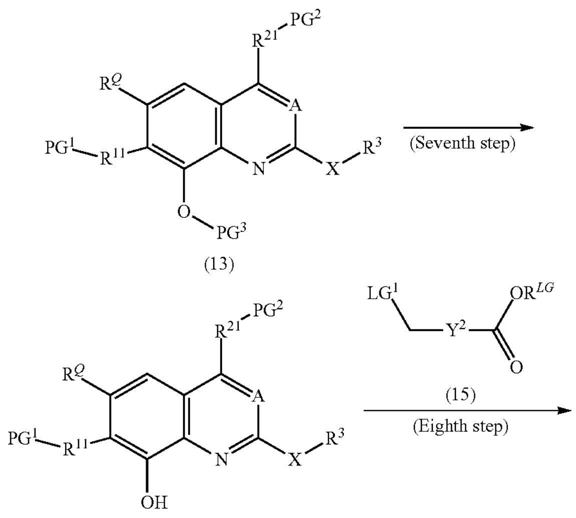

(13) (14)

-continued

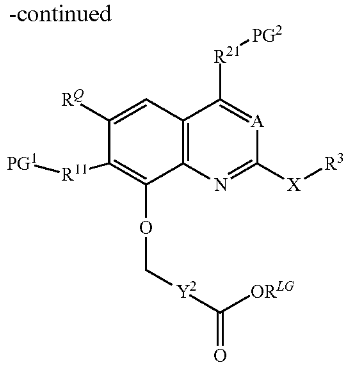

(2)-1

(In the formulae, q represents 1 or 2. The same shall apply hereinafter.)

(First Step)

This step is a method for producing a compound (16) by an ipso substitution reaction of the compound (7) and $R^{LG}$—SH. Examples of the $R^{LG}$—SH used here include $C_{1-12}$ alkylthiols, for example, ethanethiol and dodecanethiol.

The reaction conditions are the same as in the first step of the Raw Material Production Method 2.

(Second Step)

This step is a method for producing a compound (17)-1 by an ipso substitution reaction of the compound (16) and $PG^3$-OH. Examples of the $PG^3$-OH used here include benzyl alcohol, p-methoxybenzyl alcohol and 1-phenylethanol.

The reaction conditions are the same as in the first step of the Raw Material Production Method 2.

(Third Step)

This step is a method for producing a compound (18) by a Suzuki-Miyaura coupling reaction of the compound (17) including both of the compound (17)-1 obtained in the second step of this synthesis method and the compound (17)-2 obtained in (Fourth Step of Raw Material Production Method 8) described below and a boronic acid derivative composed of a $R^Q$-boronic acid group or the like.

The reaction conditions are the same as in the fourth step of the Raw Material Production Method 2.

The compound (18) (where $R^Q$ is hydrogen) can be produced by a deiodization reaction of the compound (17) with a Pd catalyst and a reducing agent.

REFERENCE

J. Org. Chem., 1977, 42, p. 3491-3494
Tetrahedron Letters 2013, 54, 5207-5210

(Fourth Step)

This step is a method for producing a compound (19) by a Suzuki-Miyaura coupling reaction of the compound (18) and the compound (12).

The reaction conditions are the same as in the fourth step of the Raw Material Production Method 2.

The compound (19) sometimes has an axial chirality and may be obtained as a mixture of stereoisomers, and each stereoisomer can be isolated by subjecting the compound (19) to separation using a common separation operation, for example, ODS column chromatography or silica gel column chromatography. The stereoisomer of the compound (19) can also be isolated by deprotecting the compound (19), isolating the stereoisomer, and then protecting it again with a protective group.

Examples of the protective group in the case of reprotection include a tetrahydro-2H-pyran-2-yl group and the like.

(Fifth Step)

This step is a method for producing a compound (20) by an oxidation reaction of the compound (19).

In this reaction, the compound (19) is treated with an oxidant in an equivalent amount or in an excess equivalent amount in a solvent inactive for the reaction, from under cooling to under heating, preferably at −20° C. to 80° C., generally for 0.1 hours to 3 days. In this reaction, oxidation with m-chloroperbenzoic acid, perbenzoic acid, peracetic acid, sodium hypochlorite or hydrogen peroxide is suitably used. Examples of the solvent include an aromatic hydrocarbon, such as benzene or toluene, an ether, such as THF, a halogenated hydrocarbon, such as chloroform or dichloromethane, DMF, DMSO, ethyl acetate, MeCN and a mixture thereof. Other examples of the oxidant include cumene hydroperoxide, Oxone, active manganese dioxide, chromic acid, potassium permanganate, sodium periodate and the like.

REFERENCE

The Chemical Society of Japan, "Jikken Kagaku Koza (Courses in Experimental Chemistry)", 5th edition, Vol. 17, Maruzen, 2004

(Sixth Step)

This step is a method for producing the compound (13) by an ipso substitution reaction of the compound (20) and a compound (8).

The reaction conditions are the same as in the first step of the Raw Material Production Method 2.

When the compound (13) has an axial chirality, the compound (13) is obtained as a mixture of stereoisomers, and each stereoisomer can be isolated by separation using a common separation operation, for example, ODS column chromatography or silica gel column chromatography.

(Seventh Step)

This step is a method for producing a compound (14) by deprotection by a catalytic hydrogenation reaction of the compound (13).

The reaction conditions are the same as in the sixth step of the Raw Material Production Method 2.

The compound (14) sometimes has an axial chirality and may be obtained as a mixture of stereoisomers, and each stereoisomer can be isolated by subjecting the compound (14) to separation using a common separation operation, for example, ODS column chromatography or silica gel column chromatography.

(Eighth Step)

This step is a method for producing a compound (2)-1 by a reaction of the compound (14) and a compound (15).

The reaction conditions are the same as in the seventh step of the Raw Material Production Method 2.

The compound (2)-1 sometimes has an axial chirality and may be obtained as a mixture of stereoisomers, and each stereoisomer can be isolated by subjecting the compound (2)-1 to separation using a common separation operation, for example, ODS column chromatography or silica gel column chromatography. The stereoisomer of the compound (2)-1 can also be isolated by deprotecting the compound (2)-1, isolating the stereoisomer, and then protecting it again with a protective group.

Examples of the protective group in the case of reprotection include a tetrahydro-2H-pyran-2-yl group and the like.

(Raw Material Production Method 4)

The production method is the third method for producing a compound (2)-1 included in the compound (2), which is a raw material of Raw Material Production Method 1.

[Chem. 148]

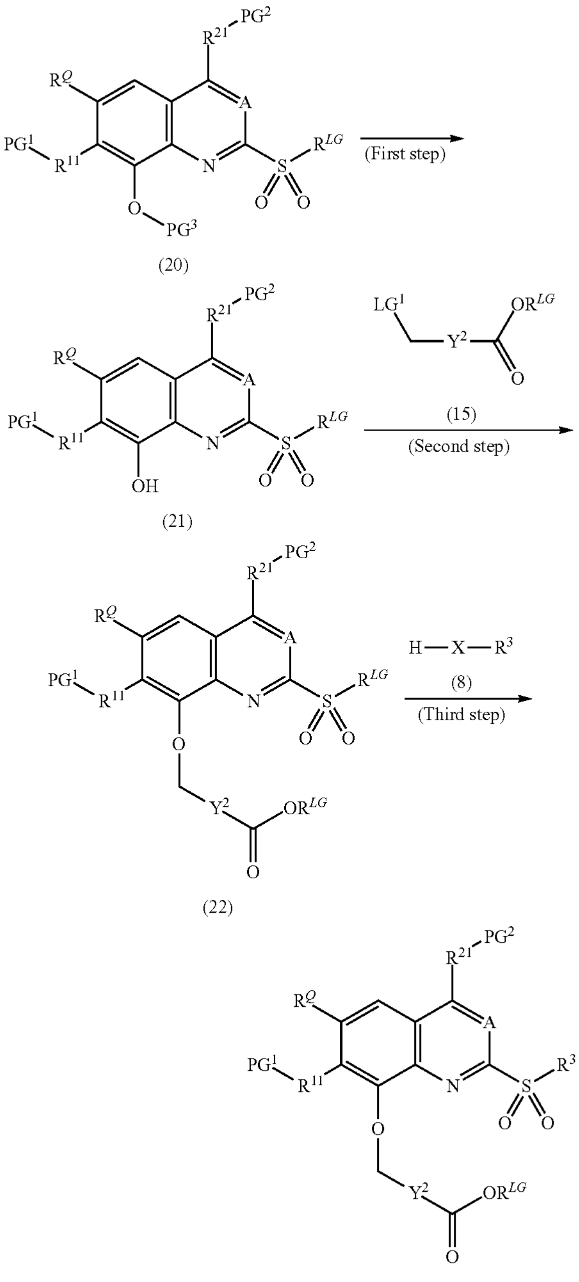

(20)
(21)
(22)
(2)-1

(First Step)

This step is a method for producing a compound (21) by deprotection by a catalytic hydrogenation reaction of the compound (20).

The reaction conditions are the same as in the sixth step of the Raw Material Production Method 2.

The compound (21) sometimes has an axial chirality and may be obtained as a mixture of stereoisomers, and each stereoisomer can be isolated by subjecting the compound (21) to separation using a common separation operation, for example, ODS column chromatography or silica gel column chromatography.

(Second Step)

This step is a method for producing a compound (22) by an alkylation reaction of the compound (21) and the compound (15).

The reaction conditions are the same as in the seventh step of the Raw Material Production Method 2.

The compound (22) sometimes has an axial chirality and may be obtained as a mixture of stereoisomers, and each stereoisomer can be isolated by subjecting the compound (22) to separation using a common separation operation, for example, ODS column chromatography or silica gel column chromatography. The stereoisomer of the compound (22) can also be isolated by deprotecting the compound (22), isolating the stereoisomer, and then protecting it again with a protective group.

Examples of the protective group in the case of reprotection include a tetrahydro-2H-pyran-2-yl group and the like.

(Third Step)

This step is a method for producing a compound (2)-1 by an ipso substitution reaction of a compound (22) and a compound (8).

The reaction conditions are the same as in the first step of the Raw Material Production Method 2.

The compound (2)-1 sometimes has an axial chirality and is obtained as a mixture of stereoisomers, and each stereoisomer can be isolated by subjecting the compound (2)-1 or a compound obtained by subjecting the compound (2)-1 to a deprotection reaction to separation using a common separation operation, for example, ODS column chromatography or silica gel column chromatography.

The reaction conditions for the deprotection reaction used here are the same as in the step described in the Production Method 1.

(Raw Material Production Method 5)

The production method is a method for producing a compound (2)-2 included in the compound (2), which is a raw material of Raw Material Production Method 1.

[Chem. 149-1]

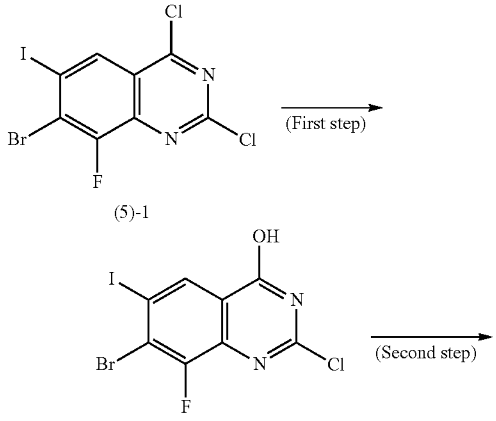

(5)-1
(23)

-continued
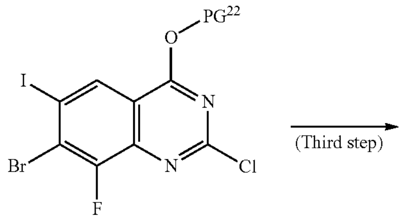
(24)
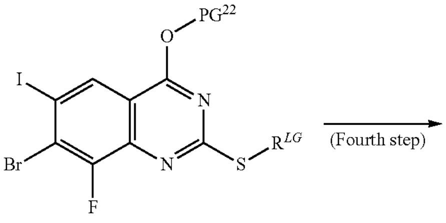
(25)
[Chem. 149-2]
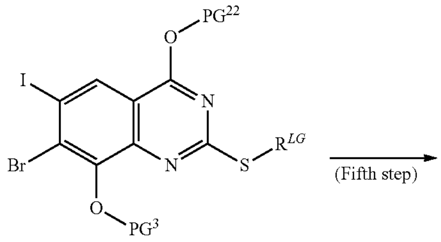
(26)
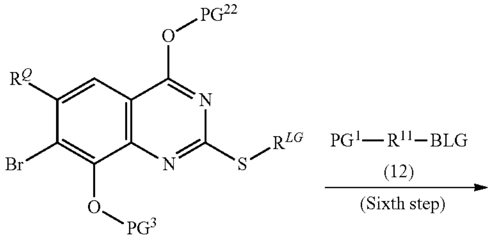
(27)
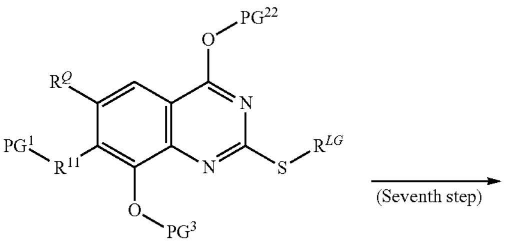
(28)
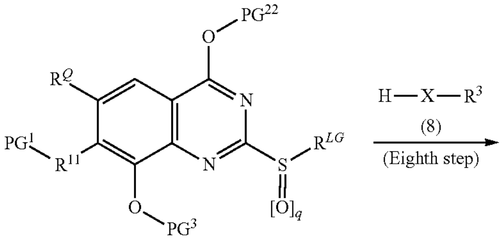
(29)
-continued
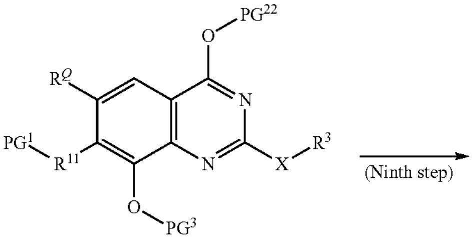
(30)
[Chem. 149-3]
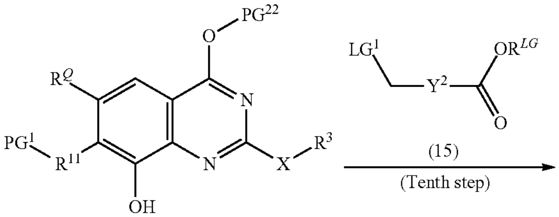
(31)
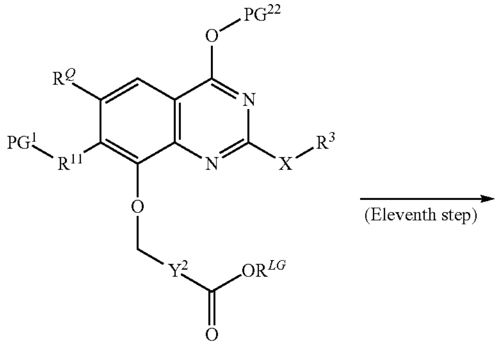
(32)
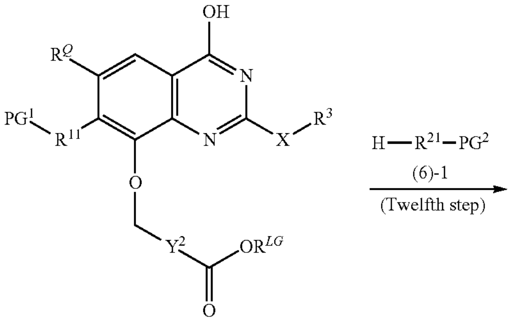
(33)
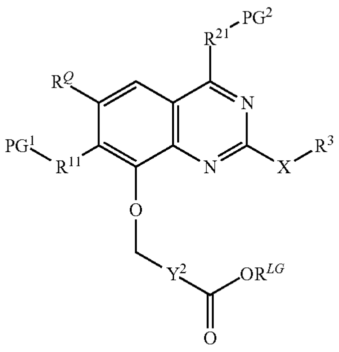
(L2)-2

(In the formulae, $PG^{22}$ represents a tert-butyl group. The same shall apply hereinafter.)

(First Step)

This step is a method for producing a compound (23) by hydrolysis of the compound (5)-1.

This reaction is performed by stirring the compound (5)-1 and a hydrolysis reagent in an equivalent amount or with one in an excess equivalent amount in a solvent inactive for the reaction under cooling to under reflux with heat, generally for 0.1 hours to 5 days. Examples of the solvent used here include, but are not particularly limited to, an alcohol, such as methanol or ethanol, acetone, DMF, THF and the like. In addition, a mixed solvent of the above solvent and water is sometimes suitable for the reaction. Examples of the hydrolysis reagent include, but are not particularly limited to, an aqueous sodium hydroxide solution, an aqueous potassium hydroxide solution, sodium hydroxide, potassium hydroxide, lithium hydroxide and the like.

For example, the following can be referred as a reference about this reaction.

The Chemical Society of Japan, "Jikken Kagaku Koza (Courses in Experimental Chemistry) (5th edition)", Vol. 16 (2005) (Maruzen)

Angew. Chem. Int. Ed. 2005, 44, p. 1378-1382.

(Second Step)

This step is a method for producing a compound (24) by protection of a hydroxy group of the compound (23) with the tert-butyl group.

This reaction is performed by stirring the compound (23) and a tert-butyl protection reagent in an equivalent amount or with one in an excess equivalent amount in a solvent inactive for the reaction under cooling to under reflux with heat, generally for 0.1 hours to 5 days. Examples of the solvent used here include, but are not particularly limited to, an ether, such as THF or DOX, a halogenated hydrocarbon, such as dichloromethane, tBuOH, DMF and the like. Examples of the tert-butyl protection reagent include, but are not particularly limited to, isobutene, 2-tert-butyl-1,3-diisopropylisourea and the like.

Moreover, the compound (24) can be produced by a dehydration condensation reaction of the compound (23) and tBuOH.

For example, the following can be referred as a reference about this reaction.

P. G. M. Wuts and T. W. Greene, "Greene's Protective Groups in Organic Synthesis", 5th edition, John Wiley & Sons Inc., 2014

Org. Lett., 2012, 14, 17, p. 4678-4681

(Third Step)

This step is a method for producing a compound (25) by an ipso substitution reaction of the compound (24) and $R^{LG}$—SH.

The reaction conditions are the same as in the first step of the Raw Material Production Method 2.

(Fourth Step)

This step is a method for producing a compound (26) by an ipso substitution reaction of the compound (25) and $PG^3$-OH.

The reaction conditions are the same as in the first step of the Raw Material Production Method 2.

(Fifth Step)

This step is a method for producing a compound (27) by a Suzuki-Miyaura coupling reaction of the compound (26) and a boronic acid derivative composed of a $R^Q$-boronic acid group or the like.

The reaction conditions are the same as in the fourth step of the Raw Material Production Method 2.

The compound (27) (where $R^Q$ is hydrogen) can be produced by a deiodization reaction of the compound (26) with a Pd catalyst and a reducing agent.

REFERENCE

J. Org. Chem., 1977, 42, p. 3491-3494

Tetrahedron Letters 2013, 54, 5207-5210

(Sixth Step)

This step is a method for producing a compound (28) by a Suzuki-Miyaura coupling reaction of the compound (27) and a compound (12).

The reaction conditions are the same as in the fourth step of the Raw Material Production Method 2.

The compound (28) sometimes has an axial chirality and may be obtained as a mixture of stereoisomers, and each stereoisomer can be isolated by subjecting the compound (28) to separation using a common separation operation, for example, ODS column chromatography or silica gel column chromatography. The stereoisomer of the compound (28) can also be isolated by deprotecting the compound (28), isolating the stereoisomer, and then protecting it again with a protective group.

Examples of the protective group in the case of reprotection include a tetrahydro-2H-pyran-2-yl group and the like.

(Seventh Step)

This step is a method for producing a compound (29) by an oxidation reaction of the compound (28).

The reaction conditions are the same as in the fifth step of the Raw Material Production Method 3.

For example, the following can be referred as a reference about this reaction.

P. G. M. Wuts and T. W. Greene, "Greene's Protective Groups in Organic Synthesis", 5th edition, John Wiley & Sons Inc., 2014

(Eighth Step)

This step is a method for producing a compound (30) by an ipso substitution reaction of a compound (29) and a compound (8).

The reaction conditions are the same as in the first step of the Raw Material Production Method 2.

(Ninth Step)

This step is a method for producing a compound (31) by deprotection by a catalytic hydrogenation reaction of the compound (30).

The reaction conditions are the same as in the sixth step of the Raw Material Production Method 2.

The compound (31) sometimes has an axial chirality and may be obtained as a mixture of stereoisomers, and each stereoisomer can be isolated by subjecting the compound (31) to separation using a common separation operation, for example, ODS column chromatography or silica gel column chromatography.

(Tenth Step)

This step is a method for producing a compound (32) by an alkylation reaction of the compound (31) and the compound (15).

The reaction conditions are the same as in the seventh step of the Raw Material Production Method 2.

The compound (32) sometimes has an axial chirality and may be obtained as a mixture of stereoisomers, and each stereoisomer can be isolated by subjecting the compound (32) to separation using a common separation operation, for example, ODS column chromatography or silica gel column chromatography. The stereoisomer of the compound (32)

can also be isolated by deprotecting the compound (32), isolating the stereoisomer, and then protecting it again with a protective group.

(Eleventh Step)

This step is a method for producing a compound (33) by subjecting the compound (32) to a deprotection reaction.

The reaction conditions are the same as in the step described in the first production method.

The compound (33) can be protected with a protective group again after deprotection. Examples of the protective group in the case of reprotection include a tetrahydro-2H-pyran-2-yl group and the like.

Further, a series of the above deprotection and protection with a protective group again may be carried out as a one step reaction.

(Twelfth Step)

This step is a method for producing a compound (2)-2 by a reaction of the compound (33) and a compound (6)-1.

In this reaction, the compound (33) and the compound (6)-1 are used in an equivalent amount or with one in an excess equivalent amount, and the mixture of the compounds is stirred in the presence of a condensing agent, in a solvent inactive for the reaction, from under cooling to under heating, preferably at −20° C. to 60° C., generally for 0.1 hours to 5 days. Examples of the solvent include an aromatic hydrocarbon, such as benzene, or toluene, an ether, such as THF or DOX, a halogenated hydrocarbon, such as chloroform or dichloromethane, an alcohol, such as methanol or ethanol, DMF, DMSO, ethyl acetate, MeCN and a mixture thereof. Examples of the condensing agent include PyBOP, HATU, CDI and the like. Performing the reaction in the presence of an organic base, such as TEA, DIPEA or NMM, or an inorganic base, such as potassium carbonate, sodium carbonate or cesium carbonate, is sometimes advantageous for smoothly promoting the reaction.

(Raw Material Production Method 6)

The production method is a method for producing a compound (13)-1 included in the compound (13), which is an intermediate of Raw Material Production Method 2.

[Chem. 150]

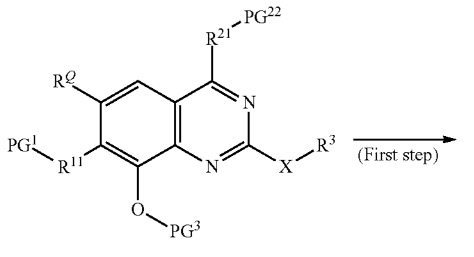

(30)

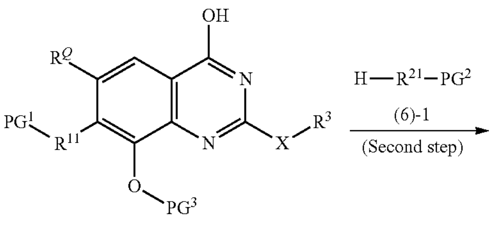

(34)

-continued

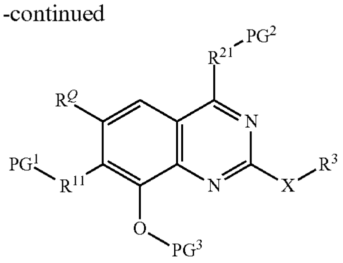

(13)-1

(First Step)

This step is a method for producing a compound (34) by subjecting the compound (30) to a deprotection reaction.

The reaction conditions are the same as in the step described in the first production method.

The compound (34) can be protected with a protective group again after deprotection. Examples of the protective group in the case of reprotection include a tetrahydro-2H-pyran-2-yl group and the like.

Further, a series of the above deprotection and protection with a protective group again may be carried out as a one step reaction.

(Second Step)

This step is a method for producing a compound (13)-1 by a reaction of the compound (34) and the compound (6)-1.

The reaction conditions are the same as in the twelfth step of the Raw Material Production Method 5.

(Raw Material Production Method 7)

This production method is a method for producing the compound (30), which is a raw material of Raw Material Compound Method 6.

[Chem. 151]

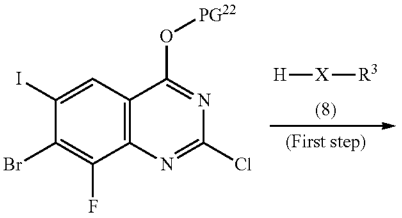

(24)

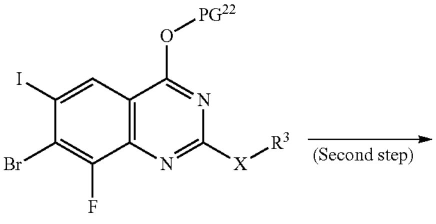

(37)

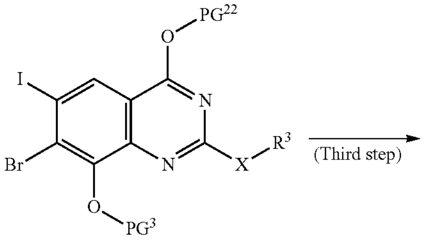

(38)

-continued

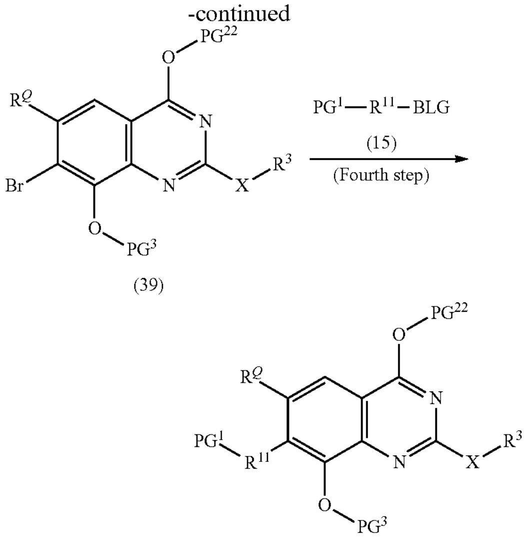

(39)

(30)

(First Step)

This step is a method for producing a compound (37) by an ipso substitution reaction of the compound (24) and the compound (8).

The reaction conditions are the same as in the first step of the Raw Material Production Method 2.

(Second Step)

This step is a method for producing a compound (38) by an ipso substitution reaction of the compound (37) and $PG^3$-OH.

The reaction conditions are the same as in the first step of the Raw Material Production Method 2.

(Third Step)

This step is a method for producing a compound (39) by a Suzuki-Miyaura coupling reaction of the compound (38) and a boronic acid derivative composed of a $R^Q$-boronic acid group or the like.

The reaction conditions are the same as in the fourth step of the Raw Material Production Method 2.

The compound (39) (where $R^Q$ is hydrogen) can be produced by a dehydrogenation reaction of the compound (38) with a Pd catalyst and a reducing agent.

REFERENCE

J. Org. Chem., 1977, 42, p. 3491-3494

Tetrahedron Letters 2013, 54, 5207-5210

(Fourth Step)

This step is a method for producing the compound (30) by a Suzuki-Miyaura coupling reaction of the compound (39) and the compound (15).

The reaction conditions are the same as in the fourth step of the Raw Material Production Method 2.

The compound (30) sometimes has an axial chirality and may be obtained as a mixture of stereoisomers, and each stereoisomer can be isolated by subjecting the compound (30) to separation using a common separation operation, for example, ODS column chromatography or silica gel column chromatography. The stereoisomer of the compound (30) can also be isolated by deprotecting the compound (30), isolating the stereoisomer, and then protecting it again with a protective group.

(Raw Material Production Method 8)

The production method is a method for producing a compound (17)-2 included in the compound (17), which is an intermediate of Raw Material Production Method 3.

[Chem. 152]

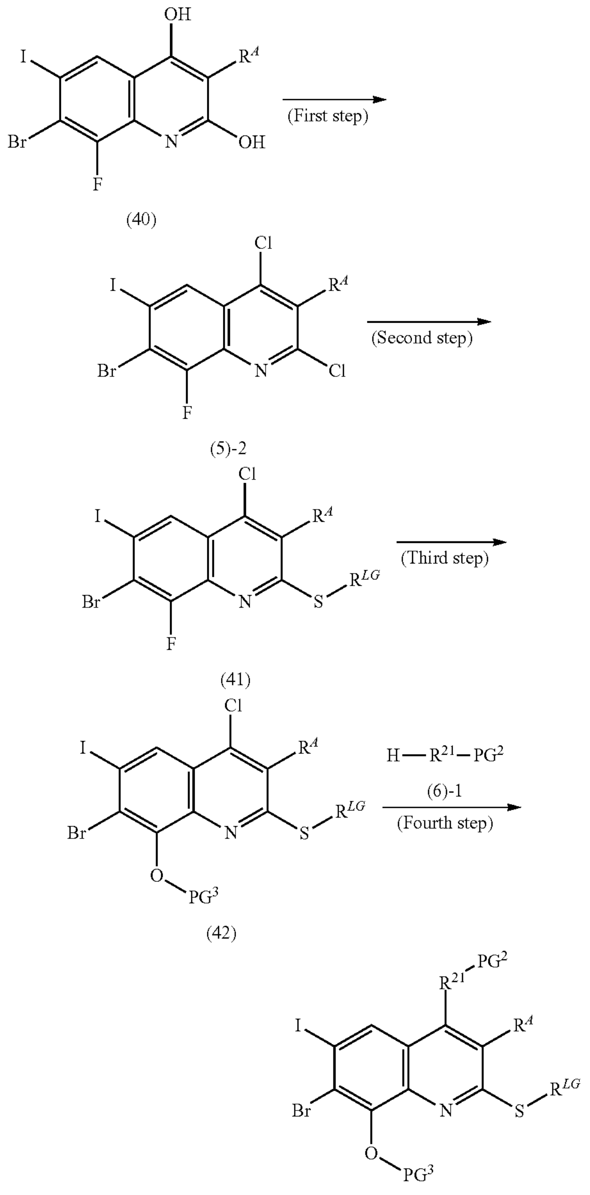

(40)

(5)-2

(41)

(42)

(17)-2

(First Step)

This step is a method for producing a compound (5)-2 by a chlorination reaction of the compound (40).

This reaction is performed by stirring a mixture of the compound (40) and a chlorinating agent in an equivalent amount or with one in an excess equivalent amount in a solvent inactive for the reaction or with no solvent, from under cooling to under reflux with heat, preferably at 60° C. to under reflux with heat, generally for 0.1 hours to 5 days. Examples of the solvent used here include, but are not particularly limited to, an aromatic hydrocarbon, such as toluene, an ether, such as THF or DOX, a halogenated hydrocarbon, such as dichloromethane, DMF, DMAc and the like. Examples of the chlorinating agent include phosphorus oxychloride, thionyl chloride the like. Performing the reaction in the presence of an organic base, such as TEA, DIPEA or NMM, is sometimes advantageous for smoothly promoting the reaction.

(Second Step)

This step is a method for producing a compound (41) by an ipso substitution reaction of the compound (5)-2 and $R^{LG}$—SH.

The reaction conditions are the same as in the first step of the Raw Material Production Method 2.

(Third Step)

This step is a method for producing a compound (42) by an ipso substitution reaction of the compound (41) and $PG^3$-OH.

The reaction conditions are the same as in the first step of the Raw Material Production Method 2.

(Fourth Step)

This step is a method for producing the compound (17)-2 by an ipso substitution reaction of the compound (42) and the compound (6)-1.

The reaction conditions are the same as in the first step of the Raw Material Production Method 2.

(Raw Material Production Method 9)

This production method is a method for producing a compound (10)-2.

[Chem. 153]

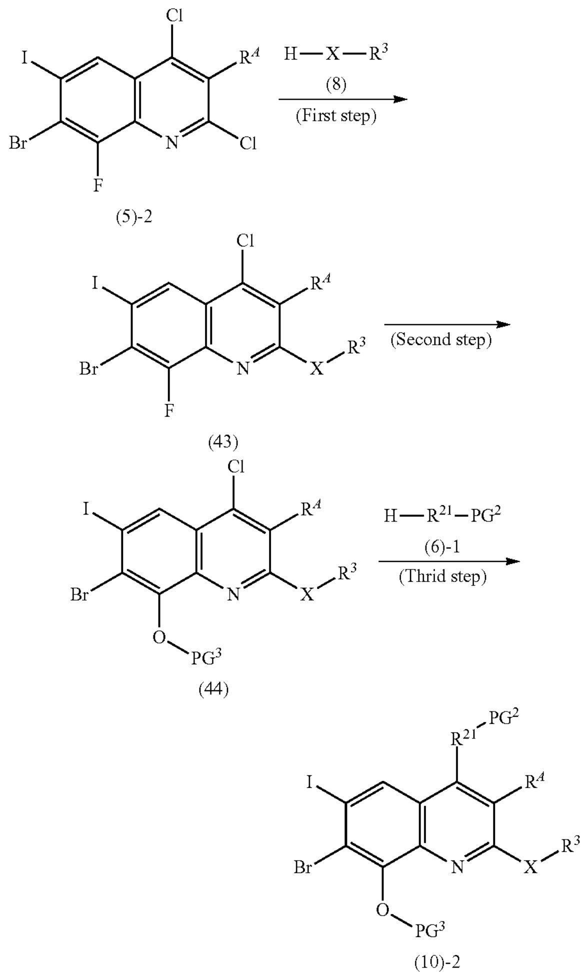

(First Step)

This step is a method for producing a compound (43) by an ipso substitution reaction of a compound (5)-2 and a compound (8).

The reaction conditions are the same as in the first step of the Raw Material Production Method 2.

Moreover, the compound (43) can be produced by the Negishi coupling of a compound in which a hydrogen atom of the compound (8) is converted to halogen and the compound (5)-2.

(Second Step)

This step is a method for producing a compound (44) by an ipso substitution reaction of the compound (43) and $PG^3$-OH.

The reaction conditions are the same as in the first step of the Raw Material Production Method 2.

(Third Step)

This step is a method for producing the compound (10)-2 by an ipso substitution reaction of a compound (44) and the compound (6)-1.

The reaction conditions are the same as in the first step of the Raw Material Production Method 2.

(Raw Material Production Method 10)

The production method is a method for producing a compound (4)-1 included in the compound (4), which is an intermediate of Raw Material Production Method 1.

[Chem. 154]

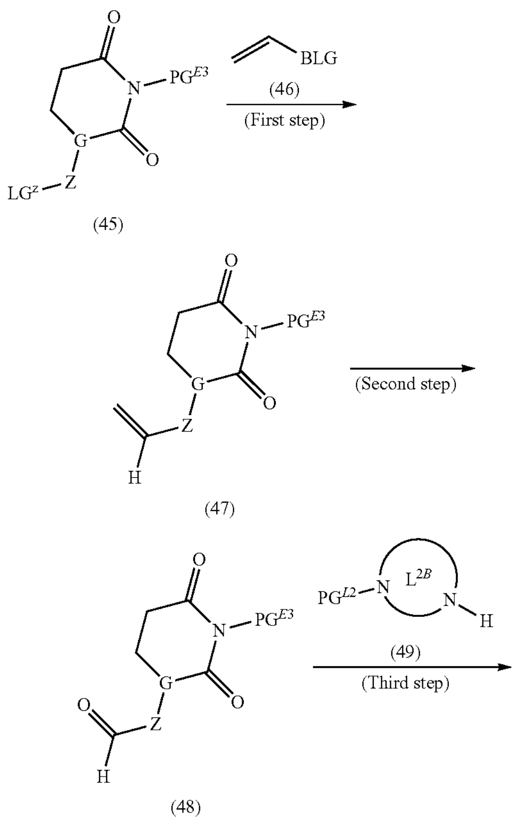

-continued

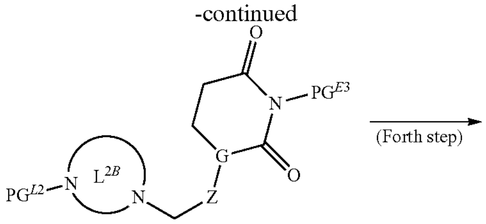

(4)-1'

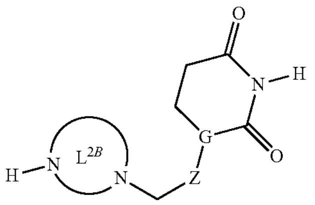

(4)-1

(In the formula, $L^{2B}$ represents piperazinediyl optionally substituted with $C_{1-3}$ alkyl, bridged piperazinediyl or 2,6-diazaspiro[3.4]octanediyl, $PG^{E3}$ and $PG^{L2}$ represent a protective group of NH, $LG^{Z}$ represents a leaving group, and BLG represents a boronic acid group, a boronic acid group protected with a protective group of boronic acid such as a boronic acid pinacol ester group or a trifluoroboric acid salt group (hereinafter sometimes described as a boronic acid group or the like). The compound (4)-1 can also be produced by a similar reaction of a compound in which the $PG^{E3}$ moiety of the compound (45) is H. Examples of the leaving group shown here include Cl, Br, a methanesulfonyloxy group, p-toluenesulfonyloxy group and the like. The same shall apply hereinafter.)

(First Step)

This step is a step of producing a compound (47) by subjecting the compound (45) and the compound (46) to Suzuki-Miyaura coupling reaction conditions.

The reaction conditions are the same as in the fourth step of the Raw Material Production Method 2.

(Second Step-1A)

This step is a step of producing a 1,2-diol compound by subjecting a compound of the compound (47) to oxidation reaction conditions.

This reaction is performed by stirring the compound of the compound (47), an oxidant and a re-oxidant in an excess equivalent amount in a solvent inactive for the reaction, from under ice-bath cooling to room temperature, generally for 1 hour to 2 days. Examples of the oxidant used here include, but are not particularly limited to, osmium(VIII) tetroxide, PI osmium(VIII) oxide, PEM-polystyrene microencapsulated osmium(VIII) oxide and the like. Examples of the re-oxidant used here include, but are not particularly limited to, NMO, trimethylamine oxide, tBuOOH, $K_3Fe(CN)_6$ and the like. Examples of the solvent used here include, but are not particularly limited to, an ether-based solvent, such as tetrahydrofuran, diethyl ether or 1,4-dioxane, a halogenated hydrocarbon, such as dichloromethane, dichloroethane or chloroform, tBuOH, acetone, acetonitrile, toluene, water and a mixture thereof.

(Second Step-1B)

This step is a step of producing the compound (48) by subjecting the compound obtained in the (second step-TA) above to oxidative cleavage reaction conditions.

This reaction is performed by stirring the compound obtained in the (second step-1A) and an oxidant in an equivalent amount or an excess equivalent amount to the compound in a solvent inactive for the reaction, from under ice-bath cooling to room temperature, generally for 1 hour to 2 days. Examples of the oxidant used here include, but are not particularly limited to, sodium periodate, periodic acid and the like. Examples of the solvent used here include, but are not particularly limited to, an ether-based solvent, such as tetrahydrofuran, diethyl ether or 1,4-dioxane, acetonitrile, water, a halogenated hydrocarbon, such as dichloromethane, dichloroethane or chloroform, and a mixture thereof. Alternatively, the (second step-TA) and (second step-1B) above can also be carried out as one-step reactions.

REFERENCE

J. Org. Chem. 1956, 21, 4, 478-479

(Second Step-2)

This step is a step of producing the compound (48) by subjecting a compound of the compound (47) to oxidation reaction conditions. This step is a method to obtain the compound (48), which is different from the second step-TA and the second step-1B.

This reaction is performed by stirring the compound of the compound (47) in a solvent inactive for the reaction from under ice-bath cooling to room temperature under an ozone atmosphere, generally for 1 hour to 1 day, and then treating it with a reducing agent. Examples of the reducing agent used here include, but are not particularly limited to, dimethyl sulfide, triphenylphosphine, metallic zinc and the like. Examples of the solvent used here include, but are not particularly limited to, an alcohol-based solvent, such as methanol or ethanol, a halogenated hydrocarbon, such as dichloromethane, dichloroethane or chloroform, ethyl acetate, a mixture thereof and the like.

(Third Step)

This step is a step of producing a compound of the compound (4)-1' by subjecting the compound (48) and the compound (49) to reductive amination reaction conditions.

This reaction is performed by stirring the compound (48) and the compound (49) in an equivalent amount or with one in an excess equivalent amount in the presence of a reducing agent and acetic acid, in a solvent inactive for the reaction, from under ice-bath cooling to room temperature, generally for 1 hour to 5 days. Examples of the reducing agent used here include, but are not particularly limited to, $NaBH(OAc)_3$, 2-picoline borane, $NaBH_3CN$ and the like. Examples of the solvent include, but are not particularly limited to, a halogenated hydrocarbon, such as dichloromethane, dichloroethane or chloroform, an ether-based solvent, such as tetrahydrofuran, diethyl ether or 1,4-dioxane, an alcohol-based solvent, such as methanol or ethanol, acetonitrile and the like.

(Fourth Step)

This step is a step of producing a compound (4)-1 by subjecting (4)-1' to deprotection conditions.

The reaction conditions are the same as in the first production method.

(Raw Material Production Method 11)

This production method is a method for producing a compound (45)-1' included in the compound (45), which is a raw material of Raw Material Production Method 10, and a compound (45)-1 in which the $PG^{E3}$ moiety of the compound (45)-1' included in the compound (45) is H.

[Chem. 155]

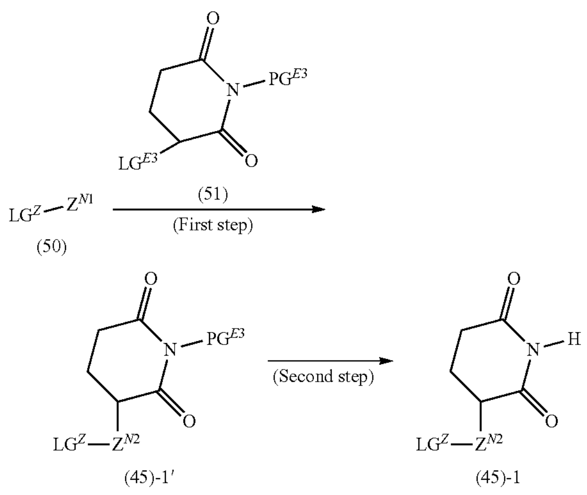

(In the formula, $LG^{E3}$ represents a leaving group. Examples of the leaving group shown here include Cl, Br, a methanesulfonyloxy group, a p-toluenesulfonyloxy group and the like. The same shall apply hereinafter.)

(First Step)

This step is a step of producing the compound (45)-1' by subjecting the compound (50) and the compound (51) to alkylation reaction conditions.

This reaction is performed by stirring the compound (50) and the compound (51) in an equivalent amount or with one in an excess equivalent amount in the presence of a base, in a solvent inactive for the reaction, from under ice-bath cooling to under reflux with heat, generally for 1 hour to 1 day. Examples of the base used here include, but are not particularly limited to, sodium hydride, tBuOK, LHMDS, NHMDS, potassium carbonate, cesium carbonate and the like. Examples of the solvent used here include, but are not particularly limited to, an ether-based solvent, such as tetrahydrofuran, diethyl ether or 1,4-dioxane, DMF, MeCN and the like.

Here, when the compound obtained by the above reaction has a protective group, the compound (45)-1' can be obtained by subjecting the compound obtained to the reaction followed by deprotection reaction conditions.

The reaction conditions are the same as in the first production method.

(Second Step)

This step is a step of producing a compound (45)-1 by subjecting (45)-1' to deprotection conditions.

The reaction conditions are the same as in the first production method.

(Raw Material Production Method 12)

This production method is a method for producing a compound (45)-2' included in the compound (45), which is a raw material in Raw Material Production Method 10, and a compound (45)-2 in which the $PG^{E3}$ moiety of the compound (45)-2' included in the compound (45) is H.

[Chem. 156]

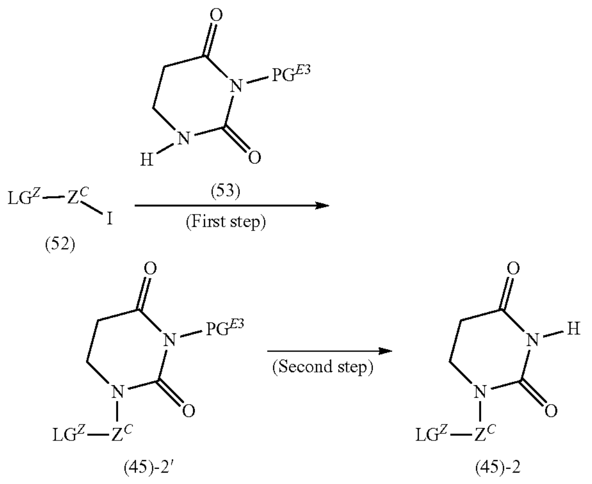

(First Step)

This step is a step of producing the compound (45)-2' by subjecting the compound (52) and the compound (53) to coupling reaction conditions using a copper catalyst.

This reaction is performed by stirring the compound (52) and the compound (53) in an equivalent amount or with one in an excess equivalent amount using a copper catalyst, a ligand and a base in a solvent inactive for the reaction, from at room temperature to under reflux with heat, generally for 1 hour to 5 days. Examples of the copper catalyst include, but are not particularly limited to, copper(I) iodide, copper (I) chloride, copper(I) oxide and the like. Examples of the ligand used here include, but are not particularly limited to, DMEDA, trans-N,N'-dimethylcyclohexane-1,2' diamine and the like. Examples of the base used here include, but are not particularly limited to, an organic base, such as diisopropylethylamine or triethylamine, and an inorganic base, such as potassium carbonate, cesium carbonate, sodium carbonate or tripotassium phosphate. Examples of the solvent used here include, but are not particularly limited to, an ether-based solvent, such as tetrahydrofuran or 1,4-dioxane, an alcohol-based solvent, such as methanol or ethanol, dimethyl sulfoxide, N,N-dimethylformamide, water and the like. In addition, heating the mixture by microwave irradiation is sometimes advantageous for smoothly promoting the reaction.

(Second Step)

This step is a step of producing a compound (45)-2 by subjecting (45)-2' to deprotection conditions.

The reaction conditions are the same as in the first production method.

(Raw Material Production Method 13)

This production method is a method for producing a compound (4)-2 included in the compound (4), which is an intermediate of Raw Material Production Method 1.

[Chem. 157]

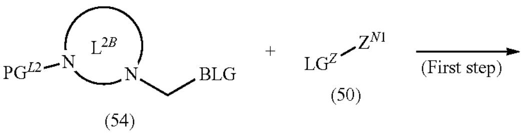

-continued

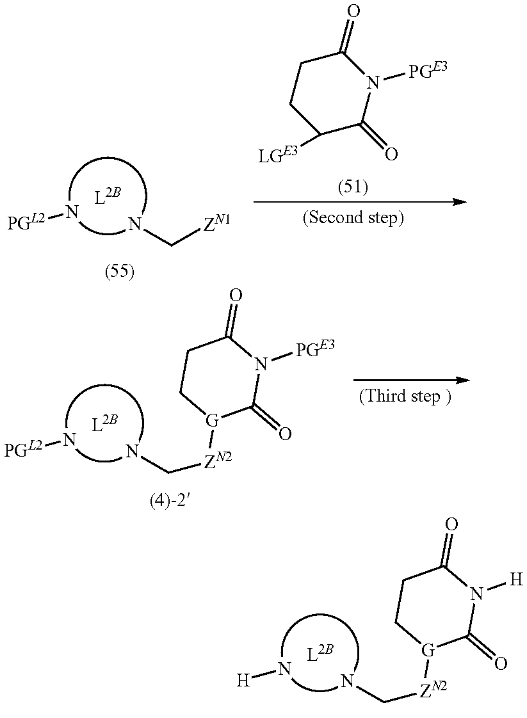

(55)

(4)-2'

(4)-2

(In the formula, a compound in which the $PG^{E3}$ moiety of the compound (4)-2' is H can also be produced by a similar reaction of a compound in which the $PG^{E3}$ moiety of the compound (51) is H. The same shall apply hereinafter.)

(First Step)

This step is a step of producing a compound (55) by subjecting the compound (54) and the compound (50) to Suzuki-Miyaura coupling reaction conditions.

The reaction conditions are the same as in the fourth step of the Raw Material Production Method 2.

(Second Step)

This step is a step of producing a compound of the compound (4)-2' by subjecting the compound (55) and the compound (51) to alkylation reaction conditions.

The reaction conditions are the same as in the first step of the Raw Material Production Method 11.

(Third Step)

This step is a step of producing a compound (4)-2 by subjecting (4)-2' to deprotection conditions.

The reaction conditions are the same as in the first production method.

(Raw Material Production Method 14)

This production method is a method for producing a compound (4)-3 included in the compound (4), which is an intermediate of Raw Material Production Method 1.

[Chem. 158]

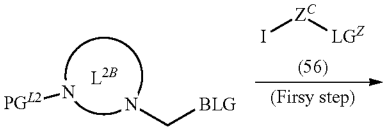

(54)

-continued

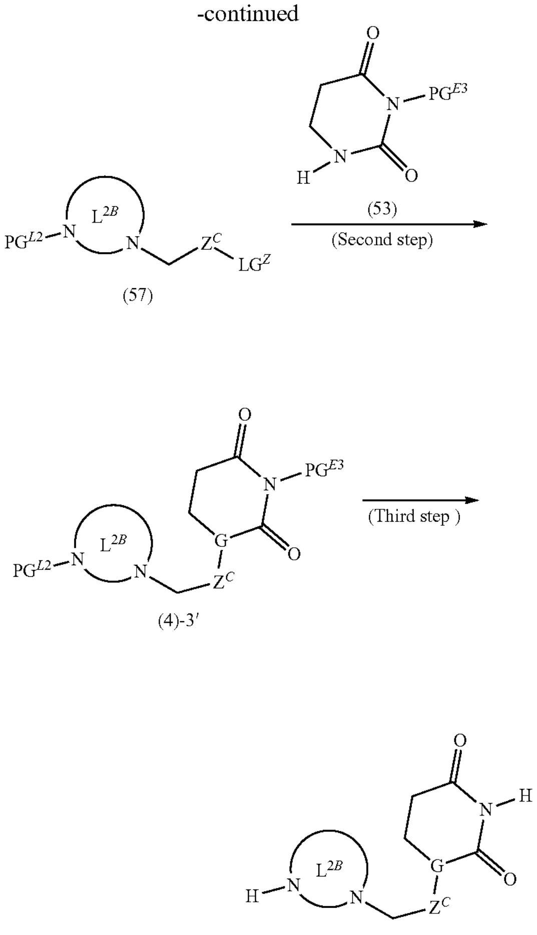

(57)

(4)-3'

(4)-3

(In the formula, $LG^Z$ represents a leaving group. Examples of the leaving group shown here include Cl, Br, a methanesulfonyloxy group, a p-toluenesulfonyloxy group and the like. The same shall apply hereinafter.)

(First Step)

This step is a step of producing a compound (57) by subjecting the compound (54) and the compound (56) to Suzuki-Miyaura coupling reaction conditions.

The reaction conditions are the same as in the fourth step of the Raw Material Production Method 2.

(Second Step)

This step is a step of producing a compound (4)-3' by subjecting the compound (57) and the compound (53) to coupling reaction conditions using a copper catalyst.

The reaction conditions are the same as in the first step of the Raw Material Production Method 12.

(Third Step)

This step is a step of producing a compound (4)-3 by subjecting (4)-3' to deprotection conditions.

The reaction conditions are the same as in the first production method.

(Raw Material Production Method 15)

This production method is a method for producing the compound (4)-1 included in the compound (4), which is an intermediate of Raw Material Production Method 1.

[Chem. 159]

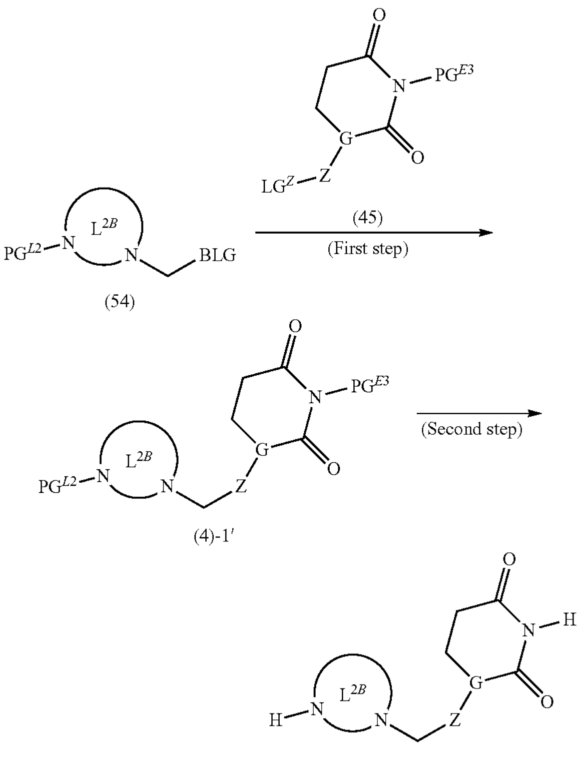

(45)
(54)
(4)-1'
(4)-1

(In the formula, the compound (4)-1 can also be produced by a similar reaction of a compound in which the $PG^{E3}$ moiety of the compound (45) is H. The same shall apply hereinafter.)

(First Step)

This step is a step of producing the compound (4)-1' by subjecting the compound (54) and the compound (45) to Suzuki-Miyaura coupling reaction conditions.

The reaction conditions are the same as in the fourth step of the Raw Material Production Method 2.

(Second Step)

This step is a step of producing the compound (4)-1 by subjecting (4)-1' to deprotection conditions.

The reaction conditions are the same as in the first production method.

(Raw Material Production Method 16)

This production method is a method for producing a compound (4)-5 included in the compound (4), which is an intermediate of Raw Material Production Method 1.

[Chem. 160]

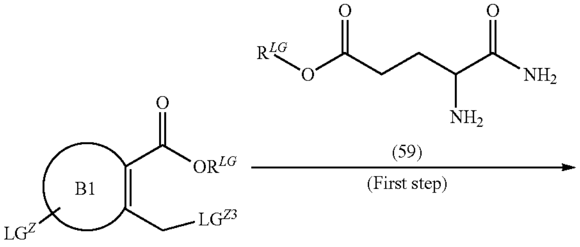

(59)
(58)

-continued

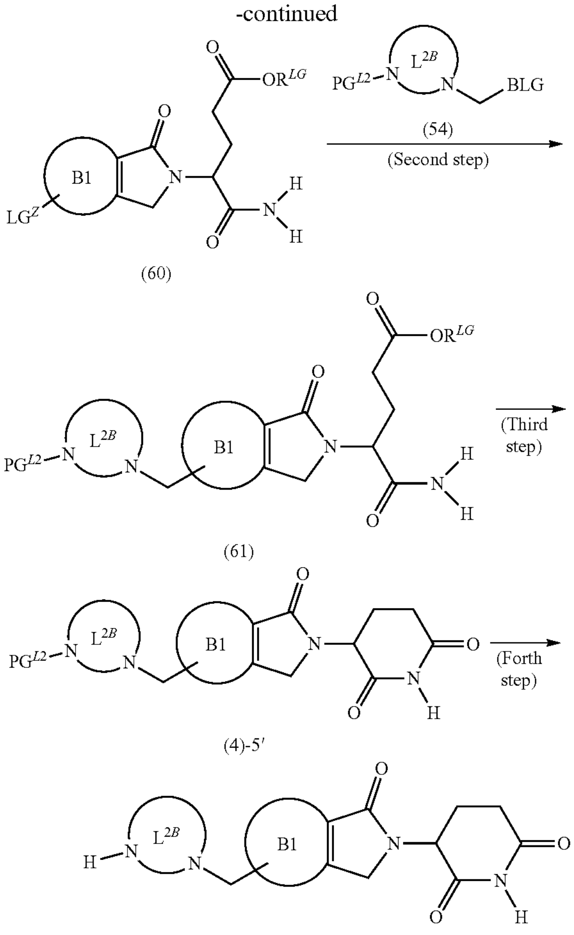

(54)
(60)
(61)
(4)-5'
(4)-5

(In the formula, $LG^{Z3}$ represents a leaving group. Examples of the leaving group shown here include Cl, Br, a methanesulfonyloxy group, a p-toluenesulfonyloxy group and the like. The same shall apply hereinafter.)

(First Step)

This step is a step of producing a compound (60) by subjecting the compound (58) and the compound (59) to cyclization reaction conditions.

This reaction is performed by stirring the compound (58) and the compound (59) in an equivalent amount or with one in an excess equivalent amount in the presence of a base, in a solvent inactive for the reaction, under cooling to under reflux with heat, generally for 1 hour to 5 days. Examples of the base used here include, but are not particularly limited to, an organic base, such as triethylamine or N,N'-diisopropylethylamine, an inorganic base, such as potassium carbonate or cesium carbonate, and the like. Examples of the solvent used here include, but are not particularly limited to, an ether-based solvent, such as tetrahydrofuran or 1,4-dioxane, N,N-dimethylformamide, and the like.

(Second Step)

This step is a step of producing a compound (61) by subjecting the compound (60) and the compound (54) to Suzuki-Miyaura coupling reaction conditions.

The reaction conditions are the same as in the fourth step of the Raw Material Production Method 2.

(Third Step)

This step is a step of producing a compound (4)-5' by subjecting the compound (61) to cyclization reaction conditions.

The reaction conditions are the same as in the third step of the Raw Material Production Method 17.

(Fourth Step)

This step is a step of producing a compound (4)-5 by subjecting the compound (4)-5' to deprotection conditions.

The reaction conditions are the same as in the first production method.

(Raw Material Production Method 17)

This production method is a method for producing a compound (4)-6. By using the compound (4)-6 instead of the compound (4) described in Raw Material Production Method 1, some of the compounds included in the compound of formula (1) can be synthesized.

[Chem. 161]

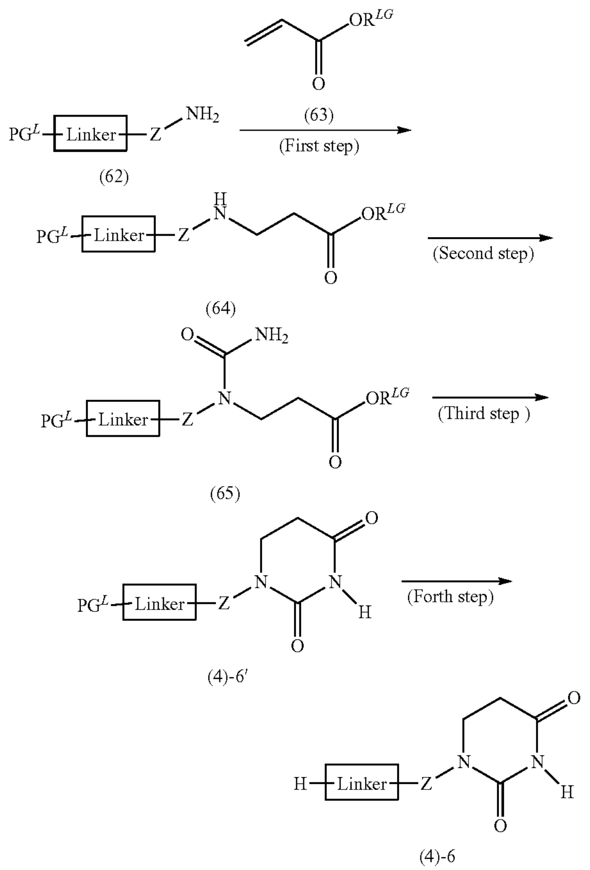

(63) (62) (64) (65) (4)-6' (4)-6

(In the formula, Linker is -($L^2$-$L^3$-$L^4$)-, $L^2$ is piperidinediyl optionally substituted with $C_{1-3}$ alkyl, piperazinediyl optionally substituted with $C_{1-3}$ alkyl, pyrrolidinediyl optionally substituted with $C_{1-3}$ alkyl, 3,8-diazabicyclo[3.2.1]octanediyl or 2,6-diazaspiro[3.4]octanediyl, $L^3$ is a bond, —N($R^{L3}$)—, $C_{1-3}$ alkylene or piperazinediyl, $L^4$ is a bond, —N($R^{L4}$)—, —O—, piperazinediyl or $C_{1-3}$ alkylene, $R^{L3}$ is H or $C_{1-3}$ alkyl, and $R^{L4}$ is H or $C_{1-3}$ alkyl, and $PG^L$ represents a protective group of NH or OH. $R^{LG}$ represents a $C_{1-12}$ alkyl group. The same shall apply hereinafter.)

(First Step)

This step is a step of producing a compound (64) by subjecting the compound (62) and the compound (63) to Michael addition conditions.

This reaction is performed by stirring the compound (62) and the compound (63) in an equivalent amount or with one in an excess equivalent amount in the presence of a base and excess acid reagent from at room temperature to under reflux with heat, generally for 1 day to 5 days. Examples of the base used here include, but are not particularly limited to, an organic base, such as 1,8-diazabicyclo[5.4.0]undec-7-ene or N,N'-diisopropylethylamine, and the like. Examples of the acid reagent used here include, but are not particularly limited to, lactic acid, trifluoroacetic acid, acetic acid and the like.

(Second Step)

This step is a step of producing a compound (65) by subjecting the compound (64) to urea-forming reaction conditions.

This reaction is performed by stirring the compound (64) in the presence of a urea-forming reagent and acid in a solvent inactive for the reaction with no solvent from at room temperature to under reflux with heat, generally for 1 day to 5 days. Examples of the urea-forming reagent used here include, but are not particularly limited to, sodium cyanate, potassium cyanate and the like. Examples of the acid used here include, but are not particularly limited to, acetic acid, hydrochloric acid, trifluoroacetic acid and the like. Examples of the solvent used here include, but are not particularly limited to, a halogenated hydrocarbon, such as dichloromethane, dichloroethane or chloroform, an ether-based solvent, such as tetrahydrofuran or 1,4-dioxane, acetic acid, toluene, water and a mixture thereof.

(Third Step)

This step is a step of producing a compound (4)-6' by subjecting the compound (65) to cyclization reaction conditions.

This reaction is performed by stirring the compound (65) in the presence of a base, in a solvent inactive for the reaction, from under ice-bath cooling to under reflux with heat, generally for 1 hour to 5 days. Examples of the base used here include, but are not particularly limited to, Triton B, potassium trimethylsilanolate, sodium ethoxide and the like. Examples of the solvent used here include, but are not particularly limited to, an ether-based solvent, such as tetrahydrofuran or 1,4-dioxane, N,N-dimethylformamide, acetonitrile and the like.

(Fourth Step)

This step is a step of producing a compound (4)-6 by subjecting the compound (4)-6' to deprotection conditions.

The reaction conditions are the same as in the first production method.

(Raw Material Production Method 18)

This production method is a method for producing the compound (67). By using the compound (67) instead of the compound (4) described in Raw Material Production Method 1, some of the compounds included in the compound of formula (1) can be synthesized.

[Chem. 162]

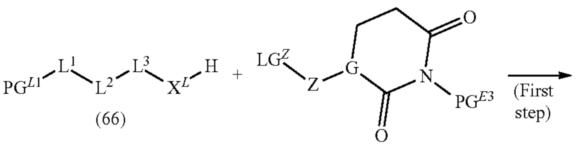

(66) (65)

-continued

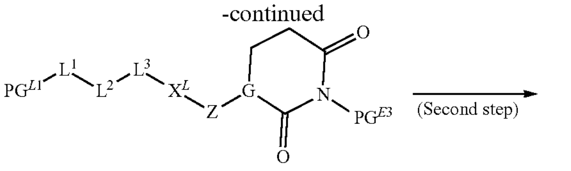

(67')

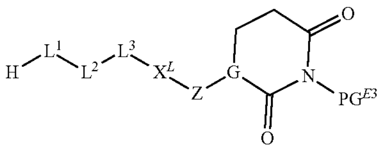

(67)

(In the formula, $L^1$ is piperidinediyl optionally substituted with $C_{1-3}$ alkyl, piperazinediyl optionally substituted with $C_{1-3}$ alkyl, pyrrolidinediyl optionally substituted with $C_{1-3}$ alkyl, 3,8-diazabicyclo[3.2.1]octanediyl or 2,6-diazaspiro[3.4]octanediyl, $L^2$ is a bond, —$N(R^{L3})$—, $C_{1-3}$ alkylene or piperazinediyl, $L^3$ is a bond, —$N(R^{L4})$—, —O—, piperazinediyl or $C_{1-3}$ alkylene, $R^{L3}$ is H or $C_{1-3}$ alkyl, and $R^{L4}$ is H or $C_{1-3}$ alkyl, and $X^L$ represents an oxygen atom or a nitrogen atom, $PG^{L1}$ represents a protective group of NH or OH, and $PG^{E3}$ represents a protective group of NH or H. The same shall apply hereinafter.)

(First Step)

This step is a step of producing a compound (67') by subjecting the compound (66) and the compound (65) to ipso reaction conditions.

The reaction conditions are the same as in the first step of the Raw Material Production Method 2.

The compound (67') can also be produced by subjecting the compound (66) and the compound (65) to coupling reaction conditions using a copper catalyst.

The reaction conditions are the same as in the first step of the Raw Material Production Method 12.

The compound (67') can also be produced by subjecting the compound (66) and the compound (65) to carbon-nitrogen bond formation reaction conditions.

This reaction is performed by adding a metal catalyst, a ligand and a base to a mixture of the compound (66) and the compound (65) in an equivalent amount or with one compound thereof in an excess equivalent amount and stirring the mixture in a solvent inactive for the reaction from at 80° C. to under reflux with heat, generally for 1 hour to 5 days.

Examples of the metallic reagent catalyst used here include, but are not particularly limited to, palladium(II) acetate, tris(dibenzylideneacetone) dipalladium, [1,1'-bis(diphenylphosphino)ferrocene]palladium (II) dichloride, [1,1'-bis(diphenylphosphino)ferrocene]palladium (II) dichloride dichloromethane adduct and the like. Examples of the ligand include, but are not particularly limited to, Xantphos, Ruphos, Xphos, BINAP and the like. Examples of the base include, but are not particularly limited to, an inorganic base, such as potassium carbonate, sodium carbonate, cesium carbonate or sodium tert-butoxide, and an organic base, such as triethylamine or N,N-diisopropylethylamine. Examples of the solvent include, but are not particularly limited to, 1,4-dioxane, toluene, N,N-dimethylformamide, a mixture thereof and the like. This reaction may be performed under microwave irradiation.

The compound (67') can also be produced by subjecting the compound (66) and the compound (65) to alkylation reaction conditions.

The reaction conditions are the same as in the first step of the Raw Material Production Method 2.

(Second Step)

This step is a step of producing a compound (67) by subjecting the compound (67') to deprotection conditions.

The reaction conditions are the same as in the first production method.

(Raw Material Production Method 19)

This production method is a method for producing the compound (1)-2 included in the compound (1), which is a raw material of the first production method.

[Chem. 163]

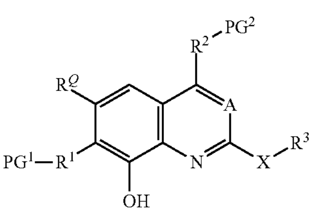

(14)

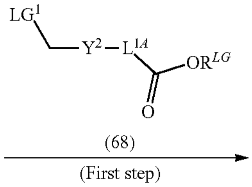

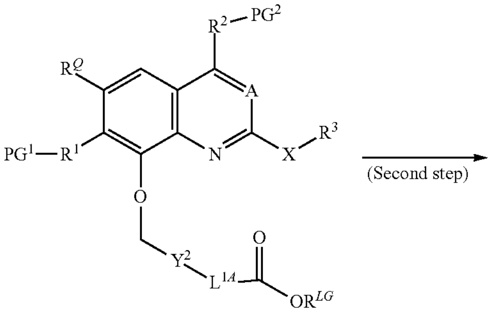

(69)

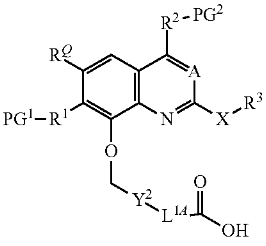

(70)

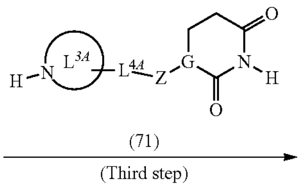

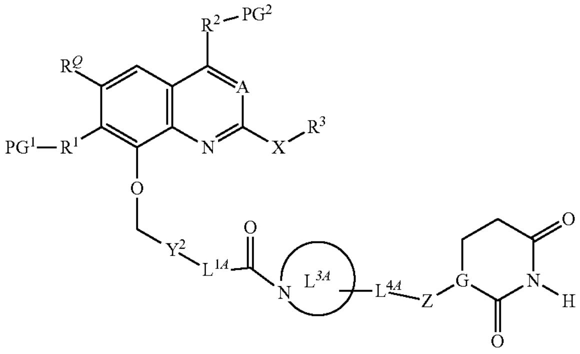

(1)-2

(In the formula, $L^{1A}$ and $L^{4A}$ represent one group selected from the group consisting of substituted heterocycloalkylene, optionally substituted heteroarylene, saturated 7-membered to 9-membered spiroheterocycloalkylene containing one or two nitrogen atoms, saturated 7-membered to 9-membered bridged heterocycloalkylene containing two nitrogen atoms and optionally substituted $C_{1-6}$ alkylene, and $L^{3A}$ represents piperidinediyl optionally substituted with $C_{1-3}$ alkyl, piperazinediyl optionally substituted with $C_{1-3}$ alkyl, pyrrolidinediyl optionally substituted with $C_{1-3}$ alkyl, bridged piperazinediyl or 2,6-diazaspiro[3.4]octanediyl. The same shall apply hereinafter.)

(First Step)

This step is a method for producing a compound (69) by an alkylation reaction of the compound (14) and the compound (68).

The reaction conditions are the same as in the seventh step of the Raw Material Production Method 2.

(Second Step)

This step is a step of producing a compound (70) by subjecting the compound (69) to hydrolysis conditions.

The reaction conditions are the same as in the first step of the Raw Material Production Method 1.

(Third Step)

This step is a step of producing a compound (1)-2 by subjecting the compound (70) and the compound (71) to condensation reaction conditions.

The reaction conditions are the same as in the second step of the Raw Material Production Method 1.

(Raw Material Production Method 20)

This production method is a method for producing a compound (74). By using the compound (74) instead of the compound (4) described in Raw Material Production Method 1, some of the compounds included in the compound of formula (1) can be synthesized.

[Chem. 164]

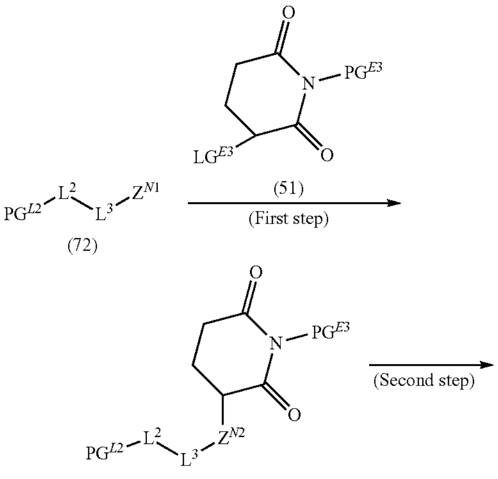

(51) (72) (73)

-continued

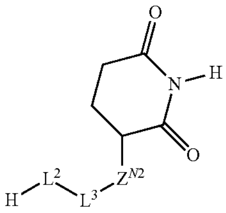

(74)

(In the formula, the compound (74) can also be produced by a similar reaction of a compound in which the $PG^{E3}$ moiety of the compound (51) is H.

(First Step)

This step is a step of producing a compound (73) by subjecting the compound (72) and the compound (51) to nucleophilic substitution conditions.

The reaction conditions are the same as in the first step of the Raw Material Production Method 11.

(Second Step)

This step is a step of producing a compound (74) by subjecting the compound (73) to deprotection conditions.

The reaction conditions are the same as in the first production method.

(Raw Material Production Method 21)

[Chem. 165]

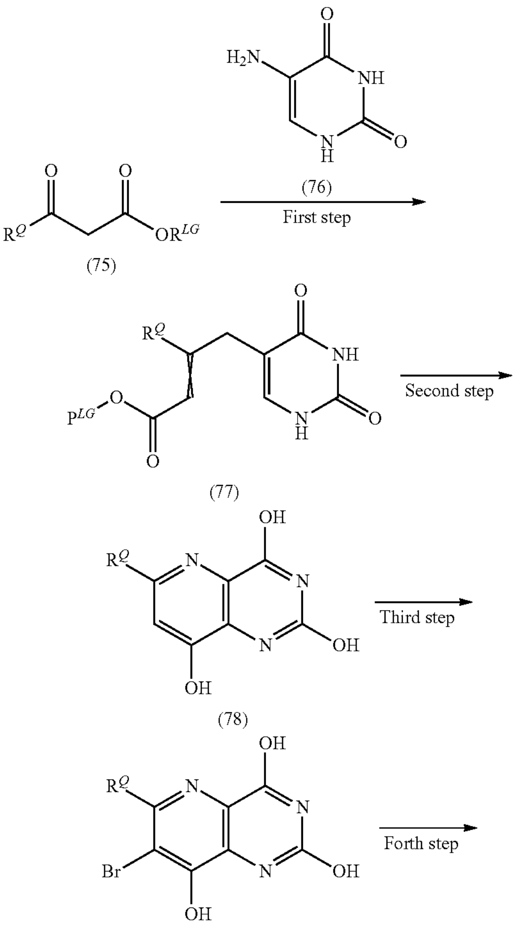

(76) (75) (77) (78) (79)

-continued

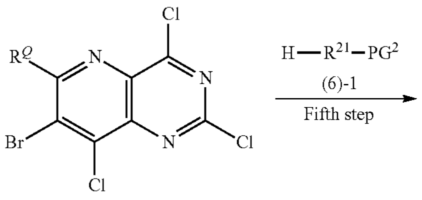

(80)

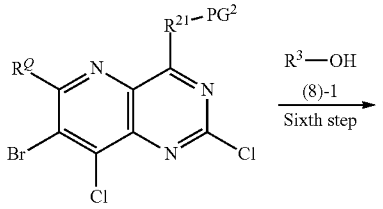

(81)

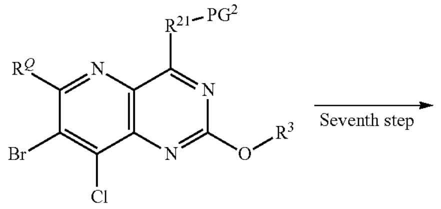

(82)

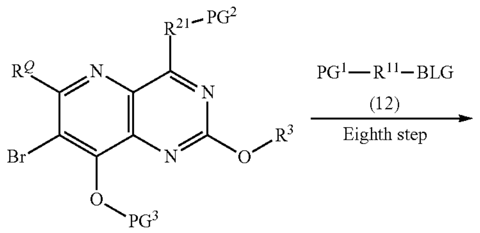

(83)

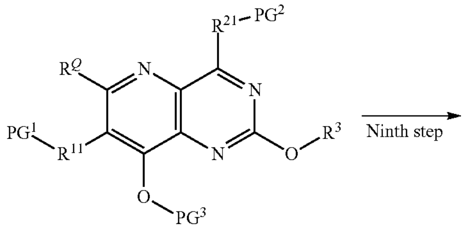

(84)

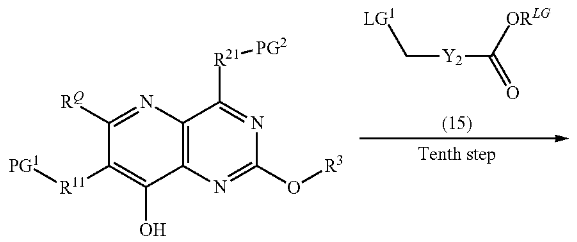

(85)

-continued

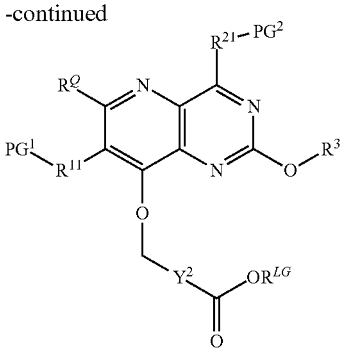

(2)-3

The production method is a method for producing a compound (2)-3 included in the compound (2), which is a raw material of Production Method 1.

(First Step)

This step is a method for producing a compound (77) by a reaction of a compound (75) and a compound (76).

The reaction is performed by converting the compound (75) to the corresponding enolate using an orthoester such as trimethyl orthoformate under acidic conditions, then adding the compound (76) and the enolate in in an equivalent amount or with one in an excess amount and stirring the mixture in a solvent inactive for the reaction, under reflux with heat, preferably at 60° C. to under reflux with heat, generally for 0.1 hours to 5 days. Examples of the solvent used here include, but are not particularly limited to, an aromatic hydrocarbon, such as toluene, an ether, such as THF or DOX, DMF, DMAc and the like.

(Second Step)

This step is a method for producing a compound (78) from the compound (77).

This reaction is performed by stirring the compound (77) in a solvent inactive for the reaction, under reflux with heat, preferably at 150° C. to under reflux with heat, generally for 0.1 hours to 5 days. Examples of the solvent used here include, but are not particularly limited to, NMP and the like.

(Third Step)

This step is a method for producing a compound (79) from the compound (78).

This reaction is performed by stirring a mixture of the compound (78) and a brominating agent in an equal amount of or with one in an excess amount in a solvent inactive for the reaction or with no solvent, from under cooling to under reflux with heat, preferably at room temperature to under reflux with heat, generally for 0.1 hours to 5 days. Examples of the solvent used here include, but are not particularly limited to, an aromatic hydrocarbon, such as toluene, an ether, such as THF or DOX, a halogenated hydrocarbon, such as dichloromethane, DMF and the like. Examples of the brominating agent include N-bromosuccinimide, N-bromosaccharin, 1,3-dibromo-5,5-dimethylhydantoin, dibromoisocyanuric acid and the like.

(Fourth Step)

This step is a method for producing a compound (80) from the compound (79).

The reaction conditions are the same as in the first step of the Raw Material Production Method 8.

(Fifth Step)

This step is a method for producing a compound (81) by an ipso substitution reaction of the compound (80) and a compound (6)-1.

The reaction conditions are the same as in the first step of the Raw Material Production Method 2.

(Sixth Step)

This step is a method for producing a compound (82) by an ipso substitution reaction of the compound (81) and a compound (8)-1.

The reaction conditions are the same as in the first step of the Raw Material Production Method 2.

(Seventh Step)

This step is a method for producing a compound (82) by an ipso substitution reaction of the compound (82) and $PG^3$-OH.

Examples of the $PG^3$-OH used here include benzyl alcohol, p-methoxybenzyl alcohol and 1-phenylethanol.

The reaction conditions are the same as in the first step of the Raw Material Production Method 2.

(Eighth Step)

This step is a method for producing a compound (84) by a Suzuki-Miyaura coupling reaction of the compound (83) and the compound (12), which is a boronic acid derivative.

The reaction conditions are the same as in the fourth step of the Raw Material Production Method 2.

When the compound (84) has an axial chirality, the compound (84) is obtained as a mixture of stereoisomers, and each stereoisomer can be isolated by separation using a common separation operation, for example, ODS column chromatography or silica gel column chromatography.

The compound (84) can be protected with a protective group again after deprotection. In addition, the compound (84) sometimes converts $PG^1$ to another protective group, followed by deprotection reaction conditions so that the compound (84) can be deprotected under different conditions from a protective group $PG^2$ to be introduced later.

The reaction conditions for the deprotection reaction used here are the same as in the step described in the Production Method 1.

Examples of the protective group of PG1 which is subsequently converted include a tetrahydro-2H-pyran-2-yl group and the like.

For example, the following can be referred as a reference about this reaction.

P. G. M. Wuts and T. W. Greene, "Greene's Protective Groups in Organic Synthesis", 5th edition, John Wiley & Sons Inc., 2014

(Ninth Step)

This step is a method for producing a compound (85) by deprotection by a catalytic hydrogenation reaction of the compound (84).

The reaction conditions are the same as in the sixth step of the Raw Material Production Method 2.

(Tenth Step)

This step is a method for producing a compound (2)-3 by a reaction of a compound (85) and a compound (15).

The reaction conditions are the same as in the seventh step of the Raw Material Production Method 2.

(Raw Material Production Method 22)

[Chem. 166]

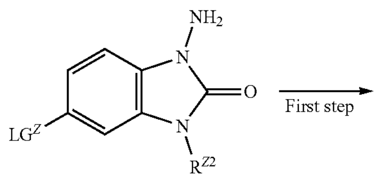

(86)

-continued

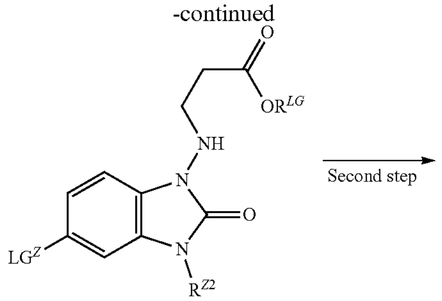

(87)

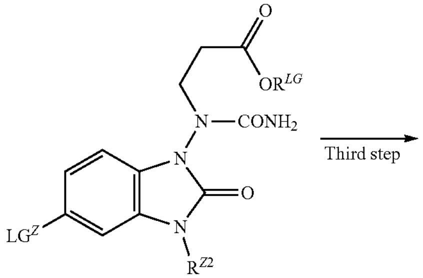

(88)

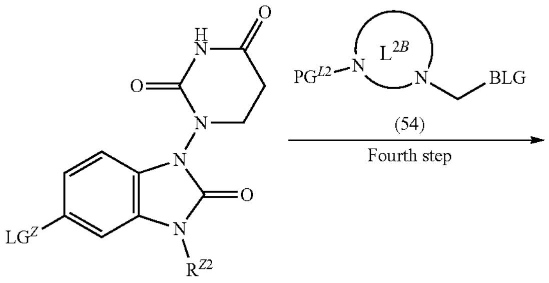

(89)

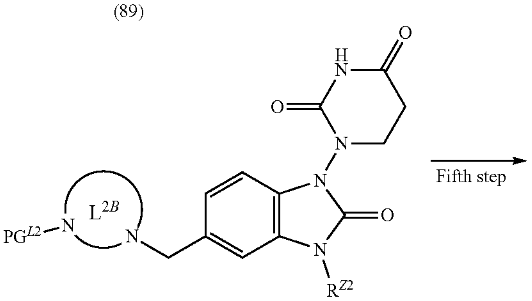

(90)

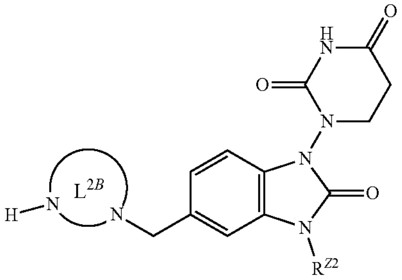

(4)-7

The production method is a method for producing a compound (4)-7 included in the compound (4), which is an intermediate of Raw Material Production Method 1.

(First Step)

This step is a method for producing a compound (87) from the compound (86).

The reaction conditions are the same as in the first step of the Raw Material Production Method 17.

(Second Step)

This step is a method for producing a compound (88) from the compound (87).

This reaction is performed by adding an ammonia reagent to the compound (87) in the presence of triphosgene and a base and stirring the mixture in a solvent inactive for the reaction at room temperature, generally for 1 day to 5 days. Examples of the ammonia reagent used here include, but are not particularly limited to, ammonia methanol solution and the like. Examples of the base used here include, but are not particularly limited to, an organic base, such as pyridine, triethylamine or N,N'-diisopropylethylamine. Examples of the solvent used here include, but are not particularly limited to, a halogenated hydrocarbon, such as dichloromethane, dichloroethane or chloroform.

(Third Step)

This step is a method for producing a compound (89) from the compound (88).

The reaction conditions are the same as in the third step of the Raw Material Production Method 17.

(Fourth Step)

This step is a step of producing a compound (90) by subjecting the compound (89) and the compound (54) to Suzuki-Miyaura coupling reaction conditions.

The reaction conditions are the same as in the fourth step of the Raw Material Production Method 2.

(Fifth Step)

This step is a step of producing a compound (4)-7 by subjecting the compound (90) to deprotection conditions.

The reaction conditions are the same as in the first production method.

(Raw Material Production Method 23)

The production method is a method for producing a compound (45)-3 included in the compound (45), which is a raw material of Raw Material Production Method 10.

[Chem. 167]

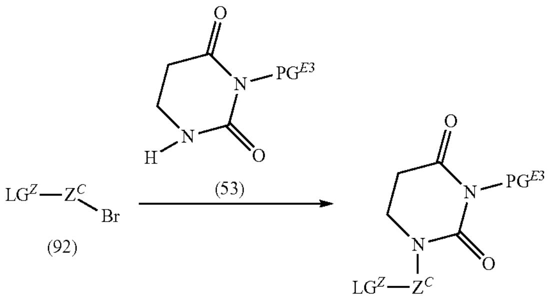

(92)

(45)-3

This step is a step of producing the compound (45)-3 by subjecting the compound (92) and the compound (53) to coupling reaction conditions using a copper catalyst.

The reaction conditions are the same as in the first step of the Raw Material Production Method 12.

The compound of the formula (I), the formula (XXI), the formula (XXII) or the formula (XXIII) is isolated and purified as a free compound, a salt, hydrate, solvate or crystal polymorphous substance thereof or a substance in the amorphous solid form. A salt of the compound of the formula (I), the formula (XXI), the formula (XXII) or the formula (XXIII) can also be produced by subjecting the compound to a salt formation reaction which is an ordinary method.

The isolation and purification are performed by applying a common chemical operation, such as extraction, fractional crystallization or various types of fraction chromatography.

Various types of isomers can be produced by selecting an appropriate raw material compound or can be separated using a difference in physiochemical properties between the isomers. For example, an optical isomer can be obtained by a general optical resolution method of a racemate (for example, fractional crystallization for inducing a racemate to a diastereomer salt with an optically active base or acid, chromatography using a chiral column or the like or the like) and can also be produced from an appropriate optically active raw material compound.

In addition, the compounds of the formula (I), the formula (XXI), the formula (XXII) or the formula (XXIII) or intermediates thereof sometimes have an axial chirality and are obtained as a mixture of stereoisomers, and each stereoisomer can be isolated by separation using a common separation operation, for example, octadecylsilyl (ODS) column chromatography or silica gel column chromatography.

The pharmacological activities of the compound of the formula (I) was confirmed by the following tests.

Test Example 1: Evaluation of KRAS Degradation Activity on Human G12D Mutant KRAS-Positive Pancreatic Cancer Line AsPC-1 (CRL-1682; ATCC)

The KRAS degradation activity of test compounds was evaluated by measuring the expression levels of KRAS G12D by Cell ELISA.

AsPC-1 cells were seeded at 20 μL per well on 384-well plates (from Greiner bio-one) to give $2.0\times10^4$ cells per well. As for the cell culture conditions, RPMI 1640 (from Sigma-Aldrich) medium containing 10% fetal bovine serum (from Cytiva) was used in the presence of 5% $CO_2$ at 37° C.

The next day, the test compounds (10 points having final concentrations in the range of 10 μM to 0.3 nM) and DMSO (from FUJIFILM Wako Pure Chemical Corporation), which was the solvent for the test compounds, as a negative control were diluted 500-fold with a fresh medium and were added at 20 μL per well. The cells were cultured overnight. The next day, the culture supernatant was removed, and 4% paraformaldehyde phosphate buffer (from FUJIFILM Wako Pure Chemical Corporation) was added at 20 μL per well. The plates were allowed to stand for 30 minutes at room temperature to thus immobilize the cells. Then, the supernatant was removed, and 0.1% Triton X-100 (from Amersham Biosciences)-containing Phosphate buffered saline (PBS; from FUJIFILM Wako Pure Chemical Corporation) was added at 20 μL per well. After allowing to stand for 10 minutes at room temperature, the supernatant was removed. PBS was added at 25 μL per well, and the supernatant was removed to thus wash each well. The washing was performed twice in total. Next, the supernatant was removed, and 0.5% sodium dodecyl sulfate (SDS; from Invitrogen)-containing PBS was added at 20 μL per well. After allowing to stand at room temperature for 10 minutes, the supernatant was removed by a centrifugal operation (using a centrifugal dehydrator machine, the supernatant was removed by the same method hereinafter). PBS was added at 25 μL per well, and the supernatant was removed to thus wash each well. The washing was performed twice in total. The supernatant was removed, and blocking solution (Intercept Blocking Buffer; from Li-COR Biosciences) was added at 20 μL per well. After allowing to stand for 30 minutes at room temperature, the supernatant was removed, and a solution obtained by diluting anti-β-actin antibody (Anti-beta Actin antibody [mAbcam 8226]-Loading Control; from abcam) 1,000-fold with blocking solution and a solution obtained by diluting anti-Ras (G12D Mutant Specific) antibody (Ras (G12D Mutant Specific) (D8H7) Rabbit mAb #14429; from Cell Signaling Technology) and anti-β-actin antibody (from abcam) 1,000-fold with blocking solution were respectively added to positive control wells and the other wells at 15 μL per well as a primary antibody. The plates were allowed to stand overnight at 4° C.

The next day, the supernatant was removed. PBS was added at 25 μL per well, and the supernatant was removed to thus wash each well. The washing was performed twice in total. The supernatant was removed, and a solution obtained by diluting Donkey anti-Mouse IgG H&L (IRDye 680RD) (from Li-COR Biosciences) and Goat anti-Rabbit IgG H&L (IRDye 800CW) (from Li-COR Biosciences) 1,000-fold with blocking solution was added at 15 μL per well as a secondary antibody. A solution obtained by diluting Donkey anti-Mouse IgG H&L (IRDye 680RD) (from Li-COR Biosciences) 1,000-fold with blocking solution was added to a positive control well as a secondary antibody. After allowing to stand for 1 hour at room temperature, the supernatant was removed. PBS was added at L per well, and the supernatant was removed to thus wash each well. The washing was performed twice in total. After removing the supernatant, the plates were dried with air at room temperature for 2 hours or more, and the 700 nm and 800 nm fluorescent signals were measured with Aerius (from Li-COR Biosciences).

After the signaling value of RAS measured at a fluorescence wavelength of 800 nm was corrected with the signaling value of p-actin measured at a fluorescence wavelength of 700 nm, with the signaling value at the time of addition of DMSO taken as 0% and with the signaling value when stained only with the anti-β-actin antibody taken as 100%, the 50% degradation concentration values ($DC_{50}$) of the amounts of KRAS were calculated by Sigmoid-Emax non-linear regression analysis based on the degradation rate up to the concentration of the compound showing Dmax, where Dmax is the degradation rate at the concentration of the compound showing highest degradation action. The results for some test compounds of the formula (I) are shown in tables below. The calculated 50% degradation value represents a degradation rate at the highest concentration evaluated (10 μM) for a compound that exceeds the concentration in the evaluation range.

In the tables presented below, Ex represents Example No. The $DC_{50}$ of Ex. 13, Ex. 15, and Ex. 16 were calculated using the molecular weights as tetrahydrochloride, and the $DC_{50}$ of Ex. 14 was calculated using the molecular weight as trihydrochloride.

TABLE 1

| Ex | $DC_{50}$ (nM) | Dmax (%) | Ex | $DC_{50}$ (nM) | Dmax (%) |
|---|---|---|---|---|---|
| 1 | 1946 | 59 | 23 | 2807 | 61 |
| 2 | 4899 | 59 | 24 | 297 | 78 |
| 3 | 53 | 83 | 25 | 856 | 70 |
| 4 | 40% at 10 μM | 40 | 26 | 5216 | 67 |
| 5 | 308 | 84 | 27 | 25% at 10 μM | 25 |
| 6 | 2731 | 49 | 28 | 5534 | 54 |
| 7 | 35 | 80 | 29 | 22 | 86 |
| 8 | 13 | 86 | 30 | 1482 | 71 |

TABLE 1-continued

| Ex | $DC_{50}$ (nM) | Dmax (%) | Ex | $DC_{50}$ (nM) | Dmax (%) |
|---|---|---|---|---|---|
| 9 | 55 | 65 | 31 | 115 | 71 |
| 10 | 8 | 86 | 32 | 46 | 78 |
| 11 | 58 | 84 | 33 | 79 | 88 |
| 12 | 18 | 82 | 34 | 202 | 85 |
| 13 | 408 | 66 | 35 | 3674 | 48 |
| 14 | 2180 | 51 | 36 | 79 | 80 |
| 15 | 406 | 60 | 37 | 30 | 87 |
| 16 | 71 | 86 | 38 | 22 | 86 |
| 17 | 4274 | 52 | 39 | 22 | 83 |
| 18 | 85 | 77 | 40 | 23 | 88 |
| 19 | 278 | 93 | 41 | 52 | 78 |
| 20 | 488 | 78 | 42 | 294 | 89 |
| 21 | 4961 | 52 | 43 | 9 | 90 |
| 22 | 114 | 84 | 44 | 41 | 74 |

Test Example 2: Evaluation of ERK Phosphorylation Inhibitory Effect on Human G12D Mutant KRAS-Positive Pancreatic Cancer Line AsPC-1

The ERK phosphorylation inhibitory effect of test compounds was evaluated by measuring phosphorylation of threonine 202 (Thr202) and tyrosine 204 (Tyr204) of ERK located downstream of the KRAS signal by Cell ELISA.

AsPC-1 cells were seeded on 384-well plates at 20 L/well to give $2.0\times10^4$ cells per well. As for the cell culture conditions, RPMI 1640 medium containing 10% fetal bovine serum was used in the presence of 5% $CO_2$ at 37° C.

The next day, the test compounds (10 points having final concentrations in the range of 10 μM to 0.3 nM), trametinib (MEK inhibitor) of a final concentration of 1 μM as positive control and DMSO, which was the solvent for the test compounds, as negative control were diluted 500-fold with a fresh medium and were added at 20 μL per well. The cells were cultured overnight. After culturing, 30% glyoxal solution (40% glyoxal [from Nacalai Tesque] was diluted with PBS) was quickly added at 30 μL per well, and the plates were allowed to stand for 120 minutes at room temperature to thus immobilize the cells. Then, the plates were centrifuged to remove the supernatant (using a centrifugal dehydrator machine, the supernatant was removed by the same method hereinafter), and 0.10% Triton X-100-containing PBS was added at 20 μL per well. After allowing to stand for 10 minutes at room temperature, the supernatant was removed, and the same operation was further repeated. Next, 0.5% SDS-containing PBS was added at 20 μL per well, and after allowing to stand at room temperature for 30 minutes, the supernatant was removed. Subsequently, blocking solution (Intercept Blocking Buffer) was added at 20 μL per well, and the plates were allowed to stand for 1 hour at room temperature. The supernatant was removed, and an ERK (Thr202/Tyr204) phosphorylation antibody (Phospho-p44/42 MAPK (Erk 1/2) (Thr202/Tyr204) (D13.14.4E) XP Rabbit mAb; from Cell Signaling Technology) diluted 2,500-fold with blocking solution was added at 15 μL per well as a primary antibody. The plates were allowed to stand at 4° C. overnight.

The next day, the supernatant was removed. 0.05% Tween-20 (from Thermo Fisher Scientific)-containing PBS was added at 50 μL per well, and the supernatant was removed to thus wash each well. The washing was performed three times in total. After washing, Goat anti-Rabbit IgG H&L (IRDye 800CW) diluted 1,000-fold with blocking solution was added at 15 μL per well as a secondary antibody, and the plates were allowed to stand for 1 hour at room temperature. The supernatant was removed, and each well was washed three times with 0.05% Tween-20-containing PBS in the same manner as after the primary antibody reaction. After removing the supernatant, the plates were dried with air at room temperature for 3 hours or more, and the 800-nm fluorescent signals were measured with Aerius.

With the signaling value at the time of addition of DMSO taken as 100% and with the signaling value at the time of addition of 1 μM trametinib taken as 0%, the 50% inhibitory concentration values ($IC_{50}$) were calculated by Sigmoid-Emax nonlinear regression analysis. The results for some test compounds of the formula (I) are shown in tables below. The calculated 50% inhibition represents the inhibition at the highest concentration evaluated (10 μM) for a compound that exceeds the concentration in the evaluation range.

In the tables presented below, Ex represents Example No. The $IC_{50}$ of Ex. 13, Ex. 15, and Ex. 16 were calculated using the molecular weights as tetrahydrochloride, and the $IC_{50}$ of Ex. 14 was calculated using the molecular weight as trihydrochloride.

TABLE 2

| Ex | $IC_{50}$ (nM) | Ex | $IC_{50}$ (nM) |
|---|---|---|---|
| 1 | 3358 | 23 | 1563 |
| 2 | 4771 | 24 | 231 |
| 3 | 94 | 25 | 668 |
| 4 | 33% at 10 μM | 26 | 2020 |
| 5 | 329 | 27 | 2768 |
| 6 | 3937 | 28 | 2189 |
| 7 | 60 | 29 | 24 |
| 8 | 21 | 30 | 1280 |
| 9 | 69 | 31 | 158 |
| 10 | 9 | 32 | 69 |
| 11 | 59 | 33 | 102 |
| 12 | 16 | 34 | 200 |
| 13 | 608 | 35 | 1507 |
| 14 | 1514 | 36 | 78 |
| 15 | 503 | 37 | 41 |
| 16 | 158 | 38 | 31 |
| 17 | 1345 | 39 | 30 |
| 18 | 250 | 40 | 30 |
| 19 | 555 | 41 | 90 |
| 20 | 1068 | 42 | 365 |
| 21 | 2283 | 43 | 13 |
| 22 | 283 | 44 | 69 |

Test Example 3: Evaluation of Non-Anchorage-Dependent Cell Growth Inhibitory Effect on Human G12D Mutant KRAS-Positive Pancreatic Cancer Line AsPC-1

The non-anchorage-dependent cell growth inhibitory effect of test compounds was evaluated by spheroid 3D cell culture.

AsPC-1 cells were seeded on low-cell-adhesive round bottom 384-well plates (PrimeSurface: from Sumitomo Bakelite) at 20 μL (or 36 L)/well to give $5\times10^2$ cells per well. As for the cell culture conditions, RPMI 1640 medium containing 10% fetal bovine serum was used in the presence of 5% $CO_2$ at 37° C.

The next day, the test compounds (10 points or 6 points having final concentrations in the range of 10 μM to 0.3 nM) and DMSO, which was the solvent for the test compounds, as a negative control were diluted 500-fold (or 100-fold) with a fresh medium and were added at 20 μL (or 4 L) per well. After culturing in the presence of 5% $CO_2$ at 37° C. for 6 days, CellTiter Glo 2.0 (from Promega) was added at 20 μL per well. After stirring with a plate mixer (from FINEPCR) at normal temperature for 1 hour, the luminescent signals were measured with ARVO X3 (from PerkinElmer).

With the signaling value in treatment with DMSO taken as 100% and with the signaling value in the medium alone without cells taken as 0%, the 50% inhibitory concentration values ($IC_{50}$) were calculated by Sigmoid-Emax nonlinear regression analysis. The results for some test compounds of the formula (I) are shown in tables below. The calculated 50% inhibition represents the inhibition at the highest concentration evaluated (10 μM) for a compound that exceeds the concentration in the evaluation range.

In the tables presented below, Ex represents Example No. The $IC_{50}$ of Ex. 13, Ex. 15, and Ex. 16 were calculated using the molecular weights as tetrahydrochloride, and the $IC_{50}$ of Ex. 14 was calculated using the molecular weight as trihydrochloride.

TABLE 3-1

| Ex | $IC_{50}$ (nM) | Ex | $IC_{50}$ (nM) |
|---|---|---|---|
| 1 | 37% at 10 μM | 23 | 1086 |
| 2 | 55% at 10 μM | 24 | 223 |
| 3 | 120 | 25 | 460 |
| 4 | 22% at 10 μM | 26 | 1349 |
| 5 | 490 | 27 | 1888 |
| 6 | 50% at 10 μM | 28 | 2017 |
| 7 | 73 | 29 | 33 |
| 8 | 27 | 30 | 1443 |
| 9 | 90 | 31 | 147 |
| 10 | 15 | 32 | 60 |
| 11 | 142 | 33 | 142 |
| 12 | 41 | 34 | 476 |
| 13 | 1224 | 35 | 1112 |
| 14 | 1119 | 36 | 159 |
| 15 | 211 | 37 | 64 |
| 16 | 73 | 38 | 51 |
| 17 | 684 | 39 | 52 |
| 18 | 217 | 40 | 46 |
| 19 | 242 | 41 | 155 |
| 20 | 884 | 42 | 399 |
| 21 | 852 | 43 | 33 |
| 22 | 128 | 44 | 123 |

TABLE 3-2

| Ex | $IC_{50}$ (nM) |
|---|---|
| 45 | 162 |
| 46 | 1277 |
| 47 | 448 |
| 48 | 161 |

Test Example 4: Evaluation of Anti-Tumor Activity in Human KRAS G12D Mutant-Positive PK-59 Pancreatic Cancer Cell Line-Derived Xenograft Mice PK-59 cells (RIKEN BioResearch Center, RCB1901) were cultured using RPMI 1640 medium containing 10% fetal bovine serum in the presence of 5% $CO_2$ at 37° C. The PK-59 cells were collected and suspended in PBS, and after adding an equal amount of Matrigel (from Becton, Dickinson and Company), 4- to 5-week-old male nude mice (BALB/c-nu (nu/nu), from Charles River Laboratories Japan) were subcutaneously inoculated with the cell suspension of 1.0 to $2.0\times10^7$ cells/mL was subcutaneously inoculated in a volume of 100 μL per mouse. About two weeks after the inoculation, the mice were divided into groups so that all the groups had approximately the same tumor volume and body weight, and administration of test compounds was started on the next day. The study was conducted for 5 mice each of a vehicle group and test compound administration groups. The compounds were dissolved in a solvent containing ethanol (from FUJIFILM Wako Pure Chemical Corporation), a 5% glucose solution (from Otsuka Pharmaceutical), 1M hydrochloric acid (from Kanto Chemical Co., Inc.), 50% (2-hydroxypropyl)-P-cyclodextrin (HP-βCD) solution (from ROQUETTE), HCO-40 (from Nikko Chemicals Co., Ltd.) and 1M sodium hydroxide solution (from Kanto Chemical Co., Inc.) at a liquid amount ratio of 4:84.4:1.1:1:9:0.5. The test compounds dissolved in the respective solvents or the solvents were administered into tail vein. The administration was performed once a week and twice in total. The tumor sizes and the body weights were measured twice a week. The tumor volumes were calculated using the following equation.

$$[\text{Tumor volume (mm}^3)]=[\text{Long diameter of tumor (mm)}]\times[\text{Short diameter of tumor (mm)}]^2\times 0.5$$

The tumor growth inhibition rate (%) by the test compounds were calculated with the tumor volumes of the test compound administration groups on the previous day of the start of the administration taken as 100% inhibition and the tumor volumes of the vehicle groups two weeks after the initial administration taken as 0% inhibition. In addition, when the tumor volume of a test compound administration group was smaller than the tumor volume on the previous day of the start of the administration, the tumor regression rate (%) by the test compound was calculated with the tumor volume on the previous day of the start of the administration taken as 0% regression and with the tumor volume 0 taken as 100% regression. The results for some test compounds of the formula (I) are shown in the following Table.

TABLE 4

| Ex | Dose (mg/kg) | Anti-Tumor Activity Two Weeks After Initial Administration |
|---|---|---|
| 8 | 3 | 28% regression |
| 10 | 3 | 28% regression |
| 12 | 3 | 35% regression |
| 29 | 3 | 5% regression |

Test Example 5: Evaluation of Inhibitory Effect on KRAS G12D/SOS/c-Raf Complex Formation Using human recombinant KRAS G12D, SOS and c-Raf proteins, the inhibitory effect of test compounds on the formation of the complex of the proteins was examined by the time-resolved fluorescence resonance energy transfer (TR-FRET) method. Biotinylated AviTag-KRAS G12D (amino acid region of 1-185, GDP) (2.5 μL; 400 nM) and test compounds dissolved in an assay buffer (50 mM HEPES [from Jena], 150 mM NaCl [from Nacalai Tesque], 5 mM $MgCl_2$ [from Thermo Fisher Scientific], 0.05% Tween 20 [from Sigma-Aldrich], pH 7.0) were added to 384-well plates (from Corning) in a liquid volume of 2.5 μL at 40,000 nM to 40 nM. Son of Sevenless (SOS) (amino acid region of 564-1049, 2.5 μL; 1.3 μM) and c-Raf (amino acid region of 51-131) GST (2.5 μL; 130 nM) containing GTP (from Sigma-Aldrich; 2 μM) were added to the plates, and the plates were allowed to stand for 1 hour at room temperature. Then, a mixture liquid (10 L) of LANCE Ulight-anti-GST (from PerkinElmer; 120 nM) and LANCE Eu-W1024 labeled Streptoavidin (from PerkinElmer; 100 ng/mL) was added, and the 620-nm and 665-nm fluorescence intensities were measured using EnVision 2104 (from PerkinElmer) under the conditions of an excitation wavelength of 337 nm. After standardizing the values with the fluorescence intensity at a reference wavelength of 620 nm, the 50% inhibitory concentrations ($IC_{50}$) were calculated by Sigmoid-Emax nonlinear regression analysis with the signaling value of the solvent treatment taken as 0% inhibition and with the signaling value without the addition of GTP taken as 100% inhibition.

As a result of the above tests, G12D mutant KRAS degradation activity was observed for some compounds of the formula (I) (Test Example 1). Moreover, inhibitory effect on complex formation (G12D mutant KRAS inhibitory effect) was observed (Test Example 5). Furthermore, inhibitory effect on phosphorylation of ERK located downstream of the KRAS signal was observed for some compounds of the formula (I) (Test Example 2). For some compounds of the formula (I), cell growth inhibitory effect on a human G12D mutant KRAS-positive pancreatic cancer line was observed (Test Example 3), and anti-tumor activity in human G12D mutant KRAS-positive pancreatic cancer line tumor-bearing mice was observed (Test Example 4). Therefore, the compounds of the formula (I) can be used for the treatment of pancreatic cancer, in particular, G12D mutant KRAS-positive pancreatic cancer, and the like.

A pharmaceutical composition that contains one or two or more compounds of the formula (I), the formula (XXI), the formula (XXII) or the formula (XXIII) or salts thereof as active ingredients can be prepared by a usually used method using an excipient usually used in the art, namely, a pharmaceutical excipient, a pharmaceutical carrier or the like.

The administration may be either oral administration with a tablet, pill, capsule, granule, powder, liquid or other agent or parenteral administration with an intraarticular, intravenous, intramuscular or other injection, a transmucosal agent, an inhalant or the like.

As a solid composition for oral administration, a tablet, powder, granular or other agent is used. In such a solid composition, one or two or more active ingredients are mixed with at least one inactive excipient. The composition may contain an inactive additive, for example, a lubricant, a disintegrator, a stabilizer or a dissolution aid, according to an ordinary method. A tablet or pill may be coated with a sugar coating or a film soluble in the stomach or intestine, as needed.

Liquid compositions for oral administration include a pharmaceutically acceptable emulsion, solution, suspension, syrup, elixir agent and the like and contain a generally used inactive diluent, for example, purified water or ethanol. The liquid composition may contain, in addition to the inactive diluent, an adjuvant, such as a solubilizer, a wetting agent or a suspending agent, a sweetening agent, a flavor, an aromatic or a preservative.

The injection agents for parenteral administration include a sterile aqueous or nonaqueous solution, suspension or emulsion agent. Examples of the aqueous solvent include distilled water for injection or physiological saline. An example of the nonaqueous solvent is an alcohol, such as EtOH. Such a composition may further contain an isotonizing agent, a preservative, a wetting agent, an emulsifier, a dispersant, a stabilizer or a dissolution aid. These are sterilized, for example, by filtration through a bacteria keeping filter, incorporation of a microbicide or irradiation. In addition, such a composition can be produced as a sterile solid composition, which is dissolved or suspended in sterile water or a sterile solvent for injection before use.

The transmucosal agent, such as an inhalant or a transnasal agent, is used in a solid, liquid or semi-solid form and can be produced according to a conventionally known method. For example, a known excipient and in addition, a pH modifier, a preservative, a surfactant, a lubricant, a stabilizer, a thickener or the like may be appropriately added. The administration can be performed using an appropriate device for inhalation or insufflation. For example, the agent can be administered using a known device, such as a metering and administering inhalation device, or an atomizer, as a compound alone or a powder of a mixture formulated, or as a solution or a suspension in combination with a medically acceptable carrier. A dry powder inhaler or the like may be for a single administration or multiple administrations, and dry powder or powder-containing capsule can be used. Alternatively, the agent may be used in a form of a pressurized aerosol spray or the like using an appropriate ejection agent, for example, a suitable gas, such as a chlorofluoroalkane or carbon dioxide.

In the case of a common oral administration, the daily dose is appropriately about 0.001 to 100 mg/kg body weight, preferably 0.1 to 30 mg/kg body weight, further preferably 0.1 to 10 mg/kg body weight, and the dose is given once or is divided into two to four times in a day. In the case of intravenous administration, the daily dose is appropriately about 0.0001 to 10 mg/kg body weight and is given once or is divided into multiple times in a day. In addition, the daily dose of a transmucosal agent is about 0.001 to 100 mg/kg body weight and is given once or is divided into multiple times in a day. The dose is appropriately decided depending on the individual case taking the symptom, age, sex and the like into account.

Depending on the route of administration, dosage form, site of administration and types of excipient and additive, the pharmaceutical composition of the present invention contains 0.01 to 100% by weight, in one embodiment, 0.01 to 50% by weight, of one or more compound of the formula (I) or salts thereof which are active ingredients.

The compounds of the formula (I), the formula (XXI), the formula (XXII) or the formula (XXIII) can be used in combination with various therapeutic agents or preventive agents for a disease to which the compounds of the formula (I), the formula (XXI), the formula (XXII) or the formula (XXIII) are considered to have an effectiveness. The combination use may be simultaneous administration or separate administration either sequential or with a desired interval. A simultaneous administration preparation may be a formulated agent or may be separately formulated.

EXAMPLES

The production method of the compounds of the formula (I), the formula (XXI), the formula (XXII) or the formula (XXIII) will be described in further detail below based on Examples. Note that the present invention is not to be limited to the compounds described in the following Examples. The production methods of raw material compounds are also shown in the Production Examples. Although the compounds described in the following Examples are specific compounds included in the formula (I), the production methods of the compounds of the formula (I) are not limited only to the production methods of specific Examples described below, and the compounds of the formula (I), the formula (XXI), the formula (XXII) or the formula (XXIII) can also be produced by a combination of the production methods or a method that is obvious to a person skilled in the art.

Note that, in this specification, a compound is sometimes named using naming software, such as ACD/Name (registered trademark, Advanced Chemistry Development, Inc.).

For the purpose of convenience, the concentration mol/L is shown as M. For example, 1 M aqueous sodium hydroxide solution means an aqueous sodium hydroxide solution of 1 mol/L.

The "amorphous solid form" described in this specification includes both a form showing no peak in the powder X-ray diffraction (XRD) pattern and a form having a low crystallinity.

XRD is measured using Empyrean under the conditions of a vacuum tube of Cu, a tube current of 40 mA, a tube voltage of 45 kV, a step width of 0.013°, a wavelength of 1.5418 Å and a measurement diffraction angle range (2θ) of 2.5 to 40°. Note that due to the nature of the data, crystal lattice spacing and overall pattern are important in determining crystal identity in powder X-ray diffraction patterns, and the error range of the diffraction angle (2θ(°)) in powder X-ray diffraction is usually ±0.2°. However, the diffraction angle and diffraction intensity may vary to some extent depending on the crystal growth direction, particle size, and measurement conditions, and should not be interpreted strictly.

Production Example 1

In THF (400 mL), 7-bromo-2,4-dichloro-8-fluoro-6-iodoquinazoline (40 g) was suspended, aqueous sodium hydroxide solution (1M, 190 mL) was added dropwise under ice-bath cooling so that the internal temperature was 10° C. or lower, and the mixture was stirred for 2 hours. The reaction solution was poured at once into an Erlenmeyer flask containing hydrochloric acid (1M, 190 mL) and ice water (about 900 g), and the mixture was stirred for about 30 minutes at room temperature (until the ice melted). The insoluble materials were filtered while washing with water and were dried under reduced pressure, thus obtaining 7-bromo-2-chloro-8-fluoro-6-iodoquinazolin-4-ol (33.56 g) as a solid.

Production Example 2

Under nitrogen flow, to a mixture of 7-bromo-2-chloro-8-fluoro-6-iodoquinazolin-4-ol (24.6 g) and THF (260 mL), which was heated to 60° C., was added 2-tert-butyl-1,3-diisopropylisourea (73.4 g) dropwise over 15 minutes. The mixture was stirred at the same temperature for 2.5 hours. After allowing to cool to room temperature, the colorless solid was separated by filtration while washing with THF (about 500 mL). The filtrate was concentrated, MeOH (210 mL) was added to the resulting solid, and the mixture was suspended and washed by stirring at room temperature for 1 hour. The solid was filtered with MeOH (100 mL) to give 7-bromo-4-tert-butoxy-2-chloro-8-fluoro-6-iodoquinazoline (23.2 g) as a solid.

Production Example 3

To a mixture of tert-butyl (1S,4S)-5-(7-bromo-2-chloro-8-fluoro-6-iodoquinazolin-4-yl)-2,5-diazabicyclo[2.2.1]heptane-2-carboxylate (38.4 g) and $CH_2Cl_2$ (500 mL) were added ethanethiol (5.3 mL) and DABCO (10.6 g) with stirring at room temperature, and the mixture was stirred under an argon atmosphere at room temperature for 17 hours. Ethanethiol (1 mL) was added, and the mixture was further stirred for 6 hours at room temperature. Then, DABCO (1.5 g) was added thereto and stirred for 3 days at room temperature, and cesium carbonate (2.1 g) was added thereto and stirred at room temperature for 22 hours. Ice water was poured into the reaction mixture, and the mixture was extracted twice with $CHCl_3$. The combined organic layer was dried over anhydrous magnesium sulfate and was concentrated under reduced pressure, thus obtaining tert-butyl (1S,4S)-5-[7-bromo-2-(ethylsulfanyl)-8-fluoro-6-iodoquinazolin-4-yl]-2,5-diazabicyclo[2.2.1]heptane-2-carboxylate (43.2 g) as a foam-like solid.

Production Example 4

To a mixture of tert-butyl (1S,4S)-5-[7-bromo-2-(ethylsulfanyl)-8-fluoro-6-iodoquinazolin-4-yl]-2,5-diazabicyclo[2.2.1]heptane-2-carboxylate (40.2 g), dehydrated THF (400 mL) and (1S)-1-phenylethane-1-ol (10 mL), which were sufficiently stirred under cooling in an ice/MeOH bath, was added tBuOK (15.3 g), and under an argon atmosphere, the mixture was stirred under cooling for 30 minutes and at room temperature for 30 minutes. Ice and saturated aqueous ammonium chloride solution were added to the reaction mixture and the mixture was extracted twice with ethyl acetate. The combined organic layer was washed with saturated aqueous sodium chloride solution, was dried over anhydrous magnesium sulfate and was concentrated under reduced pressure, thus obtaining tert-butyl (1S,4S)-5-{7-bromo-2-(ethylsulfanyl)-6-iodo-8-[(1S)-1-phenylethoxy]quinazolin-4-yl}-2,5-diazabicyclo[2.2.1]heptane-2-carboxylate (45.94 g) as a foam-like solid.

Production Example 5

Under an argon atmosphere, a mixture of tert-butyl (1S,4S)-5-{7-bromo-6-iodo-2-[(2S)-2-methoxypropoxy]-8-[(1S)-1-phenylethoxy]quinolin-4-yl}-2,5-diazabicyclo[2.2.1]heptane-2-carboxylate (1.02 g), cyclopropylboronic acid (178 mg), tripotassium phosphate (1.06 g), $PdCl_2$(dppf)-$CH_2Cl_2$ (113 mg), MeCN (15 mL) and water (3 mL) was stirred at 90° C. for 6 hours. After the mixture was allowed to cool to room temperature, ethyl acetate and water were added, and the mixture was filtered through celite (registered trademark) pad. Two layers were separated, and the aqueous layer was extracted with ethyl acetate. The combined organic layer was washed with saturated aqueous sodium chloride solution and was dried over anhydrous magnesium sulfate. The insoluble materials were removed by filtration, and the filtrate was concentrated under reduced pressure. The residue was purified by silica gel column chromatography (hexane/ethyl acetate), thus obtaining tert-butyl (1S,4S)-5-{7-bromo-6-cyclopropyl-2-[(2S)-2-methoxypropoxy]-8-[(1S)-1-phenylethoxy]quinolin-4-yl}-2,5-diazabicyclo[2.2.1]heptane-2-carboxylate (652 mg) as a foam-like solid.

Production Example 6

Under an argon atmosphere, a mixture of tert-butyl (1S,4S)-5-{7-bromo-6-cyclopropyl-2-[(2S)-2-methoxypropoxy]-8-[(1S)-1-phenylethoxy]quinolin-4-yl}-2,5-diazabicyclo[2.2.1]heptane-2-carboxylate (0.75 g), 6-fluoro-5-methyl-4-(4,4,5,5-tetramethyl-1,3,2-dioxaborolan-2-yl)-2-(triphenylmethyl)-2H-indazole (900 mg), dicyclohexyl(2',6'-diisopropoxy-1,1'-biphenyl]-2-yl)phosphine (138 mg), palladium(II) acetate (31 mg), anhydrous barium hydroxide (0.61 g), DOX (30 mL) and water (6 mL) was stirred at 50° C. for 30 minutes. 6-fluoro-5-methyl-4-(4,4,5,5-tetramethyl-1,3,2-dioxaborolan-2-yl)-2-(triphenylmethyl)-2H-indazole (600 mg) was added at the same temperature, and the mixture was further stirred at 50° C. for 1 hour. After the mixture was cooled to room temperature, ethyl acetate and water were added, and the insoluble materials were removed by filtration through celite (registered trademark) pad. The two layers of filtrate were separated, and the aqueous layer was extracted with ethyl acetate. The combined organic layer was washed with saturated aqueous sodium chloride solution and was dried over anhydrous magnesium sulfate. The insoluble materials were removed by filtration, and then the filtrate was concentrated under reduced pressure. The residue was purified by silica gel column chromatography (hexane/ethyl acetate), thus obtaining tert-butyl (1S,4S)-5-{6-cyclopropyl-7-[6-fluoro-5-methyl-2-(triphenylmethyl)-2H-indazol-4-yl]-2-[(2S)-2-methoxypropoxy]-8-[(1S)-1-phenylethoxy]quinolin-4-yl}-2,5-diazabicyclo[2.2.1]heptane-2-carboxylate (about 4:1 diastereomeric mixture derived from axial chirality, 866 mg) as a solid. MeOH (5 mL) was added to the resulting solid (866 mg). The mixture was heated to 60° C. to dissolve the solid and was stirred at room temperature for 3 days under an argon atmosphere. The precipitated solid was filtered while washing with a small amount of MeOH to give tert-butyl (1S,4S)-5-{6-cyclopropyl-7-[6-fluoro-5-methyl-2-(triphenylmethyl)-2H-indazol-4-yl]-2-[(2S)-2-methoxypropoxy]-8-[(1S)-1-phenylethoxy]quinolin-4-yl}-2,5-diazabicyclo[2.2.1]heptane-2-carboxylate (almost single diastereomer with unknown axial chirality configuration, 200 mg) as a solid.

Production Example 7

To a mixture of tert-butyl (1S,4S)-5-{(7M)-6-cyclopropyl-2-(ethylsulfanyl)-7-[6-fluoro-5-methyl-1-(oxan-2-yl)-1H-indazol-4-yl]-8-[(1S)-1-phenylethoxy]quinazolin-4-yl}-2,5-diazabicyclo[2.2.1]heptane-2-carboxylate (11.14 g) and $CH_2Cl_2$ (170 mL) was added m-chloroperbenzoic acid (about 30% water content, 7.9 g) under ice-bath cooling, and the mixture was stirred at room temperature for 1.5 hours under an argon atmosphere. Ice, saturated aqueous sodium thiosulfate solution and saturated aqueous sodium hydrogen carbonate solution were added, and the mixture was stirred at room temperature for about 20 minutes. Then, the reaction solution was diluted with $CH_2Cl_2$ and separated into layers. The organic layer was dried over anhydrous magnesium sulfate and was concentrated under reduced pressure. The residue was purified by silica gel column chromatography (hexane/ethyl acetate), thus obtaining tert-butyl (1S,4S)-5-{(7M)-6-cyclopropyl-2-(ethanesulfonyl)-7-[6-fluoro-5-methyl-1-(oxan-2-yl)-1H-indazol-4-yl]-8-[(1S)-1-phenylethoxy]quinazolin-4-yl}-2,5-diazabicyclo[2.2.1]heptane-2-carboxylate (9.02 g) as a foam-like solid.

Production Example 8

To a mixture of tert-butyl (1S,4S)-5-[(7M)-6-cyclopropyl-2-(ethanesulfonyl)-7-[6-fluoro-5-methyl-1-(oxan-2-yl)-1H-indazol-4-yl]-8-{[4-(methoxycarbonyl)phenyl]methoxy}quinazolin-4-yl]-2,5-diazabicyclo[2.2.1]heptane-2-carboxylate (300 mg), (2S)-2-methoxypropan-1-ol (40 mg) and THF (4 mL) was added tBuOK (85 mg) under cooling in an ice/MeOH bath, and the mixture was stirred at the same temperature for 30 minutes under an argon atmosphere. Ice water and aqueous ammonium chloride solution were added to the reaction mixture to quench the reaction, and the mixture was extracted with ethyl acetate twice. The combined organic layer was washed with saturated aqueous sodium chloride solution, was dried over anhydrous magnesium sulfate and was concentrated under reduced pressure. The residue was purified by silica gel column chromatography (basic silica gel, hexane/ethyl acetate), thus obtaining tert-butyl (1S,4S)-5-{(7M)-6-cyclopropyl-7-[6-fluoro-5-methyl-1-(oxan-2-yl)-1H-indazol-4-yl]-8-{[4-(methoxycarbonyl)phenyl]methoxy}-2-[(2S)-2-methoxypropoxy]quinazolin-4-yl}-2,5-diazabicyclo[2.2.1]heptane-2-carboxylate (255 mg) as a foam-like solid.

Production Example 9

Under nitrogen atmosphere, to a solution in MeOH (5 mL) and THF (5 mL) of tert-butyl (1S,4S)-5-{6-cyclopropyl-7-[6-fluoro-5-methyl-2-(triphenylmethyl)-2H-indazol-4-yl]-2-[(2S)-2-methoxypropoxy]-8-[(1S)-1-phenylethoxy]quinolin-4-yl}-2,5-diazabicyclo[2.2.1]heptane-2-carboxylate (180 mg) were added 10% Pd/C (50% water content, 40 mg) and sodium hydrogen carbonate (80 mg), and then the mixture was purged with a hydrogen atmosphere at normal temperature and was stirred at room temperature for 4 hours. The reaction mixture overlayed with nitrogen and was then filtered through celite (registered trademark) pad using MeOH, and the filtrate was concentrated under reduced pressure. The residue was purified by silica gel column chromatography (hexane/ethyl acetate), thus obtaining tert-butyl (1S,4S)-5-{6-cyclopropyl-7-[6-fluoro-5-methyl-2-(triphenylmethyl)-2H-indazol-4-yl]-8-hydroxy-2-[(2S)-2-methoxypropoxy]quinolin-4-yl}-2,5-diazabicyclo[2.2.1]heptane-2-carboxylate (160 mg) as a foam-like solid.

Production Example 10

To a mixture of tert-butyl (1S,4S)-5-{6-cyclopropyl-7-[6-fluoro-5-methyl-2-(triphenylmethyl)-2H-indazol-4-yl]-8-hydroxy-2-[(2S)-2-methoxypropoxy]quinolin-4-yl}-2,5-diazabicyclo[2.2.1]heptane-2-carboxylate (100 mg), methyl 4-(chloromethyl)benzoate (32 mg) and DMF (2 mL) was added cesium carbonate (172 mg) at room temperature, and the mixture was stirred at room temperature for 6 hours. Ethyl acetate and water were added, two layers were separated, and the aqueous layer was extracted with ethyl acetate. The combined organic layer was washed with water and saturated aqueous sodium chloride solution and was dried over anhydrous magnesium sulfate. The insoluble materials were removed by filtration, and the filtrate was concentrated under reduced pressure. The residue was purified by silica gel column chromatography (hexane/ethyl acetate), thus obtaining tert-butyl (1S,4S)-5-{6-cyclopropyl-7-[6-fluoro-5-methyl-2-(triphenylmethyl)-2H-indazol-4-yl]-8-{[4-(methoxycarbonyl)phenyl]methoxy}-2-[(2S)-2-methoxypropoxy]quinolin-4-yl}-2,5-diazabicyclo[2.2.1]heptane-2-carboxylate (90 mg) as a foam-like solid.

Production Example 11

To a mixture of methyl 4-[({(7M)-4-tert-butoxy-6-cyclopropyl-7-[6-fluoro-5-methyl-2-(triphenylmethyl)-2H-indazol-4-yl]-2-[(2S)-2-methoxypropoxy]quinazolin-8-yl}oxy)methyl]benzoate (2.51 g) and THF (30 mL) were added 3,4-dihydro-2H-pyran (2.7 mL) and 4-methylbenzene-1-sulfonic acid monohydrate (270 mg) at room temperature, and the mixture was stirred at 60° C. for 2 hours. The reaction solution was concentrated under reduced pressure, and the resulting residue was purified by silica gel column chromatography (basic silica gel, $CHCl_3$/MeOH), thus obtaining methyl 4-[({(7M)-6-cyclopropyl-7-[6-fluoro-5-methyl-1-(oxan-2-yl)-1H-indazol-4-yl]-4-hydroxy-2-[(2S)-2-methoxypropoxy]quinazolin-8-yl}oxy)methyl]benzoate (1.79 g) as a foam-like solid.

Production Example 12

To a mixture of tert-butyl (1S,4S)-5-{(7M)-6-cyclopropyl-2-(ethylsulfanyl)-7-(6-fluoro-5-methyl-1H-indazol-4-yl)-8-[(1S)-1-phenylethoxy]quinazolin-4-yl}-2,5-diazabicyclo[2.2.1]heptane-2-carboxylate (11.1 g) and THF (150 mL) were added 3,4-dihydro-2H-pyran (10 mL) and 4-methylbenzene-1-sulfonic acid monohydrate (0.7 g) with stirring at room temperature, and the mixture was stirred at room temperature for 14 hours under an argon atmosphere. Another 3,4-dihydro-2H-pyran (5 mL) and 4-methylbenzene-1-sulfonic acid monohydrate (0.3 g) were added, and the mixture was stirred at room temperature for another 5 hours. After TEA (2 mL) was added to quench the reaction, the mixture was concentrated under reduced pressure. The residue was purified by silica gel column chromatography (hexane/ethyl acetate), thus obtaining tert-butyl (1S,4S)-5-{(7M)-6-cyclopropyl-2-(ethylsulfanyl)-7-[6-fluoro-5-methyl-1-(oxan-2-yl)-1H-indazol-4-yl]-8-[(1S)-1-phenylethoxy]quinazolin-4-yl}-2,5-diazabicyclo[2.2.1]heptane-2-carboxylate (11.15 g) as a foam-like solid.

Production Example 13

Under nitrogen atmosphere, to a THF (3 mL) solution of methyl 4-[({(7M)-6-cyclopropyl-7-[6-fluoro-5-methyl-1-(oxan-2-yl)-1H-indazol-4-yl]-4-hydroxy-2-[(2S)-2-methoxypropoxy]quinazolin-8-yl}oxy)methyl]benzoate (100 mg) were added cesium carbonate (80 mg) and PyBOP (120 mg) at room temperature, and the mixture was stirred at the same temperature for 1 hour. Tert-butyl (3S)-3-hydroxypyrrolidine-1-carboxylate (60 mg) and cesium carbonate (160 mg) were added at room temperature, and the mixture was stirred at 60° C. for 3 hours. After the mixture was allowed to cool to room temperature, ethyl acetate was added, and the mixture was filtered through celite (registered trademark) pad. The filtrate was concentrated, and the resulting residue was purified silica gel column chromatography (hexane/ethyl acetate), thus obtaining tert-butyl (3S)-3-({(7M)-6-cyclopropyl-7-[6-fluoro-5-methyl-1-(oxan-2-yl)-1H-indazol-4-yl]-8-{[4-(methoxycarbonyl)phenyl]methoxy}-2-[(2S)-2-methoxypropoxy]quinazolin-4-yl}oxy)pyrrolidine-1-carboxylate (86 mg) as an oil.

Production Example 14

To a mixture of tert-butyl (1S,4S)-5-{(7M)-6-cyclopropyl-7-[6-fluoro-5-methyl-1-(oxan-2-yl)-1H-indazol-4-yl]-8-{[4-(methoxycarbonyl)phenyl]methoxy}-2-[(2S)-2-methoxypropoxy]quinazolin-4-yl}-2,5-diazabicyclo[2.2.1]heptane-2-carboxylate (252 mg), MeOH (3.4 mL) and THF (1.7 mL) was added aqueous sodium hydroxide solution (1 M, 1.7 mL) under ice-bath cooling, and the mixture was stirred at room temperature for 6 hours. Hydrochloric acid (1M, 1.77 mL) and ice water were added, and the mixture was extracted twice with $CHCl_3$/MeOH (10/1). The combined organic layer was dried over anhydrous magnesium sulfate. The solvent was removed under reduced pressure to give 4-[({(7M)-4-[(1S,4S)-5-(tert-butoxycarbonyl)-2,5-diazabicyclo[2.2.1]heptan-2-yl]-6-cyclopropyl-7-[6-fluoro-5-methyl-1-(oxan-2-yl)-1H-indazol-4-yl]-2-[(2S)-2-methoxypropoxy]quinazolin-8-yl}oxy)methyl]benzoic acid (250 mg) as a foam-like solid.

Production Example 15

To a mixture of tert-butyl (3S)-3-({(7M)-6-cyclopropyl-7-[6-fluoro-5-methyl-1-(oxan-2-yl)-1H-indazol-4-yl]-8-{[4-(methoxycarbonyl)phenyl]methoxy}-2-[(2S)-2-methoxypropoxy]quinazolin-4-yl}oxy)pyrrolidine-1-carboxylate (84 mg) and 1,2-dichloroethane (4 mL) was added trimethyltin(IV) hydroxide (100 mg) at room temperature, and the mixture was stirred at 80° C. for 24 hours. After the mixture was allowed to cool to room temperature, trimethyltin(IV) hydroxide (100 mg) was added, and the mixture was stirred at 80° C. for 48 hours. After the mixture was allowed to cool to room temperature, hydrochloric acid (1 μM) was added, and the mixture was extracted twice with $CHCl_3$/iPrOH (4/1). The combined organic layer was washed with hydrochloric acid (1M) and was dried over anhydrous sodium sulfate. The insoluble materials were removed by filtration, and the filtrate was concentrated under reduced pressure, thus obtaining 4-[({(7M)-4-{[(3S)-1-(tert-butoxycarbonyl)pyrrolidin-3-yl]oxy}-6-cyclopropyl-7-[6-fluoro-5-methyl-1-(oxan-2-yl)-1H-indazol-4-yl]-2-[(2S)-2-methoxypropoxy]quinazolin-8-yl}oxy)methyl]benzoic acid (86 mg) as an oil.

Production Example 16

To a mixture of 4-[({(7M)-4-[(1S,4S)-5-(tert-butoxycarbonyl)-2,5-diazabicyclo[2.2.1]heptan-2-yl]-6-cyclopropyl-7-[6-fluoro-5-methyl-1-(oxan-2-yl)-1H-indazol-4-yl]-2-[(2S)-2-methoxypropoxy]quinazolin-8-yl}oxy)methyl]benzoic acid (247 mg), 3-(3-methyl-5-{[(3S)-3-methylpiperazin-1-yl]methyl}-2-oxo-2,3-dihydro-1H-benzimidazol-1-yl)piperidine-2,6-dione dihydrochloride (160 mg), DIPEA (0.3 mL) and DMF (4 mL) was added HATU (230 mg) under cooling in an ice/MeOH bath, and the mixture was stirred at room temperature for 2 hours under an argon atmosphere. Ice and saturated aqueous ammonium chloride solution were added to the reaction mixture, and the mixture was extracted twice with ethyl acetate. The combined organic layer was washed with saturated aqueous sodium chloride solution, was then dried over anhydrous magnesium sulfate and was concentrated under reduced pressure. The resulting residue was purified by silica gel column chromatography ($CHCl_3$/iPrOH), thus obtaining tert-butyl (1S,4S)-5-{(7M)-6-cyclopropyl-8-({4-[(2S)-4-{[1-(2,6-dioxopiperidin-3-yl)-3-methyl-2-oxo-2,3-dihydro-1H-benzimidazol-5-yl]methyl}-2-methylpiperazine-1-carbonyl]phenyl}methoxy)-7-[6-fluoro-5-methyl-1-(oxan-2-yl)-1H-indazol-4-yl]-2-[(2S)-2-methoxypropoxy]quinazolin-4-yl}-2,5-diazabicyclo[2.2.1]heptane-2-carboxylate (273 mg) as a solid.

Production Example 17

A mixture of 7-bromo-2,4-dichloro-8-fluoro-6-iodoquinazoline (100 g), DOX (1000 mL) and THF (500 mL) was cooled with ice bath, and then DIPEA (240 mL) and tert-butyl (1S,4S)-2,5-diazabicyclo[2.2.1]heptane-2-carboxylate (48 g) were added. The mixture was stirred at room temperature overnight. Water was added to the reaction mixture, and the mixture was extracted with ethyl acetate. The organic layer was washed with an aqueous sodium chloride solution, was dried over anhydrous magnesium sulfate and was then concentrated under reduced pressure until the total amount of the solution became about 400 mL. A mixed solvent (hexane/ethyl acetate=4/1, 1000 mL) was added to the resulting solution, and the mixture was stirred at room temperature. The precipitated solid was filtered to give tert-butyl (1S,4S)-5-(7-bromo-2-chloro-8-fluoro-6-iodoquinazolin-4-yl)-2,5-diazabicyclo[2.2.1]heptane-2-carboxylate (123 g) as a solid.

Production Example 18

To a mixture of tert-butyl (1S,4S)-5-{6-cyclopropyl-2-(ethylsulfanyl)-7-[6-fluoro-5-methyl-2-(triphenylmethyl)-2H-indazol-4-yl]-8-[(1S)-1-phenylethoxy]quinazolin-4-yl}-2,5-diazabicyclo[2.2.1]heptane-2-carboxylate (about 4.5:1 mixture of isomers with regard to axial chirality, 20.63 g) and EtOH (250 mL) was added 4-methylbenzene-1-sulfonic acid monohydrate (4.8 g) with stirring at room temperature, and the mixture was stirred at room temperature for 1 hour under an argon atmosphere. Ice and saturated aqueous sodium hydrogen carbonate solution were poured into the reaction mixture, and the resulting white insoluble materials were dissolved in ethyl acetate and extracted twice with ethyl acetate. The combined organic layer was washed with saturated aqueous sodium chloride solution, was dried over anhydrous magnesium sulfate and was then concentrated under reduced pressure. The residue was purified by silica gel column chromatography (hexane/ethyl acetate), thus obtaining tert-butyl (1S,4S)-5-{(7M)-6-cyclopropyl-2-(ethylsulfanyl)-7-(6-fluoro-5-methyl-1H-indazol-4-yl)-8-[(1S)-1-phenylethoxy]quinazolin-4-yl}-2,5-diazabicyclo[2.2.1]heptane-2-carboxylate (single isomer with regard to axial chirality, 11.17 g), which was a low-polar fraction, as a foam-like solid and tert-butyl (1S,4S)-5-{(7P)-6-cyclopropyl-2-(ethylsulfanyl)-7-(6-fluoro-5-methyl-1H-indazol-4-yl)-8-[(1S)-1-phenylethoxy]quinazolin-4-yl}-2,5-diazabicyclo[2.2.1]heptane-2-carboxylate (single isomer with regard to axial chirality, 1.92 g), which was a high-polar fraction, as a foam-like solid.

Production Example 19

To a mixture of 2-amino-4-bromo-3-fluoro-5-iodobenzoic acid (10 g) and N-methyl-2-pyrrolidone (20 mL) was added trimethyl orthoacetate (10.5 mL), and the mixture was stirred at 110° C. for 12 hours. After the mixture was cooled to room temperature, MeOH (20 mL) was added, and the resulting solid was filtered while washing with ice-cooled methanol (about 60 mL) and was dried under reduced pressure, thus obtaining 2-acetamido-4-bromo-3-fluoro-5-iodobenzoic acid methyl ester (6.67 g) as a solid.

Production Example 20

Under an argon atmosphere, to a mixture of lithium bis(trimethylsilyl)amide (1.3 M THF solution, 100 mL) and THF (150 mL) was added 2-acetamido-4-bromo-3-fluoro-5-iodobenzoic acid methyl ester (18 g) portionwise under cooling in a water bath. The mixture was stirred at 40° C. for 1 hour and was then cooled to room temperature, water was added, and the mixture was washed twice with ethyl acetate. Under ice-bath cooling, the aqueous layer was acidified with hydrochloric acid (1M, 140 mL) and ice water and was stirred for a while. The precipitated solid was filtered and was dried under reduced pressure. The resulting solid was filtered while washing with methanol and was dried under reduced pressure, thus obtaining 7-bromo-8-fluoro-4-hydroxy-6-iodoquinoline-2(1H)-one (13.6 g) as a solid.

Production Example 21

Under an argon atmosphere, phosphoryl chloride (24 mL) was added to 7-bromo-8-fluoro-4-hydroxy-6-iodoquinoline-2(1H)-one (5 g), and under ice-bath cooling DIPEA (7 mL) was slowly added. The mixture was stirred at 110° C. for 1 hour. The reaction solution was cooled to room temperature and was dried at room temperature under reduced pressure. Ice water was added to the residue, and the mixture was stirred for 30 minutes. The precipitated solid was filtered, was washed with water and was then dried under reduced pressure, thus obtaining 7-bromo-2,4-dichloro-8-fluoro-6-iodoquinoline (5.03 g).

Production Example 22

Under an argon atmosphere, to a mixture of 7-bromo-2,4-dichloro-8-fluoro-6-iodoquinoline (6.4 g) and DMAc (70 mL) was added DABCO (1.8 g), and the mixture was stirred at 40° C. for 2 hours. Ethanethiol (1.4 mL) was added, and the mixture was stirred at 60° C. for 1 hour. After the mixture was cooled to room temperature, water was added, and the mixture was stirred for 5 minutes. The resulting solid was filtered and was dried under reduced pressure. The resulting solid was purified by silica gel column chromatography (hexane/ethyl acetate), thus obtaining 7-bromo-4-chloro-2-(ethylsulfanyl)-8-fluoro-6-iodoquinoline (5.76 g) as a solid.

Production Example 23

Under an argon atmosphere, to a THF (50 mL) solution of 7-bromo-4-chloro-8-fluoro-6-iodo-2-[(2S)-2-methoxypropoxy]quinoline (6.47 g) and (1S)-1-phenylethan-1-ol (3.34 mL) was added tBuOK (3.06 g) in a cooling bath (about −10° C.), and the mixture was stirred at the same temperature for 30 minutes. Saturated aqueous ammonium chloride solution was added under ice-bath cooling, and the mixture was extracted twice with ethyl acetate. The combined organic layer was washed with saturated aqueous sodium chloride solution and was dried over anhydrous magnesium sulfate. The insoluble materials were removed by filtration, and the filtrate was concentrated under reduced pressure. The residue was purified by silica gel column chromatography (hexane/ethyl acetate), thus obtaining 7-bromo-4-chloro-6-iodo-2-[(2S)-2-methoxypropoxy]-8-[(1S)-1-phenylethoxy]quinoline (4.67 g) as an oil.

Production Example 24

Under an argon atmosphere, a mixture prepared by adding tBuOK (1.59 g) to a DMAc (20 mL) solution of tert-butyl (3S)-3-hydroxypyrrolidine-1-carboxylate (2.7 g) and stirring at room temperature for 10 minutes was added dropwise to a mixture of 7-bromo-4-chloro-2-(ethylsulfanyl)-6-iodo-8-[(1S)-1-phenylethoxy]quinoline (6.46 g) and DMAc (40 mL) under ice-bath cooling, and the mixture was stirred at the same temperature for 30 minutes. Saturated aqueous ammonium chloride solution, ice and ethyl acetate were added, and the mixture was stirred to divide the mixture into layers. The aqueous layer was extracted with ethyl acetate twice. The combined organic layer was washed with saturated aqueous sodium chloride solution, was dried over anhydrous magnesium sulfate and was concentrated under reduced pressure. The residue was purified by silica gel column chromatography (hexane/ethyl acetate), thus obtaining tert-butyl (3S)-3-({7-bromo-2-(ethylsulfanyl)-6-iodo-8-[(1S)-1-phenylethoxy]quinolin-4-yl}oxy)pyrrolidine-1-carboxylate (4.6 g) as a solid.

Production Example 25

Under an argon atmosphere, to a mixture of 7-bromo-2,4-dichloro-8-fluoro-6-iodoquinoline (10 g), DABCO (3.3 g), cesium carbonate (23.3 g) and DMAc (100 mL) was added (2S)-2-methoxypropan-1-ol (3 mL), the mixture was stirred at room temperature for 1.5 hours and then at 60° C. for 12 hours. After the mixture was allowed to cool to room temperature, water and ethyl acetate were added. The mixture was stirred for a while, and then, two layers were separated. The aqueous layer was extracted with ethyl acetate. The combined organic layer was washed with saturated aqueous sodium chloride solution and was dried over anhydrous magnesium sulfate. The insoluble materials were removed by filtration, and the filtrate was concentrated. The residue was purified by silica gel column chromatography (hexane/ethyl acetate), thus obtaining 7-bromo-4-chloro-8-fluoro-6-iodo-2-[(2S)-2-methoxypropoxy]quinoline (5.97 g) as a solid.

Production Example 26

To a DMAc (5 mL) solution of 7-bromo-4-chloro-6-iodo-2-[(2S)-2-methoxypropoxy]-8-[(1S)-1-phenylethoxy]quinoline (1.6 g) were added tert-butyl (1S,4S)-2,5-diazabicyclo[2.2.1]heptane-2-carboxylate (832 mg) and potassium carbonate (768 mg) at room temperature, and the mixture was stirred at 120° C. overnight. Another tert-butyl (1S,4S)-2,5-diazabicyclo[2.2.1]heptane-2-carboxylate (278 mg) and potassium carbonate (384 mg) were added at 120° C., and the mixture was stirred at the same temperature overnight. The mixture was cooled to room temperature, saturated aqueous ammonium chloride solution was added, and the mixture was extracted twice with ethyl acetate. The combined organic layer was washed with saturated aqueous sodium chloride solution and was dried over anhydrous magnesium sulfate. The solution was concentrated under reduced pressure, and the residue was purified by silica gel column chromatography (hexane/ethyl acetate), thus obtaining tert-butyl (1S,4S)-5-{7-bromo-6-iodo-2-[(2S)-2-methoxypropoxy]-8-[(1S)-1-phenylethoxy]quinolin-4-yl}-2,5-diazabicyclo[2.2.1]heptane-2-carboxylate (1.02 g) as a foam-like solid.

Production Example 27

Under an argon atmosphere, to a $CH_2Cl_2$ (10 mL) solution of 3-hydroxy-1-[(4-methoxyphenyl)methyl]piperidine-2,6-dione (800 mg) were added trifluoromethanesulfonic anhydride (809 L) and pyridine (520 L) under ice-bath cooling, and the mixture was stirred at the same temperature for 1 hour and was concentrated under reduced pressure. The resulting residue was purified by silica gel column chromatography (hexane/ethyl acetate), thus obtaining 1-[(4-methoxyphenyl)methyl]-2,6-dioxopiperidin-3-yl trifluoromethanesulfonate (1.1 g) as an oil.

Production Example 28

Under an argon atmosphere, tBuOK (260 mg) was added to a THF (20 mL) solution of 6-bromo-1-methyl-1,3-dihydro-2H-benzimidazol-2-one (350 mg) under cooling in an ice/sodium chloride bath and stirred at the same temperature for 30 minutes. A THF (7 mL) solution of 1-[(4-methoxyphenyl)methyl]-2,6-dioxopiperidin-3-yl trifluoromethanesulfonate (700 mg) was added dropwise over 10 minutes, and the mixture was stirred at the same temperature for 30 minutes. Water was added to the reaction mixture, and the mixture was extracted with ethyl acetate three times. The combined organic layer was washed with saturated aqueous sodium chloride solution, was dried over anhydrous magnesium sulfate and was concentrated under reduced pressure. The resulting solid was filtered and washed with ethyl acetate and was dried under reduced pressure, thus obtaining 3-(5-bromo-3-methyl-2-oxo-2,3-dihydro-1H-benzimidazol-1-yl)-1-[(4-methoxyphenyl)methyl]piperidine-2,6-dione (524 mg) as a solid.

Production Example 29

To a mixture of tert-butyl 4-[(3-methyl-2-oxo-2,3-dihydro-1H-imidazo[4,5-b]pyridin-5-yl)methyl]piperazine-1-carboxylate (285 mg) and THF (3 mL) was slowly added dropwise lithium bis(trimethylsilyl)amide (1 M THF solution, 2.4 mL) under an argon atmosphere under ice-bath cooling, followed by addition of 3-bromopiperidine-2,6-dione (268 mg). Then, the mixture was stirred at 75° C. for 16 hours. After the mixture was allowed to cool to room temperature, saturated aqueous ammonium chloride solution was added, and the mixture was extracted twice with ethyl acetate. The combined organic layer was washed with saturated aqueous sodium chloride solution and was then dried over anhydrous sodium sulfate. The insoluble materials were removed by filtration, and the filtrate was concentrated under reduced pressure. The resulting residue was purified by silica gel column chromatography ($CHCl_3$/iPrOH), thus obtaining tert-butyl 4-{[1-(2,6-dioxopiperidin-3-yl)-3-methyl-2-oxo-2,3-dihydro-1H-imidazo[4,5-b]pyridin-5-yl]methyl}piperazine-1-carboxylate (106 mg) as an oil.

Production Example 30

To a mixture of 7-bromo-1,3-benzoxazol-2(3H)-one (8.5 g), 3-bromopiperidine-2,6-dione (9.9 g) and MeCN (80 mL) was added potassium carbonate (8.2 g), and the mixture was stirred at 70° C. for 12 hours. Water (600 mL) was poured into the reaction mixture, and the resulting insoluble materials were filtered while washing with water. Toluene was added to the resulting solid, and the mixture was concentrated under reduced pressure to azeotrope water. Petroleum ether/ethyl acetate (4/1) was added to the resulting crude product for trituration, and 3-(7-bromo-2-oxo-1,3-benzoxazol-3(2H)-yl)piperidine-2,6-dione (11 g) was obtained as a solid by collecting by filtration.

Production Example 32

To 3-(5-bromo-3-methyl-2-oxo-2,3-dihydro-1H-benzimidazol-1-yl)-1-[(4-methoxyphenyl)methyl]piperidine-2,6-dione (500 mg) were added trifluoroacetic acid (5 mL) and trifluoromethanesulfonic acid (5 mL), and the mixture was stirred at 60° C. for 1 hour. The solution was concentrated under reduced pressure to about half the volume, and ethyl acetate was added. The mixture was poured into saturated aqueous sodium hydrogen carbonate solution under ice-bath cooling and stirred for a while. The organic layer was separated, and the aqueous layer was extracted with ethyl acetate. The combined organic layer was washed with saturated aqueous sodium chloride solution, was dried over anhydrous magnesium sulfate and was concentrated under reduced pressure. The resulting residue was purified by silica gel column chromatography (hexane/ethyl acetate), thus obtaining 3-(5-bromo-3-methyl-2-oxo-2,3-dihydro-TH-benzimidazol-1-yl)piperidine-2,6-dione (300 mg) as a solid.

Production Example 33

Under an argon atmosphere, a mixture of 3-(5-bromo-3-methyl-2-oxo-2,3-dihydro-1H-benzimidazol-1-yl)piperidine-2,6-dione (4.32 g), potassium vinyltrifluoroborate (7.5 g), $PdCl_2$(dppf)-$CH_2Cl_2$ (1.16 g), cesium carbonate (9.2 g), DOX (50 mL) and water (5 mL) was stirred at 80° C. for 3 hours. Ethyl acetate and water were added, and the mixture was filtered through celite (registered trademark) pad. Two layers were separated, and the aqueous layer was extracted with ethyl acetate. The combined organic layer was washed with saturated aqueous sodium chloride solution, was dried over anhydrous magnesium sulfate and was concentrated under reduced pressure. The residue was purified by silica gel column chromatography (hexane/ethyl acetate). The resulting solid was filtered while washing with $iPr_2O$ and dried under reduced pressure, thus obtaining 3-(5-ethenyl-3-methyl-2-oxo-2,3-dihydro-1H-benzimidazol-1-yl)piperidine-2,6-dione (559 mg) as a solid.

Production Example 34

To a mixture of 3-(5-ethenyl-3-methyl-2-oxo-2,3-dihydro-1H-benzimidazol-1-yl)piperidine-2,6-dione (373 mg), DOX (10 mL) and water (1 mL) were added sodium periodate (570 mg), osmium tetroxide (2.5% by weight tBuOH solution, 13.3 g), 4-methylmorpholine N-oxide (88 mg) at room temperature, and the mixture was stirred at room temperature for 30 minutes. Water was added to the reaction mixture, and the mixture was extracted with ethyl acetate. The organic layer was washed with saturated aqueous sodium chloride solution, was dried over anhydrous magnesium sulfate and was concentrated under reduced pressure. The resulting residue was purified by silica gel column chromatography (hexane/ethyl acetate), thus obtaining 1-(2,6-dioxopiperidin-3-yl)-3-methyl-2-oxo-2,3-dihydro-1H-benzimidazole-5-carbaldehyde (280 mg) as a solid.

Production Example 35

In a mixed solvent of MeOH (30 mL) and $CH_2Cl_2$ (30 mL), 1-(6-ethenyl-1-methyl-1H-indazol-3-yl)-1,3-diazinane-2,4-dione (1.44 g) was dissolved at room temperature, and the mixture was stirred for 1.5 hours while bubbling ozone gas under cooling with a dry ice-acetone refrigerant. After dimethyl sulfide (1.2 mL) was added at the same temperature, the mixture was warmed to room temperature and stirred overnight. The reaction solution was concentrated under reduced pressure, and the residue was washed with a mixed solvent of ethyl acetate and MeOH, thus obtaining 3-(2,4-dioxo-1,3-diazinane-1-yl)-1-methyl-1H-indazole-6-carbaldehyde (527 mg) as a solid.

Production Example 36

Acetic acid (31 L) was added to a mixture of 1-(2,6-dioxopiperidin-3-yl)-3-methyl-2-oxo-2,3-dihydro-1H-benzimidazole-5-carbaldehyde (148 mg), tert-butyl (2S)-2-methylpiperazine-1-carboxylate (210 mg), $CH_2Cl_2$ (2 mL) and N-methyl-2-pyrrolidone (2 mL) at room temperature, and the mixture was stirred at room temperature for 30 minutes. Sodium triacetoxyborohydride (220 mg) was added at room temperature, and the mixture was stirred overnight. Water and saturated aqueous sodium hydrogen carbonate solution were added, and the mixture was stirred for a while and then extracted twice with ethyl acetate. The combined organic layer was washed with water and saturated aqueous sodium chloride solution and was dried over anhydrous magnesium sulfate. The insoluble materials were removed by filtration, and the filtrate was concentrated under reduced pressure. The resulting residue was purified by silica gel column chromatography ($CHCl_3$/iPrOH), thus obtaining tert-butyl (2S)-4-{[1-(2,6-dioxopiperidin-3-yl)-3-methyl-2-oxo-2,3-dihydro-1H-benzimidazol-5-yl]methyl}-2-methylpiperazine-1-carboxylate (224 mg) as a foam-like solid.

Production Example 37

To a mixture of tert-butyl (2S)-4-{[1-(2,6-dioxopiperidin-3-yl)-3-methyl-2-oxo-2,3-dihydro-1H-benzimidazol-5-yl]methyl}-2-methylpiperazine-1-carboxylate (200 mg) and $CH_2Cl_2$ (2 mL) was added hydrogen chloride (4 M DOX solution, 3 mL), and the mixture was stirred at room temperature overnight. $iPr_2O$ was added to the reaction mixture, and the resulting solid was filtered, was washed with $iPr_2O$ and was dried under reduced pressure, thus obtaining 3-(3-methyl-5-{[(3S)-3-methylpiperazin-1-yl]methyl}-2-oxo-2,3-dihydro-1H-benzimidazol-1-yl)piperidine-2,6-dione dihydrochloride (178 mg) as a solid.

Production Example 38

Under an argon atmosphere, 5-chloro-3-methyl-1,3-dihydro-2H-imidazo[4,5-b]pyridin-2-one (100 mg), potassium {[4-(tert-butoxycarbonyl)piperazin-1-yl]methyl}tri(fluoro)boranuide (333 mg), palladium(II) acetate (12 mg), dicyclohexyl(2',6'-dimethoxy-[1,1'-biphenyl]-2-yl)phosphine (45 mg), cesium carbonate (532 mg), DOX (2 mL) and water (0.4 mL) were mixed and was reacted at 130° C. for 1 hour under microwave irradiation. After the mixture was cooled to room temperature, water and ethyl acetate were added, and the insoluble materials were separated by filtration through celite (registered trademark) pad. Two layers were separated, and the aqueous layer was extracted with ethyl acetate. The combined organic layer was washed with saturated aqueous sodium chloride solution and was then dried over anhydrous sodium sulfate. The insoluble materials were removed by filtration, the filtrate was concentrated under reduced pressure. The resulting residue was purified by silica gel column chromatography ($CHCl_3$/MeOH), thus obtaining tert-butyl 4-[(3-methyl-2-oxo-2,3-dihydro-1H-imidazo[4,5-b]pyridin-5-yl)methyl]piperazine-1-carboxylate (120 mg) as an oil.

Production Example 39

Under an argon atmosphere, to a mixture of methyl 5-amino-4-(5-bromo-1-oxo-1,3-dihydro-2H-isoindol-2-yl)-5-oxopentanoate (209.5 mg), potassium {[(3S)-4-(tert-butoxycarbonyl)-3-methylpiperazin-1-yl]methyl}tri(fluoro)boranuide (380 mg), cesium carbonate (577 mg), water (1 mL) and DOX (5 mL) were added palladium(II) acetate (13 mg) and di(adamantan-1-yl)(butyl)phosphine (42 mg), and the mixture was stirred at 100° C. for 5 hours. After the mixture was allowed to cool to room temperature, ethyl acetate and water were added, and the insoluble materials were filtered through celite (registered trademark) pad. The filtrate was divided into layers, the aqueous layer was extracted with ethyl acetate, and the combined organic layer was dried over anhydrous sodium sulfate. The insoluble materials were removed by filtration, and the filtrate was concentrated under reduced pressure. The residue was purified by silica gel column chromatography ($CHCl_3$/MeOH), thus obtaining tert-butyl (2S)-4-{[2-(1-amino-5-methoxy-1,5-dioxopentan-2-yl)-1-oxo-2,3-dihydro-1H-isoindol-5-yl]methyl}-2-methylpiperazine-1-carboxylate (148 mg) as a foam-like solid.

Production Example 40

To a mixture of 1-[(4-bromo-3-fluorophenyl)methyl]-3-[(4-methoxyphenyl)methyl]-1,3-diazinane-2,4-dione (100 mg), potassium {[(3S)-4-(tert-butoxycarbonyl)-3-methylpiperazin-1-yl]methyl}tri(fluoro)boranuide (150 mg), cesium carbonate (240 mg), water (0.4 mL) and DOX (degassed by argon bubbling, 2 mL), mesyl[(tri-t-butylphosphine)-2-(2-aminobiphenyl)]palladium(II) (15 mg) at room temperature, and the mixture was stirred at 100° C. for 1 hour. After the mixture was allowed to cool to room temperature, ethyl acetate and water were added, and the mixture was filtered through celite (registered trademark) pad to give a filtrate. The aqueous layer was separated, and the organic layer was washed with saturated aqueous sodium chloride solution, was dried over anhydrous sodium sulfate and was filtered. The filtrate was concentrated under reduced pressure. The residue was purified by silica gel column chromatography (basic silica gel, hexane/ethyl acetate), thus obtaining tert-butyl (2S)-4-{[2-fluoro-4-({3-[(4-methoxyphenyl)methyl]-2,4-dioxo-1,3-diazinane-1-yl}methyl)phenyl]methyl}-2-methylpiperazine-1-carboxylate (59 mg) as an oil.

Production Example 41

Under an argon atmosphere, a mixture of 2-(2,6-dioxopiperidin-3-yl)-4-fluoro-1H-isoindole-1,3(2H)-dione (220 mg), tert-butyl 4-(aminomethyl)piperidine-1-carboxylate (204 mg), DIPEA (0.3 mL) and N-methyl-2-pyrrolidone (4 mL) was stirred at 80° C. for 3 hours. The mixture was allowed to cool, was then diluted with water and ethyl acetate and was separated into layers. The aqueous layer was extracted with ethyl acetate, and the combined organic layer was dried over anhydrous sodium sulfate and was then filtered and was concentrated under reduced pressure. The resulting residue was purified by silica gel column chromatography (hexane/ethyl acetate), thus obtaining tert-butyl 4-({[2-(2,6-dioxopiperidin-3-yl)-1,3-dioxo-2,3-dihydro-TH-isoindol-4-yl]amino}methyl)piperidine-1-carboxylate (86 mg) as a foam-like solid.

Production Example 42

Under an argon atmosphere, a mixture of methyl 4-bromo-2-(bromomethyl)benzoate (300 mg), methyl 4,5-diamino-5-oxopentanoate monohydrochloride (231 mg), DIPEA (0.35 mL) and DMF (6 mL) was stirred at room temperature for 24 hours. Saturated aqueous ammonium chloride solution was added to the reaction mixture under ice-bath cooling, and the mixture was diluted with water and ethyl acetate and divided into layers. The aqueous layer was extracted with ethyl acetate three times, and the combined organic layer was dried over anhydrous sodium sulfate and was then filtered and was concentrated under reduced pressure. The resulting residue was purified by silica gel column chromatography ($CHCl_3$/MeOH), thus obtaining methyl 5-amino-4-(5-bromo-1-oxo-1,3-dihydro-2H-isoindol-2-yl)-5-oxopentanoate (209.5 mg) as a solid.

Production Example 43

Under an argon atmosphere, to a mixture of tert-butyl (2S)-4-{[2-(1-amino-5-methoxy-1,5-dioxopentan-2-yl)-1-oxo-2,3-dihydro-1H-isoindol-5-yl]methyl}-2-methylpiperazine-1-carboxylate (144 mg) and THF (6 mL) was added potassium trimethylsilanolate (40 mg) under ice-bath cooling, and the mixture was stirred at the same temperature for 1 hour. Saturated aqueous ammonium chloride solution was added to the reaction mixture under ice-bath cooling, and the mixture was diluted with water and ethyl acetate and divided into layers. The aqueous layer was extracted with ethyl acetate, and the combined organic layer was dried over anhydrous sodium sulfate and was then filtered and was concentrated under reduced pressure. The resulting residue was purified by silica gel column chromatography ($CHCl_3$/MeOH), thus obtaining tert-butyl (2S)-4-{[2-(2,6-dioxopiperidin-3-yl)-1-oxo-2,3-dihydro-1H-isoindol-5-yl]methyl}-2-methylpiperazine-1-carboxylate (129 mg) as a solid.

Production Example 44

To a MeCN (20 mL) suspension of tert-butyl (2S)-4-({3-[carbamoyl(3-ethoxy-3-oxopropyl)amino]-1-methyl-1H-indazol-5-yl}methyl)-2-methylpiperazine-1-carboxylate (1.92 g) was added bnezyltrimethylammonium hydroxide (40% by weight MeOH solution, 480 mg), and the mixture was stirred at room temperature for 2 hours. The reaction solution was concentrated, and the residue was purified by silica gel column chromatography ($CHCl_3$/MeOH), thus obtaining tert-butyl (2S)-4-{[3-(2,4-dioxo-1,3-diazinan-1-yl)-1-methyl-1H-indazol-5-yl]methyl}-2-methylpiperazine-1-carboxylate (1.09 g) as a solid.

Production Example 45

To a DMF (35 mL) solution of N-iodosuccinimide (13.9 g) was added (2-methyl-2H-indazol-6-yl)methanol (2.5 g) at room temperature, and the mixture was stirred at the same temperature overnight and was then stirred at 60° C. for 2 hours. The reaction mixture was allowed to cool to room temperature and 5% aqueous sodium thiosulfate solution and saturated aqueous sodium hydrogen carbonate solution were added, and the mixture was extracted with ethyl acetate twice. The combined organic layer was washed with saturated aqueous sodium chloride solution and was dried over anhydrous magnesium sulfate. The insoluble materials were removed by filtration, the filtrate was concentrated, and the residue was washed with ethyl acetate, thus obtaining (3-iodo-2-methyl-2H-indazol-6-yl)methanol (2.19 g) as a solid.

Production Example 46

In DOX (20 mL), 3-[(4-methoxyphenyl)methyl]-1,3-diazinane-2,4-dione (1.05 g), (3-iodo-2-methyl-2H-indazol-6-yl)methanol (1.09 g), copper(I) iodide (420 mg), tripotassium phosphate (1.7 g) and racemic-(1R,2R)-cyclohexane-1,2-diamine (280 L) were suspended and was stirred at 120° C. for 3 hours under microwave irradiation. After the mixture was cooled to room temperature, ethyl acetate and water were added. Then, the mixture was filtered through celite (registered trademark) pad. The organic layer was washed with saturated aqueous sodium chloride solution, was dried over anhydrous magnesium sulfate and was then concentrated under reduced pressure. The residue was purified by silica gel column chromatography ($CHCl_3$/MeOH), thus obtaining 1-[6-(hydroxymethyl)-2-methyl-2H-indazol-3-yl]-3-[(4-methoxyphenyl)methyl]-1,3-diazinane-2,4-dione (293 mg) as a foam-like solid.

Production Example 47

To a DOX (17 mL) solution of 7-bromo-3-iodoimidazo[1,2-a]pyridine (1.7 g) and 3-[(4-methoxyphenyl)methyl]-1,3-diazinane-2,4-dione (1.5 g) were sequentially added DIPEA (4.58 mL), copper(I) iodide (1.0 g) and N,N'-dimethylethylenediamine (1.13 mL), and the mixture was stirred at 130° C. for 4 hours under nitrogen atmosphere. Water was added to the reaction mixture, and the mixture was extracted with ethyl acetate three times. The combined organic layer was dried over anhydrous sodium sulfate and was concentrated under reduced pressure. The resulting residue was purified by silica gel column chromatography (petroleum ether/ethyl acetate), thus obtaining 1-(7-bromoimidazo[1,2-a]pyridin-3-yl)-3-[(4-methoxyphenyl)methyl]-1,3-diazinane-2,4-dione (750 mg) as a solid.

Production Example 48

To a $CH_2Cl_2$ (10 mL) solution of 1-[6-(hydroxymethyl)-2-methyl-2H-indazol-3-yl]-3-[(4-methoxyphenyl)methyl]-1,3-diazinane-2,4-dione (320 mg) was added 1,1,1-triacetoxy-1,1-dihydro-1,2-benziodoxol-3-(1H)-one (470 mg) at room temperature, and the mixture was stirred for 1 hour. 5% aqueous sodium thiosulfate solution and saturated aqueous sodium hydrogen carbonate solution were added to the reaction solution. The mixture was stirred for a while and was then extracted with $CHCl_3$. The organic layer was dried over anhydrous magnesium sulfate and was then filtered and concentrated. The residue was purified by silica gel column chromatography ($CHCl_3$/MeOH), thus obtaining 3-{3-[(4-methoxyphenyl)methyl]-2,4-dioxo-1,3-diazinan-1-yl}-2-methyl-2H-indazole-6-carbaldehyde (208 mg) as a foam-like solid.

Production Example 49

To tert-butyl (2S)-4-[(3-{3-[(4-methoxyphenyl)methyl]-2,4-dioxo-1,3-diazinane-1-yl}-2-methyl-2H-indazol-6-yl)methyl]-2-methylpiperazine-1-carboxylate (153 mg) were added triisopropylsilane (165 L), trifluoroacetic acid (1 mL) and trifluoromethanesulfonic acid (1 mL) at room temperature in this order, and the mixture was stirred at room temperature overnight and was then stirred at 70° C. for 4 hours. The reaction solution was concentrated under reduced pressure, and the residue was purified by ODS column chromatography (0.1% formic acid in MeCN solution/0.1% aqueous formic acid solution). Saturated aqueous sodium hydrogen carbonate solution was added to a fraction containing the target compound, and the mixture was extracted with $CHCl_3$/iPrOH (4/1) four times. The combined organic layer was dried over anhydrous magnesium sulfate, was filtered and was concentrated, thus obtaining 1-(2-methyl-6-{[(3S)-3-methylpiperazin-1-yl]methyl}-2H-indazol-3-yl)-1,3-diazinane-2,4-dione (50 mg) as a solid.

Production Example 50

To a trifluoroacetic acid (5 mL) solution of tert-butyl (2S)-4-[(3-{3-[(4-methoxyphenyl)methyl]-2,4-dioxo-1,3-diazinane-1-yl}imidazo[1,2-a]pyridin-7-yl)methyl]-2-methylpiperazine-1-carboxylate (500 mg) was added trifluoromethanesulfonic acid (5 mL), and the mixture was stirred at 60° C. for 1 hour. The reaction mixture was concentrated under reduced pressure. Ice water (100 mL) was poured into the resulting residue, and the mixture was stirred for 5 minutes and was then extracted with ethyl acetate three times. The combined organic layer was dried over anhydrous sodium sulfate and was concentrated under reduced pressure. The resulting residue was purified by reverse phase HPLC (MeCN/0.1% aqueous formic acid solution), thus obtaining 1-(7-{[(3S)-3-methylpiperazin-1-yl]methyl}imidazo[1,2-a]pyridin-3-yl)-1,3-diazinane-2,4-dione n trifluoromethanesulfonate (185.9 mg) as a solid.

Production Example 51

Under an argon atmosphere, to a mixture of (methoxymethyl)triphenylphosphonium chloride (900 mg) and THF (7 mL) was added tBuOK (295 mg) in two portions under ice-bath cooling. The reaction mixture was stirred for 10 minutes under ice-bath cooling. Then, a mixture of 3-iodo-1-methyl-TH-indazole-5-carbaldehyde (500 mg) and THF (7 mL) was added dropwise under ice-bath cooling, and the mixture was stirred at room temperature for 45 minutes. The resulting reaction mixture was cooled with an ice bath again. Separately, a suspension obtained by adding tBuOK (295 mg) to a mixture of (methoxymethyl)triphenylphosphonium chloride (900 mg) and THF (7 mL) under ice-bath cooling and stirring for 10 minutes was added thereto, and then, the mixture was stirred at room temperature for 30 minutes. Saturated aqueous ammonium chloride solution and water were added to the reaction mixture under ice-bath cooling, and the mixture was extracted with ethyl acetate. The organic layer was dried over anhydrous magnesium sulfate, and the solvent was removed under reduced pressure. The residue was purified by silica gel column chromatography (hexane/ethyl acetate), thus obtaining 3-iodo-5-(2-methoxyethenyl)-1-methyl-TH-indazole (351 mg) as an oil.

Production Example 52

To 3-iodo-5-(2-methoxyethenyl)-1-methyl-TH-indazole (250 mg) were added water (2 mL) and formic acid (2 mL), and the mixture was stirred at 80° C. for 2 hours. The reaction mixture was concentrated under reduced pressure, and $CH_2Cl_2$ (2 mL), tert-butyl (2S)-2-methylpiperazine-1-carboxylate (200 mg), acetic acid (50 L) and sodium triacetoxyborohydride (200 mg) were added to the residue and stirred at room temperature overnight. Saturated aqueous sodium hydrogen carbonate solution was added to the reaction mixture, and the mixture was extracted with $CHCl_3$. The organic layer was dried over anhydrous magnesium sulfate, was filtered and was concentrated, thus obtaining tert-butyl (2S)-4-[2-(3-iodo-1-methyl-1H-indazol-5-yl)ethyl]-2-methylpiperazine-1-carboxylate (154 mg) as a foam-like solid.

Production Example 53

To a mixture of tert-butyl (2S)-4-[(3-cyano-4-fluorophenyl)methyl]-2-methylpiperazine-1-carboxylate (4.46 g) and propan-1-ol (40 mL) was added methylhydrazine (10 mL) at room temperature, and the mixture was stirred at 100° C. for 6 hours. The reaction solution was allowed to cool to room temperature and was then concentrated under reduced pressure. The residue was purified by silica gel column chromatography ($CHCl_3$/MeOH), thus obtaining tert-butyl (2S)-4-[(3-amino-1-methyl-1H-indazol-5-yl)methyl]-2-methylpiperazine-1-carboxylate (4.56 g) as a solid.

Production Example 54

To an EtOH (100 mL) solution of 3-bromo-2-fluorobenzonitrile (9.00 g) were added methylhydrazine sulfate (32.4 g) and TEA (75.2 mL) at 25° C., and the mixture was stirred at 110° C. for 48 hours. The reaction mixture was poured into water (300 mL) and was then concentrated under reduced pressure to remove volatiles. The resulting solid was filtered and was dried under reduced pressure. Ethyl acetate (50 mL) was added to the resulting solid, was stirred at 25° C. for 10 minutes and was milled to give 7-bromo-1-methyl-1H-indazol-3-amine (8 g) as a solid.

Production Example 55

To tert-butyl (2S)-4-[(3-amino-1-methyl-1H-indazol-5-yl)methyl]-2-methylpiperazine-1-carboxylate (3 g) were added 1,8-diazabicyclo[5.4.0]-7-undecene (1.66 mL) and lactic acid (1 g) under ice-bath cooling, the mixture was allowed to stand at room temperature for 0.5 hours. Ethyl acrylate (3 mL) was added, and the mixture was stirred at 90° C. overnight. The reaction solution was at room temperature, ethyl acetate and water were added, and the mixture was stirred for a while. The aqueous layer and the organic layer were separated, and the aqueous layer was extracted with ethyl acetate. The combined organic layer was washed with saturated aqueous sodium chloride solution, was dried over anhydrous magnesium sulfate and was concentrated. The residue was purified by silica gel chromatography ($CHCl_3$/MeOH), thus obtaining tert-butyl (2S)-4-({3-[(3-ethoxy-3-oxopropyl)amino]-1-methyl-1H-indazol-5-yl}methyl)-2-methylpiperazine-1-carboxylate (1.95 g) as an oil.

Production Example 56

To tert-butyl (2S)-4-({3-[(3-ethoxy-3-oxopropyl)amino]-1-methyl-1H-indazol-5-yl}methyl)-2-methylpiperazine-1-carboxylate (1.95 g) were added acetic acid (24 mL), water (8 mL) and sodium cyanate (830 mg) at room temperature in this order, and the mixture was stirred at the same temperature for 3 days. The reaction solution was concentrated, water and saturated aqueous sodium hydrogen carbonate solution were added to the residue, and the mixture was extracted with ethyl acetate twice. The combined organic layer was washed with saturated aqueous sodium chloride solution, was dried over anhydrous magnesium sulfate and was filtered. The filtrate was concentrated, and the residue was purified by silica gel column chromatography (basic silica gel, $CHCl_3$/MeOH), thus obtaining tert-butyl (2S)-4-({3-[carbamoyl(3-ethoxy-3-oxopropyl)amino]-1-methyl-1H-indazol-5-yl}methyl)-2-methylpiperazine-1-carboxylate (1.92 g) as a foam-like solid.

Production Example 57

To a DMF (10 mL) solution of 6-chloro-2-methyl-3-nitropyridine (1 g) were added tert-butyl 4-hydroxypiperidine-1-carboxylate (1.4 g), DABCO (720 mg) and cesium carbonate (4.72 g), and the mixture was stirred at room temperature for 2 hours. Ethyl acetate and water were added, and the organic layer was extracted. The organic layer was washed with saturated aqueous sodium chloride solution, was dried over anhydrous magnesium sulfate and was then concentrated under reduced pressure. The resulting residue was purified by silica gel column chromatography (hexane/ethyl acetate), thus obtaining tert-butyl 4-[(6-methyl-5-nitropyridin-2-yl)oxy]piperidine-1-carboxylate (447 mg) as a solid.

Production Example 58

To a mixture of sodium hydride (60% mineral oil dispersion, 500 mg) and DMAc (25 mL) was added tert-butyl 4-hydroxypiperidine-1-carboxylate (2.10 g) at 20° C., and the mixture was stirred at 20° C. for 30 minutes. 2-fluoro-4-iodo-3-methylpyridine (2.47 g) was added to the reaction mixture and was stirred at 100° C. for 1 hour. Water (5 mL) was added to the reaction mixture, and the resulting solution was purified by reverse phase HPLC (0.05% ammonia water/MeOH), thus obtaining tert-butyl 4-[(4-iodo-3-methylpyridin-2-yl)oxy]piperidine-1-carboxylate (2.85 g) as an oil.

Production Example 59

To a mixture of tert-butyl 4-[(6-methyl-5-nitropyridin-2-yl)oxy]piperidine-1-carboxylate (532 mg), DOX (10 mL) and water (2 mL) were added zinc powder (830 mg) and ammonium chloride (680 mg) under ice-bath cooling, and the mixture was stirred at room temperature for 2 hours and diluted with ethyl acetate. Celite (registered trademark) was added, and the mixture was stirred for a while. The insoluble materials were removed by filtration through celite (registered trademark) pad. The filtrate was washed with water and saturated aqueous sodium chloride solution and was dried over anhydrous magnesium sulfate. The insoluble materials were removed by filtration, and the filtrate was concentrated under reduced pressure, thus obtaining tert-butyl 4-[(5-amino-6-methylpyridin-2-yl)oxy]piperidine-1-carboxylate (480 mg) as an oil.

Production Example 60

Under nitrogen atmosphere, to a mixture of 3-iodophenol (500 mg), tert-butyl 4-(2-hydroxyethyl)piperazine-1-carboxylate (525 mg), triphenylphosphine (650 mg) and THF (5 mL) was added diisopropyl azodicarboxylate (500 L) under ice-bath cooling, and the mixture was stirred at room temperature for 1 hour. The reaction mixture was concentrated under reduced pressure, and the resulting residue was purified by silica gel column chromatography (hexane/ethyl acetate), thus obtaining tert-butyl 4-[2-(3-iodophenoxy)ethyl]piperazine-1-carboxylate (742 mg) as an oil.

Production Example 61

Under nitrogen atmosphere, to a DMF (6 mL) solution of 3-[(4-methoxyphenyl)methyl]-1,3-diazinane-2,4-dione (300 mg) was added sodium hydride (55% mineral oil dispersion, 70 mg) under ice-bath cooling, and the mixture was stirred at the same temperature for 10 minutes. 1-Bromo-4-(bromomethyl)-2-fluorobenzene (430 mg) was added at the same temperature, and the mixture was stirred for 30 minutes. Saturated aqueous ammonium chloride solution was added to the reaction mixture, and the mixture was extracted with ethyl acetate. The organic layer was washed with water and saturated aqueous sodium chloride solution, was dried over anhydrous sodium sulfate and was filtered. The filtrate was concentrated under reduced pressure. The resulting residue was purified by silica gel column chromatography (hexane/ethyl acetate), thus obtaining 1-[(4-bromo-3-fluorophenyl)methyl]-3-[(4-methoxyphenyl)methyl]-1,3-diazinane-2,4-dione (473 mg) as an oil.

Production Example 62

Under an argon atmosphere, to a mixture of tert-butyl (3S)-3-({7-bromo-2-(ethylsulfanyl)-6-iodo-8-[(1S)-1-phenylethoxy]quinolin-4-yl}oxy)pyrrolidine-1-carboxylate (1.38 g), cyclopropylboronic acid (255 mg), $PdCl_2$(dppf)-$CH_2Cl_2$ (162 mg), MeCN (15 mL) and water (3 mL) was added tripotassium phosphate (1.52 g), and the mixture was stirred at 90° C. for 6 hours. After the mixture was allowed to cool to room temperature, ethyl acetate and water were added. Two layers were separated, and the aqueous layer was extracted with ethyl acetate. The combined organic layer was washed with saturated aqueous sodium chloride solution and was dried over anhydrous magnesium sulfate. The insoluble materials were removed by filtration, and the filtrate was concentrated under reduced pressure. The residue was purified by silica gel column chromatography (hexane/ethyl acetate), thus obtaining tert-butyl (3S)-3-({7-bromo-6-cyclopropyl-2-(ethylsulfanyl)-8-[(1S)-1-phenylethoxy]quinolin-4-yl}oxy)pyrrolidine-1-carboxylate (589 mg) as a foam-like solid.

Production Example 63

A mixture of tert-butyl (1S,4S)-5-{7-bromo-2-(ethylsulfanyl)-6-iodo-8-[(1S)-1-phenylethoxy]quinazolin-4-yl}-2,5-diazabicyclo[2.2.1]heptane-2-carboxylate (45.93 g), cyclopropylboronic acid (9.8 g), tripotassium phosphate (55 g), $PdCl_2$(dppf)-$CH_2Cl_2$ (5.4 g), MeCN (360 mL), DOX (240 mL) and water (120 mL) was degassed and then purged with argon gas, and the mixture was stirred at 90° C. for 5 hours under an argon atmosphere. The reaction mixture which was allowed to cool was concentrated under reduced pressure to about half the volume, and saturated aqueous sodium hydrogen carbonate solution (100 mL) and water (300 mL) were poured into the residue and extracted twice with ethyl acetate. After the combined organic layer was washed with saturated aqueous sodium chloride solution, thiol-modified silica gel (about 10 g) and basic silica gel (about 10 g) were added, and the mixture was stirred at room temperature for 30 minutes. The insoluble materials were removed by filtration while washing with ethyl acetate, and the filtrate was concentrated under reduced pressure. The residue was purified by silica gel column chromatography (hexane/ethyl acetate), thus obtaining tert-butyl (1S,4S)-5-{7-bromo-6-cyclopropyl-2-(ethylsulfanyl)-8-[(1S)-1-phenylethoxy]quinazolin-4-yl}-2,5-diazabicyclo[2.2.1]heptane-2-carboxylate (27.74 g) as a foam-like solid.

Production Example 64

Under an argon atmosphere, a mixture of tert-butyl (3S)-3-({7-bromo-6-cyclopropyl-2-(ethylsulfanyl)-8-[(1S)-1-phenylethoxy]quinolin-4-yl}oxy)pyrrolidine-1-carboxylate (2.71 g), 6-fluoro-5-methyl-4-(4,4,5,5-tetramethyl-1,3,2-dioxaborolan-2-yl)-2-(triphenylmethyl)-2H-indazole (3.44 g), dicyclohexyl(2',6'-diisopropoxy-[1,1'-biphenyl]-2-yl)phosphine (531 mg), palladium(II) acetate (106 mg), and anhydrous barium hydroxide (2.29 g) were suspended in DOX (110 mL) and water (22 mL), the suspension was stirred at 50° C. for 15 minutes. 6-fluoro-5-methyl-4-(4,4,5,5-tetramethyl-1,3,2-dioxaborolan-2-yl)-2-(triphenylmethyl)-2H-indazole (1.6 g) was added, and the mixture was further stirred at 50° C. for 15 minutes. After the mixture was cooled to room temperature, ethyl acetate and water were added, and the insoluble materials were removed by filtration through celite (registered trademark) pad. The two layers of filtrate were separated, and the aqueous layer was extracted with ethyl acetate. The combined organic layer was washed with saturated aqueous sodium chloride solution and was dried over anhydrous magnesium sulfate. After separating the drying agent by filtration, the filtrate was concentrated under reduced pressure, and the resulting residue was purified by silica gel column chromatography (basic silica gel, hexane/ethyl acetate), thus obtaining tert-butyl (3S)-3-({6-cyclopropyl-2-(ethylsulfanyl)-7-[6-fluoro-5-methyl-2-(triphenylmethyl)-2H-indazol-4-yl]-8-[(1S)-1-phenylethoxy]quinolin-4-yl}oxy)pyrrolidine-1-carboxylate (about 5:1 diastereomeric mixture derived from axial chirality, 3.88 g) as an oil.

To tert-butyl (3S)-3-({6-cyclopropyl-2-(ethylsulfanyl)-7-[6-fluoro-5-methyl-2-(triphenylmethyl)-2H-indazol-4-yl]-8-[(1S)-1-phenylethoxy]quinolin-4-yl}oxy)pyrrolidine-1-carboxylate (about 5:1 diastereomeric mixture derived from axial chirality, 100 mg) was added MeOH (2 mL), and the mixture was heated to 70° C. to dissolve. The mixture was stirred at room temperature overnight and was further stirred for 3 days. Solid precipitation (pale yellow suspension) was observed. The solid was filtered and was washed with a small amount of MeOH, thus obtaining tert-butyl (3S)-3-({6-cyclopropyl-2-(ethylsulfanyl)-7-[6-fluoro-5-methyl-2-(triphenylmethyl)-2H-indazol-4-yl]-8-[(1S)-1-phenylethoxy]quinolin-4-yl}oxy)pyrrolidine-1-carboxylate (about 1:1 diastereomeric mixture derived from axial chirality, 21 mg) as a powder. The filtrate was concentrated, thus obtaining the desired (3S)-3-[{6-cyclopropyl-2-(ethylsulfanyl)-7-[6-fluoro-5-methyl-2-(triphenylmethyl)-2H-indazol-4-yl]-8-[(1S)-1-phenylethoxy]quinolin-4-yl}oxy)pyrrolidine-1-carboxylate (single diastereomer with unknown axial chirality configuration, 70 mg) as a solid.

Similarly, to tert-butyl (3S)-3-({6-cyclopropyl-2-(ethylsulfanyl)-7-[6-fluoro-5-methyl-2-(triphenylmethyl)-2H-indazol-4-yl]-8-[(1S)-1-phenylethoxy]quinolin-4-yl}oxy)pyrrolidine-1-carboxylate (about 5:1 diastereomeric mixture derived from axial chirality, 2.95 g) was added EtOH (6 mL), and the mixture was heated to 70° C. to dissolve. The powder of the axially chiral mixture (obtained above) was added in a trace amount at room temperature, and the mixture was stirred at room temperature overnight. The precipitated solid was filtered and was washed with a small amount of EtOH, thus obtaining tert-butyl (3S)-3-({6-cyclopropyl-2-(ethanesulfonyl)-7-(6-fluoro-5-methyl-2-(triphenylmethyl)-2H-indazol-4-yl]-8-[(1S)-1-phenylethoxy]quinolin-4-yl}oxy)pyrrolidine-1-carboxylate (about 1:1 diastereomeric mixture derived from axial chirality, 699 mg) as a colorless powder. The filtrate was concentrated, thus obtaining the desired (3S)-3-[{6-cyclopropyl-2-(ethylsulfanyl)-7-[6-fluoro-5-methyl-2-(triphenylmethyl)-2H-indazol-4-yl]-8-[(1S)-1-phenylethoxy]quinolin-4-yl}oxy)pyrrolidine-1-carboxylate (single diastereomer with unknown axial chirality configuration, 2.33 g) as a foam-like solid.

Production Example 65

A mixture of tert-butyl (1S,4S)-5-{7-bromo-6-cyclopropyl-2-(ethylsulfanyl)-8-[(1S)-1-phenylethoxy]quinazolin-4-yl}-2,5-diazabicyclo[2.2.1]heptane-2-carboxylate (17.7 g), 6-fluoro-5-methyl-4-(4,4,5,5-tetramethyl-1,3,2-dioxaborolan-2-yl)-2-(triphenylmethyl)-2H-indazole (19.6 g), palladium(II) acetate (0.7 g), dicyclohexyl(2',6'-diisopropoxy-[1,1'-biphenyl]-2-yl)phosphine (2.7 g), barium hydroxide (14.6 g), DOX (500 mL) and water (50 mL) was degassed and then purged with argon gas, and the mixture was stirred at 50° C. for 6 hours under an argon atmosphere. The reaction suspension which was allowed to cool was filtered through celite (registered trademark) pad while washing with ethyl acetate. After the filtrate was concentrated to about ¼ under reduced pressure, water was poured, and the mixture was extracted twice with ethyl acetate. The combined organic layer was washed with saturated aqueous sodium chloride solution, was then dried over anhydrous magnesium sulfate and was concentrated under reduced pressure. The residue was purified twice by silica gel column chromatography (basic silica gel, hexane/ethyl acetate), thus obtaining tert-butyl (1S,4S)-5-{6-cyclopropyl-2-(ethylsulfanyl)-7-[6-fluoro-5-methyl-2-(triphenylmethyl)-2H-indazol-4-yl]-8-[(1S)-1-phenylethoxy]quinazolin-4-yl}-2,5-diazabicyclo[2.2.1]heptane-2-carboxylate (about 4.5:1 mixture of isomers with regard to axial chirality, 20.64 g) as a foam-like solid.

Production Example 66

Under an argon atmosphere, to a $CH_2Cl_2$ (30 mL) solution of tert-butyl (3S)-3-({6-cyclopropyl-2-(ethylsulfanyl)-7-[6-fluoro-5-methyl-2-(triphenylmethyl)-2H-indazol-4-yl]-8-[(1S)-1-phenylethoxy]quinolin-4-yl}oxy)pyrrolidine-1-carboxylate (2.70 g) was added m-chloroperbenzoic acid (about 30% water content, 1.6 g) under ice-bath cooling, and the mixture was stirred at the same temperature for 1 hour. Under ice-bath cooling, an aqueous solution (10 mL) containing sodium thiosulfate pentahydrate (1.7 g) and saturated aqueous sodium hydrogen carbonate solution (40 mL) were added, and the mixture was stirred at room temperature for 30 minutes. Then, the reaction mixture was extracted with $CHCl_3$. The organic layer was dried over anhydrous magnesium sulfate and was concentrated under reduced pressure. The residue was purified by silica gel column chromatography (hexane/ethyl acetate), thus obtaining tert-butyl (3S)-3-({6-cyclopropyl-2-(ethanesulfonyl)-7-[6-fluoro-5-methyl-2-(triphenylmethyl)-2H-indazol-4-yl]-8-[(1S)-1-phenylethoxy]quinolin-4-yl}oxy)pyrrolidine-1-carboxylate (2.68 g) as a foam-like solid.

Production Example 67

To a mixture of tert-butyl (1S,4S)-5-[(7M)-6-cyclopropyl-2-(ethanesulfonyl)-7-[6-fluoro-5-methyl-1-(oxan-2-yl)-1H-indazol-4-yl]-8-{[4-(methoxycarbonyl)phenyl]methoxy}quinazolin-4-yl]-2,5-diazabicyclo[2.2.1]heptane-2-carboxylate (200 mg), tetrahydro-2H-pyran-4-ol (32 mg) and THF (4 mL) was added tBuOK (56 mg) under cooling in an ice/MeOH bath, and the mixture was stirred at the same temperature for 30 minutes under an argon atmosphere. Ice water and saturated aqueous ammonium chloride solution were added to the reaction mixture, and the mixture was extracted with ethyl acetate twice. The combined organic layer was washed with saturated aqueous sodium chloride solution, was dried over anhydrous magnesium sulfate and was concentrated under reduced pressure. The residue was purified by silica gel column chromatography (basic silica gel, hexane/ethyl acetate), thus obtaining tert-butyl (1S,4S)-5-{(7M)-6-cyclopropyl-7-[6-fluoro-5-methyl-1-(oxan-2-yl)-1H-indazol-4-yl]-8-{[4-(methoxycarbonyl)phenyl]methoxy}-2-[(oxan-4-yl)oxy]quinazolin-4-yl}-2,5-diazabicyclo[2.2.1]heptane-2-carboxylate (144 mg) as a foam-like solid.

Production Example 68

To a THF (10 mL) solution of tert-butyl (3S)-3-{[6-cyclopropyl-2-(ethanesulfonyl)-7-[6-fluoro-5-methyl-2-(triphenylmethyl)-2H-indazol-4-yl]-8-{[4-(methoxycarbonyl)phenyl]methoxy}quinolin-4-yl]oxy}pyrrolidine-1-carboxylate (835 mg) and (2S)-2-methoxypropan-1-ol (97 L) was added tBuOK (114 mg) under ice-bath cooling, and the mixture was stirred at the same temperature for 2 hours. Ice water and aqueous ammonium chloride solution were added to the reaction solution to quench the reaction, and the mixture was extracted with ethyl acetate twice. The combined organic layer was washed with saturated aqueous sodium chloride solution, was dried over anhydrous magnesium sulfate and was concentrated under reduced pressure. The resulting residue was purified by silica gel column chromatography (hexane/ethyl acetate), thus obtaining tert-butyl (3S)-3-({6-cyclopropyl-7-[6-fluoro-5-methyl-2-(triphenylmethyl)-2H-indazol-4-yl]-8-{[4-(methoxycarbonyl)phenyl]methoxy}-2-[(2S)-2-methoxypropoxy]quinolin-4-yl}]oxy}pyrrolidine-1-carboxylate (374 mg) as a foam-like solid.

Production Example 69

To a mixture of tert-butyl (1S,4S)-5-{(7M)-6-cyclopropyl-2-(ethanesulfonyl)-7-[6-fluoro-5-methyl-1-(oxan-2-yl)-1H-indazol-4-yl]-8-[(1S)-1-phenylethoxy]quinazolin-4-yl}-2,5-diazabicyclo[2.2.1]heptane-2-carboxylate (4.5 g) and MeOH (100 mL) was added 10% Pd/C (52% water content, 1 g), and the mixture was stirred at room temperature overnight under a hydrogen atmosphere at normal pressure. Celite (registered trademark) was added, and the mixture was filtered while washing with ethyl acetate and $CHCl_3$. Toluene (about 20 mL) was added to the filtrate, and the mixture was concentrated under reduced pressure. MeOH (80 mL) and 10% Pd/C (52% water content, 1.4 g) were added to the resulting solid, and the mixture was stirred at room temperature for 3 hours under a hydrogen atmosphere at normal pressure. Celite (registered trademark) was added, and the mixture was filtered while washing with ethyl acetate and $CHCl_3$. The filtrate was concentrated under reduced pressure, and the residue was purified by silica gel column chromatography (hexane/ethyl acetate), thus obtaining tert-butyl (1S,4S)-5-{(7M)-6-cyclopropyl-2-(ethanesulfonyl)-7-[6-fluoro-5-methyl-1-(oxan-2-yl)-1H-indazol-4-yl]-8-hydroxyquinazolin-4-yl}-2,5-diazabicyclo[2.2.1]heptane-2-carboxylate (3.42 g) as a foam-like solid.

Production Example 70

Under nitrogen atmosphere, to a solution in MeOH (15 mL) and THF (15 mL) of tert-butyl (3S)-3-({6-cyclopropyl-2-(ethanesulfonyl)-7-[6-fluoro-5-methyl-2-(triphenylmethyl)-2H-indazol-4-yl]-8-[(1S)-1-phenylethoxy]quinolin-4-yl}oxy)pyrrolidine-1-carboxylate (1.3 g) were added 10% Pd/C (50% water content, 300 mg) and sodium hydrogen carbonate (600 mg), and then the mixture was stirred at room temperature for 4 hours under a hydrogen atmosphere at normal pressure. The reaction mixture overlayed with nitrogen and was then filtered through celite (registered trademark) pad using MeOH, and the filtrate was concentrated under reduced pressure. Water was added to the residue, and the mixture was extracted twice with ethyl acetate. The combined organic layer was washed with saturated aqueous sodium chloride solution, was dried over anhydrous magnesium sulfate and was concentrated under reduced pressure, thus obtaining tert-butyl (3S)-3-({6-cyclopropyl-2-(ethanesulfonyl)-7-[6-fluoro-5-methyl-2-(triphenylmethyl)-2H-indazol-4-yl]-8-hydroxyquinolin-4-yl}oxy)pyrrolidine-1-carboxylate (1.16 g) as a foam-like solid.

Production Example 71

To a mixture of tert-butyl (1S,4S)-5-{(7M)-6-cyclopropyl-2-(ethanesulfonyl)-7-[6-fluoro-5-methyl-1-(oxan-2-yl)-1H-indazol-4-yl]-8-hydroxyquinazolin-4-yl}-2,5-diazabicyclo[2.2.1]heptane-2-carboxylate (3.01 g), DMF (30 mL) and methyl 4-(chloromethyl)benzoate (1 g) was added cesium carbonate (4 g) with stirring at room temperature, and the mixture was stirred under an argon atmosphere at room temperature overnight. Ice water and saturated aqueous ammonium chloride solution were added to the reaction mixture, and the mixture was extracted with ethyl acetate twice. The combined organic layer was washed with saturated aqueous sodium chloride solution, was dried over anhydrous magnesium sulfate and was concentrated under reduced pressure. The resulting residue was purified by silica gel column chromatography (basic silica gel, hexane/ethyl acetate), thus obtaining tert-butyl (1S,4S)-5-[(7M)-6-cyclopropyl-2-(ethanesulfonyl)-7-[6-fluoro-5-methyl-1-(oxan-2-yl)-1H-indazol-4-yl]-8-{[4-(methoxycarbonyl)phenyl]methoxy}quinazolin-4-yl]-2,5-diazabicyclo[2.2.1]heptane-2-carboxylate (3.32 g) as a foam-like solid.

Production Example 72

To a mixture of tert-butyl (3S)-3-({6-cyclopropyl-2-(ethanesulfonyl)-7-[6-fluoro-5-methyl-2-(triphenylmethyl)-2H-indazol-4-yl]-8-hydroxyquinolin-4-yl}]oxy)pyrrolidine-1-carboxylate (1.16 g), methyl 4-(chloromethyl)benzoate (375 mg) and DMF (12 mL) was added cesium carbonate (2 g) at room temperature, and the mixture was stirred at room temperature for 6 hours. Ethyl acetate and water were added to the reaction mixture, two layers were separated, and the aqueous layer was extracted with ethyl acetate. The combined organic layer was washed with water and saturated aqueous sodium chloride solution and was dried over anhydrous magnesium sulfate. The insoluble materials were removed by filtration, and the filtrate was concentrated under reduced pressure. Then, the resulting residue was purified by silica gel column chromatography (hexane/ethyl acetate), thus obtaining tert-butyl (3S)-3-({6-cyclopropyl-2-(ethanesulfonyl)-7-[6-fluoro-5-methyl-2-(triphenylmethyl)-2H-indazol-4-yl]-8-{[4-(methoxycarbonyl)phenyl]methoxy}quinolin-4-yl}]oxy}pyrrolidine-1-carboxylate (1.22 g) as a foam-like solid.

Production Example 73

To a mixture of tert-butyl (1S,4S)-5-{(7M)-6-cyclopropyl-7-[6-fluoro-5-methyl-1-(oxan-2-yl)-1H-indazol-4-yl]-8-{[4-(methoxycarbonyl)phenyl]methoxy}-2-[(oxan-4-yl)oxy]quinazolin-4-yl}-2,5-diazabicyclo[2.2.1]heptane-2-carboxylate (142 mg), MeOH (1 mL) and THF (1 mL) was added aqueous sodium hydroxide solution (1 M, 1 mL) under ice-bath cooling, and the mixture was stirred at room temperature for 6 hours. Under ice-bath cooling, hydrochloric acid (1M, 1 mL) was added, and the mixture was extracted twice with $CHCl_3$/MeOH (9/1). The combined organic layer was dried over anhydrous sodium sulfate. The solvent was removed under reduced pressure to give 4-[({(7M)-4-[(1S,4S)-5-(tert-butoxycarbonyl)-2,5-diazabicyclo

[2.2.1]heptan-2-yl]-6-cyclopropyl-7-[6-fluoro-5-methyl-1-(oxan-2-yl)-1H-indazol-4-yl]-2-[(oxan-4-yl)oxy]quinazolin-8-yl}oxy)methyl]benzoic acid (132 mg) as a solid.

Production Example 74

To a solution in MeOH (2 mL) and THF (2 mL) of tert-butyl (3S)-3-({6-cyclopropyl-7-[6-fluoro-5-methyl-2-(triphenylmethyl)-2H-indazol-4-yl]-8-{[4-(methoxycarbonyl)phenyl]methoxy}-2-[(2S)-2-methoxypropoxy]quinolin-4-yloxy)pyrrolidine-1-carboxylate (250 mg) was added aqueous sodium hydroxide solution (1 M, 1.2 mL) at room temperature, and the mixture was stirred at room temperature for 6 hours. Under ice-bath cooling, ethyl acetate and saturated aqueous ammonium chloride solution were added, and the organic layer was extracted, was washed with saturated aqueous sodium chloride solution, was dried over anhydrous sodium sulfate and was concentrated under reduced pressure. $iPr_2O$ was added to the resulting residue, and the precipitated solid was filtered and washed with $iPr_2O$ to give 4-{[(4-{[(3S)-1-(tert-butoxycarbonyl)pyrrolidin-3-yl]oxy}-6-cyclopropyl-7-[6-fluoro-5-methyl-2-(triphenylmethyl)-2H-indazol-4-yl]-2-[(2S)-2-methoxypropoxy]quinolin-8-yl}oxy)methyl]benzoic acid (216 mg) as a solid.

Production Example 75

To a mixture of tert-butyl (1S,4S)-5-{6-cyclopropyl-7-[6-fluoro-5-methyl-2-(triphenylmethyl)-2H-indazol-4-yl]-8-{[4-(methoxycarbonyl)phenyl]methoxy}-2-[(2S)-2-methoxypropoxy]quinolin-4-yl}-2,5-diazabicyclo[2.2.1]heptane-2-carboxylate (90 mg), MeOH (1 mL) and THF (1 mL) was added aqueous sodium hydroxide solution (1 M, 430 L) at room temperature, and the mixture was stirred at room temperature overnight. Under ice-bath cooling, ethyl acetate and saturated aqueous ammonium chloride solution were added. The organic layer was extracted and washed with saturated aqueous sodium chloride solution, was dried over anhydrous magnesium sulfate and was concentrated under reduced pressure, thus obtaining 4-[({4-[(1S,4S)-5-(tert-butoxycarbonyl)-2,5-diazabicyclo[2.2.1]heptan-2-yl]-6-cyclopropyl-7-[6-fluoro-5-methyl-2-(triphenylmethyl)-2H-indazol-4-yl]-2-[(2S)-2-methoxypropoxy]quinolin-8-yl}oxy)methyl]benzoic acid (80 mg) as a foam-like solid.

Production Example 76

To a mixture of 4-[({(7M)-4-[(1S,4S)-5-(tert-butoxycarbonyl)-2,5-diazabicyclo[2.2.1]heptan-2-yl]-6-cyclopropyl-7-[6-fluoro-5-methyl-1-(oxan-2-yl)-1H-indazol-4-yl]-2-[(oxan-4-yl)oxy]quinazolin-8-yl}oxy)methyl]benzoic acid (65 mg), 3-(3-methyl-5-{[(3S)-3-methylpiperazin-1-yl]methyl}-2-oxo-2,3-dihydro-1H-benzimidazol-1-yl)piperidine-2,6-dione dihydrochloride (41 mg), DIPEA (50 L) and DMF (1 mL) was added HATU (35 mg) under ice-bath cooling, and the mixture was stirred at room temperature for 1 hour. Ethyl acetate, water and saturated aqueous sodium hydrogen carbonate solution were added, two layers were separated, and the aqueous layer was extracted with ethyl acetate. The combined organic layer was washed twice with saturated aqueous sodium chloride solution and was then dried over anhydrous sodium sulfate. The insoluble materials were removed by filtration, and the filtrate was concentrated under reduced pressure. The residue was purified by silica gel column chromatography ($CHCl_3$/iPrOH), thus obtaining tert-butyl (1S,4S)-5-{(7M)-6-cyclopropyl-8-({4-[(2S)-4-{[1-(2,6-dioxopiperidin-3-yl)-3-methyl-2-oxo-2,3-dihydro-1H-benzimidazol-5-yl]methyl}-2-methylpiperazine-1-carbonyl]phenyl}methoxy)-7-[6-fluoro-5-methyl-1-(oxan-2-yl)-1H-indazol-4-yl]-2-[(oxan-4-yl)oxy]quinazolin-4-yl}-2,5-diazabicyclo[2.2.1]heptane-2-carboxylate (80 mg) as a solid.

Production Example 77

To a DMF (1 mL) solution of 4-{[(4-{[(3S)-1-(tert-butoxycarbonyl)pyrrolidin-3-yl]oxy}-6-cyclopropyl-7-[6-fluoro-5-methyl-2-(triphenylmethyl)-2H-indazol-4-yl]-2-[(2S)-2-methoxypropoxy]quinolin-8-yl)oxy]methyl}benzoic acid (80 mg), 3-(3-methyl-5-{[(3S)-3-methylpiperazin-1-yl]methyl}-2-oxo-2,3-dihydro-1H-benzimidazol-1-yl)piperidine-2,6-dione dihydrochloride (40 mg) and DIPEA (64 L) was added HATU (41 mg) under ice-bath cooling, and the mixture was stirred at room temperature overnight. Ethyl acetate and water were added, and the organic layer was extracted. After washing with saturated aqueous sodium chloride solution, the organic layer was dried over anhydrous magnesium sulfate, was concentrated under reduced pressure and was purified by silica gel column chromatography ($CHCl_3$/iPrOH), thus obtaining tert-butyl (3S)-3-({6-cyclopropyl-8-({4-[(2S)-4-{[1-(2,6-dioxopiperidin-3-yl)-3-methyl-2-oxo-2,3-dihydro-1H-benzimidazol-5-yl]methyl}-2-methylpiperazine-1-carbonyl]phenyl}methoxy)-7-[6-fluoro-5-methyl-2-(triphenylmethyl)-2H-indazol-4-yl]-2-[(2S)-2-methoxypropoxy]quinolin-4-yl}oxy)pyrrolidine-1-carboxylate (75 mg) as a foam-like solid.

Production Example 78

To a DMF (1 mL) solution of 4-[({4-[(1S,4S)-5-(tert-butoxycarbonyl)-2,5-diazabicyclo[2.2.1]heptan-2-yl]-6-cyclopropyl-7-[6-fluoro-5-methyl-2-(triphenylmethyl)-2H-indazol-4-yl]-2-[(2S)-2-methoxypropoxy]quinolin-8-yl}oxy)methyl]benzoic acid (76 mg), 3-(3-methyl-5-{[(3S)-3-methylpiperazin-1-yl]methyl}-2-oxo-2,3-dihydro-1H-benzimidazol-1-yl)piperidine-2,6-dione dihydrochloride (39 mg) and DIPEA (60 L) was added HATU (39 mg) under ice-bath cooling, and the mixture was stirred at room temperature for 2 hours. Water was added, and the mixture was extracted with ethyl acetate twice. The combined organic layer was washed with saturated aqueous sodium chloride solution, was then dried over anhydrous magnesium sulfate and was concentrated under reduced pressure. The residue was purified by silica gel column chromatography ($CHCl_3$/iPrOH), thus obtaining tert-butyl (1S,4S)-5-{6-cyclopropyl-8-({4-[(2S)-4-{[1-(2,6-dioxopiperidin-3-yl)-3-methyl-2-oxo-2,3-dihydro-1H-benzimidazol-5-yl]methyl}-2-methylpiperazine-1-carbonyl]phenyl}methoxy)-7-[6-fluoro-5-methyl-2-(triphenylmethyl)-2H-indazol-4-yl]-2-[(2S)-2-methoxypropoxy]quinolin-4-yl}-2,5-diazabicyclo[2.2.1]heptane-2-carboxylate (100 mg) as a foam-like solid.

Production Example 79

To a DMF (2 mL) solution of 4-[({(7M)-4-[(1S,4S)-5-(tert-butoxycarbonyl)-2,5-diazabicyclo[2.2.1]heptan-2-yl]-6-cyclopropyl-7-[6-fluoro-5-methyl-1-(oxan-2-yl)-1H-indazol-4-yl]-2-[(oxan-4-yl)oxy]quinazolin-8-yl}oxy)methyl]benzoic acid (70 mg), 1-(7-{[(3S)-3-methylpiperazin-1-yl]methyl}imidazo[1,2-a]pyridin-3-yl)-1,3-diazinane-2,4-dione n trifluoromethanesulfonate (64 mg) and DIPEA (100 L) was added HATU (63 mg) under ice-bath cooling, and the mixture was stirred at room temperature for 4 hours. The reaction mixture was diluted with $CHCl_3$ and water, two layers were separated, and the aqueous layer was extracted with $CHCl_3$. The combined organic layer was dried over anhydrous sodium sulfate, was filtered and was concentrated under reduced pressure. The residue was purified by silica gel column chromatography ($CHCl_3$/MeOH), thus obtaining tert-butyl (1S,4S)-5-{(7M)-6-cyclopropyl-8-({4-[(2S)-4-{[3-(2,4-dioxo-1,3-diazinan-1-yl)imidazo[1,2-a]pyridin-7-yl]methyl}-2-methylpiperazine-1-carbonyl] phenyl}methoxy)-7-[6-fluoro-5-methyl-1-(oxan-2-yl)-1H-indazol-4-yl]-2-[(oxan-4-yl)oxy]quinazolin-4-yl}-2,5-diazabicyclo[2.2.1]heptane-2-carboxylate (84.9 mg) as a foam-like solid.

Production Example 80

To a mixture of 4-[({(7M)-4-[(1S,4S)-5-(tert-butoxycarbonyl)-2,5-diazabicyclo[2.2.1]heptan-2-yl]-6-cyclopropyl-7-[6-fluoro-5-methyl-1-(oxan-2-yl)-1H-indazol-4-yl]-2-[(oxan-4-yl)oxy]quinazolin-8-yl}oxy)methyl]benzoic acid (70 mg), 5-[(3,8-diazabicyclo[3.2.1]octan-3-yl)methyl]-2-(2,6-dioxopiperidin-3-yl)-1H-isoindole-1,3(2H)-dione n hydrochloride (45 mg) and DMF (1 mL) were added DIPEA (60 L) and HATU (45 mg) under ice-bath cooling, and the mixture was stirred at room temperature for 2 hours. Water, saturated aqueous sodium chloride solution and ethyl acetate were added to the mixture, two layers were separated, and the aqueous layer was extracted with ethyl acetate. The combined organic layer was washed twice with saturated aqueous sodium chloride solution and was dried over anhydrous magnesium sulfate. The insoluble materials were removed by filtration, and the filtrate was concentrated under reduced pressure. The residue was purified by silica gel column chromatography ($CHCl_3$/MeOH), thus obtaining tert-butyl (1S,4S)-5-{(7M)-6-cyclopropyl-8-{[4-(3-{[2-(2,6-dioxopiperidin-3-yl)-1,3-dioxo-2,3-dihydro-TH-isoindol-5-yl]methyl}-3,8-diazabicyclo[3.2.1]octane-8-carbonyl) phenyl]methoxy}-7-[6-fluoro-5-methyl-1-(oxan-2-yl)-1H-indazol-4-yl]-2-[(oxan-4-yl)oxy]quinazolin-4-yl}-2,5-diazabicyclo[2.2.1]heptane-2-carboxylate (100 mg) as a solid.

Production Example 81

Under an argon atmosphere, to a mixture of 4-[({(7M)-4-[(1S,4S)-5-(tert-butoxycarbonyl)-2,5-diazabicyclo[2.2.1] heptan-2-yl]-6-cyclopropyl-7-[6-fluoro-5-methyl-1-(oxan-2-yl)-1H-indazol-4-yl]-2-[(oxan-4-yl)oxy]quinazolin-8-yl}oxy)methyl]benzoic acid (100 mg), 3-(5-{[(3S)-3-methylpiperazin-1-yl]methyl}-1-oxo-1,3-dihydro-2H-indazol-2-yl)piperidine-2,6-dione n hydrochloride (61 mg), DIPEA (0.1 mL) and DMF (6 mL) was added HATU (90 mg) under ice-bath cooling, and the mixture was stirred at room temperature for 3 hours. The reaction mixture was diluted with ethyl acetate and water to separate an aqueous layer. The aqueous layer was extracted with ethyl acetate, and the combined organic layer was dried over anhydrous sodium sulfate, was filtered and was concentrated under reduced pressure. The residue was purified by silica gel column chromatography ($CHCl_3$/MeOH), thus obtaining tert-butyl (1S,4S)-5-{(7M)-6-cyclopropyl-8-({4-[(2S)-4-{[2-(2,6-dioxopiperidin-3-yl)-1-oxo-2,3-dihydro-1H-isoindol-5-yl]methyl}-2-methylpiperazine-1-carbonyl] phenyl}methoxy)-7-[6-fluoro-5-methyl-1-(oxan-2-yl)-1H-indazol-4-yl]-2-[(oxan-4-yl)oxy]quinazolin-4-yl}-2,5-diazabicyclo[2.2.1]heptane-2-carboxylate (127.6 mg) as a foam-like solid.

Production Example 82

To a mixture of 4-[({(7M)-4-[(1S,4S)-5-(tert-butoxycarbonyl)-2,5-diazabicyclo[2.2.1]heptan-2-yl]-6-cyclopropyl-7-[6-fluoro-5-methyl-1-(oxan-2-yl)-1H-indazol-4-yl]-2-[(oxan-4-yl)oxy]quinazolin-8-yl}oxy)methyl]benzoic acid (130 mg), 1-(1-methyl-6-{[(3S)-3-methylpiperazin-1-yl] methyl}-1H-indazol-3-yl)-1,3-diazinane-2,4-dione n hydrochloride (76 mg), DIPEA (130 L) and DMF (1.3 mL) was added HATU (78 mg), and the mixture was stirred at room temperature overnight. Water and saturated aqueous sodium hydrogen carbonate solution were added to the reaction mixture. The mixture was stirred for a while, and the resulting solid was filtered to give tert-butyl (1S,4S)-5-{(7M)-6-cyclopropyl-8-({4-[(2S)-4-{[3-(2,4-dioxo-1,3-diazinan-1-yl)-1-methyl-1H-indazol-6-yl]methyl}-2-methylpiperazine-1-carbonyl]phenyl}methoxy)-7-[6-fluoro-5-methyl-1-(oxan-2-yl)-1H-indazol-4-yl]-2-[(oxan-4-yl)oxy] quinazolin-4-yl}-2,5-diazabicyclo[2.2.1]heptane-2-carboxylate (164 mg) as a solid.

Production Example 83

Under an argon atmosphere, a mixture prepared by adding tBuOK (1.39 g) to a dehydrated THF (40 mL) solution of (1S)-1-phenylethan-1-ol (1.56 mL) and stirring at room temperature for 30 minutes was added dropwise to a mixture of 7-bromo-4-chloro-2-(ethylsulfanyl)-8-fluoro-6-iodoquinoline (5.5 g) and dehydrated THF (40 mL) under ice-bath cooling over 20 minutes, and the mixture was stirred at the same temperature for 10 minutes. Separately, under an argon atmosphere, a mixture prepared by adding tBuOK (415 mg) to a dehydrated THF (10 mL) solution of (1S)-1-phenylethan-1-ol (0.45 mL) and stirring at room temperature for 10 minutes was slowly added dropwise to the above reaction mixture under ice-bath cooling, and the mixture was stirred at the same temperature for 10 minutes. Saturated aqueous ammonium chloride solution, ice and ethyl acetate were added to divide the mixture into layers, and the aqueous layer was extracted with ethyl acetate twice. The combined organic layer was washed with saturated aqueous sodium chloride solution and was dried over anhydrous magnesium sulfate. The insoluble materials were removed by filtration, and the filtrate was concentrated under reduced pressure. The residue was purified by silica gel column chromatography (hexane/ethyl acetate), thus obtaining 7-bromo-4-chloro-2-(ethylsulfanyl)-6-iodo-8-[(1S)-1-phenylethoxy] quinoline (4.9 g) as an oil. Slightly impure fractions were concentrated, thus obtaining 7-bromo-4-chloro-2-(ethylsulfanyl)-6-iodo-8-[(1S)-1-phenylethoxy]quinoline (1.56 g) as an oil.

Production Example 84

Under an argon atmosphere, a mixture of 1-(6-bromo-1-methyl-1H-indazol-3-yl)-1,3-diazinane-2,4-dione (600 mg), potassium vinyltrifluoroborate (995 mg), $PdCl_2$(dppf)-$CH_2Cl_2$ (152 mg), cesium carbonate (1.21 g), DOX (12.5 mL) and water (3 mL) was stirred at 80° C. for 3 hours. After the mixture was allowed to cool to room temperature, water was added, and the mixture was extracted with ethyl acetate. The organic layer was washed with saturated aqueous sodium chloride solution, was dried over anhydrous magnesium sulfate and was concentrated under reduced pressure. The resulting residue was purified by silica gel column chromatography (hexane/ethyl acetate, $CHCl_3$/MeOH), thus obtaining 1-(6-ethenyl-1-methyl-1H-indazol-3-yl)-1,3-diazinane-2,4-dione (546 mg) as a solid.

Production Example 85

To a mixture of tert-butyl 2-(2,6-dioxopiperidin-3-yl)-1,3-dioxo-2,3-dihydro-1H-isoindole-5-carbaldehyde (52 mg), 3,8-diazabicyclo[3.2.1]octane-8-carboxylate (46 mg) and $CH_2Cl_2$ (1 mL) was added acetic acid (10 L), and the mixture was stirred at room temperature for 30 minutes. Sodium triacetoxyborohydride (60 mg) was added to the reaction mixture, and the mixture was stirred at room temperature for 16 hours. The mixture was diluted with $CHCl_3$, saturated aqueous sodium hydrogen carbonate solution was added. The mixture was stirred for a while and then, two layers were separated. The aqueous layer was extracted with $CHCl_3$/MeOH (9/1). The combined organic layer was dried over anhydrous sodium sulfate. The insoluble materials were removed by filtration, and the filtrate was concentrated under reduced pressure. The resulting residue was purified by silica gel column chromatography ($CHCl_3$/MeOH), thus obtaining tert-butyl 3-{[2-(2,6-dioxopiperidin-3-yl)-1,3-dioxo-2,3-dihydro-1H-isoindol-5-yl]methyl}-3,8-diazabicyclo[3.2.1]octane-8-carboxylate (containing impurities, 84 mg) as an oil.

Production Example 86

To a mixture of 3-(2,4-dioxo-1,3-diazinan-1-yl)-1-methyl-1H-indazole-6-carbaldehyde (50 mg), acetic acid (11 L), $CH_2Cl_2$ (1 mL) and N-methyl-2-pyrrolidone (1 mL) was tert-butyl (2S)-2-methylpiperazine-1-carboxylate (115 mg), and the mixture was stirred at room temperature for 30 minutes. Sodium triacetoxyborohydride (120 mg) was added to the reaction mixture, and the mixture was stirred at room temperature for 16 hours. After the mixture was diluted with ethyl acetate, saturated aqueous sodium hydrogen carbonate solution was added. The mixture was stirred for a while to separate an aqueous layer, and then the aqueous layer was extracted with ethyl acetate. The combined organic layer was washed twice with saturated aqueous sodium chloride solution and was dried over anhydrous sodium sulfate. The insoluble materials were removed by filtration, and the filtrate was concentrated under reduced pressure. The residue was purified by silica gel column chromatography ($CHCl_3$/MeOH), thus obtaining tert-butyl (2S)-4-{[3-(2,4-dioxo-1,3-diazinan-1-yl)-1-methyl-1H-indazol-6-yl]methyl}-2-methylpiperazine-1-carboxylate (74 mg) as a foam-like solid.

Production Example 87

To a mixture of tert-butyl 3-{[2-(2,6-dioxopiperidin-3-yl)-1,3-dioxo-2,3-dihydro-1H-isoindol-5-yl]methyl}-3,8-diazabicyclo[3.2.1]octane-8-carboxylate (82 mg) and $CH_2Cl_2$ (2 mL) was added hydrogen chloride (4 M DOX solution, 1 mL) under ice-bath cooling, and the mixture was stirred at room temperature overnight. The mixture was concentrated under reduced pressure, and ethyl acetate was added to the residue. The resulting solid was filtered and was dried under reduced pressure, thus obtaining 5-[(3,8-diazabicyclo[3.2.1]octane-3-yl)methyl]-2-(2,6-dioxopiperidin-3-yl)-1H-isoindole-1,3(2H)-dione n hydrochloride (49 mg) as a solid.

Production Example 88

To a mixture of tert-butyl (2S)-4-{[2-(2,6-dioxopiperidin-3-yl)-1-oxo-2,3-dihydro-1H-isoindol-5-yl]methyl}-2-methylpiperazine-1-carboxylate (124 mg) and $CH_2Cl_2$ (8 mL) was added hydrogen chloride (4 M DOX solution, 4 mL) under ice-bath cooling, and the mixture was stirred at room temperature for 18 hours. The mixture was concentrated under reduced pressure, thus obtaining 3-(5-{[(3S)-3-methylpiperazin-1-yl]methyl}-1-oxo-1,3-dihydro-2H-indazol-2-yl)piperidine-2,6-dione n hydrochloride (125 mg) as a solid.

Production Example 89

To a mixture of tert-butyl (2S)-4-{[3-(2,4-dioxo-1,3-diazinan-1-yl)-1-methyl-TH-indazol-6-yl]methyl}-2-methylpiperazine-1-carboxylate (74 mg) and $CH_2Cl_2$ (2 mL) was added hydrogen chloride (4 M DOX solution, 2 mL), and the mixture was stirred at room temperature for 6 hours. The mixture was concentrated under reduced pressure, thus obtaining 1-(1-methyl-6-{[(3S)-3-methylpiperazin-1-yl]methyl}-1H-indazol-3-yl)-1,3-diazinane-2,4-dione n hydrochloride (75 mg) as a solid.

Production Example 90

To a mixture of 1-(7-bromoimidazo[1,2-a]pyridin-3-yl)-3-[(4-methoxyphenyl)methyl]-1,3-diazinane-2,4-dione (500 mg), potassium {[(3S)-4-(tert-butoxycarbonyl)-3-methylpiperazin-1-yl]methyl}tri(fluoro)boranuide (1.1 g), DOX (5 mL) and water (1 mL) were sequentially added di(adamantan-1-yl)(butyl)phosphine (167 mg), cesium carbonate (1.1 g) and palladium(II) acetate (52.3 mg), and the mixture was stirred at 100° C. for 12 hours. Water was added to the reaction mixture, and the mixture was extracted with ethyl acetate three times. The combined organic layer was dried over anhydrous sodium sulfate and was concentrated under reduced pressure. The resulting residue was purified by silica gel column chromatography ($CH_2Cl_2$/MeOH), thus obtaining tert-butyl (2S)-4-[(3-{3-[(4-methoxyphenyl)methyl]-2,4-dioxo-1,3-diazinan-1-yl}imidazo[1,2-a]pyridin-7-yl)methyl]-2-methylpiperazine-1-carboxylate (550 mg) as an oil.

Production Example 91

To a mixture of 4-bromo-6-fluoro-5-methyl-2-(triphenylmethyl)-2H-indazole (100 g), 4,4,4',4',5,5,5',5'-octamethyl-2,2'-bi-1,3,2-dioxaborolane (61.42 g), triphenylphosphine (10.57 g), potassium acetate (59.34 g) and DOX (1000 mL) was added palladium(II) acetate (4.52 g) under nitrogen atmosphere at room temperature. After the reaction mixture was degassed and filled with nitrogen gas three times each, the mixture was stirred at 100° C. for 12 hours under nitrogen atmosphere. After cooling, water (1500 mL) was added, and the mixture was extracted with ethyl acetate (900 mL) three times. The combined organic layer was dried over anhydrous sodium sulfate, and then the insoluble materials were removed by filtration. Activated carbon (50 g) was added to the resulting solution, and the solution was stirred at 20° C. for 1 hour and filtered while washing with ethyl acetate (50 ml) three times. The filtrate was concentrated. MeOH (200 mL) was added to the resulting residue for trituration, and 6-fluoro-5-methyl-4-(4,4,5,5-tetramethyl-1,3,2-dioxaborolan-2-yl)-2-(triphenylmethyl)-2H-indazole (110 g) was obtained as a solid by collecting by filtration and drying under reduced pressure.

Production Example 92

To a mixture of 4-bromo-6-fluoro-2-(triphenylmethyl)-2H-indazole (100 g) and 2-methyltetrahydrofuran (1000 mL) was added lithium diisopropylamide (2 M THF solution, 214.28 mL) at −78° C. under nitrogen atmosphere, and the mixture was stirred at −78° C. for 2.5 hours. Methyl iodide (26.68 mL) was added at −78° C., and the mixture was stirred at 25° C. for 2.5 hours. Water (2000 mL) was added to quench the reaction, and the mixture was extracted with ethyl acetate (800 mL) twice. The combined organic layer was dried over anhydrous sodium sulfate. Then, the insoluble materials were removed by filtration, and the filtrate was concentrated under reduced pressure. Ethyl acetate (50 mL)/petroleum ether (50 mL) were added to the resulting residue for trituration, and then 4-bromo-6-fluoro-5-methyl-2-(triphenylmethyl)-2H-indazole (81 g) was obtained as a solid by collecting by filtration and drying under reduced pressure.

Production Example 93

To a mixture of 4-bromo-6-fluoro-1H-indazole (235 g), TEA (183 mL) and $CH_2Cl_2$ (1880 mL) was added 1,1',1"-(chloromethanetriyl)tribenzene (335 g) at room temperature, and the mixture was stirred at 25° C. for 16 hours. The reaction mixture was poured into ice water (1.5 L), and the organic layer and the aqueous layer were separated. The aqueous layer was extracted with $CH_2Cl_2$ (400 mL) three times. The combined organic layer was dried over anhydrous sodium sulfate. Then, the insoluble materials were removed by filtration, and the filtrate was concentrated under reduced pressure. Petroleum ether (550 mL) was added to the resulting residue for trituration (0° C., 2 hours), and then 4-bromo-6-fluoro-2-(triphenylmethyl)-2H-indazole (508.98 g) was obtained as a solid by collecting by filtration and drying under reduced pressure.

Production Example 94

Ethanethiol (3.6 mL) and DABCO (7.7 g) were added to a $CH_2Cl_2$ (200 mL) suspension of 7-bromo-4-tert-butoxy-2-chloro-8-fluoro-6-iodoquinazoline (21 g) at room temperature, and under an argon atmosphere, the mixture was stirred at room temperature overnight. The reaction was quenched with water under ice-bath cooling. $CHCl_3$ was added, the organic layer and the aqueous layer were separated, and the aqueous layer was extracted with $CHCl_3$ three times.

The collected organic layer was dried over anhydrous sodium sulfate, was filtered and was concentrated under reduced pressure, thus obtaining 7-bromo-4-tert-butoxy-2-(ethylsulfanyl)-8-fluoro-6-iodoquinazoline (23.4 g) as a solid.

Production Example 97

To 7-bromo-4-tert-butoxy-6-cyclopropyl-2-(ethylsulfanyl)-8-[(1S)-1-phenylethoxy]quinazoline (14.21 g) were added 6-fluoro-5-methyl-4-(4,4,5,5-tetramethyl-1,3,2-dioxaborolan-2-yl)-2-(triphenylmethyl)-2H-indazole (19.3 g), palladium(II) acetate (0.67 g), dicyclohexyl(2',6'-diisopropoxy-[1,1'-biphenyl]-2-yl)phosphine (2.67 g), anhydrous barium hydroxide (14.6 g) and DOX (500 mL)/water (100 mL), degassing and argon gas substitution operations were performed several times. Then, the mixture was heated and stirred at 50° C. overnight under an argon atmosphere. The reaction suspension which was allowed to cool was filtered through celite (registered trademark) pad while washing with ethyl acetate, and the gray insoluble materials were removed by filtration. After the filtrate was concentrated to about ¼ under reduced pressure, water was added, and the mixture was extracted twice with ethyl acetate. The collected organic layer was washed with saturated aqueous sodium chloride solution, was dried over anhydrous magnesium sulfate and was concentrated under reduced pressure. The resulting residue was purified by silica gel column chromatography (hexane/ethyl acetate), thus obtaining 4-tert-butoxy-6-cyclopropyl-2-(ethylsulfanyl)-7-[6-fluoro-5-methyl-2-(triphenylmethyl)-2H-indazol-4-yl]-8-[(1S)-1-phenylethoxy]quinazoline (about 3.3:1 diastereomeric mixture derived from axial chirality, 16.44 g) as a solid.

Production Example 98

Under nitrogen flow, 4-tert-butoxy-6-cyclopropyl-2-(ethanesulfonyl)-7-[6-fluoro-5-methyl-2-(triphenylmethyl)-2H-indazol-4-yl]-8-[(1S)-1-phenylethoxy]quinazoline (about 3.3:1 diastereomeric mixture derived from axial chirality, 33.71 g) was dissolved in $CH_2Cl_2$ (500 mL), and m-chloroperbenzoic acid (about 30% water content, 22.4 g) was added under ice-bath cooling (internal temperature: 5 to 10° C.). The mixture was stirred for 2 hours at room temperature. Under ice-bath cooling, an aqueous solution (300 mL) of sodium thiosulfate pentahydrate (11 g) and saturated aqueous sodium hydrogen carbonate solution (300 mL) were poured into the reaction solution, and the mixture was stirred for 30 minutes at room temperature and was then extracted with ethyl acetate twice. The combined organic layer was washed with saturated aqueous sodium hydrogen carbonate solution and saturated aqueous sodium chloride solution, was dried over anhydrous magnesium sulfate and was filtered. The filtrate was concentrated under reduced pressure, thus obtaining 4-tert-butoxy-6-cyclopropyl-2-(ethanesulfonyl)-7-[6-fluoro-5-methyl-2-(triphenylmethyl)-2H-indazol-4-yl]-8-[(1S)-1-phenylethoxy]quinazoline (diastereomeric mixture derived from axial chirality). iPrOH (1000 mL) was added to the resulting residue, and the mixture was stirred at room temperature overnight. The resulting solid was filtered, was washed with iPrOH and was dried under reduced pressure, thus obtaining 4-tert-butoxy-6-cyclopropyl-2-(ethanesulfonyl)-7-[6-fluoro-5-methyl-2-(triphenylmethyl)-2H-indazol-4-yl]-8-[(1S)-1-phenylethoxy]quinazoline (about 1:1 diastereomeric mixture derived from axial chirality, 11.52 g) as a solid. The filtrate was concentrated under reduced pressure, thus obtaining the desired (7M)-4-tert-butoxy-6-cyclopropyl-2-(ethanesulfonyl)-7-[6-fluoro-5-methyl-2-(triphenylmethyl)-2H-indazol-4-yl]-8-[(1S)-1-phenylethoxy]quinazoline (single diastereomer, 23.29 g) as a solid.

Production Example 227

A mixture of phenyl (2E)-2-benzylidenehydrazine-1-carboxylate (200 mg), 5-bromo-2-iodoaniline (373 mg), DABCO (281 mg) and benzotrifluoride (9 mL) was stirred at 100° C. for 12 hours. After allowing to cool to room temperature, the reaction solution was concentrated under reduced pressure. DMSO (8 mL), copper(I) iodide (24 mg) and 1,10-phenanthroline (46 mg) were added to the residue, and the mixture was stirred at 100° C. for 5 hours. After allowing to cool to room temperature, the mixture was diluted with ethyl acetate and washed with water, was dried over anhydrous magnesium sulfate and was concentrated under reduced pressure, thus obtaining 1-[(E)-benzylideneamino]-5-bromo-1,3-dihydro-2H-benzimidazol-2-one (451 mg, containing impurities) as a solid.

Production Example 228

To a mixture of 1-[(E)-benzylideneamino]-5-bromo-1,3-dihydro-2H-benzimidazol-2-one (450 mg, containing impurities) obtained in Production Example 227, potassium carbonate (576 mg) and DMF (8 mL) was added methyl iodide (0.195 mL), and the mixture was stirred at room temperature for 4 hours. The mixture was diluted with ethyl acetate and washed with water. Two layers were separated, and the aqueous layer was extracted with ethyl. The combined organic layer was dried over anhydrous sodium sulfate and was concentrated under reduced pressure. The residue was purified by silica gel column chromatography (hexane/$CHCl_3$), thus obtaining 1-[(E)-benzylideneamino]-5-bromo-3-methyl-1,3-dihydro-2H-benzimidazol-2-one (201 mg) as a solid.

Production Example 229

To a mixture of 1-[(E)-benzylideneamino]-5-bromo-3-methyl-1,3-dihydro-2H-benzimidazol-2-one (197 mg) and MeOH (4 mL) was added a mixture of hydroxylamine (60 mg) and MeOH (4 mL), and the mixture was stirred under reflux with heat for 8 hours. After the reaction mixture was allowed to cool to room temperature, MeOH (7 mL) and a mixture of hydroxylamine (120 mg) and MeOH (1 mL) was added, and the mixture was stirred under reflux with heat for 8 hours. The reaction mixture was allowed to cool to room temperature and was concentrated under reduced pressure. The residue was purified by silica gel column chromatography (hexane/ethyl acetate), thus obtaining 1-amino-5-bromo-3-methyl-1,3-dihydro-2H-benzimidazol-2-one (109 mg) as a solid.

Production Example 231

To a mixture of ethyl 3-[(5-bromo-3-methyl-2-2-oxo-2,3-dihydro-1H-benzimidazol-1-yl)amino]propanoate (100 mg), $CH_2Cl_2$ (2 mL) and pyridine (48 L) was added a $CH_2Cl_2$ (1 mL) solution of triphosgene (45 mg) under ice-bath cooling, and the mixture was stirred under ice-bath cooling for 1 hour and at room temperature for 2 hours. The solution was diluted with $CH_2Cl_2$ and washed with hydrochloric acid (0.5 μM), was dried over anhydrous sodium sulfate and was concentrated under reduced pressure. Ammonia (7 M MeOH solution, 2.6 mL) was added to the residue under ice-bath cooling, and the mixture was stirred at room temperature for 2.5 hours. The mixture was concentrated under reduced pressure, thus obtaining ethyl 3-[(5-bromo-3-methyl-2-oxo-2,3-dihydro-1H-benzimidazol-1-yl)(carbamoyl)amino]propanoate (112.6 mg) as a solid.

Production Example 236

To a mixture of methyl 3-cyclopropyl-3-oxopropanoate (17 mL) and trimethyl orthoformate (20 mL) was added concentrated sulfuric acid (500 L) under ice-bath cooling, and under an argon atmosphere, the mixture was stirred at room temperature overnight. The reaction solution was concentrated and dried at room temperature under reduced pressure over 4 hours. 5-Aminopyrimidine-2,4(1H,3H)-dione (11.4 g) and DMAc (300 mL) were added to the residue at room temperature, and under an argon atmosphere, the mixture was stirred at 110° C. overnight. The reaction mixture was concentrated under reduced pressure, and water was added to the residue. The resulting solid was filtered and was dried under reduced pressure at 50° C. overnight, thus obtaining methyl 3-cyclopropyl-3-[(2,4-dioxo-1,2,3,4-tetrahydropyrimidin-5-yl)amino]prop-2-enoate (22.3 g) as a solid.

Production Example 237

Methyl 3-cyclopropyl-3-[(2,4-dioxo-1,2,3,4-tetrahydropyrimidin-5-yl)amino]prop-2-enoate (870 mg) was dissolved in NMP (17 mL) at room temperature, and the mixture was stirred under an argon atmosphere at 220° C. for 5 hours. The reaction mixture was concentrated under reduced pressure, and water was added to the residue. The resulting solid was filtered and was dried under reduced pressure at 50° C. for 1 hour, thus obtaining 6-cyclopropylpyrido[3,2-d]pyrimidine-2,4,8-triol (230 mg) as a solid.

Production Example 238

To a DMF (90 mL) solution of 6-cyclopropylpyrido[3,2-d]pyrimidine-2,4,8-triol (5.71 g) was added N-bromosuccinimide (9.3 g) under ice-bath cooling, and the mixture was stirred at room temperature overnight. Water was added thereto under ice-bath cooling. The resulting solid was filtered and was dried under reduced pressure at 50° C. for 3 hours, thus obtaining 7-bromo-6-cyclopropylpyrido[3,2-d]pyrimidine-2,4,8-triol (2.12 g) as a solid.

Production Example 239

To a mixture of 7-bromo-6-cyclopropylpyrido[3,2-d]pyrimidine-2,4,8-triol (2.11 g) and N,N-diethylaniline (3.4 mL) was added phosphorus oxychloride (38.2 g) at room temperature, and under an argon atmosphere, the mixture was stirred at 100° C. overnight. After the reaction solution was concentrated under reduced pressure, MeCN (35 mL) and DIPEA (6 mL) were added to the residue under ice-bath cooling, and the mixture was stirred for 1 minute. Then, tert-butyl (1S,4S)-2,5-diazabicyclo[2.2.1]heptane-2-carboxylate (1.96 g) was added under ice-bath cooling, and the mixture was stirred at room temperature for 1 hours. The reaction solution was concentrated under reduced pressure, and the resulting residue was purified by silica gel column chromatography (hexane/ethyl acetate), thus obtaining tert-butyl (1S,4S)-5-(7-bromo-2,8-dichloro-6-cyclopropylpyrido[3,2-d]pyrimidin-4-yl)-2,5-diazabicyclo[2.2.1]heptane-2-carboxylate (1.29 g) as a solid.

Production Example 240

Tert-butyl (1S,4S)-5-(7-bromo-2,8-dichloro-6-cyclopropylpyrido[3,2-d]pyrimidin-4-yl)-2,5-diazabicyclo[2.2.1]heptane-2-carboxylate (2.4 g), DMF (20 mL), THF (20 mL) and tetrahydro-2H-pyran-4-ol (2.2 mL) were mixed at room temperature, and under ice-bath cooling, cesium carbonate (7.6 g) and DABCO (100 mg) were added. After the mixture was stirred at 50° C. overnight under an argon atmosphere, saturated aqueous ammonium chloride solution was added under ice-bath cooling to quench the reaction. Water and ethyl acetate were added, the organic layer and the aqueous layer were separated, and the aqueous layer was extracted with ethyl acetate three times. The combined organic layer was dried over anhydrous sodium sulfate, was filtered and was concentrated under reduced. The resulting residue was purified by silica gel column chromatography (hexane/ethyl acetate), thus obtaining tert-butyl (1S,4S)-5-{7-bromo-8-chloro-6-cyclopropyl-2-[(oxan-4-yl)oxy]pyrido[3,2-d]pyrimidin-4-yl}-2,5-diazabicyclo[2.2.1]heptane-2-carboxylate (1.23 g) as a solid.

Production Example 243

To a THF (10 mL) solution of tert-butyl (1S,4S)-5-{6-cyclopropyl-7-[6-fluoro-5-methyl-2-(triphenylmethyl)-2H-indazol-4-yl]-2-[(oxan-4-yl)oxy]-8-[(1S)-1-phenylethoxy] pyrido[3,2-d]pyrimidin-4-yl}-2,5-diazabicyclo[2.2.1] heptane-2-carboxylate (470 mg) were added 4-methylbenzene-1-sulfonic acid monohydrate (60 mg) and 3,4-dihydro-2H-pyran (1.1 mL) under ice-bath cooling, and under an argon atmosphere, the mixture was stirred at room temperature overnight. After TEA (0.4 mL) was added under ice-bath cooling, the reaction solution was concentrated under reduced pressure. The residue was purified by silica gel column chromatography (basic silica gel, hexane/ethyl acetate), thus obtaining tert-butyl (1S,4S)-5-{6-cyclopropyl-7-[6-fluoro-5-methyl-1-(oxan-2-yl)-1H-indazol-4-yl]-2-[(oxan-4-yl)oxy]-8-[(1S)-1-phenylethoxy]pyrido[3,2-d]pyrimidin-4-yl}-2,5-diazabicyclo[2.2.1]heptane-2-carboxylate (291 mg) as a solid.

In the same manner as in the production methods of the Production Examples described above, the compounds shown in the tables presented later were produced. In addition, the production method, the structure and the physiochemical data of the compound of each Production Example are shown in the tables presented later.

Example 5

To a $CH_2Cl_2$ (1 mL) solution of tert-butyl (1S,4S)-5-{(7M)-6-cyclopropyl-8-{[4-(3-{[2-(2,6-dioxopiperidin-3-yl)-1,3-dioxo-2,3-dihydro-1H-isoindol-5-yl]methyl}-3,8-diazabicyclo[3.2.1]octane-8-carbonyl)phenyl]methoxy}-7-[6-fluoro-5-methyl-1-(oxan-2-yl)-1H-indazol-4-yl]-2-[(oxan-4-yl)oxy]quinazolin-4-yl}-2,5-diazabicyclo[2.2.1]heptane-2-carboxylate (98 mg) was added trifluoroacetic acid (0.5 mL) under ice-bath cooling, and the mixture was stirred at room temperature for 2 hours. The mixture was concentrated under reduced pressure, and the residue was purified by ODS column chromatography (0.1% formic acid in MeCN solution/0.1% aqueous formic acid solution). Water and saturated aqueous sodium hydrogen carbonate solution were added to a fraction containing the target compound, and the mixture was extracted twice with $CHCl_3$/MeOH (9/1). The combined organic layer was dried over anhydrous sodium sulfate, was filtered and was concentrated under reduced pressure. The resulting solid was washed with diethyl ether and was dried under reduced pressure, thus obtaining 5-[(8-{4-[({(7M)-6-cyclopropyl-4-[(1S,4S)-2,5-diazabicyclo [2.2.1]heptan-2-yl]-7-(6-fluoro-5-methyl-1H-indazol-4-yl)-2-[(oxan-4-yl)oxy]quinazolin-8-yl}oxy)methyl]benzoyl}-3,8-diazabicyclo[3.2.1]octan-3-yl)methyl]-2-(2,6-dioxopiperidin-3-yl)-1H-isoindole-1,3(2H)-dione (45 mg) as a solid.

Example 8

To a mixture of tert-butyl (1S,4S)-5-{(7M)-6-cyclopropyl-8-({4-[(2S)-4-{[1-(2,6-dioxopiperidin-3-yl)-3-methyl-2-oxo-2,3-dihydro-1H-benzimidazol-5-yl]methyl}-2-methylpiperazine-1-carbonyl]phenyl}methoxy)-7-[6-fluoro-5-methyl-1-(oxan-2-yl)-1H-indazol-4-yl]-2-[(oxan-4-yl)oxy] quinazolin-4-yl}-2,5-diazabicyclo[2.2.1]heptane-2-carboxylate (300 mg) and $CH_2Cl_2$ (2 mL) was added trifluoroacetic acid (1.2 mL) under ice-bath cooling, and the mixture was stirred at room temperature for 2 hours. The mixture was concentrated under reduced pressure, and the residue was purified by ODS column chromatography (0.1% formic acid in MeCN solution/0.1% aqueous formic acid solution). Water and saturated aqueous sodium hydrogen carbonate solution were added to a fraction containing the target compound, and the mixture was extracted twice with $CHCl_3$/iPrOH (5/1). The combined organic layer was dried over anhydrous sodium sulfate. The insoluble materials were removed by filtration, the filtrate was concentrated under reduced pressure, and the residue was again purified by ODS column chromatography (0.1% formic acid in MeCN solution/0.1% aqueous formic acid solution). Water and saturated aqueous sodium hydrogen carbonate solution were added to a fraction containing the target compound, and the mixture was extracted twice with $CHCl_3$/iPrOH (5/1). The combined organic layer was dried over anhydrous sodium sulfate. The insoluble materials were removed by filtration, and the filtrate was concentrated and dried under reduced pressure, thus obtaining 3-(5-{[(3S)-4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl) oxy]quinazolin-8-yl}oxy)methyl]benzoyl}-3-methylpiperazin-1-yl]methyl}-3-methyl-2-oxo-2,3-dihydro-TH-benzimidazol-1-yl)piperidine-2,6-dione (133 mg) as a solid.

Example 10

To tert-butyl (1S,4S)-5-{(7M)-6-cyclopropyl-8-({4-[(2S)-4-{[1-(2,6-dioxopiperidin-3-yl)-3-methyl-2-oxo-2,3-dihydro-TH-benzimidazol-5-yl]methyl}-2-methylpiperazine-1-carbonyl]phenyl}methoxy)-7-[6-fluoro-5-methyl-1-(oxan-2-yl)-1H-indazol-4-yl]-2-[(2S)-2-methoxypropoxy] quinazolin-4-yl}-2,5-diazabicyclo[2.2.1]heptane-2-carboxylate (268 mg) was added $CH_2Cl_2$ (6 mL) and was added trifluoroacetic acid (2 mL) with stirring under cooling in an ice/MeOH bath. The mixture was stirred under an argon atmosphere at room temperature for 2 hours. The mixture was concentrated under reduced pressure, and ice water and saturated aqueous sodium hydrogen carbonate solution were added. The mixture was extracted twice with $CHCl_3$/iPrOH (10/1). The combined organic layer was washed with saturated aqueous sodium chloride solution, was dried over anhydrous magnesium sulfate and was concentrated under reduced pressure. Hexane/ethyl acetate (3/1, about 5 mL) was added to the resulting solid, and the resulting precipitate was filtered while washing with the same solvent and dried under reduced pressure, thus obtaining 3-(5-{[(3S)-4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]benzoyl}-3-methylpiperazin-1-yl]methyl}-3-methyl-2-oxo-2,3-dihydro-1H-benzimidazol-1-yl) piperidine-2,6-dione (198 mg) as a solid.

Example 12

To a $CH_2Cl_2$ (1 mL) solution of tert-butyl (3S)-3-({6-cyclopropyl-8-({4-[(2S)-4-{[1-(2,6-dioxopiperidin-3-yl)-3-methyl-2-oxo-2,3-dihydro-1H-benzimidazol-5-yl]methyl}-

2-methylpiperazine-1-carbonyl]phenyl}methoxy)-7-[6-fluoro-5-methyl-2-(triphenylmethyl)-2H-indazol-4-yl]-2-[(2S)-2-methoxypropoxy]quinolin-4-yl}oxy)pyrrolidine-1-carboxylate (74 mg) was added trifluoroacetic acid (400 L) under ice-bath cooling, and the mixture was stirred at room temperature for 1 hour. The mixture was concentrated under reduced pressure, and the residue was purified by ODS column chromatography (0.1% formic acid in MeCN solution/0.1% aqueous formic acid solution). Water and saturated aqueous sodium hydrogen carbonate solution were added to a fraction containing the target compound, and the mixture was extracted twice with $CHCl_3$/iPrOH (5/1). The combined organic layer was dried over anhydrous sodium sulfate. The insoluble materials were removed by filtration, the filtrate was concentrated under reduced pressure, and $iPr_2O$ was added to the resulting residue. The precipitated solid was filtered, was washed with $iPr_2O$ and was dried under reduced pressure, thus obtaining 3-[5-({(3S)-4-[4-({[6-cyclopropyl-7-(6-fluoro-5-methyl-1H-indazol-4-yl)-2-[(2S)-2-methoxypropoxy]-4-{[(3S)-pyrrolidin-3-yl]oxy}quinolin-8-yl]oxy}methyl)benzoyl]-3-methylpiperazin-1-yl}methyl)-3-methyl-2-oxo-2,3-dihydro-1H-benzimidazol-1-yl]piperidine-2,6-dione (18 mg) as a solid.

Example 16

To a $CH_2Cl_2$ (3 mL) solution of tert-butyl (1S,4S)-5-{(7M)-6-cyclopropyl-8-({4-[(2S)-4-{[3-(2,4-dioxo-1,3-diazinan-1-yl)-1-methyl-1H-indazol-6-yl]methyl}-2-methylpiperazine-1-carbonyl]phenyl}methoxy)-7-[6-fluoro-5-methyl-1-(oxan-2-yl)-1H-indazol-4-yl]-2-[(oxan-4-yl)oxy]quinazolin-4-yl}-2,5-diazabicyclo[2.2.1]heptane-2-carboxylate (164 mg) was added trifluoroacetic acid (1 mL) under ice-bath cooling, and the mixture was stirred at room temperature for 4 hours. The mixture was concentrated under reduced pressure, and the residue was purified by ODS column chromatography (0.1% formic acid in MeCN solution/0.1% aqueous formic acid solution). A fraction containing the target compound was collected and was concentrated under reduced pressure. The resulting residue was dissolved in $CH_2Cl_2$, and hydrogen chloride (4 M ethyl acetate solution, 300 L) was added under ice-bath cooling. The mixture was stirred for a while and was concentrated under reduced pressure, thus obtaining 1-(6-{[(3S)-4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-1-methyl-1H-indazol-3-yl)-1,3-diazinane-2,4-dione n hydrochloride (71 mg) as a foam-like solid.

Example 29

To a $CH_2Cl_2$ (1 mL) solution of tert-butyl (1S,4S)-5-{6-cyclopropyl-8-({4-[(2S)-4-{[1-(2,6-dioxopiperidin-3-yl)-3-methyl-2-oxo-2,3-dihydro-1H-benzimidazol-5-yl]methyl}-2-methylpiperazine-1-carbonyl]phenyl}methoxy)-7-[6-fluoro-5-methyl-2-(triphenylmethyl)-2H-indazol-4-yl]-2-[(2S)-2-methoxypropoxy]quinolin-4-yl}-2,5-diazabicyclo[2.2.1]heptane-2-carboxylate (95 mg) was added trifluoroacetic acid (510 L) under ice-bath cooling, and the mixture was stirred at room temperature for 1 hour. The mixture was concentrated under reduced pressure, and the residue was purified by ODS column chromatography (0.1% formic acid in MeCN solution/0.1% aqueous formic acid solution). Water and saturated aqueous sodium hydrogen carbonate solution were added to a fraction containing the target compound, and the mixture was extracted twice with $CHCl_3$/iPrOH (5/1). The combined organic layer was dried over anhydrous sodium sulfate. The insoluble materials were removed by filtration, and the filtrate was concentrated and dried under reduced pressure, thus obtaining 3-(5-{[(3S)-4-{4-[({6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione (57 mg) as a solid.

Example 33

Under an argon atmosphere, a $CH_2Cl_2$ (4 mL) solution of tert-butyl (1S,4S)-5-{(7M)-6-cyclopropyl-8-({4-[(2S)-4-{[2-(2,6-dioxopiperidin-3-yl)-1-oxo-2,3-dihydro-1H-isoindol-5-yl]methyl}-2-methylpiperazine-1-carbonyl]phenyl}methoxy)-7-[6-fluoro-5-methyl-1-(oxan-2-yl)-1H-indazol-4-yl]-2-[(oxan-4-yl)oxy]quinazolin-4-yl}-2,5-diazabicyclo[2.2.1]heptane-2-carboxylate (122.5 mg) was added trifluoroacetic acid (2 mL) under ice-bath cooling, and the mixture was stirred at room temperature for 4 hours. The mixture was concentrated under reduced pressure, and the residue was purified by ODS column chromatography (0.1% formic acid in MeCN solution/0.1% aqueous formic acid solution). Saturated aqueous sodium hydrogen carbonate solution was added to a fraction containing the target compound, and the mixture was extracted with $CHCl_3$/iPrOH (4/1) four times. The combined organic layer was dried over anhydrous sodium sulfate, was filtered and was concentrated under reduced pressure. The resulting product was washed with diethyl ether, thus obtaining 3-(5-{[(3S)-4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-1-oxo-1,3-dihydro-2H-isoindol-2-yl)piperidine-2,6-dione (68 mg) as a solid.

Example 34

To a $CH_2Cl_2$ (4 mL) solution of tert-butyl (1S,4S)-5-{(7M)-6-cyclopropyl-8-({4-[(2S)-4-{[3-(2,4-dioxo-1,3-diazinan-1-yl)imidazo[1,2-a]pyridin-7-yl]methyl}-2-methylpiperazine-1-carbonyl]phenyl}methoxy)-7-[6-fluoro-5-methyl-1-(oxan-2-yl)-1H-indazol-4-yl]-2-[(oxan-4-yl)oxy]quinazolin-4-yl}-2,5-diazabicyclo[2.2.1]heptane-2-carboxylate (84.9 mg) was added trifluoroacetic acid (2 mL) under ice-bath cooling, and the mixture was stirred at room temperature for 5 hours. The mixture was concentrated under reduced pressure, and the residue was purified by ODS column chromatography (0.1% formic acid in MeCN solution/0.1% aqueous formic acid solution). The fraction containing the target compound was basified with saturated aqueous sodium hydrogen carbonate solution and was then extracted twice with $CHCl_3$/iPrOH (4/1). The combined organic layer was dried over anhydrous sodium sulfate. The insoluble materials were removed by filtration, and the filtrate was concentrated under reduced pressure. The resulting solid was washed with diethyl ether, thus obtaining 1-(7-{[(3S)-4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}imidazo[1,2-a]pyridin-3-yl)-1,3-diazinane-2,4-dione (27 mg) as a solid.

Example 49

To a mixture of 85% phosphoric acid (0.27 mL) and water (1.23 mL) was added 3-(5-{[(3S)-4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione (500 mg) under ice-bath cooling, and the mixture was stirred under ice-bath cooling for 10 minutes and at room temperature for 30 minutes to completely dissolve. The resulting aqueous solution was added dropwise to stirring EtOH (15 mL) under ice-bath cooling. The mixture was stirred at room temperature for 4 hours. The precipitated solid was filtered, was washed with EtOH and was dried under reduced pressure to give phosphate salt (649 mg) as a solid. Water (1.5 mL) was added to the resulting solid, and the mixture was stirred at room temperature for 15 minutes to completely dissolve. The resulting aqueous solution was added dropwise to stirring EtOH (15 mL) under ice-bath cooling. The mixture was stirred at room temperature for 4 hours. The precipitated solid was filtered, was washed with EtOH and was dried under reduced pressure, thus obtaining 3-(5-{[(3S)-4-{4-[({6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione n phosphate (n=about 3, 493 mg) as a solid.

Example 50

To a mixture of 85% phosphoric acid (0.28 mL) and water (1.22 mL) was added 3-(5-{[(3S)-4-{4-[({(7M)-6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione (500 mg) under ice-bath cooling, and the mixture was stirred under ice-bath cooling for 10 minutes and at room temperature for 30 minutes to completely dissolve. The resulting aqueous solution was added dropwise to stirring EtOH (15 mL) under ice-bath cooling. The mixture was stirred at room temperature for 4 hours. The precipitated solid was filtered, was washed with EtOH and was dried under reduced pressure, thus obtaining phosphate salt (543 mg) as a solid. Water (1.5 mL) was added to the resulting solid, and the mixture was stirred at room temperature for 15 minutes to completely dissolve. The resulting aqueous solution was added dropwise to stirring EtOH (15 mL) under ice-bath cooling. The mixture was stirred at room temperature for 4 hours. The precipitated solid was filtered, was washed with EtOH and was dried under reduced pressure, thus obtaining 3-(5-{[(3S)-4-{4-[({6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione n phosphate (n=about 3, 382 mg) as a solid.

In the same manner as in the production methods of the Examples described above, the Example compounds shown in the tables presented later were produced. In addition, the production method and the physiochemical data of the compound of each Example are shown in tables presented later.

In the tables presented below, the following abbreviations are sometimes used.

PEx: Production Example No., Ex: Example No., PSyn: Production Example No. produced in the same method, Syn: Example No. produced in the same method (for example, Syn: 9 represents that it was produced by the same method as for Example 9), Str: chemical structural formula (a compound with "*" in the chemical structural formula represents that the compound is single structure with regard to the axial chirality or central chirality, and a compound with "**" in the chemical structural formula represents that the compound is a mixture of geometrical isomers with a double bond), n HCl: n hydrochloride (the compound with Example No. and Production Example No. shows that the compound is monohydrochloride to tetrahydrochloride), n TfOH: n trifluoromethanesulfonate (the compound with Example No. and Production Example No. shows that the compound is monotrifluoromethanesulfonate to tritrifluoromethanesulfonate), n $H_3PO_4$: n phosphate (the compound with Example No. and Production Example No. shows that the compound is diphosphate to tetraphosphate), DAT: physiochemical data, ESI+: m/z value in mass spectrometry (ionization method ESI, $[M+H]^+$ unless otherwise specified), ESI−: m/z value in mass spectrometry (ionization method ESI, $[M-H]^-$ unless otherwise specified), NMR: δ value (ppm) of peak in $^1$H-NMR (500 MHz) in DMSO-d6 at 27° C., NMR (400 MHz): δ value (ppm) of peak in $^1$H-NMR (400 MHz) in DMSO-d6 at 27° C., NMR (90° C.): δ value (ppm) of peak in TH-NMR (500 MHz) in DMSO-d6 at 90° C., s: singlet (spectrum), d: doublet (spectrum), dd: double doublet (spectrum), t: triplet (spectrum), tt: triple triplet (spectrum), dq: double quartet (spectrum), q: quartet (spectrum), m: multiplet (spectrum), br: broad (spectrum) (example: br s).

TABLE 5-1

| PEx | Str |
|---|---|
| 1 | 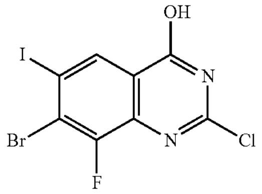 [SMILES: Oc1nc(Cl)nc2c(F)c(Br)c(I)cc12] |
| 2 | 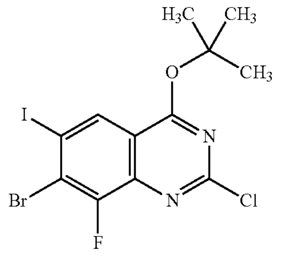 [SMILES: CC(C)(C)Oc1nc(Cl)nc2c(F)c(Br)c(I)cc12] |

TABLE 5-1-continued
| PEx | Str |
|---|---|
| 3 | 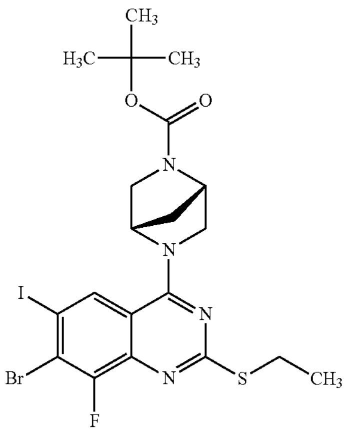 [SMILES: CCSc1nc(N2C[C@@H]3C[C@H]2CN3C(=O)OC(C)(C)C)c2cc(I)c(Br)c(F)c2n1] |
TABLE 5-1-continued
| PEx | Str |
|---|---|
| 4 | 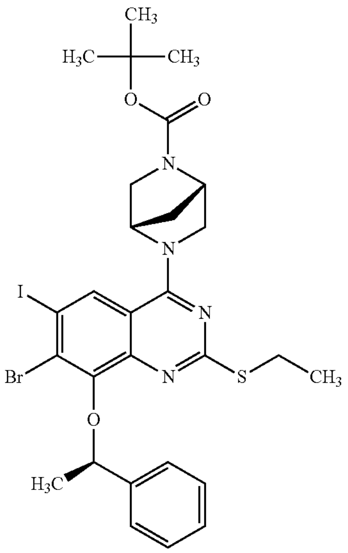 [SMILES: CCSc1nc(N2C[C@@H]3C[C@H]2CN3C(=O)OC(C)(C)C)c2cc(I)c(Br)c(O[C@H](C)c3ccccc3)c2n1] |
TABLE 5-2
| PEx | Str |
|---|---|
| 5 | 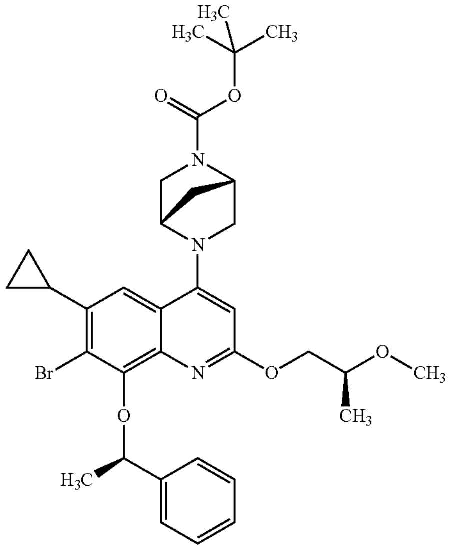 [SMILES: CO[C@@H](C)COc1cc(N2C[C@@H]3C[C@H]2CN3C(=O)OC(C)(C)C)c2cc(C3CC3)c(Br)c(O[C@H](C)c3ccccc3)c2n1] |

TABLE 5-2-continued
| PEx | Str |
| --- | --- |
| 6 | 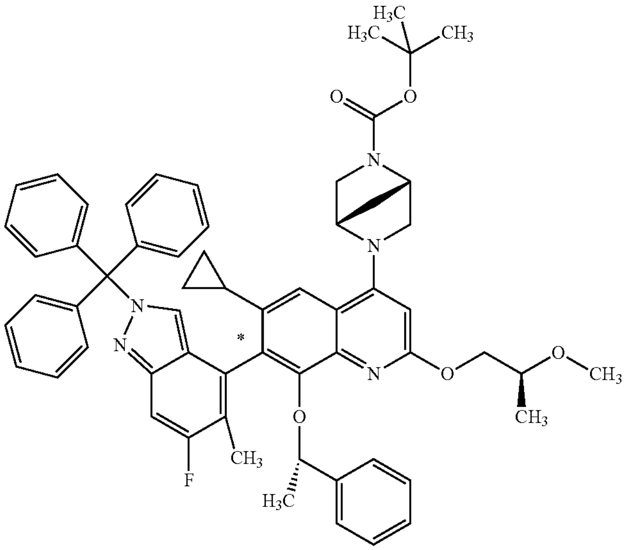 [SMILES: CO[C@@H](C)COc1cc(N2C[C@@H]3C[C@H]2CN3C(=O)OC(C)(C)C)c2cc(C3CC3)c(-c3c(C)c(F)cc4nn(C(c5ccccc5)(c5ccccc5)c5ccccc5)cc34)c(O[C@@H](C)c3ccccc3)c2n1] |
| 7 | 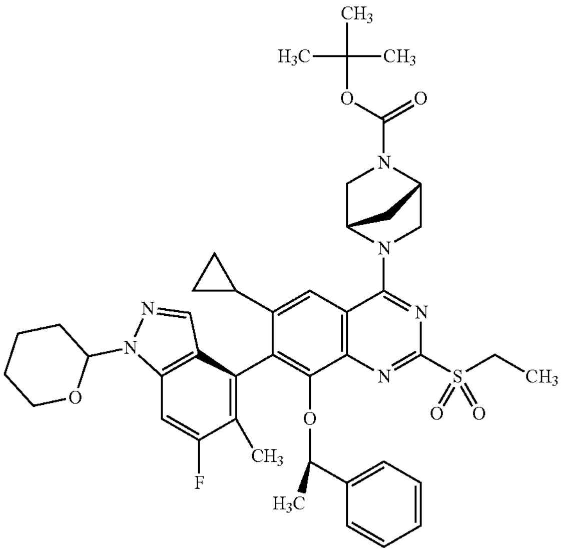 |

TABLE 5-3
| PEx | Str |
| --- | --- |
| 8 | 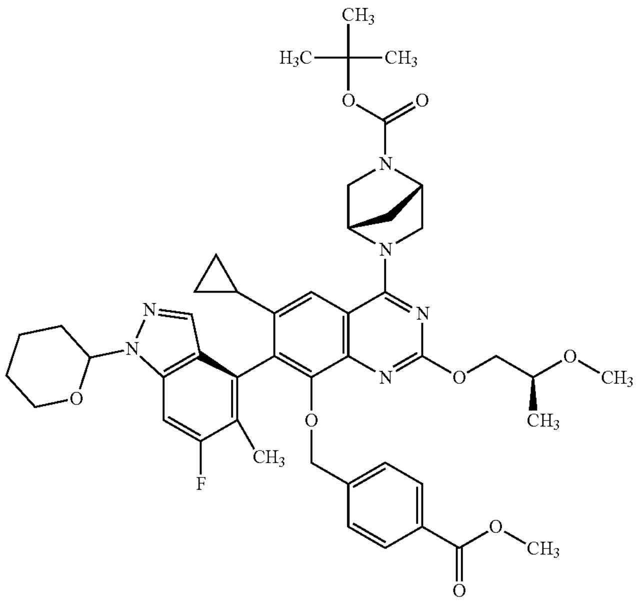 |
| 9 | 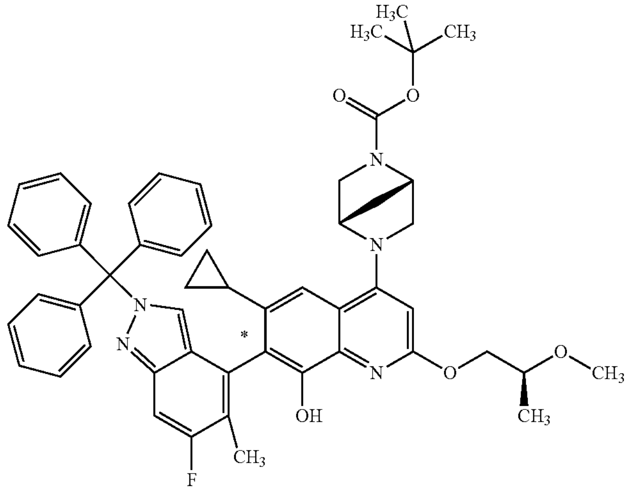 [SMILES: CO[C@@H](C)COc1cc(N2C[C@@H]3C[C@H]2CN3C(=O)OC(C)(C)C)c2cc(C3CC3)c(-c3c(C)c(F)cc4nn(C(c5ccccc5)(c5ccccc5)c5ccccc5)cc34)c(O)c2n1] |

TABLE 5-3-continued
| PEx | Str |
|---|---|
| 10 | 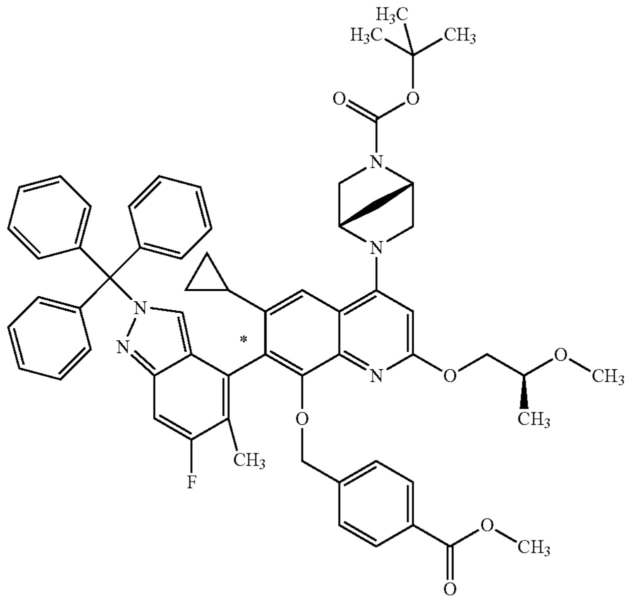 [SMILES: COC(=O)c1ccc(COc2c(-c3c(C)c(F)cc4nn(C(c5ccccc5)(c5ccccc5)c5ccccc5)cc34)c(C3CC3)cc3c(N4C[C@@H]5C[C@H]4CN5C(=O)OC(C)(C)C)cc(OC[C@H](C)OC)nc23)cc1] |
TABLE 5-4
| PEx | Str |
|---|---|
| 11 | 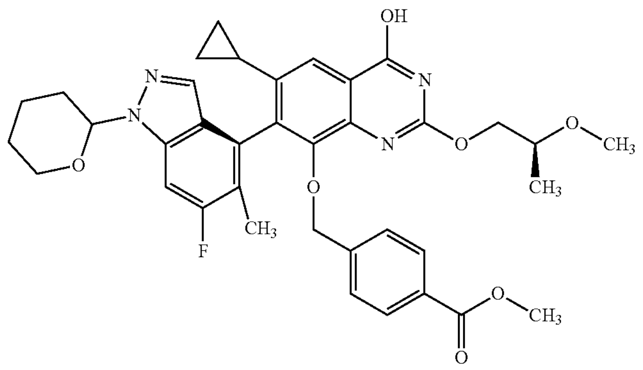 |

TABLE 5-4-continued
| PEx | Str |
| --- | --- |
| 12 | 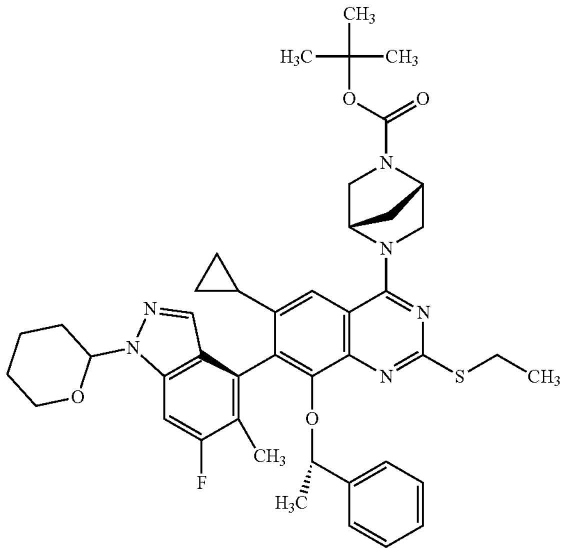 |
| 13 | 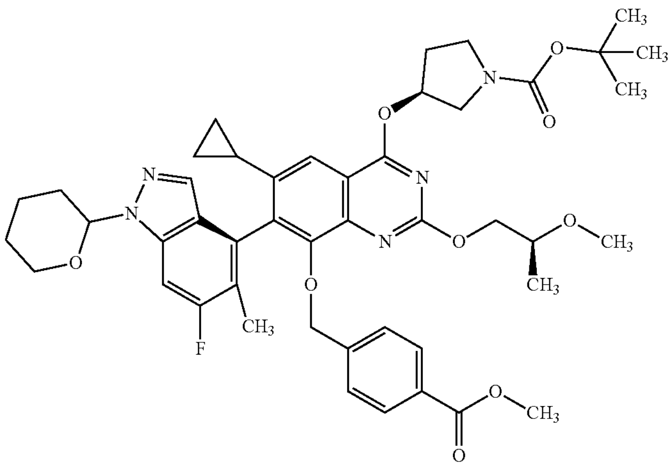 |

TABLE 5-5
| PEx | Str |
| --- | --- |
| 14 | 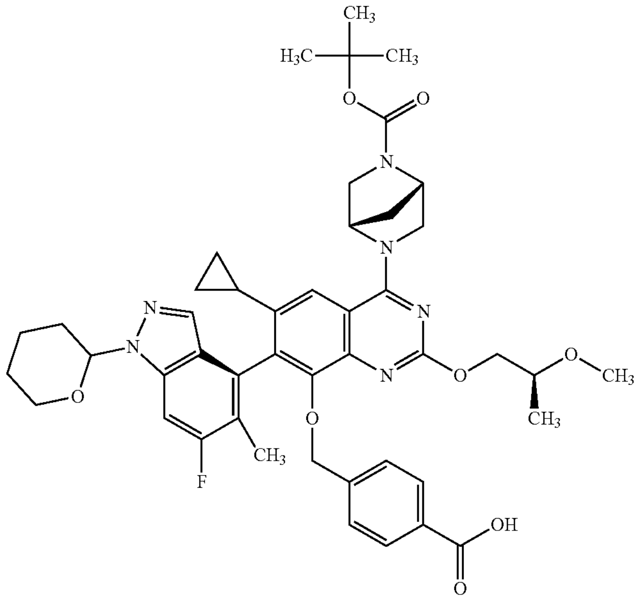 |
| 15 | 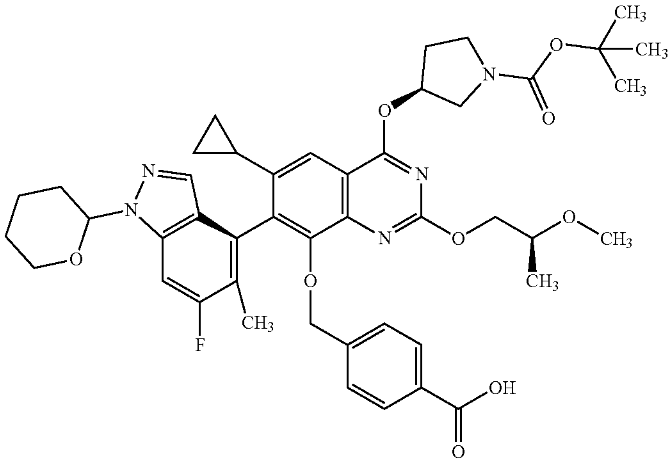 |

TABLE 5-5-continued
| PEx | Str |
|---|---|
| 16 | 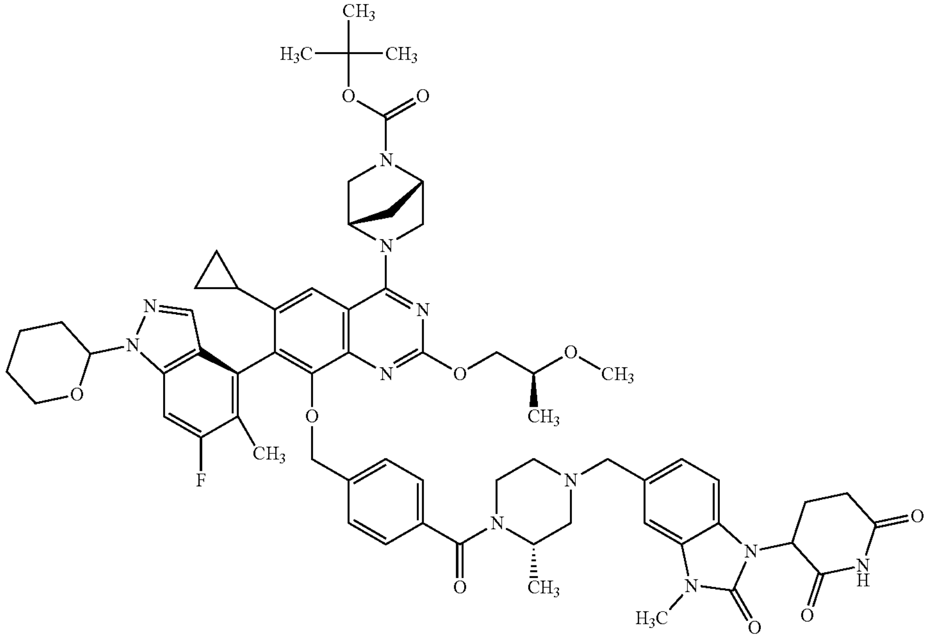 |
TABLE 5-6
| PEx | Str |
|---|---|
| 17 | 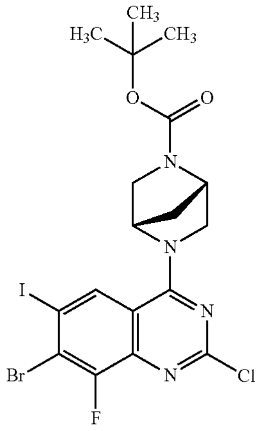 [SMILES: CC(C)(C)OC(=O)N1C[C@@H]2C[C@H]1CN2c1nc(Cl)nc2c(F)c(Br)c(I)cc12] |
TABLE 5-6-continued
| PEx | Str |
|---|---|
| 18 | 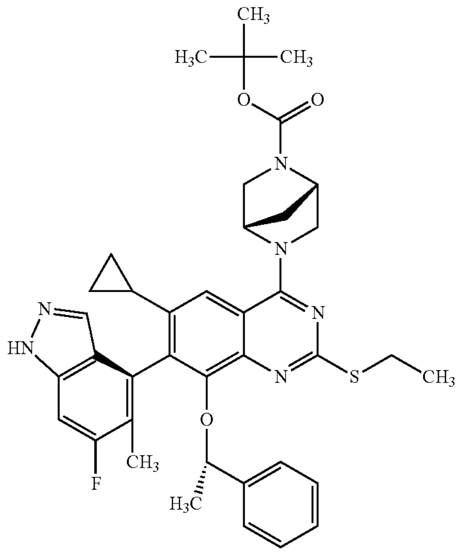 |

TABLE 5-6-continued
| PEx | Str |
|---|---|
| 19 | 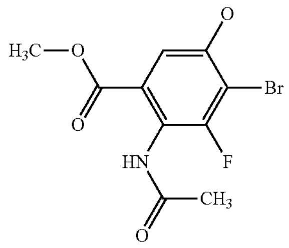 [SMILES: COC(=O)c1cc(O)c(Br)c(F)c1NC(C)=O] |
TABLE 5-7
| PEx | Str |
|---|---|
| 20 | 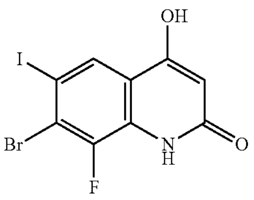 [SMILES: O=c1cc(O)c2cc(I)c(Br)c(F)c2[nH]1] |
| 21 | 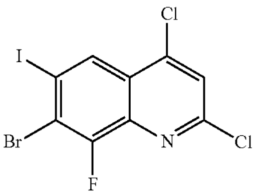 [SMILES: Fc1c(Br)c(I)cc2c(Cl)cc(Cl)nc12] |
| 22 | 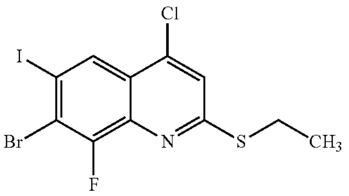 [SMILES: CCSc1cc(Cl)c2cc(I)c(Br)c(F)c2n1] |
| 23 | 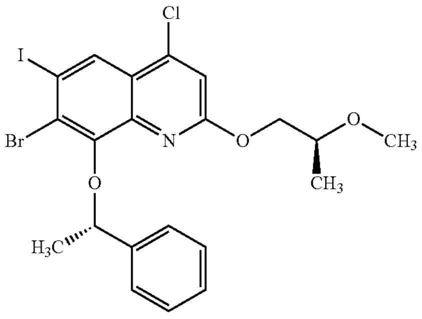 [SMILES: CO[C@@H](C)COc1cc(Cl)c2cc(I)c(Br)c(O[C@@H](C)c3ccccc3)c2n1] |
TABLE 5-7-continued
| PEx | Str |
|---|---|
| 24 | 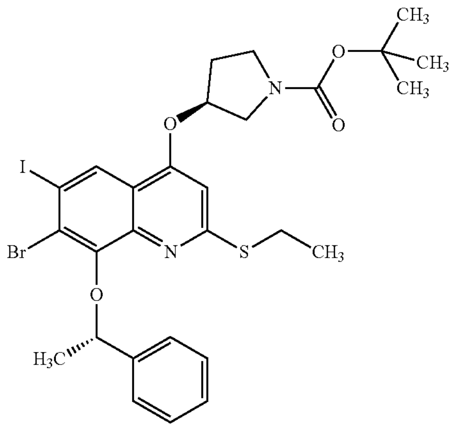 [SMILES: CCSc1cc(O[C@H]2CCN(C(=O)OC(C)(C)C)C2)c2cc(I)c(Br)c(O[C@@H](C)c3ccccc3)c2n1] |
TABLE 5-8
| PEx | Str |
|---|---|
| 25 | 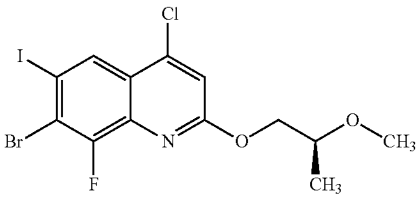 [SMILES: CO[C@@H](C)COc1cc(Cl)c2cc(I)c(Br)c(F)c2n1] |
| 26 | 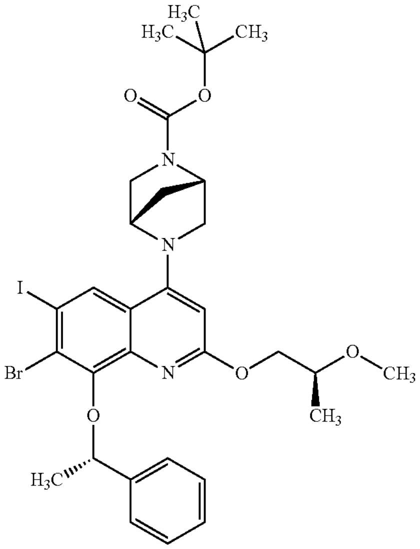 [SMILES: CO[C@@H](C)COc1cc(N2C[C@@H]3C[C@H]2CN3C(=O)OC(C)(C)C)c2cc(I)c(Br)c(O[C@@H](C)c3ccccc3)c2n1] |
| 27 | 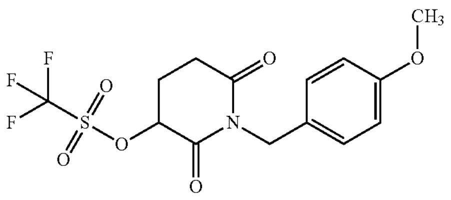 [SMILES: COc1ccc(CN2C(=O)CCC(OS(=O)(=O)C(F)(F)F)C2=O)cc1] |

TABLE 5-8-continued
| PEx | Str |
|---|---|
| 28 | 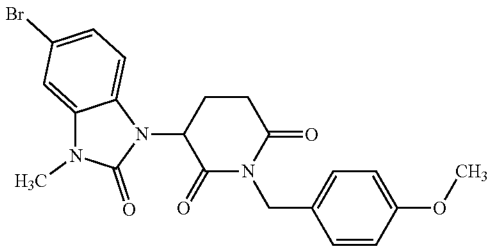 [SMILES: COc1ccc(CN2C(=O)CCC(n3c(=O)n(C)c4cc(Br)ccc43)C2=O)cc1] |
TABLE 5-9
| PEx | Str |
|---|---|
| 29 | 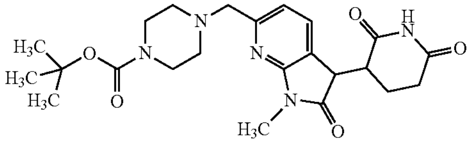 [SMILES: CN1C(=O)C(C2CCC(=O)NC2=O)c2ccc(CN3CCN(C(=O)OC(C)(C)C)CC3)nc21] |
| 30 | 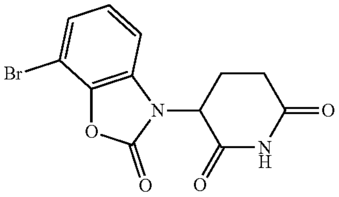 [SMILES: O=C1CCC(n2c(=O)oc3c(Br)cccc32)C(=O)N1] |
| 31 | 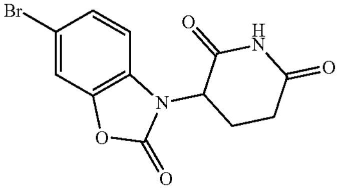 [SMILES: O=C1CCC(n2c(=O)oc3cc(Br)ccc32)C(=O)N1] |
| 32 | 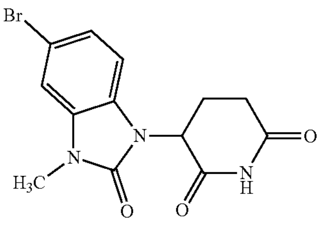 [SMILES: Cn1c(=O)n(C2CCC(=O)NC2=O)c2ccc(Br)cc21] |
| 33 | 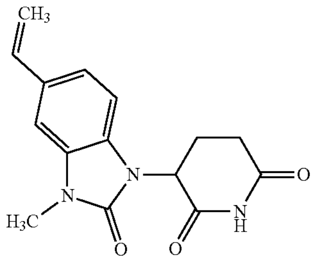 [SMILES: C=Cc1ccc2c(c1)n(C)c(=O)n2C1CCC(=O)NC1=O] |
TABLE 5-10
| PEx | Str |
|---|---|
| 34 | 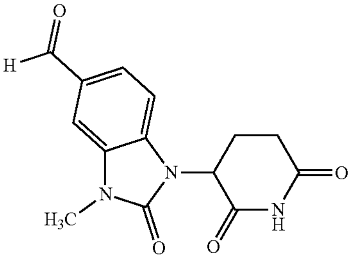 [SMILES: Cn1c(=O)n(C2CCC(=O)NC2=O)c2ccc(C=O)cc21] |
| 35 | 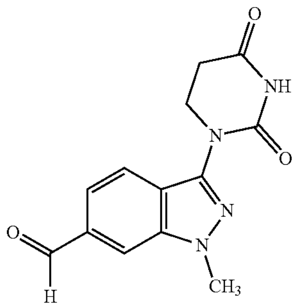 [SMILES: Cn1nc(N2CCC(=O)NC2=O)c2ccc(C=O)cc21] |
| 36 | 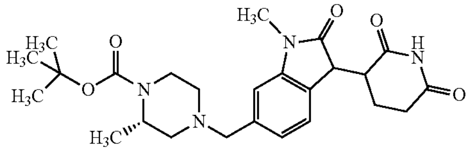 [SMILES: C[C@H]1CN(Cc2ccc3c(c2)N(C)C(=O)C3C2CCC(=O)NC2=O)CCN1C(=O)OC(C)(C)C] |
| 37 | 2 HCl 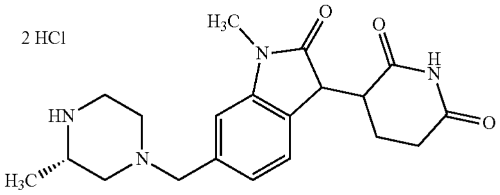 [SMILES: C[C@H]1CN(Cc2ccc3c(c2)N(C)C(=O)C3C2CCC(=O)NC2=O)CCN1] |
| 38 | 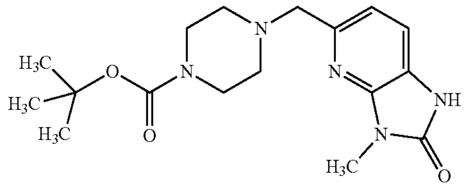 [SMILES: Cn1c(=O)[nH]c2ccc(CN3CCN(C(=O)OC(C)(C)C)CC3)nc21] |

TABLE 5-11
| PEx | Str |
|---|---|
| 39 | 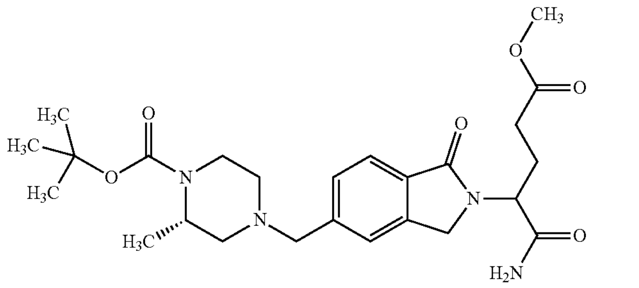 [SMILES: COC(=O)CCC(C(N)=O)N1Cc2cc(CN3CCN(C(=O)OC(C)(C)C)[C@@H](C)C3)ccc2C1=O] |
| 40 | 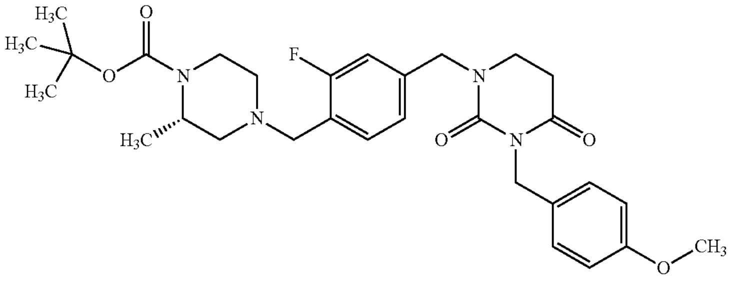 [SMILES: COc1ccc(CN2C(=O)CCN(Cc3ccc(CN4CCN(C(=O)OC(C)(C)C)[C@@H](C)C4)c(F)c3)C2=O)cc1] |
| 41 | 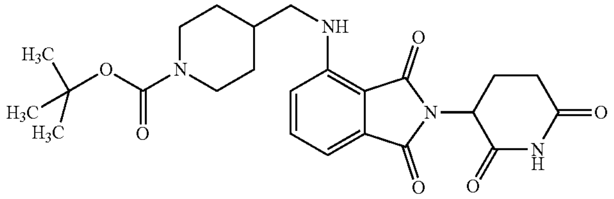 [SMILES: CC(C)(C)OC(=O)N1CCC(CNc2cccc3c2C(=O)N(C2CCC(=O)NC2=O)C3=O)CC1] |
| 42 | 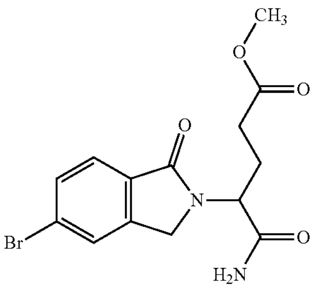 [SMILES: COC(=O)CCC(C(N)=O)N1Cc2cc(Br)ccc2C1=O] |
| 43 | 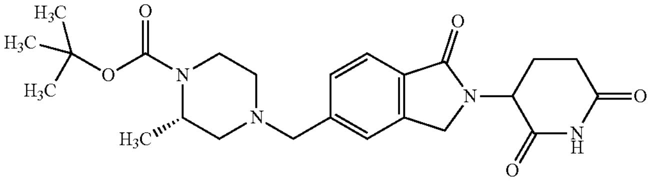 [SMILES: C[C@H]1CN(Cc2ccc3c(c2)CN(C2CCC(=O)NC2=O)C3=O)CCN1C(=O)OC(C)(C)C] |

TABLE 5-12
| PEx | Str |
|---|---|
| 44 | 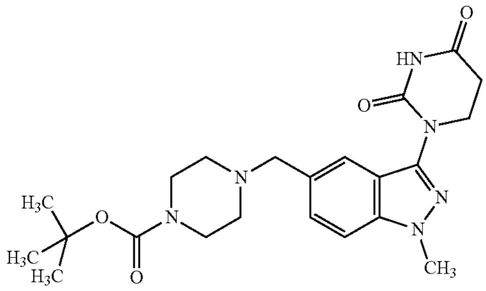 [SMILES: Cn1nc(N2CCC(=O)NC2=O)c2cc(CN3CCN(C(=O)OC(C)(C)C)CC3)ccc21] |
| 45 | 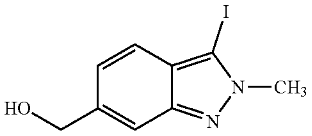 |
| 46 | 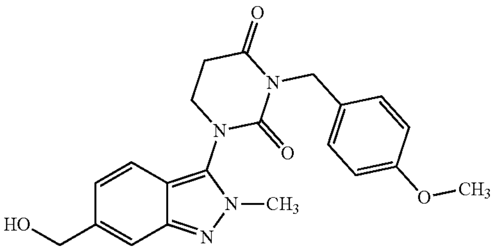 [SMILES: COc1ccc(CN2C(=O)CCN(c3c4ccc(CO)cc4nn3C)C2=O)cc1] |
| 47 | 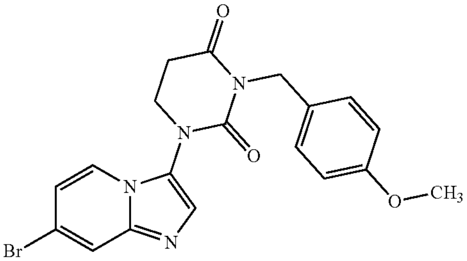 [SMILES: COc1ccc(CN2C(=O)CCN(c3cnc4cc(Br)ccn34)C2=O)cc1] |
| 48 | 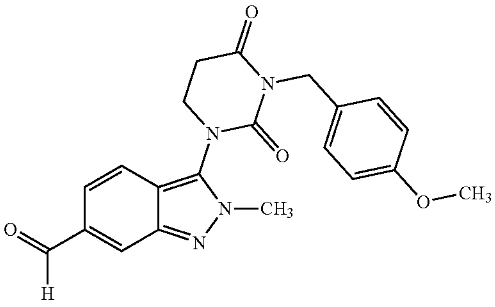 [SMILES: COc1ccc(CN2C(=O)CCN(c3c4ccc(C=O)cc4nn3C)C2=O)cc1] |
TABLE 5-13
| PEx | Str |
|---|---|
| 49 | 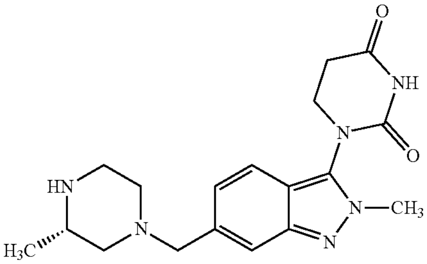 [SMILES: C[C@H]1CN(Cc2ccc3c(N4CCC(=O)NC4=O)n(C)nc3c2)CCN1] |
| 50 | *n* TfOH 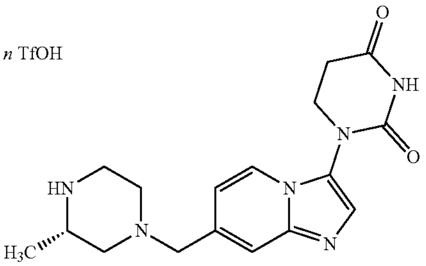 [SMILES: C[C@H]1CN(Cc2ccn3c(N4CCC(=O)NC4=O)cnc3c2)CCN1] |
| 51 | ** 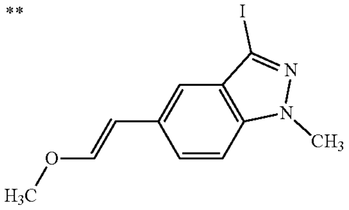 |
| 52 | 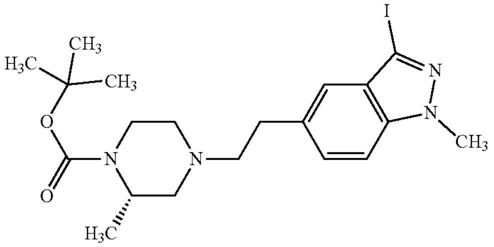 [SMILES: C[C@H]1CN(CCc2ccc3c(c2)c(I)nn3C)CCN1C(=O)OC(C)(C)C] |
| 53 | 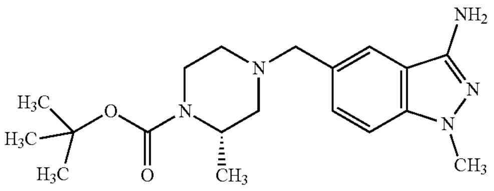 [SMILES: C[C@H]1CN(Cc2ccc3c(c2)c(N)nn3C)CCN1C(=O)OC(C)(C)C] |

TABLE 5-14
| PEx | Str |
|---|---|
| 54 | 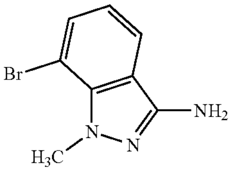 |
| 55 | 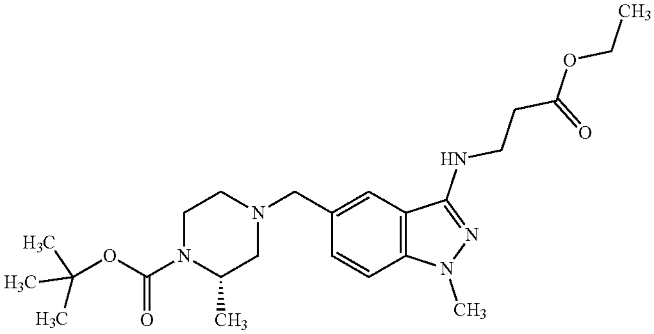 [SMILES: CCOC(=O)CCNc1nn(C)c2ccc(CN3CCN(C(=O)OC(C)(C)C)[C@@H](C)C3)cc12] |
| 56 | 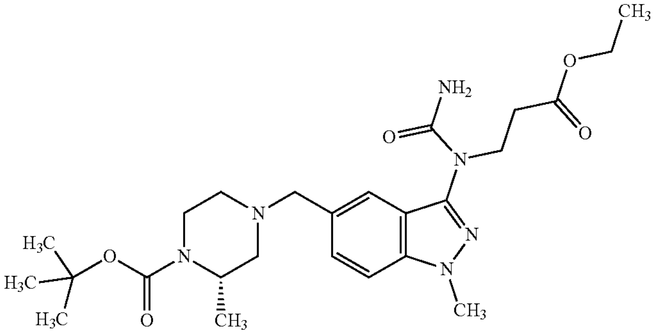 [SMILES: CCOC(=O)CCN(C(N)=O)c1nn(C)c2ccc(CN3CCN(C(=O)OC(C)(C)C)[C@@H](C)C3)cc12] |
| 57 | 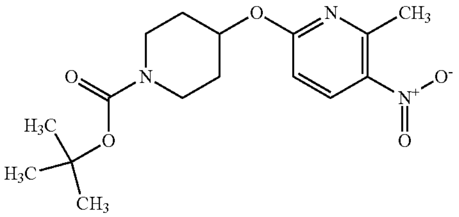 [SMILES: Cc1nc(OC2CCN(C(=O)OC(C)(C)C)CC2)ccc1[N+](=O)[O-]] |
| 58 | 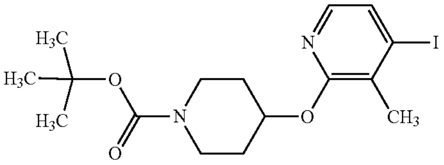 [SMILES: Cc1c(I)ccnc1OC1CCN(C(=O)OC(C)(C)C)CC1] |
TABLE 5-15
| PEx | Str |
|---|---|
| 59 | 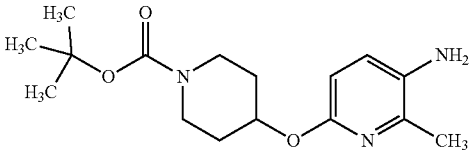 [SMILES: Cc1nc(OC2CCN(C(=O)OC(C)(C)C)CC2)ccc1N] |
TABLE 5-15-continued
| PEx | Str |
|---|---|
| 60 | 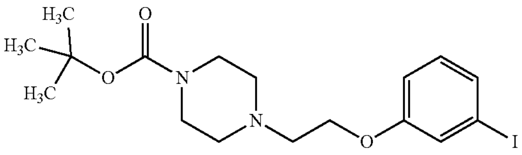 [SMILES: CC(C)(C)OC(=O)N1CCN(CCOc2cccc(I)c2)CC1] |

TABLE 5-15-continued
| PEx | Str |
|---|---|
| 61 | 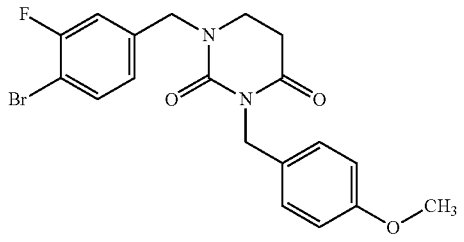 [SMILES: COc1ccc(CN2C(=O)CCN(Cc3ccc(Br)c(F)c3)C2=O)cc1] |
TABLE 5-15-continued
| PEx | Str |
|---|---|
| 62 | 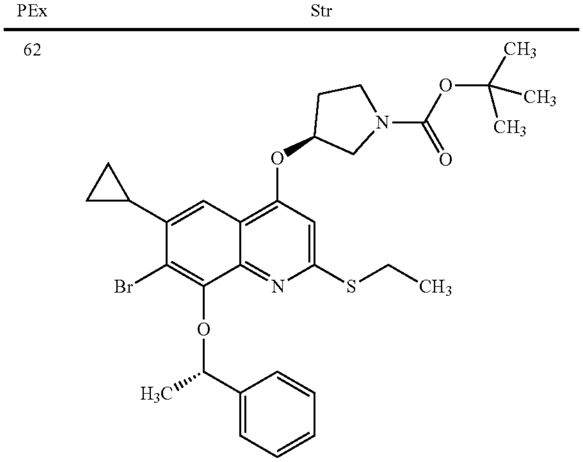 |
TABLE 5-16
| PEx | Str |
|---|---|
| 63 | 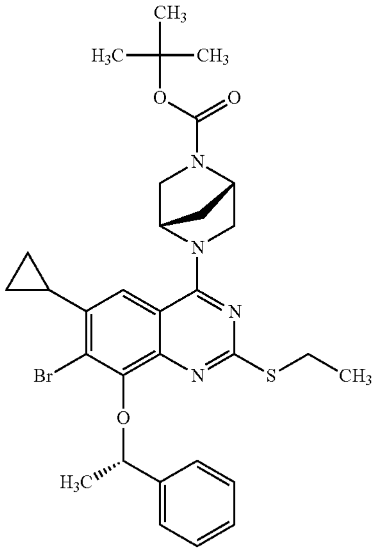 [SMILES: CCSc1nc(N2C[C@@H]3C[C@H]2CN3C(=O)OC(C)(C)C)c2cc(C3CC3)c(Br)c(O[C@@H](C)c3ccccc3)c2n1] |
| 64 | 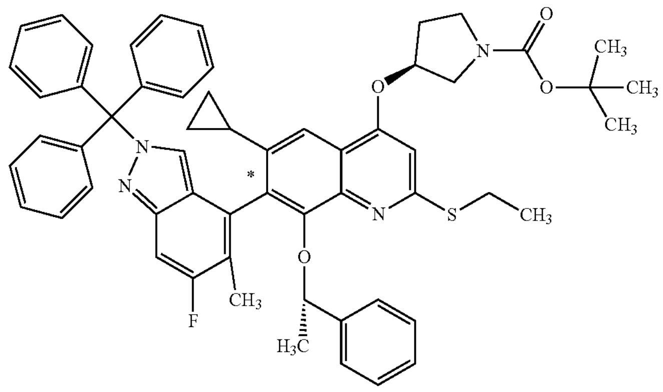 [SMILES: CCSc1cc(O[C@H]2CCN(C(=O)OC(C)(C)C)C2)c2cc(C3CC3)c(-c3c(C)c(F)cc4nn(C(c5ccccc5)(c5ccccc5)c5ccccc5)cc34)c(O[C@@H](C)c3ccccc3)c2n1] |

TABLE 5-16-continued
| PEx | Str |
|---|---|
| 65 | 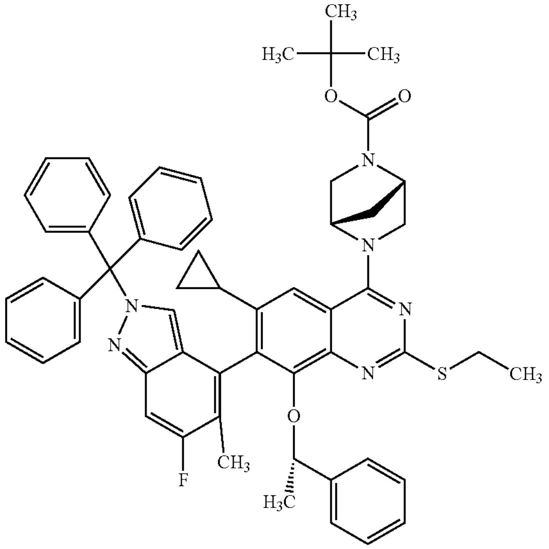 [SMILES: CCSc1nc(N2C[C@@H]3C[C@H]2CN3C(=O)OC(C)(C)C)c2cc(C3CC3)c(-c3c(C)c(F)cc4nn(C(c5ccccc5)(c5ccccc5)c5ccccc5)cc34)c(O[C@@H](C)c3ccccc3)c2n1] |
TABLE 5-17
| PEx | Str |
|---|---|
| 66 | 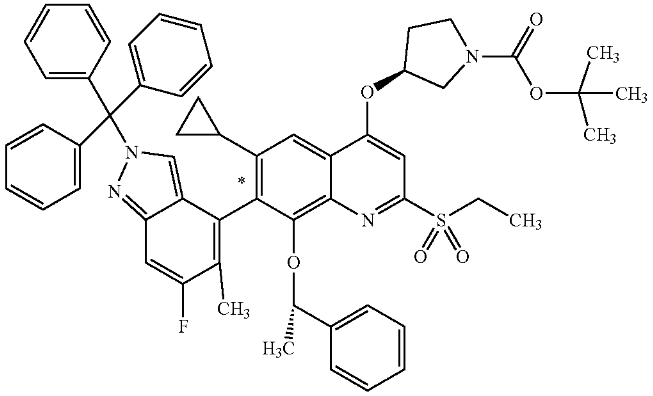 [SMILES: CCS(=O)(=O)c1cc(O[C@H]2CCN(C(=O)OC(C)(C)C)C2)c2cc(C3CC3)c(-c3c(C)c(F)cc4nn(C(c5ccccc5)(c5ccccc5)c5ccccc5)cc34)c(O[C@@H](C)c3ccccc3)c2n1] |

TABLE 5-17-continued
| PEx | Str |
|---|---|
| 67 | 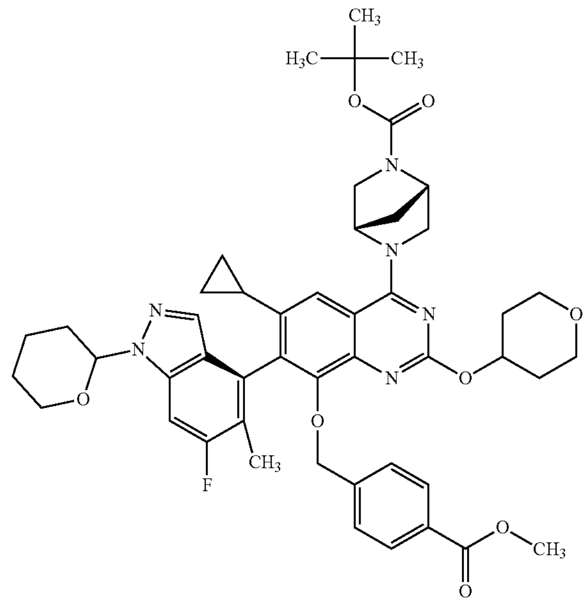 |
| 68 | 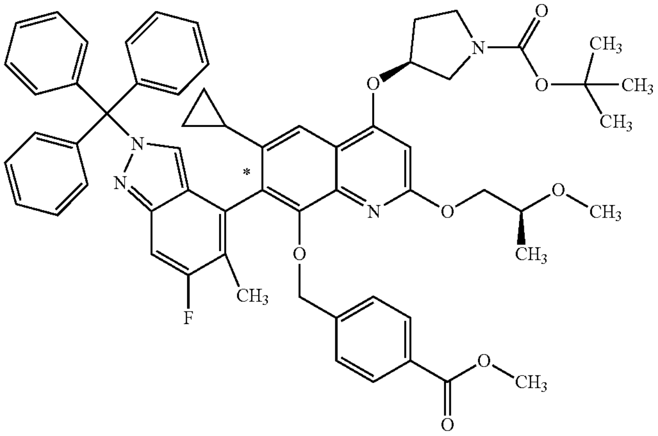 [SMILES: COC(=O)c1ccc(COc2c(-c3c(C)c(F)cc4nn(C(c5ccccc5)(c5ccccc5)c5ccccc5)cc34)c(C3CC3)cc3c(O[C@H]4CCN(C(=O)OC(C)(C)C)C4)cc(OC[C@H](C)OC)nc23)cc1] |

TABLE 5-18
| PEx | Str |
|---|---|
| 69 | 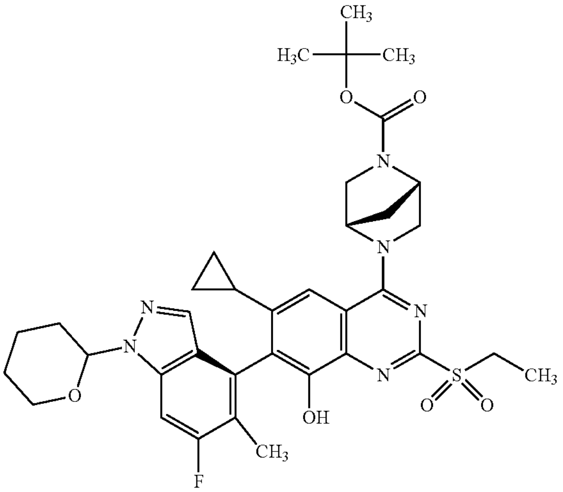 |
| 70 | 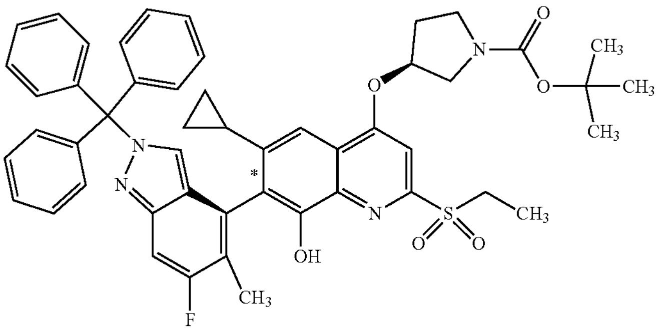 |
| 71 | 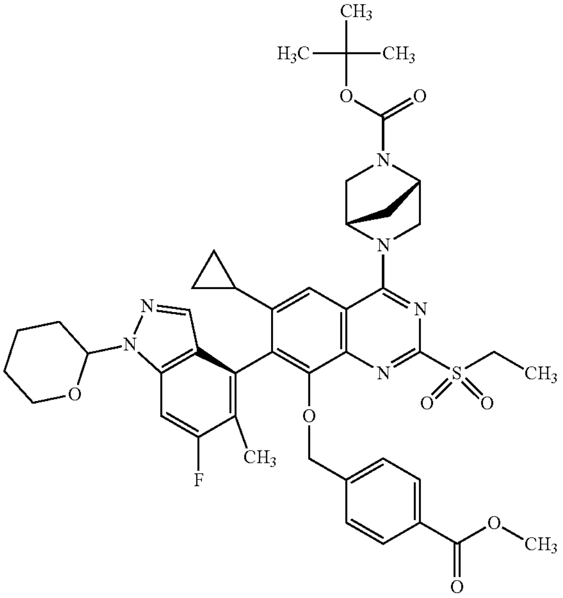 |

TABLE 5-19
| PEx | Str |
|---|---|
| 72 | 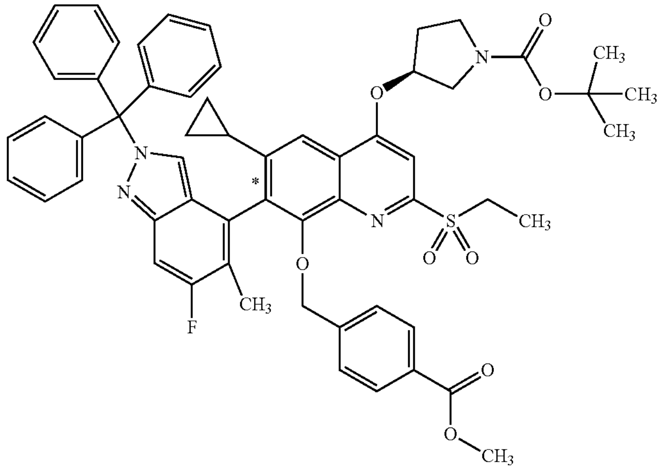 [SMILES: CCS(=O)(=O)c1cc(O[C@H]2CCN(C(=O)OC(C)(C)C)C2)c2cc(C3CC3)c(-c3c(C)c(F)cc4nn(C(c5ccccc5)(c5ccccc5)c5ccccc5)cc34)c(OCc3ccc(C(=O)OC)cc3)c2n1] |
| 73 | 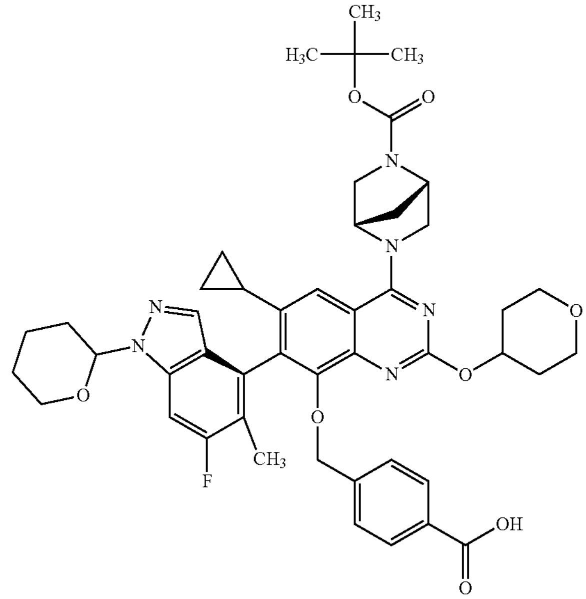 |
| 74 | 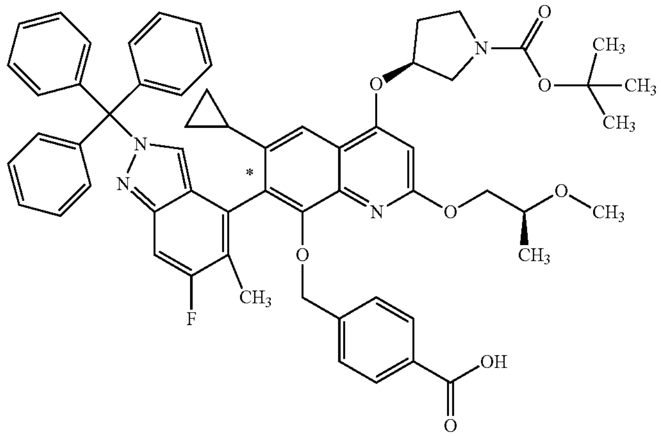 [SMILES: CO[C@@H](C)COc1cc(O[C@H]2CCN(C(=O)OC(C)(C)C)C2)c2cc(C3CC3)c(-c3c(C)c(F)cc4nn(C(c5ccccc5)(c5ccccc5)c5ccccc5)cc34)c(OCc3ccc(C(=O)O)cc3)c2n1] |

TABLE 5-20
| PEx | Str |
|---|---|
| 75 | 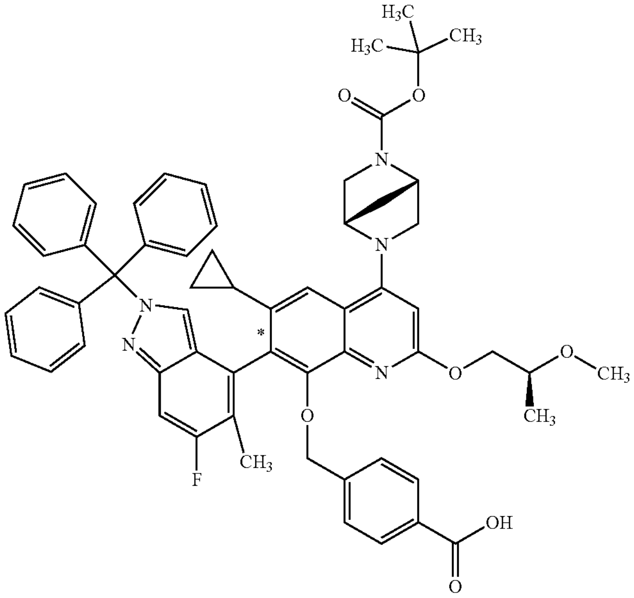 [SMILES: CO[C@@H](C)COc1cc(N2C[C@@H]3C[C@H]2CN3C(=O)OC(C)(C)C)c2cc(C3CC3)c(-c3c(C)c(F)cc4nn(C(c5ccccc5)(c5ccccc5)c5ccccc5)cc34)c(OCc3ccc(C(=O)O)cc3)c2n1] |
| 76 | 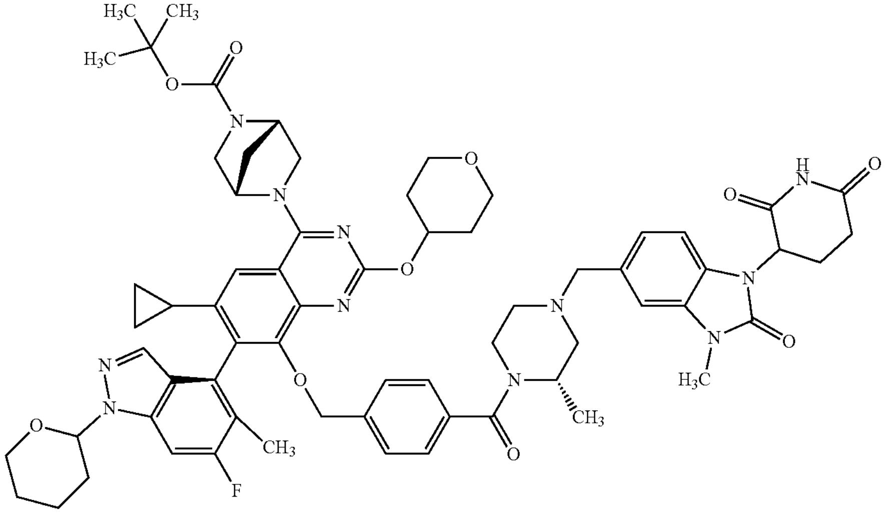 |
| 77 | 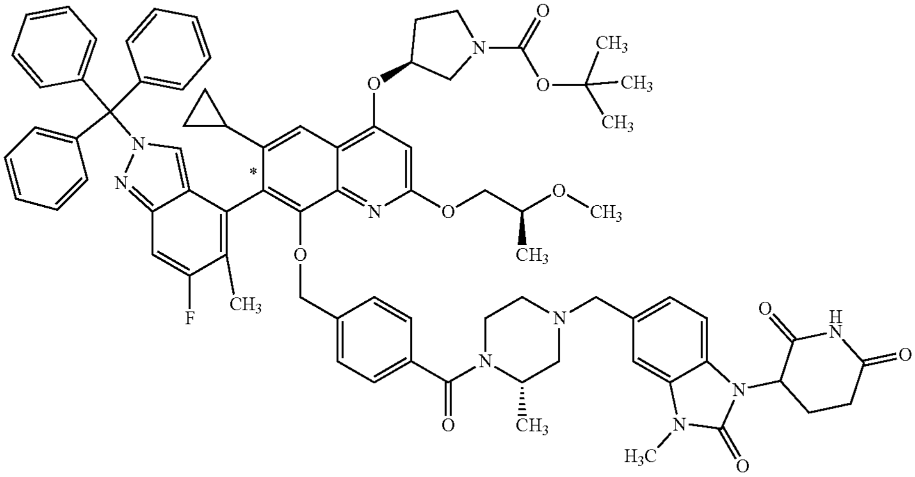 [SMILES: CO[C@@H](C)COc1cc(O[C@H]2CCN(C(=O)OC(C)(C)C)C2)c2cc(C3CC3)c(-c3c(C)c(F)cc4nn(C(c5ccccc5)(c5ccccc5)c5ccccc5)cc34)c(OCc3ccc(C(=O)N4CCN(Cc5ccc6c(c5)n(C)c(=O)n6C5CCC(=O)NC5=O)C[C@@H]4C)cc3)c2n1] |

TABLE 5-21
| PEx | Str |
|---|---|
| 78 | 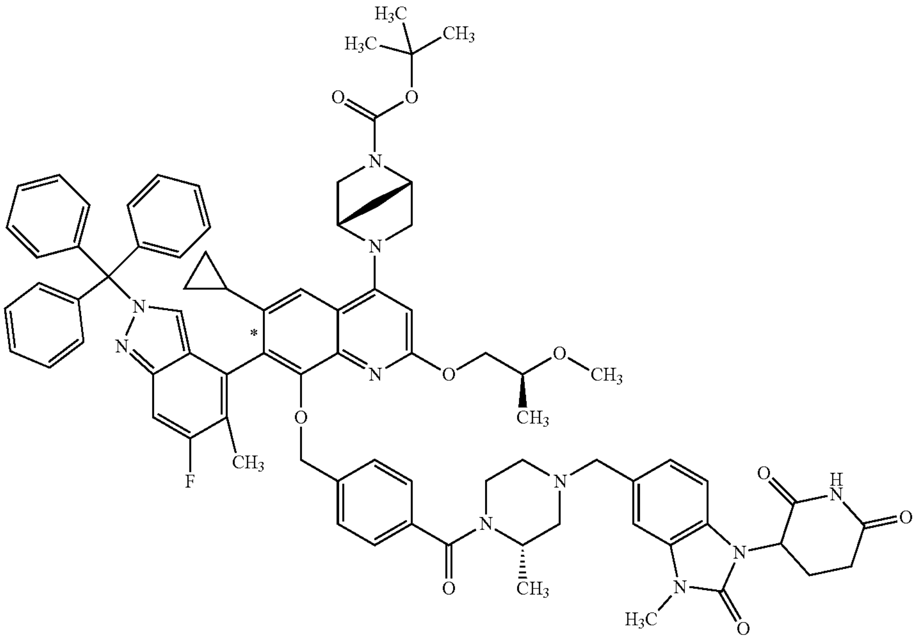 [SMILES: CO[C@@H](C)COc1cc(N2C[C@@H]3C[C@H]2CN3C(=O)OC(C)(C)C)c2cc(C3CC3)c(-c3c(C)c(F)cc4nn(C(c5ccccc5)(c5ccccc5)c5ccccc5)cc34)c(OCc3ccc(C(=O)N4CCN(Cc5ccc6c(c5)n(C)c(=O)n6C5CCC(=O)NC5=O)C[C@@H]4C)cc3)c2n1] |
| 79 | 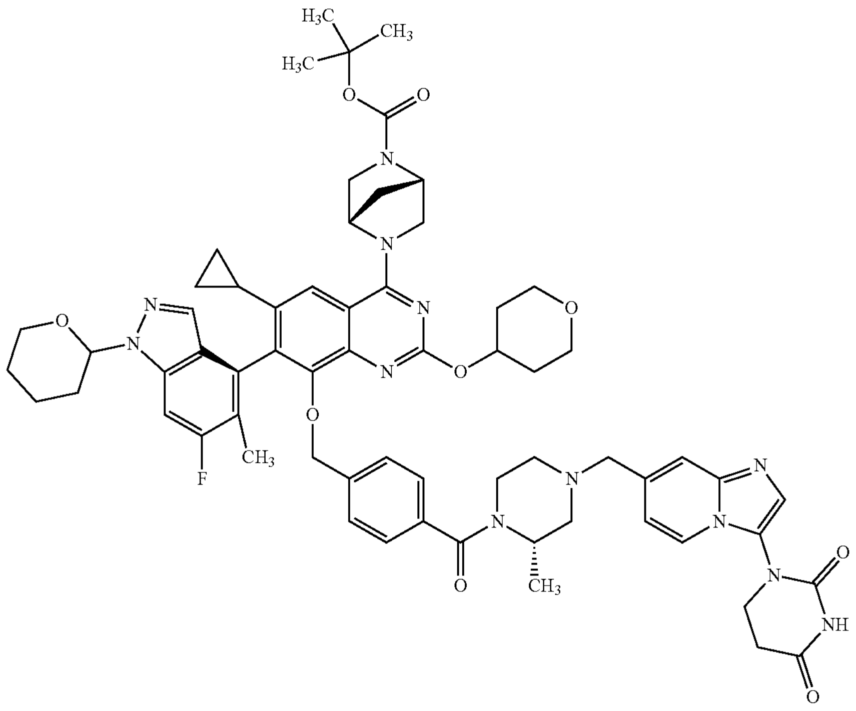 |

TABLE 5-22
| PEx | Str |
| --- | --- |
| 80 | 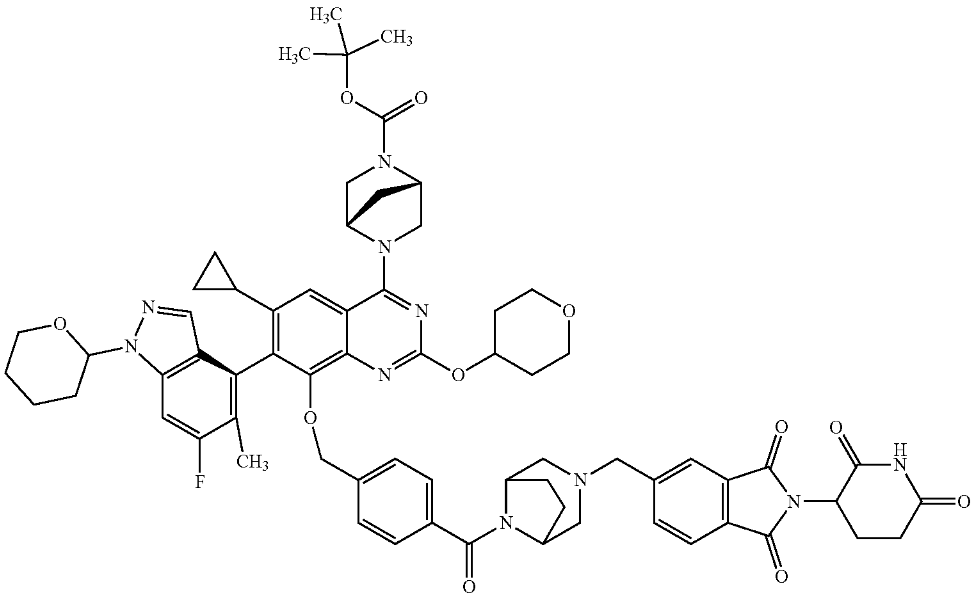 |
| 81 | 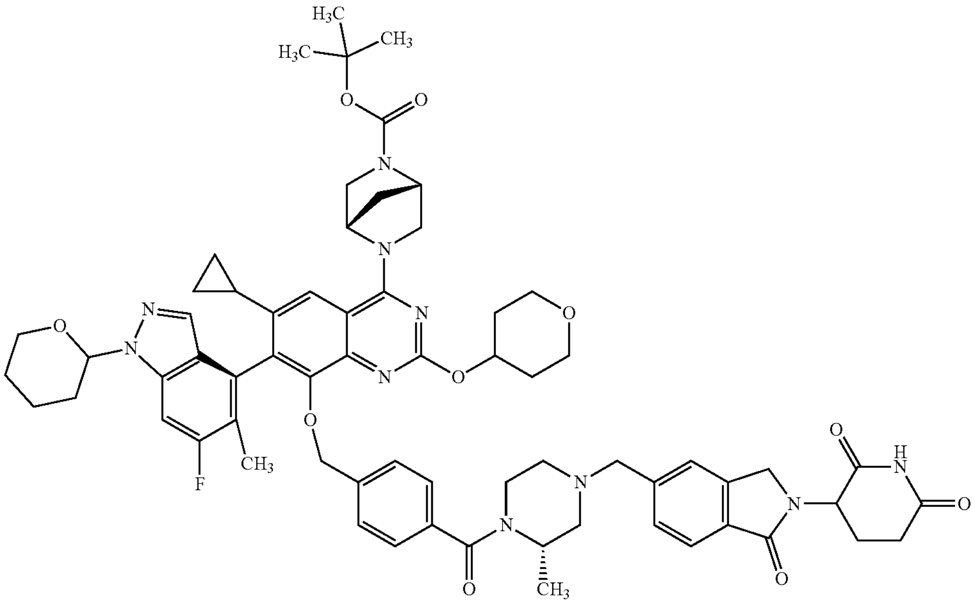 |

TABLE 5-23
| PEx | Str |
|---|---|
| 82 | 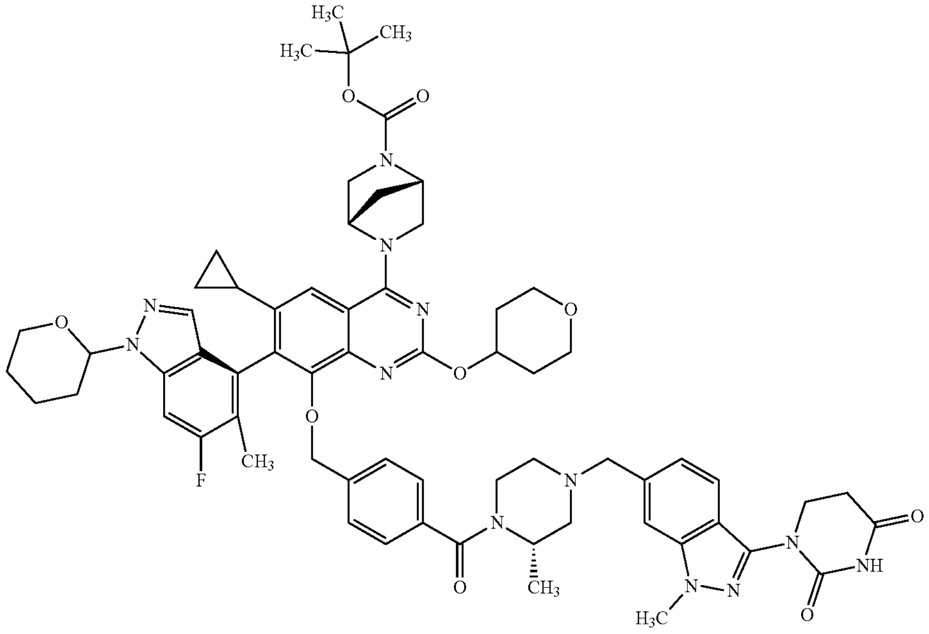 |
| 83 | 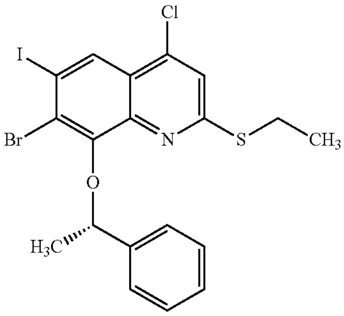 [SMILES: CCSc1cc(Cl)c2cc(I)c(Br)c(O[C@@H](C)c3ccccc3)c2n1] |
| 84 | 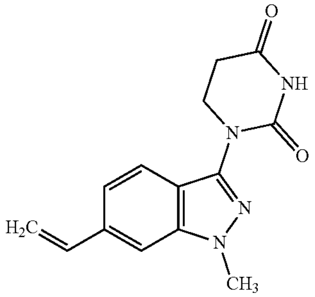 [SMILES: C=Cc1ccc2c(N3CCC(=O)NC3=O)nn(C)c2c1] |
TABLE 5-24
| PEx | Str |
|---|---|
| 85 | 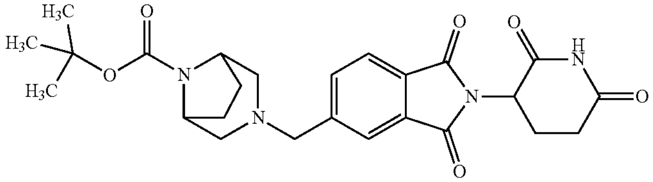 [SMILES: CC(C)(C)OC(=O)N1C2CCC1CN(Cc1ccc3c(c1)C(=O)N(C1CCC(=O)NC1=O)C3=O)C2] |

TABLE 5-24-continued
| PEx | Str |
|---|---|
| 86 | 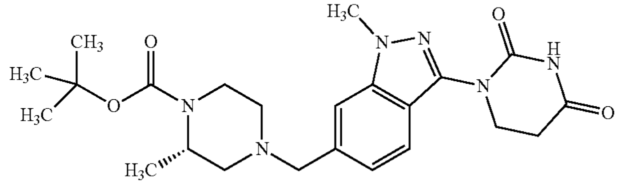 [SMILES: C[C@H]1CN(Cc2ccc3c(N4CCC(=O)NC4=O)nn(C)c3c2)CCN1C(=O)OC(C)(C)C] |
| 87 | *n* HCl 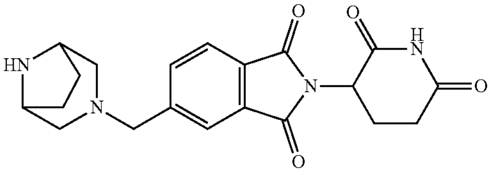 |
| 88 | *n* HCl 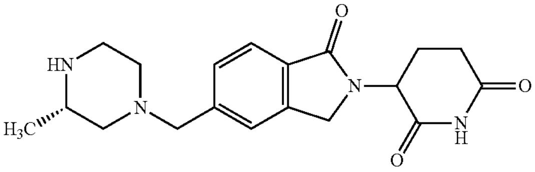 |
| 89 | *n* HCl 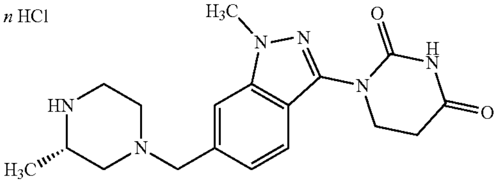 [SMILES: C[C@H]1CN(Cc2ccc3c(N4CCC(=O)NC4=O)nn(C)c3c2)CCN1] |
TABLE 5-25
| PEx | Str |
|---|---|
| 90 | 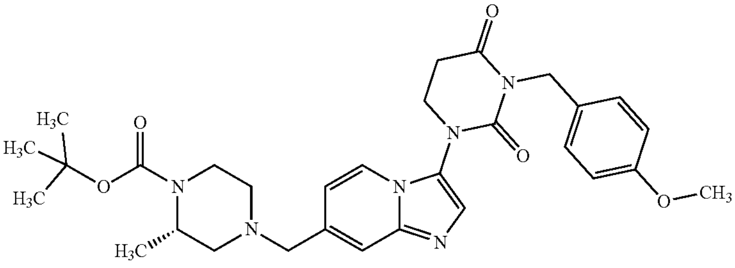 [SMILES: COc1ccc(CN2C(=O)CCN(c3cnc4cc(CN5CCN(C(=O)OC(C)(C)C)[C@@H](C)C5)ccn34)C2=O)cc1] |
| 91 | 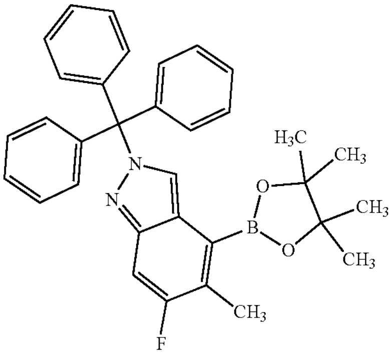 [SMILES: Cc1c(F)cc2nn(C(c3ccccc3)(c3ccccc3)c3ccccc3)cc2c1B1OC(C)(C)C(C)(C)O1] |

TABLE 5-25-continued
| PEx | Str |
|---|---|
| 92 | 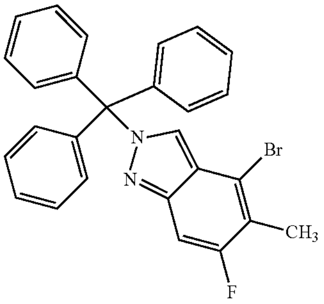 [SMILES: Cc1c(F)cc2nn(C(c3ccccc3)(c3ccccc3)c3ccccc3)cc2c1Br] |
| 93 | 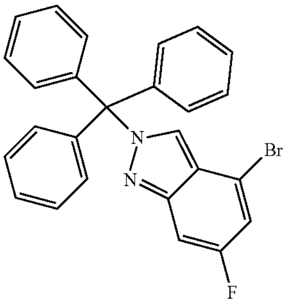 [SMILES: Fc1cc(Br)c2cn(C(c3ccccc3)(c3ccccc3)c3ccccc3)nc2c1] |
TABLE 5-26
| PEx | Str |
|---|---|
| 94 | 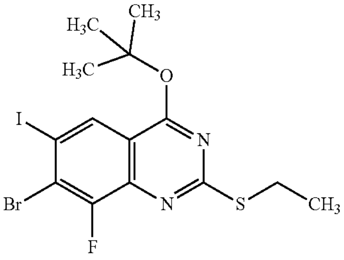 [SMILES: CCSc1nc(OC(C)(C)C)c2cc(I)c(Br)c(F)c2n1] |
| 95 | 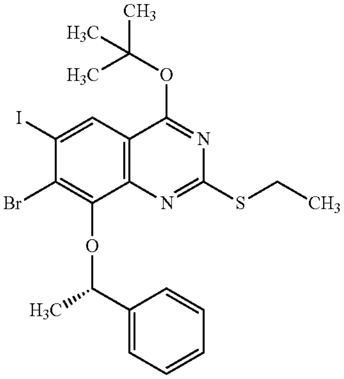 [SMILES: CCSc1nc(OC(C)(C)C)c2cc(I)c(Br)c(O[C@@H](C)c3ccccc3)c2n1] |
TABLE 5-26-continued
| PEx | Str |
|---|---|
| 96 | 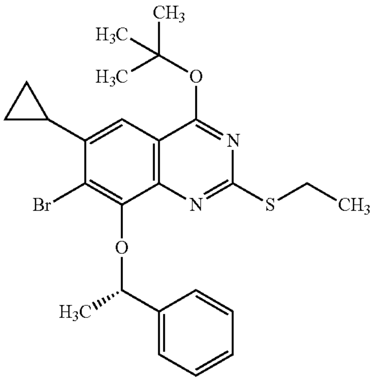 [SMILES: CCSc1nc(OC(C)(C)C)c2cc(C3CC3)c(Br)c(O[C@@H](C)c3ccccc3)c2n1] |

TABLE 5-27
| PEx | Str |
|---|---|
| 97 | 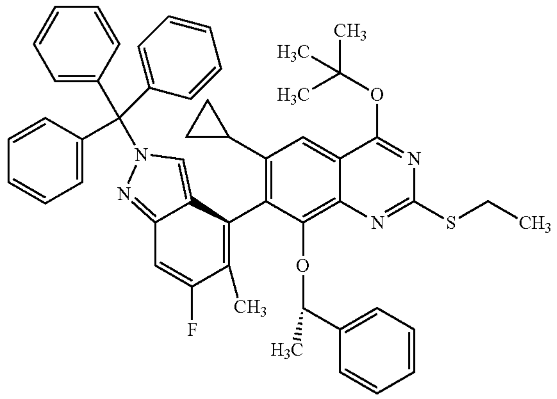 |
| 98 | 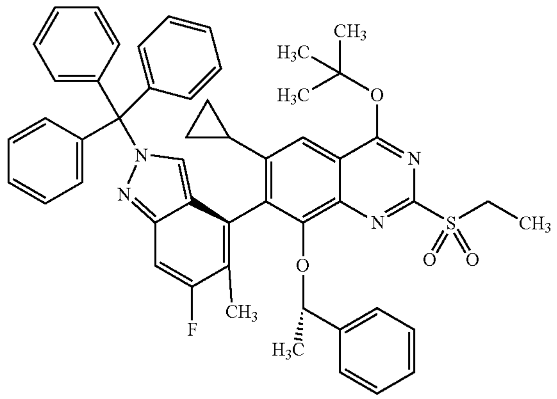 |
| 99 | 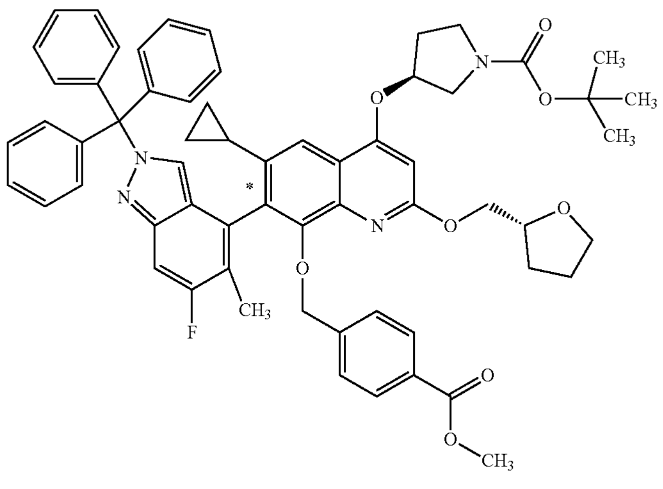 [SMILES: COC(=O)c1ccc(COc2c(-c3c(C)c(F)cc4nn(C(c5ccccc5)(c5ccccc5)c5ccccc5)cc34)c(C3CC3)cc3c(O[C@H]4CCN(C(=O)OC(C)(C)C)C4)cc(OC[C@H]4CCCO4)nc23)cc1] |

TABLE 5-28
| PEx | Str |
|---|---|
| 100 | 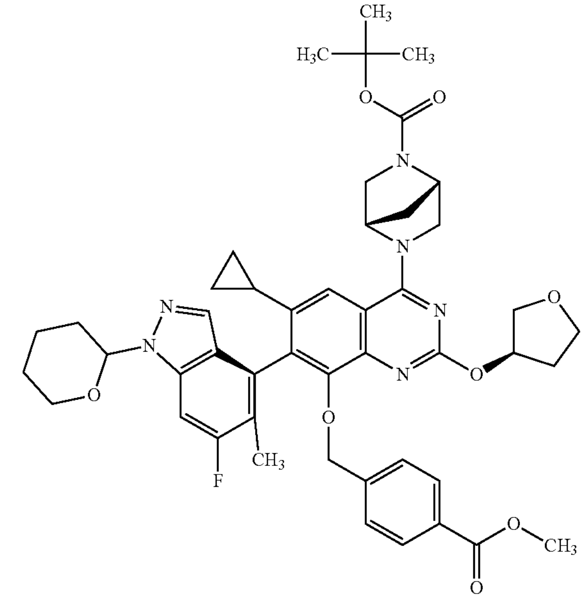 |
| 101 | 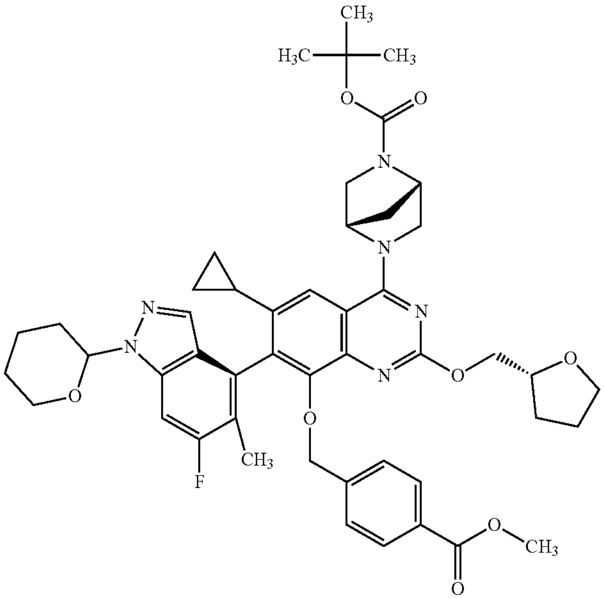 |

TABLE 5-28-continued
| PEx | Str |
| --- | --- |
| 102 | 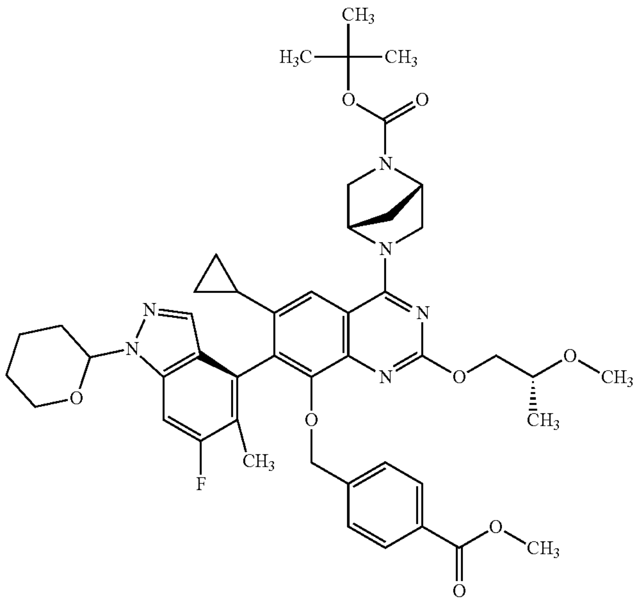 |
TABLE 5-29
| PEx | Str |
| --- | --- |
| 103 | 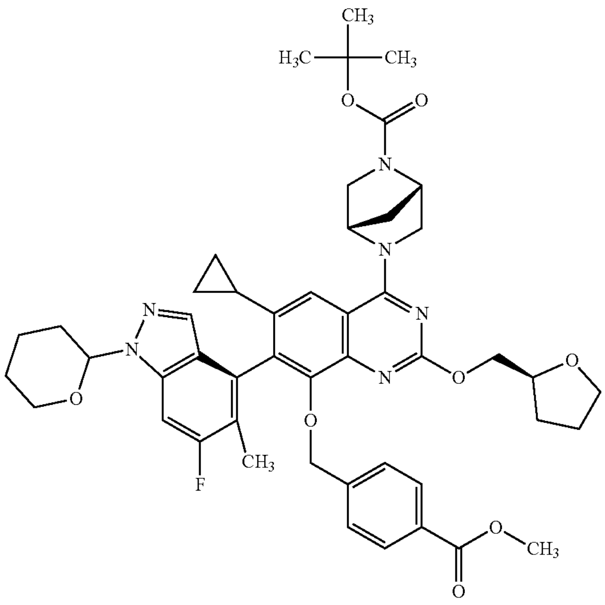 |

TABLE 5-29-continued
| PEx | Str |
|---|---|
| 104 | 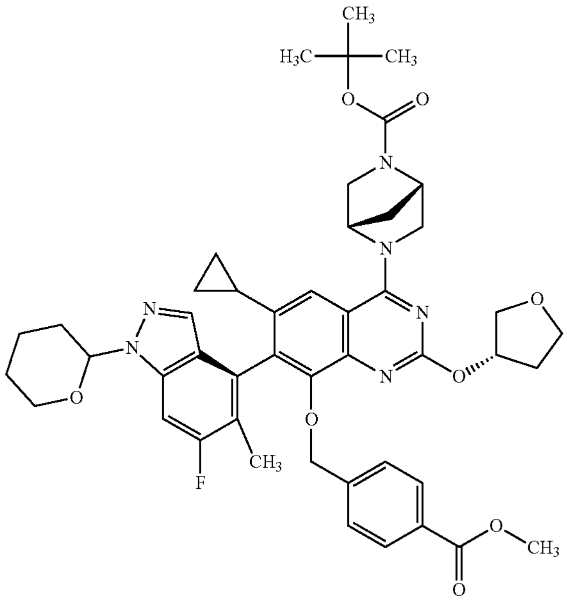 |
| 105 | 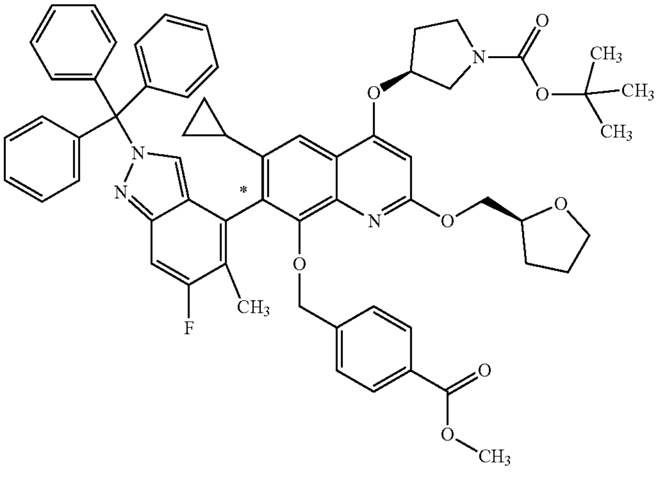 [SMILES: COC(=O)c1ccc(COc2c(-c3c(C)c(F)cc4nn(C(c5ccccc5)(c5ccccc5)c5ccccc5)cc34)c(C3CC3)cc3c(O[C@H]4CCN(C(=O)OC(C)(C)C)C4)cc(OC[C@@H]4CCCO4)nc23)cc1] |

TABLE 5-30
| PEx | Str |
|---|---|
| 106 | 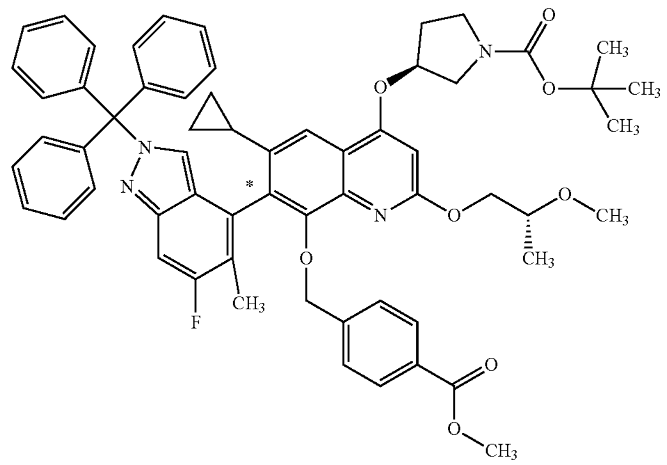 [SMILES: COC(=O)c1ccc(COc2c(-c3c(C)c(F)cc4nn(C(c5ccccc5)(c5ccccc5)c5ccccc5)cc34)c(C3CC3)cc3c(O[C@H]4CCN(C(=O)OC(C)(C)C)C4)cc(OC[C@@H](C)OC)nc23)cc1] |
| 107 | 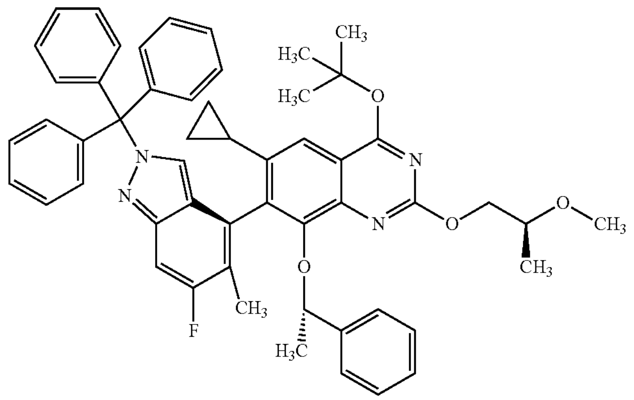 |
| 108 | 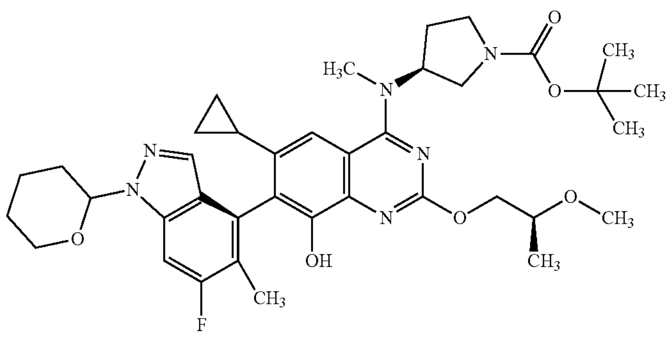 |

TABLE 5-31
| PEx | Str |
|---|---|
| 109 | 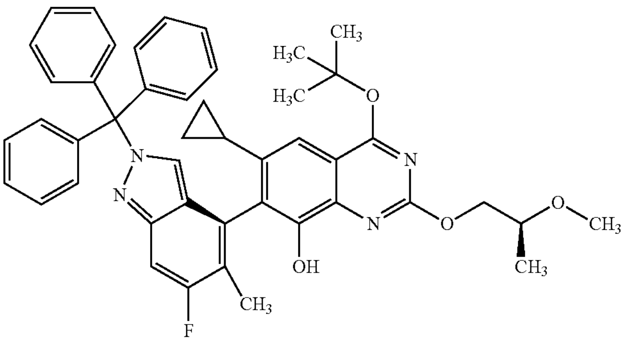 |
| 110 | 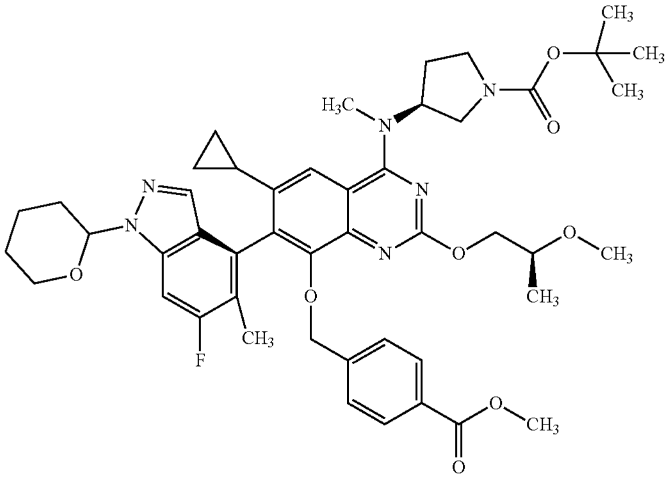 |
| 111 | 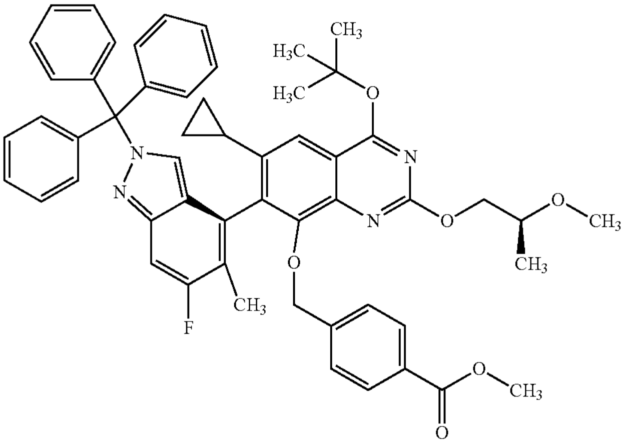 |

TABLE 5-32
| PEx | Str |
|---|---|
| 112 | 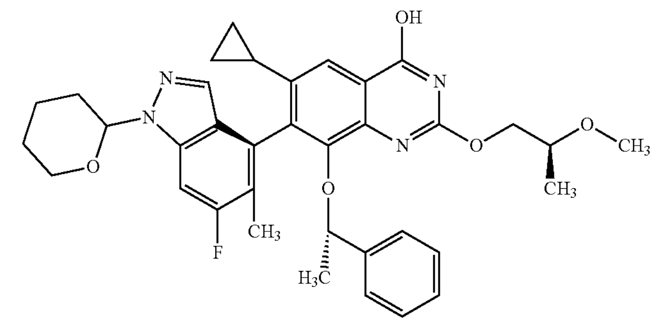 |
| 113 | 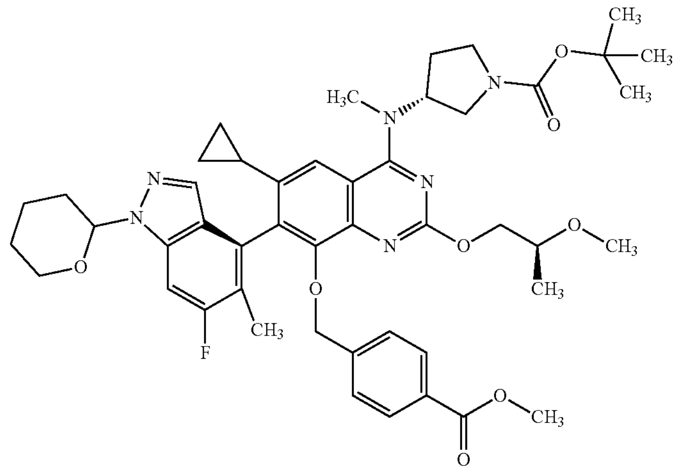 |
| 114 | 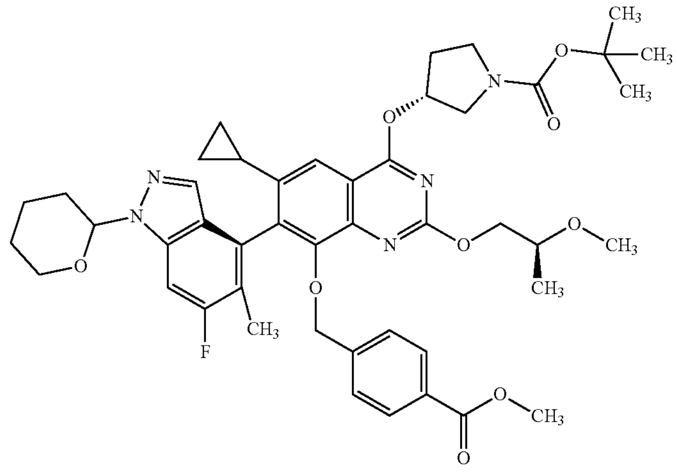 |

TABLE 5-33
| PEx | Str |
|---|---|
| 115 | 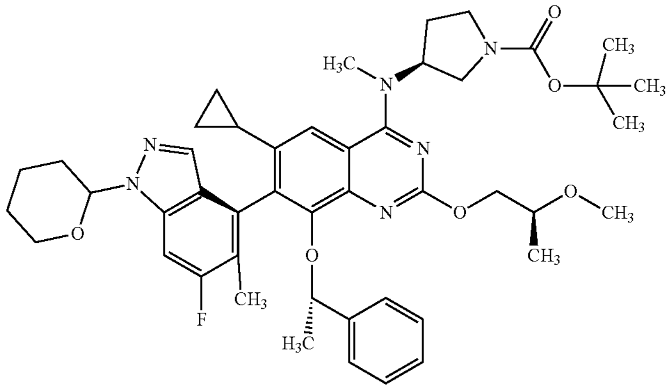 |
| 116 | 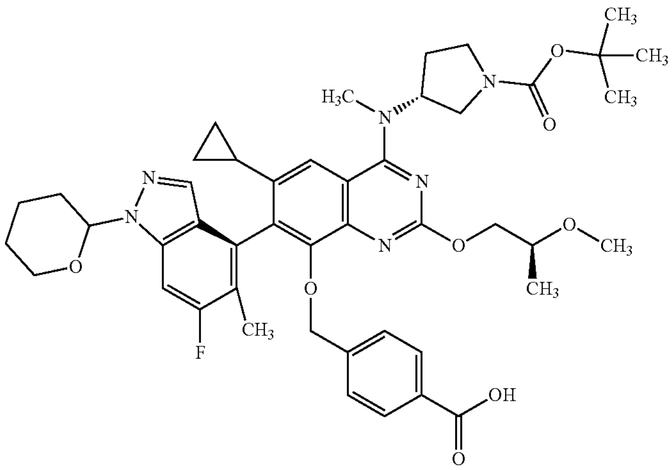 |
| 117 | 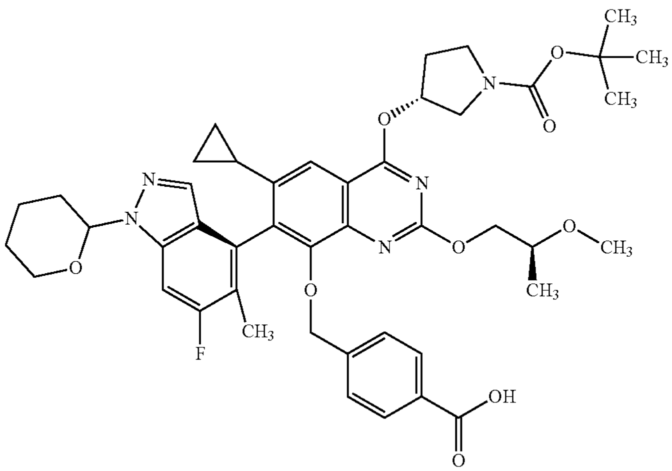 |

TABLE 5-34
| PEx | Str |
|---|---|
| 118 | 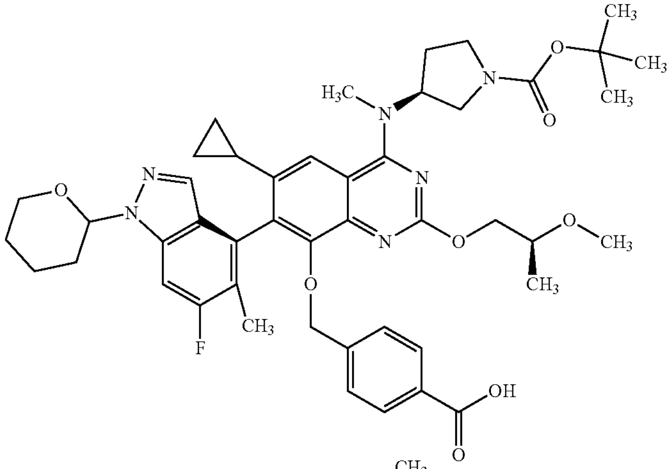 |
| 119 | 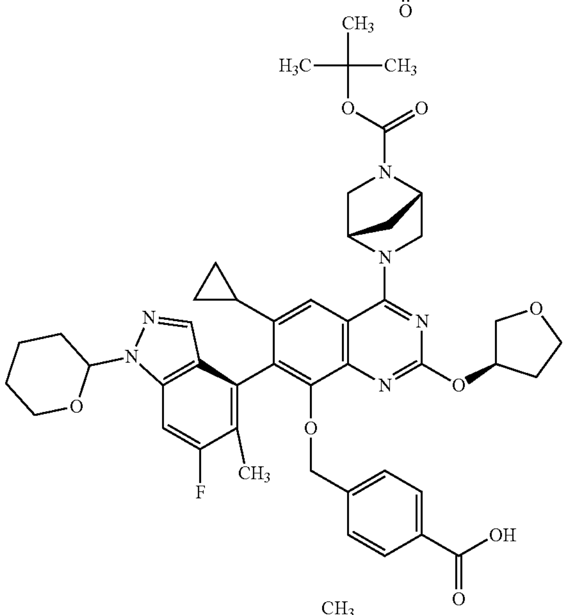 |
| 120 | 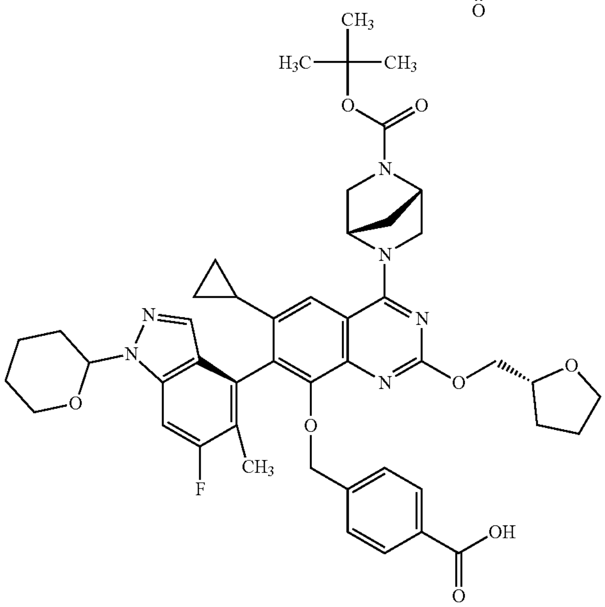 |

TABLE 5-35
| PEx | Str |
|---|---|
| 121 | 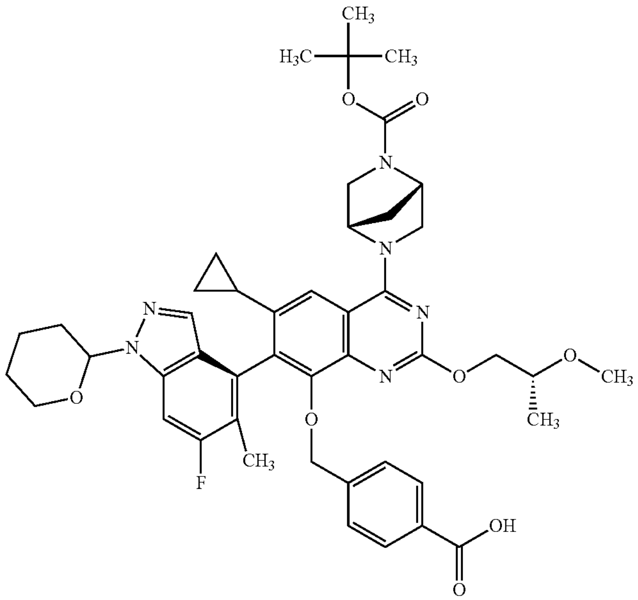 |
| 122 | 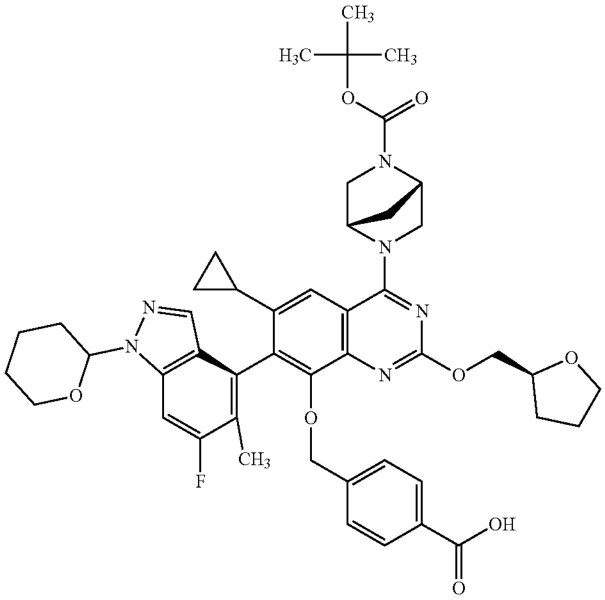 |

TABLE 5-35-continued
| PEx | Str |
|---|---|
| 123 | 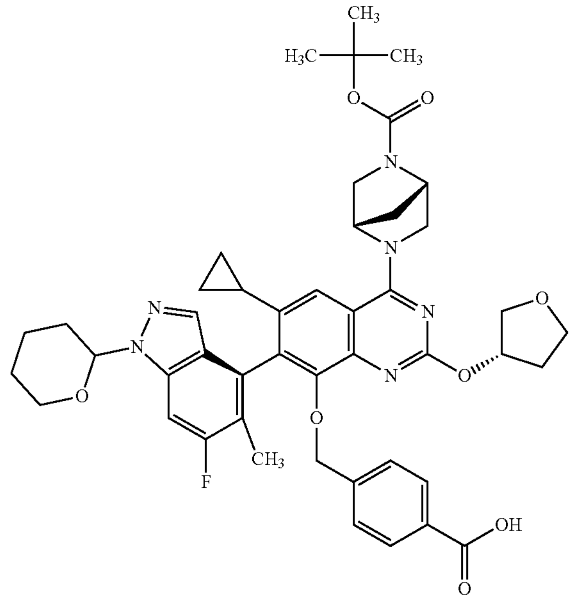 |
TABLE 5-36
| PEx | Str |
|---|---|
| 124 | 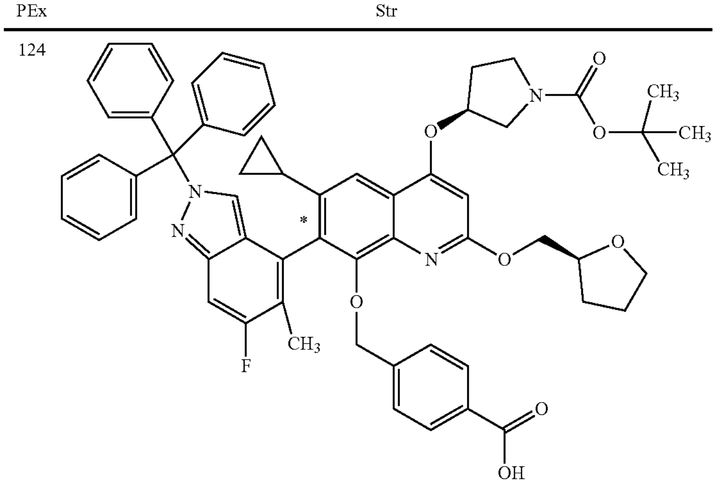 |
| 125 | 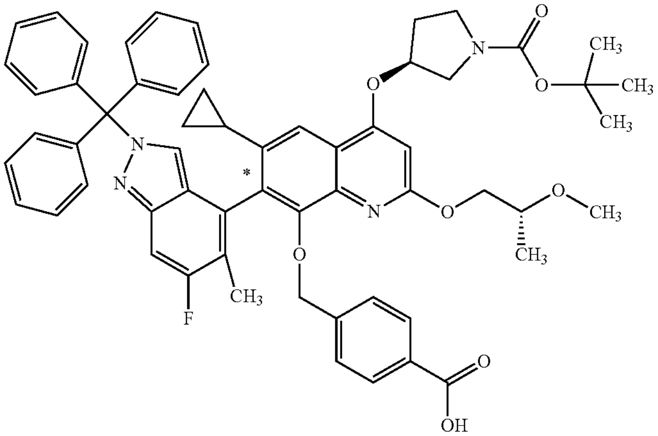 [SMILES: CO[C@H](C)COc1cc(O[C@H]2CCN(C(=O)OC(C)(C)C)C2)c2cc(C3CC3)c(-c3c(C)c(F)cc4nn(C(c5ccccc5)(c5ccccc5)c5ccccc5)cc34)c(OCc3ccc(C(=O)O)cc3)c2n1] |

TABLE 5-36-continued
| PEx | Str |
|---|---|
| 126 | 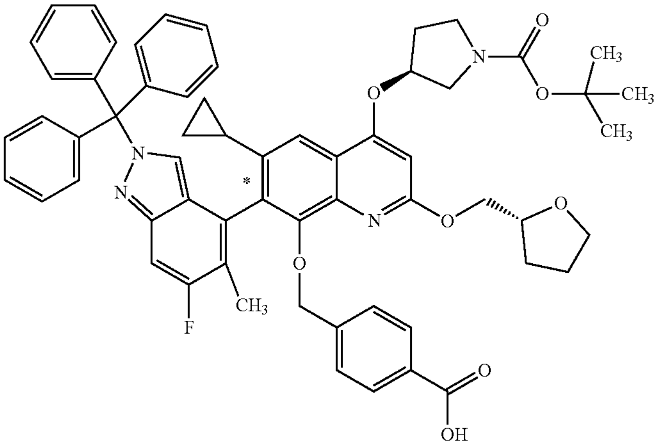 [SMILES: Cc1c(F)cc2nn(C(c3ccccc3)(c3ccccc3)c3ccccc3)cc2c1-c1c(C2CC2)cc2c(O[C@H]3CCN(C(=O)OC(C)(C)C)C3)cc(OC[C@H]3CCCO3)nc2c1OCc1ccc(C(=O)O)cc1] |
TABLE 5-37
| PEx | Str |
|---|---|
| 127 | 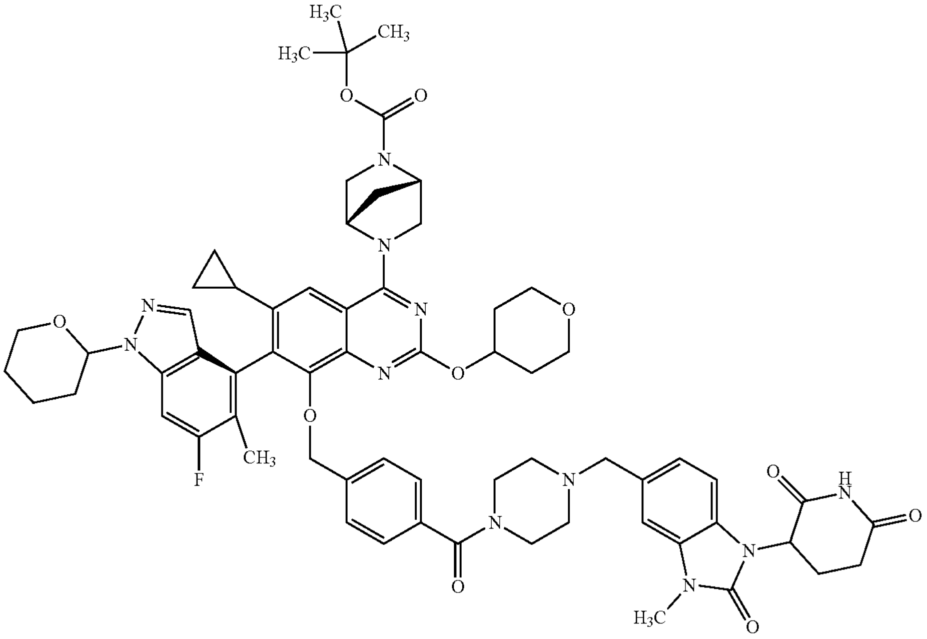 |

TABLE 5-37-continued
| PEx | Str |
|---|---|
| 128 | 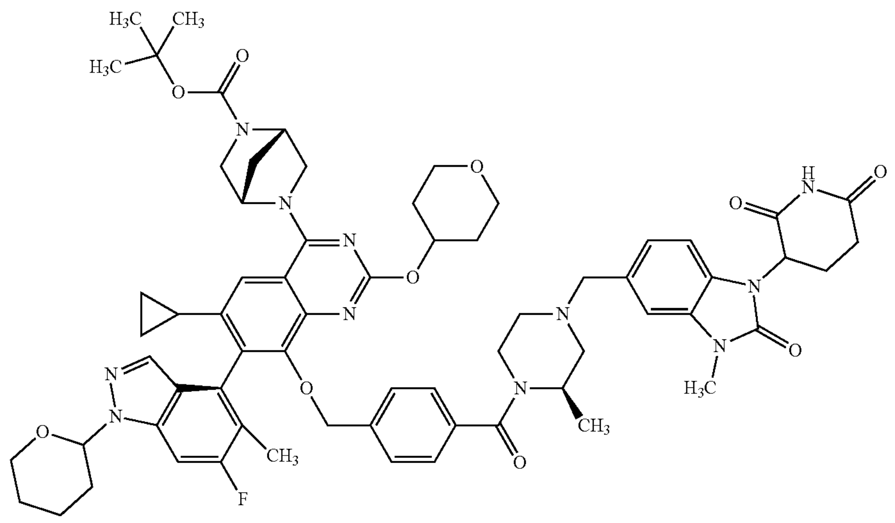 |
| 129 | 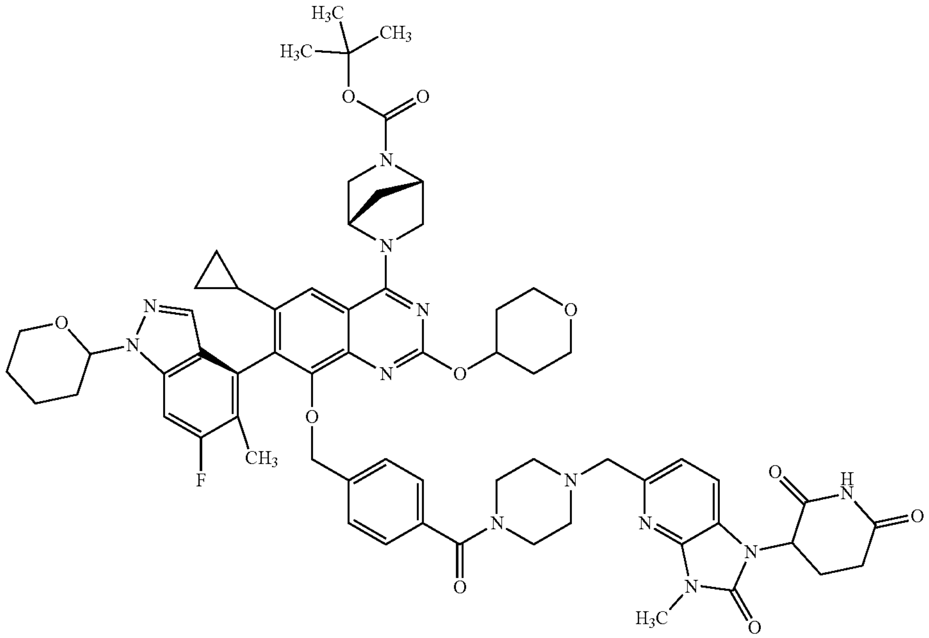 |

TABLE 5-38
| PEx | Str |
|---|---|
| 130 | 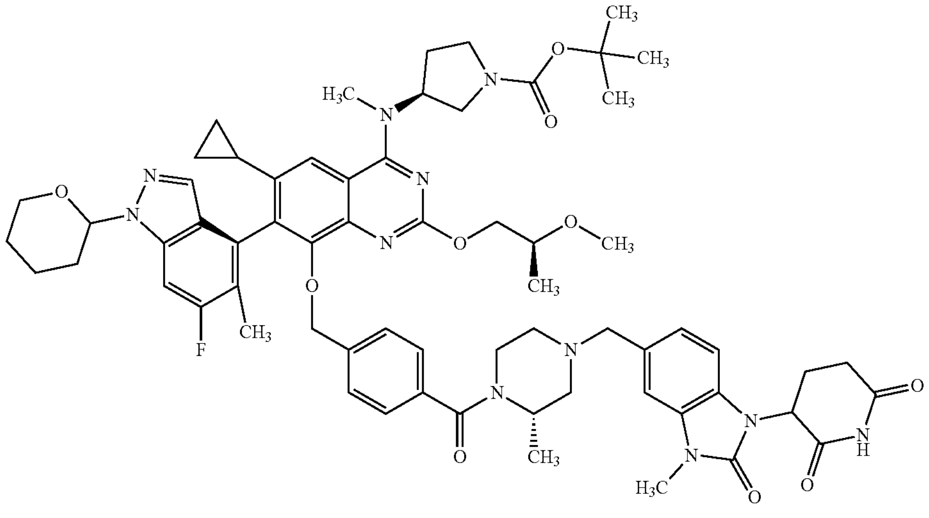 |
| 131 | 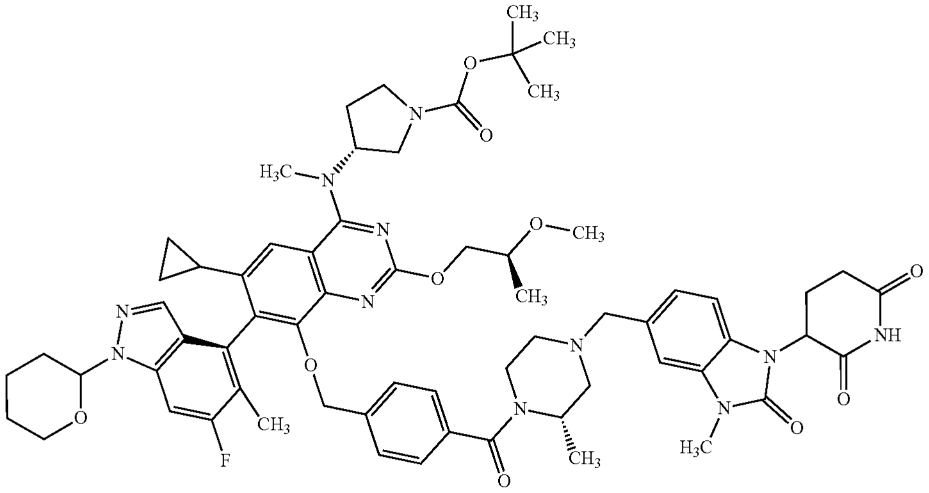 |

TABLE 5-38-continued
| PEx | Str |
|---|---|
| 132 | 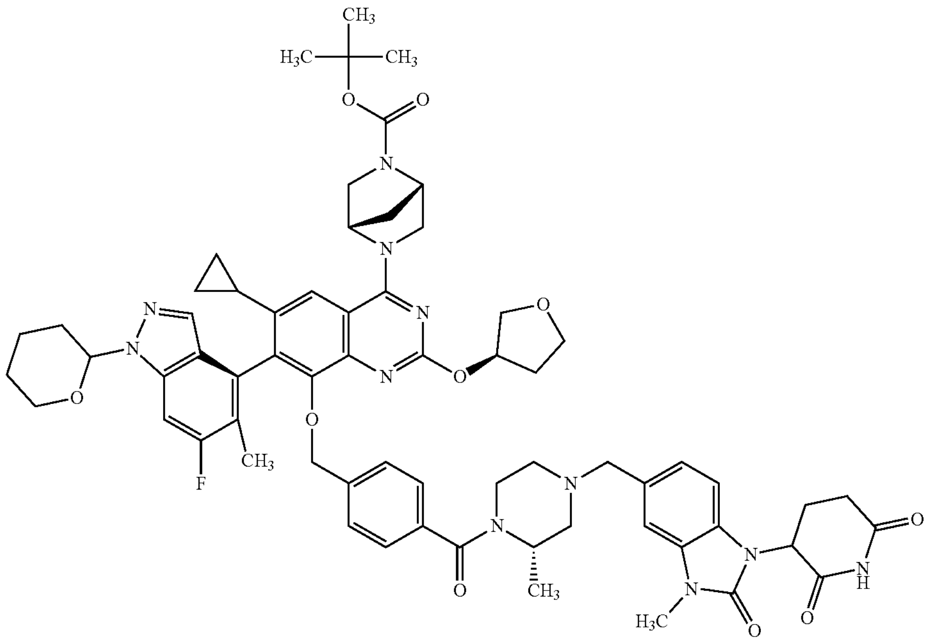 |
TABLE 5-39
| PEx | Str |
|---|---|
| 133 | 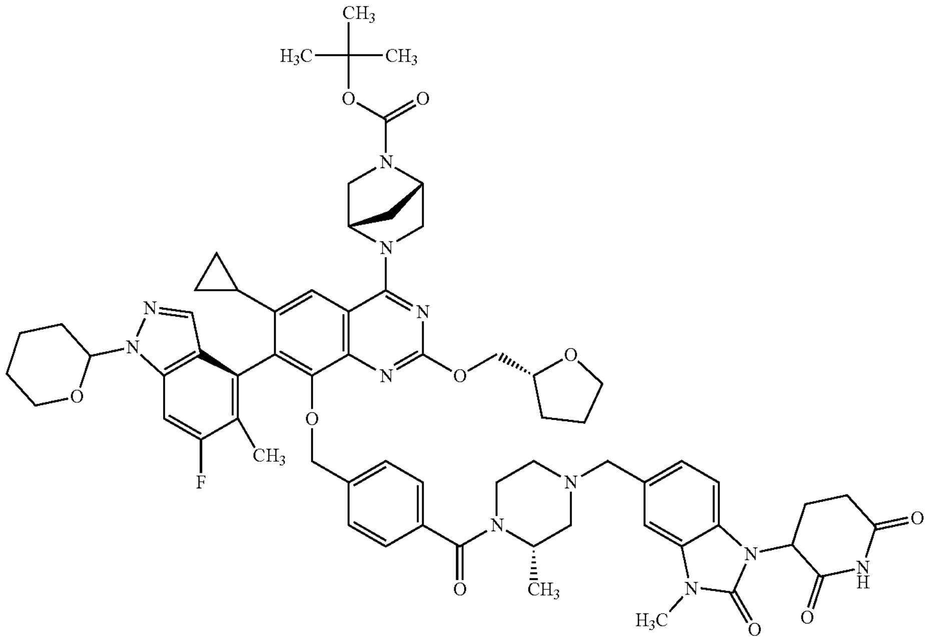 |

TABLE 5-39-continued
| PEx | Str |
| --- | --- |
| 134 | 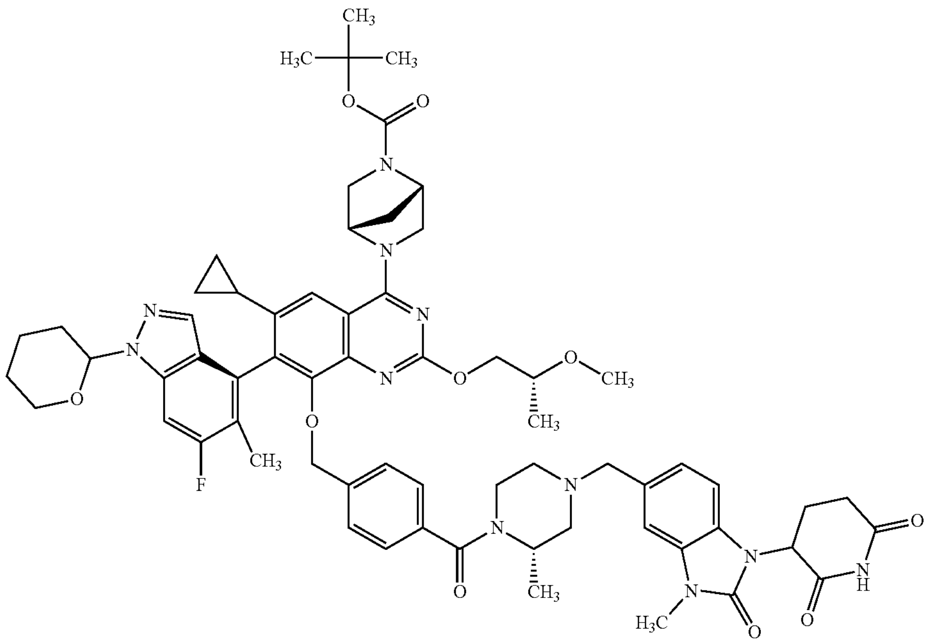 |
| 135 | 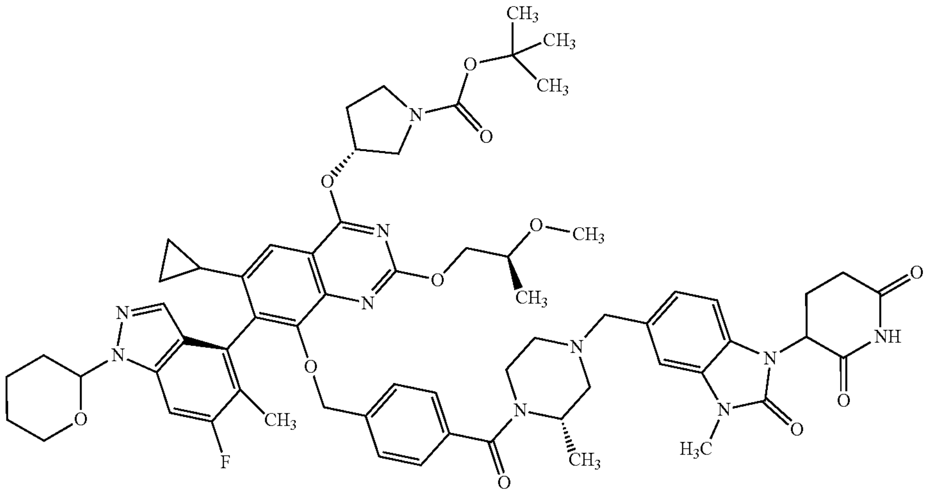 |

TABLE 5-40
| PEx | Str |
|---|---|
| 136 | 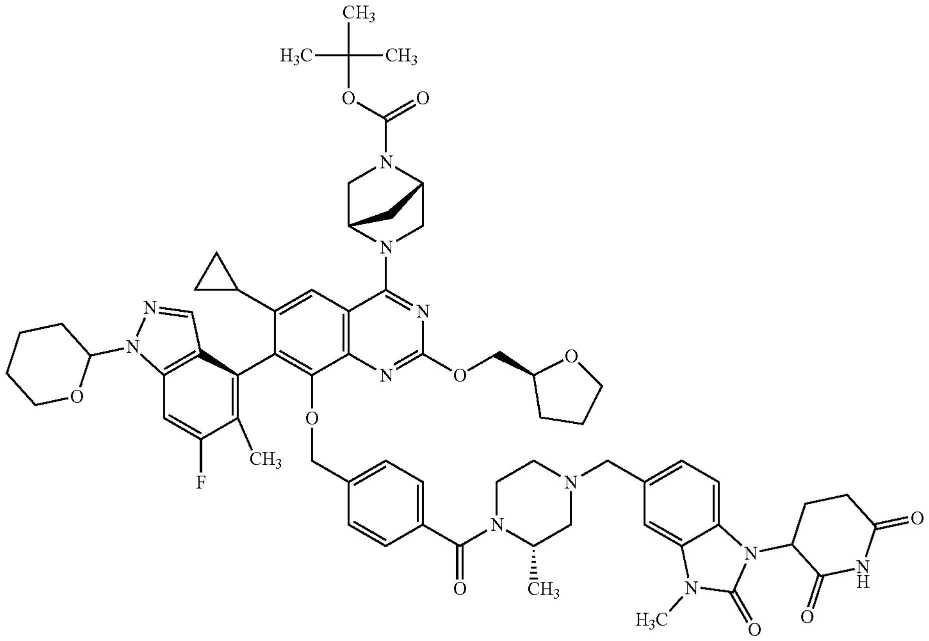 |
| 137 | 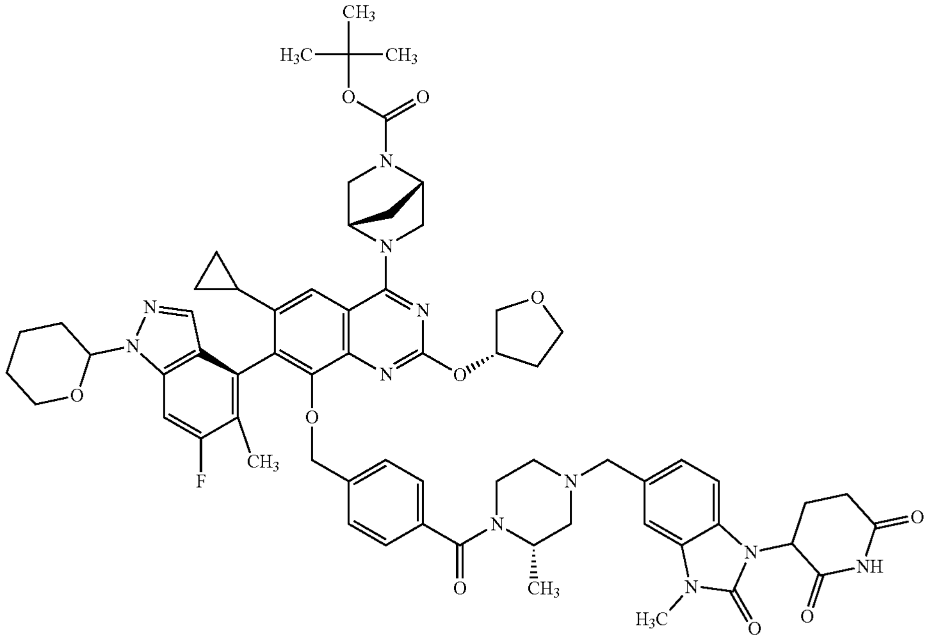 |

TABLE 5-41
| PEx | Str |
| --- | --- |
| 138 | 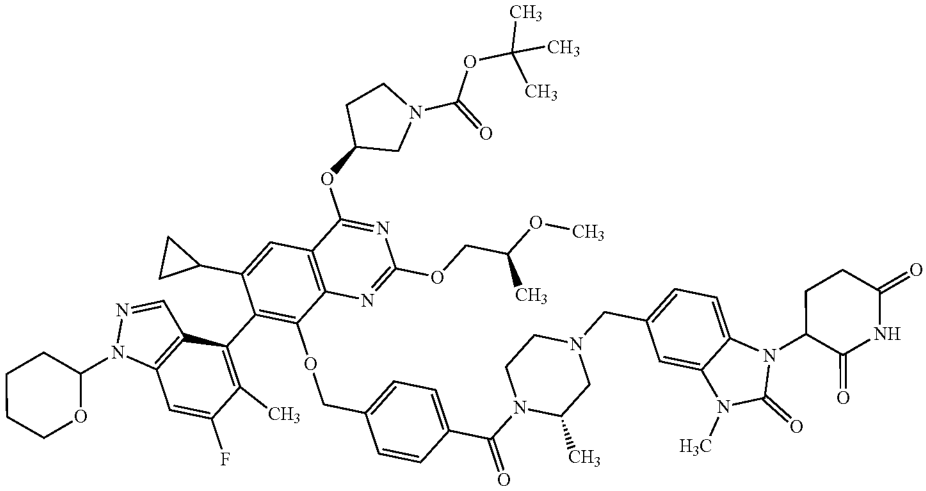 |
| 139 | 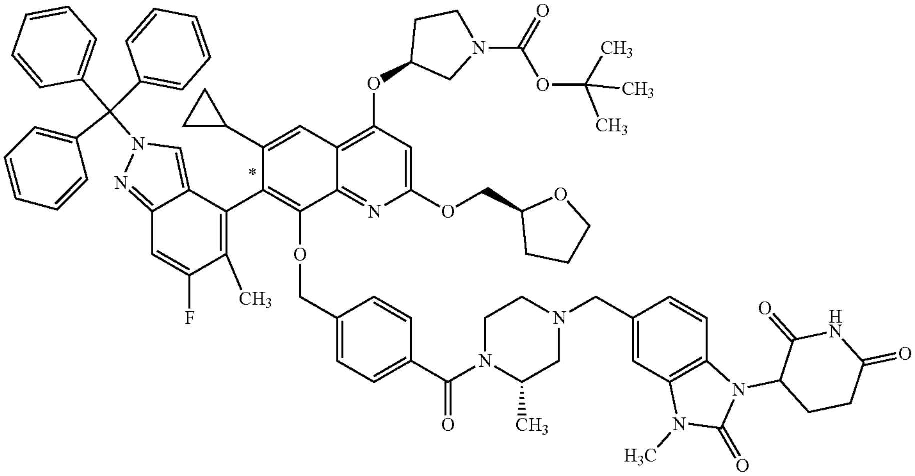 [SMILES: Cc1c(F)cc2nn(C(c3ccccc3)(c3ccccc3)c3ccccc3)cc2c1-c1c(C2CC2)cc2c(O[C@H]3CCN(C(=O)OC(C)(C)C)C3)cc(OC[C@@H]3CCCO3)nc2c1OCc1ccc(C(=O)N2CCN(Cc3ccc4c(c3)n(C)c(=O)n4C3CCC(=O)NC3=O)C[C@@H]2C)cc1] |
| 140 | 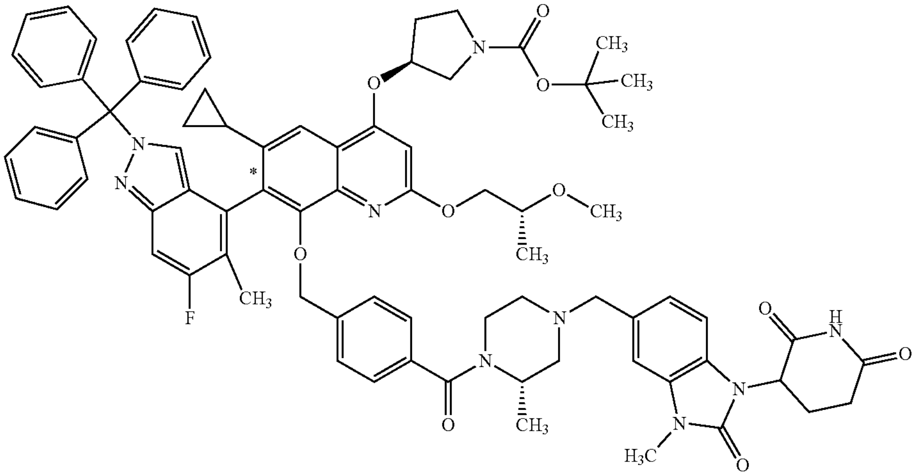 [SMILES: CO[C@H](C)COc1cc(O[C@H]2CCN(C(=O)OC(C)(C)C)C2)c2cc(C3CC3)c(-c3c(C)c(F)cc4nn(C(c5ccccc5)(c5ccccc5)c5ccccc5)cc34)c(OCc3ccc(C(=O)N4CCN(Cc5ccc6c(c5)n(C)c(=O)n6C5CCC(=O)NC5=O)C[C@@H]4C)cc3)c2n1] |

TABLE 5-42
| PEx | Str |
|---|---|
| 141 | 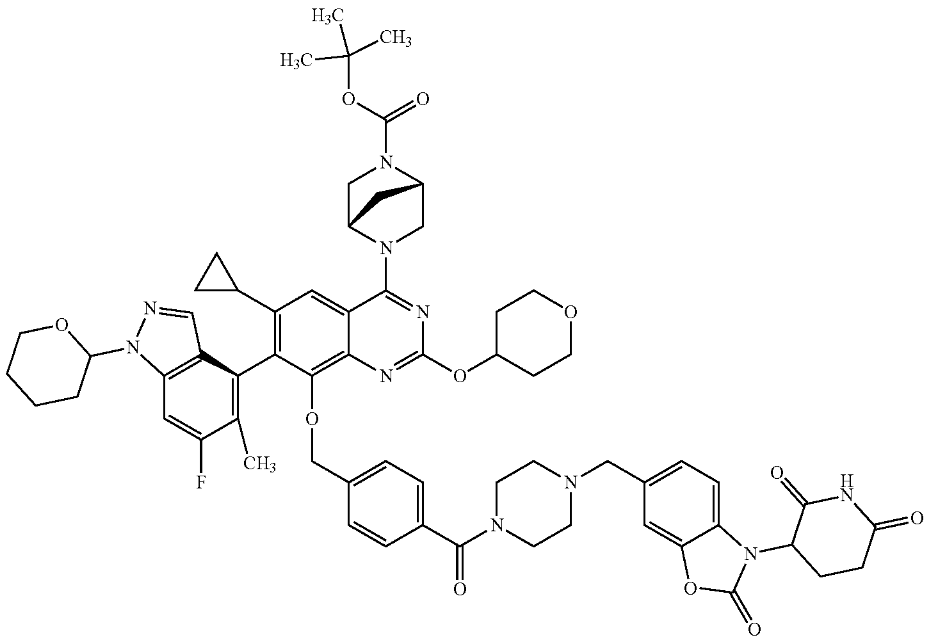 |
| 142 | 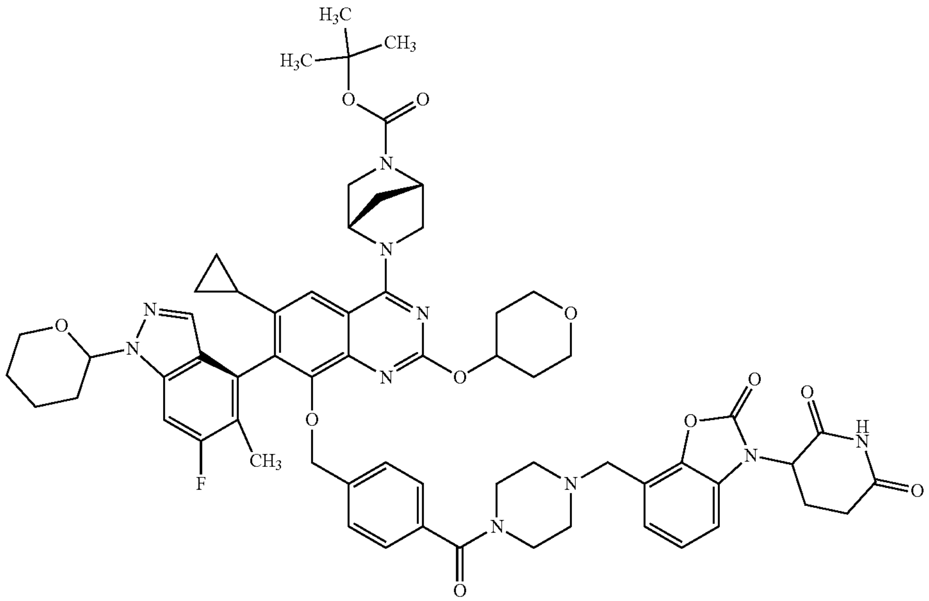 |

TABLE 5-43
| PEx | Str |
|---|---|
| 143 | 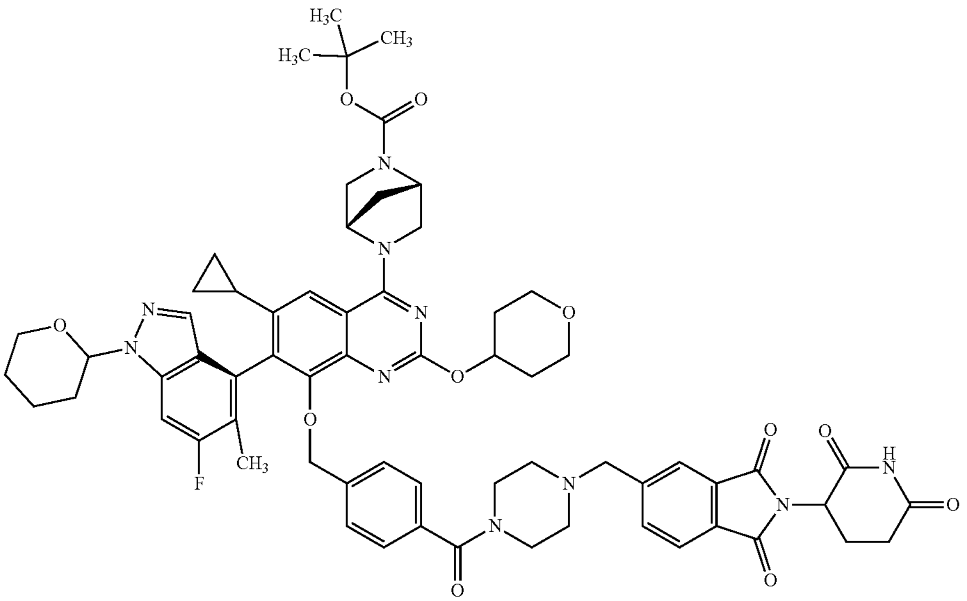 |
| 144 | 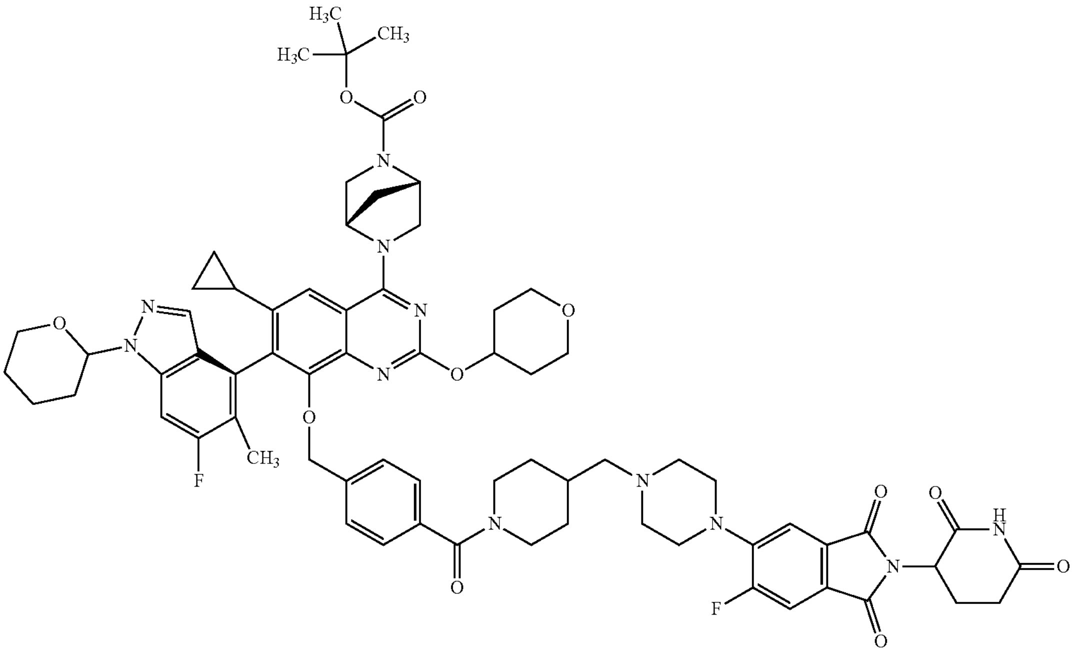 |

TABLE 5-43-continued
| PEx | Str |
|---|---|
| 145 | 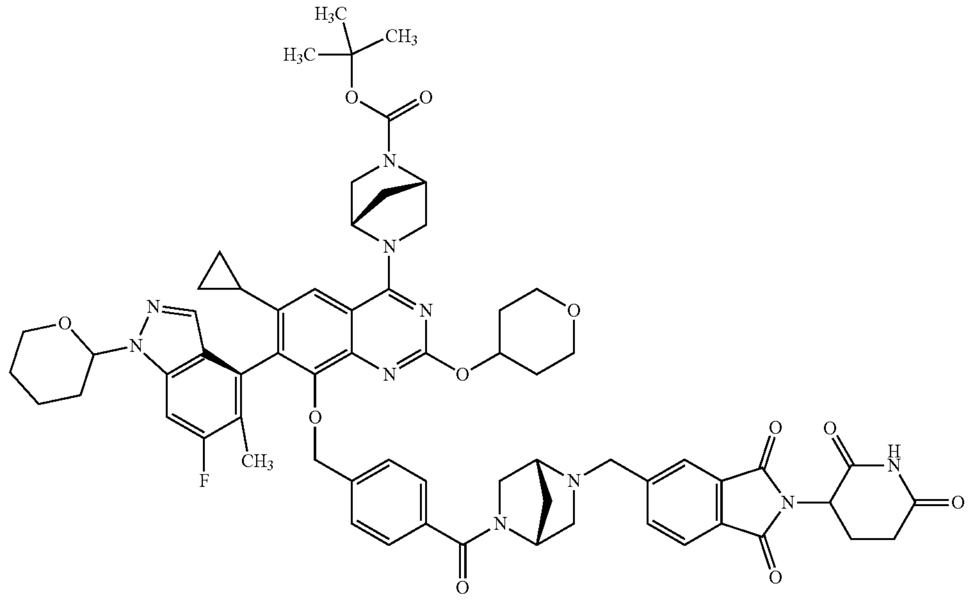 |
TABLE 5-44
| PEx | Str |
|---|---|
| 146 | 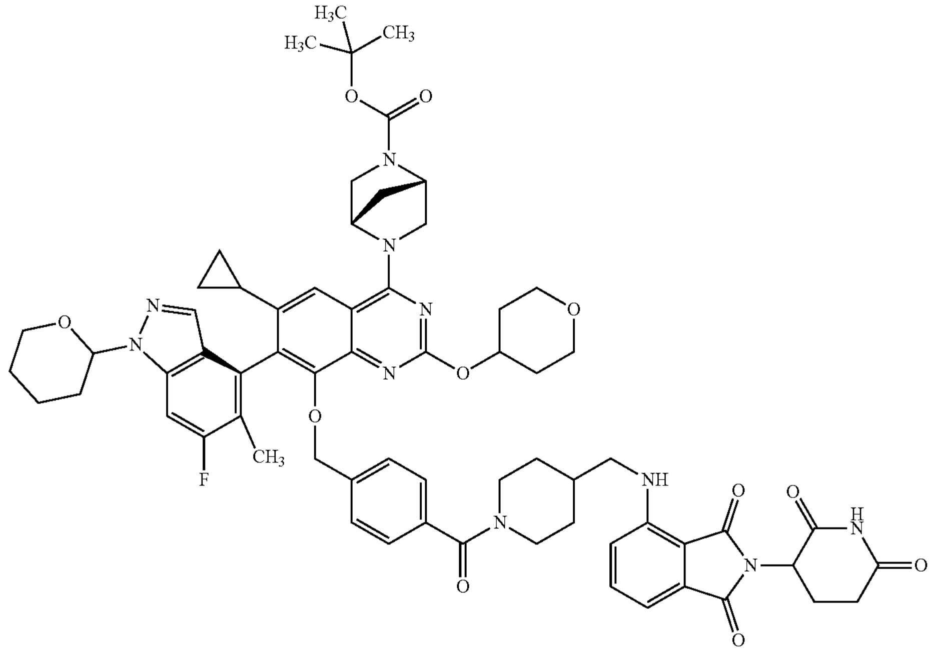 |

TABLE 5-44-continued
| PEx | Str |
|---|---|
| 147 | 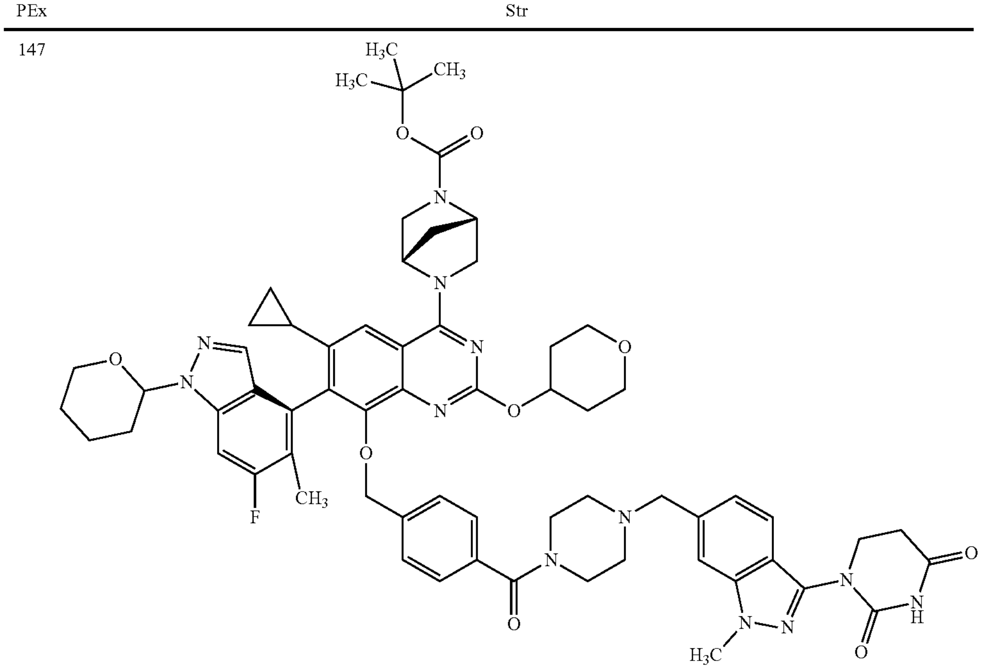 |
TABLE 5-45
| PEx | Str |
|---|---|
| 148 | 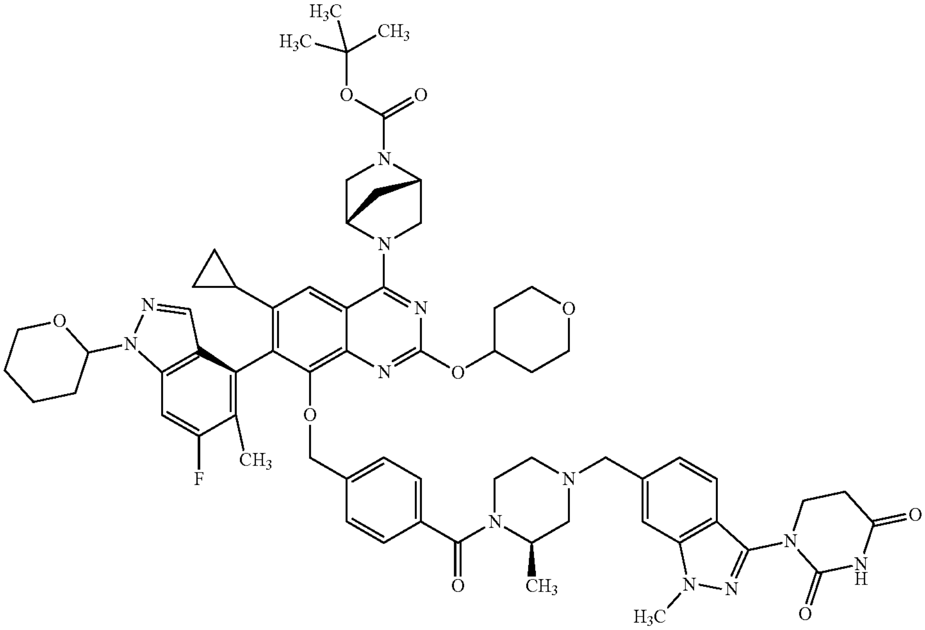 |

TABLE 5-45-continued
| PEx | Str |
|---|---|
| 149 | 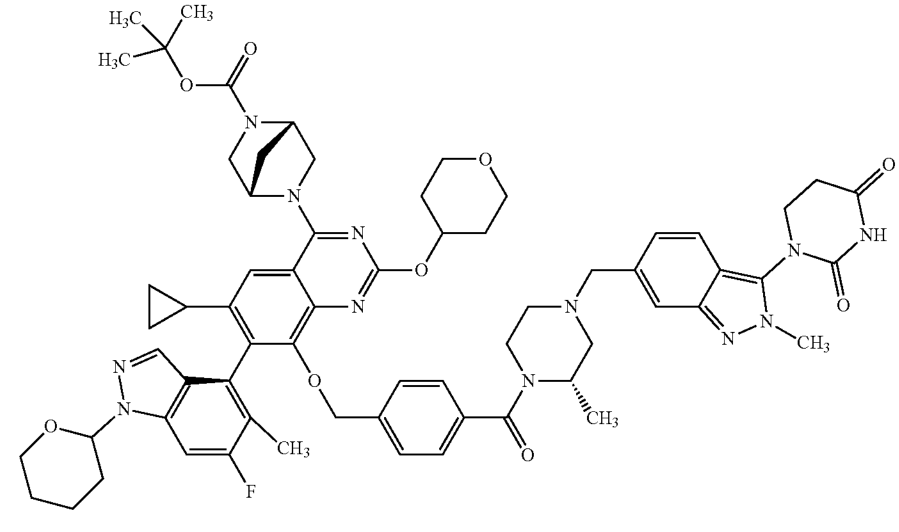 |
| 150 | 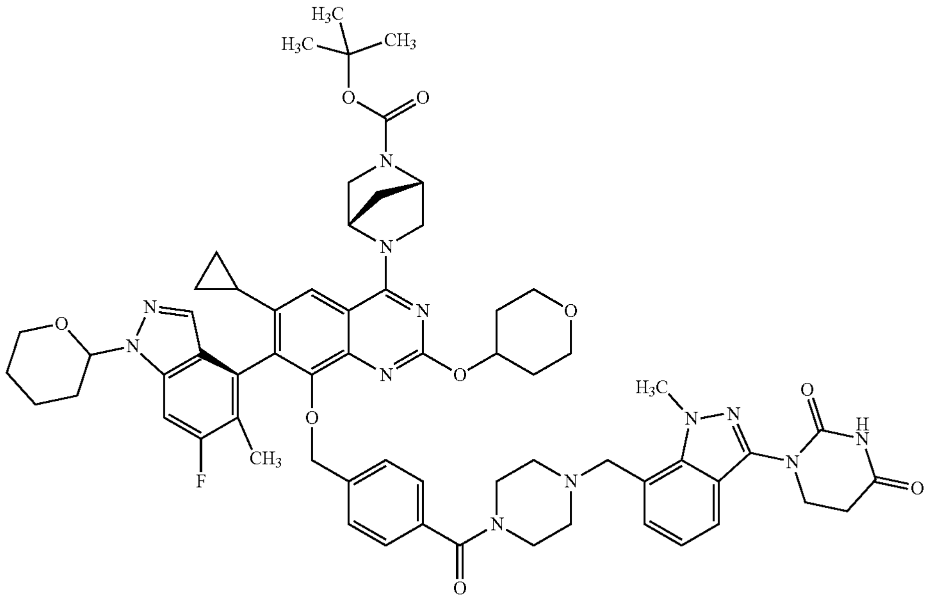 |

TABLE 5-46
| PEx | Str |
|---|---|
| 151 | 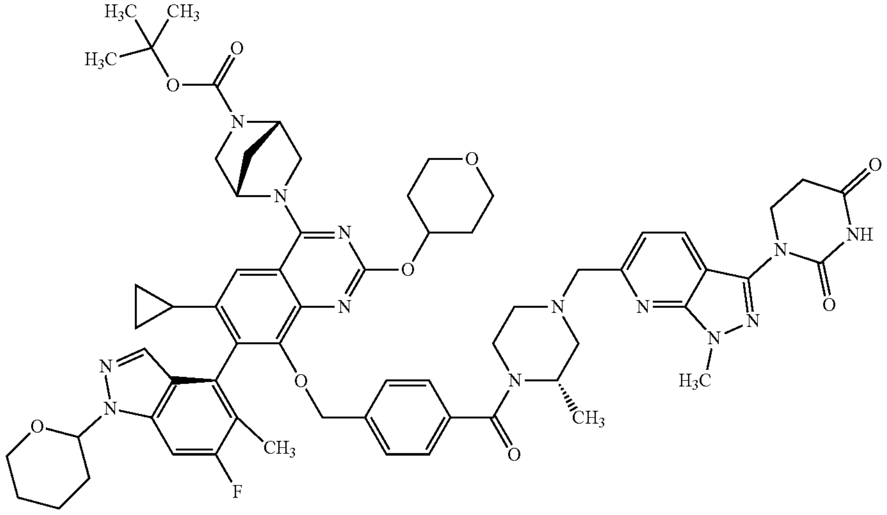 |
| 152 | 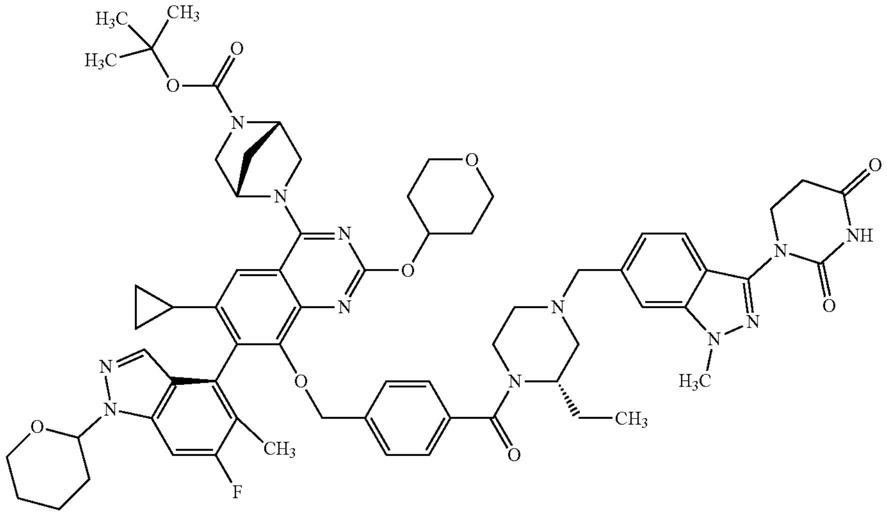 |
| 153 | 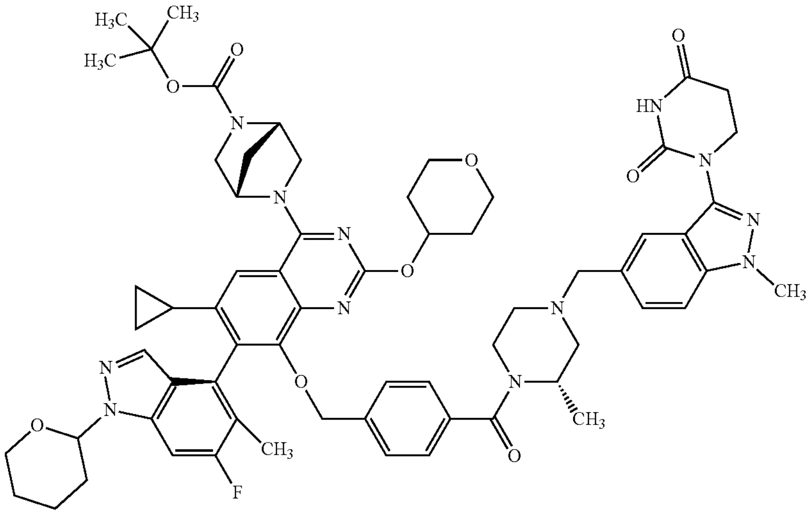 |

TABLE 5-47
| PEx | Str |
|---|---|
| 154 | 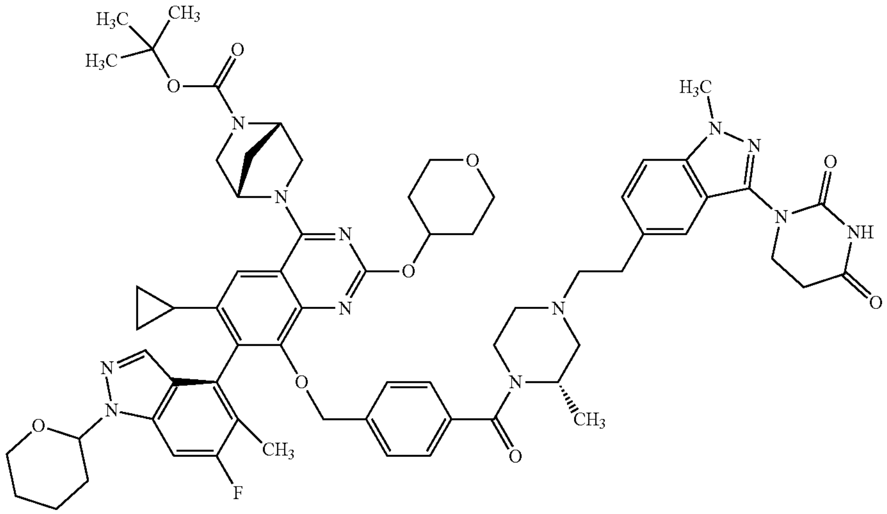 |
| 155 | 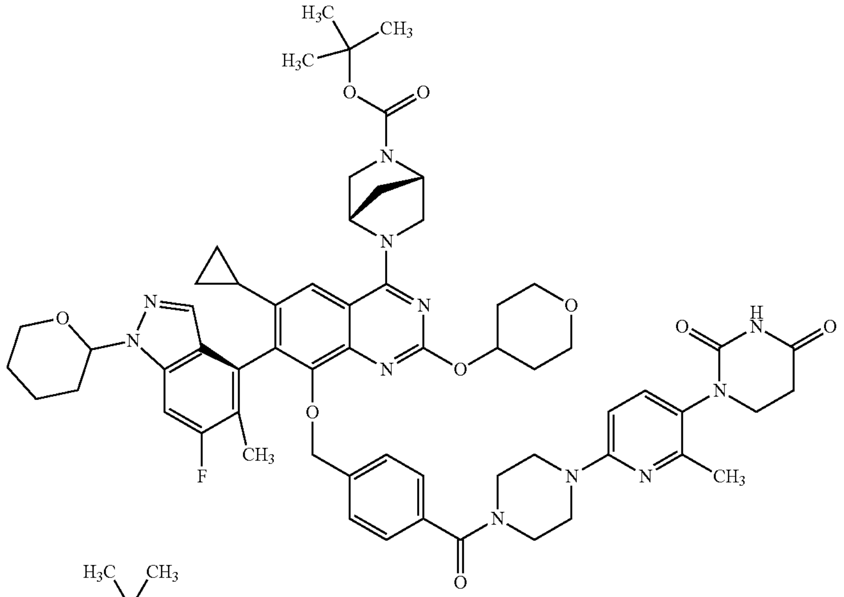 |
| 156 | 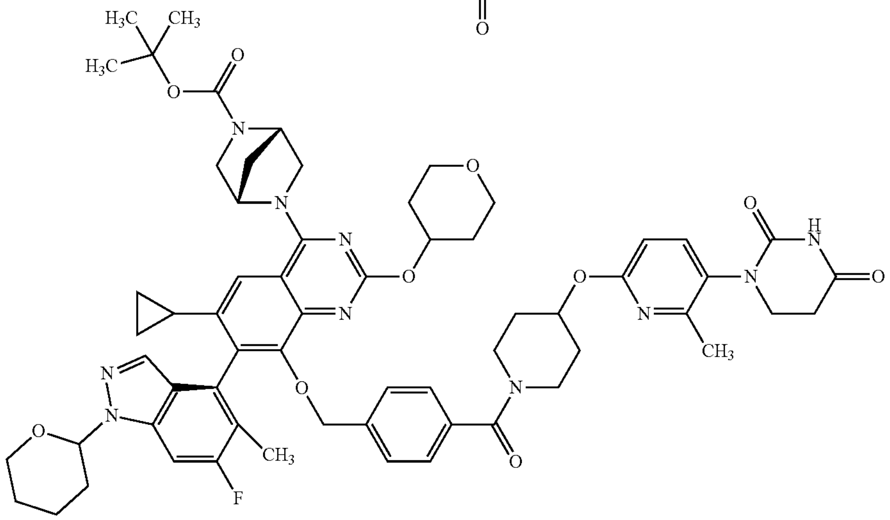 |

TABLE 5-48
| PEx | Str |
|---|---|
| 157 | 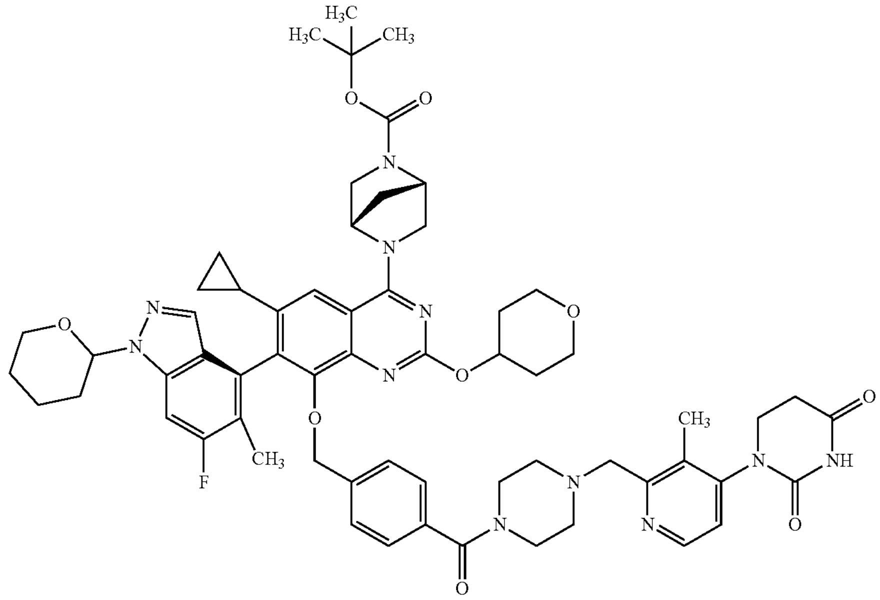 |
| 158 | 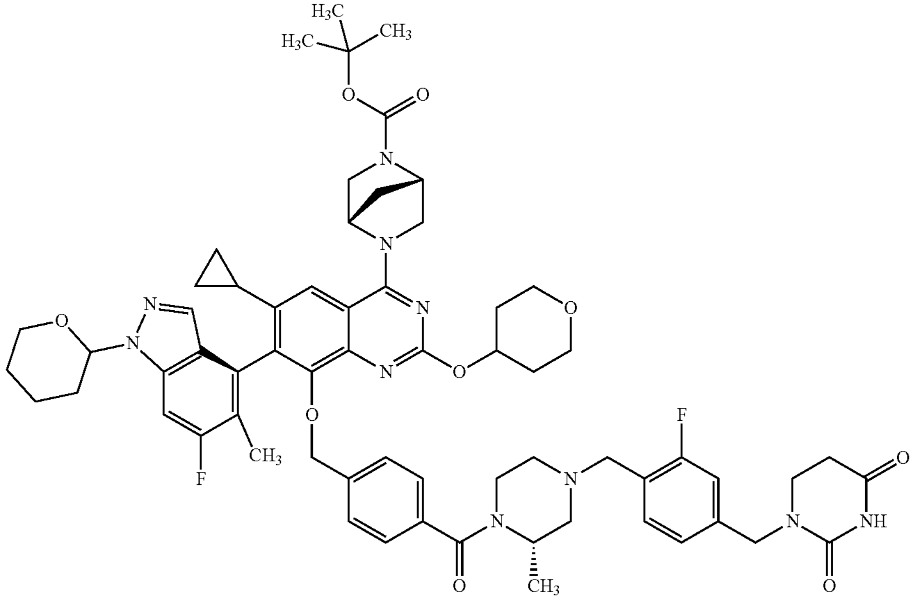 |

TABLE 5-48-continued
| PEx | Str |
|---|---|
| 159 | 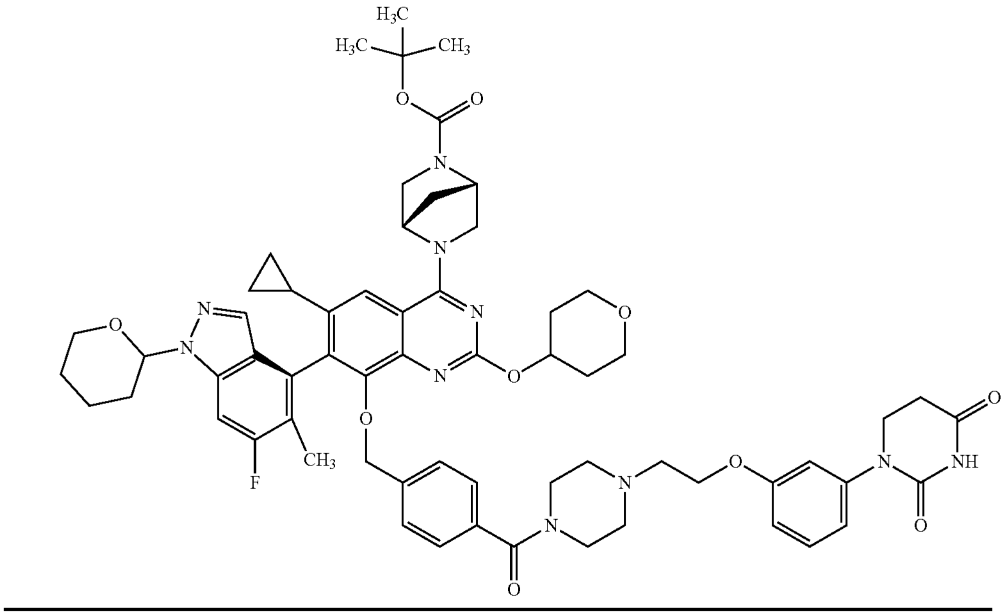 |
TABLE 5-49
| PEx | Str |
|---|---|
| 160 | 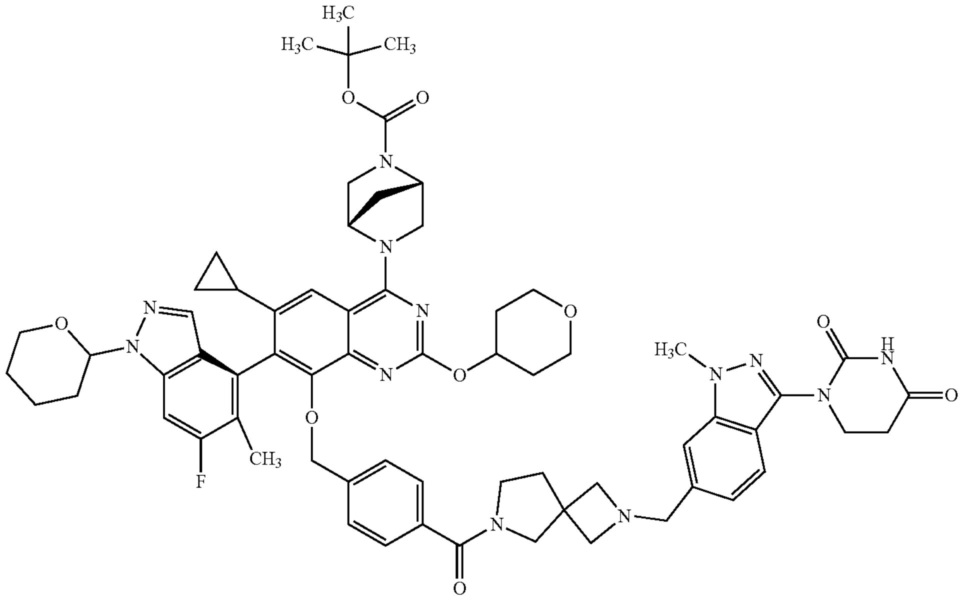 |

TABLE 5-49-continued
| PEx | Str |
|---|---|
| 161 | 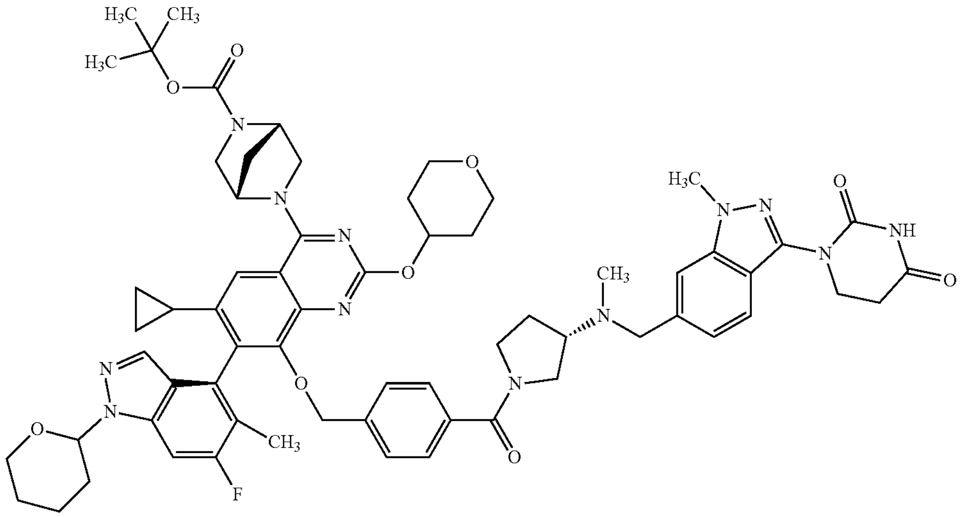 |
| 162 | 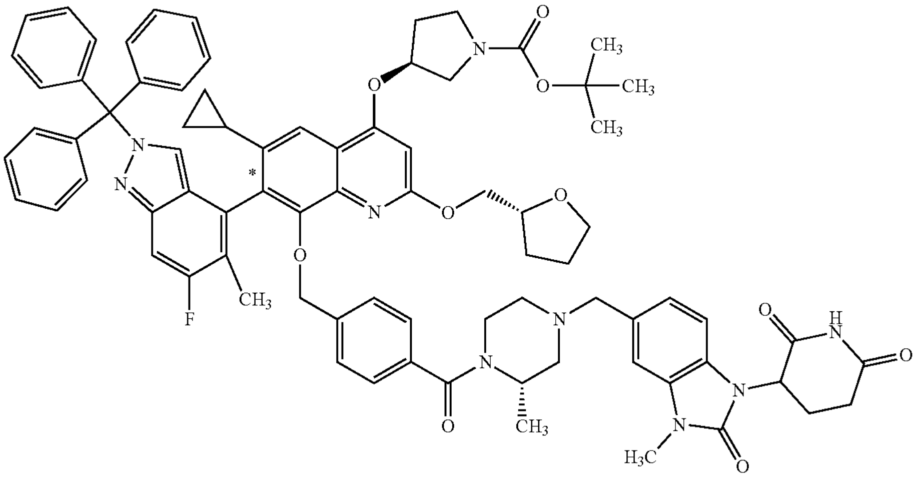 [SMILES: Cc1c(F)cc2nn(C(c3ccccc3)(c3ccccc3)c3ccccc3)cc2c1-c1c(C2CC2)cc2c(O[C@H]3CCN(C(=O)OC(C)(C)C)C3)cc(OC[C@H]3CCCO3)nc2c1OCc1ccc(C(=O)N2CCN(Cc3ccc4c(c3)n(C)c(=O)n4C3CCC(=O)NC3=O)C[C@@H]2C)cc1] |
TABLE 5-50
| PEx | Str |
|---|---|
| 163 | 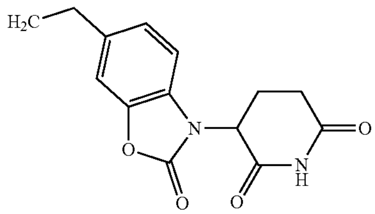 [SMILES: CCc1ccc2c(c1)oc(=O)n2C1CCC(=O)NC1=O] |
| 164 | 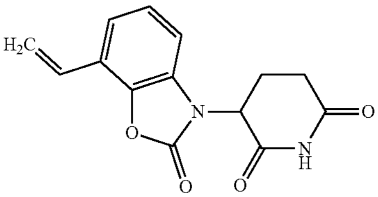 [SMILES: C=Cc1cccc2c1oc(=O)n2C1CCC(=O)NC1=O] |
TABLE 5-50-continued
| PEx | Str |
|---|---|
| 165 | 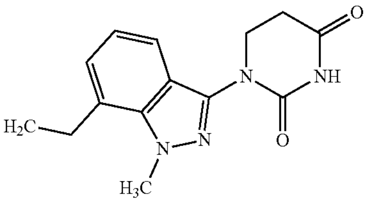 [SMILES: CCc1cccc2c(N3CCC(=O)NC3=O)nn(C)c12] |
| 166 | 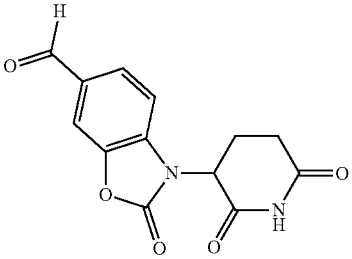 [SMILES: O=Cc1ccc2c(c1)oc(=O)n2C1CCC(=O)NC1=O] |

TABLE 5-50-continued
| PEx | Str |
|---|---|
| 167 | 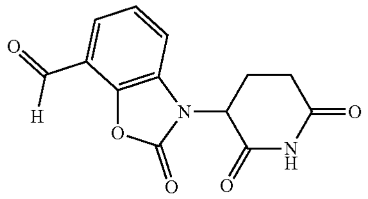 [SMILES: O=Cc1cccc2c1oc(=O)n2C1CCC(=O)NC1=O] |
TABLE 5-51
| PEx | Str |
|---|---|
| 168 | 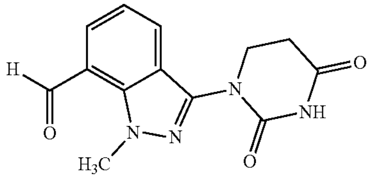 [SMILES: Cn1nc(N2CCC(=O)NC2=O)c2cccc(C=O)c21] |
| 169 | 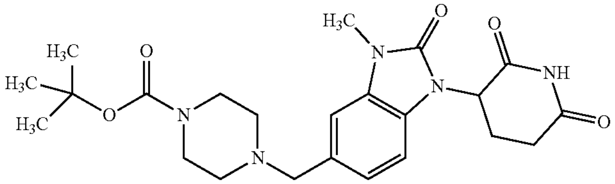 [SMILES: Cn1c(=O)n(C2CCC(=O)NC2=O)c2ccc(CN3CCN(C(=O)OC(C)(C)C)CC3)cc21] |
| 170 | 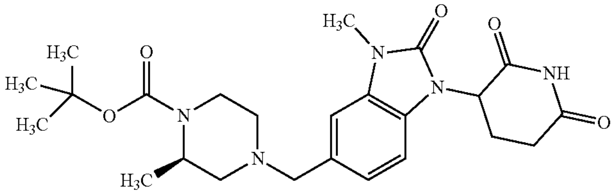 [SMILES: C[C@@H]1CN(Cc2ccc3c(c2)n(C)c(=O)n3C2CCC(=O)NC2=O)CCN1C(=O)OC(C)(C)C] |
| 171 | 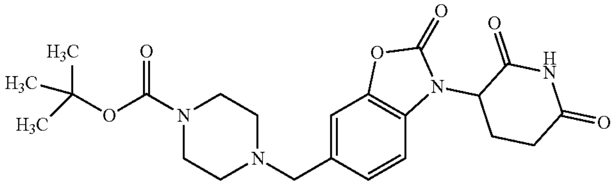 [SMILES: CC(C)(C)OC(=O)N1CCN(Cc2ccc3c(c2)oc(=O)n3C2CCC(=O)NC2=O)CC1] |
| 172 | 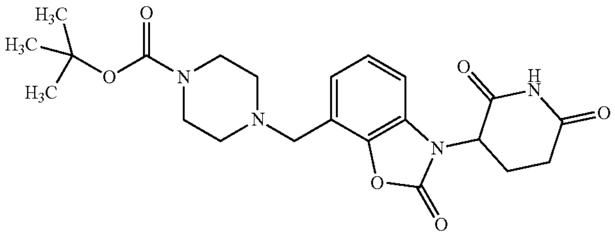 [SMILES: CC(C)(C)OC(=O)N1CCN(Cc2cccc3c2oc(=O)n3C2CCC(=O)NC2=O)CC1] |

TABLE 5-52
| PEx | Str |
|---|---|
| 173 | 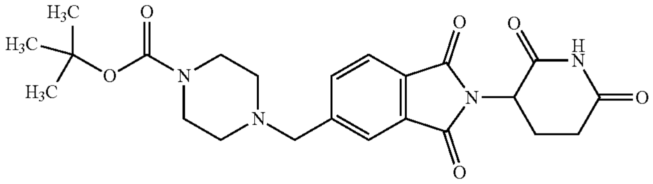 [SMILES: CC(C)(C)OC(=O)N1CCN(Cc2ccc3c(c2)C(=O)N(C2CCC(=O)NC2=O)C3=O)CC1] |
| 174 | 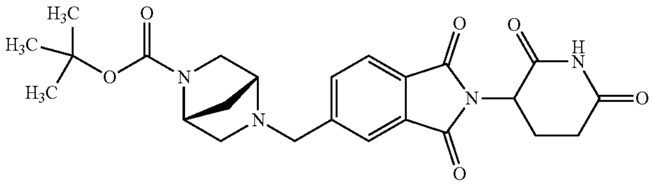 [SMILES: CC(C)(C)OC(=O)N1C[C@H]2C[C@@H]1CN2Cc1ccc2c(c1)C(=O)N(C1CCC(=O)NC1=O)C2=O] |
| 175 | 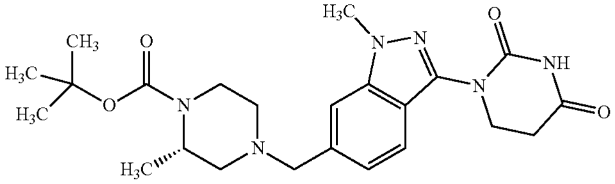 [SMILES: C[C@H]1CN(Cc2ccc3c(N4CCC(=O)NC4=O)nn(C)c3c2)CCN1C(=O)OC(C)(C)C] |
| 176 | 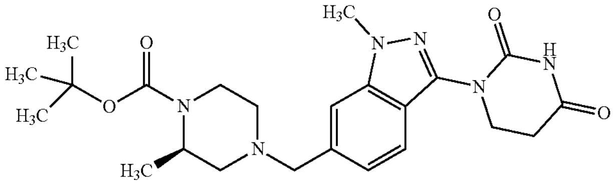 [SMILES: C[C@@H]1CN(Cc2ccc3c(N4CCC(=O)NC4=O)nn(C)c3c2)CCN1C(=O)OC(C)(C)C] |
| 177 | 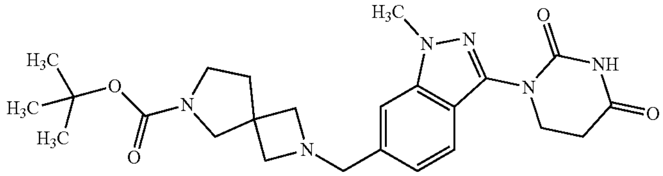 [SMILES: Cn1nc(N2CCC(=O)NC2=O)c2ccc(CN3CC4(CCN(C(=O)OC(C)(C)C)C4)C3)cc21] |
TABLE 5-53
| PEx | Str |
|---|---|
| 178 | 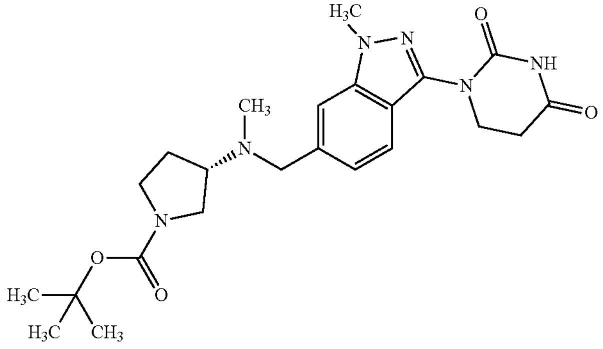 [SMILES: CN(Cc1ccc2c(N3CCC(=O)NC3=O)nn(C)c2c1)[C@H]1CCN(C(=O)OC(C)(C)C)C1] |

TABLE 5-53-continued
| PEx | Str |
|---|---|
| 179 | 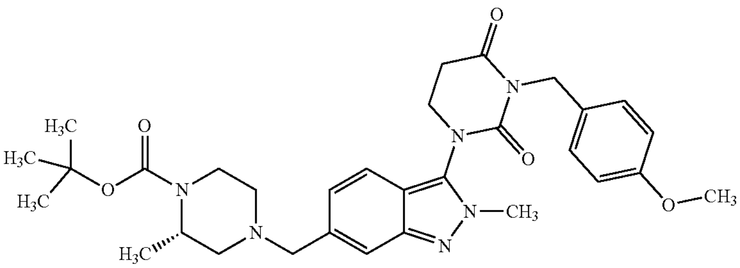 [SMILES: COc1ccc(CN2C(=O)CCN(c3c4ccc(CN5CCN(C(=O)OC(C)(C)C)[C@@H](C)C5)cc4nn3C)C2=O)cc1] |
| 180 | 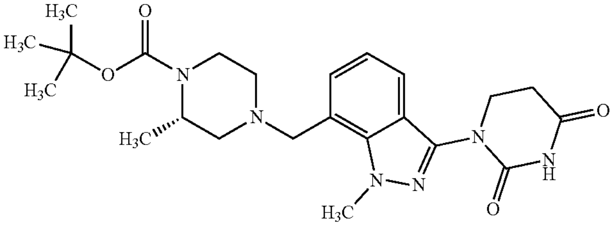 [SMILES: C[C@H]1CN(Cc2cccc3c(N4CCC(=O)NC4=O)nn(C)c23)CCN1C(=O)OC(C)(C)C] |
| 181 | 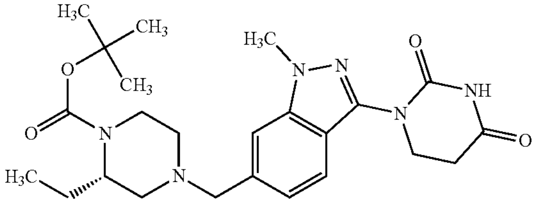 [SMILES: CC[C@H]1CN(Cc2ccc3c(N4CCC(=O)NC4=O)nn(C)c3c2)CCN1C(=O)OC(C)(C)C] |
| 182 | 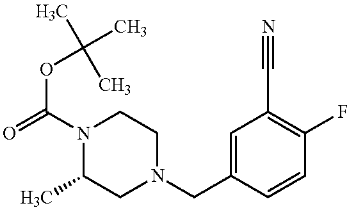 [SMILES: C[C@H]1CN(Cc2ccc(F)c(C#N)c2)CCN1C(=O)OC(C)(C)C] |
TABLE 5-54
| PEx | Str |
|---|---|
| 183 | *n* HCl 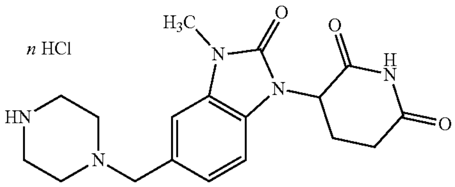 [SMILES: Cn1c(=O)n(C2CCC(=O)NC2=O)c2ccc(CN3CCNCC3)cc21] |
| 184 | *n* HCl 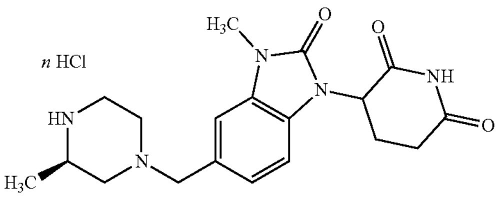 [SMILES: C[C@@H]1CN(Cc2ccc3c(c2)n(C)c(=O)n3C2CCC(=O)NC2=O)CCN1] |
TABLE 5-54-continued
| PEx | Str |
|---|---|
| 185 | *n* HCl 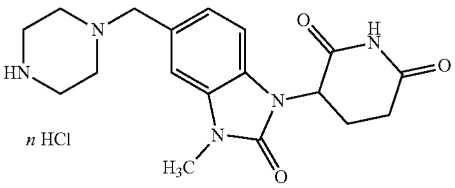 [SMILES: Cn1c(=O)n(C2CCC(=O)NC2=O)c2ccc(CN3CCNCC3)cc21] |
| 186 | *n* HCl 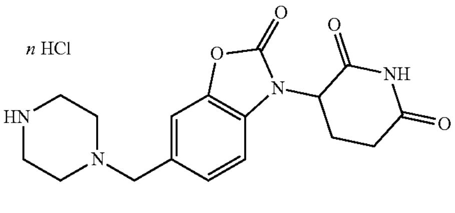 [SMILES: O=C1CCC(n2c(=O)oc3cc(CN4CCNCC4)ccc32)C(=O)N1] |

TABLE 5-54-continued
| PEx | Str |
|---|---|
| 187 | 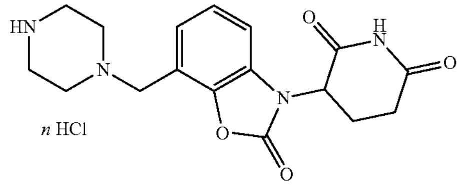 [SMILES: O=C1CCC(n2c(=O)oc3c(CN4CCNCC4)cccc32)C(=O)N1] *n* HCl |
TABLE 5-55
| PEx | Str |
|---|---|
| 188 | *n* HCl 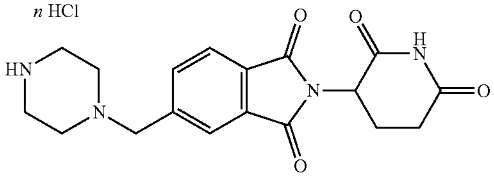 [SMILES: O=C1CCC(N2C(=O)c3ccc(CN4CCNCC4)cc3C2=O)C(=O)N1] |
| 189 | *n* HCl 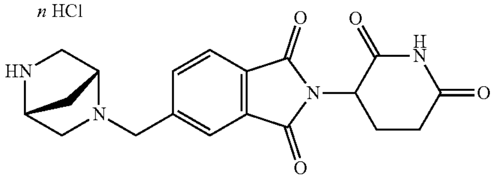 [SMILES: O=C1CCC(N2C(=O)c3ccc(CN4C[C@H]5C[C@@H]4CN5)cc3C2=O)C(=O)N1] |
| 190 | *n* HCl 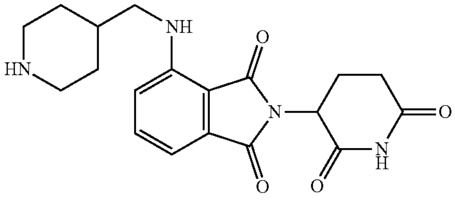 |
| 191 | *n* HCl 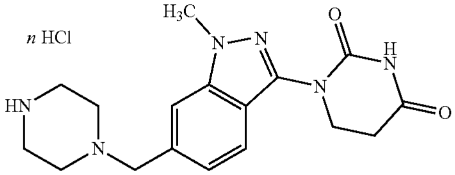 [SMILES: Cn1nc(N2CCC(=O)NC2=O)c2ccc(CN3CCNCC3)cc21] |
| 192 | *n* HCl 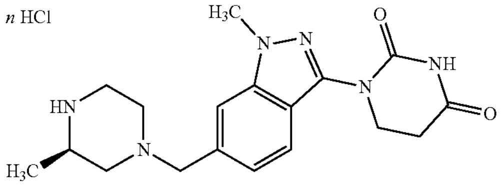 [SMILES: C[C@@H]1CN(Cc2ccc3c(N4CCC(=O)NC4=O)nn(C)c3c2)CCN1] |
TABLE 5-56
| PEx | Str |
|---|---|
| 193 | *n* HCl 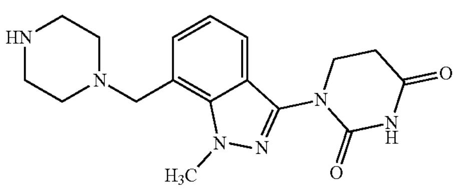 |
| 194 | *n* HCl 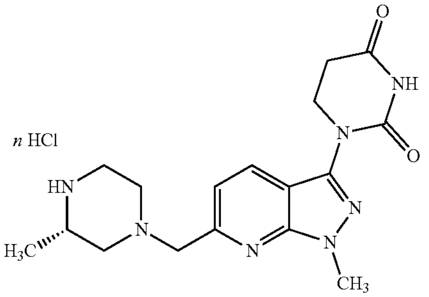 [SMILES: C[C@H]1CN(Cc2ccc3c(N4CCC(=O)NC4=O)nn(C)c3n2)CCN1] |
| 195 | *n* HCl 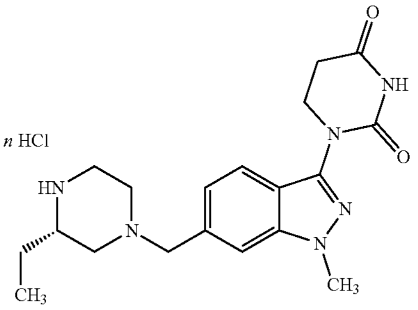 [SMILES: CC[C@H]1CN(Cc2ccc3c(N4CCC(=O)NC4=O)nn(C)c3c2)CCN1] |
| 196 | *n* HCl 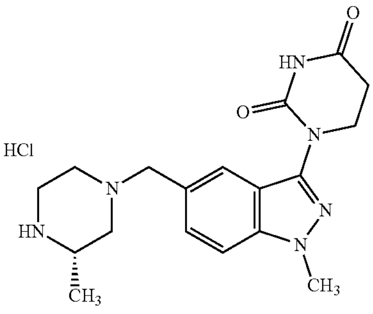 |
| 197 | *n* HCl 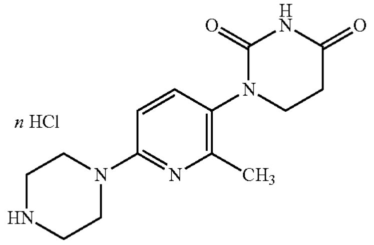 [SMILES: Cc1nc(N2CCNCC2)ccc1N1CCC(=O)NC1=O] |

TABLE 5-57
| PEx | Str |
|---|---|
| 198 | 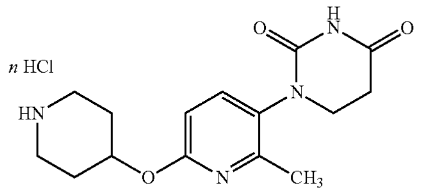 [SMILES: Cc1nc(OC2CCNCC2)ccc1N1CCC(=O)NC1=O] |
| 199 | 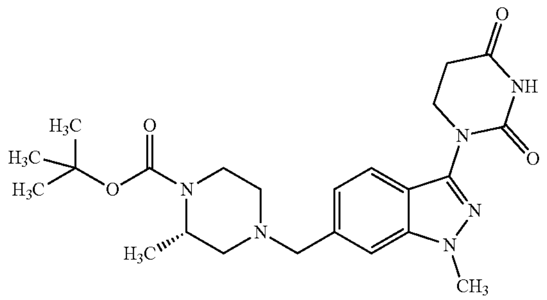 [SMILES: C[C@H]1CN(Cc2ccc3c(N4CCC(=O)NC4=O)nn(C)c3c2)CCN1C(=O)OC(C)(C)C] |
| 200 | 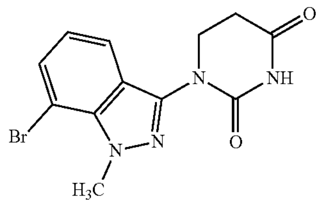 [SMILES: Cn1nc(N2CCC(=O)NC2=O)c2cccc(Br)c21] |
| 201 | 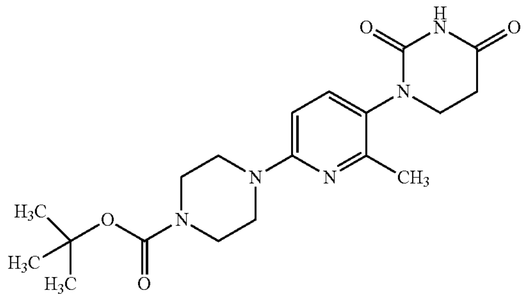 [SMILES: Cc1nc(N2CCN(C(=O)OC(C)(C)C)CC2)ccc1N1CCC(=O)NC1=O] |
| 202 | 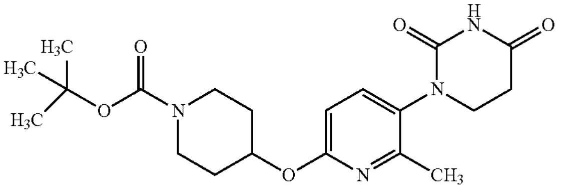 [SMILES: Cc1nc(OC2CCN(C(=O)OC(C)(C)C)CC2)ccc1N1CCC(=O)NC1=O] |

TABLE 5-58
| PEx | Str |
|---|---|
| 203 | 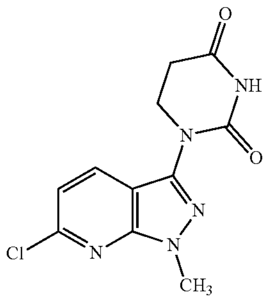 [SMILES: Cn1nc(N2CCC(=O)NC2=O)c2ccc(Cl)nc21] |
| 204 | 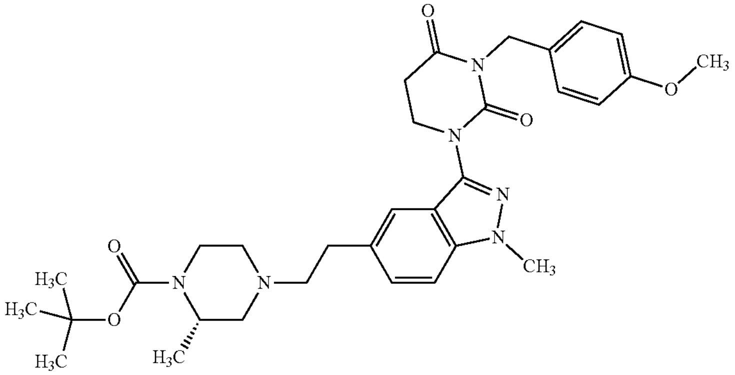 [SMILES: COc1ccc(CN2C(=O)CCN(c3nn(C)c4ccc(CCN5CCN(C(=O)OC(C)(C)C)[C@@H](C)C5)cc34)C2=O)cc1] |
| 205 | 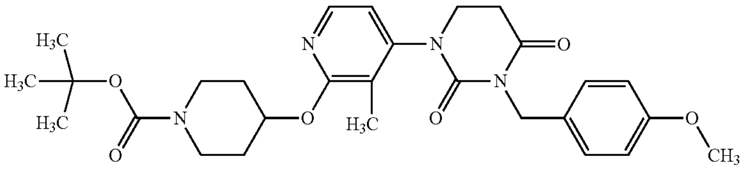 |
| 206 | 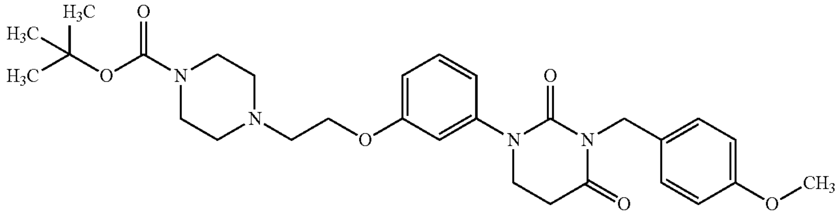 [SMILES: COc1ccc(CN2C(=O)CCN(c3cccc(OCCN4CCN(C(=O)OC(C)(C)C)CC4)c3)C2=O)cc1] |
| 207 | 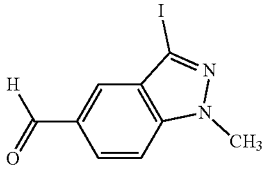 |

TABLE 5-59
| PEX | Str |
|---|---|
| 208 | 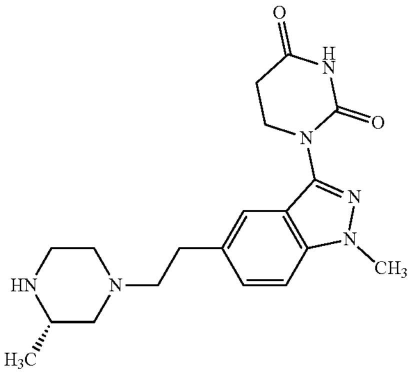 [SMILES: C[C@H]1CN(CCc2ccc3c(c2)c(N2CCC(=O)NC2=O)nn3C)CCN1] |
| 209 | 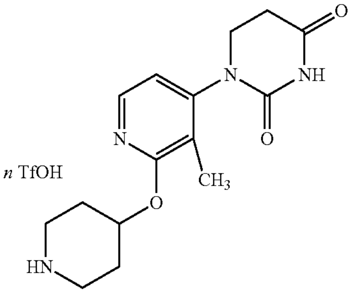 [SMILES: Cc1c(N2CCC(=O)NC2=O)ccnc1OC1CCNCC1] |
| 210 | 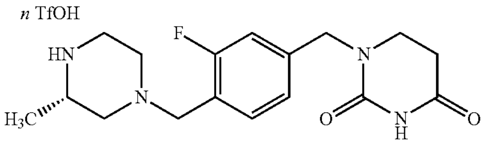 [SMILES: C[C@H]1CN(Cc2ccc(CN3CCC(=O)NC3=O)cc2F)CCN1] |
| 211 | 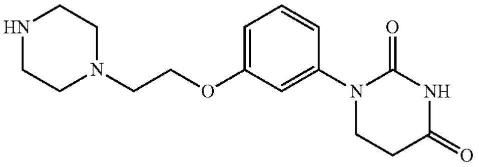 [SMILES: O=C1CCN(c2cccc(OCCN3CCNCC3)c2)C(=O)N1] |
| 212 | 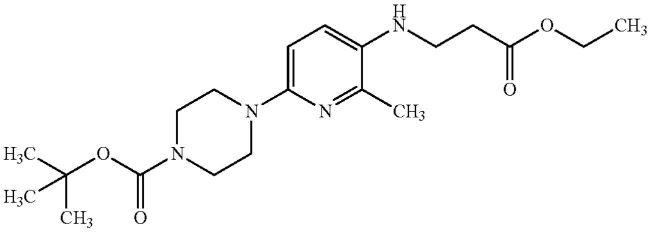 [SMILES: CCOC(=O)CCNc1ccc(N2CCN(C(=O)OC(C)(C)C)CC2)nc1C] |
TABLE 5-60
| PEx | Str |
|---|---|
| 213 | 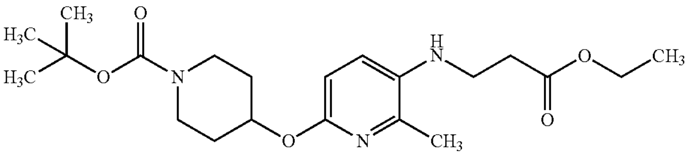 [SMILES: CCOC(=O)CCNc1ccc(OC2CCN(C(=O)OC(C)(C)C)CC2)nc1C] |

TABLE 5-60-continued
| PEx | Str |
| --- | --- |
| 214 | 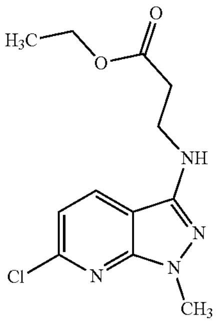 [SMILES: CCOC(=O)CCNc1nn(C)c2nc(Cl)ccc12] |
| 215 | 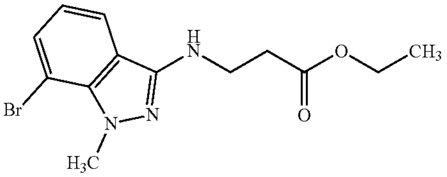 [SMILES: CCOC(=O)CCNc1nn(C)c2c(Br)cccc12] |
| 216 | 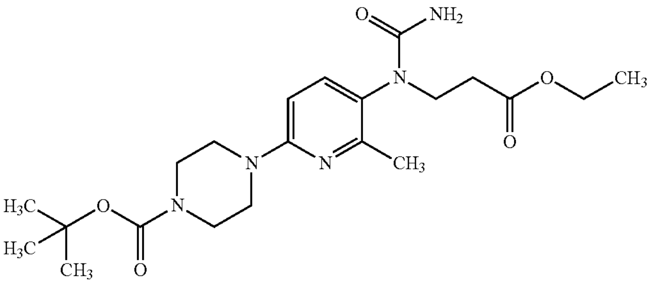 [SMILES: CCOC(=O)CCN(C(N)=O)c1ccc(N2CCN(C(=O)OC(C)(C)C)CC2)nc1C] |
| 217 | 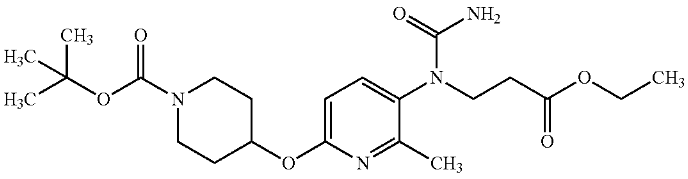 [SMILES: CCOC(=O)CCN(C(N)=O)c1ccc(OC2CCN(C(=O)OC(C)(C)C)CC2)nc1C] |
TABLE 5-61
| PEX | Str |
| --- | --- |
| 218 | 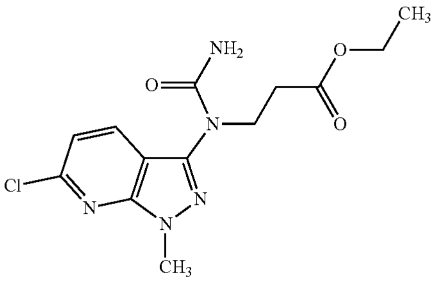 [SMILES: CCOC(=O)CCN(C(N)=O)c1nn(C)c2nc(Cl)ccc12] |
TABLE 5-61-continued
| PEX | Str |
| --- | --- |
| 219 | 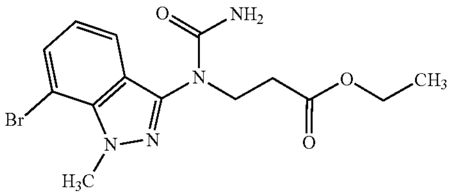 [SMILES: CCOC(=O)CCN(C(N)=O)c1nn(C)c2c(Br)cccc12] |

TABLE 5-62
| PEX | Str |
|---|---|
| 220 | 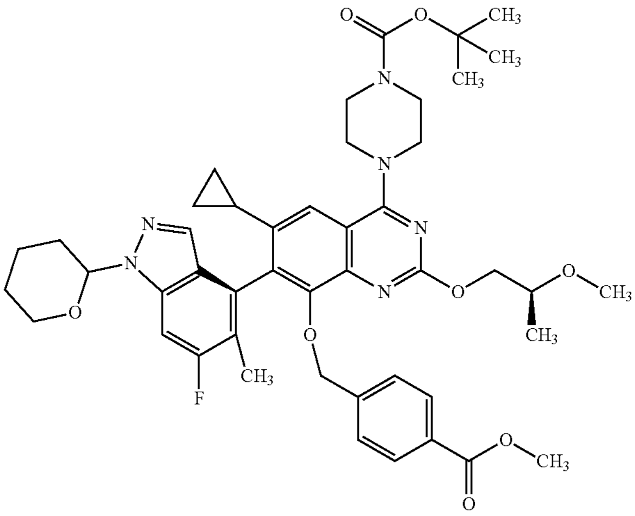 |
| 221 | 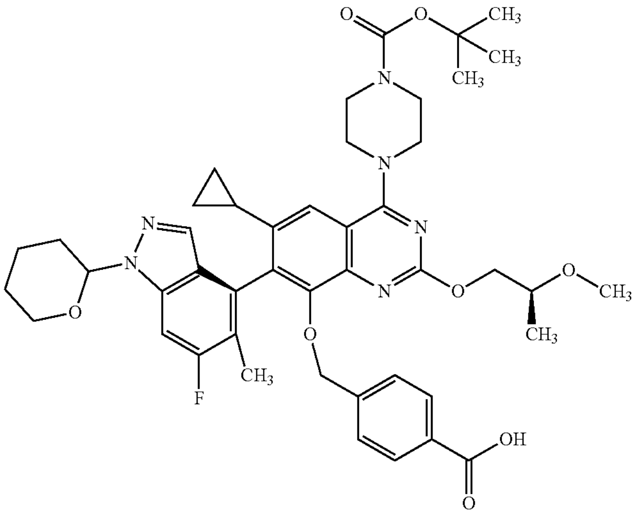 |

TABLE 5-62-continued
| PEX | Str |
| --- | --- |
| 222 | 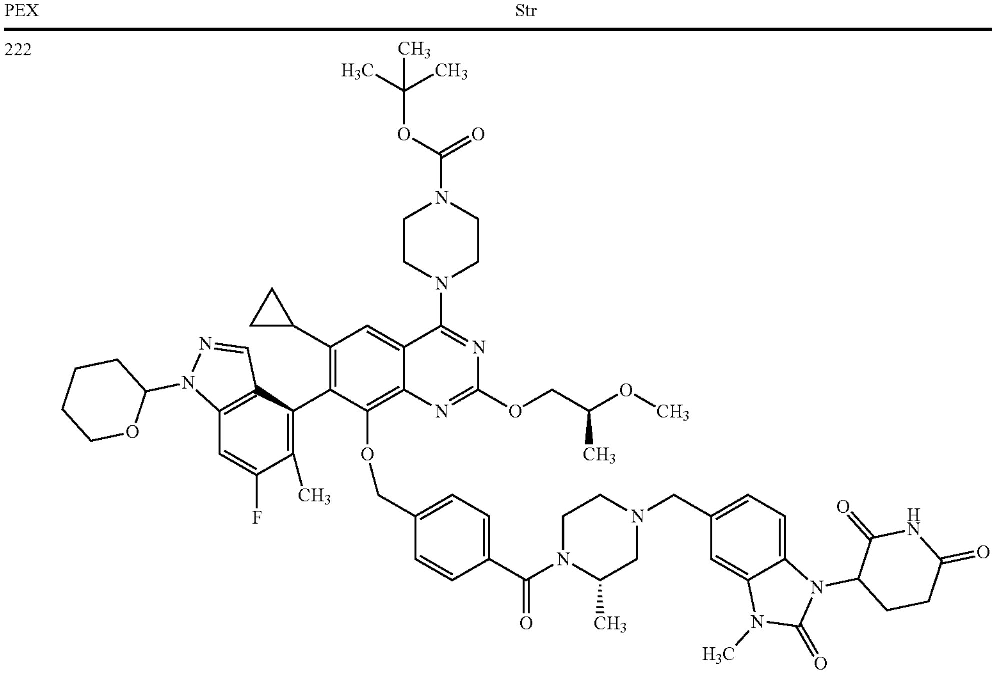 |
| 223 | 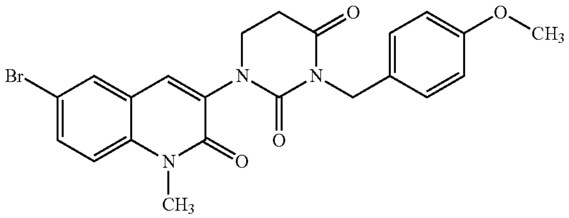 [SMILES: COc1ccc(CN2C(=O)CCN(c3cc4cc(Br)ccc4n(C)c3=O)C2=O)cc1] |
TABLE 5-63
| PEX | Str |
| --- | --- |
| 224 | 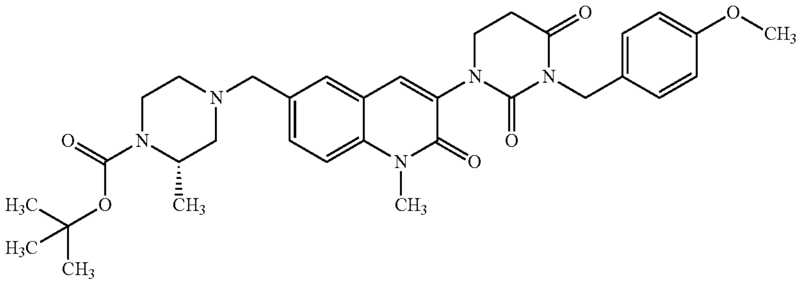 [SMILES: COc1ccc(CN2C(=O)CCN(c3cc4cc(CN5CCN(C(=O)OC(C)(C)C)[C@@H](C)C5)ccc4n(C)c3=O)C2=O)cc1] |
| 225 | 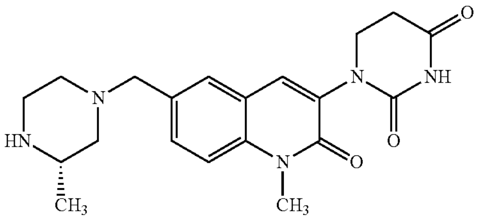 [SMILES: C[C@H]1CN(Cc2ccc3c(c2)cc(N2CCC(=O)NC2=O)c(=O)n3C)CCN1] |

TABLE 5-63-continued
| PEX | Str |
|---|---|
| 226 | 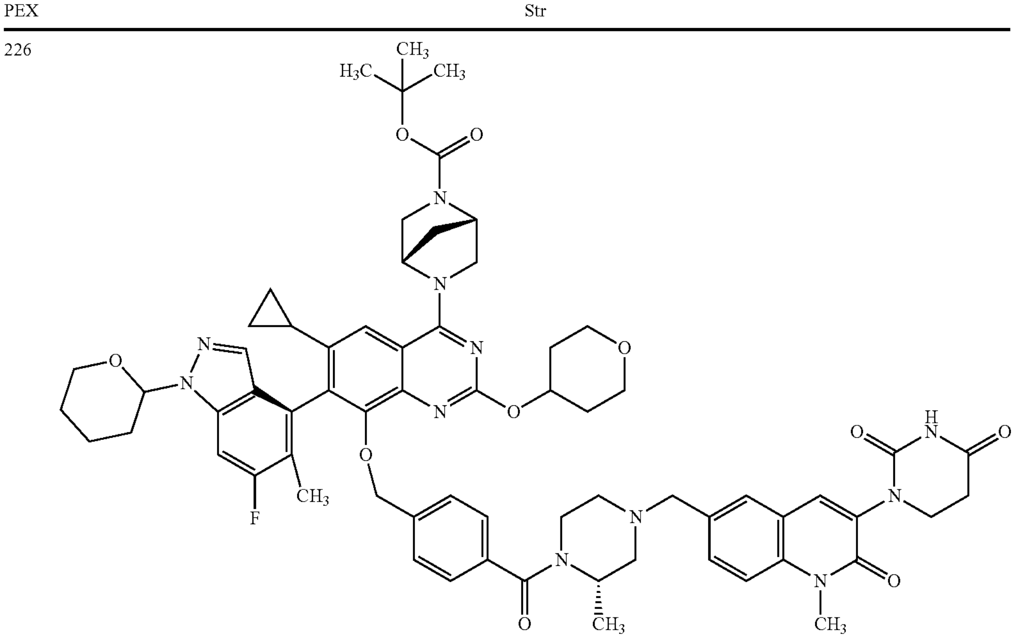 |
| 227 | 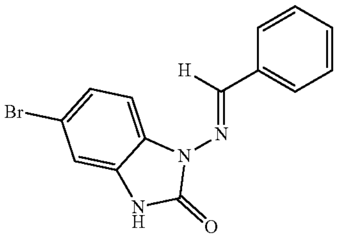 [SMILES: O=c1[nH]c2cc(Br)ccc2n1/N=C/c1ccccc1] |
| 228 | 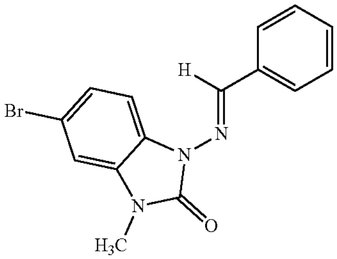 [SMILES: Cn1c(=O)n(/N=C/c2ccccc2)c2ccc(Br)cc21] |
| 229 | 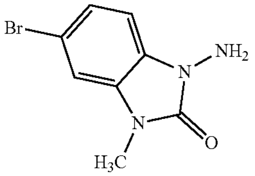 |

TABLE 5-64
| PEX | Str |
| --- | --- |
| 230 | 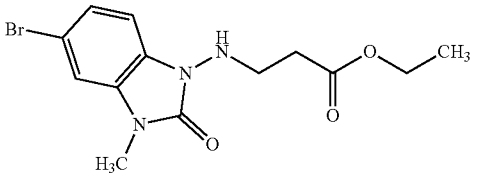 [SMILES: CCOC(=O)CCNn1c(=O)n(C)c2cc(Br)ccc21] |
| 231 | 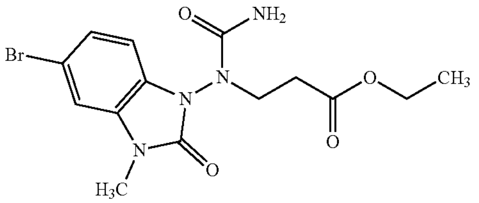 [SMILES: CCOC(=O)CCN(C(N)=O)n1c(=O)n(C)c2cc(Br)ccc21] |
| 232 | 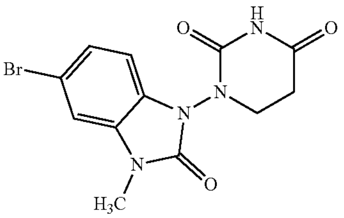 [SMILES: Cn1c(=O)n(N2CCC(=O)NC2=O)c2ccc(Br)cc21] |
TABLE 5-64-continued
| PEX | Str |
| --- | --- |
| 233 | 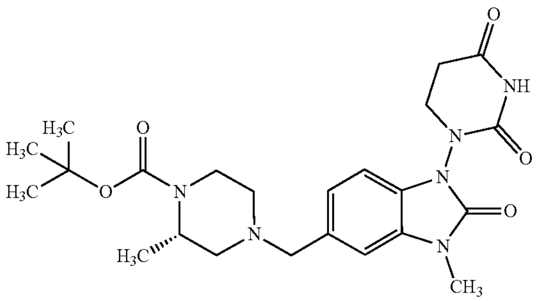 [SMILES: C[C@H]1CN(Cc2ccc3c(c2)n(C)c(=O)n3N2CCC(=O)NC2=O)CCN1C(=O)OC(C)(C)C] |
| 234 | n HCl 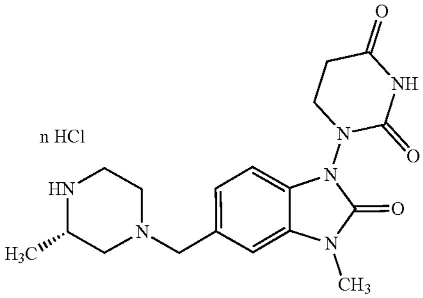 [SMILES: C[C@H]1CN(Cc2ccc3c(c2)n(C)c(=O)n3N2CCC(=O)NC2=O)CCN1] |
TABLE 5-65
| PEX | Str |
| --- | --- |
| 235 | 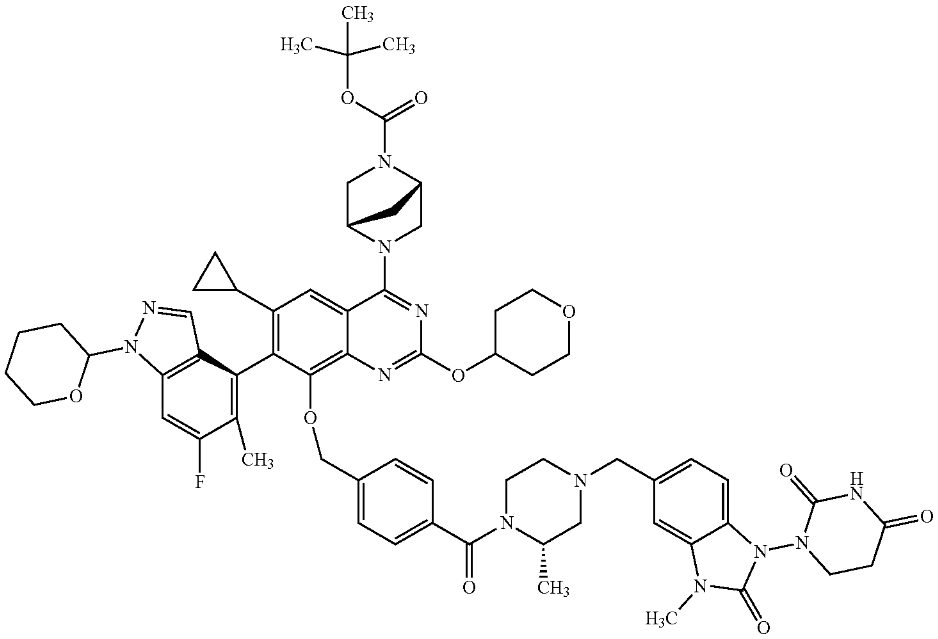 |
| 236 | 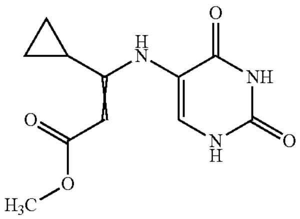 [SMILES: COC(=O)C=C(Nc1c[nH]c(=O)[nH]c1=O)C1CC1] |

TABLE 5-65-continued
| PEX | Str |
|---|---|
| 237 | 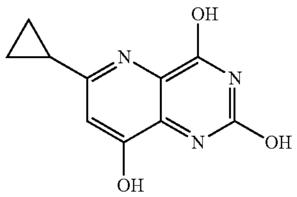 [SMILES: Oc1nc(O)c2nc(C3CC3)cc(O)c2n1] |
| 238 | 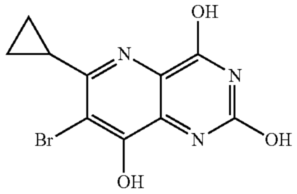 [SMILES: Oc1nc(O)c2nc(C3CC3)c(Br)c(O)c2n1] |
| 239 | 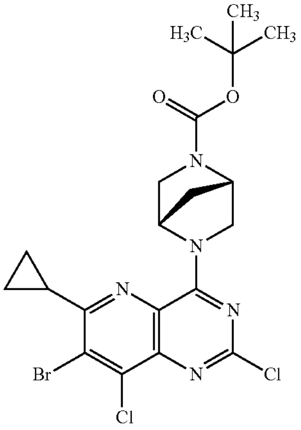 [SMILES: CC(C)(C)OC(=O)N1C[C@@H]2C[C@H]1CN2c1nc(Cl)nc2c(Cl)c(Br)c(C3CC3)nc12] |
TABLE 5-66
| PEx | Str |
|---|---|
| 240 | 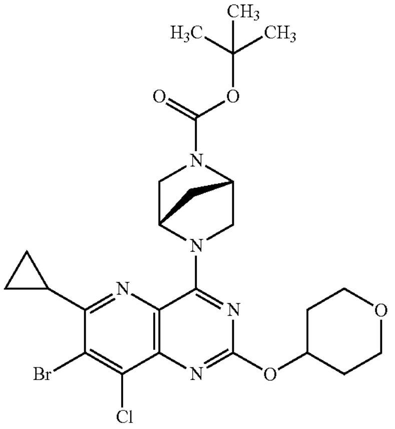 [SMILES: CC(C)(C)OC(=O)N1C[C@@H]2C[C@H]1CN2c1nc(OC2CCOCC2)nc2c(Cl)c(Br)c(C3CC3)nc12] |
TABLE 5-66-continued
| PEx | Str |
|---|---|
| 241 | 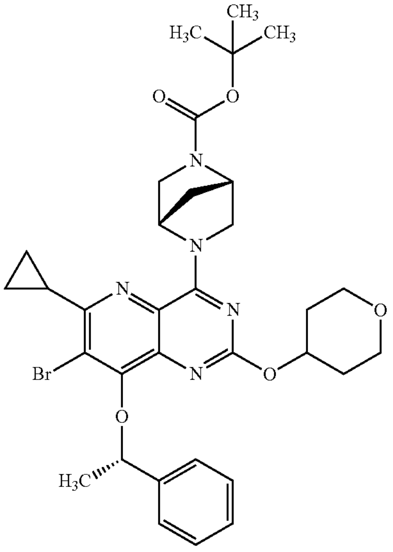 [SMILES: C[C@H](Oc1c(Br)c(C2CC2)nc2c(N3C[C@@H]4C[C@H]3CN4C(=O)OC(C)(C)C)nc(OC3CCOCC3)nc12)c1ccccc1] |

TABLE 5-66-continued
| PEx | Str |
|---|---|
| 242 | 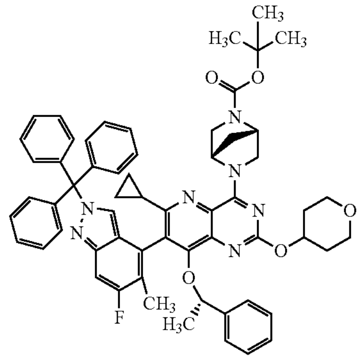 [SMILES: Cc1c(F)cc2nn(C(c3ccccc3)(c3ccccc3)c3ccccc3)cc2c1-c1c(C2CC2)nc2c(N3C[C@@H]4C[C@H]3CN4C(=O)OC(C)(C)C)nc(OC3CCOCC3)nc2c1O[C@@H](C)c1ccccc1] |
| 243 | 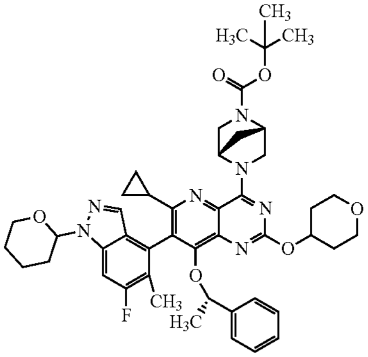 [SMILES: Cc1c(F)cc2c(cnn2C2CCCCO2)c1-c1c(C2CC2)nc2c(N3C[C@@H]4C[C@H]3CN4C(=O)OC(C)(C)C)nc(OC3CCOCC3)nc2c1O[C@@H](C)c1ccccc1] |
TABLE 5-67
| PEX | Str |
|---|---|
| 244 | 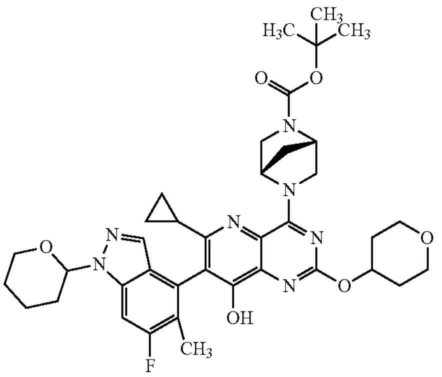 [SMILES: Cc1c(F)cc2c(cnn2C2CCCCO2)c1-c1c(C2CC2)nc2c(N3C[C@@H]4C[C@H]3CN4C(=O)OC(C)(C)C)nc(OC3CCOCC3)nc2c1O] |
TABLE 5-67-continued
| PEX | Str |
|---|---|
| 245 | 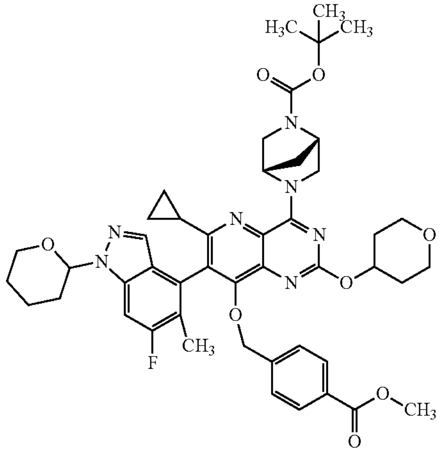 [SMILES: COC(=O)c1ccc(COc2c(-c3c(C)c(F)cc4c3cnn4C3CCCCO3)c(C3CC3)nc3c(N4C[C@@H]5C[C@H]4CN5C(=O)OC(C)(C)C)nc(OC4CCOCC4)nc23)cc1] |
| 246 | 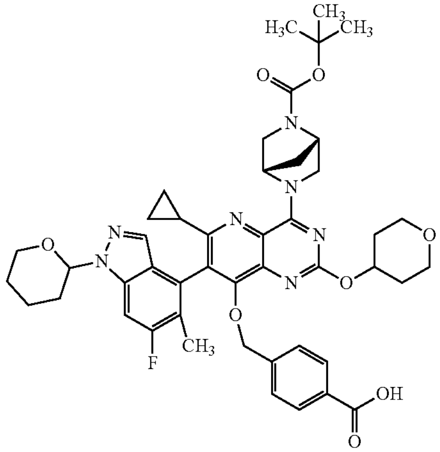 [SMILES: Cc1c(F)cc2c(cnn2C2CCCCO2)c1-c1c(C2CC2)nc2c(N3C[C@@H]4C[C@H]3CN4C(=O)OC(C)(C)C)nc(OC3CCOCC3)nc2c1OCc1ccc(C(=O)O)cc1] |

TABLE 5-68

| PEX | Str |
|---|---|
| 247 | 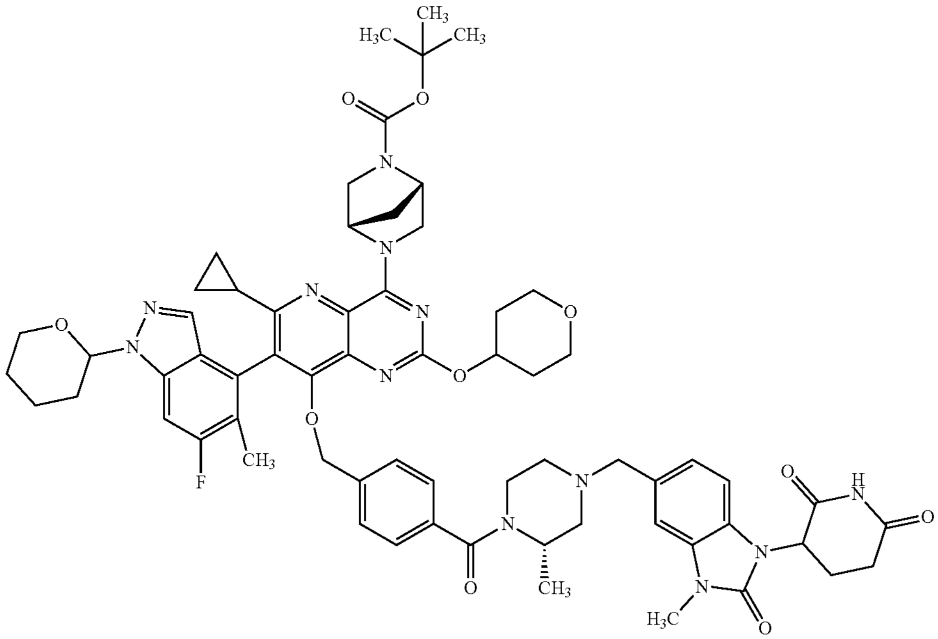 [SMILES: Cc1c(F)cc2c(cnn2C2CCCCO2)c1-c1c(C2CC2)nc2c(N3C[C@@H]4C[C@H]3CN4C(=O)OC(C)(C)C)nc(OC3CCOCC3)nc2c1OCc1ccc(C(=O)N2CCN(Cc3ccc4c(c3)n(C)c(=O)n4C3CCC(=O)NC3=O)C[C@@H]2C)cc1] |

TABLE 6-1

| PEx | PSyn | DAT |
|---|---|---|
| 1 | P1 | ESI+: 402.9, 404.9, 406.9 |
| 2 | P2 | ESI+: 480.9, 482.2 [M + Na]+ |
| 3 | P3 | ESI+: 611.1 |
| 4 | P4 | ESI+: 713.1 |
| 5 | P5 | ESI+: 654.4 |
| 6 | P6 | ESI+: 964.7 |
| 7 | P7 | ESI+: 811.5 |
| 8 | P8 | ESI+: 851.8 |
| 9 | P9 | ESI+: 860.6 |
| 10 | P10 | ESI+: 1008.5 |
| 11 | P11 | ESI+: 671.5 |
| 12 | P12 | ESI+: 779.5 |
| 13 | P13 | ESI+: 840.7 |
| 14 | P14 | ESI+: 837.7 |
| 15 | P15 | ESI+: 826.7 |
| 16 | P16 | ESI+: 1190.8 |
| 17 | P17 | ESI+: 583.1, 585.1 |
| 18 | P18 | ESI+: 695.4 NMR: 0.52-0.66 (3H, m), 0.66-0.75 (1H, m), 0.86 (3H, br d), 1.27 (3H, t), 1.30-1.46 (10H, m), 1.83 (3H, br s), 1.90-2.01 (1H, m), 2.04 (1H, br d), 2.98-3.10 (2H, m), 3.45-3.55 (2H, m), 3.67-3.82 (1H, m), 4.33 (1H, br d), 4.52-4.64 (1H, m), 5.15 (1H, br d), 6.02-6.10 (1H, m), 6.82 (2H, br d), 7.12-7.20 (3H, m), 7.31 (1H, br s), 7.37 (1H, d), 7.51-7.57 (1H, m), 13.04 (1H, br s) |
| 19 | P19 | ESI+: 417.9 |
| 20 | P20 | ESI+: 386.0 |
| 21 | P21 | ESI+: 419.8, 421.9, 423.9 |
| 22 | P22 | ESI+: 445.9, 447.9 |
| 23 | P23 | ESI+: 598.1, 600.2[M + Na]+ |
| 24 | P24 | ESI+: 699.2, 701.2 |
| 25 | P25 | ESI+: 474.0 |
| 26 | P26 | ESI+: 740.3 |
| 27 | P27 | ESI+: 382.3 |

TABLE 6-1-continued

| PEx | PSyn | DAT |
|---|---|---|
| 28 | P28 | ESI+: 460.4 |
| 29 | P29 | ESI+: 459.4 |
| 30 | P30 | ESI+: 325.0 |

TABLE 6-2

| PEx | PSyn | DAT |
|---|---|---|
| 31 | P30 | NMR (400 MHz): 2.11-2.20 (1H, m), 2.58-2.72 (2H, m), 2.79-2.93 (1H, m), 5.37 (1H, dd), 7.25 (1H, d), 7.42 (1H, dd), 7.72 (1H, d), 11.23 (1H, br s) |
| 32 | P32 | ESI+: 338.2 |
| 33 | P33 | ESI+: 286.2 |
| 34 | P34 | ESI+: 288.3 |
| 35 | P35 | ESI+: 273.1 |
| 36 | P36 | ESI+: 472.4 |
| 37 | P37 | ESI+: 372.5 |
| 38 | P38 | ESI+: 348.3 |
| 39 | P39 | ESI+: 489.5 |
| 40 | P40 | ESI+: 555.6 |
| 41 | P41 | ESI+: 471.5 |
| 42 | P42 | ESI+: 355.1 |
| 43 | P43 | ESI+: 457.5 |
| 44 | P44 | ESI+: 457.3 |
| 45 | P45 | ESI+: 289.0 |
| 46 | P46 | ESI+: 395.3 |
| 47 | P47 | ESI+: 431.0 |
| 48 | P48 | ESI+: 393.4 |
| 49 | P49 | ESI+: 357.4 |
| 50 | P50 | ESI+: 343.0 |
| 51 | P51 | ESI+: 315.0 |
| 52 | P52 | ESI+: 485.3 |
| 53 | P53 | ESI+: 360.3 |
| 54 | P54 | ESI+: 227.9 |
| 55 | P55 | ESI+: 460.5 |
| 56 | P56 | ESI+: 503.4 |
| 57 | P57 | ESI+: 360.3 [M + Na]+ |
| 58 | P58 | ESI+: 419.0 |

TABLE 6-2-continued

| PEx | PSyn | DAT |
|---|---|---|
| 59 | P59 | ESI+: 308.2 |
| 60 | P60 | ESI+: 433.2 |

TABLE 6-3

| PEx | PSyn | DAT |
|---|---|---|
| 61 | P61 | ESI+: 421.2 |
| 62 | P62 | ESI+: 613.2 |
| 63 | P63 | ESI+: 627.5 |
| 64 | P64 | ESI+: 925.3<br>NMR: 0.29-0.37 (1H, m), 0.54-0.64 (1H, m), 0.64-0.77 (2H, m), 0.78-0.87 (3H, br dd), 1.22-1.46 (13H, m), 1.83 (3H, br s), 2.20 (2H, br s), 3.07-3.26 (2H, m), 3.41-3,50 (2H, m), 3.55-3.62 (2H, m), 5.28 (1H, br s), 6.24 (1H, br s), 6.82-6.89 (2H, m), 6.91 (1H, s), 7.00-7.08 (6H, m), 7.16-7.24 (4H, m), 7.25-7.33 (9H, m), 7.33-7.37 (1H, m), 7.48 (1H, d) |
| 65 | P65 | ESI+: 937.6 |
| 66 | P66 | ESI+: 979.5 [M + Na]+ |
| 67 | P67 | ESI+: 863.6 |
| 68 | P68 | ESI+: 997.7 |
| 69 | P69 | ESI+: 707.4 |
| 70 | P70 | ESI+: 875.7 [M + Na]+ |
| 71 | P71 | ESI+: 855.5 |
| 72 | P72 | ESI+: 1001.4 |
| 73 | P73 | ESI+: 849.7 |
| 74 | P74 | ESI+: 983.6 |
| 75 | P75 | ESI+: 994.7 |
| 76 | P76 | ESI+: 1202.8 |
| 77 | P77 | ESI+: 1336.9 |
| 78 | P78 | ESI+: 1348.7 |
| 79 | P79 | ESI+: 1173.8 |
| 80 | P80 | ESI+: 1213.9 |
| 81 | P81 | ESI+: 1187.7 |
| 82 | P82 | ESI+: 1188.0 |
| 83 | P83 | ESI+: 548.0, 550.0 |
| 84 | P84 | ESI+: 271.2 |
| 85 | P85 | ESI+: 483.3 |
| 86 | P86 | ESI+: 457.6 |
| 87 | P87 | ESI+: 383.3 |
| 88 | P88 | ESI+: 357.4 |
| 89 | P89 | ESI+: 357.5 |
| 90 | P90 | ESI+: 563.3 |

TABLE 6-4

| PEx | PSyn | DAT |
|---|---|---|
| 91 | P91 | NMR: 1.21 (12H, s), 2.44 (3H, d), 7.04-7.11 (6H, m), 7.34-7.44 (9H, m), 7.49 (1H, d), 8.09 (1H, d) |
| 92 | P92 | NMR: 2.34 (3H, d), 7.07-7.13 (6H, m), 7.36-7.43 (9H, m), 7.51 (1H, d), 7.79 (1H, d) |
| 93 | P93 | NMR: 7.08-7.15 (6H, m), 7.36-7.44 (10H, m), 7.49-7.54 (1H, m), 7.89 (1H, d) |
| 94 | P94 | ESI+: 508.9 [M + Na]+ |
| 95 | P4 | ESI+: 587.2 |
| 96 | P5 | ESI+: 503.4 |
| 97 | P97 | ESI+: 813.4 |
| 98 | P98 | ESI+: 867.7 [M + Na]+<br>NMR: 0.43-0.50 (1H, m), 0.66-0.75 (1H, m), 0.77-0.89 (2H, m), 0.94 (3H, d), 1.25 (3H, t), 1.46-1.54 (1H, m), 1.75 (9H, s), 1.80 (3H, d), 3.47-3.54 (2H, m), 5.94 (1H, q), 6.90-6.94 (2H, m), 7.01-7.09 (6H, m), 7.16-7.24 (3H, m), 7.28-7.35 (9H, m), 7.35 (1H, s), 7.44 (1H, d), 7.52 (1H, d) |

TABLE 6-4-continued

| PEx | PSyn | DAT |
|---|---|---|
| 99 | P8 | ESI+: 1009.6 |
| 100 | P8 | ESI+: 849.5 |
| 101 | P8 | ESI+: 863.6 |
| 102 | P8 | ESI+: 851.6 |
| 103 | P8 | ESI+: 863.7 |
| 104 | P8 | ESI+: 849.7 |
| 105 | P8 | ESI+: 1009.5 |
| 106 | P8 | ESI+: 997.7 |
| 107 | P8 | ESI+: 841.6 |
| 108 | P9 | ESI+: 705.5 |
| 109 | P9 | ESI+: 737.6 |
| 110 | P10 | ESI+: 853.6 |
| 111 | P10 | ESI+: 907.6 [M + Na]+ |
| 112 | P11 | ESI+: 627.5 |
| 113 | P13 | ESI+: 853.6 |
| 114 | P13 | ESI+: 840.6 |
| 115 | P13 | ESI+: 809.8 |
| 116 | P14 | ESI+: 839.6 |
| 117 | P14 | ESI+: 826.7 |
| 118 | P14 | ESI+: 839.6 |
| 119 | P14 | ESI+: 835.6 |
| 120 | P14 | ESI+: 849.6 |

TABLE 6-5

| PEx | PSyn | DAT |
|---|---|---|
| 121 | P14 | ESI+: 837.6 |
| 122 | P14 | ESI+: 849.7 |
| 123 | P14 | ESI+: 835.7 |
| 124 | P14 | ESI+: 995.8 |
| 125 | P14 | ESI+: 983.7 |
| 126 | P14 | ESI+: 995.7 |
| 127 | P16 | ESI+: 1188.8 |
| 128 | P16 | ESI+: 1202.4 |
| 129 | P16 | ESI+: 1189.8 |
| 130 | P16 | ESI+: 1192.8 |
| 131 | P16 | ESI+: 1192.7 |
| 132 | P16 | ESI+: 1188.6 |
| 133 | P16 | ESI+: 1203.0 |
| 134 | P16 | ESI+: 1190.8 |
| 135 | P16 | ESI+: 1179.6 |
| 136 | P16 | ESI+: 1202.7 |
| 137 | P16 | ESI+: 1188.7 |
| 138 | P16 | ESI+: 1179.8 |
| 139 | P16 | ESI−: 1346.7 |
| 140 | P16 | ESI+: 1336.7 |
| 141 | P16 | ESI+: 1175.8 |
| 142 | P16 | ESI+: 1175.9 |
| 143 | P16 | ESI+: 1187.3 |
| 144 | P16 | ESI+: 1288.3 |
| 145 | P16 | ESI−: 1197.9 |
| 146 | P16 | ESI+: 1201.7 |
| 147 | P16 | ESI+: 1173.6 |
| 148 | P16 | ESI+: 1187.9 |
| 149 | P16 | ESI+: 1187.8 |
| 150 | P16 | ESI+: 1173.8 |
| 151 | P16 | ESI+: 1188.7 |
| 152 | P16 | ESI+: 1201.9 |
| 153 | P16 | ESI+: 1187.5 |
| 154 | P16 | ESI+: 1201.7 |
| 155 | P16 | ESI+: 1120.7 |
| 156 | P16 | ESI+: 1135.6 |
| 157 | P16 | ESI+: 1135.7 |
| 158 | P16 | ESI+: 1165.7 |
| 159 | P16 | ESI+: 1149.6 |
| 160 | P37, P16 | ESI+: 1199.7 |

TABLE 6-6

| PEx | PSyn | DAT |
|---|---|---|
| 161 | P37, P16 | ESI+: 1187.6 |
| 162 | P16 | ESI−: 1346.8 |

TABLE 6-6-continued

| PEx | PSyn | DAT |
|---|---|---|
| 163 | P33 | ESI+: 273.0 |
| 164 | P33 | ESI+: 273.0 |
| 165 | P33 | ESI+: 271.1 |
| 166 | P35 | ESI+: 275.1 |
| 167 | P35 | ESI+: 275.1 |
| 168 | P35 | ESI+: 273.1 |
| 169 | P36 | ESI+: 458.3 |
| 170 | P36 | ESI+: 472.3 |
| 171 | P36 | ESI+: 445.3 |
| 172 | P36 | ESI+: 445.3 |
| 173 | P36 | ESI+: 457.3 |
| 174 | P36 | ESI+: 469.3 |
| 175 | P36 | ESI+: 443.5 |
| 176 | P36 | ESI+: 457.4 |
| 177 | P36 | ESI+: 469.4 |
| 178 | P36 | ESI+: 457.6 |
| 179 | P36 | ESI+: 577.6 |
| 180 | P36 | ESI+: 443.5 |
| 181 | P36 | ESI+: 471.4 |
| 182 | P36 | ESI+: 334.2 |
| 183 | P37 | ESI+: 358.2 |
| 184 | P37 | ESI+: 372.2 |
| 185 | P37 | ESI+: 359.2 |
| 186 | P37 | ESI+: 345.2 |
| 187 | P37 | ESI+: 345.2 |
| 188 | P37 | ESI+: 357.1 |
| 189 | P37 | ESI+: 369.2 |
| 190 | P37 | ESI+: 371.4 |
| 191 | P37 | ESI+: 343.4 |
| 192 | P37 | ESI+: 357.5 |
| 193 | P37 | ESI+: 343.4 |
| 194 | P37 | ESI+: 358.4 |
| 195 | P37 | ESI+: 371.5 |
| 196 | P37 | ESI+: 357.3 |
| 197 | P37 | ESI+: 290.4 |
| 198 | P37 | ESI+: 305.4 |
| 199 | P39 | ESI+: 458.3 |
| 200 | P43 | ESI+: 323.0 |

TABLE 6-7

| PEx | PSyn | DAT |
|---|---|---|
| 201 | P44 | ESI+: 390.5 |
| 202 | P44 | ESI+: 405.3 |
| 203 | P44 | ESI+: 280.1 |
| 204 | P46 | ESI+: 591.5 |
| 205 | P46 | ESI+: 547.2 [M + Na]+ |

TABLE 6-7-continued

| PEx | PSyn | DAT |
|---|---|---|
| 206 | P46 | ESI+: 539.4 |
| 207 | P48 | ESI+: 286.9 |
| 208 | P50 | ESI+: 371.3 |
| 209 | P50 | ESI+: 305.1 |
| 210 | P50 | ESI+: 335.2 |
| 211 | P50 | ESI+: 319.2 |
| 212 | P55 | ESI+: 393.4 |
| 213 | P55 | ESI+: 408.5 |
| 214 | P55 | ESI+: 283.3 |
| 215 | P55 | ESI+: 327.6 |
| 216 | P56 | ESI+: 436.6 |
| 217 | P56 | ESI+: 451.4 |
| 218 | P56 | ESI+: 326.1 |
| 219 | P56 | ESI+: 370.8 |

TABLE 6-8

| PEx | PSyn | DAT |
|---|---|---|
| 220 | P13 | ESI+: 839.7 |
| 221 | P14 | ESI+: 825.7 |
| 222 | P16 | ESI+: 1178.8 |
| 223 | P46 | ESI+: 472.4 |
| 224 | P40 | ESI+: 604.6 |
| 225 | P50 | ESI+: 384.5 |
| 226 | P16 | ESI+: 1214.8 |
| 227 | P227 | ESI−: 314.3 |
| 228 | P228 | ESI+: 330.3 |
| 229 | P229 | ESI+: 242.0 |
| 230 | P55 | ESI+: 344.1 |
| 231 | P231 | ESI+: 385.2 |
| 232 | P44 | ESI−: 337.2 |
| 233 | P40 | ESI+: 473.4 |
| 234 | P37 | ESI+: 373.3 |
| 235 | P16 | ESI+: 1203.8 |
| 236 | P236 | ESI+: 252.1 |
| 237 | P237 | ESI+: 220.1 |
| 238 | P238 | ESI+: 298.0 |
| 239 | P239 | ESI+: 514.2, 516.2 |
| 240 | P240 | ESI+: 580.3, 582.2 |
| 241 | P4 | ESI+: 668.5 |
| 242 | P6 | ESI+: 978.6 |
| 243 | P11 | ESI+: 820.6 |
| 244 | P9 | ESI+: 716.5 |
| 245 | P10 | ESI+: 864.5 |
| 246 | P14 | ESI+: 850.5 |
| 247 | P16 | ESI+: 1204.7 |

TABLE 7-1

| Ex | Str |
|---|---|
| 1 | 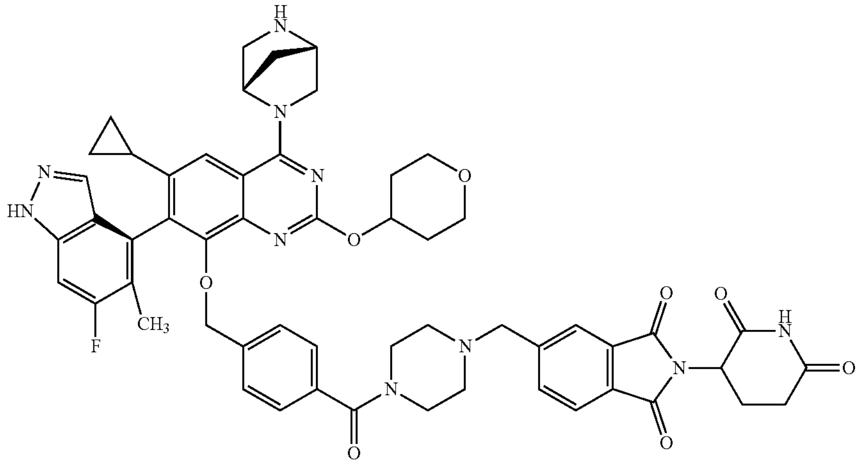 |

TABLE 7-1-continued
| Ex | Str |
| --- | --- |
| 2 | 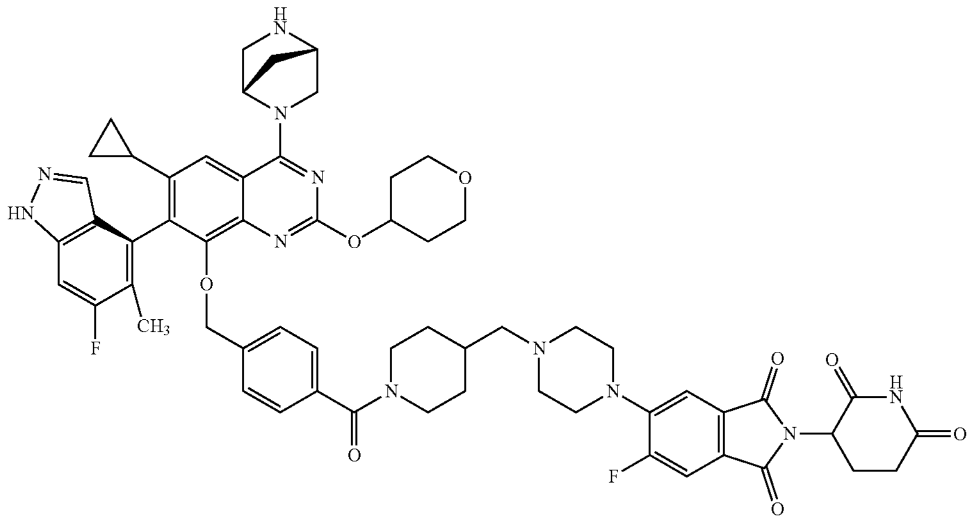 |
| 3 | 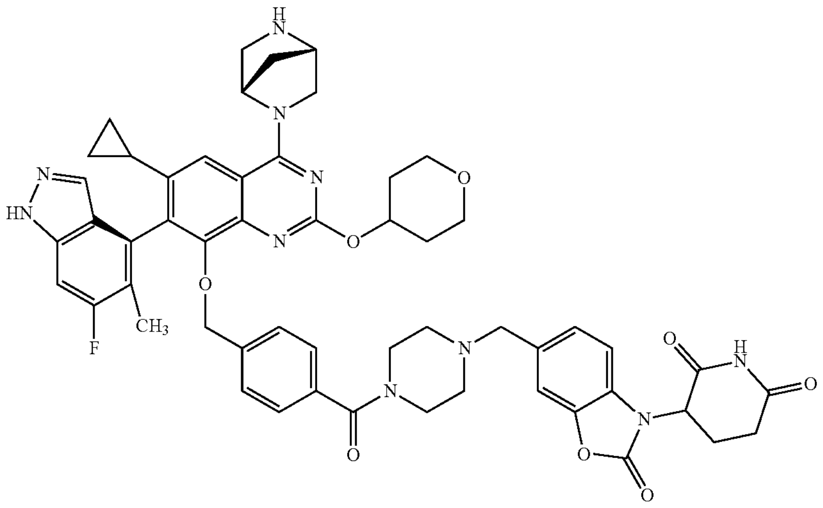 |

TABLE 7-2
| Ex | Str |
| --- | --- |
| 4 | 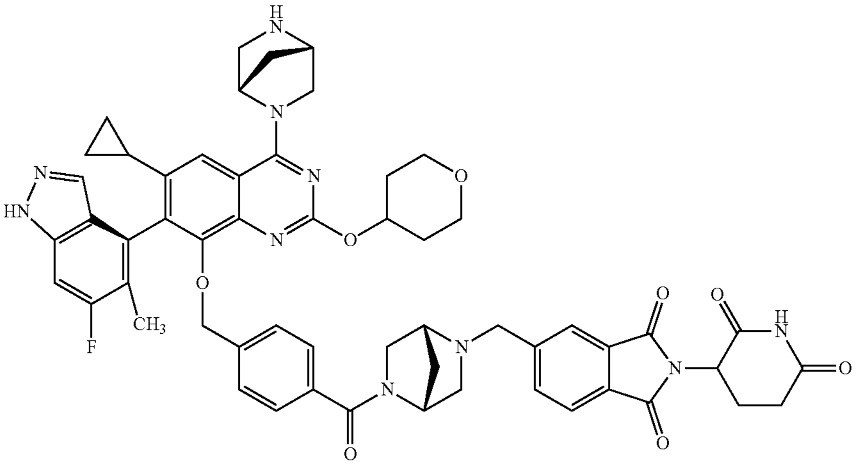 |
| 5 | 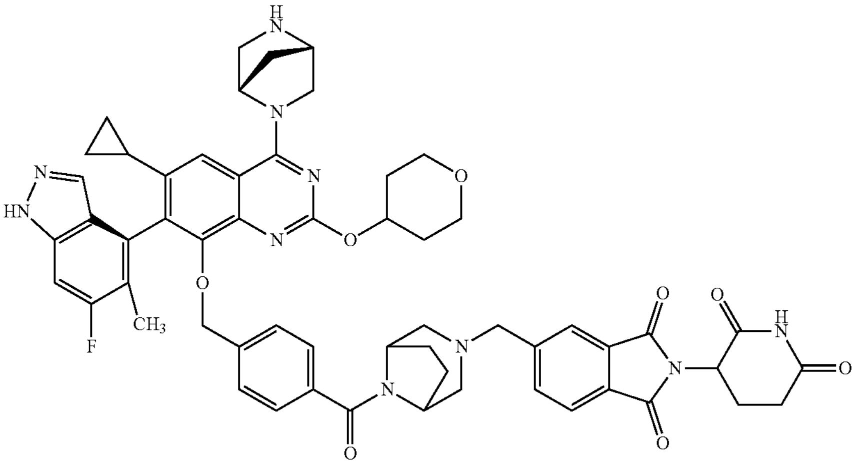 |
| 6 | 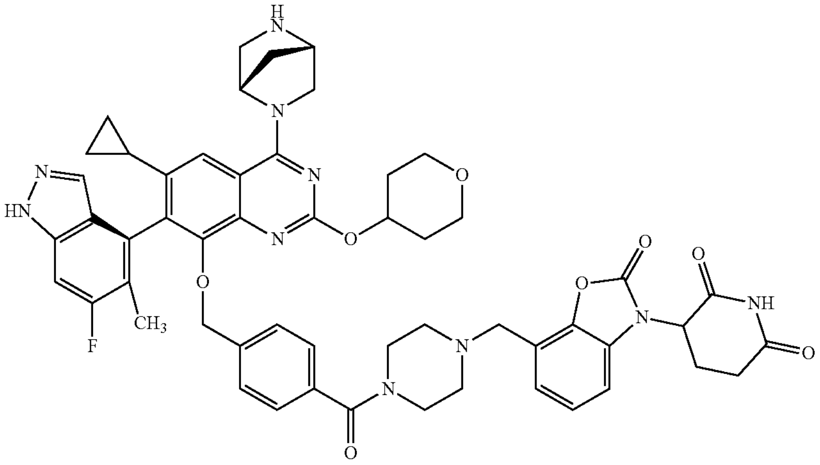 |

TABLE 7-3
| Ex | Str |
|---|---|
| 7 | 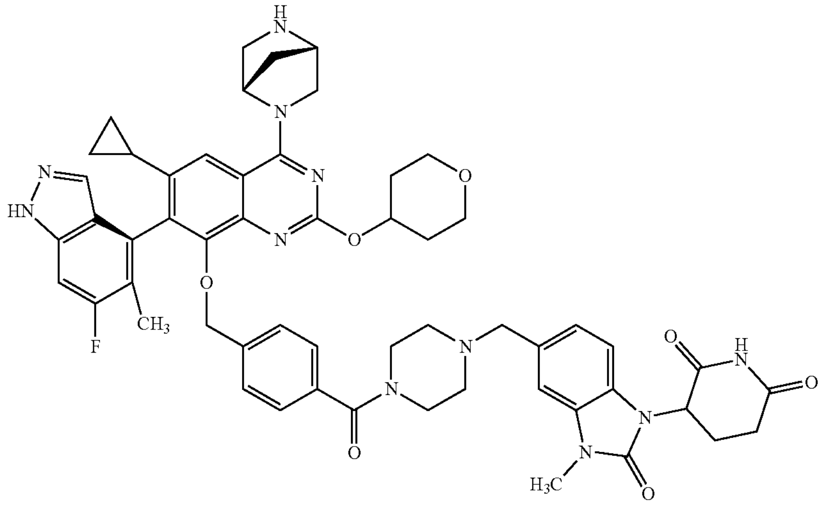 |
| 8 | 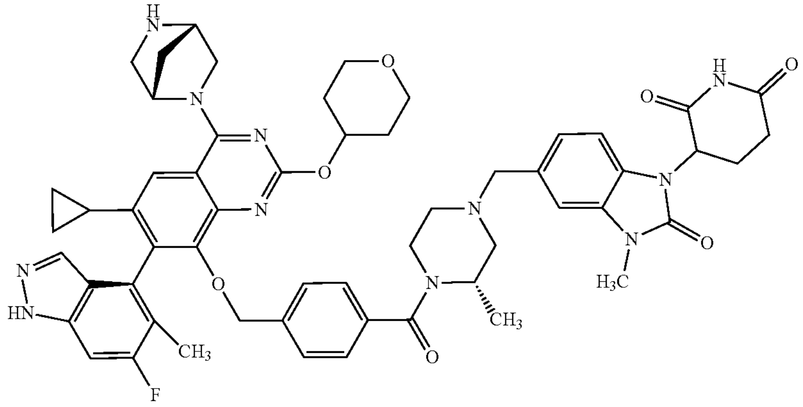 |
| 9 | 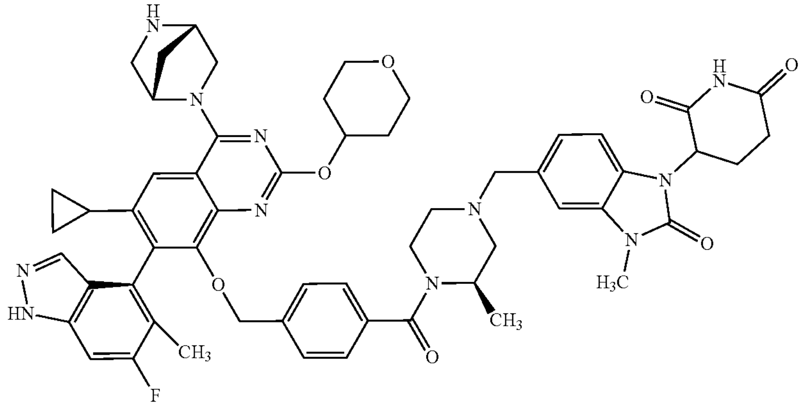 |

TABLE 7-4
| Ex | Str |
|---|---|
| 10 | 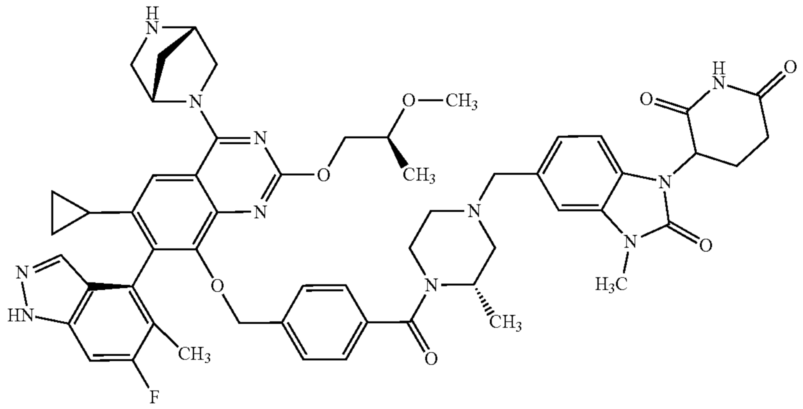 |
| 11 | 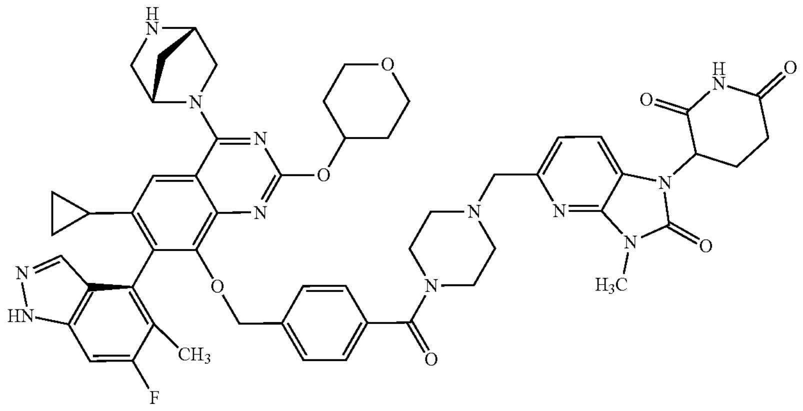 |
| 12 | 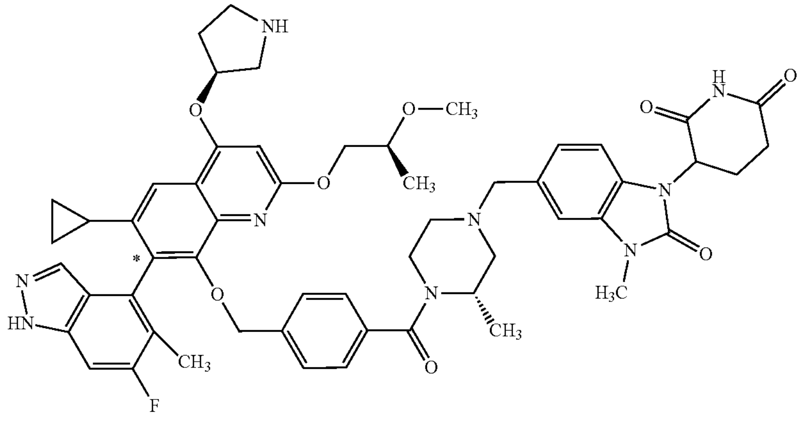 [SMILES: CO[C@@H](C)COc1cc(O[C@H]2CCNC2)c2cc(C3CC3)c(-c3c(C)c(F)cc4[nH]ncc34)c(OCc3ccc(C(=O)N4CCN(Cc5ccc6c(c5)n(C)c(=O)n6C5CCC(=O)NC5=O)C[C@@H]4C)cc3)c2n1] |

TABLE 7-5
| Ex | Str |
| --- | --- |
| 13 | 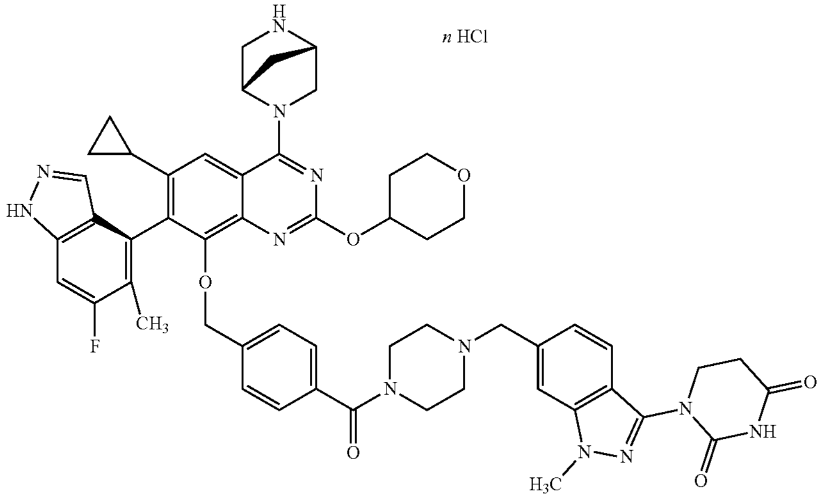 n HCl |
| 14 | 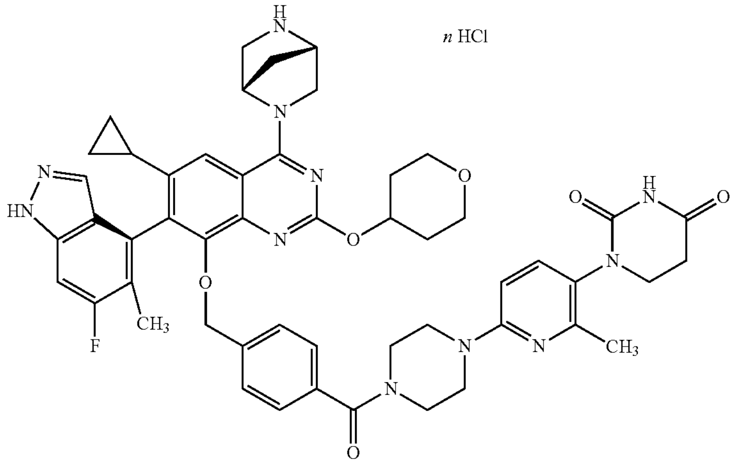 n HCl |
| 15 | 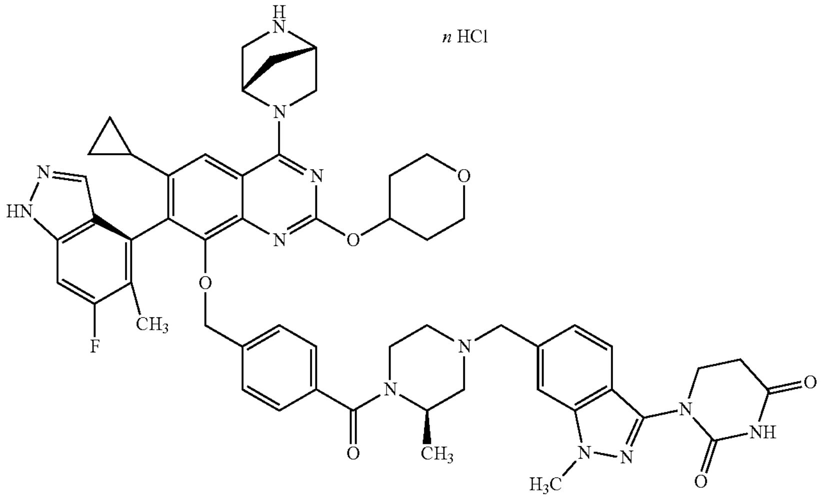 n HCl |

TABLE 7-6
| Ex | Str |
|---|---|
| 16 | 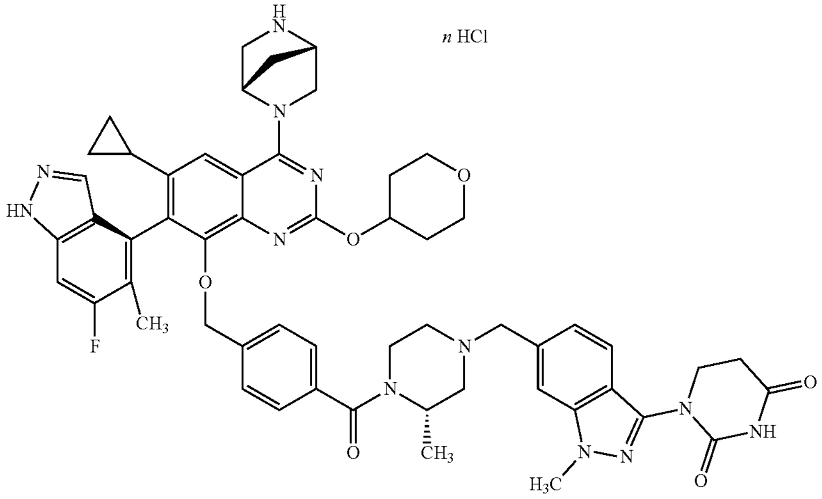 n HCl |
| 17 | 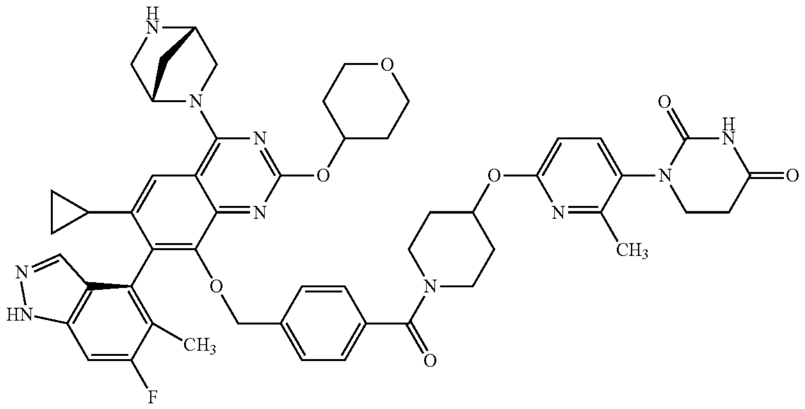 |
| 18 | 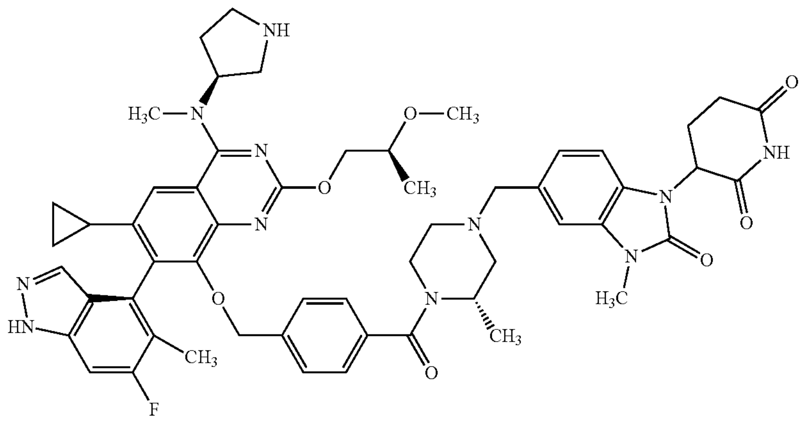 |

TABLE 7-7
| Ex | Str |
|---|---|
| 19 | 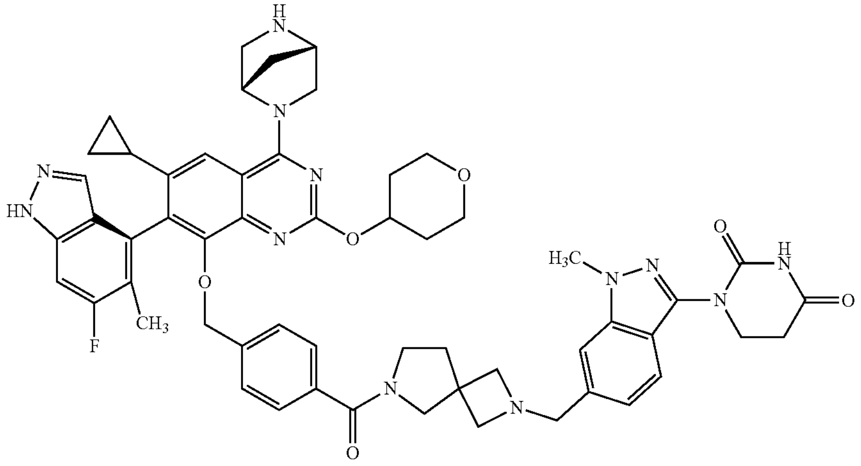 |
| 20 | 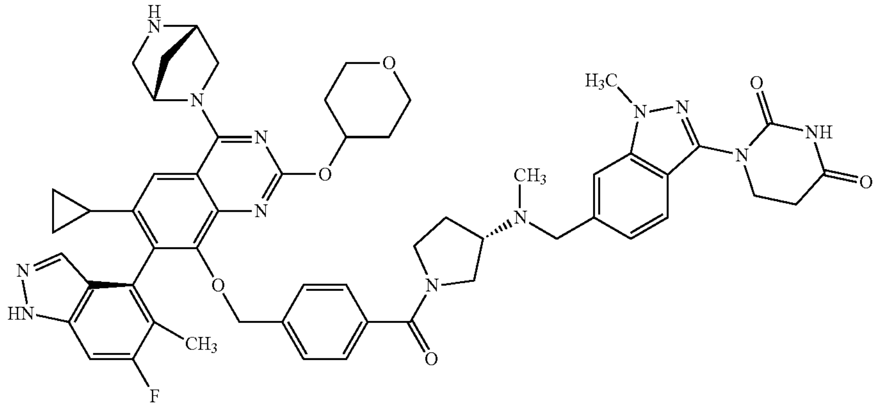 |
| 21 | 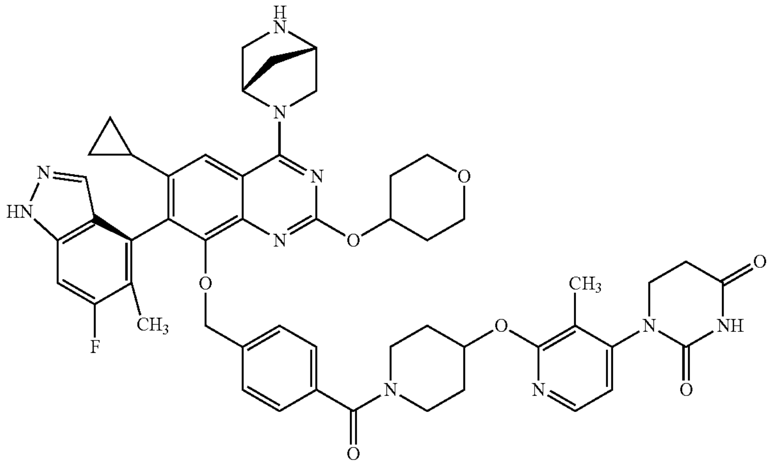 |

TABLE 7-8
| Ex | Str |
| --- | --- |
| 22 | 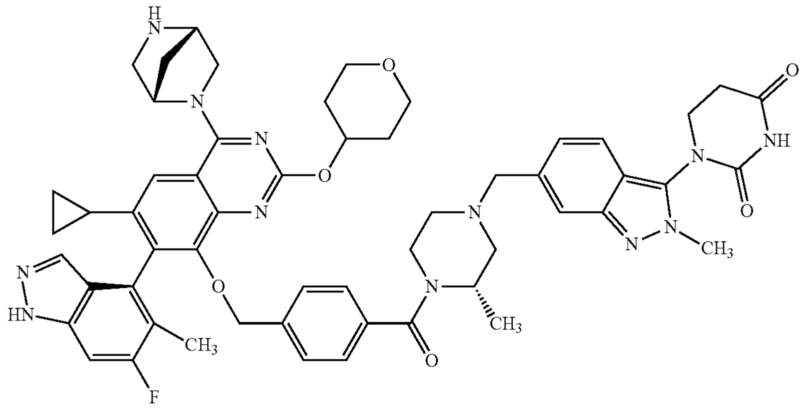 |
| 23 | 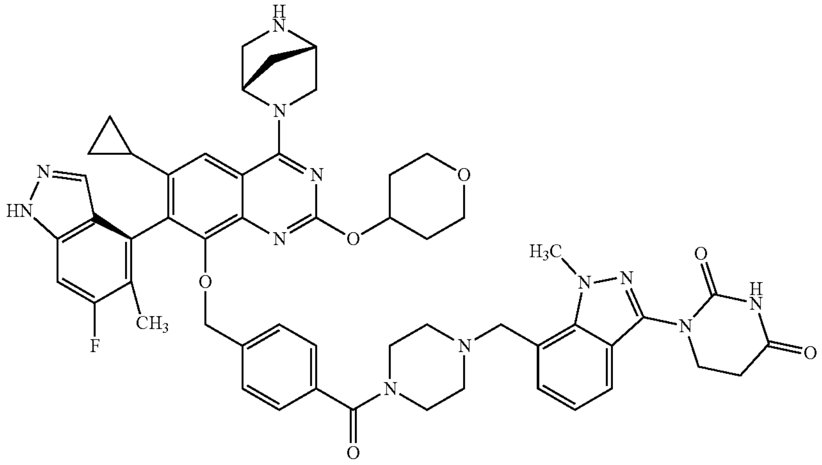 |
| 24 | 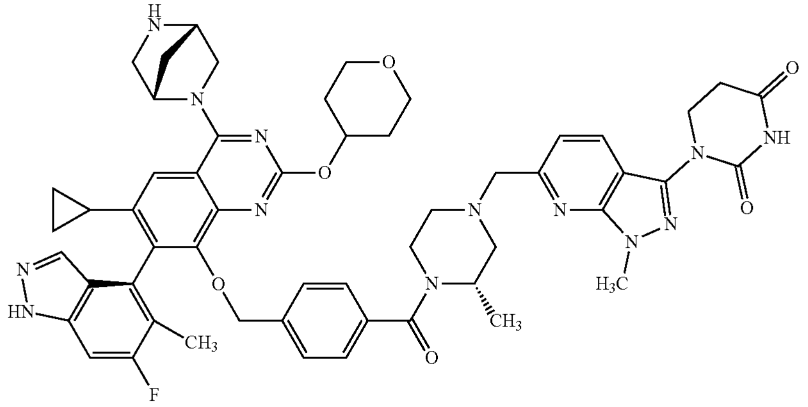 |

TABLE 7-9
| Ex | Str |
|---|---|
| 25 | 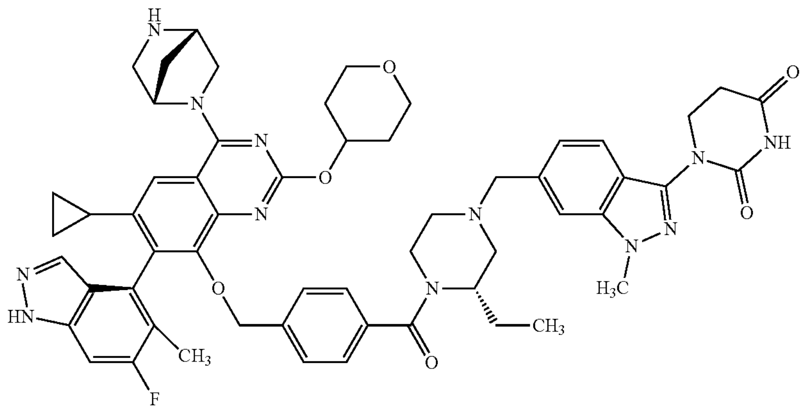 |
| 26 | 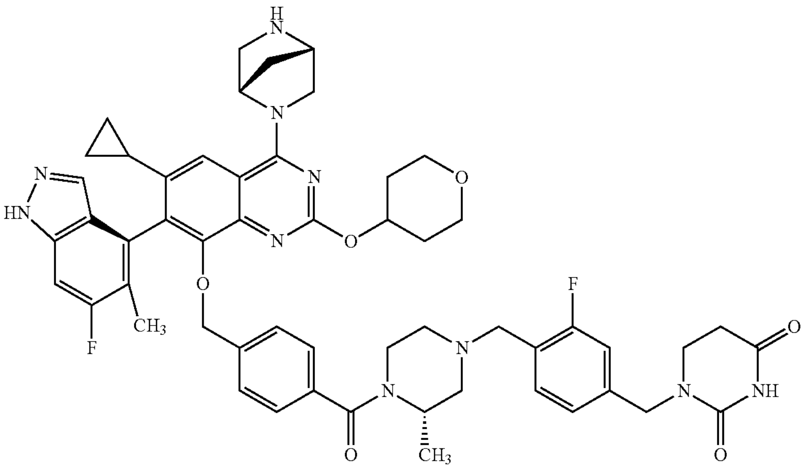 |
| 27 | 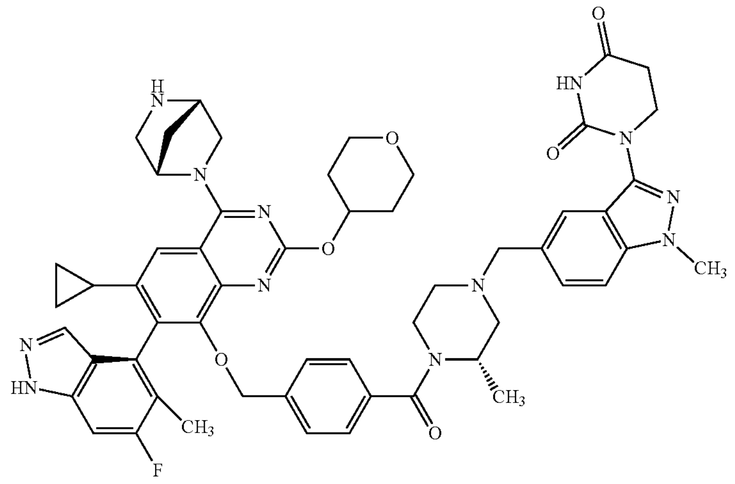 |

TABLE 7-10
| Ex | Str |
|---|---|
| 28 | 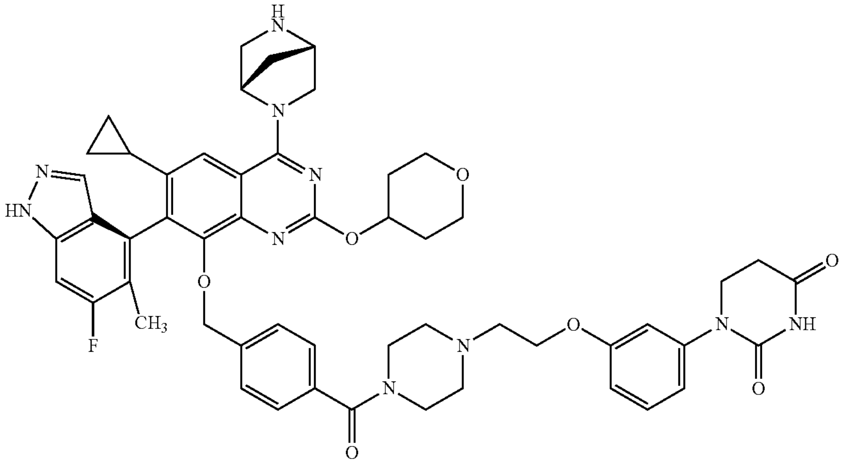 |
| 29 | 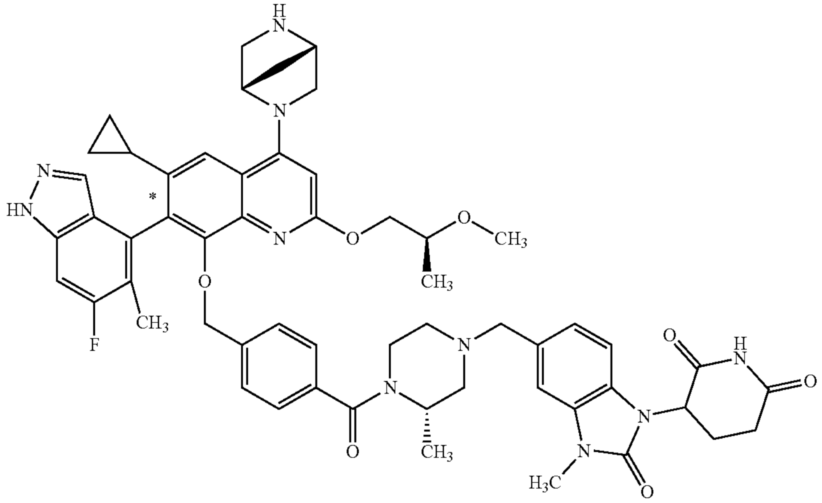 [SMILES: CO[C@@H](C)COc1cc(N2C[C@@H]3C[C@H]2CN3)c2cc(C3CC3)c(-c3c(C)c(F)cc4[nH]ncc34)c(OCc3ccc(C(=O)N4CCN(Cc5ccc6c(c5)n(C)c(=O)n6C5CCC(=O)NC5=O)C[C@@H]4C)cc3)c2n1] |
| 30 | 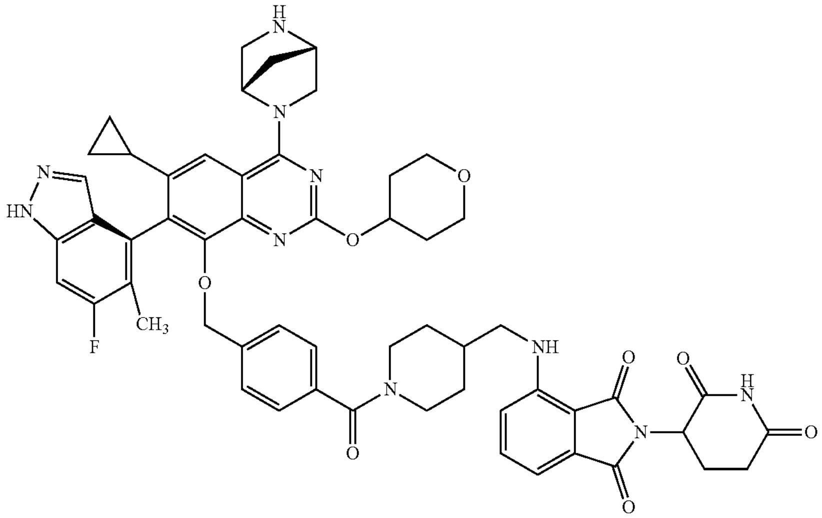 |

TABLE 7-11
| Ex | Str |
|---|---|
| 31 | 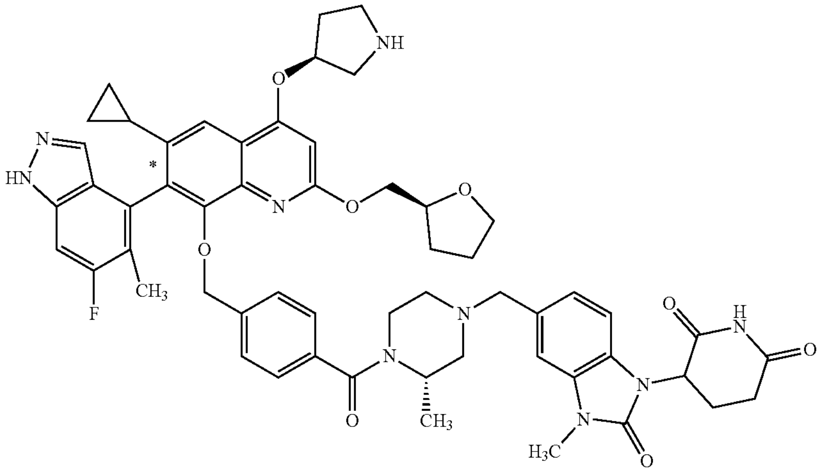 [SMILES: Cc1c(F)cc2[nH]ncc2c1-c1c(C2CC2)cc2c(O[C@H]3CCNC3)cc(OC[C@@H]3CCCO3)nc2c1OCc1ccc(C(=O)N2CCN(Cc3ccc4c(c3)n(C)c(=O)n4C3CCC(=O)NC3=O)C[C@@H]2C)cc1] |
| 32 | 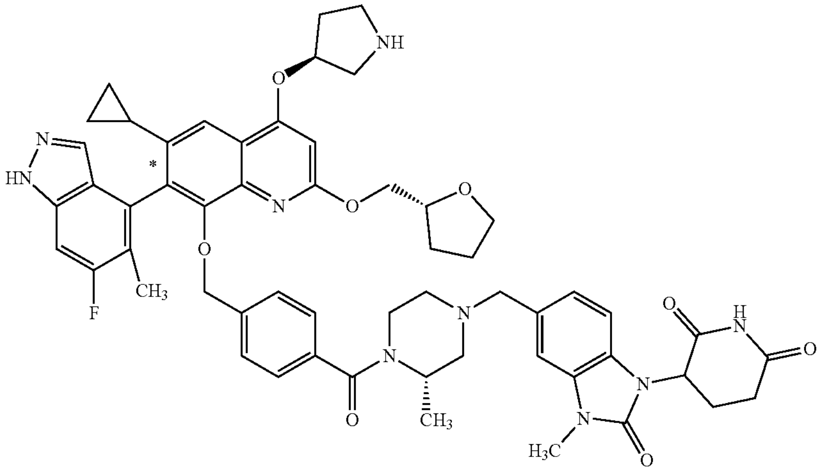 [SMILES: Cc1c(F)cc2[nH]ncc2c1-c1c(C2CC2)cc2c(O[C@H]3CCNC3)cc(OC[C@H]3CCCO3)nc2c1OCc1ccc(C(=O)N2CCN(Cc3ccc4c(c3)n(C)c(=O)n4C3CCC(=O)NC3=O)C[C@@H]2C)cc1] |
| 33 | 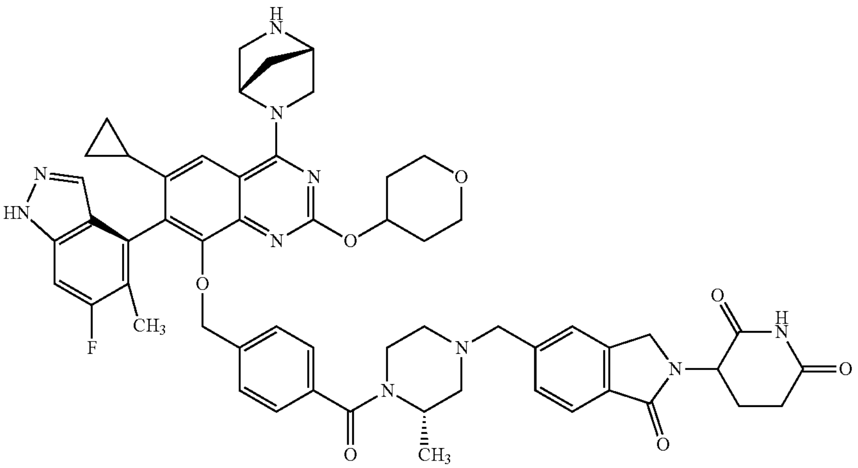 |

TABLE 7-12
| Ex | Str |
| --- | --- |
| 34 | 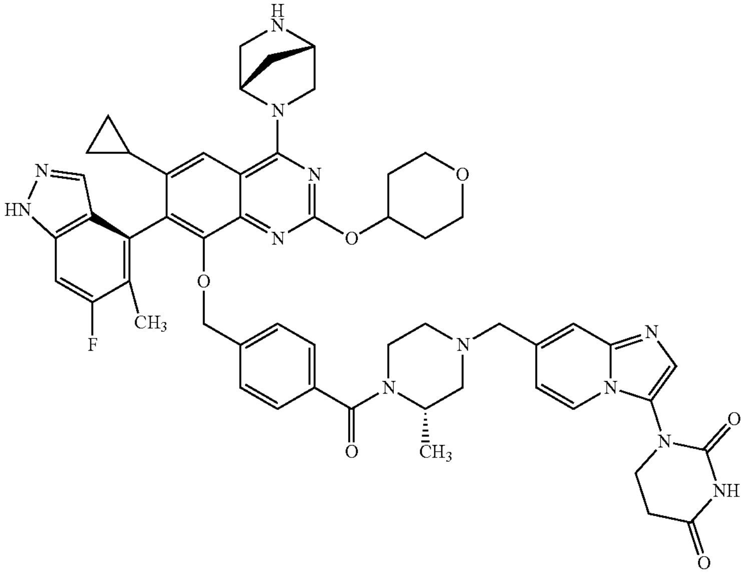 |
| 35 | 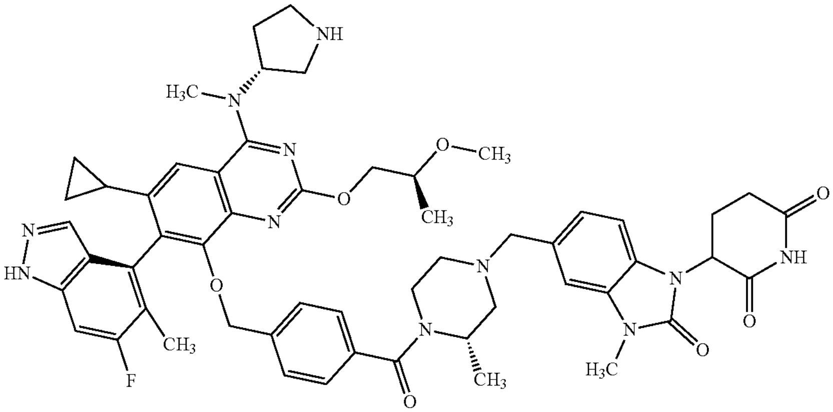 |
| 36 | 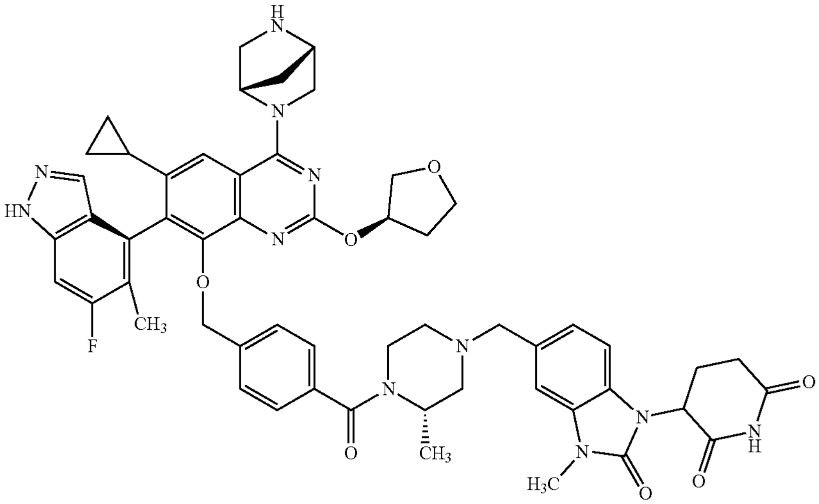 |

TABLE 7-13
| Ex | Str |
|---|---|
| 37 | 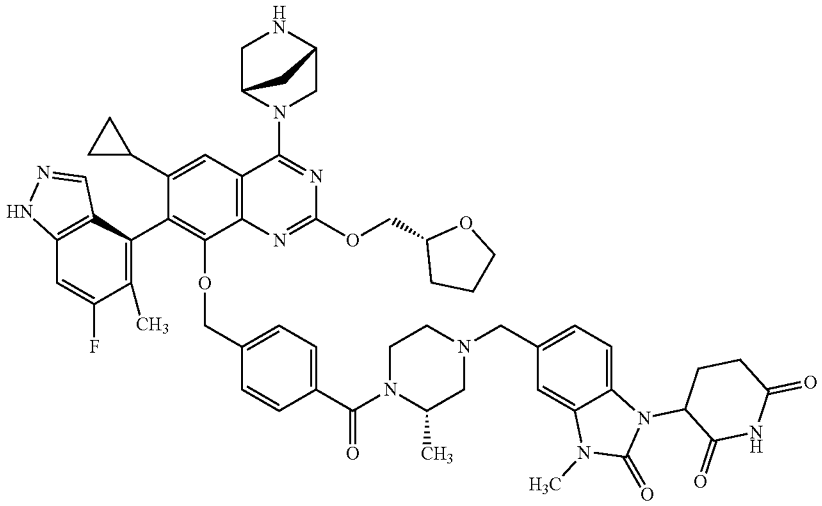 |
| 38 | 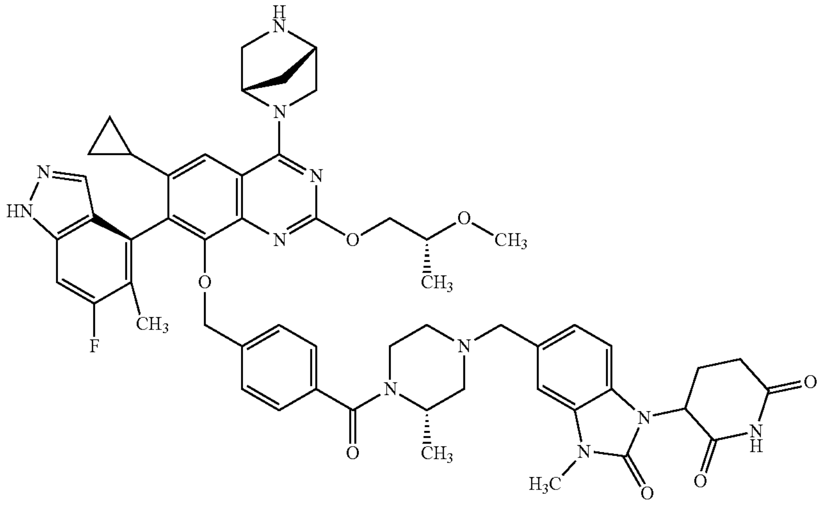 |
| 39 | 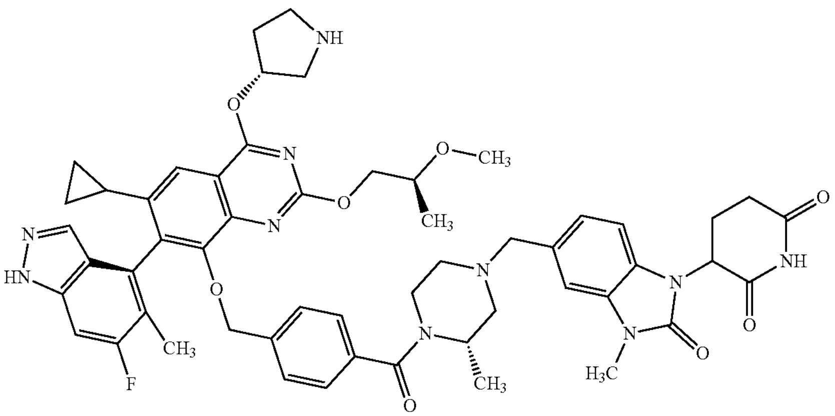 |

TABLE 7-14
| Ex | Str |
| --- | --- |
| 40 | 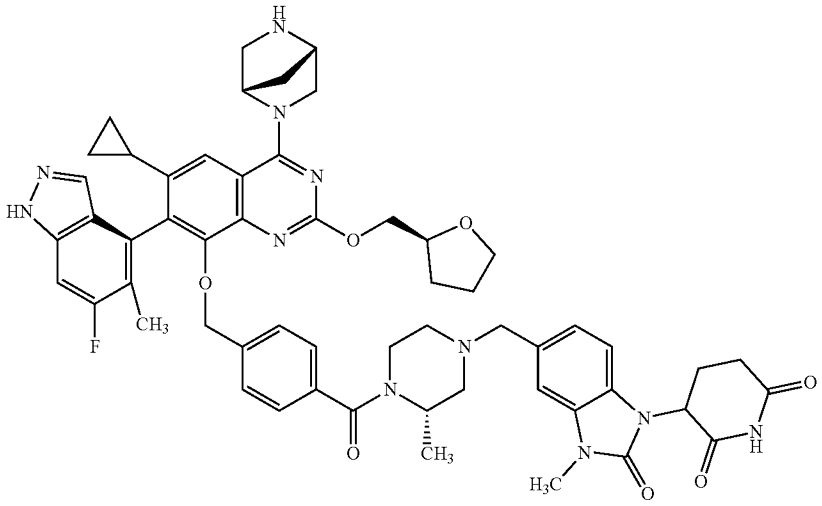 |
| 41 | 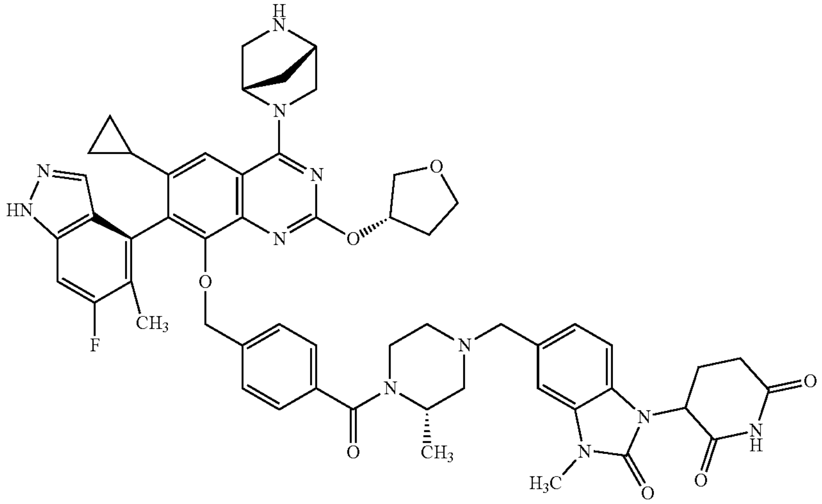 |
| 42 | 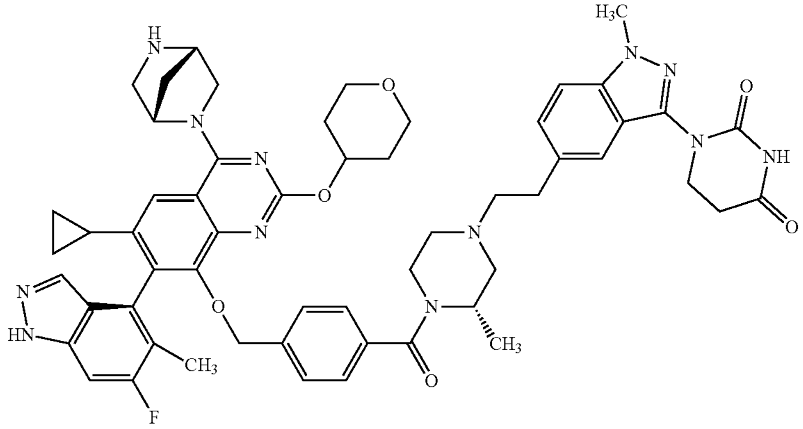 |

TABLE 7-15
| Ex | Str |
|---|---|
| 43 | 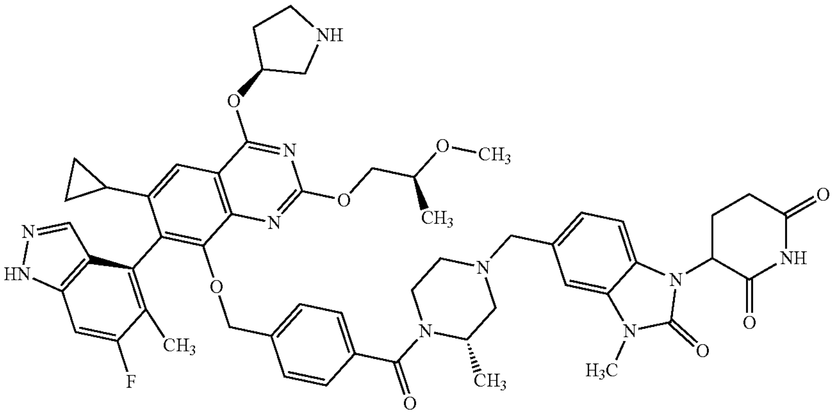 |
| 44 | 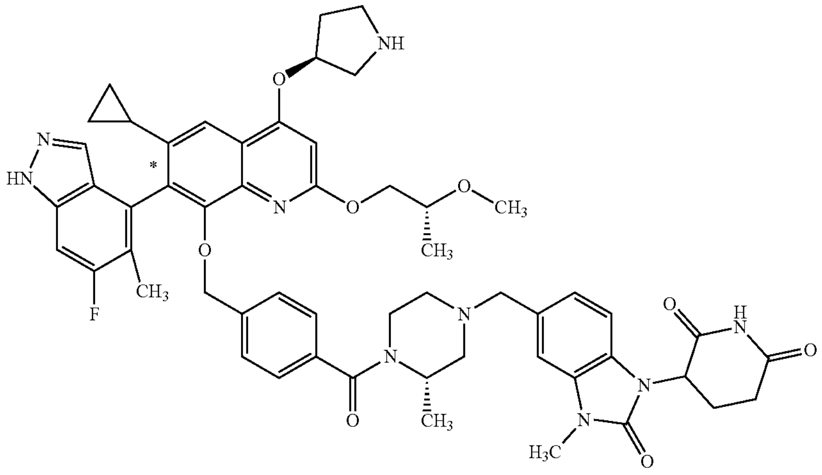 [SMILES: CO[C@H](C)COc1cc(O[C@H]2CCNC2)c2cc(C3CC3)c(-c3c(C)c(F)cc4[nH]ncc34)c(OCc3ccc(C(=O)N4CCN(Cc5ccc6c(c5)n(C)c(=O)n6C5CCC(=O)NC5=O)C[C@@H]4C)cc3)c2n1] |
TABLE 7-16
| Ex | Str |
|---|---|
| 45 | 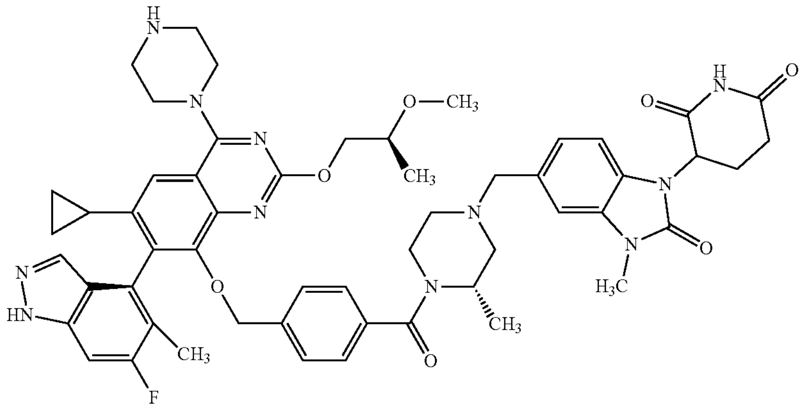 |

TABLE 7-16-continued
| Ex | Str |
|---|---|
| 46 | 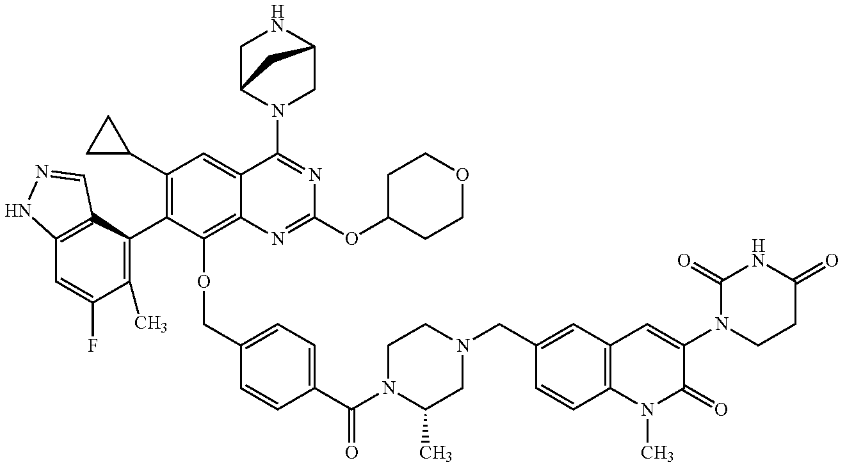 |
| 47 | 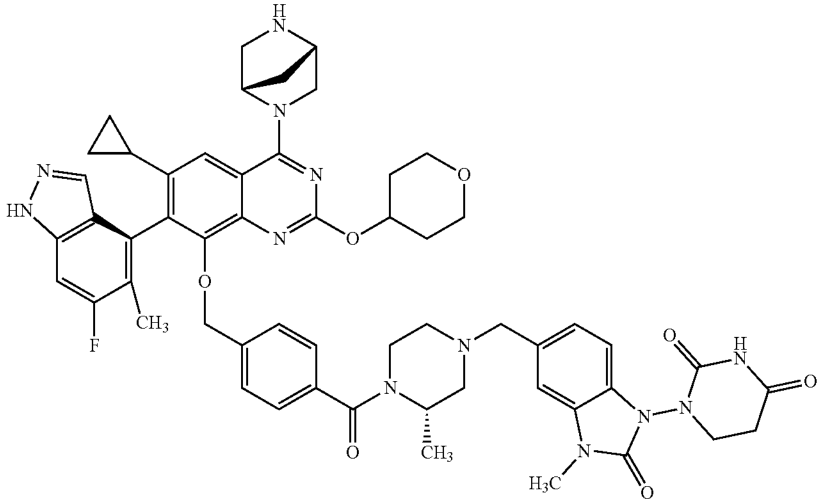 |
| 48 | 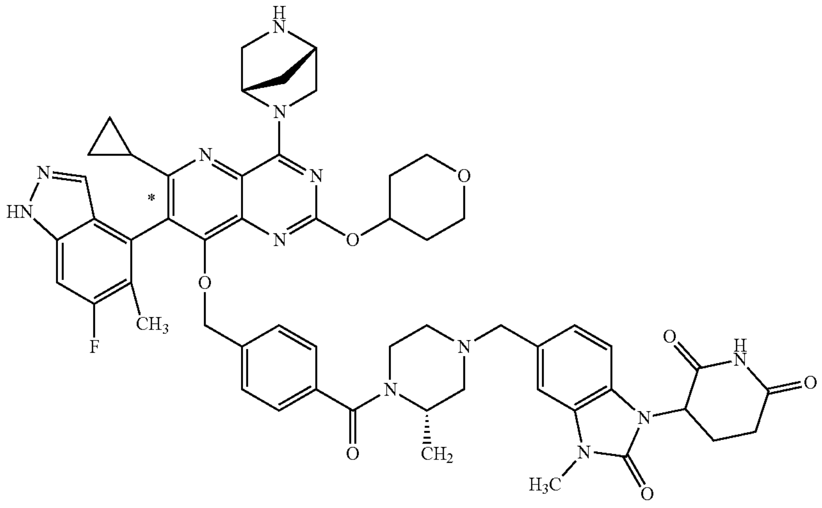 [SMILES: Cc1c(F)cc2[nH]ncc2c1-c1c(C2CC2)nc2c(N3C[C@@H]4C[C@H]3CN4)nc(OC3CCOCC3)nc2c1OCc1ccc(C(=O)N2CCN(Cc3ccc4c(c3)n(C)c(=O)n4C3CCC(=O)NC3=O)C[C@@H]2C)cc1] |

TABLE 7-17

| Ex | Str |
|---|---|
| 49 | 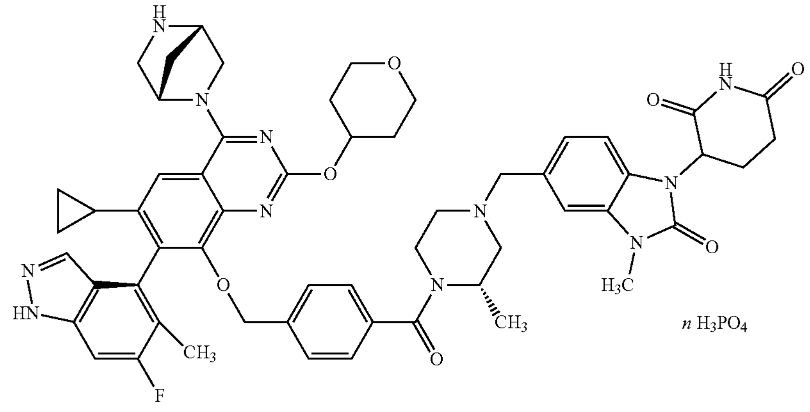 |
| 50 | 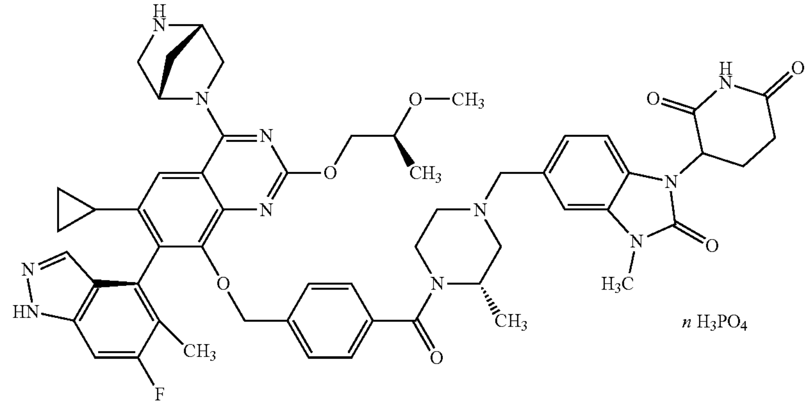 |

TABLE 8-1

| Ex | Syn | DAT |
|---|---|---|
| 1 | E5 | ESI+: 1003.3 |
| 2 | E5 | ESI−: 1102.5 |
| 3 | E5 | ESI+: 991.8 |
| 4 | E5 | ESI−: 1013.6 |
| 5 | E5 | ESI+: 1029.7 |
| 6 | E5 | ESI+: 991.4 |
| 7 | E5 | ESI+: 1004.7 |
| 8 | E8 | ESI+: 1018.6 NMR (90° C.): 0.48-0.68 (4H, m), 1.26 (3H, d), 1.37 (1H, tt), 1.62-1.71 (2H, m), 1.73 (1H, br d), 1.86 (1H, br d), 1.99 (3H, d), 1.99-2.09 (4H, m), 2.13 (1H, dd), 2.61-2.74 (3H, m), 2.80 (1H, br d), 2.83-2.93 (1H, m), 3.04 (1H, dd), 3.09-3.22 (2H, m), 3.28-3.37 (2H, m), 3.32 (3H, s), 3.46 (1H, d), 3.56 (1H, d), 3.69-3.79 (3H, m), 3.82 (2H, dq), 4.12-4.24 (1H, m), 4.16 (1H, dd), 4.81 (1H, d), 5.11 (1H, br s), 5.15 (1H, tt), 5.22-5.30 (2H, m), 6.82-6.87 (2H, m), 6.96-7.04 (2H, m), 7.07-7.11 (3H, m), 7.27 (1H, d), 7.44 (1H, d), 7.46 (1H, s), 10.71 (1H, br s), 12.78 (1H, br s) |
| 9 | E5 | ESI+: 1018.7 |
| 10 | E10 | ESI+: 1006.7 NMR (90° C.): 0.48-0.68 (4H, m), 1.12 (3H, d), 1.26 (3H, d), 1.37 (1H, tt), 1.74 (1H, br d), 1.87 (1H, br d), 1.98 (3H, d), 1.98-2.09 (2H, m), 2.12 (1H, dd), 2.60-2.74 (3H, m), 2.80 (1H, br d), 2.83-2.93 (1H, m), 3.05 (1H, dd), 3.10-3.21 (2H, m), 3.28 (3H, s), 3.32 (3H, s), 3.46 (1H, d), 3.56 (1H, d), 3.65-3.78 (4H, m), 4.13-4.22 (2H, m), 4.23-4.28 (1H, m), 4.28-4.34 (1H, m), 4.83 (1H, d), 5.12 (1H, s), 5.23-5.30 (2H, m), 6.84 (2H, d), 6.96-7.04 (2H, m), 7.04-7.10 (3H, m), 7.26 (1H, d), 7.44 (1H, d), 7.46 (1H, s), 10.73 (1H, br s), 12.77 (1H, br s) |
| 11 | E5 | ESI+: 1005.7 |
| 12 | E12 | ESI+: 994.7 NMR (90° C.): 0.48-0.68 (4H, m), 1.12 (3H, d), 1.26 (3H, d), 1.34-1.42 (1H, m), 1.92-2.09 (3H, m), 1.97 (3H, d), 2.09-2.22 (2H, m), 2.60-2.74 (3H, m), 2.80 (1H, br d), 2.83-2.93 (2H, m), 3.00-3.12 (2H, m), 3.13-3.23 (2H, m), 3.28 (3H, s), 3.32 (3H, s), 3.46 (1H, d), 3.56 (1H, d), 3.67-3.77 (2H, m), 4.18 (1H, br s), 4.30-4.39 (2H, m), 4.89-4.95 (1H, m), 5.12-5.17 (1H, m), 5.22-5.30 (2H, m), 6.43 (1H, s), 6.86 (2H, d), 6.94-7.10 (5H, m), 7.26 (1H, d), 7.42 (1H, d), 7.46 (1H, s), 12.75 (1H, br s) |

TABLE 8-2

| Ex | Syn | DAT |
|---|---|---|
| 13 | E16 | ESI+: 989.7 |
| 14 | E16 | ESI+: 936.7 |
| 15 | E16 | ESI+: 1003.6 |
| 16 | E16 | ESI+: 1003.8 |
| 17 | E5 | ESI+: 951.5 |
| 18 | E5 | ESI+: 1008.7 |
| 19 | E5 | ESI+: 1015.8 |
| 20 | E5 | ESI+: 1003.7 |
| 21 | E5 | ESI+: 951.7 |
| 22 | E5 | ESI+: 1003.6 |
| 23 | E5 | ESI+: 989.6 |

TABLE 8-2-continued

| Ex | Syn | DAT |
|---|---|---|
| 24 | E5 | ESI+: 1005.5 |
| 25 | E5 | ESI+: 1017.6 |
| 26 | E5 | ESI+: 981.5 |
| 27 | E5 | ESI+: 1003.7 |
| 28 | E5 | ESI -: 963.6 |
| 29 | E29 | ESI+: 1005.7<br>NMR (90° C.): 0.49-0.68 (4H, m), 1.10 (3H, d), 1.26 (3H, d), 1.39 (1H, tt), 1.73 (1H, br d), 1.90 (1H, br d), 1.96-2.09 (2H, m), 1.99 (3H, d), 2.12 (1H, dd), 2.61-2.74 (3H, m), 2.80 (1H, br d), 2.83-2.93 (1H, m), 2.99-3.04 (1H, m), 3.13-3.21 (1H, m), 3.23 (1H, d), 3.26 (3H, s), 3.32 (3H, s), 3.38-3.43 (1H, m), 3.46 (1H, d), 3.56 (1H, d), 3.63-3.77 (3H, m), 4.00 (1H, dd), 4.18 (1H, br s), 4.26 (1H, dd), 4.31-4.36 (1H, m), 4.50 (1H, br s), 4.81 (1H, d), 5.24-5.31 (2H, m), 6.08 (1H, s), 6.84 (2H, d), 6.96-7.04 (2H, m), 7.05-7.10 (3H, m), 7.26 (1H, d), 7.42 (1H, s), 7.43 (1H, d), 10.77 (1H, br s), 12.74 (1H, br s) |
| 30 | E5 | ESI+: 1017.7 |
| 31 | E5 | ESI+: 1006.5 |
| 32 | E5 | ESI+: 1006.5 |
| 33 | E33 | ESI+: 1003.6 |
| 34 | E34 | ESI+: 989.7 |
| 35 | E5 | ESI+: 1008.7 |
| 36 | E5 | ESI+: 1004.6 |
| 37 | E5 | ESI+: 1018.7 |
| 38 | E5 | ESI+: 1006.6 |
| 39 | E5 | ESI+: 995.8 |
| 40 | E10 | ESI+: 1018.6 |

TABLE 8-3

| Ex | Syn | DAT |
|---|---|---|
| 41 | E10 | ESI+: 1004.6 |
| 42 | E5 | ESI+: 1017.7 |
| 43 | E5 | ESI+: 995.6 |
| 44 | E5 | ESI+: 994.7 |

TABLE 8-4

| Ex | Syn | DAT |
|---|---|---|
| 45 | E5 | ESI+: 994.6 |
| 46 | E5 | ESI+: 1030.8 |
| 47 | E5 | ESI+: 1019.8 |
| 48 | E5 | ESI+: 1019.5 |
| 49 | E49 | ESI+: 1018.5 |
| 50 | E50 | ESI+: 1006.5 |

As examples of specific compounds of the formula (I) included in the present invention, compounds having any of the following structures are shown. These compounds can be produced also by the typical production methods shown above, the production methods of the Production Examples and the Examples, a combination of the production methods or a method that is obvious to a person skilled in the art.

These compounds are expected to be excellent in the degradation-inducing action on a G12D mutant KRAS protein and/or useful as a G12D mutant KRAS inhibitor and can be used as an active ingredient of a pharmaceutical composition, for example, a pharmaceutical composition for treating pancreatic cancer.

TABLE 9-1

| No. | Str |
|---|---|
| AA1 | 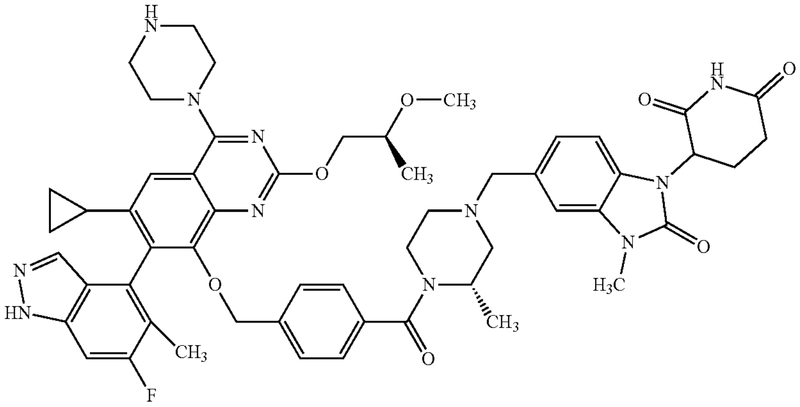 [SMILES: CO[C@@H](C)COc1nc(N2CCNCC2)c2cc(C3CC3)c(-c3c(C)c(F)cc4[nH]ncc34)c(OCc3ccc(C(=O)N4CCN(Cc5ccc6c(c5)n(C)c(=O)n6C5CCC(=O)NC5=O)C[C@@H]4C)cc3)c2n1] |

TABLE 9-1-continued
| No. | Str |
| --- | --- |
| AA2 | 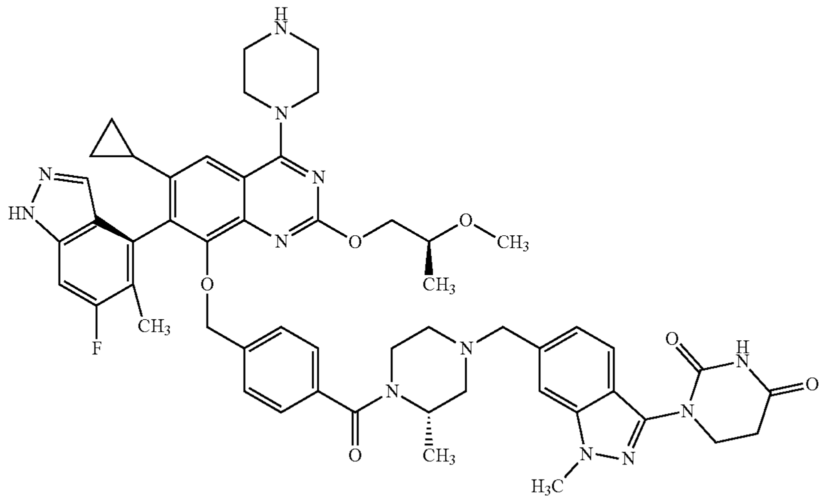 |
| AA3 | 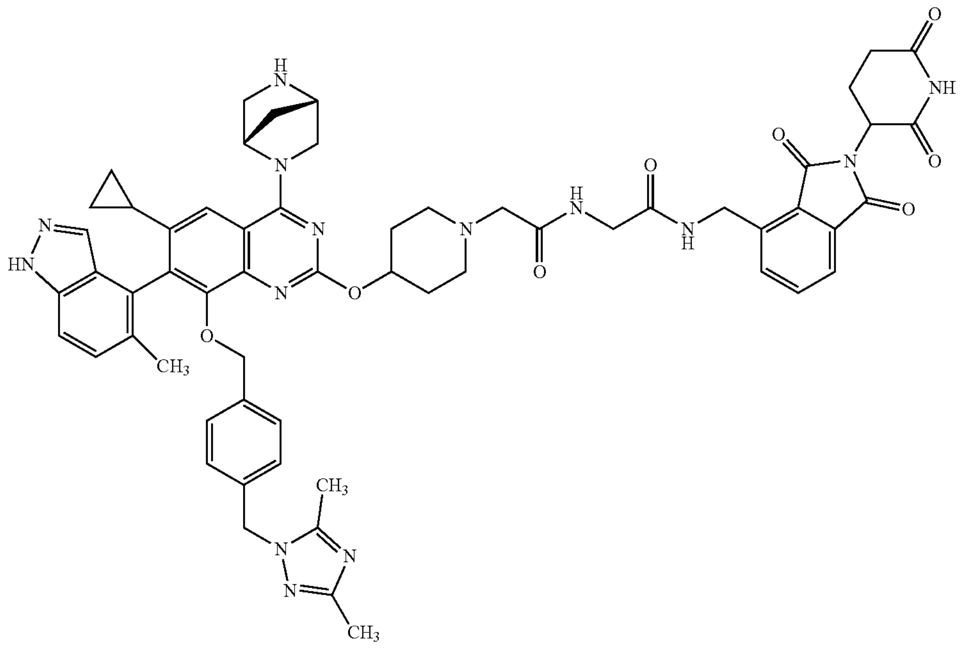 [SMILES: Cc1nc(C)n(Cc2ccc(COc3c(-c4c(C)ccc5[nH]ncc45)c(C4CC4)cc4c(N5C[C@@H]6C[C@H]5CN6)nc(OC5CCN(CC(=O)NCC(=O)NCc6cccc7c6C(=O)N(C6CCC(=O)NC6=O)C7=O)CC5)nc34)cc2)n1] |

TABLE 9-2

| No. | Str |
|---|---|
| AA4 | 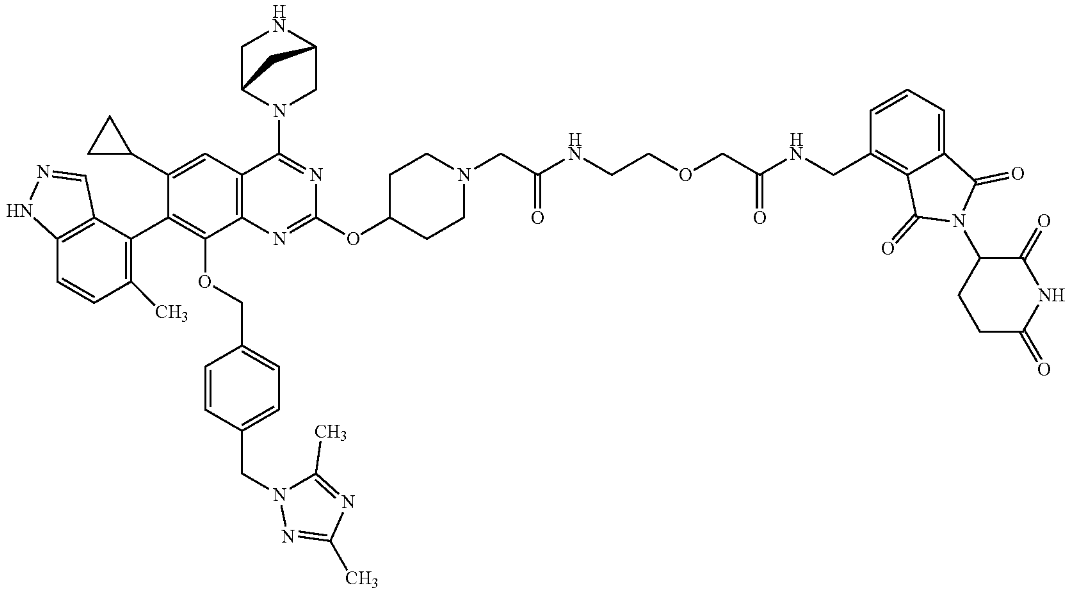 [SMILES: Cc1nc(C)n(Cc2ccc(COc3c(-c4c(C)ccc5[nH]ncc45)c(C4CC4)cc4c(N5C[C@@H]6C[C@H]5CN6)nc(OC5CCN(CC(=O)NCCOCC(=O)NCc6cccc7c6C(=O)N(C6CCC(=O)NC6=O)C7=O)CC5)nc34)cc2)n1] |
| AA5 | 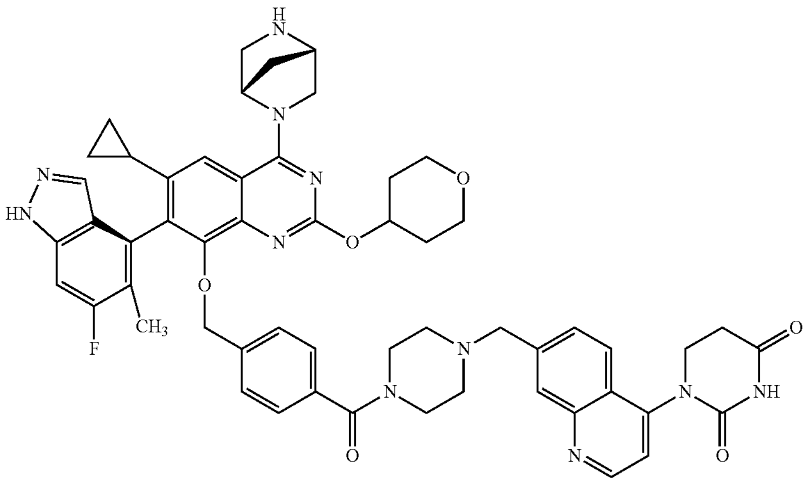 |

INDUSTRIAL APPLICABILITY

The compound or a salt thereof of the present invention is excellent in the degradation-inducing action on a G12D mutant KRAS protein, and/or is useful as a G12D mutant KRAS inhibitor and can be used as an active ingredient of a pharmaceutical composition, for example, a pharmaceutical composition for treating pancreatic cancer.

The invention claimed is:

1. A compound or a salt thereof, wherein the compound is selected from the group consisting of:

5-[(8-{4-[{{(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3,8-diazabicyclo[3.2.1]octan-3-yl)methyl]-2-(2,6-dioxopiperidin-3-yl)-1H-isoindole-1,3(2H)-dione, 3-(5-{[(3S)-4-{4-[{{(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione, 3-(5-{[(3S)-4-{4-[{{(7M)-6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione, 3-[5-({(3S)-4-[4-({[(7M)-6-cyclopropyl-7-(6-fluoro-5-methyl-1H-indazol-4-yl)-2-[(2S)-2-methoxypropoxy]-4-{[(3S)-pyrrolidin-3-yl]oxy}quinolin-8-yl]oxy}methyl)benzoyl]-3-methylpiperazin-1-yl}methyl)-3-methyl-2-oxo-2,3-dihydro-1H-benzimidazol-1-yl]piperidine-2,6-dione, 1-(6-{[(3S)-4-{4-[{{(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-1-methyl-1H-indazol-3-yl)-1,3-diazinane-2,4-dione, 3-(5-{[(3S)-4-{4-[{{(7M)-6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione, 3-(5-{[(3S)-4-{4-[{{(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-1-oxo-1,3-dihydro-2H-isoindol-2-yl)piperidine-2,6-dione, and 1-(7-{[(3S)-4-{4-[{{(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}imidazo[1,2-a]pyridin-3-yl)-1,3-diazinane-2,4-dione.

2. A pharmaceutical composition comprising at least one compound or salt thereof according to claim 1, and at least one pharmaceutically acceptable excipient.

3. The compound or a salt thereof according to claim 1, wherein the compound is:

5-[(8-{4-[{{(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3,8-diazabicyclo[3.2.1]octan-3-yl)methyl]-2-(2,6-dioxopiperidin-3-yl)-1H-isoindole-1,3(2H)-dione.

4. The compound or a salt thereof according to claim 1, wherein the compound is:

3-(5-{[(3S)-4-{4-[{{(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione.

5. The compound or a salt thereof according to claim 1, wherein the compound is:

3-(5-{[(3S)-4-{4-[{{(7M)-6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinazolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione.

6. The compound or a salt thereof according to claim 1, wherein the compound is:

3-[5-({(3S)-4-[4-{{[(7M)-6-cyclopropyl-7-(6-fluoro-5-methyl-1H-indazol-4-yl)-2-[(2S)-2-methoxypropoxy]-4-{[(3S)-pyrrolidin-3-yl]oxy}quinolin-8-yl]oxy}methyl)benzoyl]-3-methylpiperazin-1-yl}methyl)-3-methyl-2-oxo-2,3-dihydro-1H-benzimidazol-1-yl]piperidine-2,6-dione.

7. The compound or a salt thereof according to claim 1, wherein the compound is:

1-(6-{[(3S)-4-{4-[{{(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-1-methyl-1H-indazol-3-yl)-1,3-diazinane-2,4-dione.

8. The compound or a salt thereof according to claim 1, wherein the compound is:

3-(5-{[(3S)-4-{4-[{{(7M)-6-cyclopropyl-4-[(1S,4S)-2,5-diazabicyclo[2.2.1]heptan-2-yl]-7-(6-fluoro-5-methyl-1H-indazol-4-yl)-2-[(2S)-2-methoxypropoxy]quinolin-8-yl}oxy)methyl]benzoyl}-3-methylpiperazin-1-yl]methyl}-3-methyl-2-oxo-2,3-dihydro-1H-benzimidazol-1-yl)piperidine-2,6-dione.

9. The compound or a salt thereof according to claim 1, wherein the compound is:

3-(5-{[(3S)-4-{4-[{{(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}-1-oxo-1,3-dihydro-2H-isoindol-2-yl)piperidine-2,6-dione.

10. The compound or a salt thereof according to claim 1, wherein the compound is:

1-(7-{[(3S)-4-{4-[{{(7M)-6-cyclopropyl-4-[(1S,4S)-2,5-diazabicyclo[2.2.1]heptan-2-yl]-7-(6-fluoro-5-methyl-1H-indazol-4-yl)-2-[(oxan-4-yl)oxy]quinazolin-8-yl}oxy)methyl]benzoyl}-3-methylpiperazin-1-yl]methyl}imidazo[1,2-a]pyridin-3-yl)-1,3-diazinane-2,4-dione.

* * * * *